US010730826B2

(12) United States Patent
Konradi et al.

(10) Patent No.: US 10,730,826 B2
(45) Date of Patent: Aug. 4, 2020

(54) KETONE INHIBITORS OF LYSINE GINGIPAIN

(71) Applicant: CORTEXYME, INC., South San Francisco, CA (US)

(72) Inventors: Andrei W. Konradi, Burlingame, CA (US); Robert A. Galemmo, Jr., South San Francisco, CA (US); Stephen S. Dominy, Novato, CA (US); Casey C. Lynch, San Francisco, CA (US); Leslie J. Holsinger, Los Altos, CA (US)

(73) Assignee: CORTEXYME, INC., South San Francisco, CA (US)

( * ) Notice: Subject to any disclaimer, the term of this patent is extended or adjusted under 35 U.S.C. 154(b) by 0 days.

(21) Appl. No.: 16/353,786

(22) Filed: Mar. 14, 2019

(65) Prior Publication Data

US 2019/0210960 A1     Jul. 11, 2019

Related U.S. Application Data

(63) Continuation of application No. PCT/US2017/051912, filed on Sep. 15, 2017.
(Continued)

(51) Int. Cl.
*C07C 233/62* (2006.01)
*C07D 213/82* (2006.01)
*C07D 239/34* (2006.01)
*C07D 239/36* (2006.01)
*C07D 413/12* (2006.01)
*C07D 257/04* (2006.01)
*C07D 261/12* (2006.01)
*C07D 213/70* (2006.01)
*C07C 317/28* (2006.01)
*C07C 233/78* (2006.01)
*C07C 235/10* (2006.01)
*C07C 235/50* (2006.01)
*C07B 59/00* (2006.01)
*C07C 237/42* (2006.01)
*C07D 401/12* (2006.01)
*C07C 381/00* (2006.01)
*C07C 323/42* (2006.01)
*C07D 213/65* (2006.01)
*C07D 213/68* (2006.01)
*C07D 239/38* (2006.01)
*C07C 247/18* (2006.01)
*C07F 5/02* (2006.01)
*A61P 31/04* (2006.01)
*A61P 25/00* (2006.01)
*A61K 31/165* (2006.01)
(Continued)

(52) U.S. Cl.
CPC ......... *C07C 233/62* (2013.01); *A61K 31/165* (2013.01); *A61K 31/167* (2013.01); *A61K 31/41* (2013.01); *A61K 31/42* (2013.01); *A61K 31/44* (2013.01); *A61K 31/4402* (2013.01); *A61K 31/4406* (2013.01); *A61K 31/4409* (2013.01); *A61K 31/4439* (2013.01); *A61K 31/505* (2013.01); *A61K 31/513* (2013.01); *A61K 31/655* (2013.01); *A61K 45/06* (2013.01); *A61P 25/00* (2018.01); *A61P 31/04* (2018.01); *C07B 59/001* (2013.01); *C07C 233/78* (2013.01); *C07C 235/10* (2013.01); *C07C 235/50* (2013.01); *C07C 237/42* (2013.01); *C07C 245/08* (2013.01); *C07C 247/16* (2013.01); *C07C 247/18* (2013.01); *C07C 317/28* (2013.01); *C07C 323/40* (2013.01); *C07C 323/42* (2013.01); *C07C 381/00* (2013.01); *C07D 213/65* (2013.01); *C07D 213/68* (2013.01); *C07D 213/70* (2013.01); *C07D 213/81* (2013.01); *C07D 213/82* (2013.01); *C07D 239/34* (2013.01); *C07D 239/36* (2013.01); *C07D 239/38* (2013.01); *C07D 257/04* (2013.01); *C07D 261/12* (2013.01); *C07D 401/12* (2013.01); *C07D 413/12* (2013.01); *C07F 5/02* (2013.01); *C07C 2601/08* (2017.05)

(58) Field of Classification Search
CPC .................................................... C07C 233/62
USPC ......................................................... 514/151
See application file for complete search history.

(56) References Cited

U.S. PATENT DOCUMENTS 5,451,410 A   9/1995 Milstein et al.
5,523,308 A   6/1996 Costanzo
(Continued)

FOREIGN PATENT DOCUMENTS

EP   0 195 212 A2   9/1986
EP   0 272 671 A2   6/1988
(Continued)

OTHER PUBLICATIONS

Kolb et al. Liebigs Annalen der Chemie (1990), (1), 1-6. (Year: 1990).*

(Continued)

*Primary Examiner* — Kahsay Habte
(74) *Attorney, Agent, or Firm* — Kilpatrick Townsend & Stockton LLP

(57) ABSTRACT

The present invention provides compounds according to Formula I as described herein, and their use for inhibiting the lysine gingipain protease (Kgp) from the bacterium *Porphyromonas gingivalis*. Also described are gingipain activity probe compounds and methods for assaying gingipain activity are also described, as well as methods for the treatment of disorders associated with *P. gingivalis* infection, including brain disorders such as Alzheimer's disease.

11 Claims, 10 Drawing Sheets

Related U.S. Application Data

(60) Provisional application No. 62/459,456, filed on Feb. 15, 2017, provisional application No. 62/395,938, filed on Sep. 16, 2016.

(51) Int. Cl.

| | | |
|---|---|---|
| *A61K 31/167* | (2006.01) | |
| *A61K 31/41* | (2006.01) | |
| *A61K 31/42* | (2006.01) | |
| *A61K 31/44* | (2006.01) | |
| *A61K 31/4402* | (2006.01) | |
| *A61K 31/4406* | (2006.01) | |
| *A61K 31/4409* | (2006.01) | |
| *A61K 31/4439* | (2006.01) | |
| *A61K 31/505* | (2006.01) | |
| *A61K 31/513* | (2006.01) | |
| *A61K 31/655* | (2006.01) | |
| *A61K 45/06* | (2006.01) | |
| *C07C 245/08* | (2006.01) | |
| *C07C 247/16* | (2006.01) | |
| *C07C 323/40* | (2006.01) | |
| *C07D 213/81* | (2006.01) | |

(56) References Cited

U.S. PATENT DOCUMENTS

| | | | |
|---|---|---|---|
| 5,827,866 | A | 10/1998 | Costanzo et al. |
| 6,323,219 | B1 | 11/2001 | Costanzo |
| 7,071,184 | B2 | 7/2006 | Cummings et al. |
| 7,183,260 | B2 | 2/2007 | Karanewsky et al. |
| 9,758,473 | B2 | 9/2017 | Konradi et al. |
| 9,988,375 | B2 | 6/2018 | Konradi et al. |
| 10,301,301 | B2 | 5/2019 | Konradi et al. |
| 2003/0008829 | A1 | 1/2003 | Costanzo et al. |
| 2005/0059607 | A1 | 3/2005 | Breslav et al. |
| 2006/0084613 | A1 | 4/2006 | Ternansky et al. |
| 2016/0096830 | A1 | 4/2016 | Konradi et al. |
| 2017/0349537 | A1 | 12/2017 | Konradi et al. |
| 2018/0346460 | A1 | 12/2018 | Konradi et al. |
| 2019/0322659 | A1 | 10/2019 | Konradi et al. |

FOREIGN PATENT DOCUMENTS

| | | |
|---|---|---|
| EP | 530167 A1 | 3/1993 |
| JP | 01-163162 A | 6/1989 |
| RU | 2419626 C2 | 5/2011 |
| WO | 92/04371 A1 | 3/1992 |
| WO | 93/00926 A1 | 1/1993 |
| WO | 94/04172 A1 | 3/1994 |
| WO | 96/19483 A1 | 6/1996 |
| WO | 96/30035 A1 | 10/1996 |
| WO | 96/30396 A1 | 10/1996 |
| WO | 96/37497 A1 | 11/1996 |
| WO | 96/40741 A1 | 12/1996 |
| WO | 96/40742 A1 | 12/1996 |
| WO | 97/17363 A1 | 5/1997 |
| WO | 98/05333 A1 | 2/1998 |
| WO | 98/09987 A1 | 3/1998 |
| WO | 99/26925 A1 | 6/1999 |
| WO | 99/41276 A1 | 8/1999 |
| WO | 00/44733 A1 | 8/2000 |
| WO | 00/55124 A2 | 9/2000 |
| WO | 2005/334458 A1 | 3/2007 |
| WO | 2007/137080 A2 | 11/2007 |
| WO | 2009/103432 A2 | 8/2009 |
| WO | 2014/031784 A1 | 2/2014 |
| WO | 2014/145257 A2 | 9/2014 |
| WO | 2016/057413 A2 | 4/2016 |
| WO | 2018/053353 A1 | 3/2018 |
| WO | 2018/209132 A1 | 11/2018 |

OTHER PUBLICATIONS

Adang et al., "Unique Overlap in the Prerequisites for Thrombin Inhibition and Oral Bioavailability Resulting in Potent Oral Antithrombotic,s," J. Med. Chem., 2002, vol. 45, pp. 4419-4432.

Berg et al., "Design and evaluation of *Trypanosome brucei* metacaspase inhibitors," Bioorg. Med. Chem. Lett., Mar. 15, 2010; 20(6): 2001-2006.

Bialas et al., "Exploring the Sn Binding Pockets in Gingipains by Newly Developed Inhibitors: Structure-Based Design, Chemistry, and Activity," Journal of Medicinal Chemistry, 2006, vol. 49, No. 5, pp. 1744-1753.

Bland et al. Journal of the Chemical Society D: Chemical Communications 1971, 17, 1024-1025.

CAS Registry Entry for Registry No. 190903-94-7, which entered STN on Jul. 9, 1997.

CAS Registry Entry for Registry No. 190904-52-0, which entered STN on Jul. 9, 1997.

CAS Registry Entry for Registry No. 607393-00-0, which entered STN on Oct. 21, 2003.

Chauhan, Satendra S., "Enantioselective synthesis of (L)-Fmoc-α-Me-Lys(Boc)-OH via diastereoselective alkylation of oxazinone as a chiral auxiliary," Tetrahedron Letters, 2009, vol. 50, pp. 6913-6915.

Constanzo et al., "In-Depth Study of Tripeptide-Based α-Ketoheterocycles as Inhibitors of Thrombin. Effective Utilization of the $S_1$' Subsite and Its Implications to to Structure-Based Drug Design", Journal of Medicinal Chemistry, vol. 48, No. 6, Mar. 1, 2005, pp. 1-2.

Costanzo et al., "Potent, small-molecule inhibitors of human mast cell tryptase. Antiasthmatic action of a dipeptide-based transition-state analogue containing a benzothiazole keton," J. Med. Chem., Aug. 28, 2003;46(18), pp. 3865-3876.

Curtis et al., "Attenuation of the Virulence of *Porphyromonas gingivalis* by Using a Specific Synthetic Kgp Protease Inhibitor," Infection and Immunity, Dec. 2002, vol. 70., No. 12, pp. 6968-6975.

Duchene et al., "Analysis of Subpocket Selectivity and Identification of Potent Selective Inhibitors for Matriptase and Matriptasli-2," J. Med. Chem., vol. 57, Nov. 11, 2014, pp. 10198-10204.

Kadowaki et al., "Suppression of Pathogenicity of *Porphyromonas gingivalis* by Newly Developed Gingipain Inhibitors," Mol Pharmacol, 2004, vol. 66, No. 6, pp. 1599-1606.

Karukurichi et al., "Examination of the New A-(2'z-fluoro)vinyl Trigger With Lysine Decarboxylase: The Absolute Stereochemistry Dictates The Reaction Course", J.Am. Chem, Soc, vol. 129, No. 2, 2007, pp. 258-259.

Kataoka et al., "A novel, potent dual inhibitor of Arg-gingipains and Lys-gingipain as a promising agent for periodontal disease therapy," FASEB J, 2014, vol. 28, 3564-3578.

Ko et al., "Universal Peptidomimetics", J.Am. Chem. Soc, vol. 133, No. 3, 2011, pp. 462-477.

McGrath et al., "Structure-Guided Design of Peptide-Based Tryptase Inhibitors," Biochemistry, 2006, vol. 45, No. 19, pp. 5964-5973.

Mogami et al., "Effect of Thrombin on Human Amnion Mesenchymal Cells", Mouse Fetal Membranes, and Preterm Birth, The Journal of Biological Chemistry, vol. 289, No. 19, May 9, 2014, pp. 13295-13307.

"PubChem CID 11666347," compound listed Oct. 26, 2006, 9 pages.

PCT/US2017/051912 , "International Search Report," dated Jan. 18, 2018, 4 pages.

Sengupta et al., "Synthesis and biological evaluation of novel oxalamido derivatives as caspase-3 inhibitors," Indian J. Chem. Sec B, vol. 50B, Jul. 2011, pp. 901-905.

Singhrao et al., "Oral Inflammation, Tooth Loss, Risk Factors, and Association with Progression of Alzheimer's Disease," Journal of Alzheimer's Disease, 2014, vol. 42, pp. 723-737.

Teno et al., "Development of Active Center-Directed Inhibitors against Plasmin," Chem. Pharm. Bull., 1991, vol. 39(9), pp. 2340-2346.

(56) References Cited

OTHER PUBLICATIONS

Wang et al., "Solid-Phase Synthesis of Peptide Vinyl Sulfones as Potential Inhibitors and Activity-Based Probes of Cysteine Proteases", Organic Letters. vol. 5, No. 5, Feb. 12, 2003, pp. 737-740.

* cited by examiner

KETONE INHIBITORS OF LYSINE GINGIPAIN

CROSS-REFERENCES TO RELATED APPLICATIONS

This application is a continuation of International Patent Application No. PCT/US2017/051912, filed Sep. 15, 2017, which claims priority to U.S. Provisional Pat. Appl. No. 62/395,938, filed on Sep. 16, 2016, and U.S. Provisional Pat. Appl. No. 62/459,456, filed on Feb. 15, 2017, the disclosures of which are herein incorporated by reference in their entirety for all purposes.

BACKGROUND OF THE INVENTION

Infection with the bacteria *Porphyromonas gingivalis* has been linked to the development of periodontal disease, Alzheimer's and other brain disorders, cardiovascular disease, diabetes, cancer, liver disease, kidney disease, preterm birth, arthritis, pneumonia and other disorders. *P. gingivalis* is an anaerobic asaccharolytic gram-negative rod bacterium that is known to infect the oral cavity and translocate systemically into coronary arteries, aorta, placental tissue, the brain, the kidneys, and the liver. The bacterium has also been identified in cancerous tissues and a mechanism has been proposed by which gingipains can trigger immortalization and metastasis. See: Gandhimadhi, et al. *Journal of Indian Society of Periodontology.* 2010; 14(2):114-120; Liao, et al., *Med Hypotheses,* 2009. 72(6): 732-5; Byrne, et al., *Oral Microbiol Immunol,* 2009. 24(6): 469-77; Mahindra, et al., *J Maxillofac Oral Surg,* 2009. 8(2): 108-13; Stelzel, et al., *J. Periodontol,* 2002. 73(8): 868-70; Katz, et al., *Journal of Dental Research,* 2009. 88(6): 575-578; Poole, et al., *J Alzheimers Dis,* 2015, 43(1): 67-80; Ishikawa, et al., *Biochim Biophys Acta,* 2013. 1832(12): 2035-2043; Inaba, et al., *Cellular Microbiology,* 2014. 16(1): 131-145.

*P. gingivalis* produces proteases called gingipains, including Arginine Gingipain A (RgpA), Arginine Gingipain B (RgpB) and Lysine Gingipain (Kgp). Gingipains contribute to many functions of the organism including its survival and virulence. Gingipains can be secreted, transported to outer membrane surfaces of *P. gingivalis*, or released in outer membrane vesicles by the bacterium. Gingipains degrade a broad range of proteins (e.g., immunoglobulins, proteinase inhibitors, actin, and collagen) which can lead to cytoskeleton collapse and apoptosis in many types of cells, and inhibition of gingipains has been found to prevent *P. gingivalis*-induced cell death. See: Travis, et al., *Adv Exp Med Biol,* 2000. 477: 455-65; Sheets, et al., *Infect Immun,* 2005. 73(3): 1543-52; Sheets, et al., *Infect Immun,* 2006. 74(10): 5667-78; Stathopoulou, et al., *BMC Microbiol,* 2009. 9: 107. New compounds for the inhibition of gingipain activity and the treatment of diseases associated with gingipain activity and *P. gingivalis* infection are needed. In addition, compounds for the detection and quantification of gingipain activity are needed in order to effectively diagnose subjects infected with *P. gingivalis*, to identify new therapeutic agents, and to develop new methods for treating gingipain-mediated diseases. The present invention addresses these needs.

BRIEF SUMMARY OF THE INVENTION

In a first embodiment, the invention provides compounds according to Formula I:

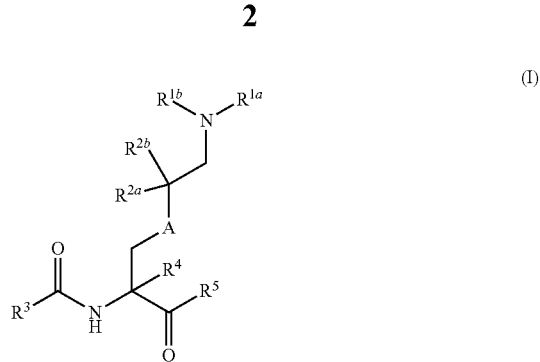

or a pharmaceutically acceptable salt thereof, wherein:

A is selected from —$CH_2$— and —O—;

$R^{1a}$ and $R^{1b}$ are each independently selected from hydrogen, $C_{1-4}$ alkyl, and an amine protecting group;

$R^{2a}$ and $R^{2b}$ are each independently selected from hydrogen, halogen, $C_{1-4}$ haloalkyl, and $C_{1-4}$ haloalkoxy;

$R^3$ is selected from $C_{3-8}$ cycloalkyl, $C_{3-8}$ alkyl, 3- to 12-membered heterocyclyl, $C_{6-10}$ aryl, 5- to 12-membered heteroaryl, and a reporter moiety wherein $R^3$ is optionally substituted with one or more $R^{3a}$ substituents;

each $R^{3a}$ is independently selected from halogen, —CN, —$NO_2$, —$N_3$, —OH, $C_{1-4}$ alkyl, $C_{1-4}$ haloalkyl, $C_{1-4}$ alkoxy, $C_{1-4}$ haloalkoxy, —N($R^c$)$_2$, —$N^+(R^b)_3$, —$(CH_2)_kC(O)R^b$, —$NR^c(CH_2)_uC(O)R^b$, —$O(CH_2)_uC(O)R^b$, —$(CH_2)_kCONR^cR^c$, —$(CH_2)_kNR^c(O)R^b$, —$NR^c(CH_2)_uCONR^cR^c$, —$NR^c(CH_2)_uNR^cC—(O)R^b$, —$O(CH_2)_uCONR^cR^c$, and —$O(CH_2)_uNR^cC(O)R^b$, and optionally substituted triazolyl;

each $R^b$ is independently selected from $C_{1-4}$ alkyl, $C_{1-4}$ haloalkyl, and $C_{1-4}$ deuteroalkyl;

each $R^c$ is independently selected from hydrogen and $C_{1-8}$ alkyl;

each subscript k is independently selected from 0, 1, 2, 3, 4, 5, and 6;

each subscript u is independently selected from 1, 2, 3, 4, 5, and 6;

$R^4$ is selected from hydrogen and $C_{1-4}$ alkyl;

$R^5$ is selected from —$CH_2R^{5a}$, —$CHS(O)(R^{5b})_2$, and $C_{1-6}$ haloalkyl;

$R^{5a}$ is selected from —O—$R^6$, —S—$R^7$, —SO—$R^7$, —$SO_2$—$R^7$, —N($R^8$)$_2$, 5- to 12-membered heteroaryl, and 3- to 12-membered heterocyclyl, wherein 5- to 12-membered heteroaryl is optionally substituted with one or more members independently selected from halogen, $C_{1-3}$ alkyl, and $C_{1-3}$ haloalkyl, and 3- to 12-membered heterocyclyl is optionally substituted with one or more members independently selected from oxo, halogen, $C_{1-3}$ alkyl, and $C_{1-3}$ haloalkyl;

each $R^{5b}$ is independently selected $C_{1-6}$ alkyl;

$R^6$ and $R^7$ are selected from phenyl, $C_{1-6}$ alkyl, $C_{1-6}$ haloalkyl, and 5- to 12-membered heteroaryl, wherein phenyl is substituted with 1-5 halogens, and wherein 5- to 12-membered heteroaryl is optionally substituted with one or more halogen, $C_{1-3}$ alkyl, or $C_{1-3}$ haloalkyl;

each $R^8$ is independently selected $C_{1-6}$ alkyl; and
$R^5$ optionally comprises a quenching moiety $R^9$;
provided that $R^5$ is other than 2,3,5,6-tetrafluorophenoxymethyl.

In a related embodiment, the invention provides pharmaceutical compositions including one or more compounds of the invention and one or more pharmaceutically acceptable excipients.

In another embodiment, the invention provides methods for treating a disease or condition associated with *P. gingivalis* infection. The methods include administering an effective amount of a compound or a composition of the invention to a subject in need thereof. In some embodiments, brain disorder (e.g., Alzheimer's disease), periodontal disease, diabetes, a cardiovascular disease, arthritis, rheumatoid arthritis, osteoarthritis, infectious arthritis, psoriatic arthritis, elevated risk of preterm birth, pneumonia, cancer, a kidney disease, a liver disease, a retinal disorder, and glaucoma.

In another embodiment, the invention provides compounds comprising a reporter moiety and a gingipain-reactive moiety as well as method for detecting gingipain activity in a biological sample. The methods include: forming a mixture comprising the biological sample and a compound as described above under conditions sufficient for a gingipain to react with the gingipain reactive moiety of the compound; detecting the reporter moiety of the compound in the mixture; and determining that a gingipain is present in the biological sample when the reporter moiety is detected.

BRIEF DESCRIPTION OF THE DRAWINGS

FIG. 5B shows that activity probes of the invention are useful for characterization of tissue slices. A gingival tissue slice from a patient with periodontal disease is stained with immunofluorescence agent CAB102, a polyclonal antibody to Kgp. A separate sequential tissue section yields a fluorescence signal after incubation with the activity probe 15a.

FIG. 6A shows a fluorescence image of an SDS-PAGE gel containing samples from human Jurkat cells with or without infection by *P. gingivalis* W83. Samples were reacted with fluorescent probe 15a or non-fluorescent Kgp inhibitor compound 73 (N-[7-amino-2-oxo-1-(2,3,5,6-tetrafluorophenoxy)heptan-3-yl]cyclopentanecarboxamide) prior to SDS-PAGE. Lane 1: cells only. Lane 2: cells+probe 15a. Lane 3: cells+probe 15a, *P. gingivalis* multiplicity of infection (MOI): 100. Lane 4: cells+pre-incubation with compound 73 followed by probe 15a, MOI: 100. Lane 5: cells+probe 15a, MOI: 10. Lane 6: cells+pre-incubation with compound 73 followed by probe 15a, MOI: 10. Lane 7: purified Kgp+probe 15a. Lane 8: purified Kgp+lysis buffer without probe 15a.

DETAILED DESCRIPTION OF THE INVENTION

I. General

Figure 1:
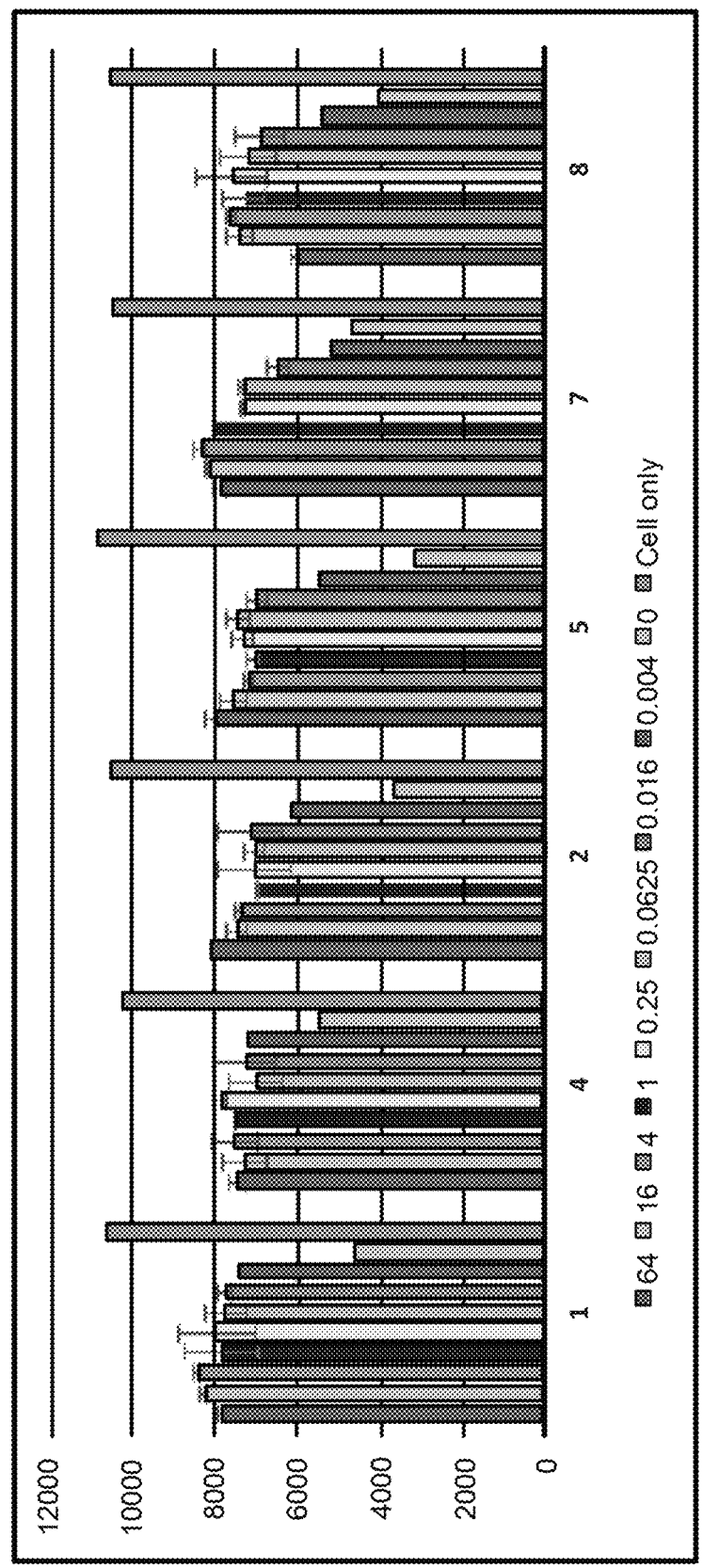
FIG. 1 shows that Kgp inhibitors of the invention protect SH-SY5Y neuroblastoma cells from *P. gingivalis*-induced cell death.

The present invention provides potent compounds for inhibiting *P. gingivalis* lysine gingipain (Kgp). The invention is based in part on the surprising discovery that certain inhibitors exhibit increased selectivity for Kgp over endogenous proteases such as cathepsins, while also exhibiting activity that is comparable to previously known compounds. Furthermore, compounds of the invention provide improved pharmacokinetic properties when compared with previously known compounds. The compounds can be used to prevent cell death, inflammation, and other pathological processes in a variety of diseases associated with *P. gingivalis* infection, including aging-related conditions such as Alzheimer's disease.

II. Definitions

As used herein, the terms "*Porphyromonas gingivalis*" and "*P. gingivalis*" refer to the gram-negative asaccharolytic bacterium that is recognized as a key causative microbe in the pathogenesis of periodontitis and related conditions. "*P. gingivalis* infection" refers to the invasion and colonization of *P. gingivalis* in a bodily tissue such as the gums or the brain. *P. gingivalis* infection is frequently characterized by subsequent tissue injury and disease.

As used herein, the term "gingipain" refers to cysteine proteases expressed by *P. gingivalis* having trypsin-like specificity (i.e., Lys-Xaa and Arg-Xaa). Gingipains are recognized as the major virulence factors of *P. gingivalis* and contribute to bacterial attachment and colonization, nutrient acquisition, evasion of host defenses, and tissue invasion. The terms "arginine gingipain" and "Rgp" are used interchangeably to refer to the *P. gingivalis* arginine-specific gingipains RgpA and RgpB, classified under EC number EC 3.4.22.37. The rgpA and rgpB gene-translation products, RgpA and RgpB, share a caspase-like protease domain (specific for Arg-Xaa peptide bonds) and an immunoglobulin-like domain. In RgpA, the protease and immunoglobulin-like domains are followed by a large C-terminal extension containing hemagglutinin-adhesin domains.

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. Unless otherwise specified, "substituted alkyl" groups can be substituted with one or more groups selected from halo, hydroxy, amino, alkylamino, amido, acyl, nitro, cyano, and alkoxy.

As used herein, the term "alkoxy," by itself or as part of another substituent, refers to a group having the formula —OR, wherein R is alkyl.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. Unless otherwise specified, "substituted cycloalkyl" groups can be substituted with one or more groups selected from halo, hydroxy, amino, alkylamino, amido, acyl, nitro, cyano, and alkoxy. The term "lower cycloalkyl" refers to a cycloalkyl radical having from three to seven carbons including, for example, cyclopropyl, cyclobutyl, cyclopentyl, cyclohexyl, and cycloheptyl.

As used herein, the term "alkylene" refers to an alkyl group, as defined above, linking at least two other groups (i.e., a divalent alkyl radical). The two moieties linked to the alkylene group can be linked to the same carbon atom or different carbon atoms of the alkylene group. The term "cycloalkylene" refers to a cycloalkyl group, as defined above, linking at least two other groups (i.e., a divalent cycloalkyl radical). The two moieties linked to the cycloalkylene group can be linked to the same carbon atom or different carbon atoms of the cycloalkylene group.

As used herein, the term "alkylthio," by itself or as part of another substituent, refers to a group having the formula —SR, wherein R is alkyl.

As used herein, the term "heteroalkyl," by itself or as part of another substituent, refers to an alkyl group of any suitable length and having from 1 to 3 heteroatoms such as N, O and S. For example, heteroalkyl can include ethers, thioethers and alkyl-amines. Additional heteroatoms can also be useful, including, but not limited to, B, Al, Si and P. The heteroatoms can be oxidized to form moieties such as, but not limited to, —S(O)— and —S(O)$_2$—. The heteroatom portion of the heteroalkyl can replace a hydrogen atom of the alkyl group to form a hydroxy, thio or amino group. Alternatively, the heteroatom portion can be the connecting atom, or be inserted between two carbon atoms.

As used herein, the term "heteroalkylene" refers to a heteroalkyl group, as defined above, linking at least two other groups (i.e., a divalent heteroalkyl radical). The two moieties linked to the heteroalkylene group can be linked to the same atom or different atoms of the heteroalkylene group. The term "heterocyclylene" refers to a cycloalkyl group, as defined above, linking at least two other groups (i.e., a divalent heterocyclyl radical). The two moieties linked to the heterocyclylene group can be linked to the same atom or different atoms of the heterocyclylene group.

As used herein, the terms "halo" and "halogen," by themselves or as part of another substituent, refer to a fluorine, chlorine, bromine, or iodine atom.

As used herein, the term "haloalkyl," by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

As used herein, the term "haloalkoxy," by itself or as part of another substituent, refers to an alkoxy group where some or all of the hydrogen atoms are replaced with halogen atoms.

As used herein, the term "halocycloalkyl," by itself or as part of another substituent, refers to a cycloalkyl group where some or all of the hydrogen atoms are replaced with halogen atoms.

As used herein, the term "deuteroalkyl," by itself or as part of another substituent, refers to an alkyl group where some or all of the hydrogen atoms are replaced with deuterium atoms. As for alkyl groups, deuteroalkyl groups can have any suitable number of carbon atoms, such as $C_{1-6}$. In some instances, the term "perdeutero" can be used to define a compound or radical where all the hydrogens are replaced with deuterium.

As used herein, the term "aryl," by itself or as part of another substituent, refers to an aromatic ring system having any suitable number of carbon ring atoms and any suitable number of rings. Aryl groups can include any suitable number of carbon ring atoms, such as $C_6$, $C_7$, $C_8$, $C_9$, $C_{10}$, $C_{11}$, $C_{12}$, $C_{13}$, $C_{14}$, $C_{15}$ or $C_{16}$, as well as $C_{6-10}$, $C_{6-12}$, or $C_{6-14}$. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. Unless otherwise specified, "substituted aryl" groups can be substituted with one or more groups selected from halo, hydroxy, amino, alkylamino, amido, acyl, nitro, cyano, and alkoxy.

As used herein, the term "arylene" refers to an aryl group, as defined above, linking at least two other groups (i.e., a divalent aryl radical).

As used herein, the term "heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can be oxidized to form moieties such as, but not limited to, —S(O)— and —S(O)$_2$—. Heteroaryl groups can include any number of ring atoms, such as $C_{5-6}$, $C_{3-8}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of heteroatoms can be included in the heteroaryl groups, such as 1, 2, 3, 4; or 5, or 1 to 2, 1 to 3, 1 to 4, 1 to 5, 2 to 3, 2 to 4, 2 to 5, 3 to 4, or 3 to 5. For example, heteroaryl groups can be $C_{5-8}$ heteroaryl, wherein 1 to 4 carbon ring atoms are replaced with heteroatoms; or $C_{5-8}$ heteroaryl, wherein 1 to 3 carbon ring atoms are replaced with heteroatoms; or $C_{5-6}$ heteroaryl, wherein 1 to 4 carbon ring atoms are replaced with heteroatoms; or $C_{5-6}$ heteroaryl, wherein 1 to 3 carbon ring atoms are replaced with heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. Unless otherwise specified, "substituted heteroaryl" groups can be substituted with one or more groups selected from halo, hydroxy, amino, alkylamino, amido, acyl, nitro, cyano, and alkoxy.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

As used herein, the term "heteroarylene" refers to a heteroaryl group, as defined above, linking at least two other groups (i.e., a divalent heteroaryl radical).

As used herein the term "heterocyclyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —S(O)$_2$—. Heterocyclyl groups can include any number of ring atoms, such as, $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of carbon ring atoms can be replaced with heteroatoms in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclyl groups can be unsubstituted or substituted. Unless otherwise specified, "substituted heterocyclyl" groups can be substituted with one or more groups selected from halo, hydroxy, amino, oxo (=O), alkylamino, amido, acyl, nitro, cyano, and alkoxy.

The heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocyclyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "amine protecting group" refers to a chemical moiety that renders an amino group unreactive, but is also removable so as to restore the amino group. Examples of amine protecting groups include, but are not limited to, benzyloxycarbonyl; 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethylchroman-6-sulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. Other amine protecting groups are known to those of skill in the art including, for example, those described by Green and Wuts (*Protective Groups in Organic Synthesis*, 4$^{th}$ Ed. 2007, Wiley-Interscience, New York).

As used herein, the term "carbonyl," by itself or as part of another substituent, refers to —C(O)—, i.e., a carbon atom double-bonded to oxygen and bound to two other groups in the moiety having the carbonyl.

As used herein, the term "amino" refers to a moiety —NR$_2$, wherein each R group is H or alkyl. An amino moiety can be ionized to form the corresponding ammonium cation. "Dialkylamino" refers to an amino moiety wherein each R group is alkyl.

As used herein, the term "sulfonyl" refers to a moiety —SO$_2$R, wherein the R group is alkyl, haloalkyl, or aryl. An amino moiety can be ionized to form the corresponding ammonium cation. "Alkylsulfonyl" refers to an amino moiety wherein the R group is alkyl.

As used herein, the term "hydroxy" refers to the moiety —OH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion.

As used herein, the term "amido" refers to a moiety —NRC(O)R or —C(O)NR$_2$, wherein each R group is H or alkyl.

As used herein, the term "nitro" refers to the moiety —NO$_2$.

As used herein, the term "oxo" refers to an oxygen atom that is double-bonded to a compound (i.e., O=).

As used herein, the term "pharmaceutically acceptable excipient" refers to a substance that aids the administration of an active agent to a subject. By "pharmaceutically acceptable," it is meant that the excipient is compatible with the other ingredients of the formulation and is not deleterious to the recipient thereof. Pharmaceutical excipients useful in the present invention include, but are not limited to, binders, fillers, disintegrants, lubricants, glidants, coatings, sweeteners, flavors and colors.

As used herein, the term "salt" refers to acid or base salts of the compounds of the invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

As used herein, the term "gingipain reactive moiety" refers to a chemical functional group in a compound that reacts with a gingipain active site thiol so as to form a covalently modified gingipain, or to a chemical functional group in a compound that interacts with a gingipain so as to form a non-covalent gingipain/compound complex. Examples of gingipain reactive moieties include, but are not limited to, haloacetamide groups (including chloroacetamides and iodoacetamides), maleimide groups, benzothiazolyl-carbonyl groups, and phenoxymethyl groups (including halogenated phenoxymethyl groups).

As used herein, the term "reporter moiety" refers to a chemical functional group in compound that can be detected using techniques including, but not limited to, optical methods (e.g., fluorescence or UV-vis absorbance) and biochemical methods (e.g., with immunochemical reagent such as an antibody).

As used herein, the terms "treat," "treatment," and "treating" refer to any indicia of success in the treatment or amelioration of an injury, pathology, condition, or symptom (e.g., cognitive impairment), including any objective or subjective parameter such as abatement; remission; diminishing of symptoms or making the symptom, injury, pathology or condition more tolerable to the patient; reduction in the rate of symptom progression; decreasing the frequency or duration of the symptom or condition; or, in some situations, preventing the onset of the symptom. The treatment or amelioration of symptoms can be based on any objective or subjective parameter; including, e.g., the result of a physical examination.

As used herein the terms "effective amount" and "therapeutically effective amount" refer to a dose of a compound such as a Kgp inhibitor that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); Goodman & Gilman's The Pharmacological Basis of Therapeutics, 11th Edition, 2006, Brunton, Ed., McGraw-Hill; and *Remington: The Science and Practice of Pharmacy*, 21st Edition, 2005, Hendrickson, Ed., Lippincott, Williams & Wilkins).

As used herein, the term "Alzheimer's disease" refers to a progressive disease of the central nervous system in humans and other mammals. It is manifested by dementia (especially in the elderly); disorientation; loss of memory; difficulty with language, calculation, or visual-spatial skills; and psychiatric manifestations. Alzheimer's disease is associated with progressive neurodegeneration and characteristic pathology, namely beta amyloid plaques and tau tangles.

As used herein, the term "osteoarthritis" refers to a chronic degenerative joint disease that results from breakdown of joint cartilage, synovial tissue, and underlying bone.

As used herein, the term "subject" refers to animals such as mammals, including, but not limited to, primates (e.g., humans), cows, sheep, goats, horses, dogs, cats, rabbits, rats, mice and the like.

III. Inhibitors of Lysine Gingipain

The present invention provides compounds for inhibition of *P. gingivalis*. In a first embodiment, the invention provides compounds according to Formula I:

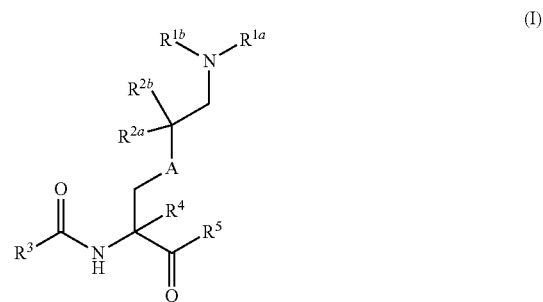

(I)

or a pharmaceutically acceptable salt thereof, wherein:
A is selected from —CH$_2$— and —O—;
$R^{1a}$ and $R^{1b}$ are each independently selected from hydrogen, C$_{1-4}$ alkyl, and an amine protecting group;
$R^{2a}$ and $R^{2b}$ are each independently selected from hydrogen, halogen, C$_{1-4}$ haloalkyl, and C$_{1-4}$ haloalkoxy;
$R^3$ is selected from C$_{3-8}$ cycloalkyl, C$_{3-8}$ alkyl, 3- to 12-membered heterocyclyl, C$_{6-10}$ aryl, 5- to 12-membered heteroaryl, and a reporter moiety wherein $R^3$ is optionally substituted with one or more $R^{3a}$ substituents;
each $R^{3a}$ is independently selected from halogen, —CN, —NO$_2$, —N$_3$, —OH, C$_{1-4}$ alkyl, C$_{1-4}$ haloalkyl, C$_{1-4}$ alkoxy,
C$_{1-4}$ haloalkoxy, —N(R$^c$)$_2$, —N$^+$(R$^b$)$_3$, —(CH$_2$)$_k$C(O)R$^b$, —NR$^c$(CH$_2$)$_u$C(O)R$^b$, —O(CH$_2$)$_u$C(O)R$^b$, —(CH$_2$)$_k$CONR$^c$R$^c$, —(CH$_2$)$_k$NR$^c$C(O)R$^b$, —NR$^c$(CH$_2$)$_u$CONR$^c$R$^c$, —NR$^c$(CH$_2$)$_u$NR$^c$C—(O)R$^b$, —O(CH$_2$)$_u$CONR$^c$R$^c$, and —O(CH$_2$)$_u$NR$^c$(O)R$^b$, and optionally substituted triazolyl;
each $R^b$ is independently selected from C$_{1-4}$ alkyl, C$_{1-4}$ haloalkyl, and C$_{1-4}$ deuteroalkyl;
each $R^c$ is independently selected from hydrogen and C$_{1-8}$ alkyl;
each subscript k is independently selected from 0, 1, 2, 3, 4, 5, and 6;
each subscript u is independently selected from 1, 2, 3, 4, 5, and 6;
$R^4$ is selected from hydrogen and C$_{1-4}$ alkyl;
$R^5$ is selected from —CH$_2$R$^{5a}$, —CHS(O)(R$^{5b}$)$_2$, and C$_{1-6}$ haloalkyl;
$R^{5a}$ is selected from —O—R$^6$, —S—R$^7$, —SO—R$^7$, —SO$_2$—R$^7$, —N(R$^8$)$_2$,
5- to 12-membered heteroaryl, and 3- to 12-membered heterocyclyl,
wherein 5- to 12-membered heteroaryl is optionally substituted with one or more members independently selected from halogen, C$_{1-3}$ alkyl, and C$_{1-3}$ haloalkyl, and
3- to 12-membered heterocyclyl is optionally substituted with one or more members independently selected from oxo, halogen, C$_{1-3}$ alkyl, and C$_{1-3}$ haloalkyl;

each $R^{5b}$ is independently selected $C_{1-6}$ alkyl;
$R^6$ and $R^7$ are selected from phenyl, $C_{1-6}$ alkyl, $C_{1-6}$ haloalkyl, and
5- to 12-membered heteroaryl,
wherein phenyl is substituted with 1-5 halogens, and
wherein 5- to 12-membered heteroaryl is optionally substituted with one or more halogen, $C_{1-3}$ alkyl, or $C_{1-3}$ haloalkyl;
each $R^8$ is independently selected $C_{1-6}$ alkyl; and
$R^5$ optionally comprises a quenching moiety $R^9$;
provided that $R^5$ is other than 2,3,5,6-tetrafluorophenoxymethyl.

In some embodiments:
A is selected from —$CH_2$— and —O—;
$R^{1a}$ and $R^{1b}$ are each independently selected from hydrogen, $C_{1-4}$ alkyl, and an amine protecting group;
$R^{2a}$ and $R^{2b}$ are each independently selected from hydrogen, halogen, $C_{1-4}$ haloalkyl, and $C_{1-4}$ haloalkoxy;
$R^3$ is selected from $C_{3-8}$ cycloalkyl, $C_{3-8}$ alkyl, $C_{6-10}$ aryl, $C_{5-12}$ heteroaryl, and $C_{3-12}$ heterocyclyl, wherein $R^3$ is optionally substituted with one or more $R^{3a}$ substituents;
each $R^{3a}$ is independently selected from halogen, —CN, —$NO_2$, —$N_3$, —OH, $C_{1-4}$ alkyl, $C_{1-4}$ haloalkyl, $C_{1-4}$ alkoxy, $C_{1-4}$ haloalkoxy, —$N(R^c)_2$, —$(CH_2)_kC(O)R^b$, —$NR^c(CH_2)_uC(O)R^b$, —$O(CH_2)_uC(O)R^b$, —$(CH_2)_k$CONR$^c$R$^c$, —$(CH_2)_kNR^c(O)R^b$, —$NR^c(CH_2)_u$CONR$^c$R$^c$, —$NR^c(CH_2)_uNR^c(O)R^b$, —$O(CH_2)_u$ CONR$^c$R$^c$, and —$O(CH_2)_uNR^cC(O)R^b$, and optionally substituted triazolyl;
each $R^b$ is independently selected from $C_{1-4}$ alkyl, $C_{1-4}$ haloalkyl, and $C_{1-4}$ deuteroalkyl;
each W is independently selected from hydrogen and $C_{1-8}$ alkyl;
each subscript k is independently selected from 0, 1, 2, 3, 4, 5, and 6;
each subscript u is independently selected from 1, 2, 3, 4, 5, and 6;
$R^4$ is selected from hydrogen and $C_{1-4}$ alkyl;
$R^5$ is selected from $C_{1-6}$ haloalkyl and —$CH_2R^{5a}$;
$R^{5a}$ is selected from —O—$R^6$, —S—$R^7$, —SO—$R^7$, —$SO_2$—$R^7$, —$N(R^8)_2$, and $C_{5-12}$ heteroaryl;
$R^6$ is selected from phenyl, $C_{1-6}$ alkyl, $C_{1-6}$ haloalkyl, and $C_{5-12}$ heteroaryl,
wherein phenyl is substituted with 1-5 halogens, and
wherein $C_{5-12}$ heteroaryl is optionally substituted with halogen or $C_{1-3}$ haloalkyl;
$R^7$ is selected from phenyl, $C_{1-6}$ alkyl, $C_{1-6}$ haloalkyl, and $C_{5-12}$ heteroaryl,
wherein phenyl is optionally substituted with 1-5 halogens, and
wherein $C_{5-12}$ heteroaryl is optionally substituted with halogen or $C_{1-3}$ haloalkyl; and
each $R^8$ is independently selected $C_{1-6}$ alkyl;
provided that when $R^5$ is other than 2,3,5,6-tetrafluorophenoxymethyl.

Compounds of the invention can be prepared in protected form (i.e., compounds wherein at least one of $R^{1a}$ and $R^{1b}$ is an amine protecting group). A number of suitable protecting groups—as described, for example, by Green and Wuts (*Protective Groups in Organic Synthesis*, 4$^{th}$ Ed. 2007, Wiley-Interscience, New York)—can be used. In some embodiments, $R^{1a}$ is H and $R^{1b}$ is selected from benzyloxycarbonyl; 9-fluorenylmethyloxycarbonyl; tert-butyloxycarbonyl; and allyloxycarbonyl. In some embodiments, $R^{1a}$ is H and $R^{1b}$ is tert-butyloxycarbonyl. Compounds can also be prepared in alkylated form (i.e., compounds wherein at least one of $R^{1a}$ and $R^{1b}$ is an alkyl group). One or both of $R^{1a}$ and $R^{1b}$ can be, for example, methyl, ethyl, n-propyl, isopropyl, n-butyl, or t-butyl.

In some embodiments, $R^{1a}$ and $R^{1b}$ are H; $R^{2a}$ and $R^{2b}$ are independently selected from hydrogen and fluoro; and A is —$CH_2$—.

In some embodiments, $R^{1a}$ and $R^{1b}$ are H; $R^{2a}$ and $R^{2b}$ are independently selected from hydrogen and fluoro; A is —$CH_2$—; and $R^4$ is selected from hydrogen and $C_{1-4}$ alkyl. In some such embodiments, $R^4$ is selected from hydrogen and methyl. In some such embodiments, $R^4$ is hydrogen.

In some embodiments, A is —$CH_2$—; $R^{2a}$ is hydrogen; $R^{2b}$ is hydrogen or fluoro; and $R^{1a}$ and $R^{1b}$ are H. In some embodiments, A is —$CH_2$—; $R^{2a}$ is hydrogen; $R^{2b}$ is fluoro; and $R^{1a}$ and $R^{1b}$ are H.

In some embodiments, the invention provides compounds having a structure according to Formula Ia:

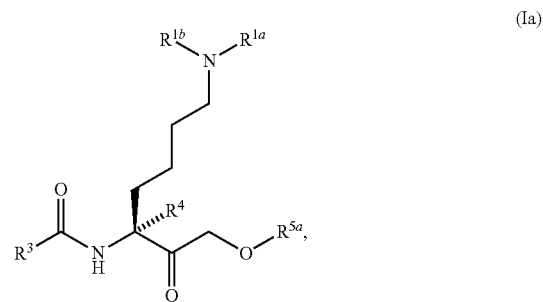

(Ia)

and pharmaceutically acceptable salt thereof.

In some embodiments, the invention provides compound of Formula I or Formula Ia and pharmaceutically acceptable salts thereof, wherein $R^3$ is selected from $C_{3-8}$ cycloalkyl, $C_{3-8}$ alkyl, $C_{6-10}$ aryl, $C_{5-12}$ heteroaryl, and $C_{3-12}$ heterocyclyl, each of which is optionally substituted with one or more $R^{3a}$ substituents. For example, $R^3$ can be cyclopropyl, cyclobutyl, cyclopentyl, cyclohexyl, cycloheptyl, or cyclooctyl. $R^3$ can be n-propyl, isopropyl, n-butyl, isobutyl, sec-butyl, tert-butyl, n-pentyl, branched pentyl, n-hexyl, branched hexyl, n-heptyl, branched heptyl, n-octyl, or branched octyl. In some embodiments, $R^3$ is selected from unsubstituted or substituted cyclobutyl, unsubstituted or substituted cyclopentyl, and unsubstituted or substituted cyclohexyl. In some embodiments, $R^3$ is unsubstituted or substituted isopropyl.

In some embodiments, $R^3$ is selected from unsubstituted or substituted phenyl and unsubstituted or substituted naphthyl. In some embodiments, $R^3$ is selected from unsubstituted or substituted pyrrolyl, unsubstituted or substituted pyridinyl, unsubstituted or substituted imidazolyl, unsubstituted or substituted pyrazolyl, unsubstituted or substituted triazolyl, unsubstituted or substituted pyrazinyl, unsubstituted or substituted triazinyl, unsubstituted or substituted indolyl, unsubstituted or substituted isoindolyl, and unsubstituted or substituted quinolinyl.

In some embodiments, $R^3$ is selected from cyclopentyl and phenyl, each of which is optionally substituted with one or more $R^{3a}$ substituents. In some such embodiments, each $R^{3a}$ is independently selected from halogen, —$N_3$, $C_{1-4}$ alkyl, $C_{1-4}$ haloalkyl, $C_{1-4}$ alkoxy, $C_{1-4}$ haloalkoxy, and —$NR^cC(O)R^b$. In some embodiments, $R^3$ is cyclopentyl.

In some embodiments, the invention provides compound of Formula I or Formula Ia and pharmaceutically acceptable salts thereof, wherein $R^3$ is selected from $C_{3-8}$ alkyl, $C_{3-8}$ cycloalkyl, $C_{6-10}$ aryl, $C_{5-12}$ heteroaryl, and $C_{3-12}$ heterocyclyl, each of which is optionally substituted with one or more $R^{3a}$ substituents. In some such embodiments, $R^3$ is selected from isopropyl, cyclopentyl, phenyl, pyridin-2-yl, pyridin-3-yl, and pyridin-4-yl, each of which is optionally substituted with one or more $R^{3a}$ substituents. In some such embodiments, each $R^{3a}$ is independently selected from halogen, $-N_3$, $C_{1-4}$ alkyl, $C_{1-4}$ haloalkyl, $C_{1-4}$ alkoxy, $C_{1-4}$ haloalkoxy, $C_{1-4}$ alkoxy, $C_{1-4}$ haloalkoxy, $-N(R^c)_2$, $-N^+(R^b)_3$, and $-NR^cC(O)R^b$.

In some embodiments, $R^3$ is cyclopentyl. In some embodiments, $R^3$ is cyclopentyl and $R^5$ is selected from the substituents in embodiments (A), embodiments (B), embodiments (C), embodiments (D), embodiments (E), embodiments (F), embodiments (G), embodiments (H), embodiments (J), or embodiments (K) as set forth below.

In some embodiments, $R^3$ is $C_{3-8}$ alkyl (e.g., n-propyl, isopropyl, n-butyl, isobutyl, sec-butyl, tert-butyl, n-pentyl, and the like) substituted with $C_{1-4}$ alkoxy (e.g., methoxy, ethoxy, isopropoxy, tert-butoxy, and the like). In some embodiments, $R^3$ is methoxypropyl. In some embodiments, $R^3$ is (2-methoxy)-propan-2-yl. In some embodiments, $R^3$ is (2-methoxy)propan-2-yl and $R^5$ is selected from the substituents in embodiments (A), embodiments (B), embodiments (C), embodiments (D), embodiments (E), embodiments (F), embodiments (G), embodiments (H), embodiments (J), or embodiments (K) as set forth below.

In some embodiments, $R^3$ is unsubstituted phenyl or $R^3$ is phenyl substituted with one or more halogen, $-N_3$, $C_{1-4}$ haloalkoxy, and/or $-NR^cC(O)R^b$. In some such embodiments, $R^5$ is selected from the substituents in embodiments (A), embodiments (B), embodiments (C), embodiments (D), embodiments (E), embodiments (F), embodiments (G), embodiments (H), embodiments (J), or embodiments (K) as set forth below.

In some embodiments, $R^3$ is unsubstituted pyridinyl (i.e., pyridin-2-yl, pyridin-3-yl, or pyridin-4-yl) or pyridinyl substituted with one or more halogen, $-N(R^c)_2$, and/or $-N^+(R^b)_3$. In some such embodiments, $R^5$ is selected from the substituents in embodiments (A), embodiments (B), embodiments (C), embodiments (D), embodiments (E), embodiments (F), embodiments (G), embodiments (H), embodiments (J), or embodiments (K) as set forth below.

Compounds containing azide groups (e.g., compounds wherein $R^{3a}$ is $-N_3$) can be modified with further functional groups via reaction with a complementary reaction partner such as an alkyne-bearing compound or a phosphine-bearing compound. Reaction of azides and alkynes via [3+2] cycloaddition, commonly referred to as "click chemistry," can be used to install a variety of substituted triazole groups in the compounds of the invention. Accordingly, some embodiments of the invention provide compounds wherein linking moiety -$L^3$- is an optionally substituted triazolyl moiety according to the formula:

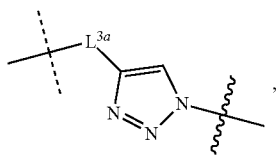

wherein the wavy line is point of connection to $R^{3a}$ and the dashed line is the point of connection to $R^{3c}$.

In some embodiments, the linking moiety $L^{3a}$ has a structure-$L^{3b}$-$L^{3c}$-, wherein Lab and $L^{3c}$ are independently selected from a bond, a divalent polymer moiety, and linear or branched, saturated or unsaturated $C_{1-30}$ alkyl;
- wherein one or more carbon atoms in the $C_{1-30}$ alkyl are optionally and independently replaced by O, S, $NR^a$;
- wherein two or more groupings of adjacent carbon atoms in the $C_{1-30}$ alkyl are optionally and independently replaced by $-NR^a(CO)-$ or $-(CO)NR^a-$; and
- wherein two or more groupings of adjacent carbon atoms in the $C_{1-30}$ alkyl are optionally and independently replaced by a 4- to 8-membered, divalent carbocycle or a 4- to 8-membered, divalent heterocycle having one to four heteroatoms selected from O, S, and N;
- and wherein each $R^a$ is independently selected from H and $C_{1-6}$ alkyl.

In some embodiments, the functional group $R^{3c}$ is selected from a chromophore, a fluorophore, and a binding moiety (e.g., biotin, glutathione, and the like), as described in more detail below.

In certain embodiments, $R^3$ and the carbonyl to which it is bonded form a moiety other than a naturally-occurring amino acid residue (an L amino acid residue) or an isomer of a naturally-occurring amino acid residue (a D amino acid residue). In some embodiments, $R^3$ and the carbonyl to which it is bonded form a moiety other than asparaginyl, substituted asparaginyl, glutaminyl (i.e., a glutamine residue), substituted glutaminyl (i.e., a substituted glutamine residue), glutamyl (i.e., a glutamic acid residue), substituted glutamyl (i.e., a substituted glutamic acid residue), isoleucinyl, substituted isoleucinyl, leucinyl, substituted leucinyl, lysinyl, substituted lysinyl, methioninyl, substituted methioninyl, prolinyl, substituted prolinyl, threoninyl, substituted threoninyl, valinyl, or substituted valinyl. The substituted amino acid residues may be present in larger peptide groups having two or more amino acid residues linked via amine bonds.

In some embodiments, the invention provides compounds of Formula I or Formula Ia and pharmaceutically acceptable salts thereof, wherein $R^4$ is hydrogen or methyl. In some such embodiments, $R^5$ is $-CH_2R^{5a}$ and $R^{5a}$ is selected from $C_{5-12}$ heteroaryl and $-O-R^6$. In some such embodiments, $R^{5a}$ is $-O$-phenyl wherein phenyl is substituted with 1-5 halogens. In some such embodiments, $R^4$ is hydrogen.

In some embodiments, $R^{5a}$ in compounds of Formula I or Formula Ia is selected from $-S-R^7$, $-SO-R^7$, $-SO_2-R^7$, $C_{5-12}$ heteroaryl, and $-N-R^8$. In some embodiments, $R^{5a}$ is selected from $-O-R^6$, $C_{5-12}$ heteroaryl, and $-N-R^8$. In some embodiments, $R^{5a}$ is selected from $-O-R^6$, $-S-R^7$, $-SO-R^7$, $-SO_2-R^7$, and $-N-R^8$. In some embodiments, $R^{5a}$ is selected from $-O-R^6$, $-S-R^7$, $-SO-R^7$, $-SO_2-R^7$, and $C_{5-12}$ heteroaryl.

In some embodiments (A), $R^{5a}$ in compounds of Formula I or Formula Ia is selected from $C_{1-6}$ haloalkoxy (i.e., $-O-R^6$ wherein $R^6$ is $C_{1-6}$ haloalkyl), $C_{1-6}$ alkylthio (i.e., $-S-R^7$ wherein $R^7$ is $C_{1-6}$ alkyl), $C_{1-6}$ haloalkythio (i.e., $-S-R^7$ wherein $R^7$ is $C_{1-6}$ haloalkyl), $C_{1-6}$ alkylsufonyl (i.e., $-SO_2-R^7$ wherein $R^7$ is $C_{1-6}$ alkyl), ($C_{1-6}$ dialkyl)amino (i.e., $-NR^8$), $C_{5-12}$ heteroaryl, 3- to 12-membered heterocyclyl, $-O$-phenyl wherein phenyl is substituted with 1-5 halogens, and $-S$-phenyl wherein phenyl is optionally substituted with 1-5 halogens. In embodiments (A), $R^3$ can be any of the substituents or groups of substituents set forth above.

In some embodiments (B), $R^{5a}$ in compounds of Formula I or Formula Ia is selected from $C_{1-6}$ alkoxy, $C_{1-6}$ alkylthio, $C_{1-6}$ haloalkythio, $C_{1-6}$ alkylsufonyl, ($C_{1-6}$ dialkyl)amino, $C_{5-12}$ heteroaryl, 3- to 12-membered heterocyclyl, —O-phenyl wherein phenyl is substituted with 1-5 halogens, and —S-phenyl wherein phenyl is optionally substituted with 1-5 halogens. In embodiments (B), $R^3$ can be any of the substituents or groups of substituents set forth above.

In some embodiments (C), $R^{5a}$ in compounds of Formula I or Formula Ia is selected from $C_{1-6}$ alkoxy, $C_{1-6}$ haloalkoxy, $C_{1-6}$ haloalkythio, $C_{1-6}$ alkylsufonyl, ($C_{1-6}$ dialkyl)amino, $C_{5-12}$ heteroaryl, 3- to 12-membered heterocyclyl, —O-phenyl wherein phenyl is substituted with 1-5 halogens, and —S-phenyl wherein phenyl is optionally substituted with 1-5 halogens. In embodiments (C), $R^3$ can be any of the substituents or groups of substituents set forth above.

In some embodiments (D), $R^{5a}$ in compounds of Formula I or Formula Ia is selected from $C_{1-6}$ alkoxy, $C_{1-6}$ haloalkoxy, $C_{1-6}$ alkylthio, $C_{1-6}$ alkylsufonyl, ($C_{1-6}$ dialkyl)amino, $C_{5-12}$ heteroaryl, 3- to 12-membered heterocyclyl, —O-phenyl wherein phenyl is substituted with 1-5 halogens, and —S-phenyl wherein phenyl is optionally substituted with 1-5 halogens. In embodiments (D), $R^3$ can be any of the substituents or groups of substituents set forth above.

In some embodiments (E), $R^{5a}$ in compounds of Formula I or Formula Ia is selected from $C_{1-6}$ alkoxy, $C_{1-6}$ haloalkoxy, $C_{1-6}$ alkylthio, $C_{1-6}$ haloalkythio, ($C_{1-6}$ dialkyl)amino, $C_{5-12}$ heteroaryl, 3- to 12-membered heterocyclyl, —O-phenyl wherein phenyl is substituted with 1-5 halogens, and —S-phenyl wherein phenyl is optionally substituted with 1-5 halogens. In embodiments (E), $R^3$ can be any of the substituents or groups of substituents set forth above.

In some embodiments (F), $R^{5a}$ in compounds of Formula I or Formula Ia is selected from $C_{1-6}$ alkoxy, $C_{1-6}$ haloalkoxy, $C_{1-6}$ alkylthio, $C_{1-6}$ haloalkythio, $C_{1-6}$ alkylsufonyl, $C_{5-12}$ heteroaryl, 3- to 12-membered heterocyclyl, —O-phenyl wherein phenyl is substituted with 1-5 halogens, and —S-phenyl wherein phenyl is optionally substituted with 1-5 halogens. In embodiments (F), $R^3$ can be any of the substituents or groups of substituents set forth above.

In some embodiments (G), $R^{5a}$ in compounds of Formula I or Formula Ia is selected from $C_{1-6}$ alkoxy, $C_{1-6}$ haloalkoxy, $C_{1-6}$ alkylthio, $C_{1-6}$ haloalkythio, $C_{1-6}$ alkylsufonyl, ($C_{1-6}$ dialkyl)amino, 3- to 12-membered heterocyclyl, —O-phenyl wherein phenyl is substituted with 1-5 halogens, and —S-phenyl wherein phenyl is optionally substituted with 1-5 halogens. In embodiments (G), $R^3$ can be any of the substituents or groups of substituents set forth above.

In some embodiments (H), $R^{5a}$ in compounds of Formula I or Formula Ia is selected from $C_{1-6}$ alkoxy, $C_{1-6}$ haloalkoxy, $C_{1-6}$ alkylthio, $C_{1-6}$ haloalkythio, $C_{1-6}$ alkylsufonyl, ($C_{1-6}$ dialkyl)amino, $C_{5-12}$ heteroaryl, 3- to 12-membered heterocyclyl, and —S-phenyl wherein phenyl is optionally substituted with 1-5 halogens. In embodiments (H), $R^3$ can be any of the substituents or groups of substituents set forth above.

In some embodiments (J), $R^{5a}$ in compounds of Formula I or Formula Ia is selected from $C_{1-6}$ alkoxy, $C_{1-6}$ haloalkoxy, $C_{1-6}$ alkylthio, $C_{1-6}$ haloalkythio, $C_{1-6}$ alkylsufonyl, ($C_{1-6}$ dialkyl)amino, $C_{5-12}$ heteroaryl, 3- to 12-membered heterocyclyl, and —O-phenyl wherein phenyl is substituted with 1-5 halogens. In embodiments (J), $R^3$ can be any of the substituents or groups of substituents set forth above.

In some embodiments (K), $R^{5a}$ in compounds of Formula I or Formula Ia is selected from $C_{1-6}$ alkoxy, $C_{1-6}$ haloalkoxy, $C_{1-6}$ alkylthio, $C_{1-6}$ haloalkythio, $C_{1-6}$ alkylsufonyl, ($C_{1-6}$ dialkyl)amino, $C_{5-12}$ heteroaryl, —O-phenyl wherein phenyl is substituted with 1-5 halogens, and —S-phenyl wherein phenyl is optionally substituted with 1-5 halogens. In embodiments (K), $R^3$ can be any of the substituents or groups of substituents set forth above.

In some embodiments, each halogen in $R^{5a}$ is independently selected from F and $C_1$. In some embodiments, each halogen in $R^{5a}$ is F.

In some embodiments, $R^{5a}$ is a moiety having the structure:

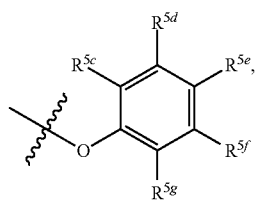

wherein $R^{5b}$, $R^{5c}$, $R^{5d}$, $R^{5e}$, and $R^{5f}$ are independently selected from hydrogen and halogen, and the wavy line represents the point of connection to the compound.

In some embodiments:

$R^{5c}$ is halogen, $R^{5d}$ is H, $R^{5e}$ is H, $R^{5f}$ is H, and $R^{5g}$ is H; or $R^{5c}$ is H, $R^{5d}$ is halogen, $R^{5e}$ is H, $R^{5f}$ is H, and $R^{5g}$ is H; or $R^{5c}$ is H, $R^{5d}$ is H, $R^{5e}$ is halogen, $R^{5f}$ is H, and $R^{5g}$ is H; or $R^{5c}$ is H, $R^{5d}$ is H, $R^{5e}$ is H, $R^{5f}$ is halogen, and $R^{5g}$ is H; or $R^{5c}$ is H, $R^{5d}$ is H, $R^{5e}$ is H, $R^{5f}$ is H, and $R^{5g}$ is halogen; or $R^{5c}$ is halogen, $R^{5d}$ is halogen, $R^{5e}$ is H, $R^{5f}$ is H, and $R^{5g}$ is H; or $R^{5c}$ is halogen, $R^{5d}$ is H, $R^{5e}$ is halogen, $R^{5f}$ is H, and $R^{5g}$ is H; or $R^{5c}$ is halogen, $R^{5d}$ is H, $R^{5e}$ is H, $R^{5f}$ is halogen, and $R^{5g}$ is H; or $R^{5c}$ is halogen, $R^{5d}$ is H, $R^{5e}$ is H, $R^{5f}$ is H, and $R^{5g}$ is halogen; or $R^{5c}$ is H, $R^{5d}$ is halogen, $R^{5e}$ is halogen, $R^{5f}$ is H, and $R^{5g}$ is H; or $R^{5c}$ is H, $R^{5d}$ is halogen, $R^{5e}$ is H, $R^{5f}$ is halogen, and $R^{5g}$ is H; or $R^{5c}$ is H, $R^{5d}$ is halogen, $R^{5e}$ is H, $R^{5f}$ is H, and $R^{5g}$ is halogen; or $R^{5c}$ is H, $R^{5d}$ is H, $R^{5e}$ is halogen, $R^{5f}$ is halogen, and $R^{5g}$ is H; or $R^{5c}$ is H, $R^{5d}$ is H, $R^{5e}$ is halogen, $R^{5f}$ is H, and $R^{5g}$ is halogen; or $R^{5c}$ is H, $R^{5d}$ is H, $R^{5e}$ is H, $R^{5f}$ is halogen, and $R^{5g}$ is halogen; or $R^{5c}$ is halogen, $R^{5d}$ is halogen, $R^{5e}$ is halogen, $R^{5f}$ is H, and $R^{5g}$ is H; or $R^{5c}$ is halogen, $R^{5d}$ is halogen, $R^{5e}$ is H, $R^{5f}$ is halogen, and $R^{5g}$ is H; or $R^{5c}$ is halogen, $R^{5d}$ is halogen, $R^{5e}$ is H, $R^{5f}$ is H, and $R^{5g}$ is halogen; or $R^{5c}$ is halogen, $R^{5d}$ is H, $R^{5e}$ is halogen, $R^{5f}$ is halogen, and $R^{5g}$ is H; or $R^{5c}$ is halogen, $R^{5d}$ is H, $R^{5e}$ is halogen, $R^{5f}$ is H, and $R^{5g}$ is halogen; or $R^{5c}$ is halogen, $R^{5d}$ is H, $R^{5e}$ is H, $R^{5f}$ is halogen, and $R^{5g}$ is halogen; or $R^{5c}$ is H, $R^{5d}$ is halogen, $R^{5e}$ is halogen, $R^{5f}$ is halogen, and $R^{5g}$ is H; or $R^{5c}$ is H, $R^{5d}$ is halogen, $R^{5e}$ is halogen, $R^{5f}$ is H, and $R^{5g}$ is halogen; or
$R^{5c}$ is H, $R^{5d}$ is halogen, $R^{5e}$ is H, $R^{5f}$ is halogen, and $R^{5g}$ is halogen; or
$R^{5c}$ is H, $R^{5d}$ is H, $R^{5e}$ is halogen, $R^{5f}$ is halogen, and $R^{5g}$ is halogen; or
$R^{5c}$ is H, $R^{5d}$ is halogen, $R^{5e}$ is halogen, $R^{5f}$ is halogen, and $R^{5g}$ is halogen; or
$R^{5c}$ is halogen, $R^{5d}$ is H, $R^{5e}$ is halogen, $R^{5f}$ is halogen, and $R^{5g}$ is halogen; or
$R^{5c}$ is halogen, $R^{5d}$ is halogen, $R^{5e}$ is halogen, $R^{5f}$ is H, and $R^{5g}$ is halogen; or
$R^{5c}$ is halogen, $R^{5d}$ is halogen, $R^{5e}$ is halogen, $R^{5f}$ is halogen, and $R^{5g}$ is H.

In some embodiments:
$R^{5c}$ is F or Cl, $R^{5d}$ is H, $R^{5e}$ is H, $R^{5f}$ is H, and $R^{5g}$ is H; or
$R^{5c}$ is H, $R^{5d}$ is F or Cl, $R^{5e}$ is H, $R^{5f}$ is H, and $R^{5g}$ is H; or
$R^{5c}$ is H, $R^{5d}$ is H, $R^{5e}$ is F or Cl, $R^{5f}$ is H, and $R^{5g}$ is H; or
$R^{5c}$ is H, $R^{5d}$ is H, $R^{5e}$ is H, $R^{5f}$ is F or Cl, and $R^{5g}$ is H; or
$R^{5c}$ is H, $R^{5d}$ is H, $R^{5e}$ is H, $R^{5f}$ is H, and $R^{5g}$ is F or Cl; or
$R^{5c}$ is F or Cl, $R^{5d}$ is F or Cl, $R^{5e}$ is H, $R^{5f}$ is H, and $R^{5g}$ is H; or
$R^{5c}$ is F or Cl, $R^{5d}$ is H, $R^{5e}$ is F or Cl, $R^{5f}$ is H, and $R^{5g}$ is H; or
$R^{5c}$ is F or Cl, $R^{5d}$ is H, $R^{5e}$ is H, $R^{5f}$ is F or Cl, and $R^{5g}$ is H; or
$R^{5c}$ is F or Cl, $R^{5d}$ is H, $R^{5e}$ is H, $R^{5f}$ is H, and $R^{5g}$ is F or Cl; or
$R^{5c}$ is H, $R^{5d}$ is F or Cl, $R^{5e}$ is F or Cl, $R^{5f}$ is H, and $R^{5g}$ is H; or
$R^{5c}$ is H, $R^{5d}$ is F or Cl, $R^{5e}$ is H, $R^{5f}$ is F or Cl, and $R^{5g}$ is H; or
$R^{5c}$ is H, $R^{5d}$ is F or Cl, $R^{5e}$ is H, $R^{5f}$ is H, and $R^{5g}$ is F or Cl; or
$R^{5c}$ is H, $R^{5d}$ is H, $R^{5e}$ is F or Cl, $R^{5f}$ is F or Cl, and $R^{5g}$ is H; or
$R^{5c}$ is H, $R^{5d}$ is H, $R^{5e}$ is F or Cl, $R^{5f}$ is H, and $R^{5g}$ is F or Cl; or
$R^{5c}$ is H, $R^{5d}$ is H, $R^{5e}$ is H, $R^{5f}$ is F or Cl, and $R^{5g}$ is F or Cl; or
$R^{5c}$ is F or Cl, $R^{5d}$ is F or Cl, $R^{5e}$ is F or Cl, $R^{5f}$ is H, and $R^{5g}$ is H; or
$R^{5c}$ is F or Cl, $R^{5d}$ is F or Cl, $R^{5e}$ is H, $R^{5f}$ is F or Cl, and $R^{5g}$ is H; or
$R^{5c}$ is F or Cl, $R^{5d}$ is F or Cl, $R^{5e}$ is H, $R^{5f}$ is H, and $R^{5g}$ is F or Cl; or
$R^{5c}$ is F or Cl, $R^{5d}$ is H, $R^{5e}$ is F or Cl, $R^{5f}$ is F or Cl, and $R^{5g}$ is H; or
$R^{5c}$ is F or Cl, $R^{5d}$ is H, $R^{5e}$ is F or Cl, $R^{5f}$ is H, and $R^{5g}$ is F or Cl; or
$R^{5c}$ is F or Cl, $R^{5d}$ is H, $R^{5e}$ is H, $R^{5f}$ is F or Cl, and $R^{5g}$ is F or Cl; or
$R^{5c}$ is H, $R^{5d}$ is F or Cl, $R^{5e}$ is F or Cl, $R^{5f}$ is F or Cl, and $R^{5g}$ is H; or
$R^{5c}$ is H, $R^{5d}$ is F or Cl, $R^{5e}$ is F or Cl, $R^{5f}$ is H, and $R^{5g}$ is F or Cl; or
$R^{5c}$ is F or Cl, $R^{5d}$ is H, $R^{5e}$ is F or Cl, $R^{5f}$ is F or Cl, and $R^{5g}$ is F or Cl; or
$R^{5c}$ is F or Cl, $R^{5d}$ is F or Cl, $R^{5e}$ is F or Cl, $R^{5f}$ is H, and $R^{5g}$ is F or Cl; or
$R^{5c}$ is F or Cl, $R^{5d}$ is F or Cl, $R^{5e}$ is F or Cl, $R^{5f}$ is F or Cl, and $R^{5g}$ is H.

In some embodiments:
$R^{5c}$ is F, $R^{5d}$ is H, $R^{5e}$ is H, $R^{5f}$ is H, and $R^{5g}$ is H; or
$R^{5c}$ is H, $R^{5d}$ is F, $R^{5e}$ is H, $R^{5f}$ is H, and $R^{5g}$ is H; or
$R^{5c}$ is H, $R^{5d}$ is H, $R^{5e}$ is F, $R^{5f}$ is H, and $R^{5g}$ is H; or
$R^{5c}$ is H, $R^{5d}$ is H, $R^{5e}$ is H, $R^{5f}$ is F, and $R^{5g}$ is H; or
$R^{5c}$ is H, $R^{5d}$ is H, $R^{5e}$ is H, $R^{5f}$ is H, and $R^{5g}$ is F; or
$R^{5c}$ is F, $R^{5d}$ is F, $R^{5e}$ is H, $R^{5f}$ is H, and $R^{5g}$ is H; or
$R^{5c}$ is F, $R^{5d}$ is H, $R^{5e}$ is F, $R^{5f}$ is H, and $R^{5g}$ is H; or
$R^{5c}$ is F, $R^{5d}$ is H, $R^{5e}$ is H, $R^{5f}$ is F, and $R^{5g}$ is H; or
$R^{5c}$ is F, $R^{5d}$ is H, $R^{5e}$ is H, $R^{5f}$ is H, and $R^{5g}$ is F; or
$R^{5c}$ is H, $R^{5d}$ is F, $R^{5e}$ is F, $R^{5f}$ is H, and $R^{5g}$ is H; or
$R^{5c}$ is H, $R^{5d}$ is F, $R^{5e}$ is H, $R^{5f}$ is F, and $R^{5g}$ is H; or
$R^{5c}$ is H, $R^{5d}$ is F, $R^{5e}$ is H, $R^{5f}$ is H, and $R^{5g}$ is F; or
$R^{5c}$ is H, $R^{5d}$ is H, $R^{5e}$ is F, $R^{5f}$ is F, and $R^{5g}$ is H; or
$R^{5c}$ is H, $R^{5d}$ is H, $R^{5e}$ is F, $R^{5f}$ is H, and $R^{5g}$ is F; or
$R^{5c}$ is H, $R^{5d}$ is H, $R^{5e}$ is H, $R^{5f}$ is F, and $R^{5g}$ is F; or
$R^{5c}$ is F, $R^{5d}$ is F, $R^{5e}$ is F, $R^{5f}$ is H, and $R^{5g}$ is H; or
$R^{5c}$ is F, $R^{5d}$ is F, $R^{5e}$ is H, $R^{5f}$ is F, and $R^{5g}$ is H; or
$R^{5c}$ is F, $R^{5d}$ is H, $R^{5e}$ is F, $R^{5f}$ is H, and $R^{5g}$ is F; or
$R^{5c}$ is F, $R^{5d}$ is H, $R^{5e}$ is F, $R^{5f}$ is F, and $R^{5g}$ is H; or
$R^{5c}$ is F, $R^{5d}$ is H, $R^{5e}$ is H, $R^{5f}$ is F, and $R^{5g}$ is F; or
$R^{5c}$ is F, $R^{5d}$ is H, $R^{5e}$ is H, $R^{5f}$ is H, and $R^{5g}$ is F; or
$R^{5c}$ is H, $R^{5d}$ is F, $R^{5e}$ is F, $R^{5f}$ is F, and $R^{5g}$ is H; or
$R^{5c}$ is H, $R^{5d}$ is F, $R^{5e}$ is F, $R^{5f}$ is H, and $R^{5g}$ is F; or
$R^{5c}$ is H, $R^{5d}$ is F, $R^{5e}$ is H, $R^{5f}$ is F, and $R^{5g}$ is F; or
$R^{5c}$ is H, $R^{5d}$ is H, $R^{5e}$ is F, $R^{5f}$ is F, and $R^{5g}$ is F; or
$R^{5c}$ is H, $R^{5d}$ is F, $R^{5e}$ is F, $R^{5f}$ is F, and $R^{5g}$ is F; or
$R^{5c}$ is F, $R^{5d}$ is H, $R^{5e}$ is F, $R^{5f}$ is F, and $R^{5g}$ is F; or
$R^{5c}$ is F, $R^{5d}$ is F, $R^{5e}$ is F, $R^{5f}$ is H, and $R^{5g}$ is F; or
$R^{5c}$ is F, $R^{5d}$ is F, $R^{5e}$ is F, $R^{5f}$ is F, and $R^{5g}$ is H.

In certain embodiments, $R^{5a}$ is not 2,3,5,6-tetrafluorophenoxy.

In some embodiments, the invention provides compound of Formula I and pharmaceutically acceptable salts thereof, wherein $R^{5a}$ is selected from 2-fluorophenoxy; 3-fluorophenoxy; 4-fluorophenoxy; 2,3-difluorophenoxy; 2,4-difluorophenoxy; 2,5-difluorophenoxy; 2,6-difluorophenoxy; 3,4-difluorophenoxy; 3,5-difluorophenoxy; 2,3,6-trifluorophenoxy; and 2,3,5-trifluorophenoxy. In some such embodiments, $R^{5a}$ is selected from 2-fluorophenoxy; 3 fluorophenoxy; 2,3-difluorophenoxy; 2,5-difluorophenoxy; 2,6-difluorophenoxy; 3,5-difluorophenoxy; 2,3,6-trifluorophenoxy; and 2,3,5-trifluorophenoxy. In some such embodiments, $R^{5a}$ is selected from 2,6-difluorophenoxy and 2,3,6-trifluorophenoxy.

In some embodiments, the invention provides compound of Formula Ia and pharmaceutically acceptable salts thereof, wherein $R^{5a}$ is selected from 2-fluorophenoxy; 3-fluorophenoxy; 4-fluorophenoxy; 2,3-difluorophenoxy; 2,4-difluorophenoxy; 2,5-difluorophenoxy; 2,6-difluorophenoxy; 3,4-difluorophenoxy; 3,5-difluorophenoxy; 2,3,6-trifluorophenoxy; and 2,3,5-trifluorophenoxy. In some such embodiments, $R^{5a}$ is selected from 2-fluorophenoxy; 3 fluorophenoxy; 2,3-difluorophenoxy; 2,5-difluorophenoxy; 2,6-difluorophenoxy; 3,5-difluorophenoxy; 2,3,6-trifluorophenoxy; and 2,3,5-trifluorophenoxy. In some such embodiments, $R^{5a}$ is selected from 2,6-difluorophenoxy and 2,3,6-trifluorophenoxy.

In some embodiments, the invention provides compounds of Formula I or Formula Ia and pharmaceutically acceptable salts thereof, wherein $R^{5a}$ is selected from —N($R^8$)$_2$, 5- to 12-membered heteroaryl, and 3- to 12-membered heterocyclyl, wherein to 12-membered heteroaryl is optionally substituted with one or more members independently selected from halogen, $C_{1-3}$ alkyl, and $C_{1-3}$ haloalkyl, and 3- to 12-membered heterocyclyl is optionally substituted with one or more members independently selected from oxo, halogen, $C_{1-3}$ alkyl, and $C_{1-3}$ haloalkyl.

In some embodiments, $R^{5a}$ is 5- to 12-membered heteroaryl or 3- to 12-membered heterocyclyl. $R^{5a}$ can be, for example, pyrrolyl, pyridinyl, imidazolyl, pyrazolyl, triazolyl, tetrazolyl, pyrazinyl, triazinyl, indolyl, isoindolyl, or quinolinyl. In some embodiments, $R^{5a}$ is tetrazolyl (e.g., 1H-tetrazol-1-yl or 2H-tetrazol-2-yl). In some embodiments, $R^{5a}$ is 6-oxopyrimidin-1(6H)-yl. In some embodiments, $R^{5a}$ is tetrazolyl or 6-oxopyrimidin-1(6H)-yl, and $R^3$ is selected from (2-methoxy)propan-2-yl, unsubstituted phenyl, phenyl substituted with one or more halogen, —$N_3$, $C_{1-4}$ haloalkoxy, and/or —$NR^cC(O)R^b$, unsubstituted pyridinyl, and pyridinyl substituted with one or more halogen, —$N(R^c)_2$, and/or —$N^+(R^b)_3$.

In some embodiments, $R^{5a}$ is —$N(R^8)_2$, wherein each $R^8$ is independently selected $C_{1-6}$ alkyl. In such embodiments, each $R^8$ can independently be, e.g., methyl, ethyl, n-propyl, isopropyl, n-butyl, isobutyl, sec-butyl, tert-butyl, n-pentyl, isopentyl, or n-hexyl. In some embodiments, $R^{5a}$ is dimethylamino. In some embodiments, $R^{5a}$ is dimethylamino and $R^3$ is selected from (2-methoxy)propan-2-yl, unsubstituted phenyl, phenyl substituted with one or more halogen, —$N_3$, $C_{1-4}$ haloalkoxy, and/or —$NR^cC(O)R^b$, unsubstituted pyridinyl, and pyridinyl substituted with one or more halogen, —$N(R^c)_2$, and/or —$N^+(R^b)_3$.

In some embodiments, $R^{5a}$ is —O—$R^6$, wherein $R^6$ is $C_{1-6}$ haloalkyl. In such embodiments, $R^6$ can be, e.g., chloromethyl, dichloromethyl, trichloromethyl, fluoromethyl, difluoromethyl, trifluoromethyl, 2,2,2-trichloroethyl, 2,2,2-trifluoroethyl, pentachloroethyl, pentafluoroethyl, 1,1,1,3,3,3-hexachloropropyl, 1,1,1,3,3,3-hexafluoropropyl, or the like. In some embodiments, $R^{5a}$ is selected from 2,2,2-trifluoroethoxy and 1,1,1,3,3,3-hexafluoroisopropoxy. In some such embodiments, $R^3$ is selected from (2-methoxy)propan-2-yl, unsubstituted phenyl, phenyl substituted with one or more halogen, —$N_3$, $C_{1-4}$ haloalkoxy, and/or —$NR^cC(O)R^b$, unsubstituted pyridinyl, and pyridinyl substituted with one or more halogen, —$N(R^c)_2$, and/or —$N^+(R^b)_3$.

In some embodiments, $R^{5a}$ is —O—$R^6$, and $R^6$ is 5- to 12-membered heteroaryl, which is optionally substituted with one or more members independently selected from halogen, $C_{1-3}$ alkyl, and $C_{1-3}$ haloalkyl. When $R^{5a}$ is —O—$R^6$, for example, $R^6$ can be isoxazolyl, oxazolyl, imidazolyl, pyrazolyl, pyridinyl, oxazinyl, pyrimidinyl, pyrazinyl, pyridazinyl. In some embodiments, $R^{5a}$ is —O—$R^6$ and $R^6$ is selected from pyridin-2-yl, pyridin-3-yl, pyridin-4-yl, isoxazol-3-yl, isoxazol-4-yl, isoxazol-5-yl, pyrimidin-2-yl, pyrimidin-4-yl, pyrimidin-5-yl, and pyrimidin-6-yl. In some embodiments, $R^{5a}$ is —O—$R^6$ and $R^6$ is selected from isoxazol-3-yl, pyridin-3-yl, pyridin-4-yl, 2,6-dimethylpyridin-5-yl, and 2-methylpyrimidin-5-yl. In some embodiments, $R^{5a}$ is —O—$R^6$, $R^6$ is selected from isoxazol-3-yl, pyridin-3-yl, pyridin-4-yl, 2,6-dimethylpyridin-5-yl, and 2-methylpyrimidin-5-yl, and $R^3$ is selected from (2-methoxy)propan-2-yl, unsubstituted phenyl, phenyl substituted with one or more halogen, —$N_3$, $C_{1-4}$ haloalkoxy, and/or —$NR^cC(O)R^b$, unsubstituted pyridinyl, and pyridinyl substituted with one or more halogen, —$N(R^c)_2$, and/or —$N^+(R^b)_3$.

In some embodiments, $R^5$ is selected from —$CH_2R^{5a}$ and —$CHS(O)(R^{5b})_2$. In some embodiments, $R^5$ is —$CHS(O)(R^{5b})_2$ (e.g., dimethyl(oxo)-$\lambda^6$-sulfanylidene). In some embodiments, $R^5$ is —$CH_2R^{5a}$, $R^{5a}$ is selected from —S—$R^7$ and —$SO_2$—$R^7$, and $R^7$ is $C_{1-6}$ alkyl. In such embodiments, $R^7$ can be, e.g., methyl, ethyl, n-propyl, isopropyl, n-butyl, isobutyl, sec-butyl, tert-butyl, n-pentyl, isopentyl, or n-hexyl. In some embodiments, $R^{5a}$ is methylthio. In some embodiments, $R^{5a}$ is methylsulfonyl. In some embodiments, $R^{5a}$ is methylthio or methylsulfonyl, and $R^3$ is selected from (2-methoxy)propan-2-yl, unsubstituted phenyl, phenyl substituted with one or more halogen, —$N_3$, $C_{1-4}$ haloalkoxy, and/or —$NR^cC(O)R^b$, unsubstituted pyridinyl, and pyridinyl substituted with one or more halogen, —$N(R^c)_2$, and/or —$N^+(R^b)_3$.

In some embodiments, $R^{5a}$ is —S—$R^7$, and $R^7$ is 5- to 12-membered heteroaryl, which is optionally substituted with one or more members independently selected from halogen, $C_{1-3}$ alkyl, and $C_{1-3}$ haloalkyl. When $R^{5a}$ is —S—$R^7$, for example, $R^7$ can be isoxazolyl, oxazolyl, imidazolyl, pyrazolyl, pyridinyl, oxazinyl, pyrimidinyl, pyrazinyl, pyridazinyl. In some embodiments, $R^{5a}$ is —S—$R^7$ and $R^7$ is selected from pyridin-2-yl, pyridin-3-yl, pyridin-4-yl, isoxazol-3-yl, isoxazol-4-yl, isoxazol-5-yl, pyrimidin-2-yl, pyrimidin-4-yl, pyrimidin-5-yl, and pyrimidin-6-yl. In some embodiments, $R^{5a}$ is —S—$R^7$ and $R^7$ is selected from isoxazol-3-yl, pyridin-3-yl, pyridin-4-yl, 2,6-dimethylpyridin-5-yl, and 2-methylpyrimidin-5-yl. In some embodiments, $R^{5a}$ is —S—$R^7$, $R^7$ is selected from pyridin-3-yl, pyridin-4-yl, 2,6-dimethylpyridin-5-yl, and 2-methylpyrimidin-5-yl, and $R^3$ is selected from (2-methoxy)propan-2-yl, unsubstituted phenyl, phenyl substituted with one or more halogen, —$N_3$, $C_{1-4}$ haloalkoxy, and/or —$NR^cC(O)R^b$, unsubstituted pyridinyl, and pyridinyl substituted with one or more halogen, —$N(R^c)_2$, and/or —$N+(R^b)_3$.

In some embodiments, $R^5$ is $C_{1-6}$ haloalkyl. $R^5$ can be, e.g., chloromethyl, dichloromethyl, trichloromethyl, fluoromethyl, difluoromethyl, trifluoromethyl, 2,2,2-trichloroethyl, 2,2,2-trifluoroethyl, pentachloroethyl, pentafluoroethyl, 1,1,1,3,3,3-hexachloropropyl, 1,1,1,3,3,3-hexafluoropropyl, or the like. In some embodiments, $R^5$ is difluoromethyl. In some embodiments, $R^5$ is difluoromethyl and $R^3$ is selected from (2-methoxy)propan-2-yl, unsubstituted phenyl, phenyl substituted with one or more halogen, —$N_3$, $C_{1-4}$ haloalkoxy, and/or —$NR^cC(O)R^b$, unsubstituted pyridinyl, and pyridinyl substituted with one or more halogen, —$N(R^c)_2$, and/or —$N^+(R^b)_3$.

In some embodiments, the invention provides compounds of Formula I or Formula Ia and pharmaceutically acceptable salts thereof, wherein $R^5$ is haloalkyl. For example, $R^5$ can be chloromethyl, dichloromethyl, trichloromethyl, difluoromethyl, or trifluoromethyl.

In some embodiments, the invention provides a compound as set forth in Table 1 below or a pharmaceutically acceptable salt thereof

TABLE 1

Lysine gingipain inhibitors.

| Compound No. | Compound Structure |
| --- | --- |
| 1 | 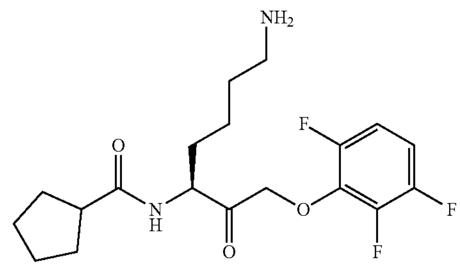 [SMILES: NCCCC[C@H](NC(=O)C1CCCC1)C(=O)COc1c(F)ccc(F)c1F] |
| 1a | 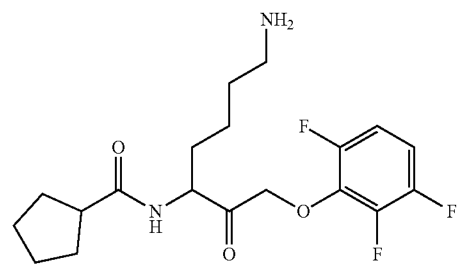 [SMILES: NCCCCC(NC(=O)C1CCCC1)C(=O)COc1c(F)ccc(F)c1F] |
| 2 | 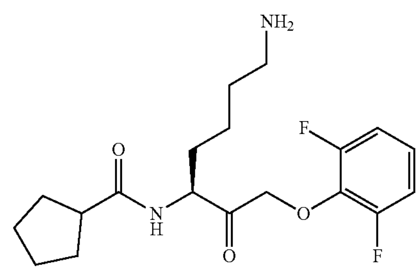 [SMILES: NCCCC[C@H](NC(=O)C1CCCC1)C(=O)COc1c(F)cccc1F] |
| 2a | 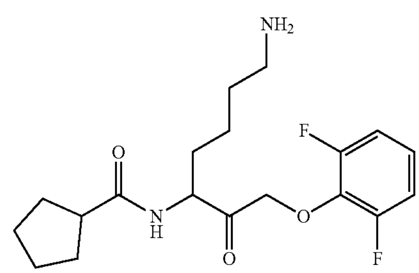 |
| 2b | 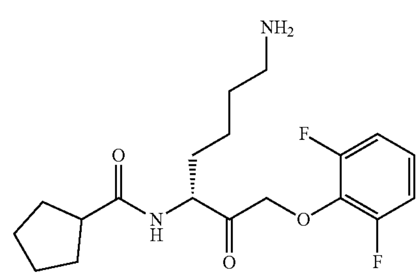 [SMILES: NCCCC[C@@H](NC(=O)C1CCCC1)C(=O)COc1c(F)cccc1F] |

TABLE 1-continued

Lysine gingipain inhibitors.

| Compound No. | Compound Structure |
|---|---|
| 3 | (S)-N-(1-(2-fluorophenoxy)-6-amino-2-oxohexan-3-yl)cyclopentanecarboxamide |
| 3a | (R)-N-(1-(2-fluorophenoxy)-6-amino-2-oxohexan-3-yl)cyclopentanecarboxamide |
| 4 | (S)-N-(6-amino-1-(2,3,5-trifluorophenoxy)-2-oxohexan-3-yl)cyclopentanecarboxamide |
| 4a | (R)-N-(6-amino-1-(2,3,5-trifluorophenoxy)-2-oxohexan-3-yl)cyclopentanecarboxamide |
| 5 | (S)-N-(6-amino-1-(2,3-difluorophenoxy)-2-oxohexan-3-yl)cyclopentanecarboxamide |

TABLE 1-continued
Lysine gingipain inhibitors.
| Compound No. | Compound Structure |
|---|---|
| 5a | 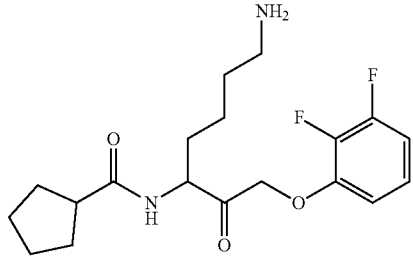 [SMILES: NCCCCC(NC(=O)C1CCCC1)C(=O)COc1cccc(F)c1F] |
| 6 | 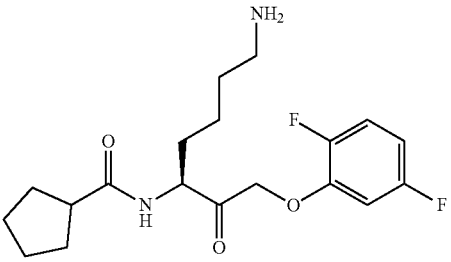 [SMILES: NCCCC[C@H](NC(=O)C1CCCC1)C(=O)COc1cc(F)ccc1F] |
| 6a | 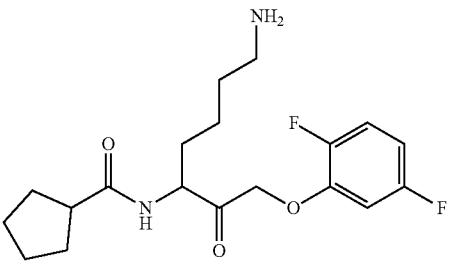 [SMILES: NCCCCC(NC(=O)C1CCCC1)C(=O)COc1cc(F)ccc1F] |
| 7 | 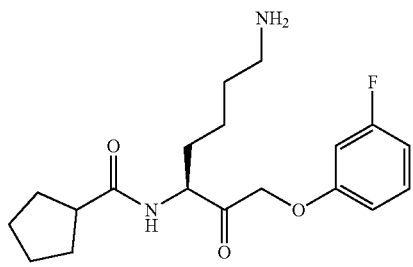 [SMILES: NCCCC[C@H](NC(=O)C1CCCC1)C(=O)COc1cccc(F)c1] |
| 7a | 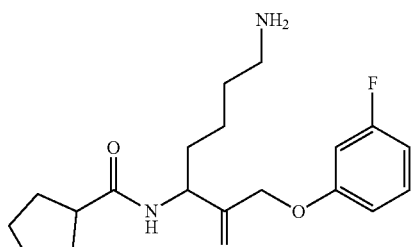 |

TABLE 1-continued
Lysine gingipain inhibitors.
| Compound No. | Compound Structure |
|---|---|
| 8 | 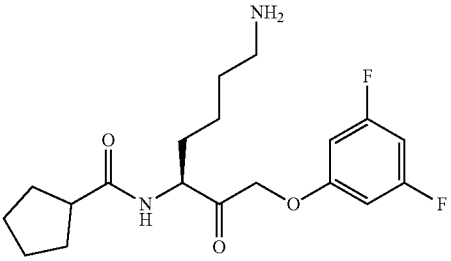 [SMILES: NCCCC[C@H](NC(=O)C1CCCC1)C(=O)COc1cc(F)cc(F)c1] |
| 8a | 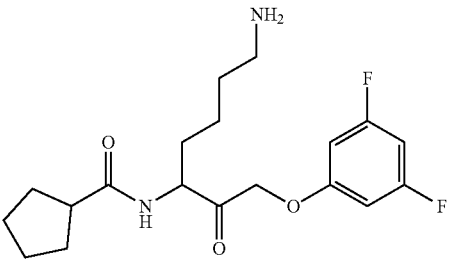 [SMILES: NCCCCC(NC(=O)C1CCCC1)C(=O)COc1cc(F)cc(F)c1] |
| 9 | 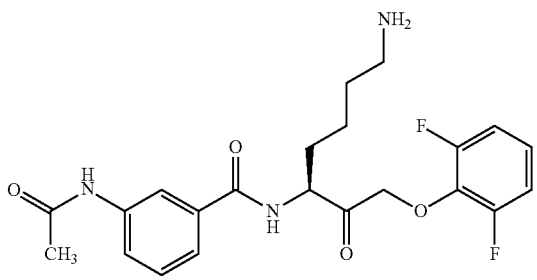 [SMILES: [2H]C([2H])([2H])C(=O)Nc1cccc(C(=O)N[C@@H](CCCCN)C(=O)COc2c(F)cccc2F)c1] |
| 9a | 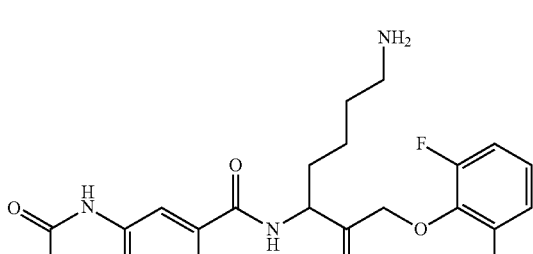 |
| 10 | 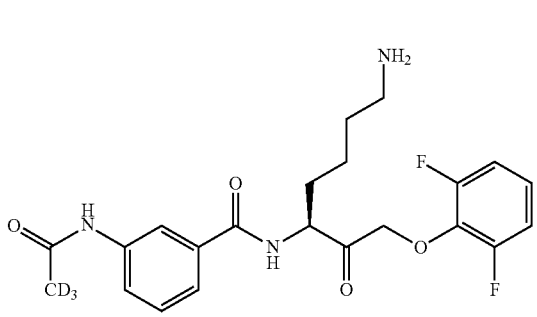 |

TABLE 1-continued

Lysine gingipain inhibitors.

| Compound No. | Compound Structure |
|---|---|
| 10a | 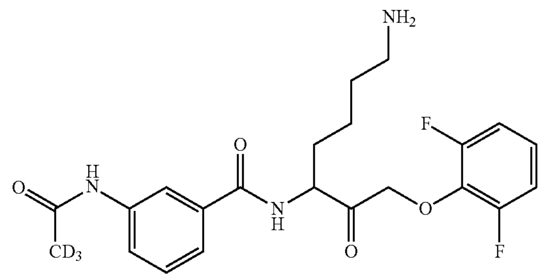 [SMILES: [2H]C([2H])([2H])C(=O)Nc1cccc(C(=O)NC(CCCCN)C(=O)COc2c(F)cccc2F)c1] |
| 11 | 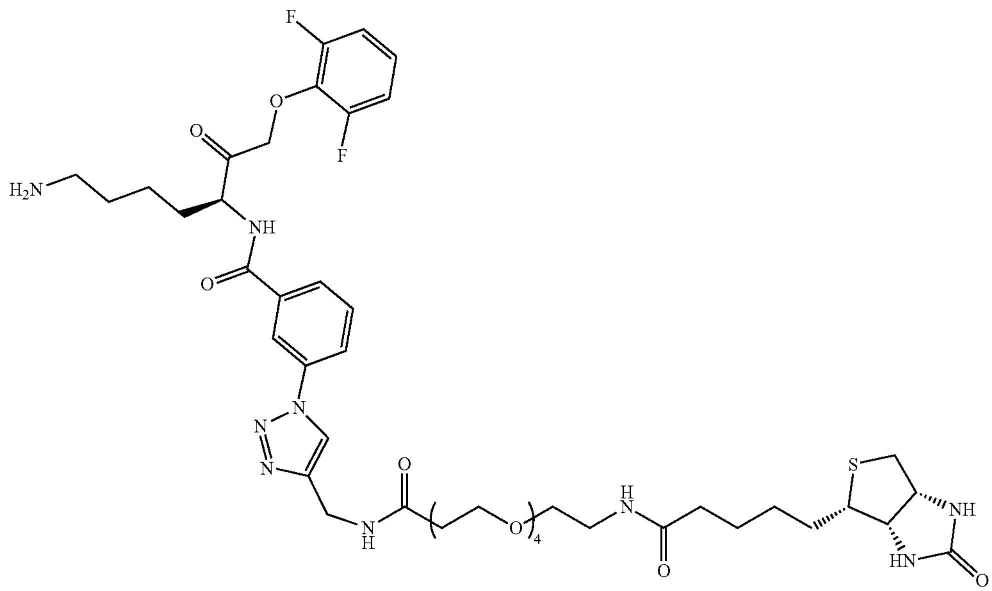 |
| 11a | 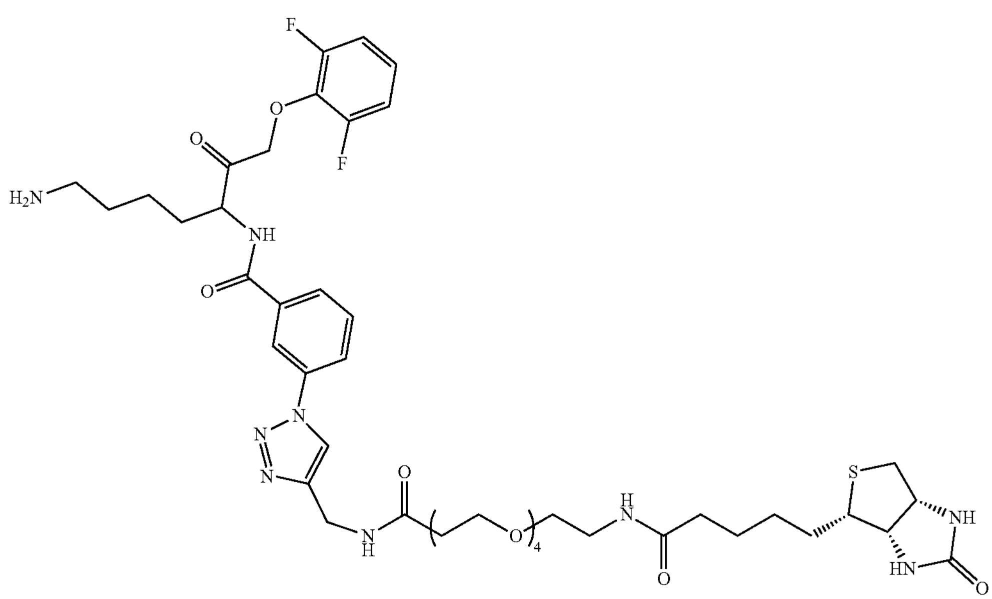 |

TABLE 1-continued

Lysine gingipain inhibitors.

| Compound No. | Compound Structure |
| --- | --- |
| 12 | 3-azidobenzamide linked to (S)-lysine-derived ketone with CH₂-O-(2,6-difluorophenyl) group |
| 12a | 3-azidobenzamide linked to lysine-derived ketone with CH₂-O-(2,6-difluorophenyl) group (no stereochemistry specified) |
| 13 | cyclopentanecarboxamide linked to (S)-lysine-derived ketone with CH₂-(1H-tetrazol-1-yl) group |
| 13a | cyclopentanecarboxamide linked to lysine-derived ketone with CH₂-(1H-tetrazol-1-yl) group (no stereochemistry specified) |
| 14 | cyclopentanecarboxamide linked to (S)-lysine-derived ketone with CH₂-(2H-tetrazol-2-yl) group |

TABLE 1-continued

Lysine gingipain inhibitors.

| Compound No. | Compound Structure |
| --- | --- |
| 14a | (cyclopentanecarbonyl)amino-lysine ketomethylene tetrazole derivative |
| 15 | 2,6-difluorophenoxy lysine ketone benzamide triazole BODIPY conjugate |
| 15a | 2,6-difluorophenoxy lysine ketone benzamide triazole BODIPY conjugate (stereoisomer) |
| 16 | (cyclopentanecarbonyl)amino-lysine thiomethyl ketone |

TABLE 1-continued

Lysine gingipain inhibitors.

| Compound No. | Compound Structure |
|---|---|
| 16a | 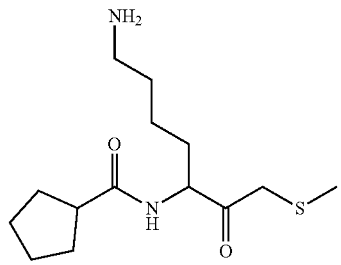 [SMILES: CSCC(=O)C(CCCCN)NC(=O)C1CCCC1] |
| 17 | 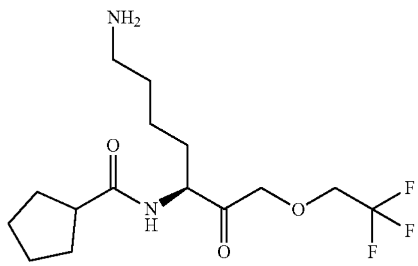 [SMILES: NCCCC[C@H](NC(=O)C1CCCC1)C(=O)COCC(F)(F)F] |
| 17a | 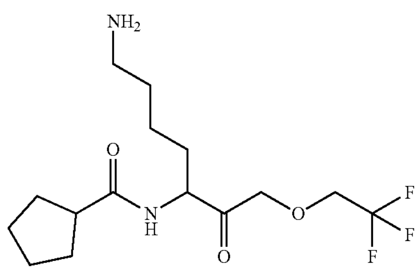 [SMILES: NCCCCC(NC(=O)C1CCCC1)C(=O)COCC(F)(F)F] |
| 18 | 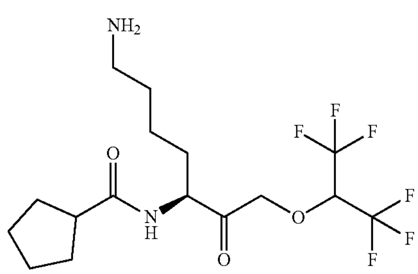 [SMILES: NCCCC[C@H](NC(=O)C1CCCC1)C(=O)COC(C(F)(F)F)C(F)(F)F] |
| 18a | 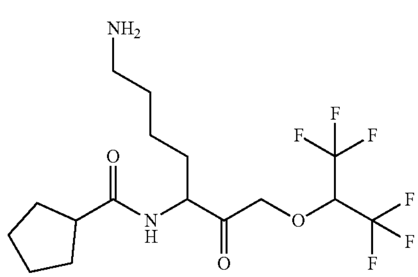 [SMILES: NCCCCC(NC(=O)C1CCCC1)C(=O)COC(C(F)(F)F)C(F)(F)F] |

TABLE 1-continued

Lysine gingipain inhibitors.

| Compound No. | Compound Structure |
|---|---|
| 19 | 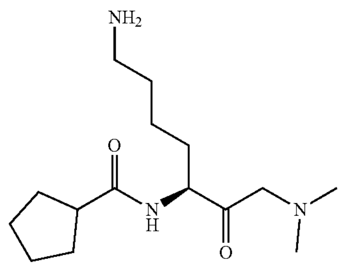 [SMILES: CN(C)CC(=O)[C@H](CCCCN)NC(=O)C1CCCC1] |
| 19a | 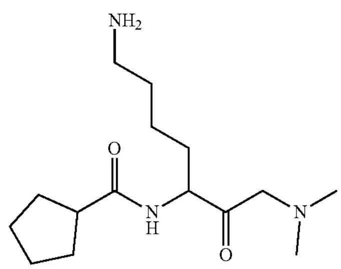 [SMILES: CN(C)CC(=O)C(CCCCN)NC(=O)C1CCCC1] |
| 20 | 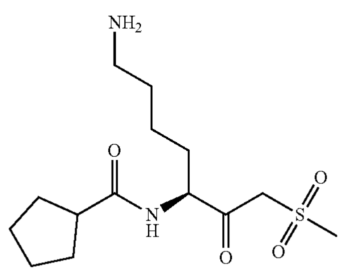 [SMILES: CS(=O)(=O)CC(=O)[C@H](CCCCN)NC(=O)C1CCCC1] |
| 20a | 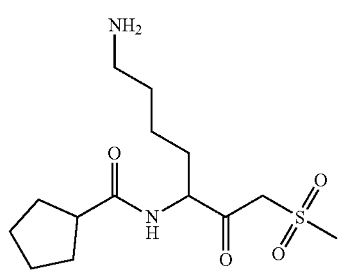 [SMILES: CS(=O)(=O)CC(=O)C(CCCCN)NC(=O)C1CCCC1] |
| 21 | 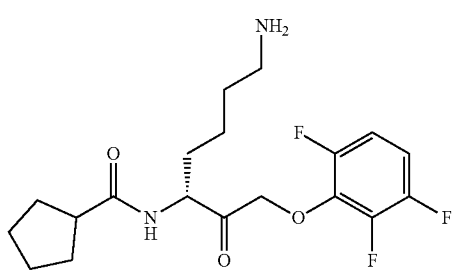 [SMILES: NCCCC[C@@H](NC(=O)C1CCCC1)C(=O)COc1c(F)ccc(F)c1F] |

TABLE 1-continued
Lysine gingipain inhibitors.
| Compound No. | Compound Structure |
| --- | --- |
| 26 | 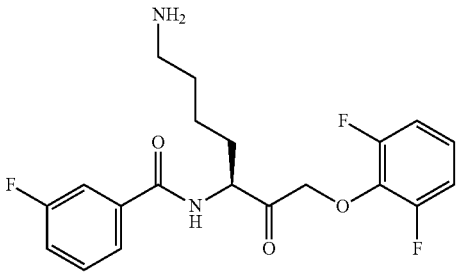 [SMILES: NCCCC[C@H](NC(=O)c1cccc(F)c1)C(=O)COc1c(F)cccc1F] |
| 26a | 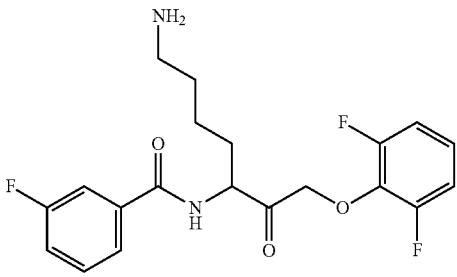 [SMILES: NCCCCC(NC(=O)c1cccc(F)c1)C(=O)COc1c(F)cccc1F] |
| 27 | 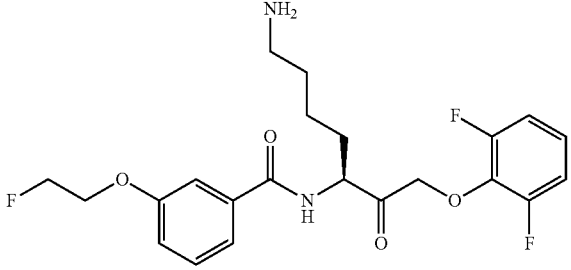 [SMILES: NCCCC[C@H](NC(=O)c1cccc(OCCF)c1)C(=O)COc1c(F)cccc1F] |
| 27a | 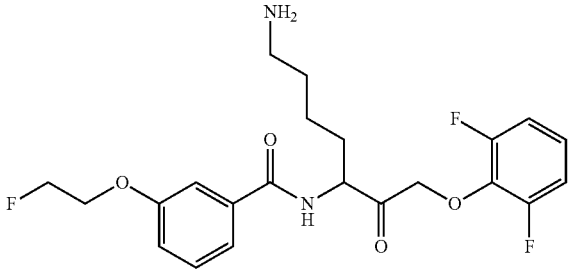 [SMILES: NCCCCC(NC(=O)c1cccc(OCCF)c1)C(=O)COc1c(F)cccc1F] |
| 28 | 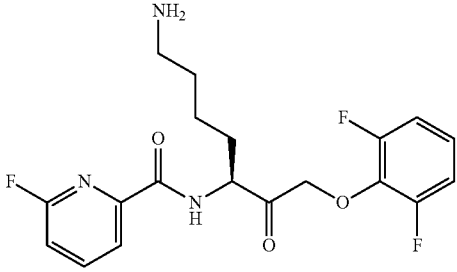 |

US 10,730,826 B2
TABLE 1-continued
Lysine gingipain inhibitors.
| Compound No. | Compound Structure |
|---|---|
| 28a | 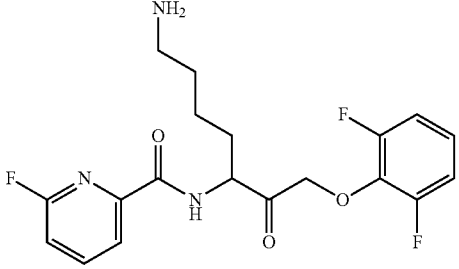 |
| 29 | 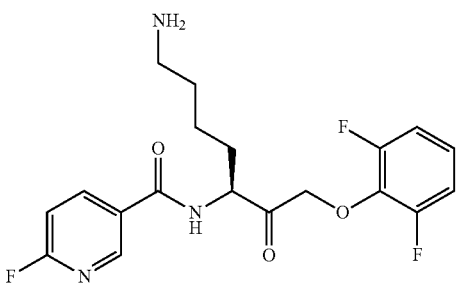 [SMILES: NCCCC[C@H](NC(=O)c1ccc(F)nc1)C(=O)COc1c(F)cccc1F] |
| 29a | 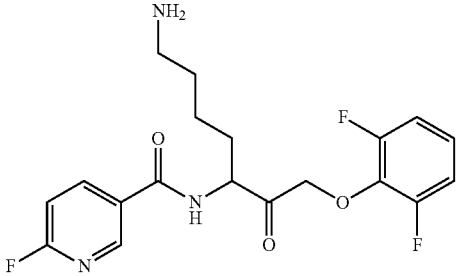 [SMILES: NCCCCC(NC(=O)c1ccc(F)nc1)C(=O)COc1c(F)cccc1F] |
| 30 | 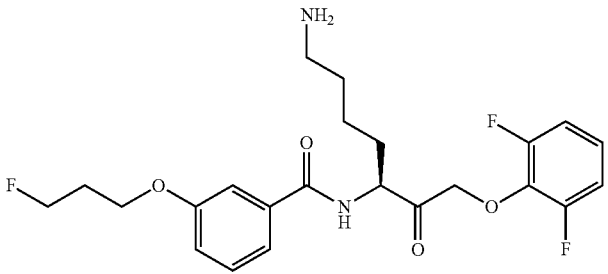 [SMILES: NCCCC[C@H](NC(=O)c1cccc(OCCCF)c1)C(=O)COc1c(F)cccc1F] |
| 30a | 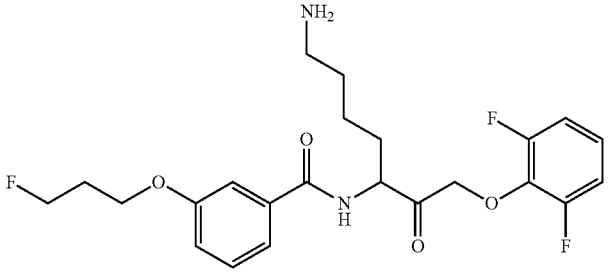 [SMILES: NCCCCC(NC(=O)c1cccc(OCCCF)c1)C(=O)COc1c(F)cccc1F] |

TABLE 1-continued

Lysine gingipain inhibitors.

| Compound No. | Compound Structure |
|---|---|
| 31 | 2-fluoropyridine-4-carboxamide of (S)-lysine α-(2,6-difluorophenoxy)methyl ketone |
| 31a | 2-fluoropyridine-4-carboxamide of (R)-lysine α-(2,6-difluorophenoxy)methyl ketone |
| 32 | 2-fluoropyridine-3-carboxamide of (S)-lysine α-(2,6-difluorophenoxy)methyl ketone |
| 32a | 2-fluoropyridine-3-carboxamide of (R)-lysine α-(2,6-difluorophenoxy)methyl ketone |
| 33 | 3-azidobenzamide of (S)-lysine α-(2,6-difluorophenoxy)methyl ketone |

TABLE 1-continued
Lysine gingipain inhibitors.
| Compound No. | Compound Structure |
|---|---|
| 33a | 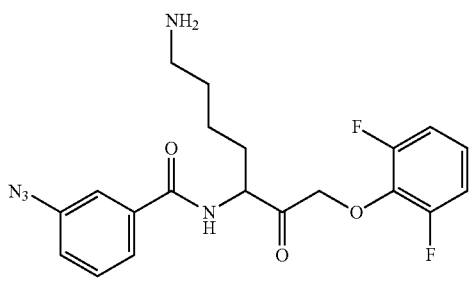 [SMILES: [N-]=[N+]=Nc1cccc(C(=O)NC(CCCCN)C(=O)COc2c(F)cccc2F)c1] |
| 34 | 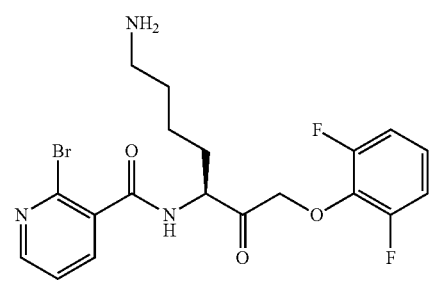 [SMILES: NCCCC[C@H](NC(=O)c1cccnc1Br)C(=O)COc1c(F)cccc1F] |
| 34a | 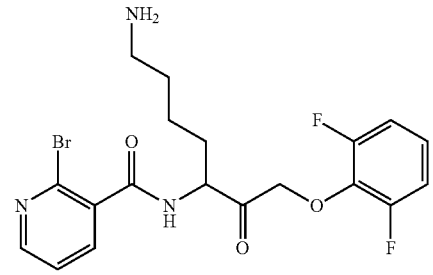 [SMILES: NCCCCC(NC(=O)c1cccnc1Br)C(=O)COc1c(F)cccc1F] |
| 35 | 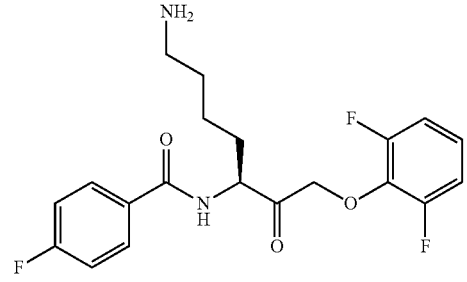 [SMILES: NCCCC[C@H](NC(=O)c1ccc(F)cc1)C(=O)COc1c(F)cccc1F] |
| 35a | 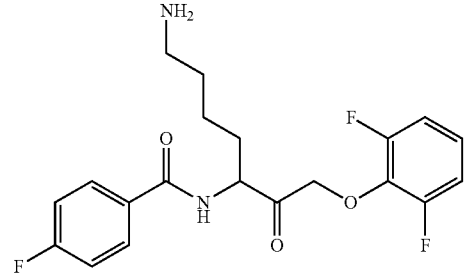 [SMILES: NCCCCC(NC(=O)c1ccc(F)cc1)C(=O)COc1c(F)cccc1F] |

TABLE 1-continued

Lysine gingipain inhibitors.

| Compound No. | Compound Structure |
|---|---|
| 36 | ![structure] |
| 36a | ![structure] |
| 37 | ![structure] |
| 37a | ![structure] |

TABLE 1-continued
Lysine gingipain inhibitors.
| Compound No. | Compound Structure |
|---|---|
| 38 | 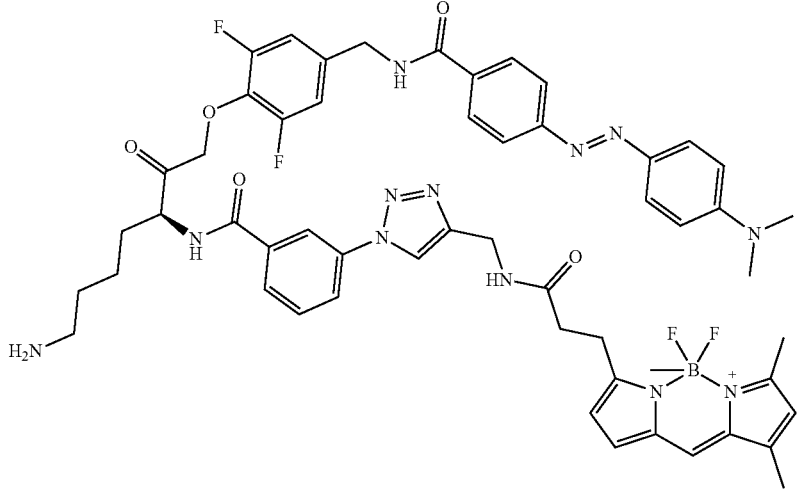 |
| 38a | 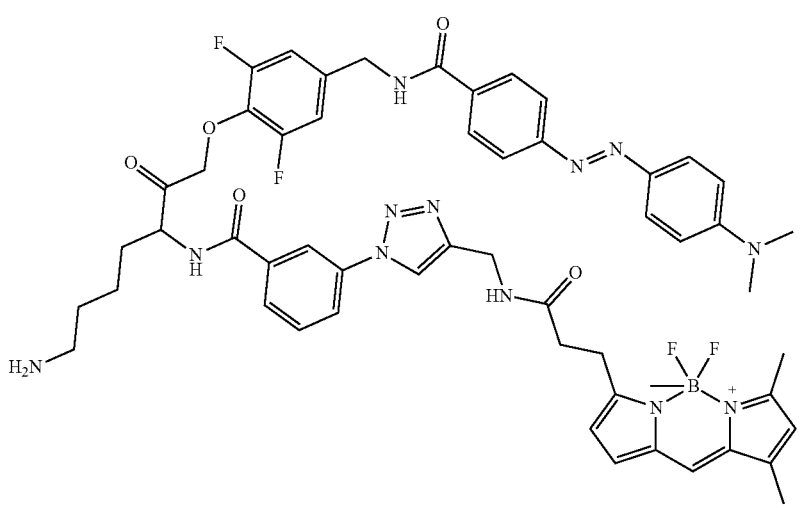 |
| 39 | 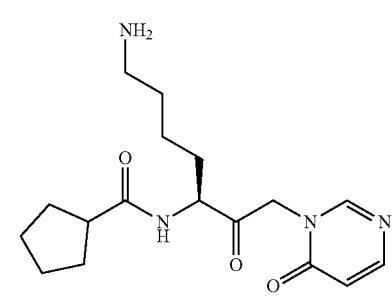 [SMILES: NCCCC[C@H](NC(=O)C1CCCC1)C(=O)Cn1cnccc1=O] |

TABLE 1-continued
Lysine gingipain inhibitors.
| Compound No. | Compound Structure |
|---|---|
| 39a | 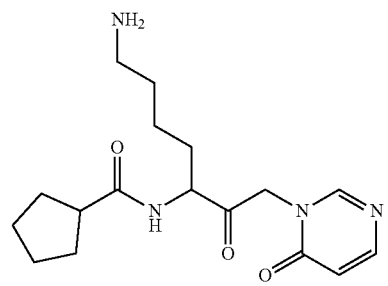 [SMILES: NCCCCC(NC(=O)C1CCCC1)C(=O)Cn1cnccc1=O] |
| 40 | 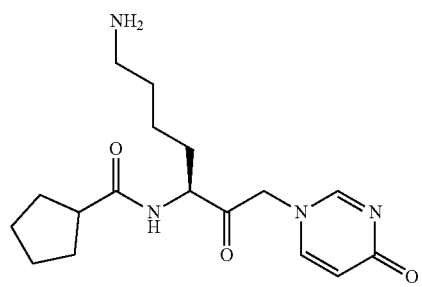 [SMILES: NCCCC[C@H](NC(=O)C1CCCC1)C(=O)Cn1ccc(=O)nc1] |
| 40a | 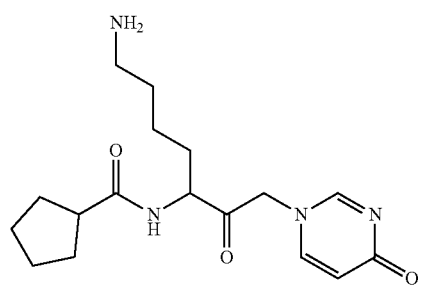 [SMILES: NCCCCC(NC(=O)C1CCCC1)C(=O)Cn1ccc(=O)nc1] |
| 41 | 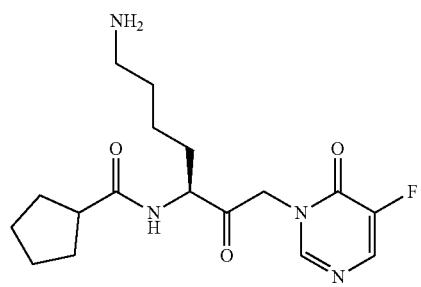 [SMILES: NCCCC[C@H](NC(=O)C1CCCC1)C(=O)Cn1cncc(F)c1=O] |
| 41a | 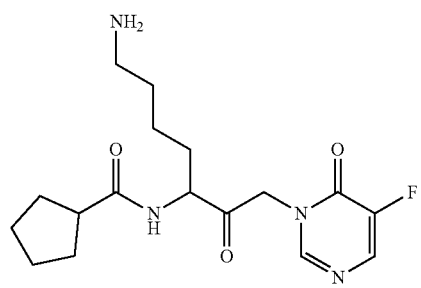 [SMILES: NCCCCC(NC(=O)C1CCCC1)C(=O)Cn1cncc(F)c1=O] |

TABLE 1-continued
Lysine gingipain inhibitors.
| Compound No. | Compound Structure |
|---|---|
| 42 | 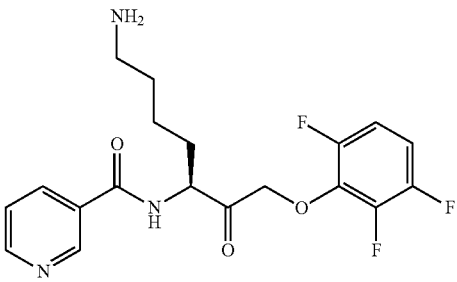 [SMILES: NCCCC[C@H](NC(=O)c1cccnc1)C(=O)COc1c(F)ccc(F)c1F] |
| 42a | 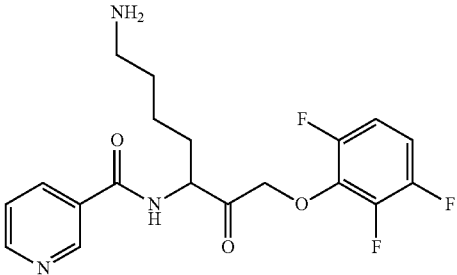 [SMILES: NCCCCC(NC(=O)c1cccnc1)C(=O)COc1c(F)ccc(F)c1F] |
| 43 | 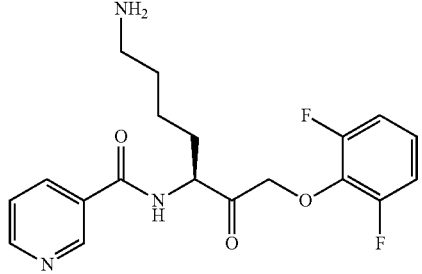 [SMILES: NCCCC[C@H](NC(=O)c1cccnc1)C(=O)COc1c(F)cccc1F] |
| 43a | 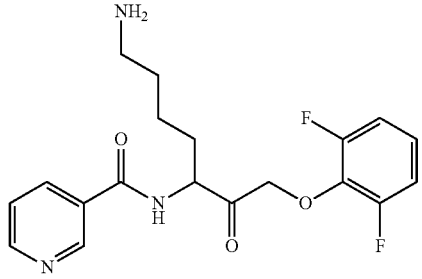 [SMILES: NCCCCC(NC(=O)c1cccnc1)C(=O)COc1c(F)cccc1F] |
| 44 | 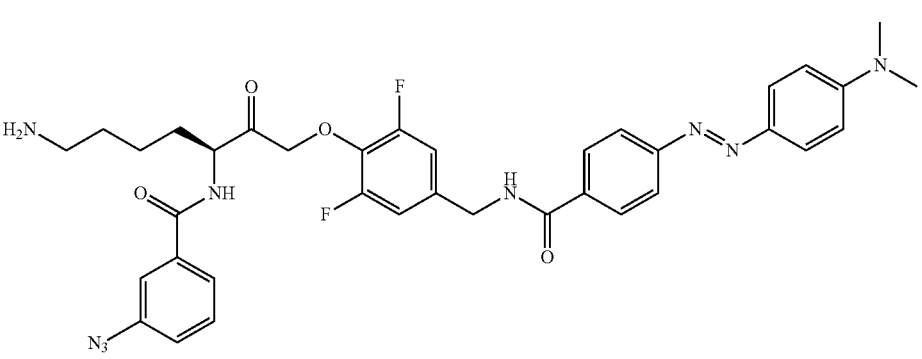 [SMILES: CN(C)c1ccc(/N=N/c2ccc(C(=O)NCc3cc(F)c(OCC(=O)[C@H](CCCCN)NC(=O)c4cccc(N=[N+]=[N-])c4)c(F)c3)cc2)cc1] |

TABLE 1-continued
Lysine gingipain inhibitors.
| Compound No. | Compound Structure |
|---|---|
| 44a | 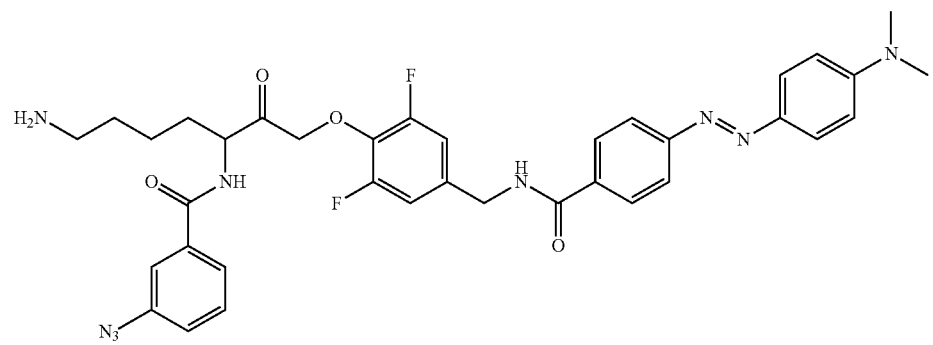 [SMILES: CN(C)c1ccc(/N=N/c2ccc(C(=O)NCc3cc(F)c(OCC(=O)C(CCCCN)NC(=O)c4cccc(N=[N+]=[N-])c4)c(F)c3)cc2)cc1] |
| 45 | 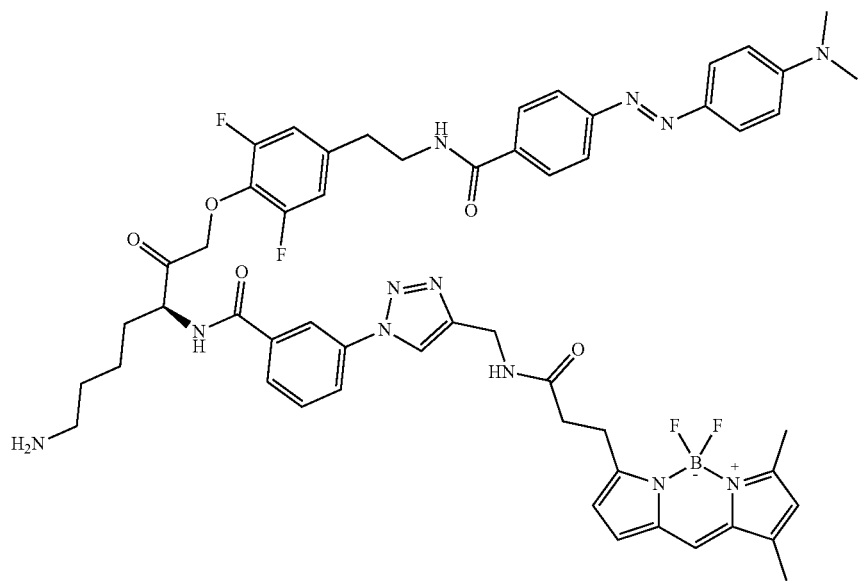 |
| 45a | 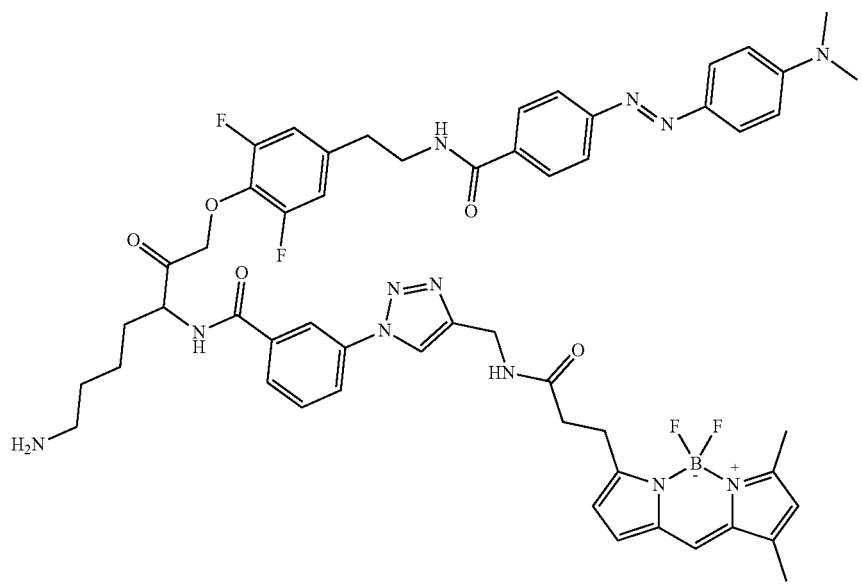 |

TABLE 1-continued
Lysine gingipain inhibitors.
| Compound No. | Compound Structure |
| --- | --- |
| 46 | 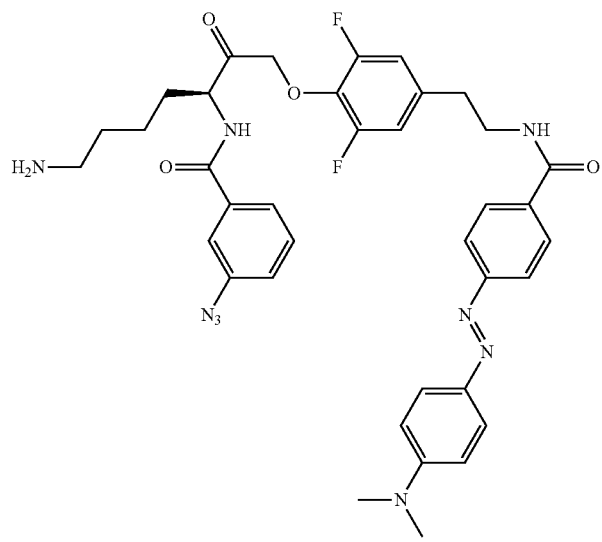 [SMILES: CN(C)c1ccc(/N=N/c2ccc(C(=O)NCCc3cc(F)c(OCC(=O)[C@H](CCCCN)NC(=O)c4cccc(N=[N+]=[N-])c4)c(F)c3)cc2)cc1] |
| 46a | 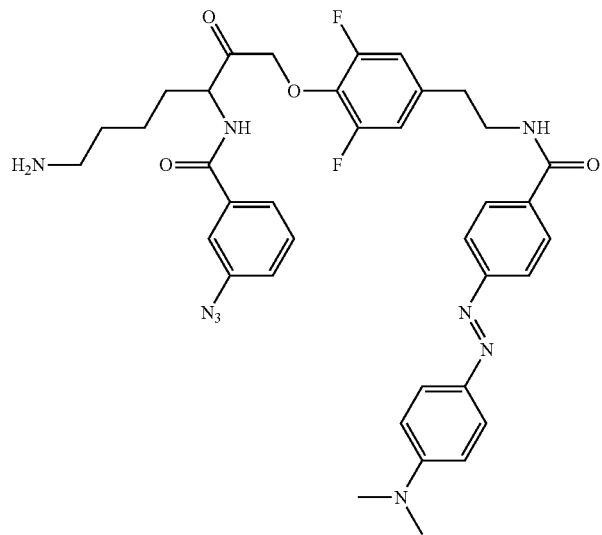 [SMILES: CN(C)c1ccc(/N=N/c2ccc(C(=O)NCCc3cc(F)c(OCC(=O)C(CCCCN)NC(=O)c4cccc(N=[N+]=[N-])c4)c(F)c3)cc2)cc1] |
| 47 | 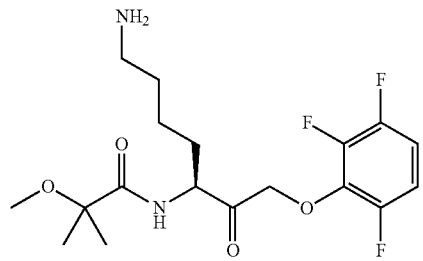 [SMILES: COC(C)(C)C(=O)N[C@@H](CCCCN)C(=O)COc1c(F)ccc(F)c1F] |

TABLE 1-continued
Lysine gingipain inhibitors.
| Compound No. | Compound Structure |
|---|---|
| 47a | 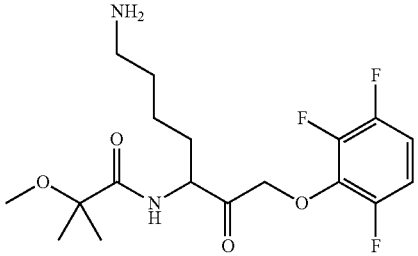 [SMILES: COC(C)(C)C(=O)NC(CCCCN)C(=O)COc1c(F)ccc(F)c1F] |
| 48 | 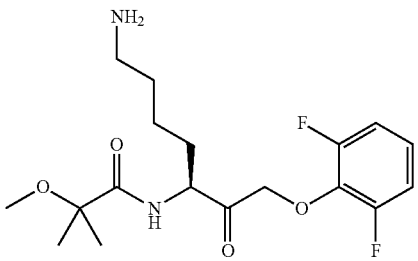 [SMILES: COC(C)(C)C(=O)N[C@@H](CCCCN)C(=O)COc1c(F)cccc1F] |
| 48a | 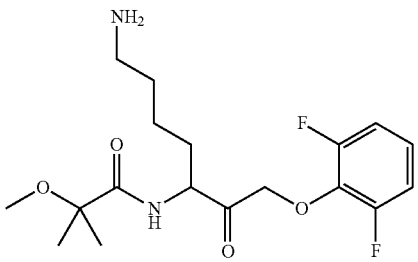 [SMILES: COC(C)(C)C(=O)NC(CCCCN)C(=O)COc1c(F)cccc1F] |
| 49 | 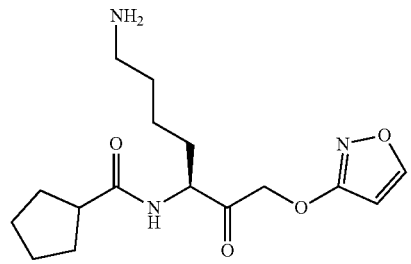 [SMILES: NCCCC[C@H](NC(=O)C1CCCC1)C(=O)COc1ccon1] |
| 49a | 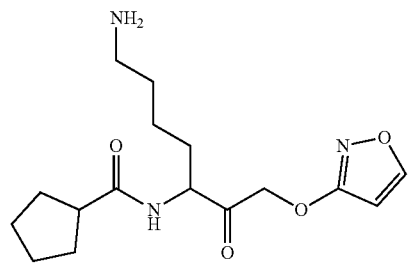 [SMILES: NCCCCC(NC(=O)C1CCCC1)C(=O)COc1ccon1] |

TABLE 1-continued

Lysine gingipain inhibitors.

| Compound No. | Compound Structure |
| --- | --- |
| 50 | 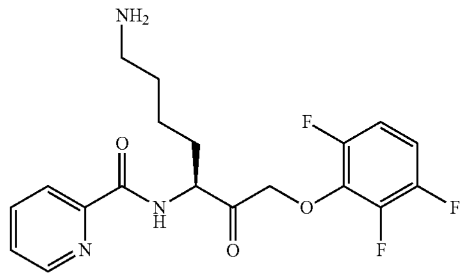 [SMILES: NCCCC[C@H](NC(=O)c1ccccn1)C(=O)COc1c(F)ccc(F)c1F] |
| 50a | 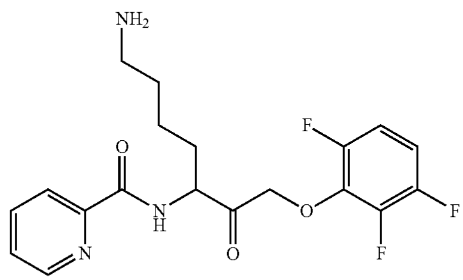 [SMILES: NCCCCC(NC(=O)c1ccccn1)C(=O)COc1c(F)ccc(F)c1F] |
| 51 | 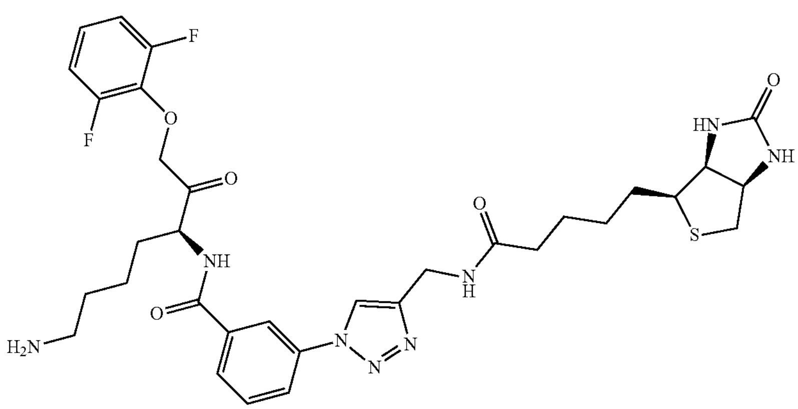 [SMILES: NCCCC[C@H](NC(=O)c1cccc(-n2cc(CNC(=O)CCCC[C@@H]3SC[C@@H]4NC(=O)N[C@@H]43)nn2)c1)C(=O)COc1c(F)cccc1F] |
| 51a | 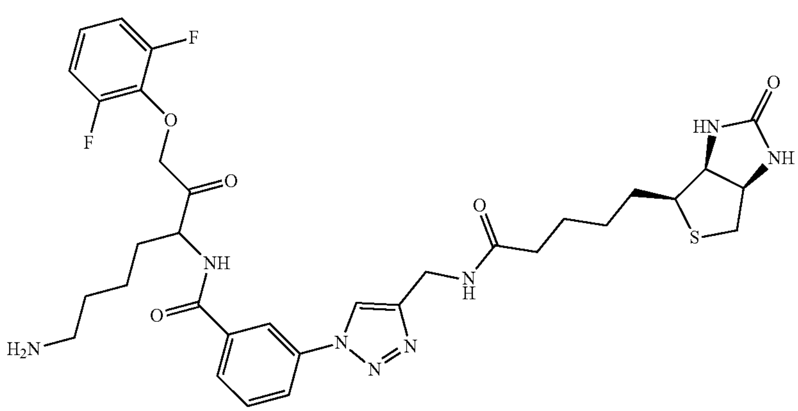 [SMILES: NCCCCC(NC(=O)c1cccc(-n2cc(CNC(=O)CCCC[C@@H]3SC[C@@H]4NC(=O)N[C@@H]43)nn2)c1)C(=O)COc1c(F)cccc1F] |

TABLE 1-continued
Lysine gingipain inhibitors.
| Compound No. | Compound Structure |
|---|---|
| 52 | 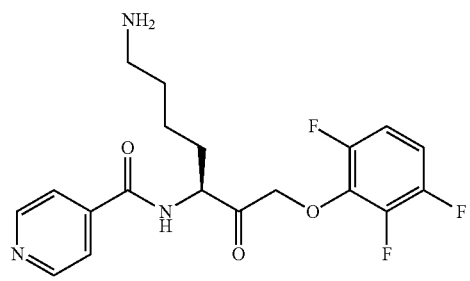 [SMILES: NCCCC[C@H](NC(=O)c1ccncc1)C(=O)COc1c(F)ccc(F)c1F] |
| 52a | 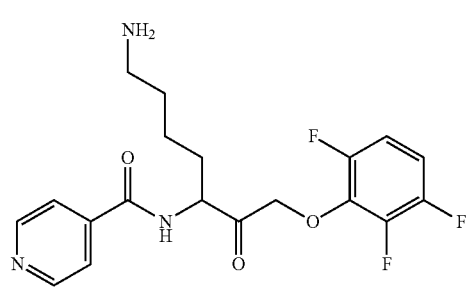 [SMILES: NCCCCC(NC(=O)c1ccncc1)C(=O)COc1c(F)ccc(F)c1F] |
| 53 | 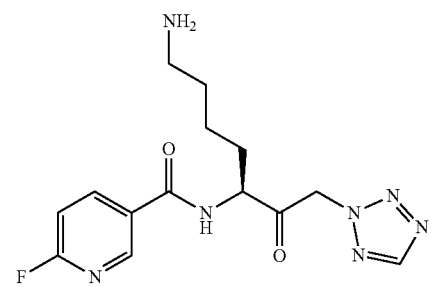 [SMILES: NCCCC[C@H](NC(=O)c1ccc(F)nc1)C(=O)Cn1ncnn1] |
| 53a | 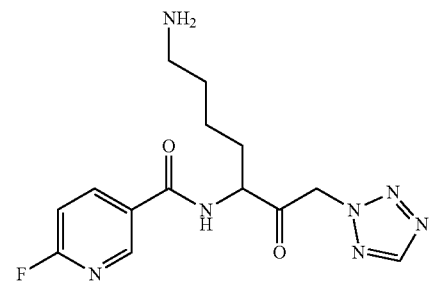 [SMILES: NCCCCC(NC(=O)c1ccc(F)nc1)C(=O)Cn1ncnn1] |
| 54 | 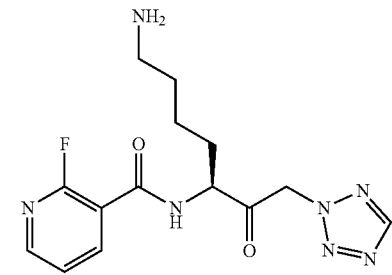 [SMILES: NCCCC[C@H](NC(=O)c1cccnc1F)C(=O)Cn1ncnn1] |

TABLE 1-continued
Lysine gingipain inhibitors.
| Compound No. | Compound Structure |
|---|---|
| 54a | 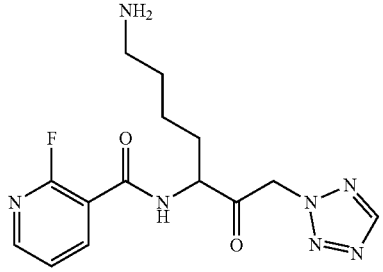 [SMILES: NCCCCC(NC(=O)c1cccnc1F)C(=O)Cn1ncnn1] |
| 55 | 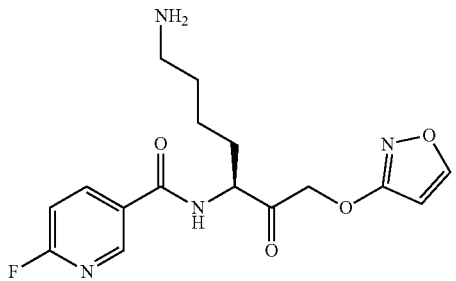 [SMILES: NCCCC[C@H](NC(=O)c1ccc(F)nc1)C(=O)COc1ccon1] |
| 55a | 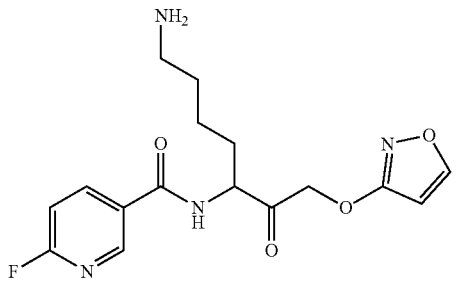 [SMILES: NCCCCC(NC(=O)c1ccc(F)nc1)C(=O)COc1ccon1] |
| 56 | 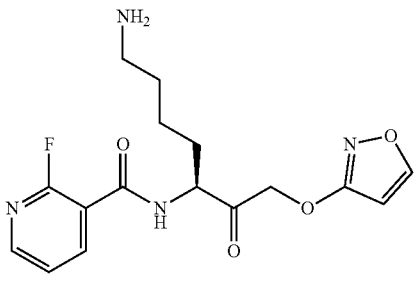 [SMILES: NCCCC[C@H](NC(=O)c1cccnc1F)C(=O)COc1ccon1] |
| 56a | 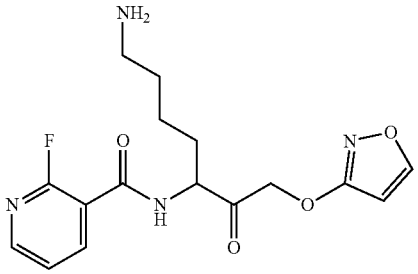 [SMILES: NCCCCC(NC(=O)c1cccnc1F)C(=O)COc1ccon1] |

TABLE 1-continued
Lysine gingipain inhibitors.
| Compound No. | Compound Structure |
|---|---|
| 57 | 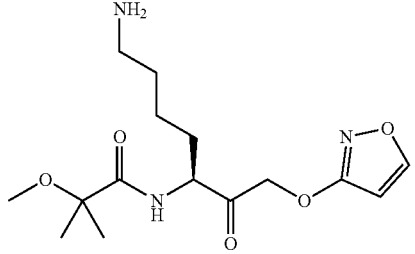 [SMILES: COC(C)(C)C(=O)N[C@@H](CCCCN)C(=O)COc1ccon1] |
| 57a | 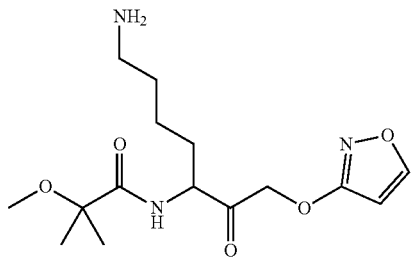 [SMILES: COC(C)(C)C(=O)NC(CCCCN)C(=O)COc1ccon1] |
| 58 | 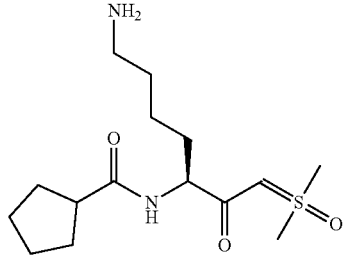 [SMILES: CS(C)(=O)=CC(=O)[C@H](CCCCN)NC(=O)C1CCCC1] |
| 58a | 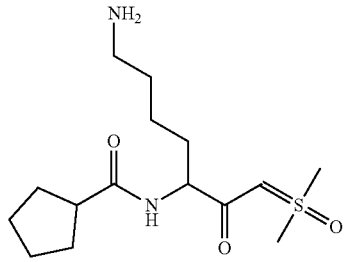 [SMILES: CS(C)(=O)=CC(=O)C(CCCCN)NC(=O)C1CCCC1] |
| 59 | 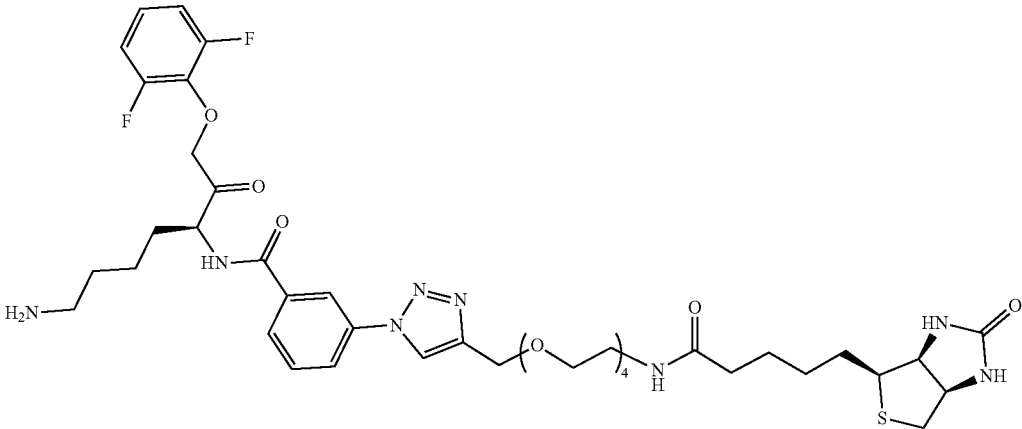 |

US 10,730,826 B2
TABLE 1-continued
Lysine gingipain inhibitors.
| Compound No. | Compound Structure |
|---|---|
| 59a | 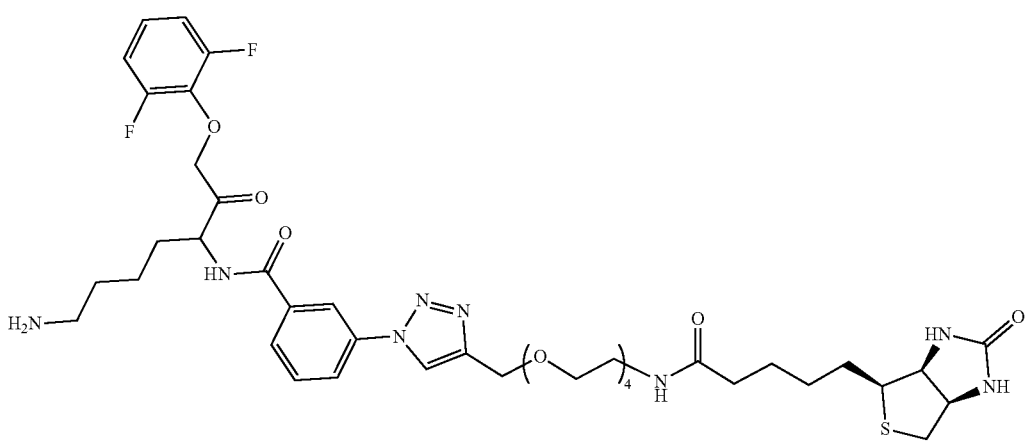 |
| 60 | 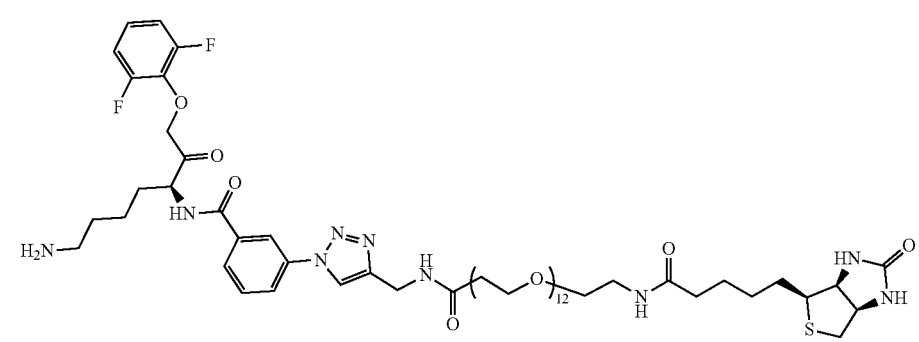 |
| 60a | 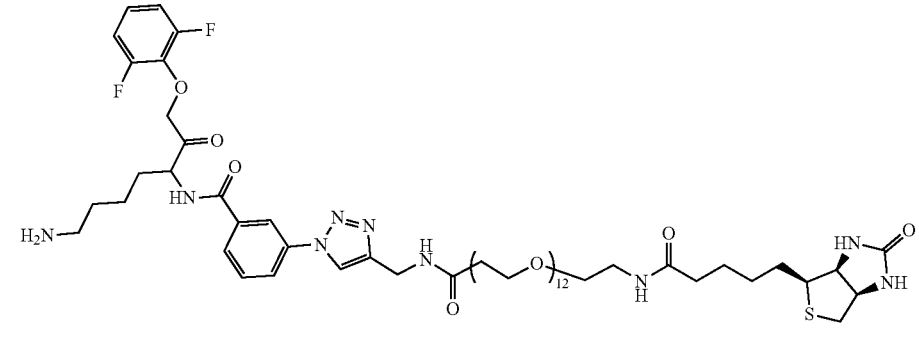 |
| 61 | 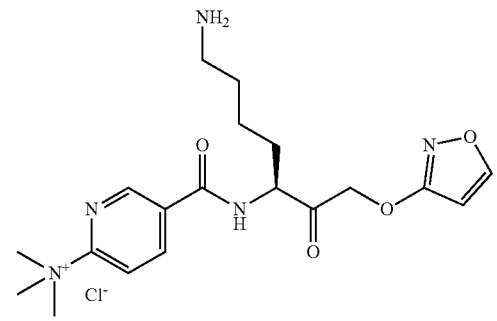 [SMILES: C[N+](C)(C)c1ccc(C(=O)N[C@@H](CCCCN)C(=O)COc2ccon2)cn1 ; [Cl-]] |

TABLE 1-continued
Lysine gingipain inhibitors.
| Compound No. | Compound Structure |
|---|---|
| 61a | 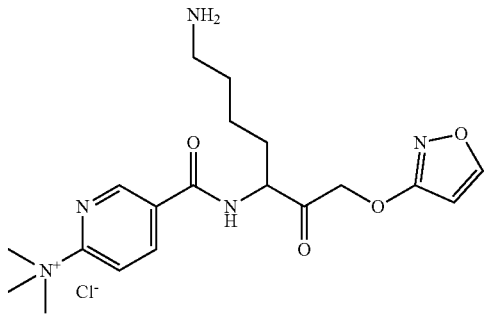 [SMILES: C[N+](C)(C)c1ccc(C(=O)NC(CCCCN)C(=O)COc2ccon2)cn1 ; [Cl-]] |
| 62 | 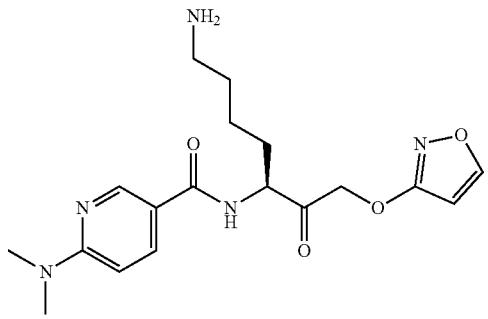 [SMILES: CN(C)c1ccc(C(=O)N[C@@H](CCCCN)C(=O)COc2ccon2)cn1] |
| 62a | 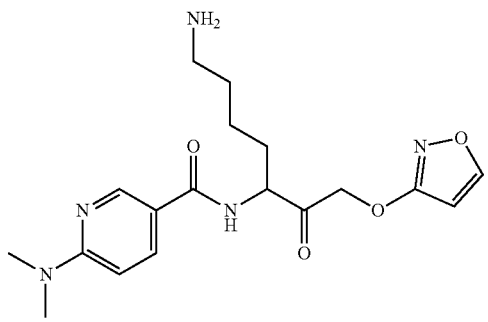 [SMILES: CN(C)c1ccc(C(=O)NC(CCCCN)C(=O)COc2ccon2)cn1] |
| 63 | 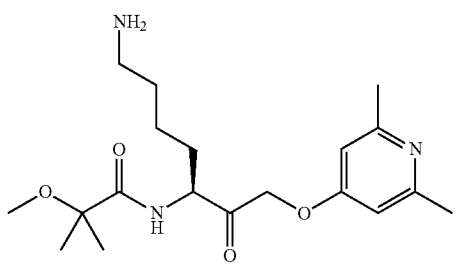 |
| 63a | 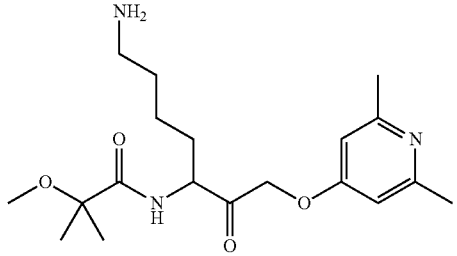 |

TABLE 1-continued

Lysine gingipain inhibitors.

| Compound No. | Compound Structure |
|---|---|
| 64 | 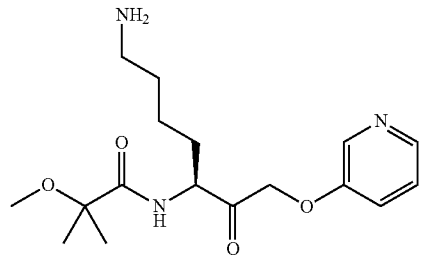 [SMILES: COC(C)(C)C(=O)N[C@@H](CCCCN)C(=O)COc1cccnc1] |
| 64a | 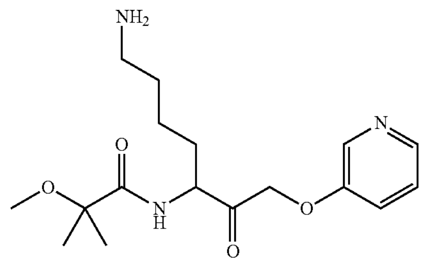 [SMILES: COC(C)(C)C(=O)NC(CCCCN)C(=O)COc1cccnc1] |
| 65 | 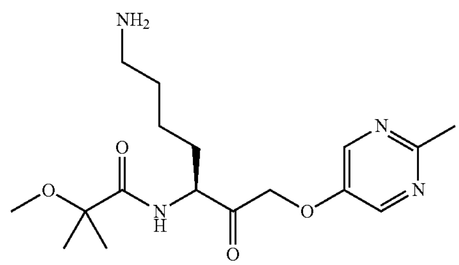 |
| 65a | 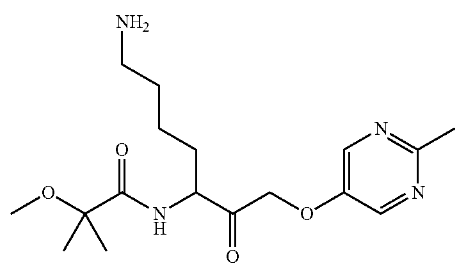 |
| 66 | 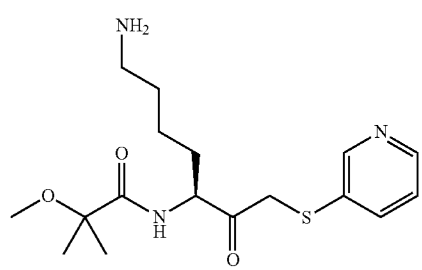 |

TABLE 1-continued
Lysine gingipain inhibitors.
| Compound No. | Compound Structure |
| --- | --- |
| 66a | 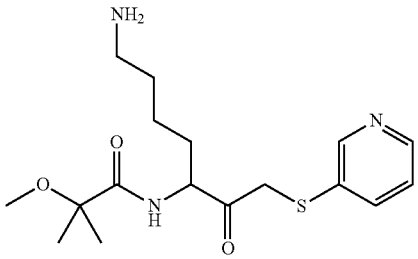 [SMILES: COC(C)(C)C(=O)NC(CCCCN)C(=O)CSc1cccnc1] |
| 67 | 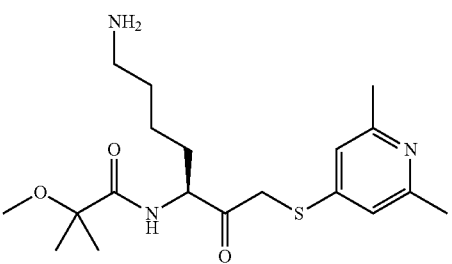 |
| 67a | 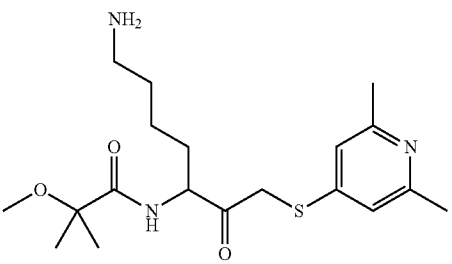 |
| 68 | 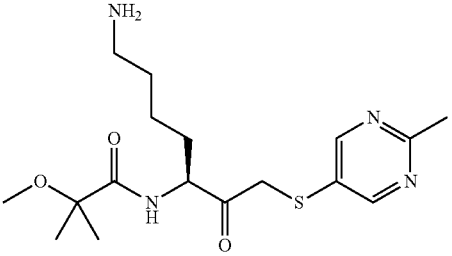 |
| 68a | 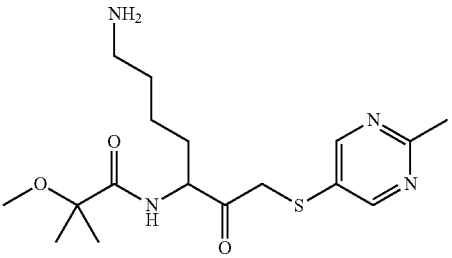 |

TABLE 1-continued
Lysine gingipain inhibitors.
| Compound No. | Compound Structure |
|---|---|
| 69 | 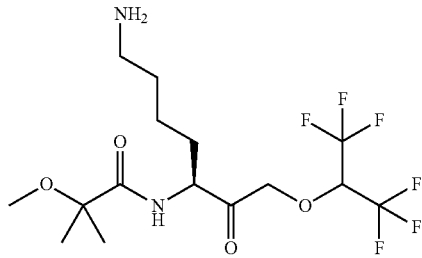 [SMILES: COC(C)(C)C(=O)N[C@@H](CCCCN)C(=O)COC(C(F)(F)F)C(F)(F)F] |
| 69a | 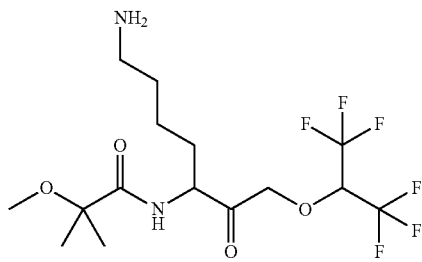 [SMILES: COC(C)(C)C(=O)NC(CCCCN)C(=O)COC(C(F)(F)F)C(F)(F)F] |
| 70 | 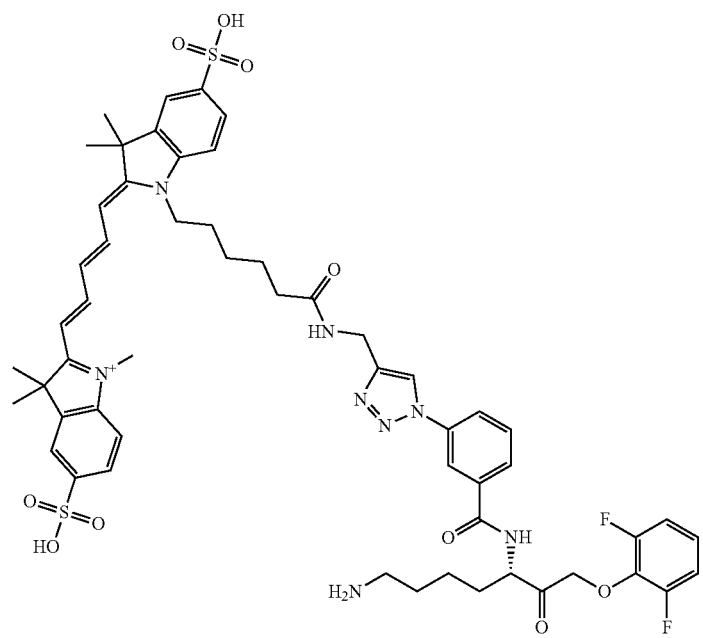 [SMILES: C[N+]1=C(/C=C/C=C/C=C2\N(CCCCCC(=O)NCc3cn(-c4cccc(C(=O)N[C@@H](CCCCN)C(=O)COc5c(F)cccc5F)c4)nn3)c3ccc(S(=O)(=O)O)cc3C2(C)C)C(C)(C)c2cc(S(=O)(=O)O)ccc21] |

TABLE 1-continued
Lysine gingipain inhibitors.
| Compound No. | Compound Structure |
|---|---|
| 70a | 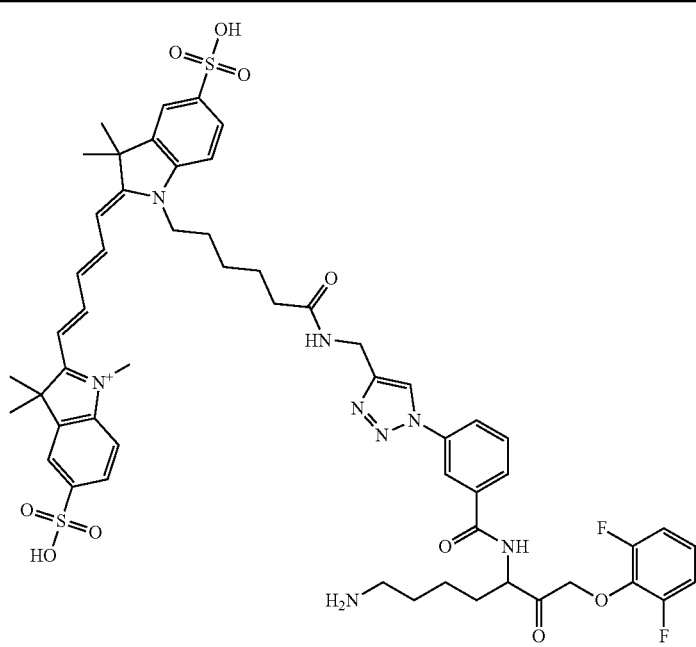 |
| 71 | 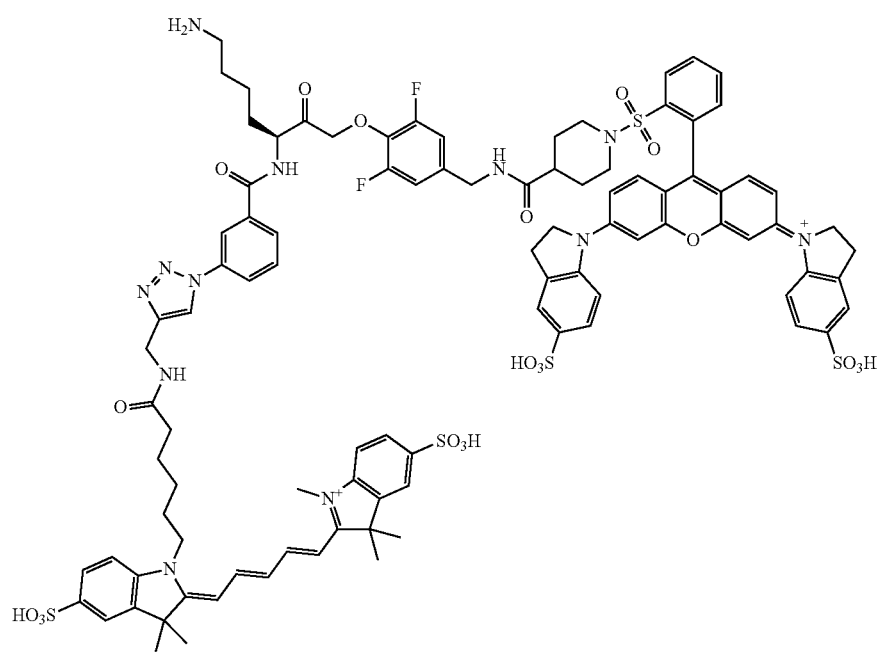 |

TABLE 1-continued
Lysine gingipain inhibitors.
| Compound No. | Compound Structure |
|---|---|
| 71a | 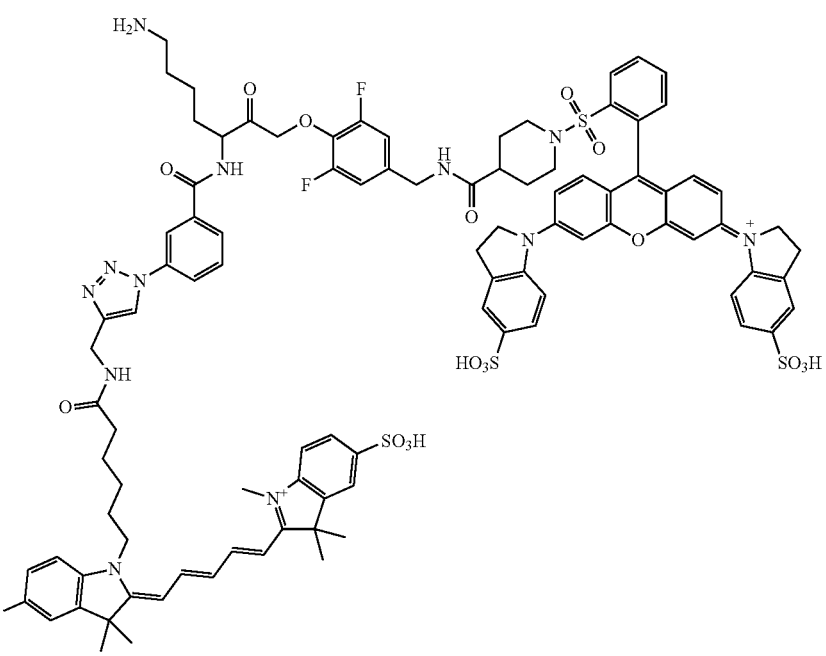 |
| 72 | 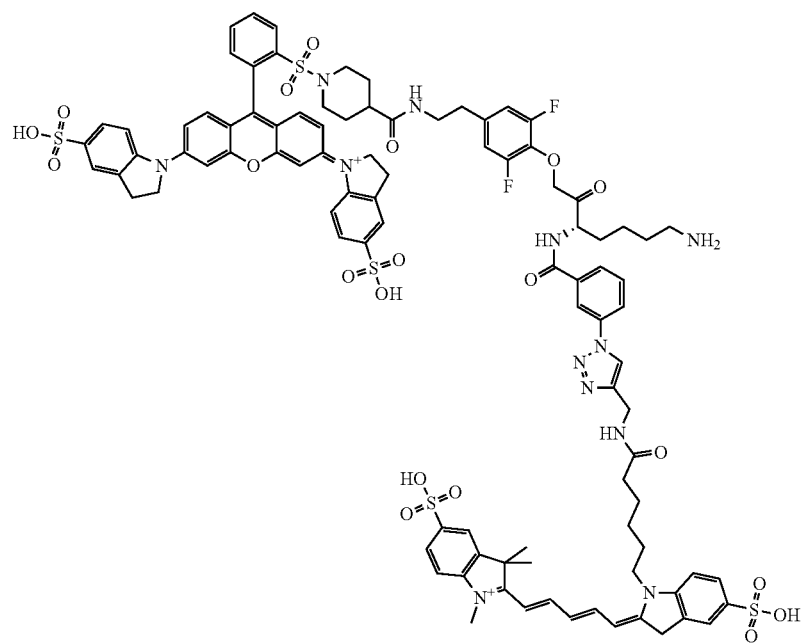 [SMILES: C[N+]1=C(/C=C/C=C/C=C2/Cc3cc(S(=O)(=O)O)ccc3N2CCCCCC(=O)NCc2cn(-c3cccc(C(=O)N[C@@H](CCCCN)C(=O)COc4c(F)cc(CCNC(=O)C5CCN(S(=O)(=O)c6ccccc6-c6c7cc/c(=[N+]8\CCc9cc(S(=O)(=O)O)ccc98)cc-7oc7cc(N8CCc9cc(S(=O)(=O)O)ccc98)ccc67)CC5)cc4F)c3)nn2)C(C)(C)c2cc(S(=O)(=O)O)ccc21] |

TABLE 1-continued
Lysine gingipain inhibitors.
| Compound No. | Compound Structure |
|---|---|
| 72a | 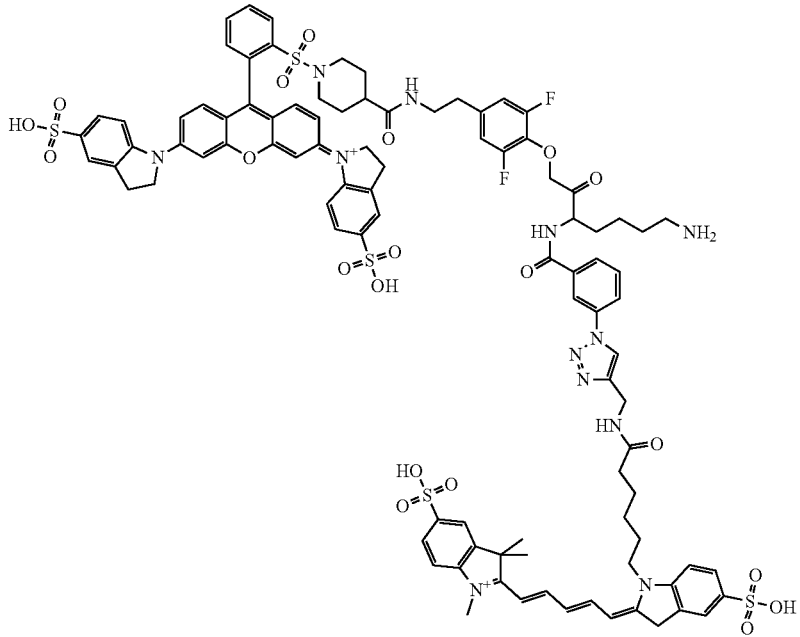 [SMILES: C[N+]1=C(/C=C/C=C/C=C2/Cc3cc(S(=O)(=O)O)ccc3N2CCCCCC(=O)NCc2cn(-c3cccc(C(=O)NC(CCCCN)C(=O)COc4c(F)cc(CCNC(=O)C5CCN(S(=O)(=O)c6ccccc6-c6c7cc/c(=[N+]8\CCc9cc(S(=O)(=O)O)ccc98)cc-7oc7cc(N8CCc9cc(S(=O)(=O)O)ccc98)ccc67)CC5)cc4F)c3)nn2)C(C)(C)c2cc(S(=O)(=O)O)ccc21] |
In some embodiments, the compound is selected from:
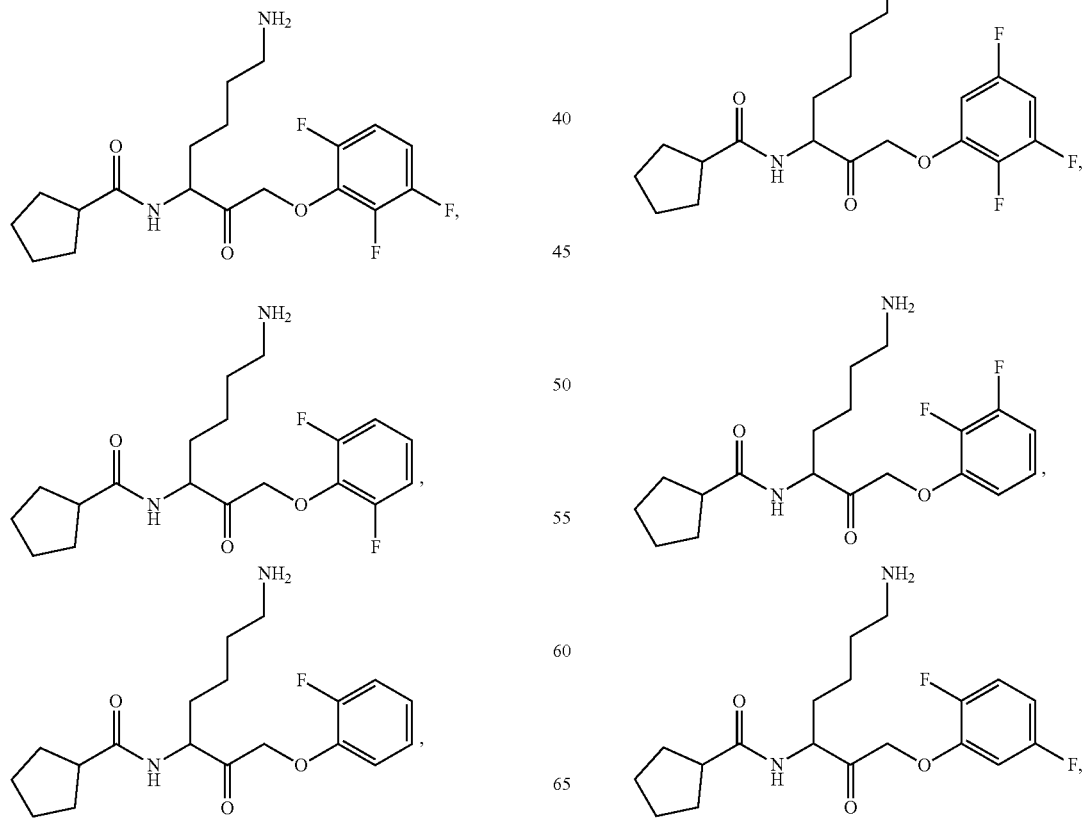

87
-continued
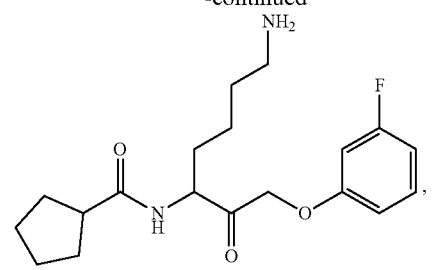
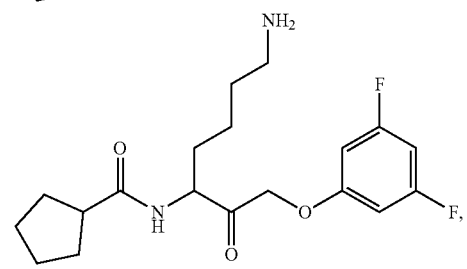
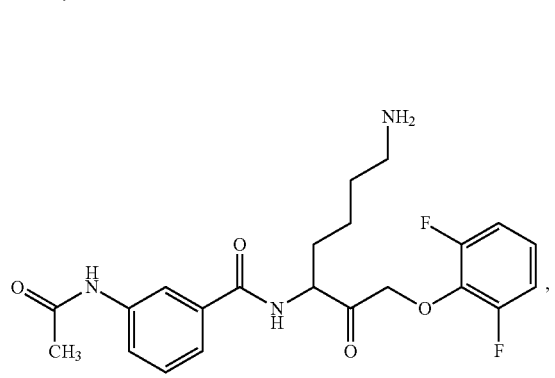
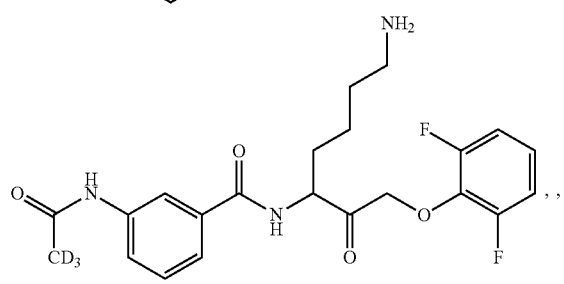
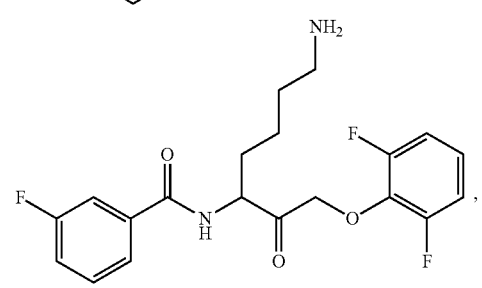
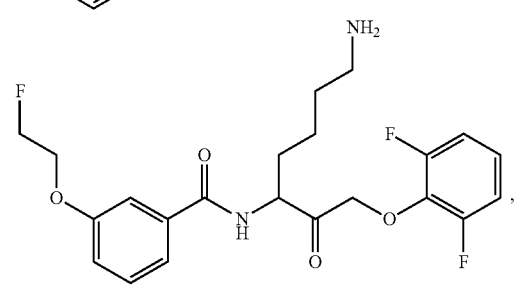
88
-continued
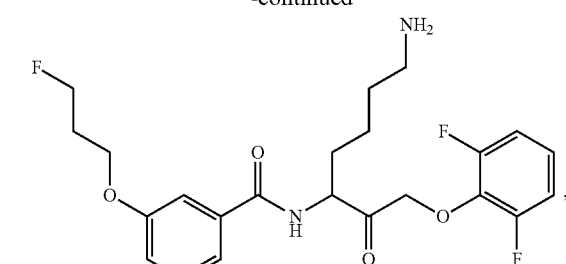
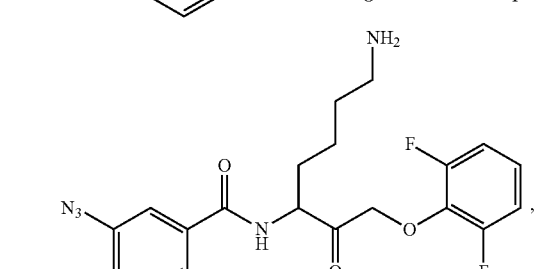
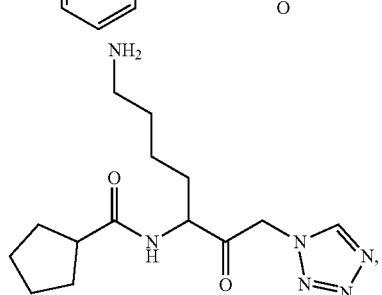
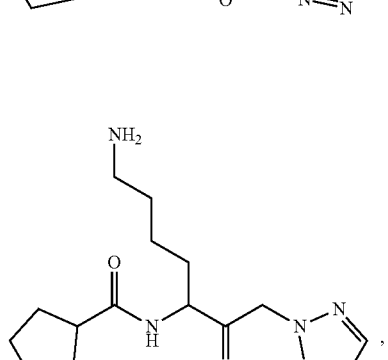
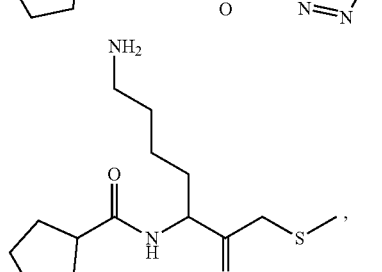
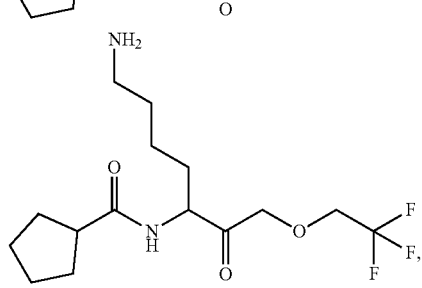

89
-continued
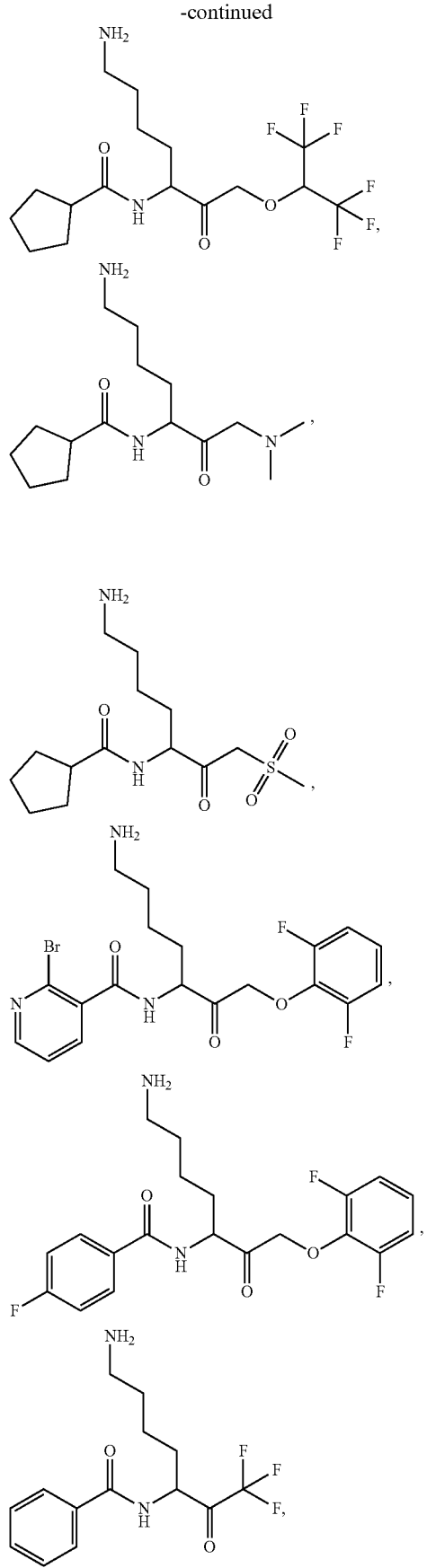
90
-continued
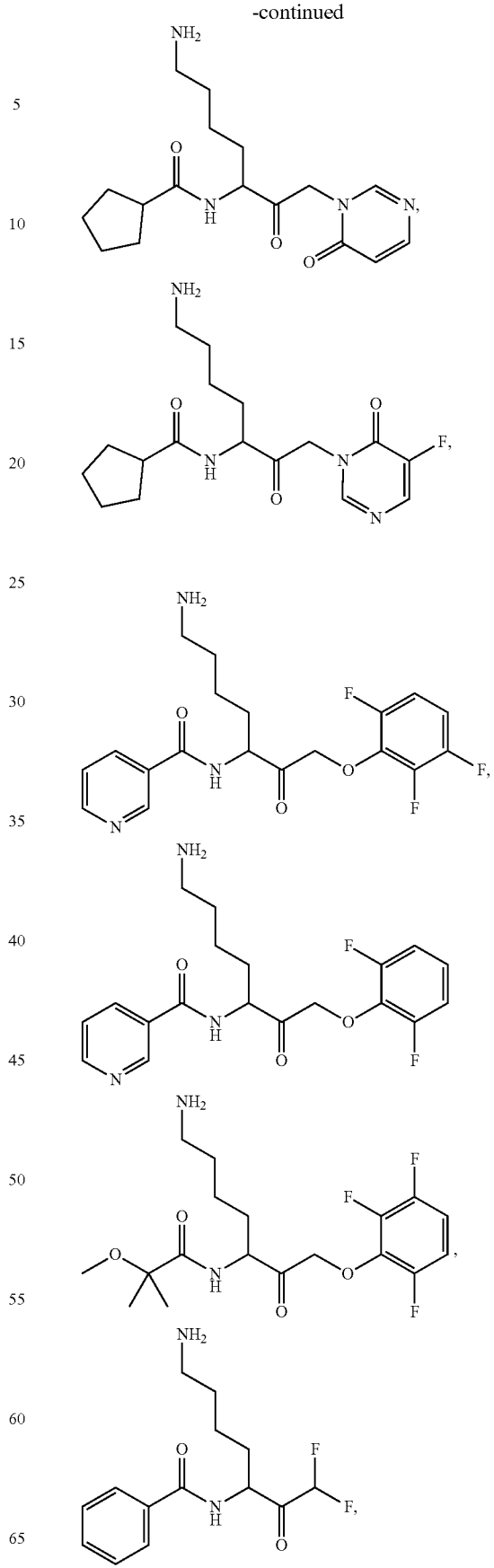

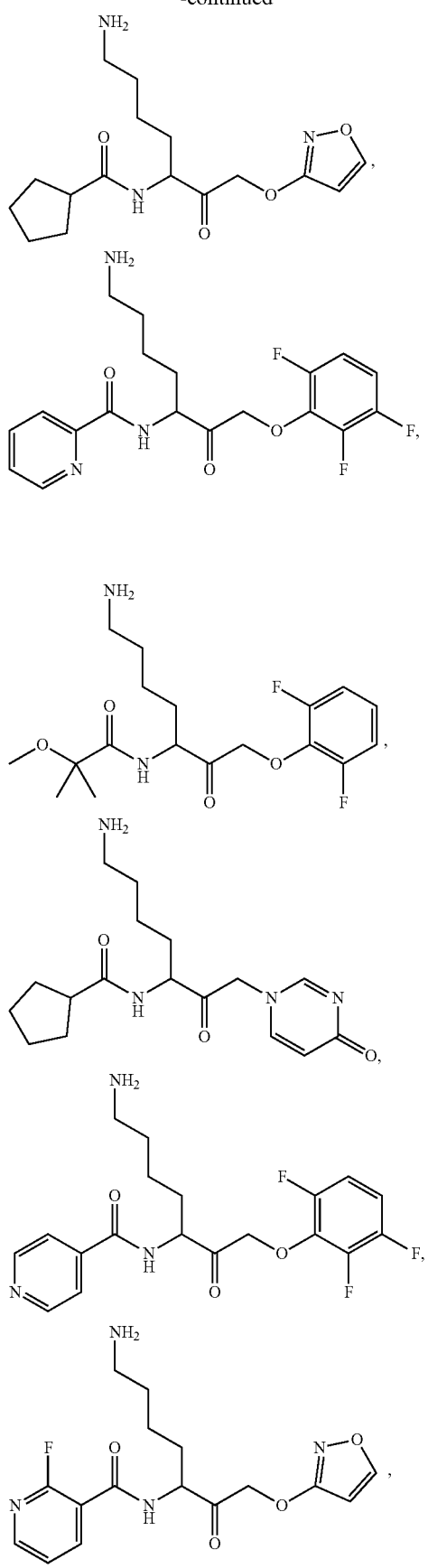
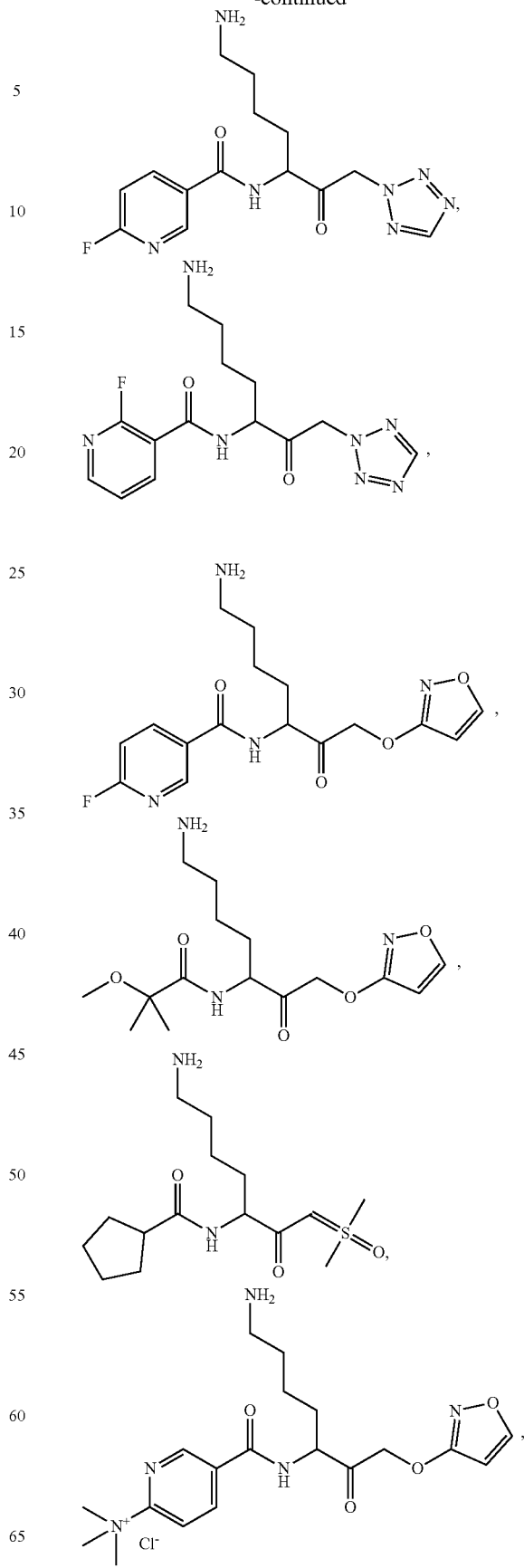

93
-continued
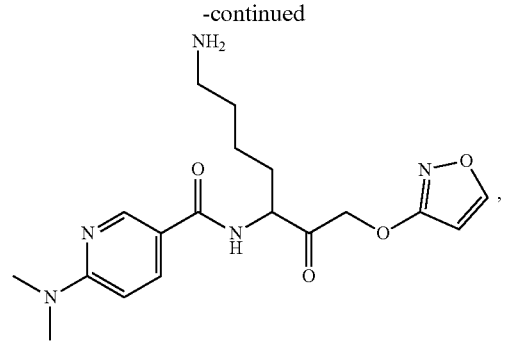
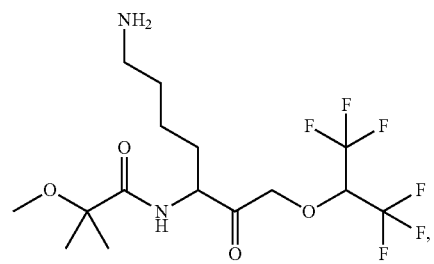
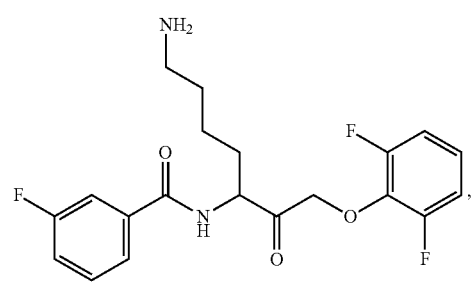
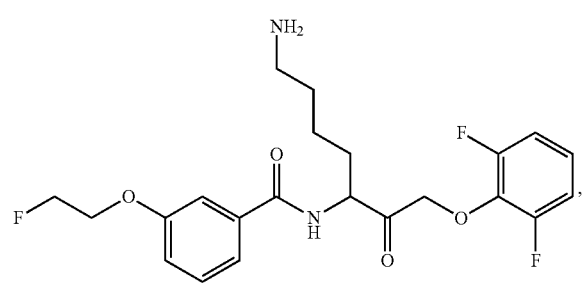
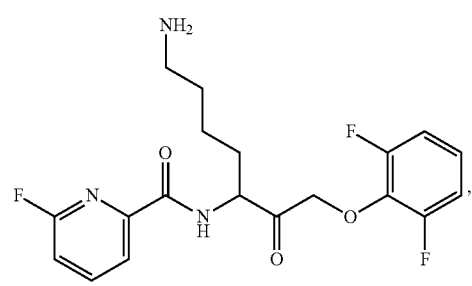
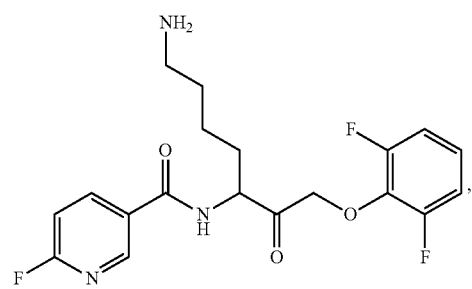
94
-continued
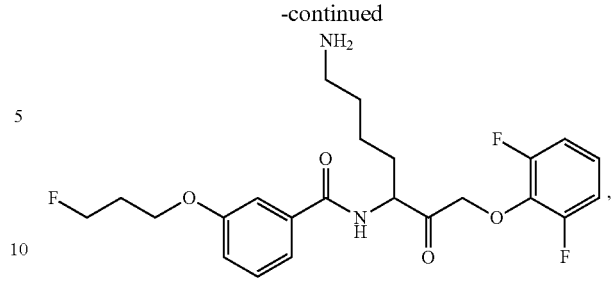
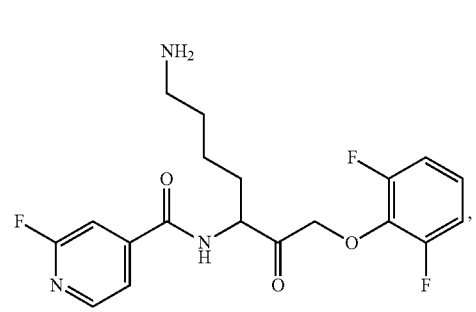
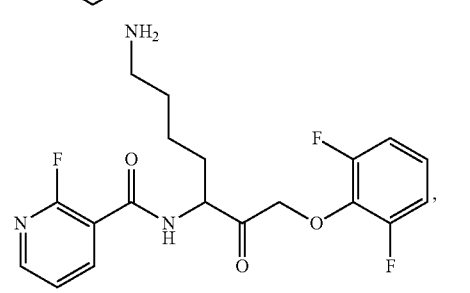
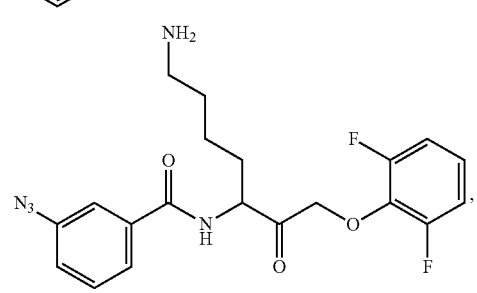
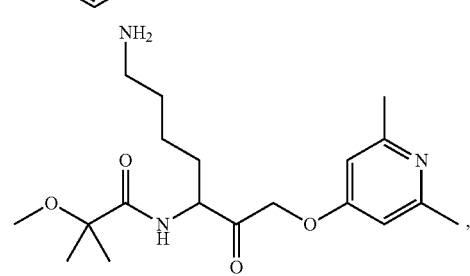
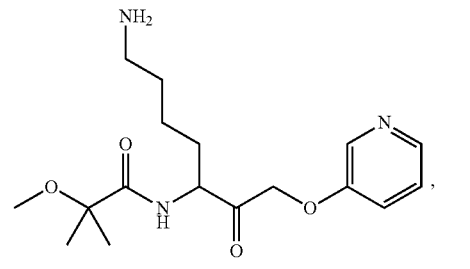

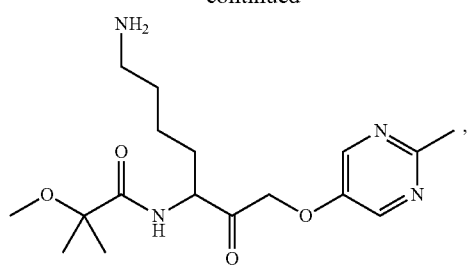
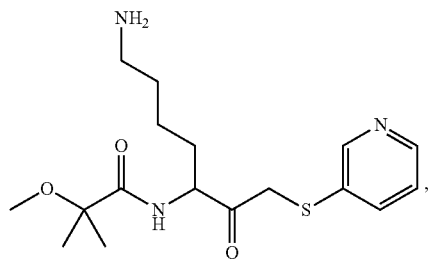
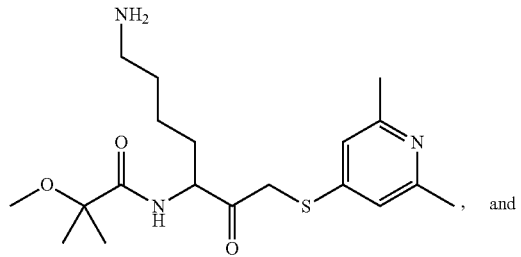, and
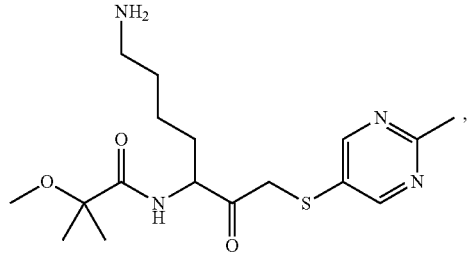
and pharmaceutically acceptable salts thereof.
In some embodiments, the compound is selected from:
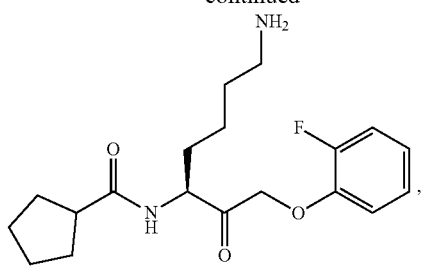
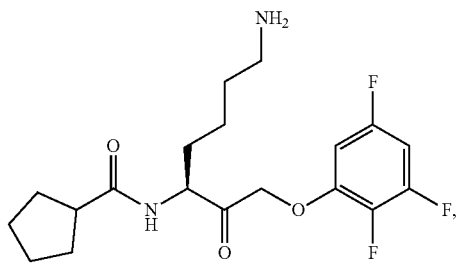
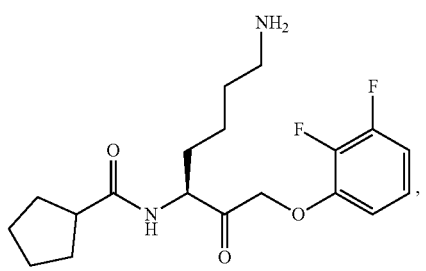
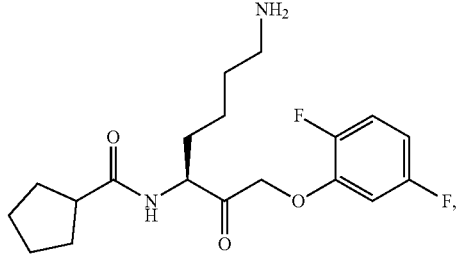
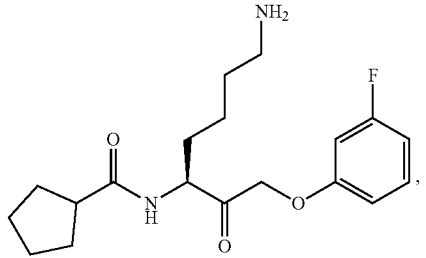
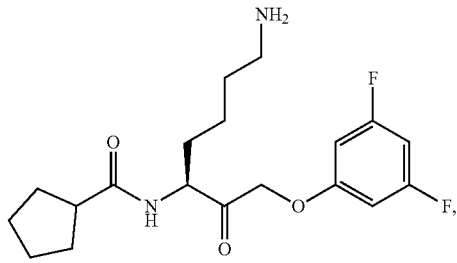

97
-continued
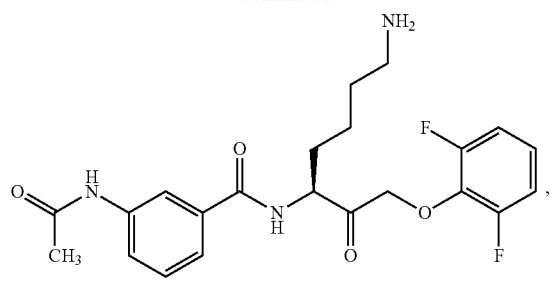
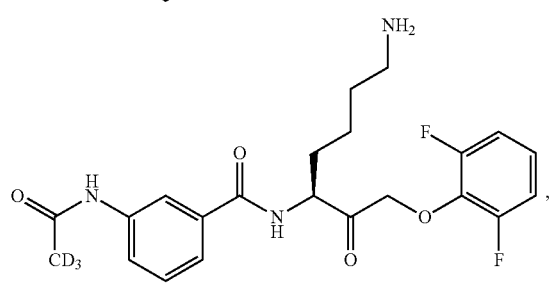
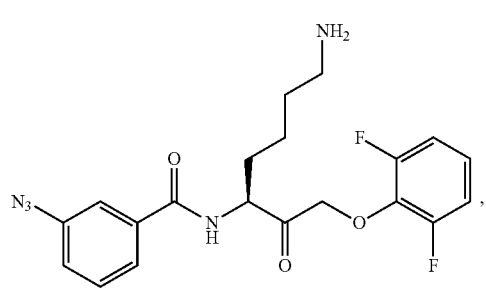
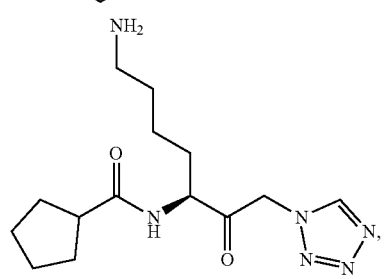
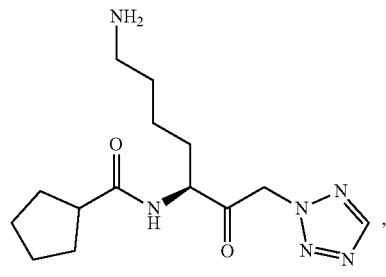
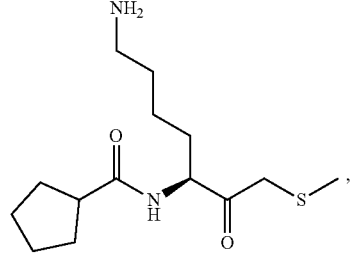
98
-continued
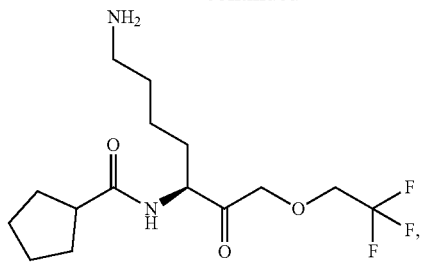
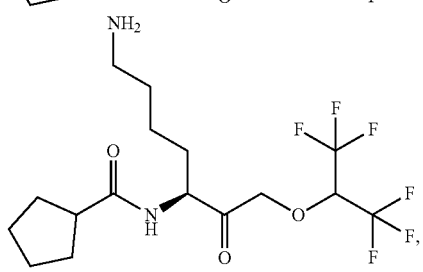
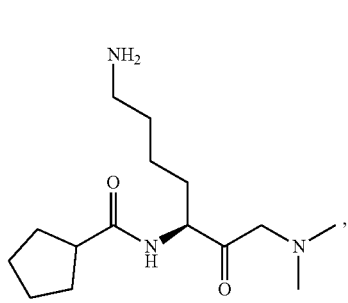
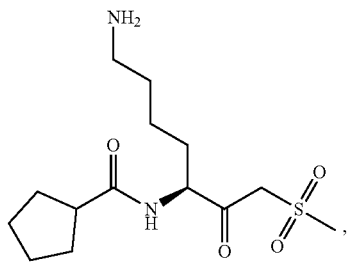
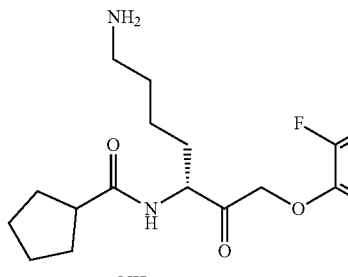
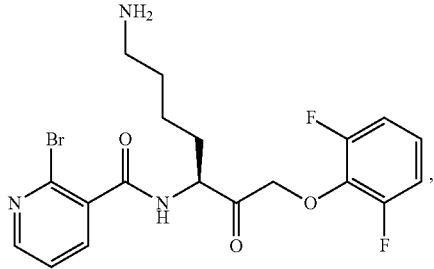

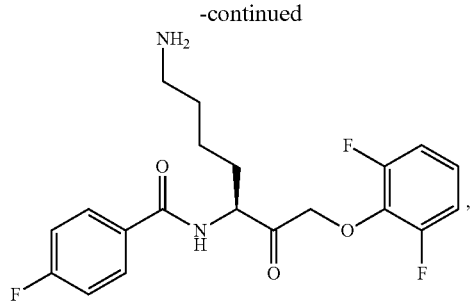
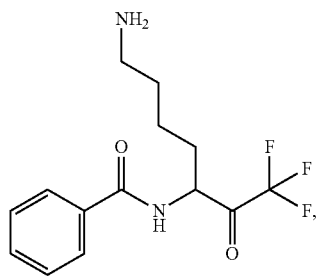
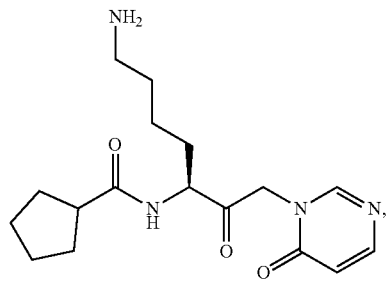
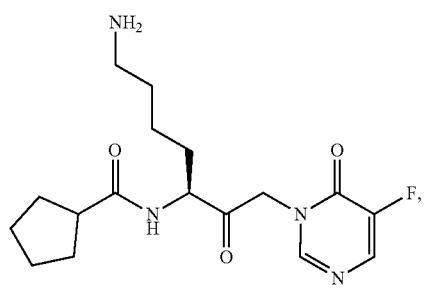
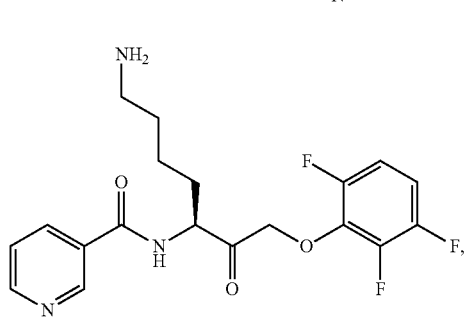
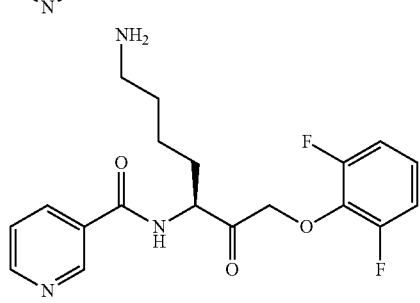
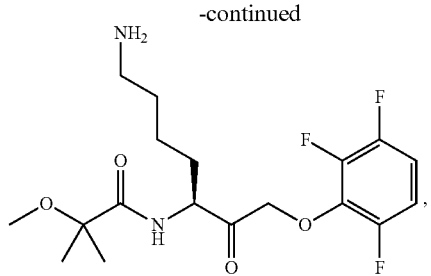
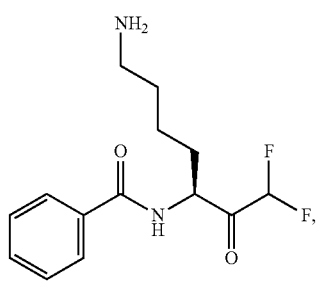
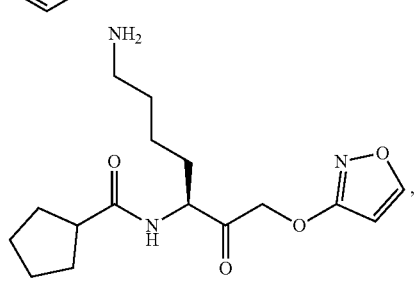
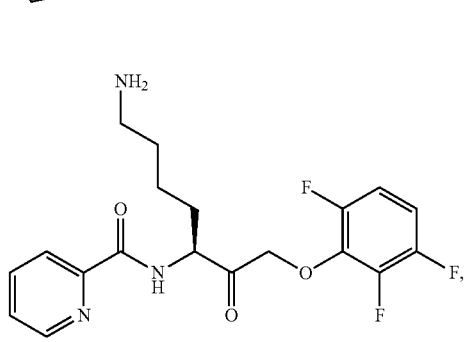
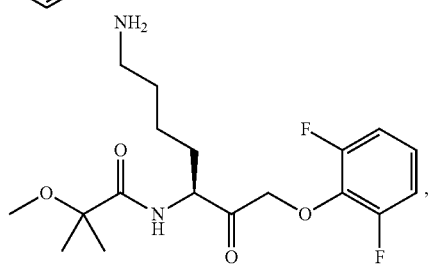
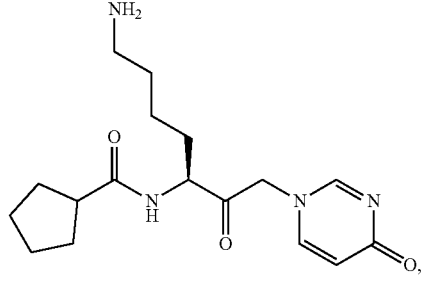

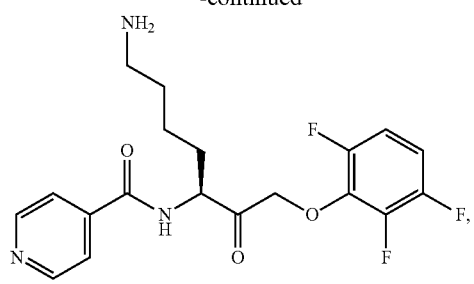
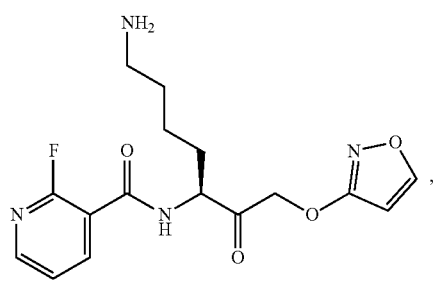
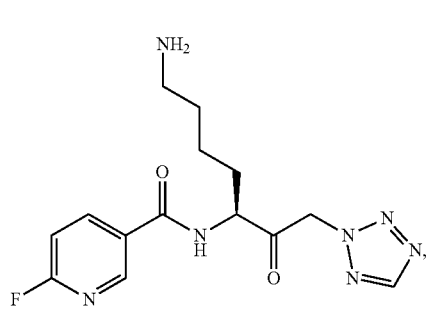
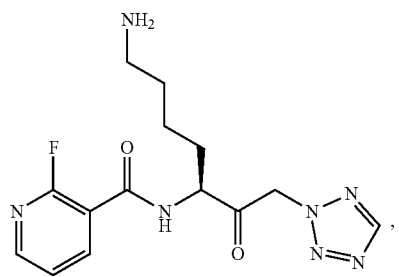
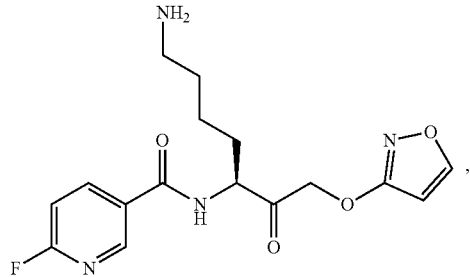
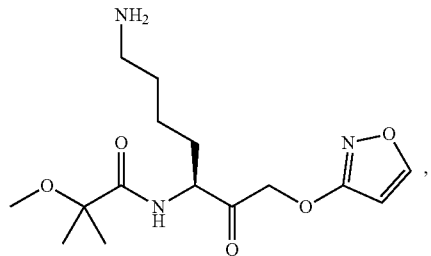
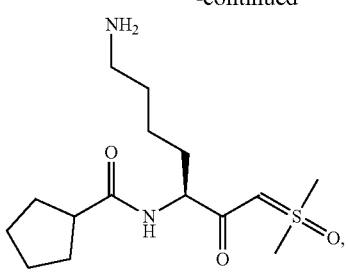
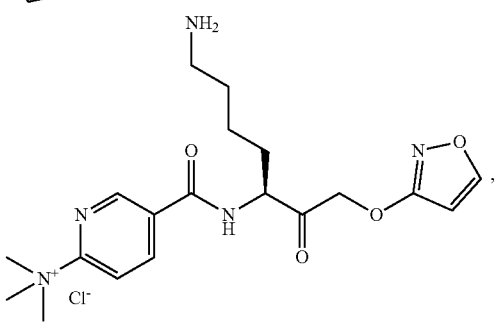
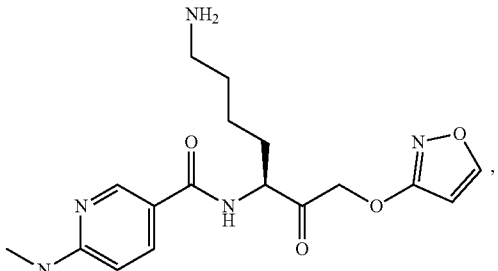
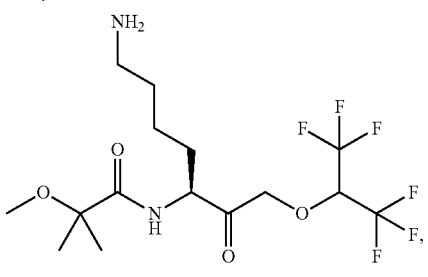
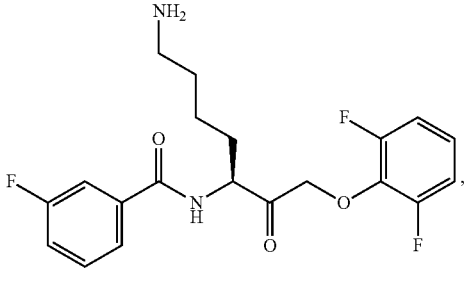
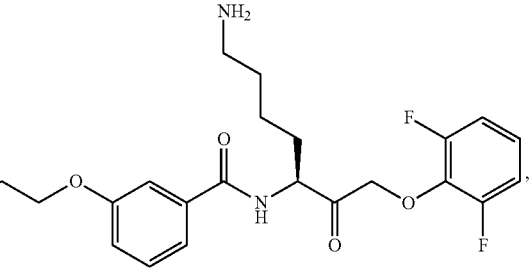

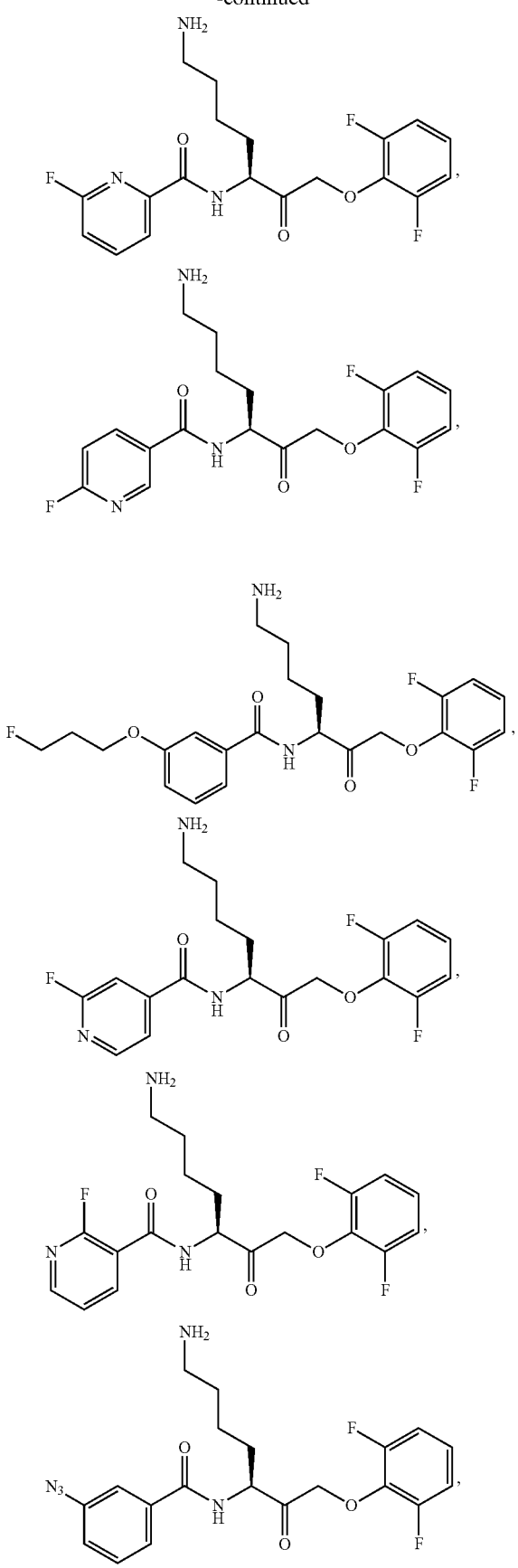
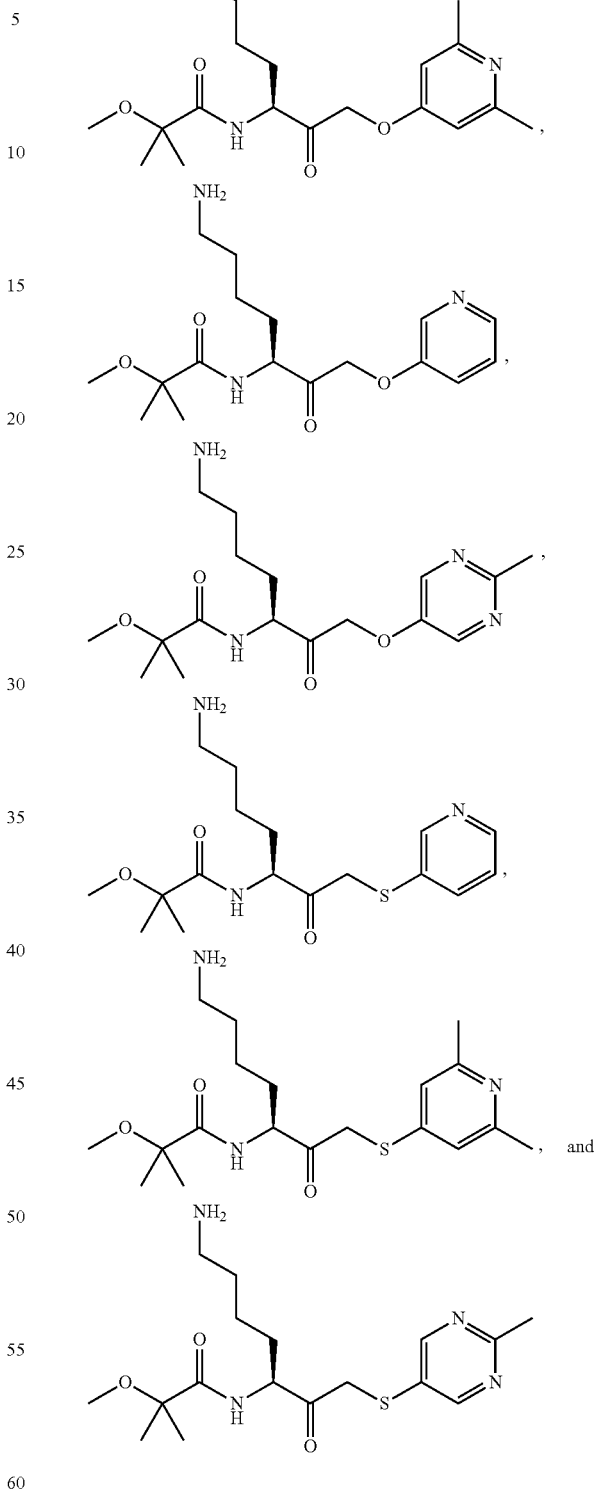
and pharmaceutically acceptable salts thereof.
The compounds described herein and methods of using them encompass the preparation and use of therapeutically active enantiomers or diastereomers of the described compounds. All such enantiomers and diastereomers of these compounds are included in the scope of the invention. Such compounds can be used as mixtures (e.g., racemic mixtures) or as isolated enantiomers or diastereomers.

Compounds of the invention can be prepared so as to include radionuclides for use in diagnostic imaging application such as positron emission tomography (PET) and single-photon emission computed tomography (SPECT). For example, Kgp inhibitors as described herein can be prepared so as to include one or more radionuclides selected from oxygen-15 ($^{15}O$), nitrogen-13 ($^{13}N$), carbon-11 ($^{11}C$), iodine-131 ($^{131}I$), and fluorine-18 ($^{18}F$). Such radiolabeled compounds can be used for PET imaging. Compounds of the invention can also be prepared in deuterated form (i.e., having one or more deuterium atoms, $^{2}H$, in place of one more hydrogen atoms), tritiated form (i.e., having one or more tritium atoms, $^{3}H$, in place of one more hydrogen atoms), or $^{14}C$-labeled form (i.e., having one or more $^{14}C$ atoms in place of one more carbon atoms).

Compounds of the invention can be prepared using starting materials A1 as shown in Scheme 1. In A1, preferred $R^9$ and $R^{1c}$ groups can be manipulated using chemical conditions that do not affect the other. For example, $R^{1c}$=benzyl can be removed by hydrogen and a palladium-carbon catalyst, but $R^{1c}$ is not affected by trifluoroacetic acid, whereas $R^9$=t-butyl can be removed by trifluoroacetic acid, but $R^9$ is not affected by hydrogen and a palladium-carbon catalyst. Other appropriate, complimentary combinations of $R^9$ and $R^{1c}$ and methods for their selective modification are known in the art.

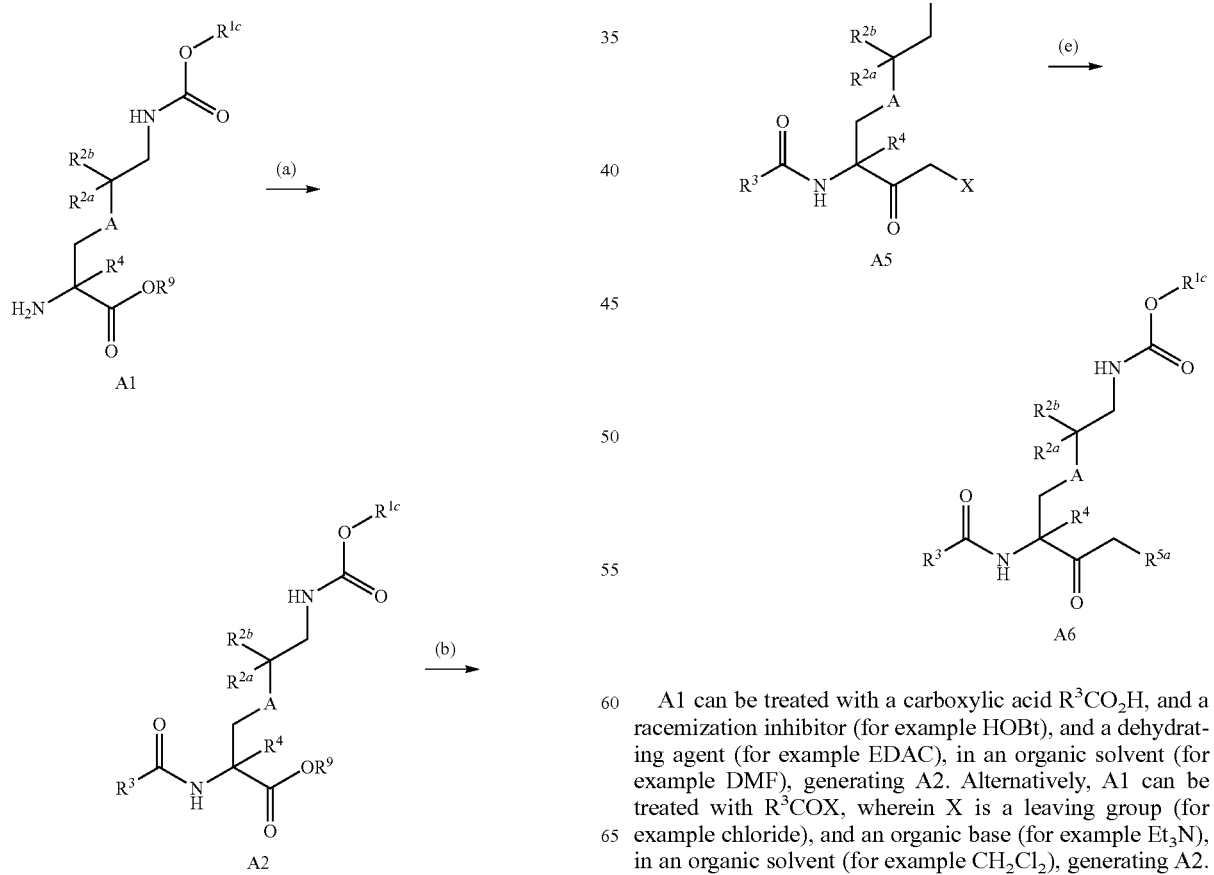

A1 can be treated with a carboxylic acid $R^3CO_2H$, and a racemization inhibitor (for example HOBt), and a dehydrating agent (for example EDAC), in an organic solvent (for example DMF), generating A2. Alternatively, A1 can be treated with $R^3COX$, wherein X is a leaving group (for example chloride), and an organic base (for example $Et_3N$), in an organic solvent (for example $CH_2Cl_2$), generating A2. A variety of applicable carboxylic acids ($R^3CO_2H$) and derivatives thereof (R³COX) are commercially available, or can be prepared according to known methods. R⁹ can be removed by appropriate chemical conditions generating A3. A3 can be reacted with a chloroformate (e.g., isobutyl chloroformate, ethyl chloroformate, and the like) followed by diazomethane to provide A4. A4 can be converted to A5 via treatment with a hydrohalic acid (i.e., HX wherein X is a halogen such as Cl, Br, or I). Displacement of the halide from A5 using a compound Rya-H (e.g., a halogenated phenol or a heteroaromatic compound) in the presence of a base can provide protected compound A6, which can be deprotected provide the product of Formula I. Alternatively, carboxylic acid A3 can be N-acylated and cyclized to afford the corresponding 5(4H)-oxazolone. The oxazolone can be further reacted with an anhydride of an α-fluorinated carboxylic acid (e.g., trifluoroacetic anhydride) to provide a C-acylated 5(4H)-oxazolone which is decarbonylated using oxalic acid to form compounds of Formula I wherein R⁵ is haloalkyl (see, Kolb, et al. *Liebigs. Ann. Chem.,* 1990, pp. 1-6; Kolb, et al. *Tet. Lett.* 1986, (27): pp. 1579-1582 and pp. 4437-4440).

Preparation of certain examples of Formula (I) will require initial preparation of unnatural amino acids that feature side-chains that are not present in any of the amino acids that occur in proteins. A wide variety of methods have been published for preparation of amino acids that feature unnatural side-chains, including the most useful and important methods F1-4 as summarized below.

Although not illustrated in F1-3, the amine and carboxylate groups are typically protected before application of these methods, and the protection is removed after construction of the unnatural side-chain. In F1, a natural side-chain (R) is modified to form an unnatural side-chain (R'). The natural amino acids serine, glutamic acid, and methionine would be especially for preparation of certain examples of Formulas (I) and (II). In F2, a metalated glycine derivative is treated with an alkylating agent (R'X) to install the unnatural side-chain (R'). In some instances, the metalated glycine derivative is generated by treating a glycine derivative with a strongly basic metalating agent (for example lithium diisopropylamide or potassium t-butoxide). In other instances, the starting glycine derivative is sufficiently acidic that a much

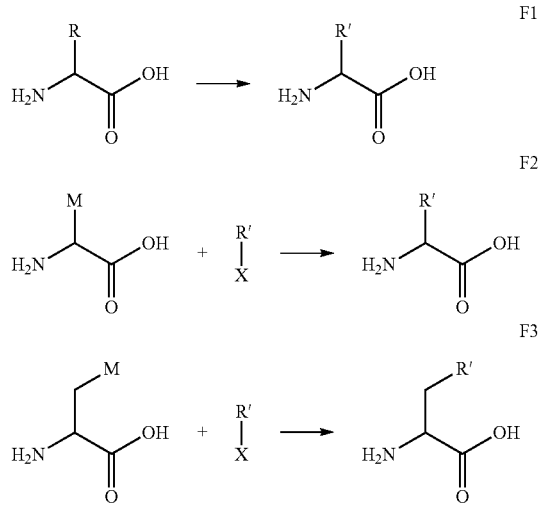

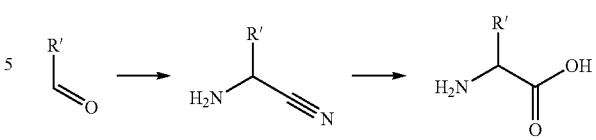

less basic metalating agent (for example potassium carbonate) is satisfactory. In the latter instances the metalated glycine derivative may exist as a dissociated ion pair, rather than as the covalently bonded species illustrated in F2. In F3, a metalated alanine derivative is treated with an alkylating agent (R'X) to install the unnatural side-chain (R'). In most instances, the metalated alanine derivative is generated by treating a halogenated alanine derivative with a low valent metal (for example zinc dust). In many instances, a soluble palladium catalyst is utilized to facilitate F3. In F4, an aldehyde (R'CHO) is reacted with a source of ammonia and a source of cyanide, to generate an amino-nitrile, which is subsequently hydrolyzed to generate an amino-acid featuring an unnatural sidechain (R').

Although not illustrated in F1-3, the amine and carboxylate groups are typically protected before application of these methods, and the protection is removed after construction of the unnatural side-chain. In F1, a natural side-chain (R) is modified to form an unnatural side-chain (R'). The natural amino acids serine, glutamic acid, and methionine would be especially for preparation of certain examples of Formulas (I) and (II). In F2, a metalated glycine derivative is treated with an alkylating agent (R'X) to install the unnatural side-chain (R'). In some instances, the metalated glycine derivative is generated by treating a glycine derivative with a strongly basic metalating agent (for example lithium diisopropylamide or potassium t-butoxide). In other instances, the starting glycine derivative is sufficiently acidic that a much less basic metalating agent (for example potassium carbonate) is satisfactory. In the latter instances the metalated glycine derivative may exist as a dissociated ion pair, rather than as the covalently bonded species illustrated in F2. In F3, a metalated alanine derivative is treated with an alkylating agent (R'X) to install the unnatural side-chain (R'). In most instances, the metalated alanine derivative is generated by treating a halogenated alanine derivative with a low valent metal (for example zinc dust). In many instances, a soluble palladium catalyst is utilized to facilitate F3. In F4, an aldehyde (R'CHO) is reacted with a source of ammonia and a source of cyanide, to generate an amino-nitrile, which is subsequently hydrolyzed to generate an amino-acid featuring an unnatural sidechain (R').

After application of appropriate methods to prepare amino acids that feature unnatural sidechains, these amino acids can be appropriately protected, as described above, and then appropriate methods can be applied to generate intermediates and products wherein the lysine side-chain has been replaced with an unnatural side-chain. Thus, suitable methods are available to provide the variations of $CH_2AC(R^{2a})(R^{2b})CH_2N(R^{1a})(R^{1b})$ that are specified for Formula (I).

IV. Pharmaceutical Compositions and Administration of Lysine Gingipain Inhibitors In a related aspect, the invention provides a pharmaceutical composition comprising a compound of Formula I and a pharmaceutically acceptable excipient.

The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

Pharmaceutical compositions containing compounds of the invention can be formulated for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semipermeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

Kgp inhibitors can also be administered topically as a solution, ointment, cream, gel, or suspension, as well as in mouth washes, eye-drops, and the like. Still further, transdermal delivery of Kgp inhibitors can be accomplished by means of iontophoretic patches and the like.

Pharmaceutical compositions containing Kgp inhibitors can also be in the form of a sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butane diol. In addition, sterile, fixed oils can be used as a solvent or suspending medium. For this purpose any bland fixed oil can be employed including synthetic monoglycerides, diglycerides, or triglycerides.

In some embodiments, a Kgp inhibitor can be formulated with a polymer such as Pluronic F127 and delivered subcutaneously. Pluronic is a hydrogel that solidifies at body temperature and can provide extended drug delivery over periods of time lasting from days to weeks.

Aqueous suspensions can contain one or more Kgp inhibitors in admixture with excipients including, but not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate. Dispersible powders and granules (suitable for preparation of an aqueous suspension by the addition of water) can contain one or more Kgp inhibitors in admixture with a dispersing agent, wetting agent, suspending agent, or combinations thereof. Oily suspensions can be formulated by suspending an Kgp inhibitor in a vegetable oil (e.g., arachis oil, olive oil, sesame oil or coconut oil), or in a mineral oil (e.g., liquid paraffin). Oily suspensions can contain one or more thickening agents, for example beeswax, hard paraffin, or cetyl alcohol. These compositions can be preserved by the addition of an anti-oxidant such as ascorbic acid.

The pharmaceutical compositions of the invention can also be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

The use of hybrid molecules to promote active transport or nanoparticles can be used in certain embodiments to increase blood brain barrier transport. For example liposomes, proteins, engineered peptide compounds or antibodies that bind to the receptors that transport proteins across the blood brain barrier including LPR-1 receptor, transferrin receptor, EGF-like growth factor or glutathione transporter can be used to increase penetration into the brain. Physical techniques including osmotic opening, ultrasound, lasers, sphenopalantine ganglion stimulation, direct intracranial, intrathecal, or intraventricular delivery via a pump can be used.

Pharmaceutical compositions according to the invention can also include one or more additional active agents useful in the treatment of conditions associated with $P.$ $gingivalis$ infection. In certain embodiments, the invention provides a pharmaceutical composition comprising one or more Kgp inhibitors as described herein in combination with one or more additional active agents for treatment of Alzheimer's disease. Several therapeutics are in development and in clinical use for treatment of Alzheimer's disease. Therapeutic strategies include lowering circulating levels of β-amyloid and tau (as described in more detail below), stabilizing microtubules, removing atherosclerotic plaques, modulating autophagy, modulating neurotransmitter levels, and inhibiting GABA(A) α5 receptors. Such therapeutics can maintain and/or restore cognitive function in subjects with Alzheimer's disease; slow the decline of cognitive function; and promote neuroplasticity and recovery of the brain.

Active agents that can be combined with Kgp inhibitors in pharmaceutical compositions include, but are not limited to, antibiotics (i.e., bacteriocidal compounds and bacteriostatic compounds), cholinesterase inhibitors, alpha-7 nicotinic receptor modulators, serotonin modulators, NMDA modulators, Aβ-targeted therapies, ApoE-targeted therapies, microglia-targeted therapies, blood/brain barrier-targeted therapies, tau-targeted therapies, complement-targeted therapies, and anti-inflammatories.

Any suitable antibiotic can be combined with one or more Kgp inhibitors in the pharmaceutical compositions of the invention. In certain embodiments, the invention provides a pharmaceutical composition containing one more Kgp inhibitors and an antibiotic having a P. gingivalis $MIC_{50}$ of less than 25 µg/ml. For example, the P. gingivalis $MIC_{50}$ of the antibiotic can be less than 20 µg/ml, less than 15 µg/ml, less than 10 µg/ml, less than 8 µg/ml, less than 6 µg/ml, or less than 5 µg/ml. In some embodiments, the P. gingivalis $MIC_{50}$ of the antibiotic is less than 1 µg/ml. In some embodiments, the P. gingivalis $MIC_{50}$ of the antibiotic is less than 0.2 µg/ml.

Examples of bacteriocidal and bacteriostatic compounds include, but are not limited to: quinolones (e.g., moxifloxacin, gemifloxacin, ciprofloxacin, oflaxacin, trovafloxacin, sitafloxacin, and the like), β-lactams (e.g., penicillins such as amoxicillin, amoxacilin-clavulanate, piperacillin-tazobactam, penicillin G, and the like; and cephalosporins such as ceftriaxone and the like), macrolides (e.g., erythromycin, azithromycin, clarithromycin, and the like), carbapenems (e.g., doripenem, imipenem, meropinem, ertapenem, and the like), thiazolides (e.g., tizoxanidine, nitazoxanidine, RM 4807, RM 4809, and the like), tetracyclines (e.g., tetracycline, minocycline, doxycycline, eravacycline, and the like), clindamycin, metronidazole, and satranidazole. Bacteriocidal and bacteriostatic compounds also include agents that inhibit or otherwise interfere with formation of biofilms by anaerobic, gram-negative bacteria; such agents include oxantel, morantel, thiabendazole, and the like. Compositions of the invention can contain one or more Kgp inhibitors with one or more (e.g., two, three, four, five, six, or more) bacteriocidal/bacteriostatic compounds. Compositions containing bacteriocidal/bacteriostatic compounds can further contain a chlorhexidine (e.g., chlorhexidine digluconate) alone or in combination with a zinc compound (e.g., zinc acetate), can also be used in combination with the administered antibiotics.

In some embodiments, a combination of a penicillin (e.g., amoxicillin) and metronidazole or a combination of penicillin (e.g., amoxicillin), metronidazole and a tetracycline is used. In some embodiments, the antibiotic is selected from minocycline, doxycycline, metronidazole, amoxicillin, clindamycin, augmentin, satranidazole, and combinations thereof.

Examples of suitable cholinesterase inhibitors include, but are not limited to, donepezil, donepezil/memantine, galantamine, rivastigmine, and tacrine, as well as pharmaceutically acceptable salts thereof. Examples of suitable serotonin modulators include, but are not limited to, idalopirdine, RVT-101, citalopram, escitalopram, fluoxetine, fluvoxamine, paroxetine, and sertraline, as well as pharmaceutically acceptable salts thereof. Examples of suitable alpha-7 nicotinic receptor modulators include, but are not limited to, alpha-7 agonists such as encenicline and APN1125. Suitable NMDA modulators include, but are not limited to, NMDA receptor antagonists such as memantine and derivatives thereof.

Pharmaceutical compositions of the invention can also contain active agents that are directed to biomolecular targets associated with neurological diseases. Such targets include beta amyloid peptides (also referred to as beta amyloid, abeta, or Aβ), apolipoprotein E (also referred to as ApoE), and microtubule-associated tau (also referred to as tau proteins, or simply as tau).

Aβ-targeted therapies include inhibitors of Aβ production (such as beta-secretase inhibitors, gamma-secretase inhibitors, alpha-secretase activators), inhibitors of Aβ aggregation, inhibitors of Aβ oligomerization, and up-regulators of Aβ clearance, among others (see, e.g., Jia, et al. *BioMed Research International,* 2014. Article ID 837157, 22 pages). Examples of Aβ-targeted therapies include but are not limited to, antibodies, pioglitazone, begacestat, atorvastatin, simvastatin, etazolate, and tramiprosate, as well as pharmaceutically acceptable salts thereof.

Examples of ApoE-targeted therapies include, but are not limited to retinoid X receptor agonists (see, Cramer, et al., *Science* 2012. 335(6075): 1503-1506) and others described by Liu et al. (*Nat Rev Neurol.* 2013. 9(2): 106-118). Tau-targeted therapies include, but are not limited to, methylthioninium, leuco-methylthioninium, antibodies and those described by Lee, et al. (*Cold Spring Harb Perspect Med* 2011; 1:a006437).

Pharmaceutical compositions of the invention can also contain complement-targeted therapies. Such therapies target components of the complement system involved in the innate immune response. Complement targeted therapies include, but are not limited to, those described by Ricklin and Lambris (*Nat. Biotechnology* 2007. 25(11): 1265-1275).

Examples of suitable anti-inflammatories include, but are not limited to, NSAIDs such as apazone, diclofenac, ibuprofen, indomethacin, ketoprofen, nabumetone, naproxen, piroxicam, and sulindac, as well as pharmaceutically acceptable salts thereof.

V. Methods for Inhibiting Gingipains and Treating Conditions Associated with P. gingivalis Infection In another embodiment, the invention provides a method of inhibiting a gingipain. The method includes contacting the gingipain with an effective amount of a compound as described herein. In certain embodiments, the gingipain is a lysine gingipain (i.e., Kgp or a variant containing one or more amino acid substitutions, deletions, and/or other peptide sequence variations). Inhibiting the gingipain generally includes contacting the gingipain with an amount of the compound sufficient to reduce the activity of the gingipain as compared to the gingipain activity in the absence of the compound. For example, contacting the gingipain with the gingipain inhibitor can result in from about 1% to about 99% gingipain inhibition (i.e., the activity of the inhibited gingipain ranges from 99% to 1% of the gingipain activity in the absence of the compound). The level of gingipain inhibition can range from about 1% to about 10%, or from about 10% to about 20%, or from about 20% to about 30%, or from about 30% to about 40%, or from about 40% to about 50%, or from about 50% to about 60%, or from about 60% to about 70%, or from about 70% to about 80%, or from about 80% to about 90%, or from about 90% to about 99%. The level of gingipain inhibition can range from about 5% to about 95%, or from about 10% to about 90%, or from about 20% to about 80%, or from about 30% to about 70%, or from about 40% to about 60%. In some embodiments, contacting the gingipain with a compound as described herein will result in complete (i.e., 100%) gingipain inhibition.

As described above, infection with P. gingivalis and gingipain activity have been linked to the development of periodontal disease, Alzheimer's and other brain disorders, cardiovascular disease, diabetes, cancer, liver disease, kidney disease, preterm birth, arthritis, pneumonia and other disorders. See: Bostanci, et al. FEMS Microbiol Lett, 2012. 333(1): 1-9; Ghizoni, et al. *J Appl Oral Sci,* 2012. 20(1): 104-12; Gatz, et al. *Alzheimers Dement,* 2006. 2(2): 110-7; Stein, et al. *J Am Dent Assoc,* 2007. 138(10): 1314-22; quiz 1381-2; Noble, et al. *J Neurol Neurosurg Psychiatry,* 2009. 80(11): 1206-11; Sparks Stein, et al. *Alzheimers Dement,* 2012. 8(3): 196-203; Velsko, et al. *PLoS ONE,* 2014. 9(5): e97811; Demmer, et al. *J Dent Res,* 2015. 94(9S): 201-S-11S; Atanasova and Yilmaz. *Molecular Oral Microbiology,* 2014. 29(2): 55-66; Yoneda, et al. *BMC Gastroenterol,* 2012. 12: 16.

Extracellular proteases produced by *P. gingivalis,* including Arginine Gingipain A (RgpA), Arginine Gingipain B (RgpB), and Lysine Gingipain (Kgp), can also degrade a broad range of proteins in connective tissue and plasma (e.g., collagen, immunoglobulins, and proteinase inhibitors, etc.). Gingipains can enter systemic circulation and/or synoviocytes and chondrocytes, and they can also cause disruption to the kallikrein-kinin cascade, blood coagulation, and host defense systems. Patients with gingipains in their joints and circulatory system may be subject to gingipain-induced death of synovial cells and/or chondrocytes, contributing to osteoarthritis.

It has recently been discovered that RgpB and Kgp can infiltrate human and dog joints, contributing to the development of osteoarthritis. It is believed that *P. gingivalis* and gingipains can infiltrate joint tissues via a number of routes. Gingipains can be secreted, transported to outer membrane surfaces of *P. gingivalis,* or released in outer membrane vesicles by the bacterium. *P. gingivalis* has previously been identified in periodontal tissues, coronary arteries, aorta, and recently, the liver—release of *P. gingivalis* and/or gingipains from any of these niches into the systemic circulation could result in translocation of *P. gingivalis* and/or gingipains to the joints. See: Travis, et al. *Adv Exp Med Biol,* 2000. 477: 455-65; Byrne, et al. *Oral Microbiol Immunol,* 2009. 24(6): 469-77; Mahendra, et al. *J Maxillofac Oral Surg,* 2009. 8(2): 108-13; Stelzel. *Periodontol,* 2002. 73(8): 868-70; Ishikawa, et al. *Biochim Biophys Acta,* 2013. 1832(12): 2035-2043.

*P. gingivalis* and/or gingipains may also enter joints by degrading the endothelial cells protecting the blood/joint barrier, or by a traumatic event to the joint, such as a meniscus injury, which permanently or transiently reduces the integrity of the joint tissues. Such a disruption in traumatic joint injury for example, may contribute to the infiltration of *P. gingivalis* and/or gingipains in infected individuals and subsequent development of chronic osteoarthritis. People who are at a high risk of traumatic joint injury, including athletes in contact sports like football, could be preventatively treated with gingipain inhibitors to reduce the risk of trauma-related osteoarthritis.

*P. gingivalis* and gingipains may also reach the joint through other mechanisms including active transport, passive transport or macrophage delivery. Osteoarthritis resulting from any of these mechanisms can be limited to a single joint or present in multiple joints.

Similar to humans, *P. gingivalis* infection and periodontal disease is one of the most common infectious diseases affecting adult dogs and cats. Dogs and cats with *P. gingivalis* infection and gingipains in their joints and circulatory system may experience periodontal disease and osteoarthritis due to gingipain-induced cell death, which could be treated or prevented according to the methods of the invention. Aged dogs spontaneously develop many features of osteoarthritis, including a common inflammatory knee arthritis associated with degeneration of the anterior cruciate ligament (ACL). A study by Muir et al. of dogs with inflammatory knee arthritis and ACL degeneration detected DNA from a range of bacterial species in 37% of knee joints from affected dogs. Muir et al. hypothesized that bacteria may be an important causative factor in the pathogenesis of inflammatory arthritis in dogs. In the Muir et al. study, DNA from *P. gingivalis* was not detected in the dog joints. See, Muir, et al. *Microb Pathog,* 2007. 42(2-3): 47-55. However, similar to humans, *P. gingivalis* is a common oral pathogen affecting adult dogs, and could potentially translocate from the oral cavity to joint tissues as a result of bacteremia. *P. gingivalis* has been demonstrated to infect chondrocytes in vitro causing chondrocyte apoptosis, indicating a pathway for cartilage loss in osteoarthritis of both dogs and humans. See: Rohner, et al. *Calcif Tissue Int,* 2010. 87(4): p. 333-40; Houle, et al. *FEMS Microbiol Lett,* 2003. 221(2): p. 181-5; Kataoka, et al. *FASEB J,* 2014. 28: 3564-3578; Pischon, et al. *Ann Rheum Dis,* 2009. 68(12): p. 1902-7.

Kgp inhibitors can therefore be used to treat diseases and conditions, such as brain disorders, caused by or otherwise affected by *P. gingivalis.* Accordingly, another aspect of the invention provides a method of treating a disease or condition associated with *P. gingivalis* infection. The method includes administering an effective amount of a compound or a composition of the invention, as described above, to a subject in need thereof.

In certain embodiments, compounds of the invention inhibit active Kgp in the brain of a mammal, e.g., a human or an animal (e.g., a dog), and are cytoprotective or neuroprotective. By "neuroprotective," it is meant that the compounds prevent aberrant changes to neurons or death of neurons. Compounds of the invention are therefore useful, e.g., in treatment of a brain disorder (e.g., a neurodegenerative disease (e.g., Alzheimer's disease, Down's syndrome, epilepsy, autism, Parkinson's disease, essential tremor, fronto-temporal dementia, progressive supranuclear palsy, amyotrophic lateral sclerosis, Huntington's disease, multiple sclerosis, mild cognitive impairment, age associated memory impairment, chronic traumatic encephalopathy, stroke, cerebrovascular disease, Lewy Body disease, multiple system atrophy, schizophrenia and depression, etc.), diabetes, cardiovascular disease, arthritis, rheumatoid arthritis, osteoarthritis, infectious arthritis, psoriatic arthritis, retinal disorders (e.g., age related macular degeneration) and glaucoma.

In some embodiments, the disease or condition is selected from a brain disorder, periodontal disease, diabetes, a cardiovascular disease, arthritis, rheumatoid arthritis, osteoarthritis, preterm birth, pneumonia, cancer, a kidney disease, a liver disease, a retinal disorder, and glaucoma.

In some embodiments, the disease or condition is a brain disorder.

In some embodiments, the brain disorder is selected from Alzheimer's disease, Down's syndrome, epilepsy, autism, Parkinson's disease, essential tremor, fronto-temporal dementia, progressive supranuclear palsy, amyotrophic lateral sclerosis, Huntington's disease, multiple sclerosis, mild cognitive impairment, age associated memory impairment, chronic traumatic encephalopathy, stroke, cerebrovascular disease, Lewy Body disease, multiple system atrophy, schizophrenia, and depression.

In some embodiments, the brain disorder is Alzheimer's disease.

In some embodiments, the method further includes administering to the subject one or more active agents selected from a cholinesterase inhibitor, a serotonin modulator, an NMDA modulator, an Aβ targeted therapy, an ApoE targeted therapy, a microglia targeted therapy, a blood brain barrier targeted therapy, a tau targeted therapy, a complement targeted therapy, and an anti-inflammatory.

In some embodiments, the disease or condition is periodontal disease. In some embodiments, the disease or condition is a liver disease. In some embodiments, the liver disease is non-alcoholic steatohepatitis. In some embodiments, the disease or condition is a retinal disorder. In some embodiments, the retinal disorder is age-related macular degeneration.

In some embodiments, the disease or condition is cancer. In some embodiments, the cancer is breast cancer, oral cancer, pancreatic cancer, or glioblastoma multiforme.

Kgp inhibitors as described herein can be administered at any suitable dose in the methods of the invention. In general, a Kgp inhibitor is administered at a dose ranging from about 0.1 milligrams to about 1000 milligrams per kilogram of a subject's body weight (i.e., about 0.1-1000 mg/kg). The dose of Kgp inhibitor can be, for example, about 0.1-1000 mg/kg, or about 1-500 mg/kg, or about 25-250 mg/kg, or about 50-100 mg/kg. The dose of Kgp inhibitor can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg. The dosages can be varied depending upon the requirements of the patient, the severity of the disorder being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the seizure disorder.

Kgp inhibitors can be administered for periods of time which will vary depending upon the nature of the particular disorder, its severity, and the overall condition of the subject to whom the Kgp inhibitor is administered. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a subject can be monitored for changes in his or her condition and for alleviation of the symptoms of the disorder. The dosage of the Kgp inhibitor can either be increased in the event the subject does not respond significantly to a particular dosage level, or the dose can be decreased if an alleviation of the symptoms of the disorder is observed, or if the disorder has been remedied, or if unacceptable side effects are seen with a particular dosage.

A therapeutically effective amount of a Kgp inhibitor can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 144, 168, 192, 216, or 240 hours (i.e., 3, 4, 5, 6, 7, 8, 9, or 10 days). In certain embodiments, administration of one or more Kgp inhibitors is conducted in a chronic fashion over periods ranging from several months to several years. Accordingly, some embodiments of the invention provide a method of treating a disease or condition associated with *P. gingivalis* infection as described above, wherein the compound is administered to the subject for at least one year. In some embodiments, the compound is administered to the subject for at least 10 years. In some embodiments, the compound is administered to the subject for at least 60 years.

Administration of Kgp inhibitors according to the methods of the invention typically results in the reduction of circulating levels of active Kgp in a subject and/or the reduction of active Kgp in the brain. In certain embodiments, administration of a Kgp inhibitor according to the methods of the invention results in at least a 20% reduction of circulating levels of active Kgp and/or at least a 20% reduction of active Kgp in the brain. For example, the circulating levels of Kgp and/or the levels of Kgp in the brain are preferably reduced by from about 25% to about 95%, or from about 35% to about 95%, or from about 40% to about 85%, or from about 40% to about 80% as compared to the corresponding levels of Kgp 24 hours prior to the first administration of the Kgp inhibitor.

Kgp inhibitors can be administered alone or in combination with one or more additional therapeutically active agents, as described above. The one or more additional therapeutically effective agents include, e.g.: (i) a pharmaceutically acceptable agent which inhibits RgpA, RgpB, and/or Kgp production, translocation of RgpA, RgpB, and/or Kgp into systemic circulation or brain, and/or pathological (e.g., neurotoxic effects) of RgpA, RgpB, and/or Kgp in a mammal; (ii) an antibacterial agent which is bacteriostatic or bacteriocidal with respect to *P. gingivalis*; (iii) one or more antibodies which bind to RgpA, RgpB and/or Kgp (e.g., 18E6, which binds to the first half of the immunoglobulin domain of RgpB; Kgp-specific monoclonal antibody, 7B9, which recognizes an epitope within the Kgp catalytic domain; the RgpA antibody 61Bg 1.3, humanized versions of any of the foregoing, etc.); (iv) epitopes of antibodies which bind to RgpA, RgpB and/or Kgp or other proteins expressed by *P. gingivalis*; and (v) combinations of any of the foregoing.

The additional therapeutically active agents also include Aβ peptides level reducers, pathogenic level tau reducers, microtubule stabilizers, agents capable or removing atherosclerotic plaques, agents that lower circulating levels of β-amyloid and tau, modulators of autophagy, neurotransmitter level regulators, GABA(A) α5 receptors inhibitors, and additional agents that help maintain and/or restore cognitive function and functional deficits of Alzheimer's disease, and/or slow down decline in cognitive functions and functional deficits in Alzheimer's disease.

Pharmaceutical compositions of the invention can contain one or more Kgp inhibitors as described herein in combination with ritonavir (RTV), which can increase bioavailability and increase blood brain barrier penetration. For example, ritonavir is commonly combined with oral peptidic HIV protease inhibitors to increase plasma levels by inhibiting the P450 3A4 enzyme and thus decreasing first-pass metabolism (see, Walmsley, et al., *N Engl J Med,* 2002. 346(26): 2039-46). In addition, RTV binds to P-glycoprotein, a transmembrane efflux pump that is found in many tissues, including the blood brain barrier, allowing co-administered compounds better access to the brain (see, Marzolini, et al., *Mol Pharm,* 2013. 10(6): 2340-9). Therefore, a combination of RTV and Kgp inhibitors can be used to increase plasma concentrations and brain levels of the gingipain inhibitors. As described in U.S. patent application Ser. No. 14/875,416, oral administration of RTV 15 minutes prior to the Kgp inhibitor Kyt-36 increases the half-life therefore it is expected that RTV will also increase the half-life of other Kgp inhibitors.

In some embodiments, compounds of the invention can be administered with natural gingipain inhibitors including melabaricone C, isolated from nutmeg or polyphenolic compounds derived from plants, such as cranberry, green tea, apple, and hops can be administered in conjunction for treatment or prevention of brain disorders. Naturally and unnaturally occurring antimicrobial peptides including: κ-casein peptide (109-137) 34, histatin 5, and CL(14-25), CL(K25A) and CL(R24A, K25A), can also be administered in conjunction with the Kgp inhibitors of the invention. (see, e.g., Taniguchi et al., *Biopolymers,* 2014. 102(5): 379-89).

Kgp inhibitors as described herein can be administered with antibodies targeting gingipains or other *P. gingivalis* proteins. Antibodies may rely on damage to the blood brain barrier for access to the brain or peripheral interference with gingipains and *P. gingivalis* propagation. Antibodies can also help to stimulate the efficacy of the immune system in clearing the bacteria. New or existing antibodies to RgpA, RgpB, or Kgp can be utilized including 18E6 and 7B9. An RgpA antibody 61BG 1.3 has previously demonstrated efficacy topically in prevention of recolonization by *P. gingivalis* after periodontal treatment. See, Booth et al., *Infect Immun,* 1996. 64(2): 422-7. Antibodies would preferably be humanized for use in humans. Methods known to those in the field for delivery of biologics to improve half-life and brain penetration can be used including, but not limited to, intravenous delivery, subcutaneous delivery, intranasal delivery, intrathecal delivery, intra-articular delivery, vector transport, and direct brain delivery.

The methods of the invention also encompass administration of Kgp inhibitors as described herein with one or more of the following additional therapeutically active agents or pharmaceutically acceptable salts thereof: an arginine derivative; histatin 5; baculovirus p35; a single point mutant of cowpox viral cytokine-response modifier (CrmA (Asp>Lys)); phenylalanyl-ureido-citrullinyl-valyl-cycloarginal (FA-70C1); (acycloxy)methyl ketone (Cbz-Phe-Lys-CH$_2$OCO-2,4,6-Me$_3$Ph); peptidyl chloro-methyl ketones (e.g., chloromethyl ketone derivatives of arginine, chloromethyl ketone derivatives of lysine, and the like); fluoro-methyl ketones; bromo-methyl ketones; ketopeptides; 1-(3-phenylpropionyl)piperidine-3(R,S)-carboxylic acid [4-amino-1(S)-(benzothiazole-2-carbonyl)butyl]amide (A71561); azapeptide fumaramide; aza-peptide Michael acceptors; benzamidine compounds; acyclomethylketone; activated factor X inhibitors (e.g., DX-9065a); cranberry nondialyzable fraction; cranberry polyphenol fraction; pancreatic trypsin inhibitor; Cbz-Phe-Lys-CH$_2$O—CO-2,4,6-Me$_3$-Ph; E-64; chlorhexidine; zinc (e.g., zinc acetate); or a combination of two, three or more of any of foregoing. In some of these embodiments, Zn can enhance potency and selectivity of the compounds (e.g., chlorhexidine, benzamidine, etc.) used in the methods of the invention.

A Kgp inhibitor of the invention can be administered in the same composition as an additional therapeutically active agent. Alternatively, the additional therapeutically active agent can be administered separately before, concurrently with, or after administration of the Kgp inhibitor.

VI. Gingipain Activity Probes

In a related embodiment, the invention provides a compound comprising a reporter moiety and a gingipain-reactive moiety, or a pharmaceutically acceptable salt thereof. In some embodiments, the gingipain-reactive moiety is a Kgp-reactive moiety. In some embodiments, the gingipain-reactive moiety is an Rgp-reactive moiety.

In some embodiments, the gingipain-reactive moiety binds reversibly to a target gingipain. In some embodiments, the gingipain-reactive moiety binds irreversibly to a target gingipain.

In some embodiments, the Kgp-reactive moiety further comprises a quenching moiety.

In some embodiments, the reporter moiety is selected from a fluorophore, a fluorogenic moiety, a chromophore, a chromogenic moiety, a biotin, a digoxigenin, a peptide tag such as a FLAG peptide, an oligonucleotide, and a polynucleotide.

As used herein, the term "FLAG peptide" refers to an oligopeptide or a polypeptide containing the amino acid sequence Asp-Tyr-Lys-Asp-Asp-Asp-Asp-Lys (i.e., DYKDDDDK). FLAG peptides and variants thereof are described for example, in U.S. Pat. No. 4,703,004 to Hopp, et al., which patent is incorporated herein by reference. Other peptides that can be used in place of a FLAG peptide include, but are not limited to, HA peptide tags containing the sequence Tyr-Pro-Tyr-Asp-Val-Pro-Asp-Tyr-Ala (i.e., YPYDVPDYA), His$_6$ peptide tags containing the sequence His-His-His-His-His-His (i.e., HHHHHH), and Myc peptide tags containing the sequence Glu-Gln-Lys-Leu-Ile-Ser-Glu-Glu-Asp-Leu (i.e., EQKLISEEDL). The peptide tags can be recognized by antibodies or other binding moieties for use with colorimetric reagents, chemiluminescent reagents, or the like for convenient identification and/or quantification. Likewise, the reporter moiety can contain a nucleotide (e.g., RNA, single-stranded DNA, or double-stranded DNA) which can be recognized by a complementary primary or other complementary nucleotide for detection by a PCR technique (e.g., quantitative PCR) as described, for example, in WO 2016/019929 (Navratil, et al.), which publication is incorporated herein by reference. Useful DNA sequences include, but are not limited to,

CCTGCCAGTTGAGCATTTTTATCTGCCACCTTCTCCACCAGACAAAAGC

TGGAAA;

CACTCTGTGCTCGTTGCTACAC;
and

CAGACAGCAAGCAGCACTACAC.

As used herein, the term "digoxigenin" refers to 3-[(3S,5R,8R,9S,10S,12R,13S, 14S,17R)-3,12,14-trihydroxy-10,13-dimethyl-1,2,3,4,5,6,7,8,9,11,12,15,16,17-tetradecahydrocyclopenta[a]phenanthren-17-yl]-2H-furan-5-one (CAS Registry No. 1672-46-4) and substituted analogs thereof. As used herein, the term "biotin" refers to 5-[(3aS,4S,6aR)-2-oxohexahydro-1H-thieno[3,4-d]imidazol-4-yl]pentanoic acid (CAS Registry No. 58-85-5) and substituted analogs thereof.

In some embodiments, the compound has a structure according to Formula I set forth above, wherein R$^3$ is a reporter moiety. In some embodiments, the compound has a structure according to Formula II:

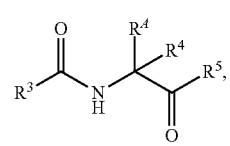

(II)

or a pharmaceutically acceptable salt thereof, wherein:
$R^4$ is a sidechain IIa:

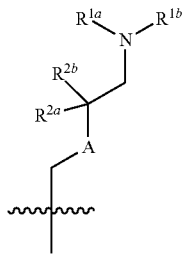
(IIa)

or a sidechain IIb:

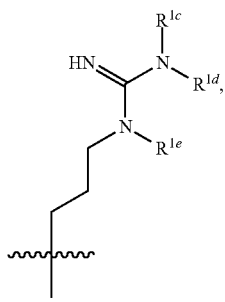
(IIb)

wherein the wavy line represents the point of connection to Formula II;

A is selected from —CH$_2$— and —O—;

$R^{1a}$, $R^{1b}$, $R^{1c}$, $R^{1d}$, and $R^{1e}$ are each independently selected from hydrogen, C$_{1-4}$ alkyl, and an amine protecting group;

$R^{2a}$ and $R^{2b}$ are each independently selected from hydrogen, halogen, C$_{1-4}$ haloalkyl, and C$_{1-4}$ haloalkoxy;

$R^3$ is the reporter moiety;

$R^4$ is selected from hydrogen and C$_{1-4}$ alkyl; and $R^5$ is the gingipain-reactive moiety, wherein the gingipain-reactive moiety optionally comprises a quenching moiety $R^9$.

Compounds of the invention can be prepared in protected form (i.e., compounds wherein at least one of $R^{1a}$, $R^{1b}$, $R^{1c}$, $R^{1d}$, and $R^{1e}$ is an amine protecting group). A number of suitable protecting groups—as described, for example, by Green and Wuts (*Protective Groups in Organic Synthesis*, 4$^{th}$ Ed. 2007, Wiley-Interscience, New York)—can be used. In some embodiments, $R^{1a}$ is H and $R^{1b}$ is selected from benzyloxycarbonyl; 9-fluorenylmethyloxycarbonyl; tert-butyloxycarbonyl; and allyloxycarbonyl. In some embodiments, $R^{1a}$ is H and $R^{1b}$ is tert-butyloxycarbonyl. Compounds can also be prepared in alkylated form (i.e., compounds wherein at least one of $R^{1a}$ and $R^{1b}$ is an alkyl group). One or both of $R^{1a}$ and $R^{1b}$ can be, for example, methyl, ethyl, n-propyl, isopropyl, n-butyl, or t-butyl.

In some embodiments, the compound has a structure according to Formula III:

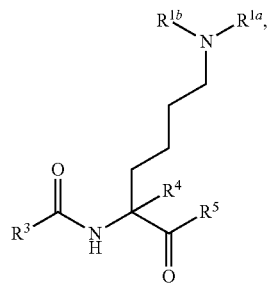
(III)

or a pharmaceutically acceptable salt thereof.

In some embodiments:

$R^5$ is selected from C$_{1-6}$ haloalkyl, —CH$_2$—O—$R^6$, —CH$_2$—S—$R^7$, —CH$_2$—SO—$R^7$, —CH$_2$—SO$_2$—$R^7$, —CH$_2$—N(R$^8$)$_2$, and —CH$_2$—C$_{5-12}$ heteroaryl;

$R^6$ and $R^6$ are selected from phenyl, C$_{1-6}$ alkyl, C$_{1-6}$ haloalkyl, and C$_{5-12}$ heteroaryl,
wherein phenyl is substituted with 1-5 halogens, and
wherein C$_{5-12}$ heteroaryl is optionally substituted with halogen or C$_{1-3}$ haloalkyl; and $R^8$ is independently selected C$_{1-6}$ alkyl.

In some embodiments the gingipain reactive moiety $R^5$ is —CH$_2$—O-phenyl, and phenyl is substituted with 1-5 halogens. In some embodiments, phenyl is optionally substituted with a quenching moiety $R^9$. In some embodiments, the gingipain reactive moiety has the formula:

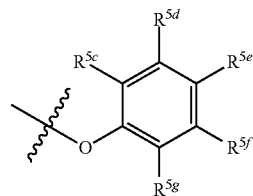

wherein the wavy line represents the point of connect to Formula II or Formula III.

In some embodiments:

$R^{5c}$ is halogen, $R^{5d}$ is H, $R^{5e}$ is H, $R^{5f}$ is H, and $R^{5g}$ is H; or $R^{5c}$ is H, $R^{5d}$ is halogen, $R^{5e}$ is H, $R^{5f}$ is H, and $R^{5g}$ is H; or $R^{5c}$ is H, $R^{5d}$ is H, $R^{5e}$ is halogen, $R^{5f}$ is H, and $R^{5g}$ is H; or $R^{5c}$ is H, $R^{5d}$ is H, $R^{5e}$ is H, $R^{5f}$ is halogen, and $R^{5g}$ is H; or $R^{5c}$ is H, $R^{5d}$ is H, $R^{5e}$ is H, $R^{5f}$ is H, and $R^{5g}$ is halogen; or $R^{5c}$ is halogen, $R^{5d}$ is halogen, $R^{5e}$ is H, $R^{5f}$ is H, and $R^{5g}$ is H; or $R^{5c}$ is halogen, $R^{5d}$ is H, $R^{5e}$ is halogen, $R^{5f}$ is H, and $R^{5g}$ is H; or $R^{5c}$ is halogen, $R^{5d}$ is H, $R^{5e}$ is H, $R^{5f}$ is halogen, and $R^{5g}$ is H; or $R^{5c}$ is halogen, $R^{5d}$ is H, $R^{5e}$ is H, $R^{5f}$ is H, and $R^{5g}$ is halogen; or $R^{5c}$ is H, $R^{5d}$ is halogen, $R^{5e}$ is halogen, $R^{5f}$ is H, and $R^{5g}$ is H; or $R^{5c}$ is H, $R^{5d}$ is halogen, $R^{5e}$ is H, $R^{5f}$ is halogen, and $R^{5g}$ is H; or $R^{5c}$ is H, $R^{5d}$ is halogen, $R^{5e}$ is H, $R^{5f}$ is H, and $R^{5g}$ is halogen; or
$R^{5c}$ is H, $R^{5d}$ is H, $R^{5e}$ is halogen, $R^{5f}$ is halogen, and $R^{5g}$ is H; or
$R^{5c}$ is H, $R^{5d}$ is H, $R^{5e}$ is halogen, $R^{5f}$ is H, and $R^{5g}$ is halogen; or
$R^{5c}$ is H, $R^{5d}$ is H, $R^{5e}$ is H, $R^{5f}$ is halogen, and $R^{5g}$ is halogen; or
$R^{5c}$ is halogen, $R^{5d}$ is halogen, $R^{5e}$ is halogen, $R^{5f}$ is H, and $R^{5g}$ is H; or
$R^{5c}$ is halogen, $R^{5d}$ is halogen, $R^{5e}$ is H, $R^{5f}$ is halogen, and $R^{5g}$ is H; or
$R^{5c}$ is halogen, $R^{5d}$ is halogen, $R^{5e}$ is H, $R^{5f}$ is H, and $R^{5g}$ is halogen; or
$R^{5c}$ is halogen, $R^{5d}$ is H, $R^{5e}$ is halogen, $R^{5f}$ is halogen, and $R^{5g}$ is H; or
$R^{5c}$ is halogen, $R^{5d}$ is H, $R^{5e}$ is halogen, $R^{5f}$ is H, and $R^{5g}$ is halogen; or
$R^{5c}$ is halogen, $R^{5d}$ is H, $R^{5e}$ is H, $R^{5f}$ is halogen, and $R^{5g}$ is halogen; or
$R^{5c}$ is H, $R^{5d}$ is halogen, $R^{5e}$ is halogen, $R^{5f}$ is halogen, and $R^{5g}$ is H; or
$R^{5c}$ is H, $R^{5d}$ is halogen, $R^{5e}$ is halogen, $R^{5f}$ is H, and $R^{5g}$ is halogen; or
$R^{5c}$ is H, $R^{5d}$ is halogen, $R^{5e}$ is H, $R^{5f}$ is halogen, and $R^{5g}$ is halogen; or
$R^{5c}$ is H, $R^{5d}$ is H, $R^{5e}$ is halogen, $R^{5f}$ is halogen, and $R^{5g}$ is halogen; or
$R^{5c}$ is H, $R^{5d}$ is halogen, $R^{5e}$ is halogen, $R^{5f}$ is halogen, and $R^{5g}$ is halogen; or
Rye is halogen, $R^{5d}$ is H, $R^{5e}$ is halogen, $R^{5f}$ is halogen, and $R^{5g}$ is halogen; or
$R^{5c}$ is halogen, $R^{5d}$ is halogen, $R^{5e}$ is halogen, $R^{5f}$ is H, and $R^{5g}$ is halogen; or
$R^{5c}$ is halogen, $R^{5d}$ is halogen, $R^{5e}$ is halogen, $R^{5f}$ is halogen, and $R^{5g}$ is H;
wherein H or halogen in one of $R^{5c}$, $R^{5d}$, $R^{5e}$, $R^{5f}$, and $R^{5g}$ is optionally replaced with a quenching moiety $R^9$.

In some embodiments:
$R^{5c}$ is F or Cl, $R^{5d}$ is H, $R^{5e}$ is H, $R^{5f}$ is H, and $R^{5g}$ is H; or
$R^{5c}$ is H, $R^{5d}$ is F or Cl, $R^{5e}$ is H, $R^{5f}$ is H, and $R^{5g}$ is H; or
$R^{5c}$ is H, $R^{5d}$ is H, $R^{5e}$ is F or Cl, $R^{5f}$ is H, and $R^{5g}$ is H; or
$R^{5c}$ is H, $R^{5d}$ is H, $R^{5e}$ is H, $R^{5f}$ is F or Cl, and $R^{5g}$ is H; or
$R^{5c}$ is H, $R^{5d}$ is H, $R^{5e}$ is H, $R^{5f}$ is H, and $R^{5g}$ is F or Cl; or
$R^{5c}$ is F or Cl, $R^{5d}$ is F or Cl, $R^{5e}$ is H, $R^{5f}$ is H, and $R^{5g}$ is H; or
$R^{5c}$ is F or Cl, $R^{5d}$ is H, $R^{5e}$ is F or Cl, $R^{5f}$ is H, and $R^{5g}$ is H; or
$R^{5c}$ is F or Cl, $R^{5d}$ is H, $R^{5e}$ is H, $R^{5f}$ is F or Cl, and $R^{5g}$ is H; or
$R^{5c}$ is F or Cl, $R^{5d}$ is H, $R^{5e}$ is H, $R^{5f}$ is H, and $R^{5g}$ is F or Cl; or
$R^{5c}$ is H, $R^{5d}$ is F or Cl, $R^{5e}$ is F or Cl, $R^{5f}$ is H, and $R^{5g}$ is H; or
$R^{5c}$ is H, $R^{5d}$ is F or Cl, $R^{5e}$ is H, $R^{5f}$ is F or Cl, and $R^{5g}$ is H; or
$R^{5c}$ is H, $R^{5d}$ is F or Cl, $R^{5e}$ is H, $R^{5f}$ is H, and $R^{5g}$ is F or Cl; or
$R^{5c}$ is H, $R^{5d}$ is H, $R^{5e}$ is F or Cl, $R^{5f}$ is F or Cl, and $R^{5g}$ is H; or
$R^{5c}$ is H, $R^{5d}$ is H, $R^{5e}$ is F or Cl, $R^{5f}$ is H, and $R^{5g}$ is F or Cl; or
$R^{5c}$ is H, $R^{5d}$ is H, $R^{5e}$ is H, $R^{5f}$ is F or Cl, and $R^{5g}$ is F or Cl; or
$R^{5c}$ is F or Cl, $R^{5d}$ is F or Cl, $R^{5e}$ is F or Cl, $R^{5f}$ is H, and $R^{5g}$ is H; or
$R^{5c}$ is F or Cl, $R^{5d}$ is F or Cl, $R^{5e}$ is H, $R^{5f}$ is F or Cl, and $R^{5g}$ is H; or
$R^{5c}$ is F or Cl, $R^{5d}$ is F or Cl, $R^{5e}$ is H, $R^{5f}$ is H, and $R^{5g}$ is F or Cl; or
$R^{5c}$ is F or Cl, $R^{5d}$ is H, $R^{5e}$ is F or Cl, $R^{5f}$ is F or Cl, and $R^{5g}$ is H; or
$R^{5c}$ is F or Cl, $R^{5d}$ is H, $R^{5e}$ is F or Cl, $R^{5f}$ is H, and $R^{5g}$ is F or Cl; or
$R^{5c}$ is F or Cl, $R^{5d}$ is H, $R^{5e}$ is H, $R^{5f}$ is F or Cl, and $R^{5g}$ is F or Cl; or
$R^{5c}$ is H, $R^{5d}$ is F or Cl, $R^{5e}$ is F or Cl, $R^{5f}$ is F or Cl, and $R^{5g}$ is H; or
$R^{5c}$ is H, $R^{5d}$ is F or Cl, $R^{5e}$ is F or Cl, $R^{5f}$ is H, and $R^{5g}$ is F or Cl; or
$R^{5c}$ is H, $R^{5d}$ is F or Cl, $R^{5e}$ is H, $R^{5f}$ is F or Cl, and $R^{5g}$ is F or Cl; or
$R^{5c}$ is H, $R^{5d}$ is H, $R^{5e}$ is F or Cl, $R^{5f}$ is F or Cl, and $R^{5g}$ is F or Cl; or
$R^{5c}$ is H, $R^{5d}$ is F or Cl, $R^{5e}$ is F or Cl, $R^{5f}$ is F or Cl, and $R^{5g}$ is F or Cl; or
$R^{5c}$ is F or Cl, $R^{5d}$ is H, $R^{5e}$ is F or Cl, $R^{5f}$ is F or Cl, and $R^{5g}$ is F or Cl; or
$R^{5c}$ is F or Cl, $R^{5d}$ is F or Cl, $R^{5e}$ is F or Cl, $R^{5f}$ is H, and $R^{5g}$ is F or Cl; or
$R^{5c}$ is F or Cl, $R^{5d}$ is F or Cl, $R^{5e}$ is F or Cl, $R^{5f}$ is F or Cl, and $R^{5g}$ is H;
wherein H or F, or Cl in one of $R^{5c}$, $R^{5d}$, $R^{5e}$, $R^{5f}$ and $R^{5g}$ is optionally replaced with a quenching moiety $R^9$.

In certain embodiments, the gingipain reactive moiety is not 2,3,5,6-tetrafluorophenoxymethyl.

In some embodiments, the compound has a structure according to Formula IIIa:

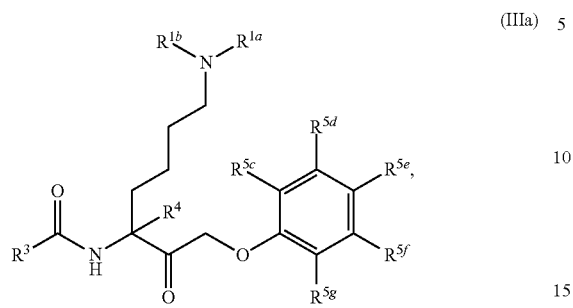

or a pharmaceutically acceptable salt thereof, wherein:
one of $R^{5c}$, $R^{5d}$, $R^{5e}$, $R^{5f}$, and $R^{5g}$ is selected from hydrogen, halogen, and a quenching moiety; and
four of $R^{5c}$, $R^{5d}$, $R^{5e}$, $R^{5f}$ and $R^{5g}$ are independently selected from hydrogen and halogen;
provided that at least one of $R^{5c}$, $R^{5d}$, $R^{5e}$, $R^{5f}$, and $R^{5g}$ is halogen.

In some embodiments, the invention provides compounds with quenching moieties included in $R^5$. Such compounds include, but are not limited to:

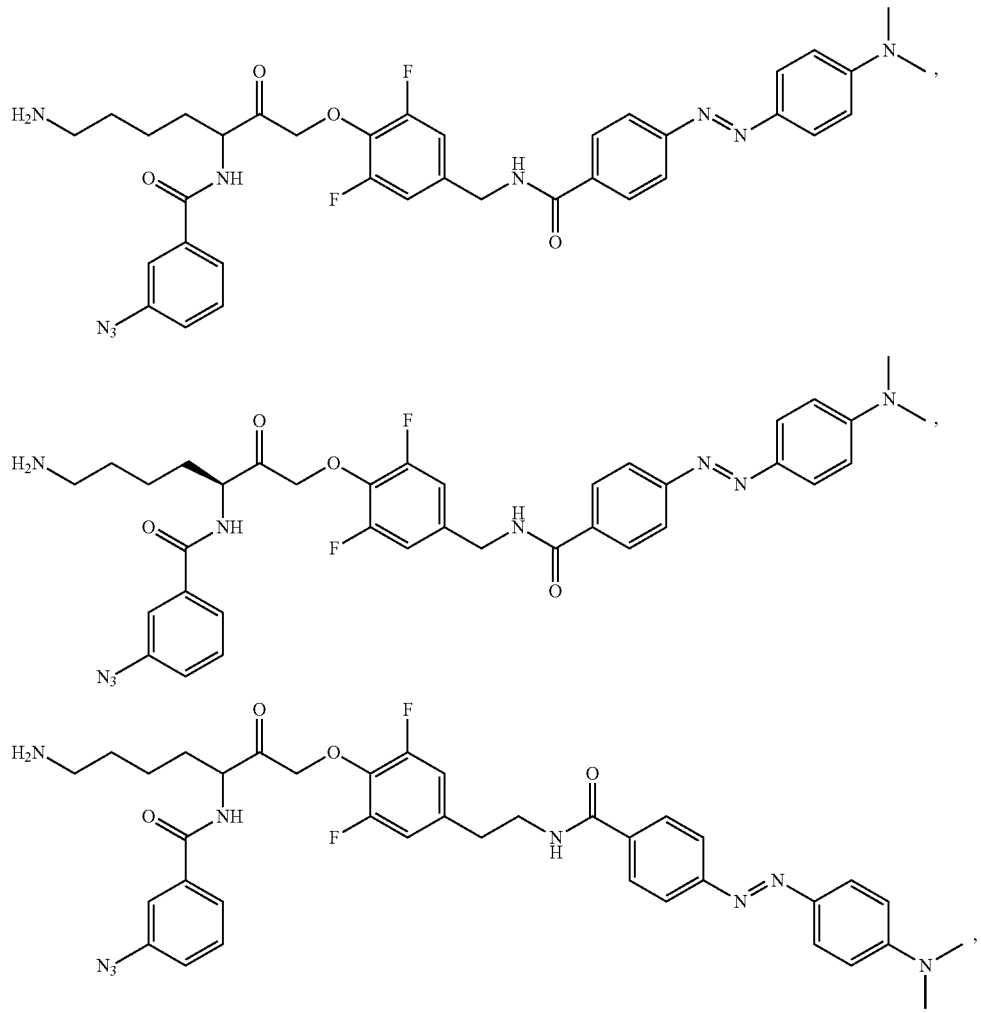

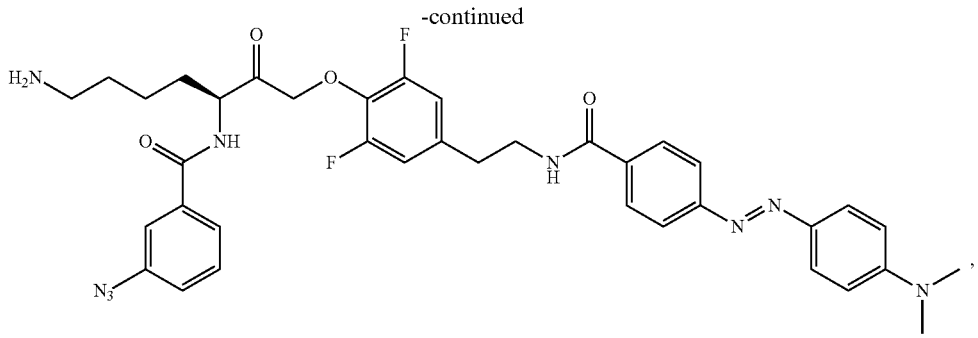

and pharmaceutically acceptable salts thereof.

In some embodiments, the compound has a structure according to Formula IV:

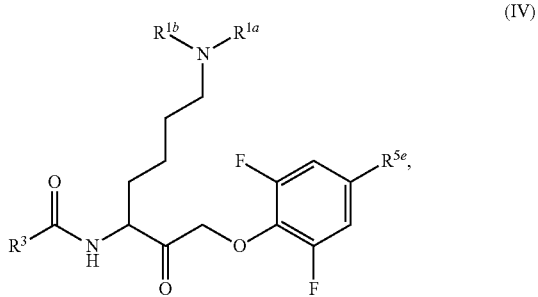

(IV)

or a pharmaceutically acceptable salt thereof, wherein:

$R^{5e}$ is selected from H and a quenching moiety -$L^9$-$R^{9a}$;

$L^9$ is a linking moiety; and $R^{9a}$ is selected from an azobenzene, a xanthylium, an anthroquinone, and a viologen.

In some embodiments, the reporter moiety $R^3$ is —$R^{3b}$-$L^3$-$R^{3c}$, wherein:

$R^{3b}$ is selected from $C_{3-8}$ alkylene, $C_{3-8}$ cycloalkylene, $C_{3-12}$ heterocyclylene, $C_{6-10}$ arylene, and $C_{5-12}$ heteroarylene;

$L^3$ is a linking moiety; and $R^{3c}$ is selected from a chromophore or a fluorophore.

Reporting moieties containing a chromophore or a fluorophore can be useful for detecting labeled gingipains using UV-visible absorption spectroscopy or fluorimetry as described below. Any suitable chromophore or fluorophore can be used in the compounds of the invention. In general, suitable chromophores and fluorophores have a reactive group (e.g., a carboxylate moiety, an amino moiety, a haloalkyl moiety, or the like) that can be covalently bonded to the compounds of Formula II directly or via one or more linking groups. Examples of suitable chromophores and fluorophores include, but are not limited to, those described in U.S. Pat. Nos. 7,687,282; 7,671,214; 7,446,202; 6,972,326; 6,716,979; 6,579,718; 6,562,632; 6,399,392; 6,316,267; 6,162,931; 6,130,101; 6,005,113; 6,004,536; 5,863,753; 5,846,737; 5,798,276; 5,723,218; 5,696,157; 5,658,751; 5,656,449; 5,582,977; 5,576,424; 5,573,909; and 5,187,288, which patents are incorporated herein by reference in their entirety.

In some embodiments, $R^{3c}$ is a boron-dipyrromethene moiety having the structure:

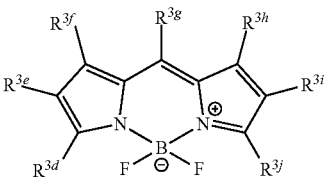

wherein six of $R^{3d}$, $R^{3e}$, $R^{3f}$, $R^{3g}$, $R^{3h}$, $R^{3i}$, and $R^{3j}$ are independently selected from H, halogen, $C_{1-6}$ alkyl, $C_{3-8}$ cycloalkyl, $C_{6-10}$ aryl, $C_{7-16}$ arylalkyl, $C_{1-6}$ acyl, and —$SO_3H$; and wherein one of $R^{3d}$, $R^{3e}$, $R^{3f}$, $R^{3g}$, $R^{3h}$, $R^{3i}$, and $R^{3j}$ is the linking moiety -$L^3$-.

In some embodiments, $R^{3d}$ and $R^{3f}$ are independently selected $C_{1-6}$ alkyl (e.g., methyl or ethyl), and one of $R^{3h}$, $R^{3i}$, and $R^{3j}$ is the linking moiety -$L^3$-. In some embodiments, $R^{3d}$ and $R^{3f}$ are methyl and $R^{3j}$ is the linking moiety -$L^3$-.

In some embodiments, $R^{3c}$ is a cyanine moiety having the structure:

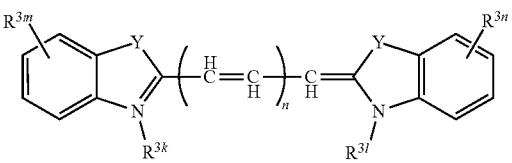

wherein $R^{3k}$ and $R^{3l}$ are independently selected from H, $C_{1-6}$ alkyl, $(CH_2)_tCOOH$, $(CH_2)_tSO_3H$, and linking moiety $L^3$;

each subscript t is independently an integer from 1 to 10;

$R^{3m}$ and $R^{3n}$ are independently selected from H, halogen, $C_{1-6}$ alkyl, —$SO_3H$, —$PO_3H_2$, —$OPO_3H_2$, —COOH, and linking moiety $L^3$;

each Y is independently selected from O, S, $C(R^{3p})_2$, —CH=CH—, and $NR^{3p}$, where each $R^{3p}$ is independently H or $C_{1-6}$ alkyl; and subscript n is an integer from 1 to 6, provided that one and only one of $R^{3k}$, $R^{3l}$, $R^{3m}$, and $R^{3n}$ is the linking moiety -$L^3$-.

In some embodiments, $R^{3c}$ is a coumarin moiety having the structure:

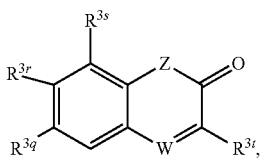

wherein
W is N or CR$^{3u}$;
Z is O, S, or NR$^{3v}$; and
each of R$^{3q}$, R$^{3s}$, R$^{3t}$, R$^{3u}$ is independently selected from H, halogen, C$_{1-6}$ alkyl, —CN, —CF$_3$, —COOR$^{3v}$, —CON(R$^{3v}$)$_2$, —OR$^{3v}$, and linking moiety -L$^3$-;
R$^{3r}$ is selected from —OR$^{3v}$ and —N(R$^{3v}$)$_2$
each R$^{3v}$ is independently selected from H, C$_{1-6}$ alkyl, and linking moiety -L$^3$-;
provided that one and only one of R$^{3q}$, R$^{3s}$, R$^{3t}$, R$^{3u}$, and R$^{3v}$ is the linking moiety -L$^3$-.

In some embodiments, R$^{3c}$ is a xanthene moiety having the structure:

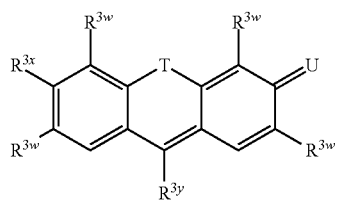

wherein:
T is selected from O, S, C(R$^{3z}$)$_2$, and NR$^{3z}$;
U is O or N(R$^{3z}$)$_2$;
each R$^{3w}$ is independently selected from H, halogen, C$_{1-6}$ alkyl, —SO$_3$H, and linking moiety -L$^3$-;
R$^{3x}$ is selected from H, —OH, —OR$^{3z}$, —N(R$^{3z}$)$_2$, and linking moiety -L$^3$-;
R$^{3y}$ is selected from H, C$_{1-6}$ alkyl, R$^{3aa}$, and linking moiety -L$^3$-;
each R$^{3z}$ is independently H or C$_{1-6}$ alkyl; and
R$^{3aa}$ is selected from

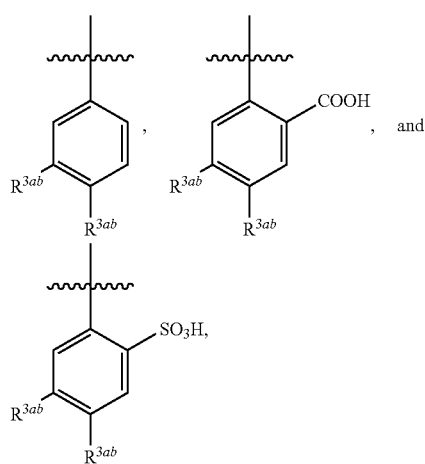

wherein:
each R$^{3ab}$ is independently selected from H and linking moiety -L$^3$-;
provided that one and only one of R$^{3w}$, R$^{3x}$, R$^{3y}$, and R$^{3ab}$ is linking moiety -L$^3$-.

In some embodiments, R$^{3c}$ is a fluorescein, wherein T and U are O; R$^{3x}$ is OH, and R$^{3y}$ is:

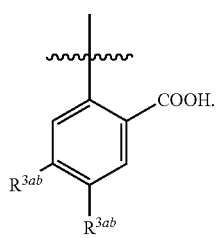

In some embodiments, the xanthene moiety is an eosin, wherein T and U are O; R$^{3x}$ is OH, each R$^{3w}$ is halogen (e.g., bromo), and R$^{3y}$ is:

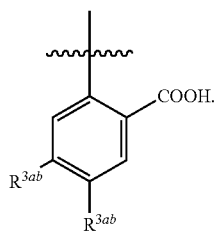

In some embodiments, the xanthene moiety is a rhodamine, wherein T is O; U is N(R$^{3z}$)$_2$ (e.g., =NH$_2^+$); R$^{3x}$ is —N(R$^{3z}$)$_2$ (e.g., —NH$_2$), and R$^{3y}$ is:

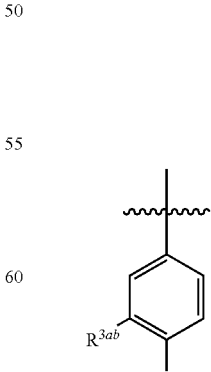

In some embodiments, the xanthene moiety is a rhodamine having the structure:

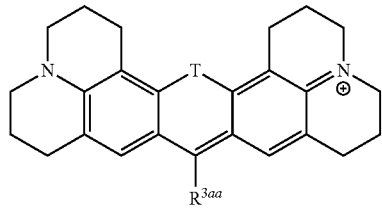

wherein $R^{3aa}$ is selected from

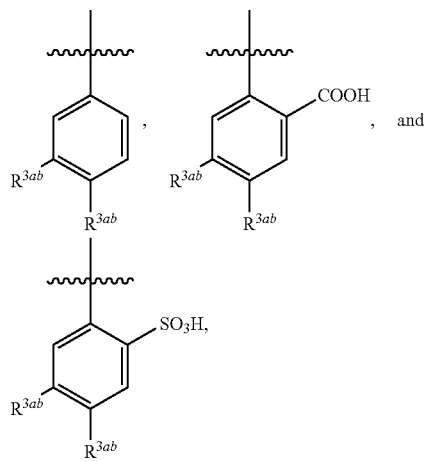

one $R^{3ab}$ is H, and the other $R^{3ab}$ is linking moiety -$L^3$-.

In some embodiments, the invention provides compounds according to Formula II wherein the reporter moiety $R^3$ is —$R^{3b}$-$L^3$-$R^{3c}$, wherein:

$R^{3b}$ is selected from $C_{3-8}$ alkylene, $C_{3-8}$ cycloalkylene, $C_{3-12}$ heterocyclylene, $C_{6-10}$ arylene, and $C_{5-12}$ heteroarylene;

$L^3$ is a linking moiety; and $R^{3c}$ is selected from a biotin, a digoxigenin, and an antibody epitope.

In some embodiments, the reporter moiety $R^3$ is —$R^{3b}$-$L^3$-$R^{3c}$, wherein:

$R^{3b}$ is selected from $C_{3-8}$ alkylene, $C_{3-8}$ cycloalkylene, $C_{3-12}$ heterocyclylene, $C_{6-10}$ arylene, and $C_{5-12}$ heteroarylene;

$L^3$ is a linking moiety; and $R^{3c}$ is selected from a fluorescein, a rhodamine, an eosin, a cyanine, a boron-dipyrromethene, a coumarin, a biotin, a digoxigenin, a FLAG peptide (or other peptide tag), an oligonucleotide, and a polynucleotide.

One of skill in the art will appreciate that compounds containing azide groups (e.g., compounds wherein $R^{3a}$ is —$N_3$) can be modified with further functional groups via reaction with a complementary reaction partner such as an alkyne-bearing compound or a phosphine-bearing compound. Reaction of azides and alkynes via [3+2] cycloaddition, commonly referred to as "click chemistry," can be used to install a variety of substituted triazole groups in the compounds of the invention. Accordingly, some embodiments of the invention provide compounds wherein linking moiety -$L^3$- is an optionally substituted triazolyl moiety according to the formula:

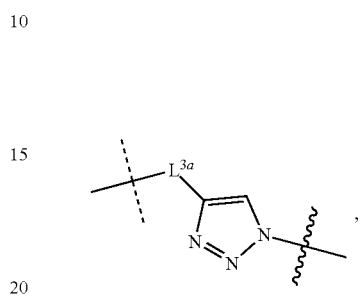

wherein the wavy line is point of connection to $R^{3a}$ and the dashed line is the point of connection to $R^{3c}$.

In some embodiments, $L^{3a}$ has a structure-$L^{ab}$-$L^{3c}$-, wherein:

$L^{3b}$ and $L^{3c}$ are independently selected from a bond, a divalent polymer moiety, and linear or branched, saturated or unsaturated $C_{1-30}$ alkyl;

one or more carbon atoms in the $C_{1-30}$ alkyl is optionally and independently replaced by O, S, $NR^a$;

two or more groupings of adjacent carbon atoms in the $C_{1-30}$ alkyl are optionally and independently replaced by —$NR^a(CO)$— or —$(CO)NR^a$—;

two or more groupings of adjacent carbon atoms in the $C_{1-30}$ alkyl are optionally and independently replaced by a 4- to 8-membered, divalent carbocycle or a 4- to 8-membered, divalent heterocycle having one to four heteroatoms selected from O, S, and N; and each $R^a$ is independently selected from H and $C_{1-6}$ alkyl.

In some embodiments, the compound has a structure according to Formula V:

(V)

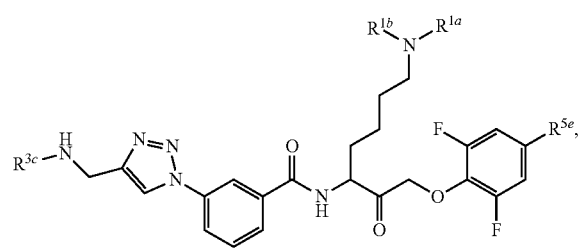

or a pharmaceutically acceptable salt thereof, wherein:

$R^{5e}$ is selected from H and —C(O)NH—$(CH_2)_x$—$R^{9a}$; and subscript x is an integer ranging from 1 to 4.

In some embodiments, the compound is selected from:
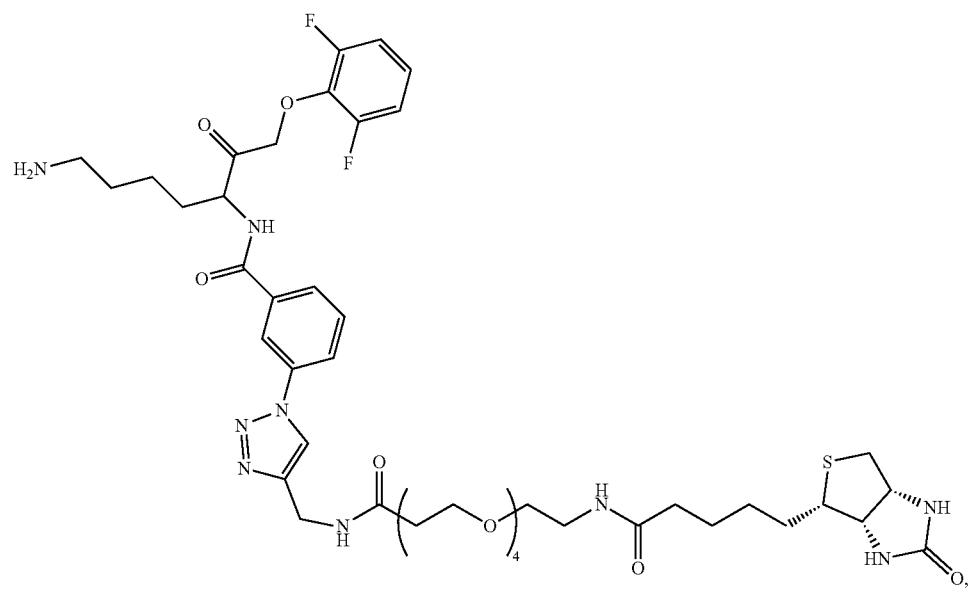
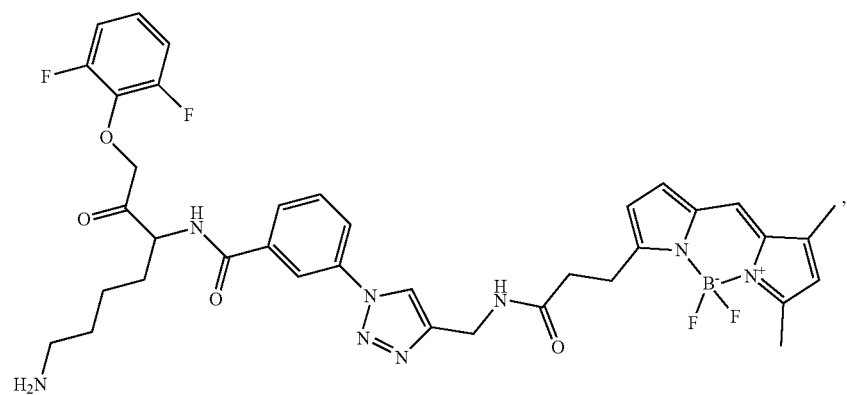
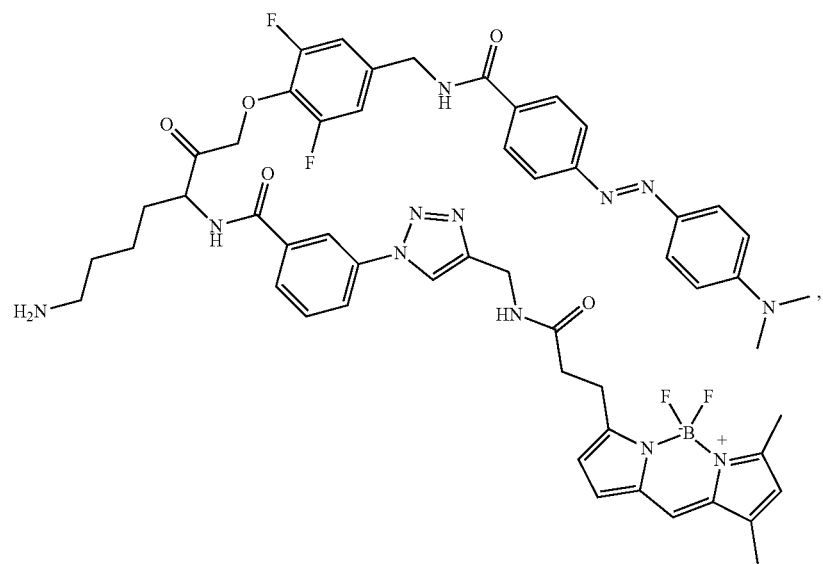

133
134
-continued
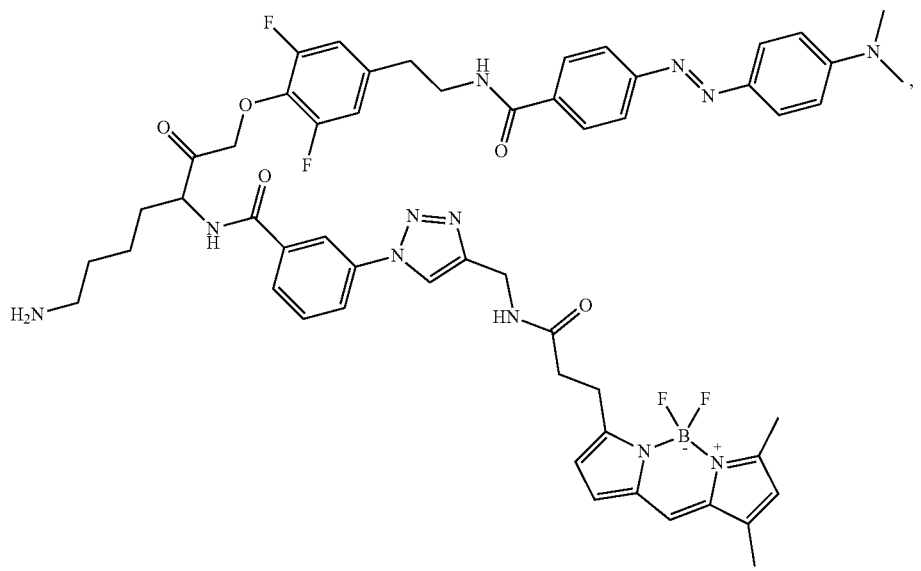
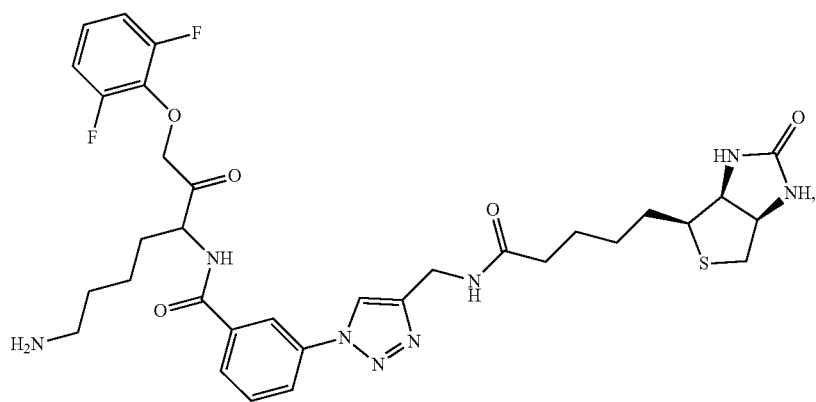
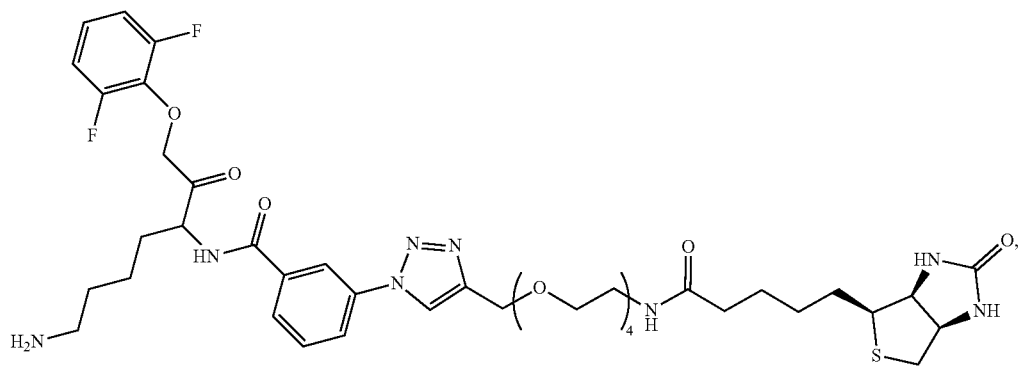

-continued
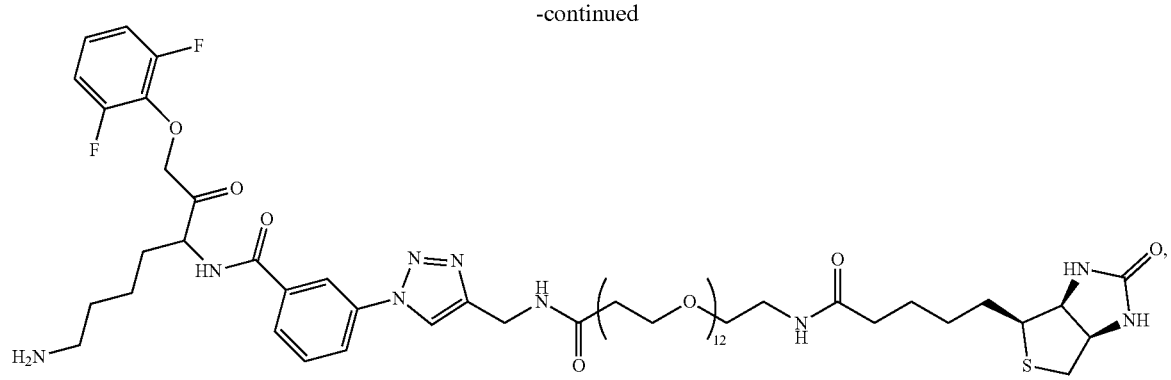
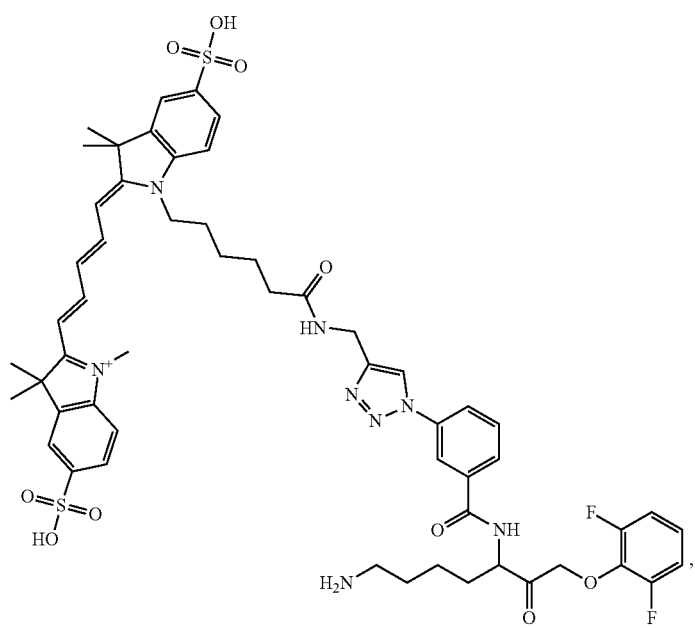
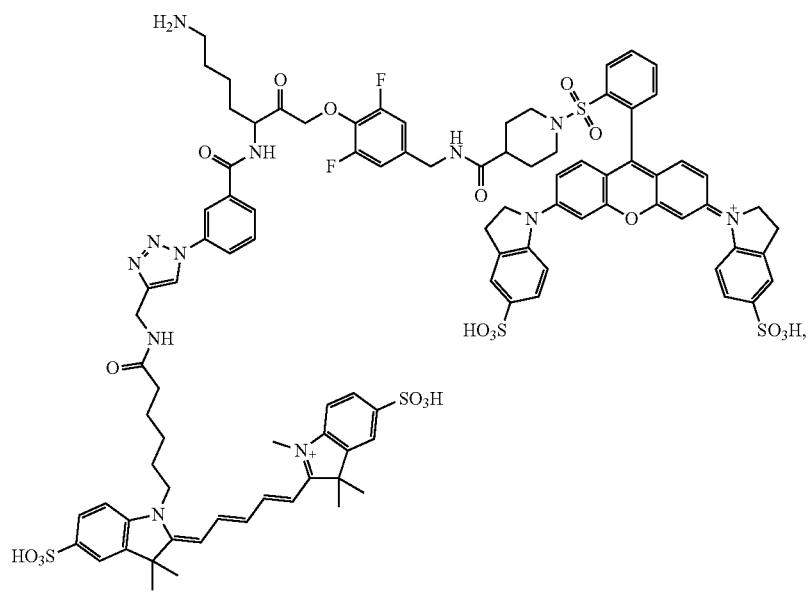

-continued
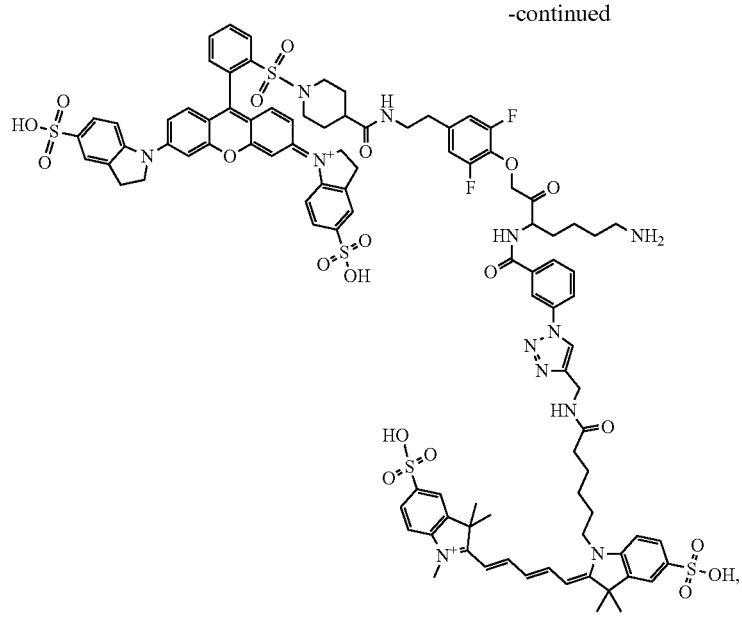
and pharmaceutically acceptable salts thereof.
In some embodiments, the compound is selected from:
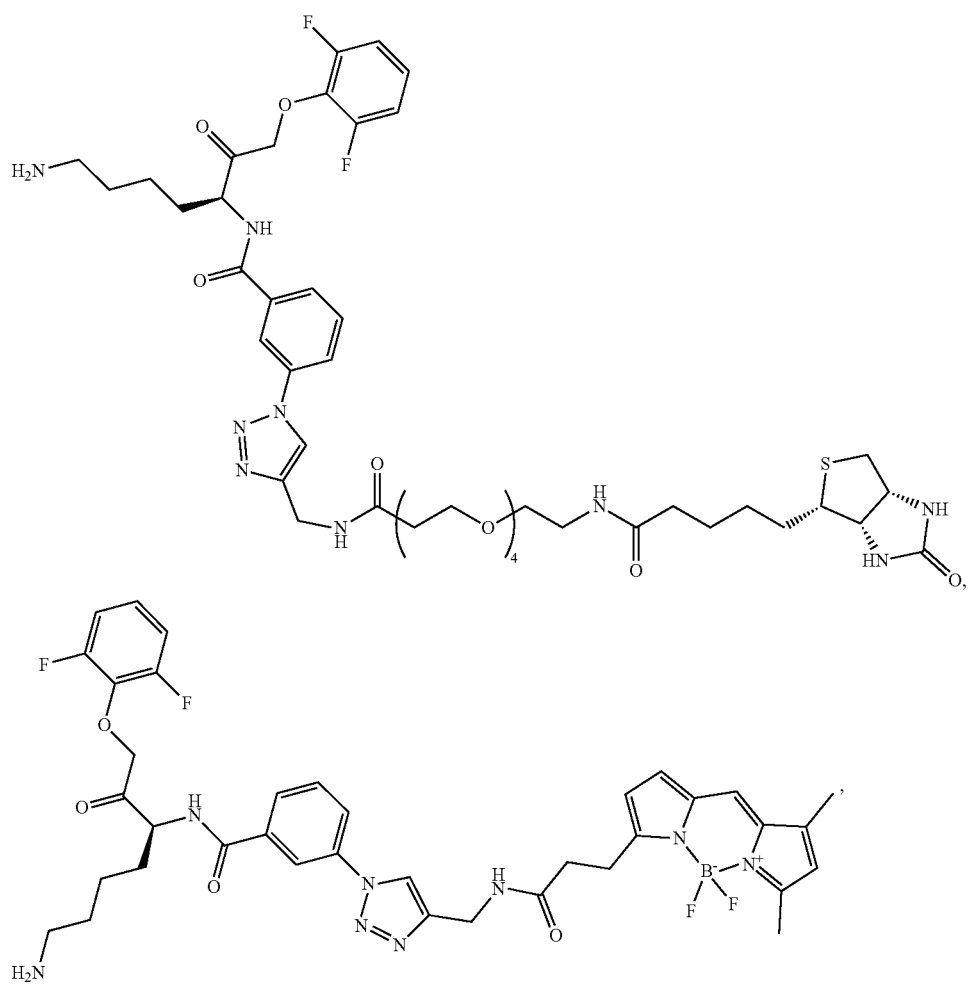

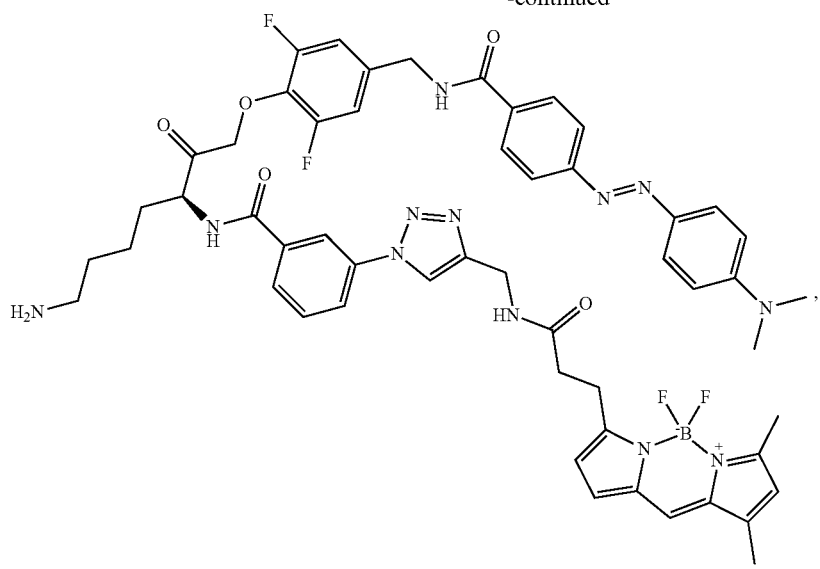
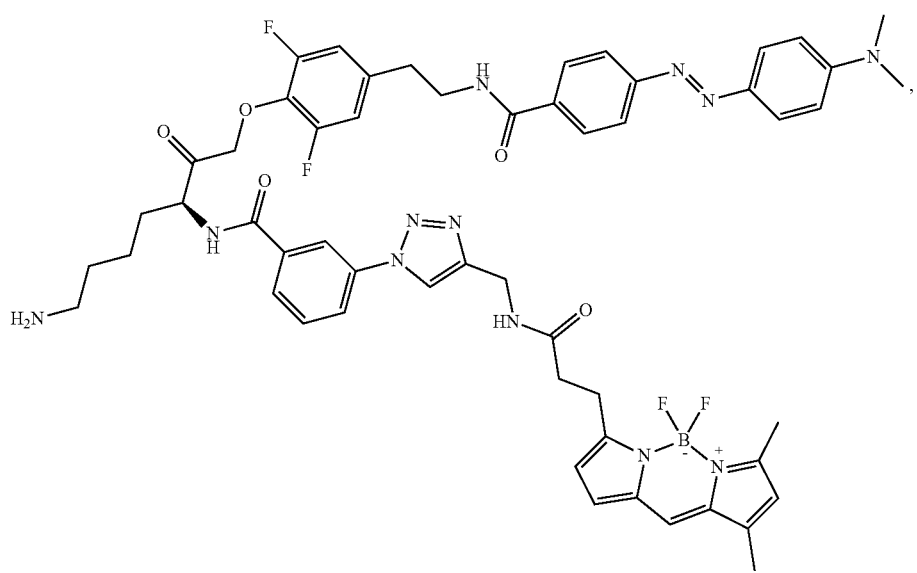
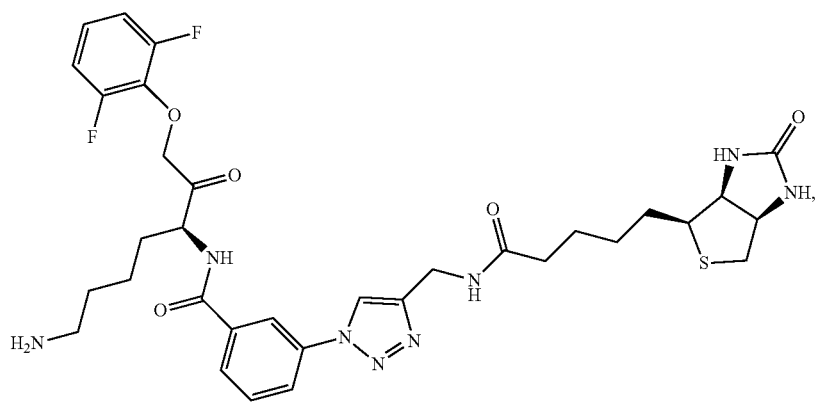

-continued
141
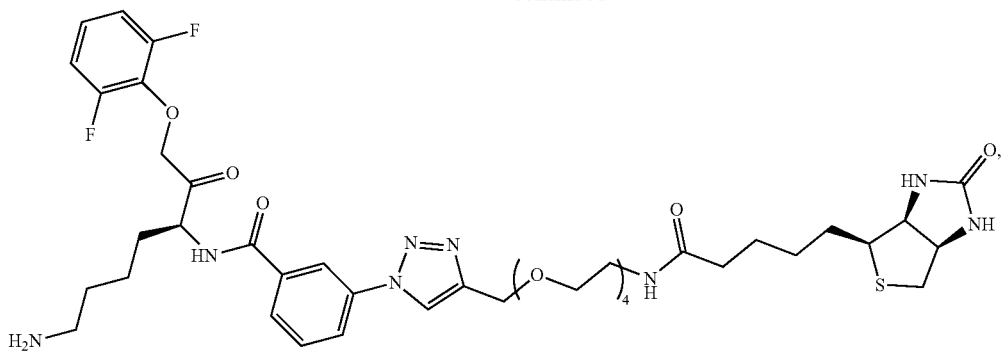
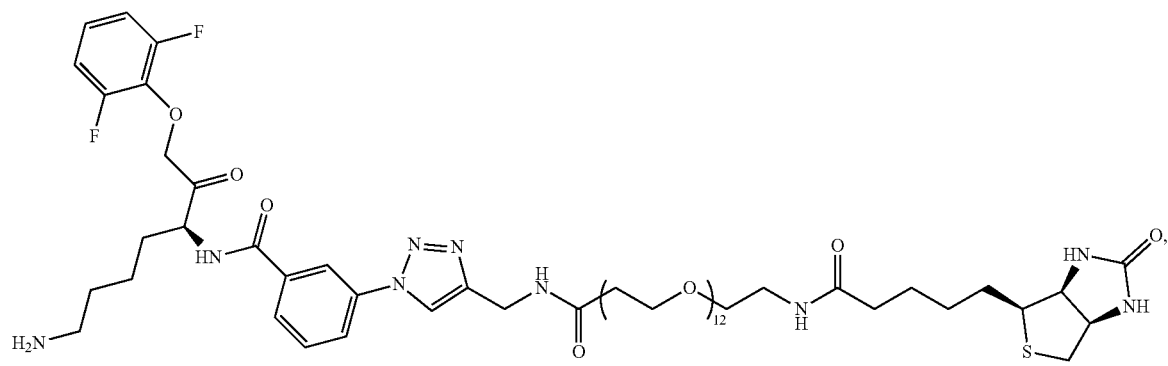
142
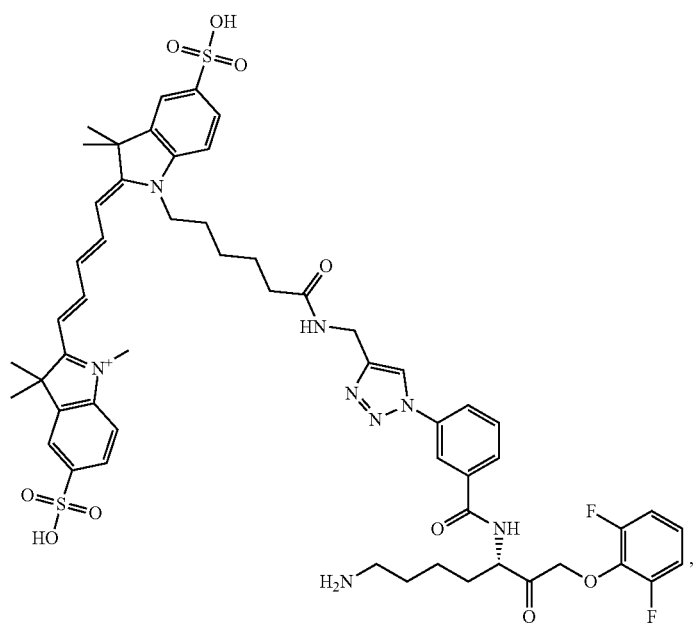

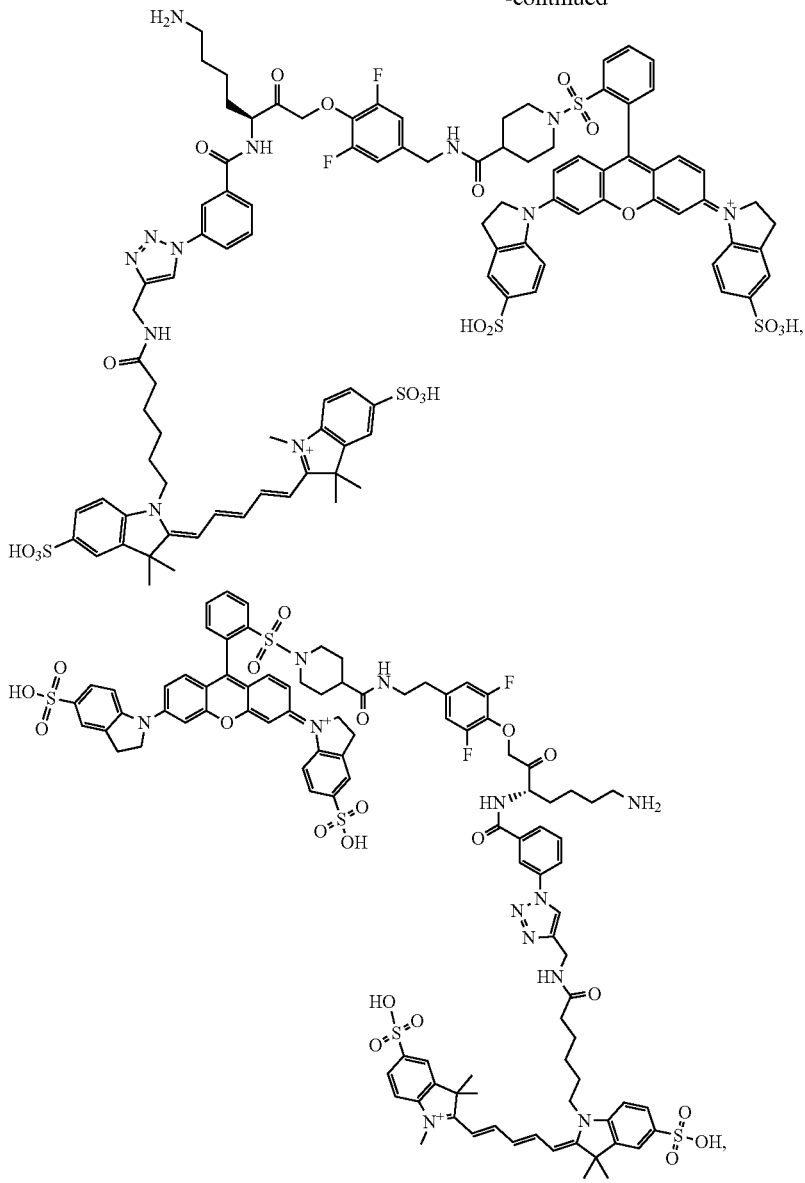

and pharmaceutically acceptable salts thereof.

VII. Methods for Probing Gingipain Activity

In another embodiment, the invention provides a method of detecting gingipain activity in a biological sample. The method includes: forming a mixture comprising the biological sample and a compound as described above under conditions sufficient for a gingipain to react with the gingipain reactive moiety of the compound; detecting the reporter moiety of the compound in the mixture; and determining that a gingipain is present in the biological sample when the reporter moiety is detected. In some embodiments, the method further includes removing unreacted compound from the mixture prior to detecting the reporter moiety of the compound in the mixture.

Any suitable biological sample can be assayed using the methods of the invention. Examples of suitable biological samples include, but are not limited to, tissue samples (e.g., gingival tissue samples or brain tissue samples), cell samples (e.g., mammalian cells obtained via buccal swab in the mouth of a patient or bacterial cells cultured from a human sample), blood or serum samples, and saliva samples.

The manner in which the biological sample and a gingipain activity probe are brought into contact with each other will depend, in part, on factors such as the type of sample being assayed and the method by which the reporter moiety in the activity probe is detected. When gingipain activity is to be detected in a cell sample, for example, cells can be suspended in an aqueous buffer (e.g., phosphate-buffered saline, citrate-phosphate buffers, and the like) and combined in a mixture containing the gingipain activity probe and an optional co-solvent (e.g., dimethylsulfoxide, N,N-dimethylformamide, and the like) such that the activity probe reacts with gingipains present in the cell sample. The activity probe will typically be used in concentrations ranging from around 1 μM to around 5 mM, and the cells will be incubated at temperatures ranging from around 4° C. to around 40° C. for a period of time ranging from a few minutes to several hours, or longer. The cells can be collected from the mixture via centrifugation after the incubation period, and unreacted activity probe can be removed from the mixture by repeated resuspension and centrifugation of the cells in a suitable volume of buffer. The cells can then be examined with a light microscope or fluorescence microscope, and detection of a colorimetric or fluorescent reporter moiety can be used to determine the presence and/or localization of gingipains in the cells.

The wavelength or wavelengths at which a colorimetric or fluorescent reporter moiety is detected will depend on factors including, but not limited to, the structure of the activity probe and the conditions under which the sample is analyzed. UV-visible absorption by reporter moieties can be measured, for example, at wavelengths ranging from about 190 nm to about 1100 nm (e.g., between 190 and 380 nm, or between 380 and 750 nm). Fluorescent reporter moieties can be excited at wavelengths ranging from about 300 nm to about 800 nm, and the resulting fluorescence emission can be detected as wavelengths ranging from about 350 nm to about 800 nm. Other absorption wavelengths, excitation wavelengths, and emission wavelengths can be used for detection of labeled gingipains, depending on the particular activity probe or sample employed. The reporter moiety can be detected by means that include visible inspection, photographic film, or use of instrumentation such as fluorimeters, quantum counters, plate readers, microscopes and flow cytometers. Instrumentation for UV-vis absorption-based and fluorescence-based methods, as well as optical properties of colorimetric and fluorescent moieties, are known to those of skill in the art as described, for example, in *The Molecular Probes™ Handbook*, 11$^{th}$ *Edition* (2010).

In certain embodiments, a gingipain activity probe contains a quenching moiety that prevents detection of an absorbance signal and/or a fluorescence signal from a reporter moiety on the probe prior to binding a gingipain. For example, an activity probe with a fluorescein, rhodamine, or cyanine reporter moiety can contain a gingipain-reactive moiety comprising an aminobenzene quenching moiety such as dabcyl. The proximity of the reporter moiety and the quenching moiety prior to reaction with a target gingipain will prevent fluorescence detection, which can advantageously reduce background signal. Release of the quenching moiety upon reaction of the gingipain-reactive moiety with the target gingipain then allows for detection of the fluorescent reporter moiety.

A biological sample obtained from a subject can be used to prepare a cell lysate or tissue lysate, and the lysate can be combined with an activity probe as described above such that gingipains in the lysate react with the probe. Unreacted activity probe may be removed from the lysate mixture via gel filtration, and gingipains can be identified in the mixture via detection of the reporter moiety via UV-vis absorption spectroscopy or fluorimetry. Alternatively, labeled gingipains can be separated from unreacted activity probe and other mixture components via electrophoresis (e.g., SDS-PAGE, capillary electrophoresis, isoelectric focusing, and the like). Labeled gingipains can be detected in a resolved sample such as a polyacrylamide gel by detecting a colorimetric or fluorescent activity probe. If a biotin, a FLAG peptide, or another affinity-based reporter moiety is used, the gel can be probed with a labeled binding partner such as streptavidin-fluorescein or a labeled antibody (or a primary/secondary antibody pair) to detect labeled gingipains in the resolved sample. If necessary, labeled gingipains can be transferred by electroblotting from a polyacrylamide gel or other resolved sample to a suitable support material such as nitrocellulose, polyvinylidene fluoride (PVDF), or the like prior to the detection step.

A tissue sample can be obtained from a subject, sectioned, and mounted for treatment with a gingipain activity probe. The sample may be freshly frozen, and optionally fixed with ethanol, formalin, or another suitable fixative prior to treatment with the gingipain activity probe. Unreacted activity probe may be removed from the tissue sample by immersing the mounted sample in one or more portions of water or buffer prior to detection of the reporter moiety. The use of probes with a quenching moiety can enable the detection of a signal in tissue samples without the necessity to remove any unreacted activity probe. Labeled gingipains can be detected using a light microscope or fluorescence microscope as described above in conjunction with one or more labeled binding partners if necessary.

When gingipains are labeled with an activity probe having an affinity-based reporter moiety (e.g., a biotin, a digoxigenin, a FLAG peptide, or other epitope), labeled gingipains can be separated from complex mixtures (e.g., a cell lysate or tissue lysate) using a binding partner immobilized on a suitable support. As a non-limiting example, gingipains can be modified with a biotin activity probe and bound to streptavidin beads (e.g., crosslinked polysaccharides, porous silica gel, magnetic particles, or the like bearing covalently or non-covalently bound streptavidin). The beads with bound gingipains can be isolated from the mixture via physical means such as centrifugation or filtration prior to detection of the reporter moiety in the activity probe. Surfaces bearing antibodies specific for a reporter moiety epitope (e.g., a FLAG peptide) can be used for binding and detecting labeled antibodies via techniques including, but not limited to, ELISA (including sandwich ELISA and competitive ELISA) and surface plasmon resonance analysis.

VIII. Examples

Example 1. Preparation of (S)—N-(7-amino-2-oxo-1-(2,3,6-trifluorophenoxy)heptan-3-yl)cyclopentanecarboxamide (1) hydrochloride

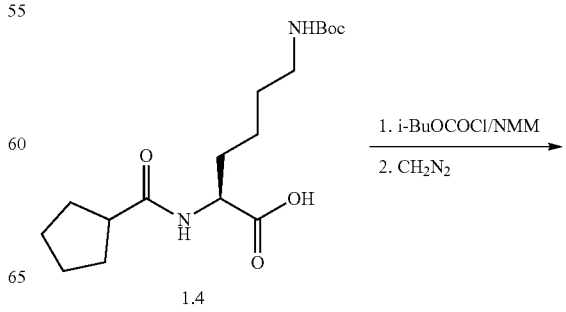

1.4

-continued

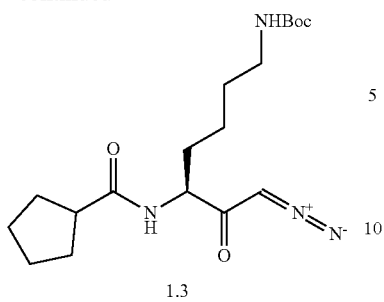

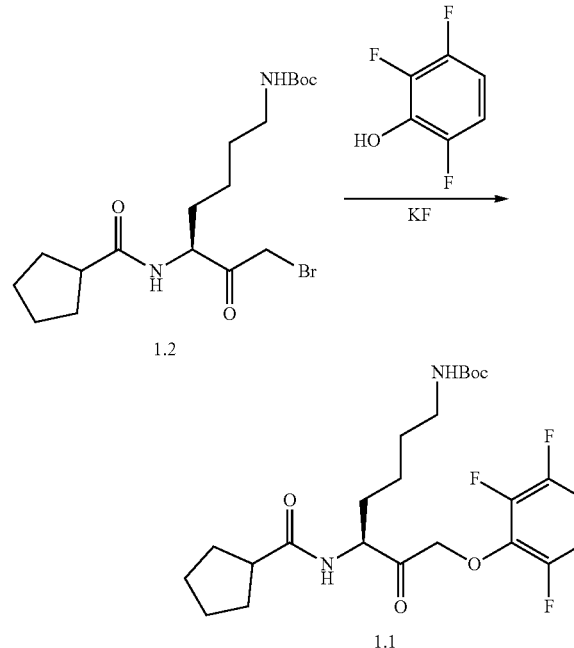

To a mixture of compound 1.4 (23.0 g, 67.2 mmol, 1.00 eq) in THF (200 mL) was added NMM (6.79 g, 67.2 mmol, 7.38 mL, 1.00 eq), isobutyl carbonochloridate (9.17 g, 67.2 mmol, 8.82 mL, 1.00 eq), and diazomethane (5.65 g, 134 mmol, 2.00 eq) at −40° C. under $N_2$ (15 psi). The mixture was stirred at 0° C. for 30 min. LCMS showed the reaction was completed. $H_2O$ (200 mL) was added to the reaction and extracted with two 300-mL portions of ethyl acetate. The combined organic phase was washed with two 200-mL portions of brine (200, dried with anhydrous $Na_2SO_4$, filtered and concentrated under vacuum to provide crude compound 1.3 (30.0 g, crude) as a yellow oil.

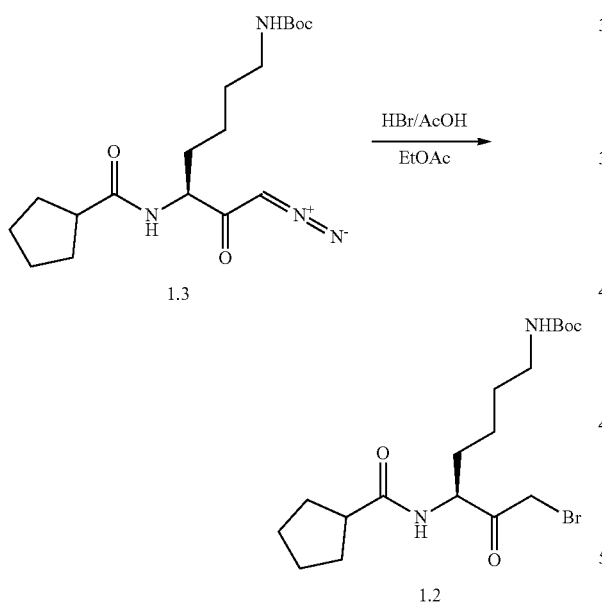

To a mixture of compound 1.3 (20.0 g, 54.6 mmol, 1.00 eq) in EtOAc (300 mL) was added hydrogen bromide (29.8 g, 121.7 mmol, 20.0 mL, 33% purity, 2.23 eq) at −20° C. under $N_2$ (15 psi). The mixture was stirred at −20° C. for 10 min. TLC (petroleum ether:ethyl acetate=0:1) showed the reaction was completed. The reaction was basified by addition of saturated $NaHCO_3$ until the pH of the mixture reached 8, and the mixture was extracted with three 500-mL portions of EtOAc. The combined organic phase was washed with two 200-mL portions of brine, dried over anhydrous $Na_2SO_4$, filtered and concentrated under vacuum to afford crude compound 1.2 (15.0 g, crude) as a yellow solid.

To a mixture of compound 1.2 (4.00 g, 9.54 mmol, 1.00 eq) in DMF (40.0 mL) was added 2,6-difluorophenol (1.49 g, 11.4 mmol, 1.20 eq) and KF (1.66 g, 28.6 mmol, 670 μL, 3.00 eq) at 25° C. The mixture was stirred at 25° C. for 3 h. TLC (petroleum ether:ethyl acetate=1:1) showed the reaction was completed. $H_2O$ (150 mL) was added to the mixture and extracted with two 200-mL portions of ethyl acetate. The combined organic phase was washed with two 100-mL portions of brine, dried with anhydrous $Na_2SO_4$, filtered, and concentrated under vacuum. The residue was purified by silica gel chromatography (petroleum ether:ethyl acetate=100:1, 5:1) to afford compound 1.1 (2.50 g, 5.35 mmol, 56.1% yield) as a yellow solid.

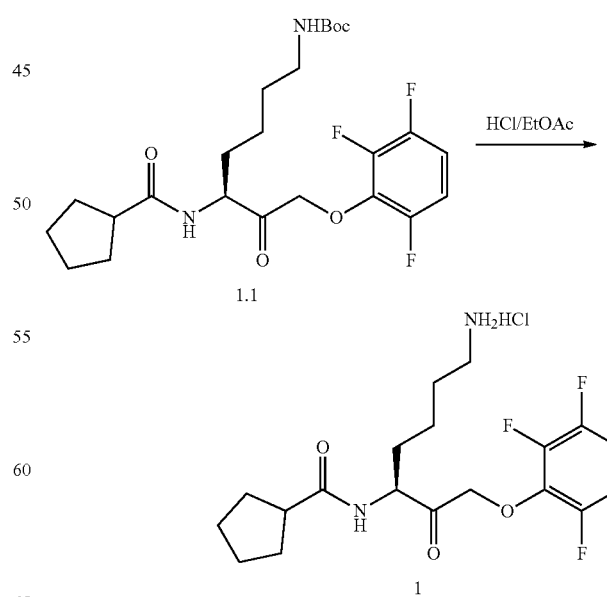

To a mixture of compound 1.1 (4.00 g, 8.22 mmol, 1.00 eq) in EtOAc (3.00 mL) was added HCl/EtOAc (40.0 mL) at 25° C. The mixture was stirred at 25° C. for 2 h. TLC (petroleum ether:ethyl acetate=2:1) showed the reaction was completed. The mixture was concentrated in reduced pressure to provide (S)—N-(7-amino-2-oxo-1-(2,3,6-trifluorophenoxy)heptan-3-yl)cyclopentanecarboxamide 1 hydrochloride salt (1.34 g, 3.16 mmol) as a light yellow solid. LCMS (ESI): m/z: [M+H] calcd for $C_{19}H_{25}N_2F_3O_3$: 387.2; found 387.1; RT=2.508 min. $^1$H NMR (400 MHz, DMSO-d$_6$) δ ppm 1.21-1.83 (m, 15H) 2.60-2.81 (m, 3H) 4.30 (ddd, J=9.70, 7.17, 4.52 Hz, 1H) 5.02-5.22 (m, 2H) 7.12-7.24 (m, 2H) 7.98 (br s, 3H) 8.32 (d, J=7.28 Hz, 1H).

Example 2. Preparation of (S)—N-(7-amino-1-(2,6-difluorophenoxy)-2-oxoheptan-3-yl)cyclopentanecarboxamide (2) hydrochloride

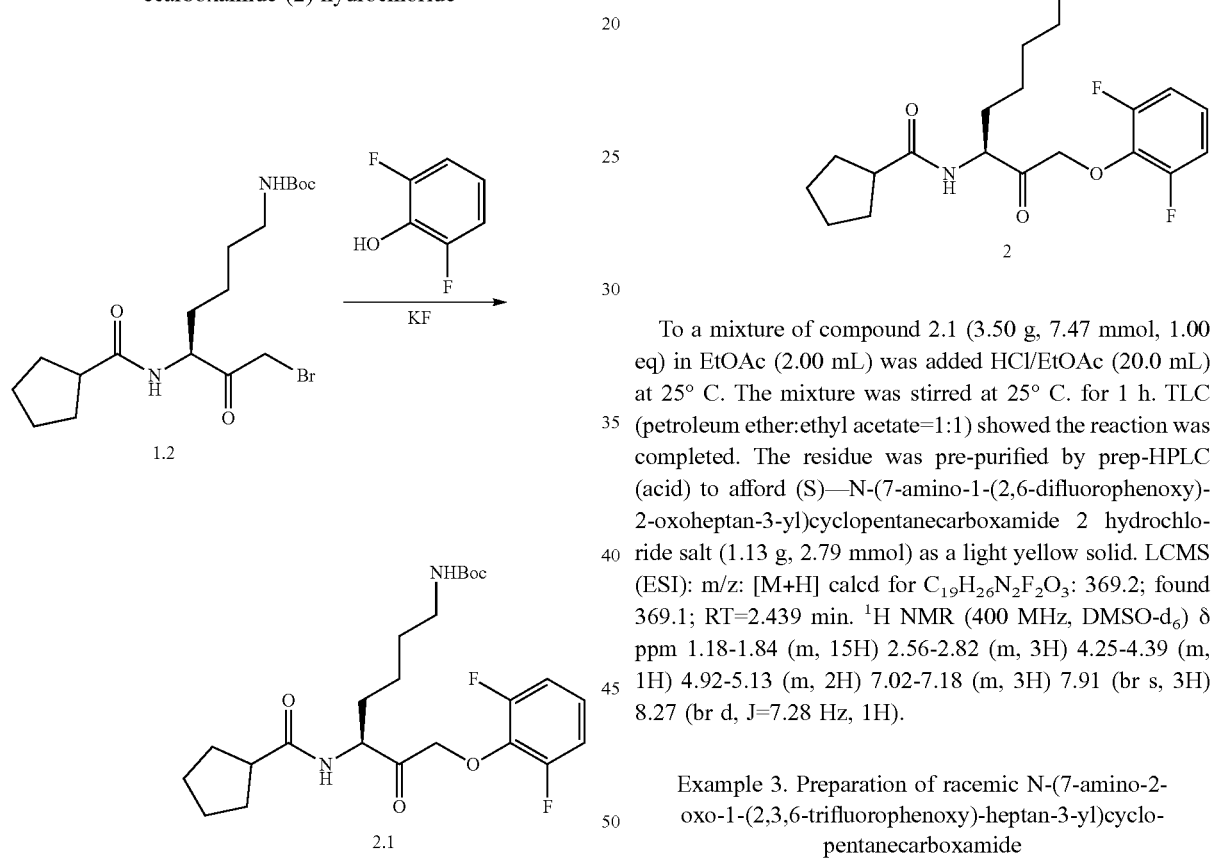

Compound 1.2 (4.00 g, 9.54 mmol, 1.00 eq) was prepared as described above and combined with DMF (40.0 mL), 2,6-difluorophenol (1.49 g, 11.5 mmol, 1.20 eq), and KF (1.66 g, 28.6 mmol, 670 μL, 3.00 eq) at 25° C. The mixture was stirred at 25° C. for 3 h. TLC (petroleum ether:ethyl acetate=1:1) showed the reaction was completed. H$_2$O (150 mL) was added to the mixture and extracted with ethyl acetate (100 mL*2). The combined organic phase was washed with brine (100 mL*2), dried with anhydrous Na$_2$SO$_4$, filtered and concentrated under vacuum. The residue was purified by silica gel chromatography (petroleum ether:ethyl acetate=100:1, 5:1) to afford compound 2.1 (2.50 g, 5.35 mmol, 56.1% yield) as a yellow solid.

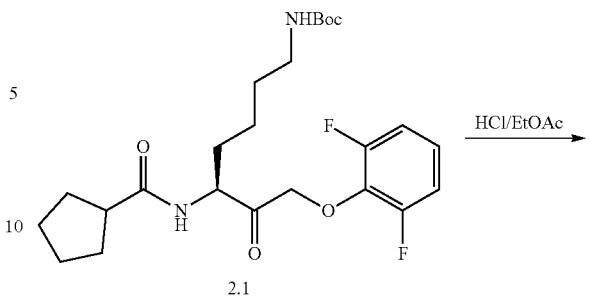

To a mixture of compound 2.1 (3.50 g, 7.47 mmol, 1.00 eq) in EtOAc (2.00 mL) was added HCl/EtOAc (20.0 mL) at 25° C. The mixture was stirred at 25° C. for 1 h. TLC (petroleum ether:ethyl acetate=1:1) showed the reaction was completed. The residue was pre-purified by prep-HPLC (acid) to afford (S)—N-(7-amino-1-(2,6-difluorophenoxy)-2-oxoheptan-3-yl)cyclopentanecarboxamide 2 hydrochloride salt (1.13 g, 2.79 mmol) as a light yellow solid. LCMS (ESI): m/z: [M+H] calcd for $C_{19}H_{26}N_2F_2O_3$: 369.2; found 369.1; RT=2.439 min. $^1$H NMR (400 MHz, DMSO-d$_6$) δ ppm 1.18-1.84 (m, 15H) 2.56-2.82 (m, 3H) 4.25-4.39 (m, 1H) 4.92-5.13 (m, 2H) 7.02-7.18 (m, 3H) 7.91 (br s, 3H) 8.27 (br d, J=7.28 Hz, 1H).

Example 3. Preparation of racemic N-(7-amino-2-oxo-1-(2,3,6-trifluorophenoxy)-heptan-3-yl)cyclopentanecarboxamide

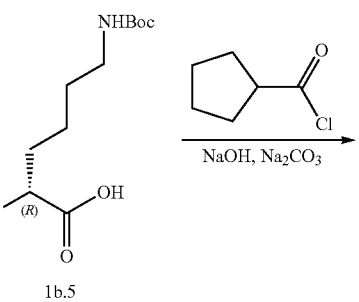

-continued

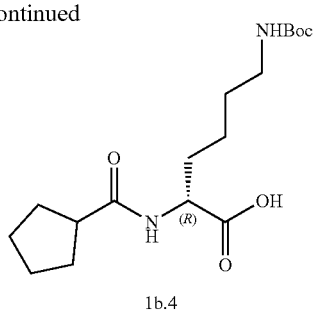
1b.4

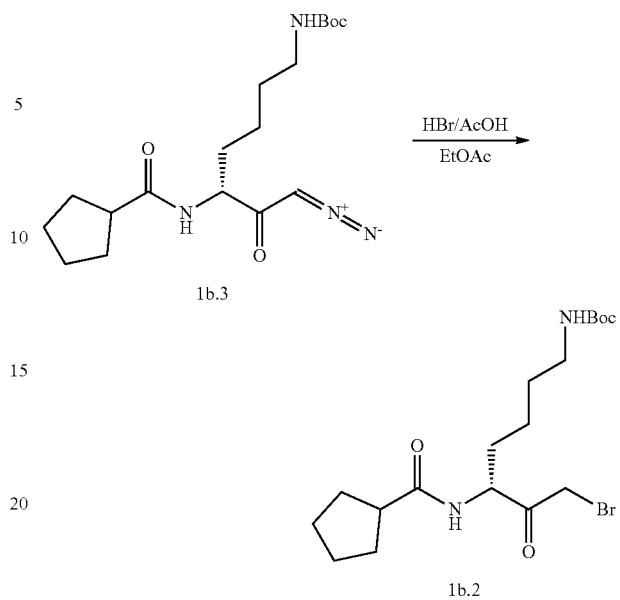
1b.3 → 1b.2

To a mixture of cyclopentanecarboxylic acid (4.40 g, 38.6 mmol, 4.19 mL, 0.95 eq) in DCM (50.0 mL) was added (COCl)₂ (5.87 g, 46.3 mmol, 4.05 mL, 1.14 eq) at 15° C. The mixture was stirred at 15° C. for 30 min. Then it was concentrated under vacuum to form a residue which was dissolved in EtOAc (40.0 mL). The resulting solution was added dropwise to a mixture of compound 1b.5 (10.0 g, 40.6 mmol, 1.00 eq), Na₂CO₃ (5.16 g, 48.7 mmol, 1.20 eq), and NaOH (1.64 g, 41.0 mmol, 1.01 eq) in H₂O (80.0 mL) at 0° C. Then the mixture was stirred at 15° C. for 14 hours. LCMS showed the reaction was completed. The ethyl acetate was removed, and the remaining solution was cooled to 0° C. prior to adjustment of the pH to 6-7 with solid KHSO₄. The mixture was filtered to collect compound 1b.4 (12.0 g, 35.0 mmol, 86.3% yield) as a white solid.

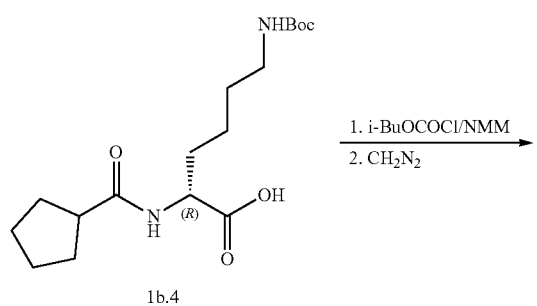
1b.4

To a mixture of compound 1b.4 (12.0 g, 35.0 mmol, 1.00 eq) in THF (300 mL) was added NMM (3.54 g, 35.0 mmol, 3.85 mL, 1.00 eq) isobutyl carbonochloridate (4.79 g, 35.0 mmol, 4.61 mL, 1.00 eq), and diazomethane (2.95 g, 70.1 mmol, 2.00 eq) at −40° C. under N₂ (15 psi). The mixture was stirred at 0° C. for 30 min. TLC (petroleum ether:ethyl acetate=0:1) showed the reaction was completed. H₂O (100 mL) was added to the reaction and extracted with two 200-mL portions of ethyl acetate. The combined organic phase was washed with two 100-mL portions of brine, dried with anhydrous Na₂SO₄, filtered, and concentrated under vacuum to provide compound 1b.3 (13.7 g, crude) as a yellow oil.

To a mixture of compound 1b.3 (13.7 g, 37.4 mmol, 1.00 eq) in EtOAc (140 mL) was added hydrogen bromide (20.9 g, 85.3 mmol, 14.0 mL, 33% purity, 2.28 eq) at −20° C. under N₂ (15 psi). The mixture was stirred at −20° C. for 10 min. TLC (petroleum ether:ethyl acetate=2:1) showed the reaction was completed. The reaction was basified by sat. NaHC$_{O3}$ until the pH reach 8, and the mixture was extracted with three 200-mL portions of EtOAc. The combined organic phase was washed with two 100-mL portions of brine, dried over anhydrous Na₂SO₄, filtered, and concentrated under vacuum to afford compound 1b.2 (8.80 g, crude) as a yellow solid.

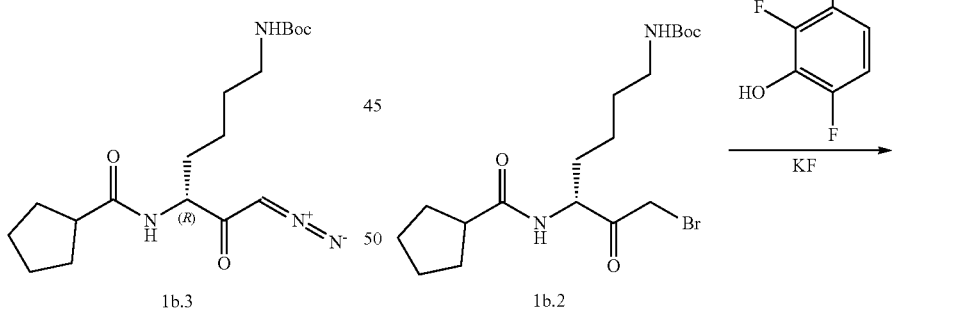
1b.2 → 21.1

To a mixture of compound 1b.2 (400 mg, 954 μmol, 1.00 eq) in DMF (10.0 mL) was added KF (166 mg, 2.86 mmol, 67.0 μL, 3.00 eq) and 2,3,6-trifluorophenol (170 mg, 1.14 mmol, 1.20 eq) at 25° C. The mixture was stirred at 25° C. for 10 h. TLC (petroleum ether:ethyl acetate=2:1) showed the reaction was completed. Then the mixture was diluted with H₂O (10 mL) and extracted with three 10-mL portions of EtOAc. The organic layers were combined, washed with brine (10 mL), dried over Na₂SO₄, filtered, and concentrated under reduced pressure to afford compound 21.1 (400 mg, 822 μmol, 86.2% yield) as a yellow oil.

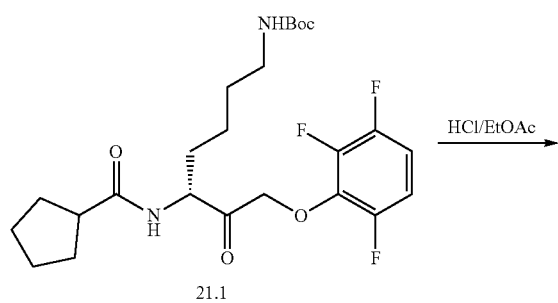

To a mixture of compound 21.1 (400 mg, 822 μmol, 1.00 eq) in EtOAc (5.00 mL) was added HCl/EtOAc (822 μmol, 15.0 mL, 1.00 eq) at 25° C. The mixture was stirred at 25° C. for 30 min. TLC (petroleum ether:ethyl acetate=2:1) showed the reaction was completed. The reaction was concentrated under reduced pressure. The residue was purified by prep-HPLC to provide compound 21 trifluoroacetate salt (90.0 mg, 213 μmol, 25.9% yield) as a light yellow solid.

Compound 1 (36 mg) and compound 21 (36 mg) were mixed with water (2 mL) and MeOH (0.5 mL). Then, the solvent was removed by lyophilization to provide racemic N-(7-amino-2-oxo-1-(2,3,6-trifluorophenoxy)heptan-3-yl)cyclopentanecarboxamide trifluoroacetate salt (72 mg).

Example 4. Preparation of racemic N-(7-amino-1-(2,6-difluorophenoxy)-2-oxoheptan-3-yl)cyclopentanecarboxamide

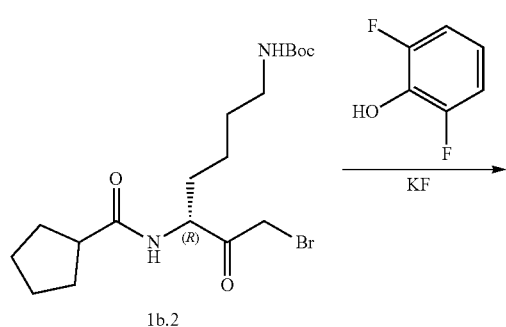

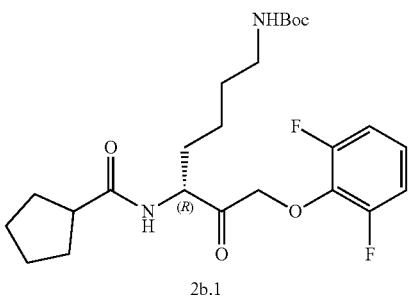

Compound 1b.2 (400 mg, 954 μmol, 1.00 eq), prepared as described above, was combined with DMF (10.0 mL) KF (166 mg, 2.86 mmol, 67.0 μL, 3.00 eq), and 2,6-difluorophenol (149 mg, 1.14 mmol, 1.20 eq) at 25° C. The mixture was stirred at 25° C. for 10 h. TLC (petroleum ether:ethyl acetate=2:1) showed the reaction was completed. The mixture was diluted with H₂O (10 mL) and extracted with three 10-mL portions of EtOAc. The organic layers were combined, washed with brine (10 mL), dried over Na₂SO₄, filtered, and concentrated under reduced pressure to provide crude 2b.1 (400 mg, crude) as a yellow oil.

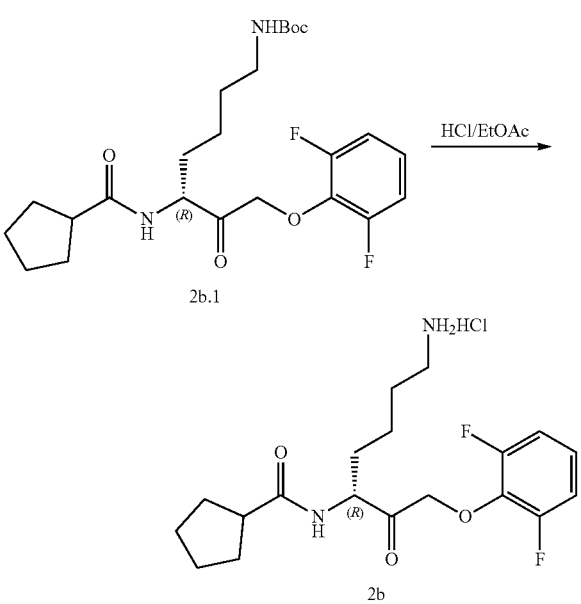

To a mixture of 2b.1 (400 mg, 856 μmol, 1.00 eq) in EtOAc (5.00 mL) was added HCl/EtOAc (856 μmol, 15.0 mL, 1.00 eq) at 25° C. The mixture was stirred at 25° C. for 30 min. TLC (petroleum ether:ethyl acetate=2:1) showed the reaction was completed. The mixture was concentrated under reduced pressure, and the resulting residue was purified by prep-HPLC to afford compound 2b trifluoroacetate salt (70.0 mg, 173 μmol, 20.2% yield) as a light yellow solid.

A racemic mixture of N-(7-amino-1-(2,6-difluorophenoxy)-2-oxoheptan-3-yl)cyclopentanecarboxamide trifluoroacetate salt (55 mg) was prepared by combining compound 2 and compound 2b as described above for compound 1 and compound 21.

Example 5. Preparation of (S)—N-(7-amino-1-(2-fluorophenoxy)-2-oxoheptan-3-yl)cyclo-pentanecarboxamide (3)

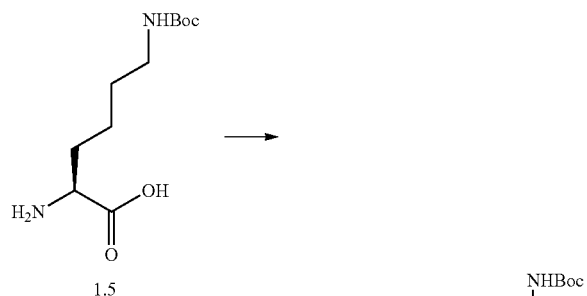

To a mixture of compound 1.5 (10.00 g, 40.60 mmol, 1.00 eq) and cyclopentanecarbonyl chloride (5.92 g, 44.66 mmol, 5.43 mL, 1.10 eq) in EtOAc (20.00 mL) was added Na$_2$CO$_3$ (5.16 g, 48.72 mmol, 1.20 eq) and NaOH (1.64 g, 41.01 mmol, 1.01 eq) in H$_2$O (80.00 mL) at 0° C. under N$_2$. The mixture was stirred at 10° C. for 3 hours. EtOAc was removed and then the solution was cooled to 0° C., and the pH was adjusted to 6-7 with HCl (1N). The suspension was filtered, and the filter cake was washed with 50 mL of PE and dried under vacuum to afford compound 1.4 (10.60 g, 30.96 mmol, 76.26% yield) as a white solid. LCMS (ESI): m/z: [M+H] calcd for C$_{17}$H$_{30}$N$_2$O$_5$: 343.4; found 343.2; RT=1.022 min.

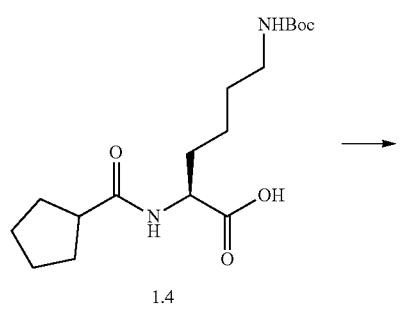

To a mixture of compound 1.4 (2.00 g, 5.84 mmol, 1.00 eq) in THF (20.00 mL) was added NMM (708.86 mg, 7.01 mmol, 770.50 μL, 1.20 eq) and isobutyl carbonochloridate (797.61 mg, 5.84 mmol, 766.93 μL, 1.00 eq) in one portion at −20° C. under N$_2$. The mixture was stirred at −20° C. for 1 hour. A diazomethane solution in Et$_2$O (20 ml) was added at 0° C. and stirred for 2 hours. The mixture was diluted with H$_2$O (20 mL) and extracted with EtOAc (3×20 mL). The organic layers were combined, dried over Na$_2$SO$_4$, filtered, and concentrated under reduced pressure to give a residue, which was purified by silica gel chromatography (PE/EtOAc=1/1) to afford compound 1.3 (130.00 mg, 354.76 μmol) as a yellow solid. LCMS (ESI): m/z: [M+H] calcd for C$_{18}$H$_{30}$N$_4$O$_4$: 367.4; found 339.2; RT=0.772 min.

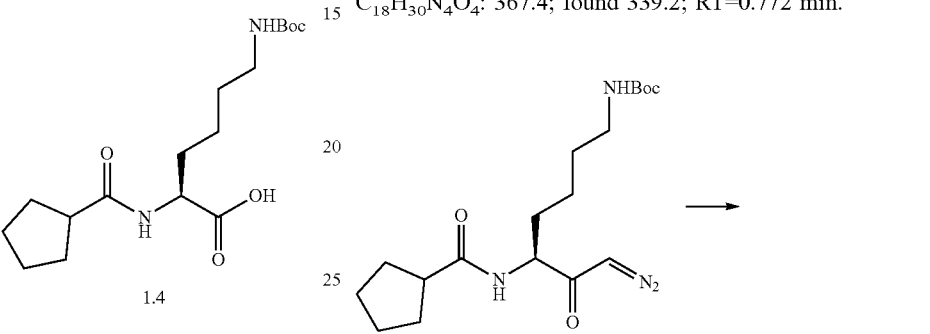

To a mixture of compound 1.3 (130.00 mg, 354.75 μmol, 1.00 eq) in EtOAc (1.00 mL) was added HBr/AcOH (150.00 μL, 33% purity) in one portion at −20° C. under N$_2$. The mixture was stirred at −20° C. for 10 mins under N$_2$, basified with sat. NaHCO$_3$ to pH=8, and extracted with EtOAc (3×10 mL). The organic layers were combined, dried over Na$_2$SO$_4$, filtered, and concentrated to afford compound 1.2 (100.00 mg, 238.46 μmol, 67.22% yield) as a white solid. LCMS (ESI): m/z: [M+H] calcd for C$_{18}$H$_{31}$N$_2$O$_4$: 420.3; found 316.2; RT=0.709 min.

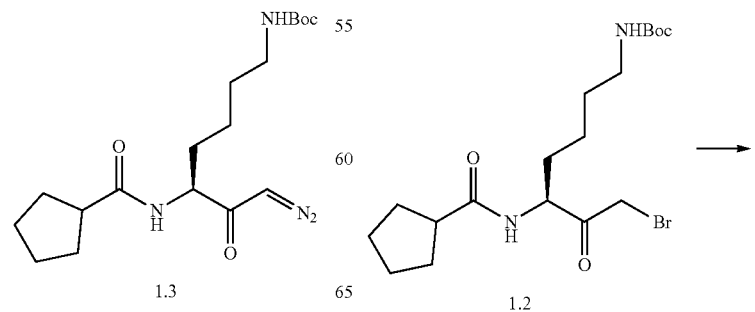

-continued

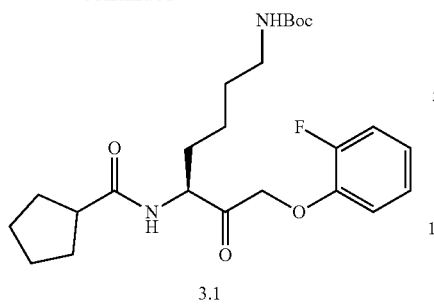

3.1

To a mixture of compound 1.2 (50.00 mg, 119.23 μmol, 1.00 eq) and 2-fluorophenol (13.37 mg, 119.23 μmol, 11.05 μL, 1.00 eq) in DMF (1.00 mL) was added KF (20.78 mg, 357.69 μmol, 8.38 μL, 3.00 eq) in one portion at 20° C. under $N_2$. The mixture was stirred at 20° C. for 15 hours. The aqueous phase was extracted with EtOAc (3×5 mL 3). The combined organic phase was washed with brine (3 mL), dried with anhydrous $Na_2SO_4$, filtered, and concentrated under vacuum. Then the residue was purified by prep-HPLC (TFA condition) to afford compound 3.1 (15.00 mg, 33.29 μmol, 27.92% yield) as a yellow oil. LCMS (ESI): m/z: [M+H] calcd for $C_{24}H_{36}N_2O_5F$: 451.5; found 451.4; RT=0.929 min.

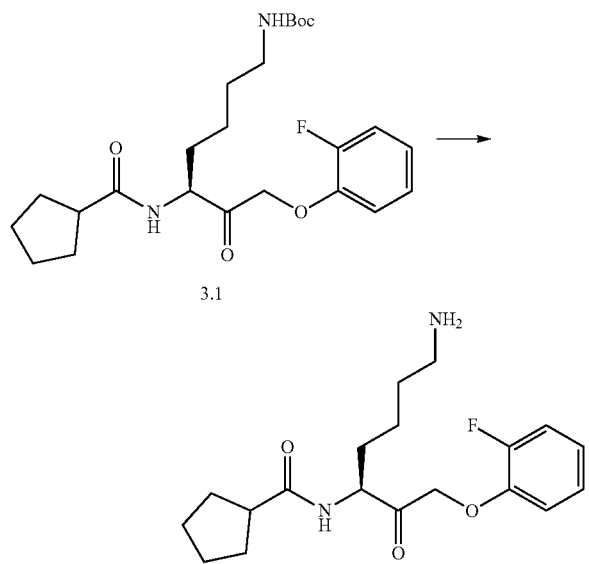

A mixture of compound 3.1 (15.00 mg, 33.29 μmol, 1.00 eq) in HCl/EtOAc (1.00 mL) was stirred at 20° C. for 3 hours. The solution was evaporated to remove organic solvents. The residual aqueous solution was lyophilized to afford compound 3 hydrochloride salt (2.00 mg, 5.71 μmol, 17.14% yield) as a white solid. LCMS (ESI): m/z: [M+H] calcd for $C_{19}H_{28}N_2O_3F$: 351.4; found 351.3; RT=2.477 min. $^1$H NMR (400 MHz, DMSO-$d_6$) δ ppm 1.25-1.83 (m, 17H) 2.61-2.87 (m, 4H) 4.24-4.43 (m, 1H) 4.95-5.13 (m, 2H) 6.87-7.27 (m, 4H) 7.83 (br s, 3H) 8.31 (d, J=6.90 Hz, 1H).

Example 6. Preparation of (S)—N-(7-amino-2-oxo-1-(2,3,5-trifluorophenoxy)heptan-3-yl)cyclopentanecarboxamide (4)

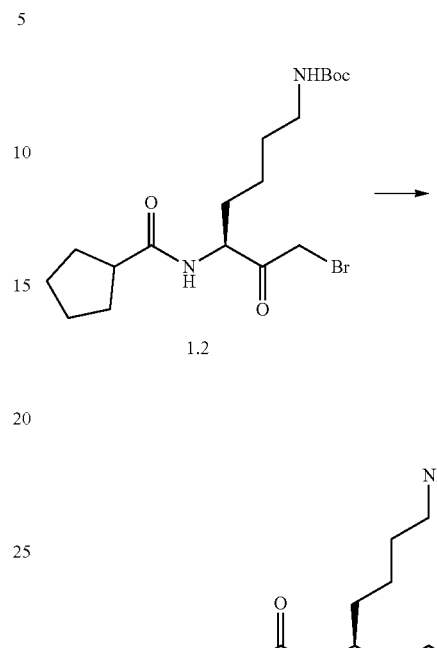

1.2

4.1

To a mixture of compound 1.2 (100.00 mg, 238.46 μmol, 1.00 eq) and 2,3,5-trifluorophenol (42.37 mg, 286.15 μmol, 1.20 eq) in DMF (1.00 mL) was added KF (41.56 mg, 715.38 μmol, 16.76 μL, 3.00 eq) in one portion at 25° C. under $N_2$. The mixture was stirred at 25° C. for 15 hours. The reaction mixture was poured into $H_2O$ (50 mL), and the aqueous phase was extracted with EtOAc (3×20 mL). The combined organic phase was washed with brine (5 mL), dried with anhydrous $Na_2SO_4$, filtered, and concentrated under vacuum. Then the residue was purified by prep-HPLC (TFA condition) to afford compound 4.1 (50.00 mg, 102.77 μmol, 43.10% yield) as a white solid. LCMS (ESI): m/z: [M+H] calcd for $C_{24}H_{33}N_2F_3O_5$: 487.2; found 487.3; RT=0.936 min.

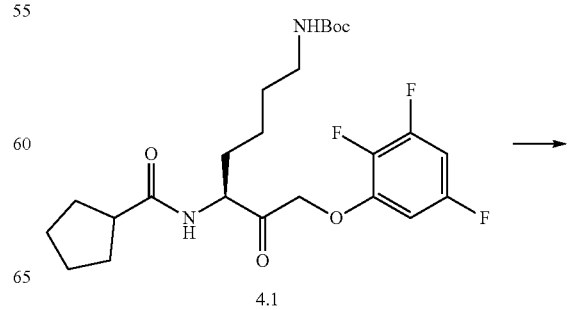

4.1

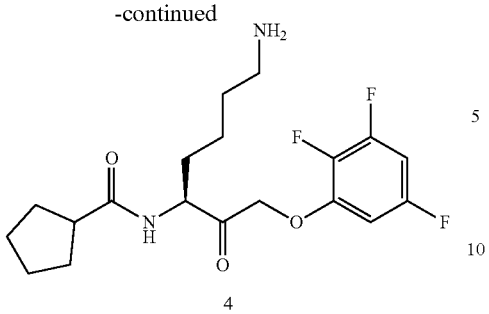
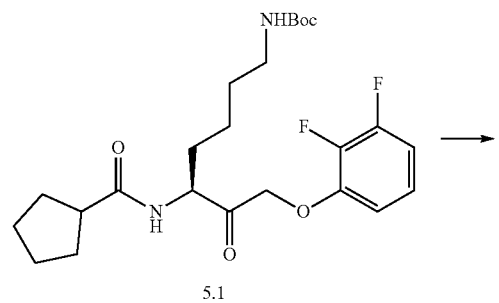

A mixture of compound 4.1 (50.00 mg, 102.77 μmol, 1.00 eq) in HCl/EtOAc (2.00 mL) was stirred under $N_2$ at 20° C. for 15 hours. The solution was evaporated to remove organic solvents. The residual aqueous solution was lyophilized to afford compound 4 hydrochloride salt (30.00 mg, 77.64 μmol, 75.55% yield) as a white solid. LCMS (ESI): m/z: [M+H] calcd for $C_{19}H_{25}N_2F_3O_3$: 387.2; found 387.2; RT=2.321 min. $^1$H NMR (400 MHz, DMSO-$d_6$) δ ppm 1.24-1.85 (m, 15H) 2.63-2.83 (m, 3H) 4.20-4.35 (m, 1H) 5.18 (d, J=1.32 Hz, 2H) 6.83-7.14 (m, 2H) 7.98 (br s, 3H) 8.44 (d, J=6.62 Hz, 1H).

Example 7. Preparation of (S)—N-(7-amino-1-(2,3-difluorophenoxy)-2-oxoheptan-3-yl)cyclopentanecarboxamide (5)

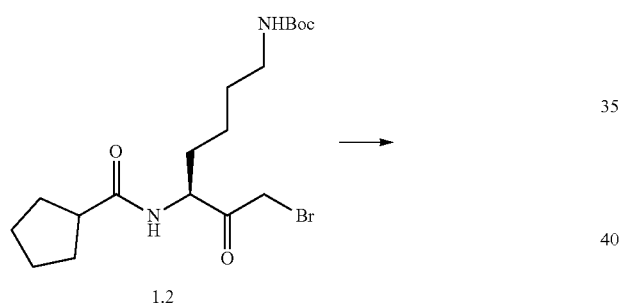

To a mixture of compound 1.2 (100.00 mg, 238.46 μmol, 1.00 eq) in DMF (1.00 mL) was added KF (41.56 mg, 715.38 μmol, 16.76 μL, 3.00 eq) and 2,3-difluorophenol (37.23 mg, 286.15 μmol, 1.20 eq) in one portion at 20° C. under $N_2$. The mixture was stirred at 20° C. for 15 hours. The reaction mixture was poured into $H_2O$ (5 mL), and the aqueous phase was extracted with EtOAc (3×5 mL). The combined organic phase was washed with brine (3 mL), dried with anhydrous $Na_2SO_4$, and filtered and concentrated under vacuum. Then the residue was purified by prep-HPLC (TFA condition) to afford compound 5.1 (50.00 mg, 106.72 μmol, 44.75% yield) as a white solid.

A mixture of compound 5.1 (50.00 mg, 106.72 μmol, 1.00 eq) in HCl/EtOAc (2.00 mL) was stirred under $N_2$ at 20° C. for 15 hours. The solution was evaporated to remove organic solvents. The residual aqueous solution was lyophilized to afford compound 5 hydrochloride salt (15.00 mg, 40.71 μmol, 38.15% yield) as a white solid. LCMS (ESI): m/z: [M+H] calcd for $C_{19}H_{26}N_2F_2O_3$: 369.2; found 369.2; RT=2.246 min. $^1$H NMR (400 MHz, DMSO-$d_6$) δ ppm 1.23-1.83 (m, 15H) 2.62-2.83 (m, 3H) 4.32 (ddd, J=9.59, 6.73, 4.63 Hz, 1H) 5.03-5.19 (m, 2H) 6.77-7.14 (m, 3H) 7.90 (br s, 3H) 8.36 (d, J=6.83 Hz, 1H).

Example 8. Preparation of (S)—N-(7-amino-1-(2,5-difluorophenoxy)-2-oxoheptan-3-yl)cyclopentanecarboxamide (6)

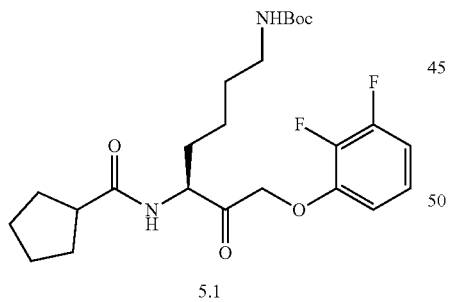

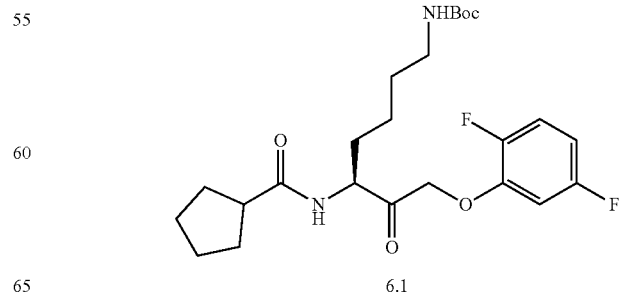

To a mixture of compound 1.2 (100.00 mg, 238.46 µmol, 1.00 eq) in DMF (1.00 mL) was added KF (41.56 mg, 715.38 µmol, 16.76 µL, 3.00 eq) and 2,5-difluorophenol (37.23 mg, 286.15 µmol, 1.20 eq) in one portion at 20° C. under $N_2$. The mixture was stirred at 20° C. for 15 hours. The reaction mixture was poured into $H_2O$ (5 mL), and the aqueous phase was extracted with EtOAc (5 mL*3). The combined organic phase was washed with brine (3 mL), dried with anhydrous $Na_2SO_4$, filtered, and concentrated under vacuum. Then the residue was purified by prep-HPLC (TFA condition) to afford compound 6.1 (41.00 mg, 87.51 µmol, 36.70% yield) as a white solid.

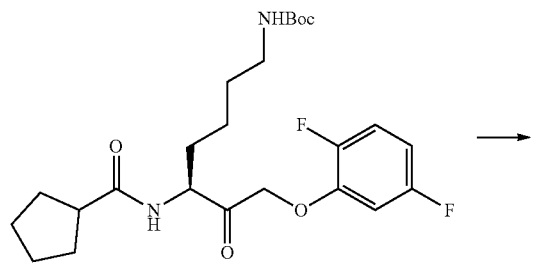

6.1

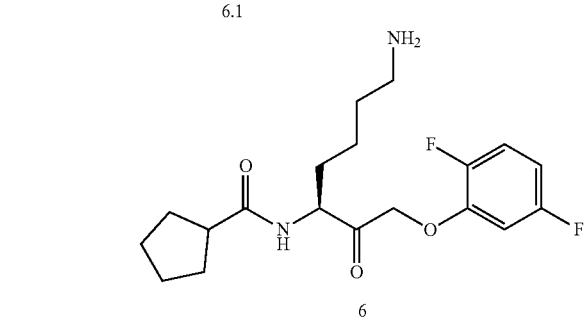

6

A mixture of compound 6.1 (41.00 mg, 87.51 µmol, 1.00 eq) in HCl/EtOAc (2.00 mL) was stirred under $N_2$ at 20° C. for 15 hours. The solution was evaporated to remove organic solvents. The residual aqueous solution was lyophilized to afford compound 6 hydrochloride salt (17.00 mg, 46.14 µmol, 52.73% yield) as a white solid. LCMS (ESI): m/z: [M+H] calcd for $C_{19}H_{26}N_2F_2O_3$: 369.2; found 369.2; RT=2.239 min. $^1$H NMR (400 MHz, DMSO-$d_6$) δ ppm 1.10-1.85 (m, 16H) 2.62-2.84 (m, 3H) 4.31 (br t, J=10.23 Hz, 1H) 5.02-5.18 (m, 2H) 6.69-7.33 (m, 3H) 7.85 (br s, 3H) 8.35 (br d, J=6.65 Hz, 1H).

Example 9. Preparation of (S)—N-(7-amino-1-(3-fluorophenoxy)-2-oxoheptan-3-yl)cyclopentanecarboxamide (7)

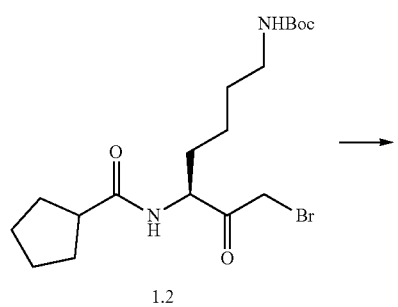

1.2

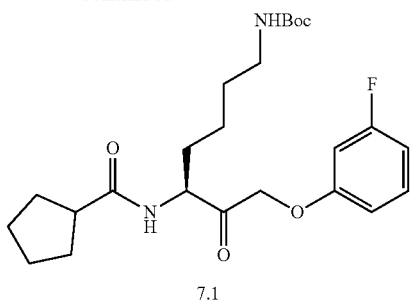

7.1

To a mixture of compound 1.2 (100.00 mg, 238.46 µmol, 1.00 eq) in DMF (1.00 mL) was added KF (41.56 mg, 715.38 µmol, 16.76 µL, 3.00 eq) and 3-fluorophenol (32.08 mg, 286.15 µmol, 26.30 µL, 1.20 eq) in one portion at 20° C. under $N_2$. The mixture was stirred at 20° C. for 15 hours. The reaction mixture was poured into $H_2O$ (5 mL), the aqueous phase was extracted with EtOAc (3×5 mL). The combined organic phase was washed with brine (3 mL), dried with anhydrous $Na_2SO_4$, filtered and concentrated under vacuum. Then the residue was purified by prep-HPLC (TFA condition) to afford compound 7.1 (47.00 mg, 104.32 µmol, 43.75% yield) as a white solid.

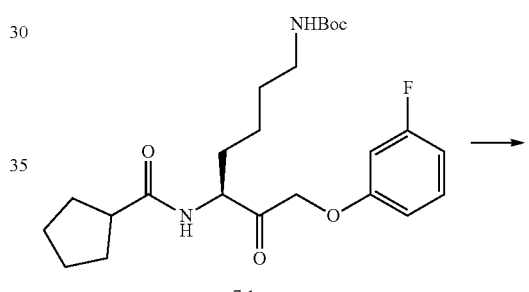

7.1

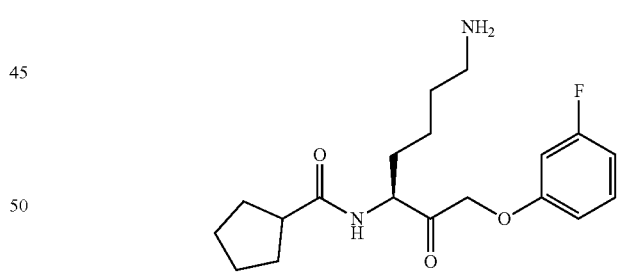

7

A mixture of compound 7.1 (47.00 mg, 104.32 µmol, 1.00 eq) in HCl/EtOAc (2.00 mL) was stirred under $N_2$ at 20° C. for 15 hours. The solution was evaporated to remove organic solvents. The residual aqueous solution was lyophilized to afford compound 7 hydrochloride salt (20.00 mg, 57.07 µmol, 54.71% yield) as a white solid. LCMS (ESI): m/z: [M+H] calcd for $C_{19}H_{27}N_2FO_3$: 351.2; found 351.2; RT=2.205 min. $^1$H NMR (400 MHz, DMSO-$d_6$) δ ppm 1.19-1.85 (m, 15H) 2.60-2.87 (m, 3H) 4.33 (ddd, J=9.43, 6.67, 4.85 Hz, 1H) 4.93-5.13 (m, 2H) 6.61-6.88 (m, 3H) 7.68 (br s, 3H) 8.27 (d, J=6.84 Hz, 1H).

163

Example 10. Preparation of (S)—N-(7-amino-1-(3,5-difluorophenoxy)-2-oxoheptan-3-yl)cyclopentanecarboxamide (8)

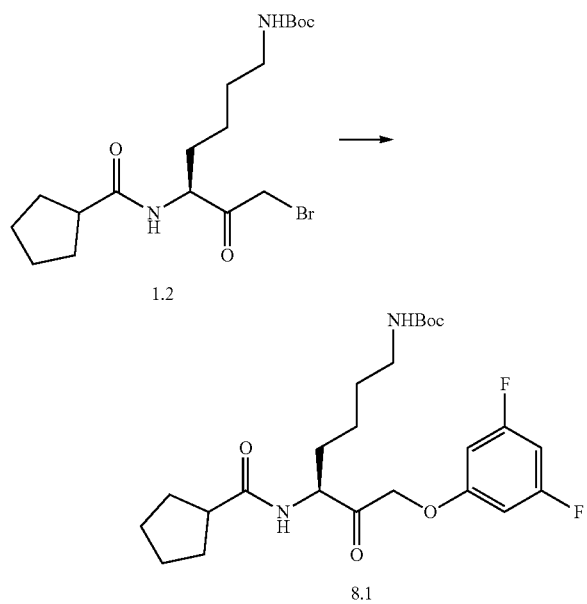

To a mixture of compound 1.2 (100.00 mg, 238.46 µmol, 1.00 eq) in DMF (1.00 mL) was added KF (41.56 mg, 715.38 µmol, 16.76 µL, 3.00 eq) and 3,5-difluorophenol (37.23 mg, 286.15 µmol, 1.20 eq) in one portion at 20° C. under N$_2$. The mixture was stirred at 20° C. for 15 hours. The reaction mixture was poured into H$_2$O (5 mL), and the aqueous phase was extracted with EtOAc (3×5 mL). The combined organic phase was washed with brine (3 mL), dried with anhydrous Na$_2$SO$_4$, filtered, and concentrated under vacuum. Then the residue was purified by prep-HPLC (TFA condition) to afford compound 8.1 (50.00 mg, 106.72 µmol, 44.75% yield) as a white solid.

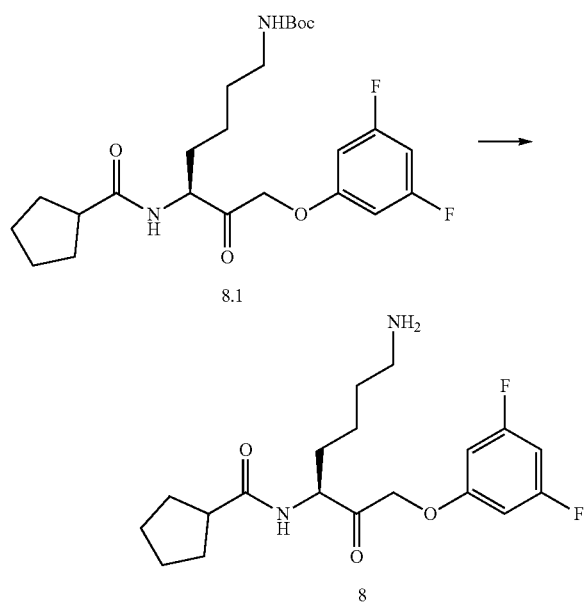

A mixture of compound 8.1 (50.00 mg, 106.72 µmol, 1.00 eq) in HCl/EtOAc (2.00 mL) was stirred under N$_2$ at 20° C. for 4 hours. The solution was evaporated to remove organic solvents. The residual aqueous solution was lyophilized to afford compound 8 hydrochloride salt (20.00 mg, 54.29 µmol, 50.87% yield) as a white solid. LCMS (ESI): m/z: [M+H] calcd for C$_{19}$H$_{26}$N$_2$F$_2$O$_3$: 369.2; found 369.1; RT=2.750 min. $^1$H NMR (400 MHz, DMSO-d$_6$) δ ppm 1.24-1.82 (m, 15H) 2.61-2.83 (m, 3H) 4.32 (ddd, J=9.43, 6.67, 4.85 Hz, 1H) 4.96-5.08 (m, 2H) 6.67 (dd, J=9.48, 2.21 Hz, 2H) 6.79 (tt, J=9.43, 2.26 Hz, 1H) 7.67 (br s, 3H) 8.26 (d, J=6.84 Hz, 1H).

Example 11. Preparation of (R)-3-(acetamido-2,2,2-d3)-N-(7-amino-1-(2,6-difluorophenoxy)-2-oxoheptan-3-yl)benzamide (10)

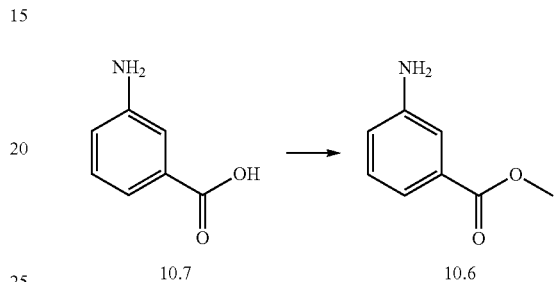

To a solution of compound 10.7 (10.00 g, 72.92 mmol, 1.00 eq) in MeOH (100.00 mL) was added SOCl$_2$ (17.35 g, 145.84 mmol, 10.58 mL, 2.00 eq) in one portion at 0° C. under N$_2$. The mixture was stirred at 65° C. for 15 hours. The reaction mixture was poured into H$_2$O (20 mL), and the aqueous phase was extracted with EtOAc (3×10 mL). The combined organic phase was washed with brine (5 mL), dried with anhydrous Na$_2$SO$_4$, filtered, and concentrated under vacuum to afford compound 10.6 (13.10 g, crude) as a white solid. LCMS (ESI): m/z: [M+H] calcd for C$_8$H$_9$NO$_2$: 152.1; found 152.2; RT=1.191 min. $^1$H NMR (400 MHz, methanol-d$_4$) δ ppm 3.35 (s, 3H) 3.95 (s, 3H) 7.65-7.72 (m, 2H) 8.07 (s, 1H) 8.10-8.16 (m, 1H)

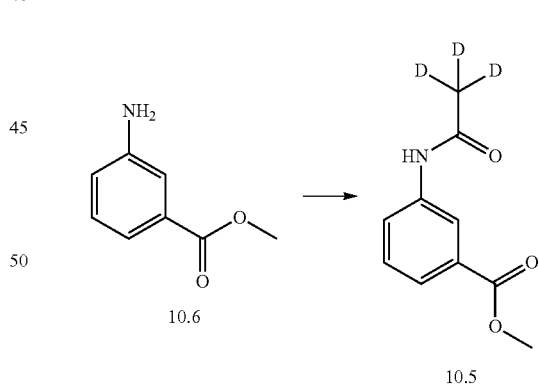

To a mixture of compound 10.6 (3.77 g, 24.97 mmol, 1.00 eq), HOBt (3.71 g, 27.47 mmol, 1.10 eq), and EDCI (4.79 g, 24.97 mmol, 1.00 eq) in DMF (50.00 mL) was added DIEA (16.14 g, 124.85 mmol, 21.80 mL, 5.00 eq) and deuterio 2,2,2-trideuterioacetate (1.60 g, 24.97 mmol, 1.00 eq) in one portion at 0° C. under N$_2$. The mixture was stirred at 15° C. for 15 hours. The reaction mixture was poured into H$_2$O (20 mL), and the aqueous phase was extracted with EtOAc (3×10 mL). The combined organic phase was washed with brine (5 mL), dried with anhydrous Na$_2$SO$_4$, filtered, and concentrated under vacuum. The residue was purified by column chromatography (SiO$_2$, petroleum ether/ethyl acetate=10:1 to 2:1) to afford compound 10.5 (2.90 g, 14.78 mmol, 59.19% yield) as a colorless oil. LCMS (ESI): m/z: [M+H] calcd for C$_{10}$H$_8$D$_3$NO$_3$: 197.1; found 197.2; RT=0.634 min. $^1$H NMR (400 MHz, chloroform-d) δ ppm 3.91 (s, 3H) 7.41 (t, J=7.94 Hz, 1H) 7.51 (br s, 1H) 7.78 (d, J=7.72 Hz, 1H) 7.92 (br d, J=8.16 Hz, 1H) 8.01 (s, 1H).

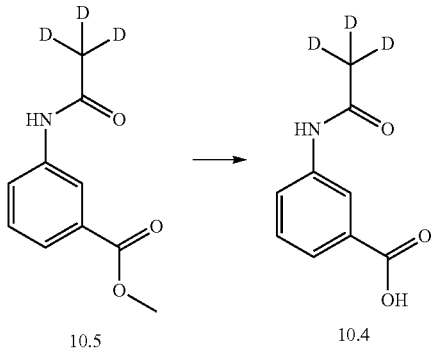 [SMILES: [2H]C([2H])([2H])C(=O)Nc1cccc(C(=O)OC)c1 ; [2H]C([2H])([2H])C(=O)Nc1cccc(C(=O)O)c1]

To a solution of compound 10.5 (2.90 g, 14.78 mmol, 1.00 eq) in MeOH (36.00 mL) was added NaOH (1.18 g, 29.56 mmol, 2.00 eq) in H$_2$O (12.00 mL) in one portion at 15° C. under N$_2$. The mixture was stirred at 15° C. for 15 hours. EtOAc was removed and then the solution was cooled to 0° C., and the pH was adjusted to 6-7 with HCl (1N). The suspension was filtered and the filter cake was washed with 50 mL of PE and dried under vacuum to afford compound 10.4 (2.10 g, crude) as a white solid. $^1$H NMR (400 MHz, methanol-d$_4$) δ ppm 7.41 (t, J=7.94 Hz, 1H) 7.75 (dt, J=7.72, 1.32 Hz, 1H) 7.82 (ddd, J=8.05, 2.21, 0.99 Hz, 1H) 8.21 (t, J=1.87 Hz, 1H).

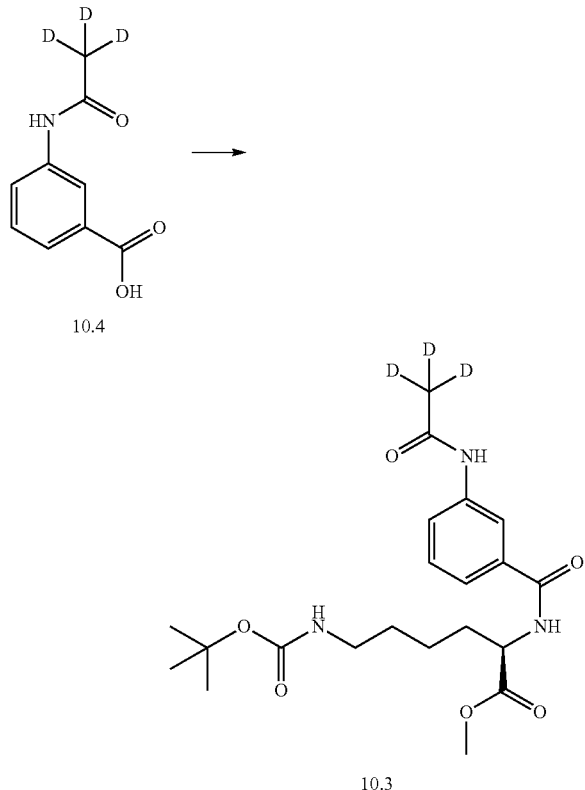

To a mixture of compound 10.4 (1.00 g, 5.49 mmol, 1.00 eq), HOBt (815.81 mg, 6.04 mmol, 1.10 eq), and EDCI (1.16 g, 6.04 mmol, 1.10 eq) in DMF (2.00 mL) was added DIEA (2.84 g, 21.96 mmol, 3.83 mL, 4.00 eq) and methyl (2S)-2-amino-6-(tert-butoxycarbonylamino)hexanoate (1.43 g, 5.49 mmol, 1.00 eq) in one portion at 0° C. under N$_2$. The mixture was stirred at 15° C. for 15 hours. The reaction mixture was poured into H$_2$O (30 mL), the aqueous phase was extracted with EtOAc (3×30 mL). The combined organic phase was washed with brine (5 mL), dried with anhydrous Na$_2$SO$_4$, filtered and concentrated under vacuum. The residue was purified by column chromatography (SiO$_2$, petroleum ether/ethyl acetate=4:1 to 0:1) to afford compound 10.3 (1.90 g, 4.48 mmol, 81.53% yield) as a light yellow solid. LCMS (ESI): m/z: [M+H] calcd for C$_{21}$H$_{28}$D$_3$N$_3$O$_6$: 425.2; found 325.3; RT=0.757 min. $^1$H NMR (400 MHz, chloroform-d) δ ppm 1.31-1.54 (m, 14H) 1.70-1.97 (m, 2H) 2.11-2.19 (m, 1H) 3.00-3.12 (m, 2H) 3.71 (s, 3H) 4.64-4.81 (m, 2H) 7.11 (br d, J=7.50 Hz, 1H) 7.28-7.36 (m, 1H) 7.47 (br d, J=7.28 Hz, 1H) 7.75 (br s, 1H) 7.95 (br d, J=7.72 Hz, 1H) 8.47 (br s, 1H).

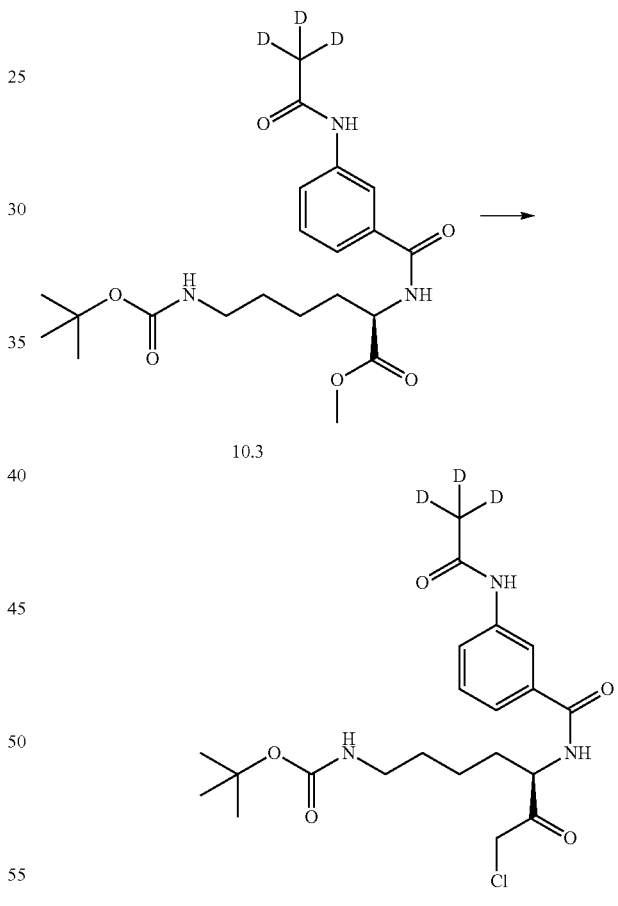

To a solution of DIPA (760.95 mg, 7.52 mmol, 1.06 mL, 4.00 eq) in THF (15.00 mL) was added n-BuLi (481.73 mg, 7.52 mmol, 4.00 eq) at 0° C. under N$_2$. After 0.5 h, compound 10.3 (800.00 mg, 1.88 mmol, 1.00 eq) and chloro(iodo)methane (1.33 g, 7.52 mmol, 545.83 μL, 4.00 eq) were added to the mixture at −78° C. under N2. The resulting mixture was stirred at −78° C. for 1.5 hrs. Water (20 mL) was added, and the mixture was extracted with EtOAc (3×20 mL). The combined organic layers were washed with brine (10 mL), dried over Na₂SO₄, filtered, and concentrated under reduced pressure to afford compound 10.2 (900.00 mg, crude) as a dark brown oil. LCMS (ESI): [M+H] calcd for $C_{21}H_{27}D_3ClN_3O_5$: 442.2; found 339.3; RT=0.748 min. ¹H NMR (400 MHz, chloroform-d) δ ppm 1.35-1.59 (m, 17H) 1.67 (br s, 3H) 1.76-2.02 (m, 3H) 3.11 (br d, J=6.17 Hz, 2H) 3.77 (s, 3H) 4.60-4.82 (m, 2H) 6.87 (br s, 1H) 7.40 (br t, J=7.61 Hz, 1H) 7.52 (br s, 1H) 7.66-7.82 (m, 2H) 7.92 (br s, 1H).

NMR (400 MHz, chloroform-d) δ ppm 1.41 (br s, 18H) 1.80 (br s, 2H) 2.08-2.24 (m, 2H) 3.13 (br s, 3H) 4.91 (br s, 3H) 5.24 (br s, 1H) 6.88-7.05 (m, 5H) 7.37-7.46 (m, 3H) 7.56 (br s, 2H) 7.78 (br s, 1H) 7.93 (br s, 1H)

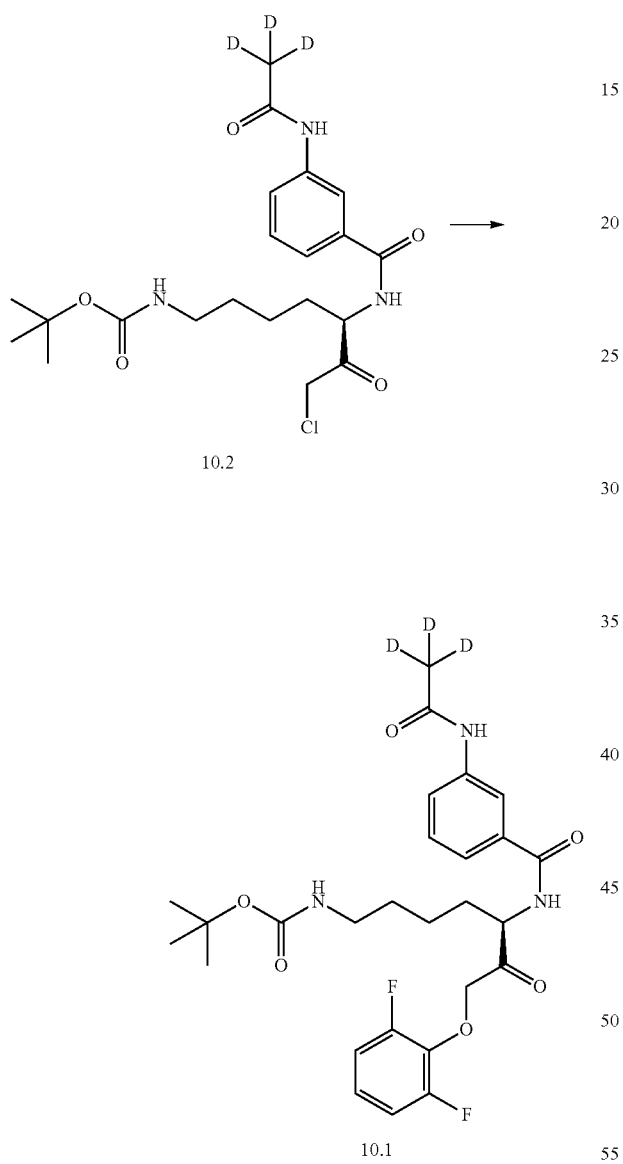

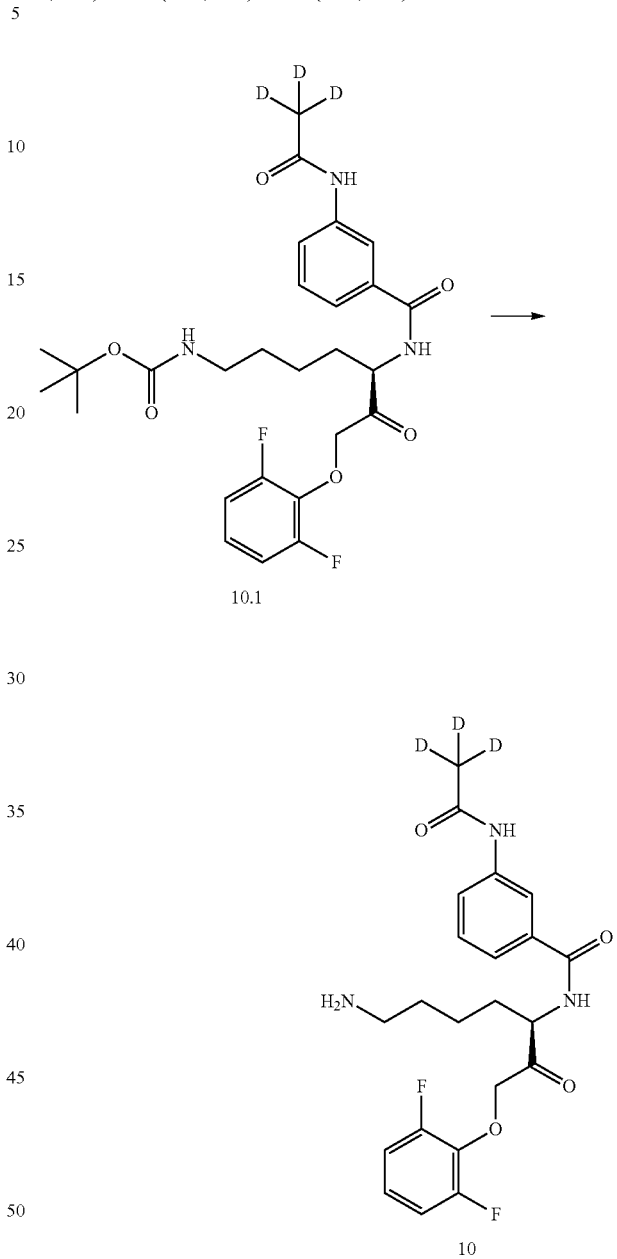

To a mixture of compound 10.2 (200.00 mg, 451.52 μmol, 1.00 eq) and 2,6-difluorophenol (58.74 mg, 451.52 μmol, 1.00 eq) in DMF (4.00 mL) was added DIEA (175.06 mg, 1.35 mmol, 236.57 μL, 3.00 eq) in one portion at 20° C. under N₂. The mixture was stirred at 20° C. for 15 hours. The residue was purified by prep-HPLC (TFA condition) to afford compound 10.1 (20.00 mg, 37.27 μmol, 8.26% yield) as a dark brown solid. LCMS (ESI): m/z: [M+H] calcd for $C_{27}H_{30}D_3F_2N_3O_6$: 537.3; found 481.3; RT=1.208 min. ¹H To a solution of compound 10.1 (10.00 mg, 18.64 μmol, 1.00 eq) in DCM (10.00 mL) was added TFA (3.08 g, 27.01 mmol, 2.00 mL, 1449.18 eq) in one portion at 20° C. under N₂. The mixture was stirred at 20° C. for 4 hours, filtered, and concentrated under vacuum. The residue was purified by prep-HPLC (TFA condition) to afford compound 10 trifluoroacetate salt (1.00 mg, 2.29 μmol, 12.29% yield) as a dark brown solid. LCMS (ESI): m/z: [M+H] calcd for $C_{22}H_{22}D_3F_2N_3O_4$: 437.2; found 437.3; RT=2.042 min. ¹H NMR (400 MHz, methanol-d₄) δ ppm 1.48-1.87 (m, 5H) 2.13 (br s, 1H) 2.91-2.99 (m, 2H) 4.90-5.08 (m, 5H) 6.94-7.12 (m, 3H) 7.39-7.46 (m, 1H) 7.54-7.65 (m, 2H) 8.13 (s, 1H).

Example 12. Preparation of Biotinylated Gingipain Inhibitor (11)

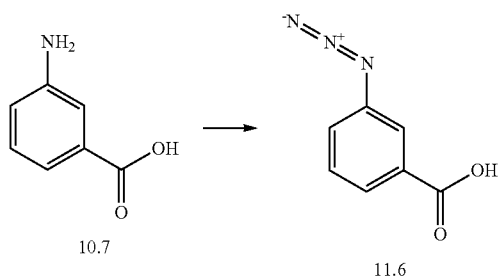

To a solution of compound 10.7 (5.00 g, 36.46 mmol, 1.00 eq) in CH$_3$CN (50.00 mL) was added t-BuONO (5.64 g, 54.69 mmol, 6.48 mL, 1.50 eq) and TMSN$_3$ (5.04 g, 43.75 mmol, 5.73 mL, 1.20 eq) in one portion at 0° C. under N$_2$. The mixture was stirred at 15° C. for 1 hour, filtered, and concentrated under vacuum. H$_2$O (20 mL) was added, and the aqueous phase was extracted with EtOAc (3×10 mL). The combined organic phase was washed with brine (5 mL), dried with anhydrous Na$_2$SO$_4$, filtered, and concentrated under vacuum to afford compound 11.6 (4.00 g, crude) as a white solid. LCMS (ESI): m/z: [M+H] calcd for C$_7$H$_5$N$_3$O$_2$: 164.0; found 164.1; RT=0.705 min. $^1$H NMR (400 MHz, chloroform-d) δ ppm 2.71 (d, J=9.48 Hz, 1H) 6.93-6.98 (m, 1H) 7.27-7.32 (m, 1H) 7.44-7.57 (m, 1H) 7.79-7.84 (m, 1H) 7.90-7.95 (m, 1H).

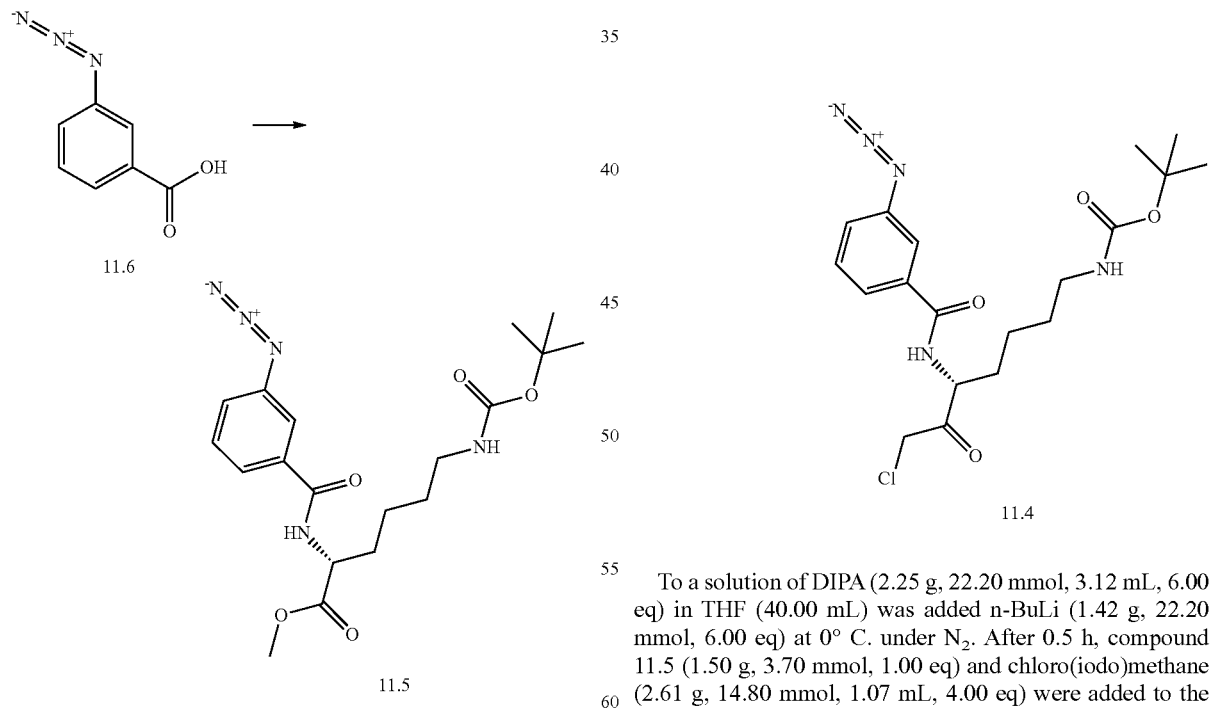

To a mixture of compound 11.6 (2.00 g, 12.26 mmol, 1.00 eq), HOBt (1.82 g, 13.49 mmol, 1.10 eq), and EDCI (2.59 g, 13.49 mmol, 1.10 eq) in DMF (40.00 mL) was added methyl (2S)-2-amino-6-(tert-butoxycarbonylamino)hexanoate (3.19 g, 12.26 mmol, 1.00 eq) and DIEA (6.34 g, 49.04 mmol, 8.57 mL, 4.00 eq) in one portion at 0° C. under N$_2$.

The mixture was stirred at 15° C. for 4 hours. The reaction mixture was poured into H$_2$O (20 mL). The aqueous phase was extracted with EtOAc (3×50 mL). The combined organic phase was washed with brine (5 mL), dried with anhydrous Na$_2$SO$_4$, filtered, and concentrated under vacuum. The residue was purified by column chromatography (SiO$_2$, petroleum ether/ethyl acetate=10:1 to 2:1) to afford compound 11.5 (3.50 g, 8.63 mmol, 70.39% yield) as a white solid. LCMS (ESI): m/z: [M+H] calcd for C$_{19}$H$_{27}$N$_5$O$_5$: 406.2; found 350.2; RT=0.840 min. $^1$H NMR (400 MHz, chloroform-d) δ ppm 1.39 (s, 10H) 1.46-1.56 (m, 3H) 1.75-2.00 (m, 2H) 3.05-3.14 (m, 2H) 3.77 (s, 3H) 4.64 (br s, 1H) 4.72-4.80 (m, 1H) 6.94 (br d, J=7.06 Hz, 1H) 7.14 (ddd, J=8.05, 2.32, 0.88 Hz, 1H) 7.40 (t, J=7.83 Hz, 1H) 7.47-7.56 (m, 2H)

To a solution of DIPA (2.25 g, 22.20 mmol, 3.12 mL, 6.00 eq) in THF (40.00 mL) was added n-BuLi (1.42 g, 22.20 mmol, 6.00 eq) at 0° C. under N$_2$. After 0.5 h, compound 11.5 (1.50 g, 3.70 mmol, 1.00 eq) and chloro(iodo)methane (2.61 g, 14.80 mmol, 1.07 mL, 4.00 eq) were added to the mixture at −78° C. under N$_2$. The resulting mixture was stirred at −78° C. for 1.5 hrs. The reaction mixture was added to water (20 mL), and the solution was extracted with EtOAc (3×20 mL). The combined organic layers were washed with brine (10 mL), dried over Na$_2$SO$_4$, filtered, and concentrated under reduced pressure to give a residue to afford compound 11.4 (1.50 g, crude) as a dark brown oil.

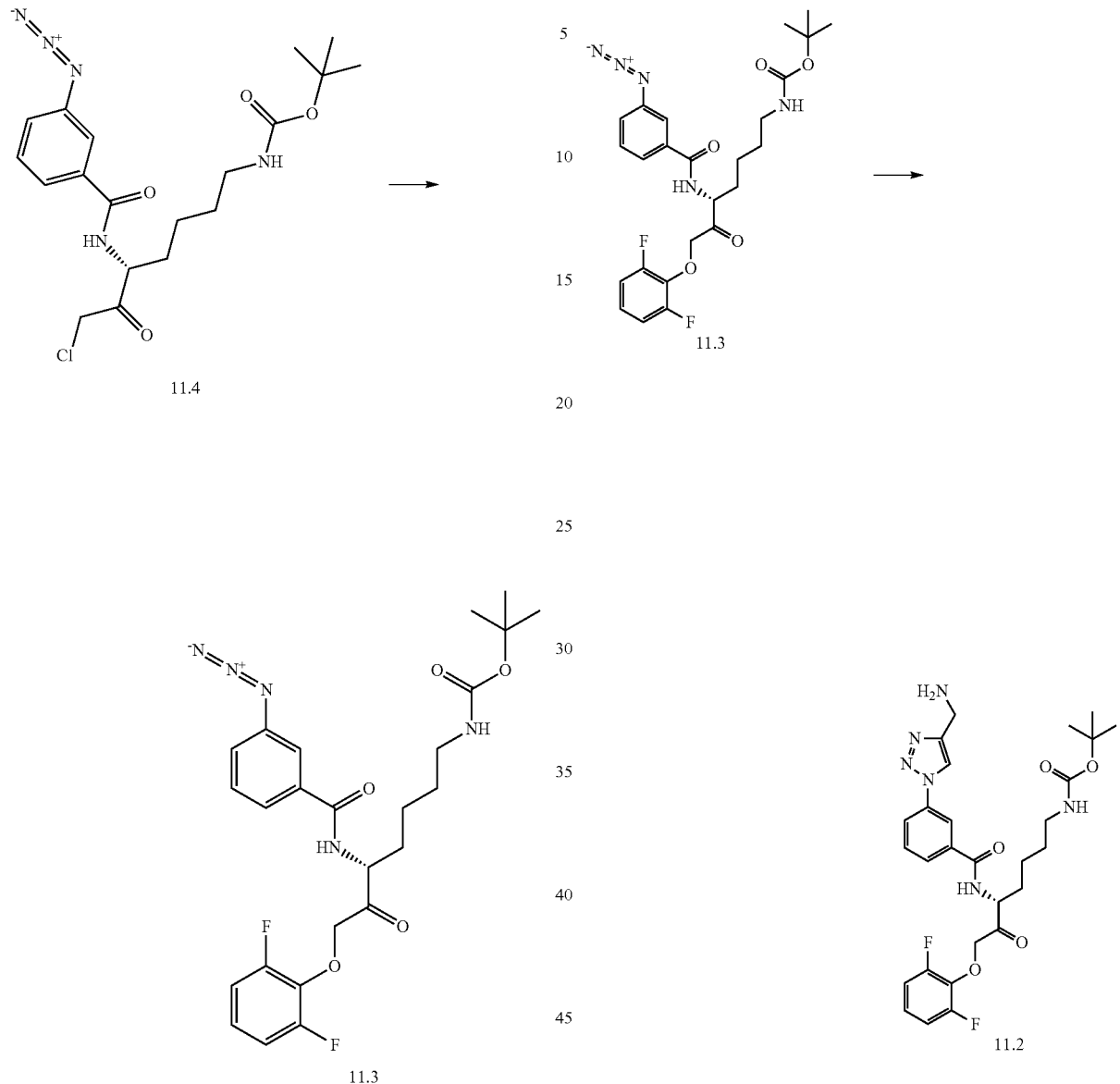

To a mixture of compound 11.4 (1.50 g, 3.54 mmol, 1.00 eq) and 2,6-difluorophenol (460.34 mg, 3.54 mmol, 1.00 eq) in DMF (15.00 mL) was added DIEA (1.37 g, 10.62 mmol, 1.85 mL, 3.00 eq) in one portion at 20° C. under $N_2$. The mixture was stirred at 20° C. for 15 hours. The reaction mixture was added to water (20 mL), and the solution was extracted with EtOAc (3×20 mL). The combined organic layers were washed with brine (10 mL), dried over $Na_2SO_4$, filtered, and concentrated under reduced pressure to give a residue. The residue was purified by column chromatography ($SiO_2$, petroleum ether/ethyl acetate=10:1 to 2:1) to afford compound 11.3 (400.00 mg, 772.92 μmol, 21.83% yield) as a light yellow oil. LCMS (ESI): m/z: [M+H] calcd for $C_{25}H_{29}F_2N_5O_5$: 518.2; found 518.3; RT=0.912 min.

To a mixture of compound 11.3 (270.00 mg, 521.72 μmol, 1.00 eq) and prop-2-yn-1-amine (28.74 mg, 521.72 μmol, 33.41 μL, 1.00 eq) in $CH_3CN$ (4.00 mL) was added $CuSO_4$ (4.16 mg, 26.09 μmol, 4.00 μL, 0.05 eq) and sodium ascorbate (20.67 mg, 104.34 μmol, 0.20 eq) in one portion at 20° C. under $N_2$. The mixture was stirred at 20° C. for 15 hours. The residue was purified by prep-HPLC (TFA conditions) to afford compound 11.2 (70.00 mg, 122.25 μmol, 23.43% yield) as a dark brown oil. LCMS (ESI): m/z: [M+H] calcd for $C_{28}H_{34}F_2N_6O_5$: 573.3; found 573.5; RT=0.846 min. $^1$H NMR (400 MHz, chloroform-d) δ ppm 1.19-1.69 (m, 8H) 2.04 (br s, 1H) 2.67-3.25 (m, 3H) 4.45 (br s, 1H) 4.72-5.15 (m, 2H) 6.78-7.09 (m, 2H) 7.58-8.01 (m, 2H) 8.16-8.49 (m, 1H) 8.63-9.26 (m, 1H).

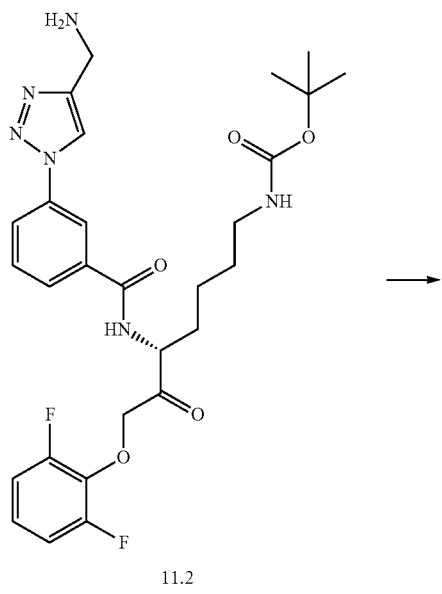

11.2

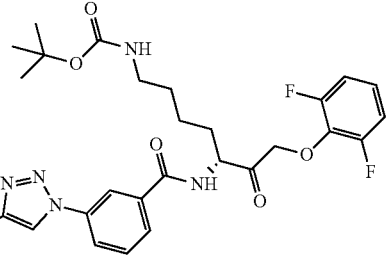

11.1

To a mixture of BIOTIN-DPEG(4)-COOH (34.34 mg, 69.86 μmol, 1.00 eq), HOBt (9.44 mg, 69.86 μmol, 1.00 eq), and EDCI (13.39 mg, 69.86 μmol, 1.00 eq) in DMF (1.00 mL) was added compound 11.2 (40.00 mg, 69.86 μmol, 1.00 eq) and DIEA (36.11 mg, 279.44 μmol, 48.80 μL, 4.00 eq) in one portion at 0° C. under $N_2$. The mixture was stirred at 20° C. for 15 hours. The residue was purified by prep-HPLC (TFA conditions) to afford compound 11.1 (20.00 mg, 19.12 μmol, 27.37% yield) as a white solid. LCMS (ESI): m/z: [M+H] calcd for $C_{49}H_{69}F_2N_9O_{12}S$: 1046.5; found 1046.3; RT=1.115 min. $^1$H NMR (400 MHz, DMSO-$d_6$) δ ppm 1.21-1.34 (m, 12H) 1.35-1.75 (m, 9H) 1.85 (br dd, J=9.59, 3.64 Hz, 1H) 2.05 (t, J=7.39 Hz, 2H) 2.35-2.42 (m, 1H) 2.38 (t, J=6.50 Hz, 1H) 2.53-2.60 (m, 2H) 2.80 (dd, J=12.35, 5.07 Hz, 1H) 2.89 (br d, J=5.95 Hz, 2H) 3.08 (ddd, J=8.49, 6.06, 4.63 Hz, 1H) 3.16 (q, J=5.88 Hz, 2H) 3.44-3.50 (m, 15H) 3.62 (t, J=6.50 Hz, 3H) 4.11 (dd, J=7.72, 4.41 Hz, 1H) 4.29 (dd, J=7.72, 4.41 Hz, 1H) 4.40 (d, J=5.73 Hz, 2H) 4.59-4.67 (m, 1H) 5.06-5.20 (m, 2H) 6.76 (br t, J=5.51 Hz, 1H) 7.06-7.14 (m, 3H) 7.71 (t, J=8.05 Hz, 1H) 7.82 (t, J=5.62 Hz, 1H) 7.95-8.00 (m, 1H) 8.06 (ddd, J=8.16, 2.21, 0.88 Hz, 1H) 8.36 (t, J=1.76 Hz, 1H) 8.45 (t, J=5.51 Hz, 1H) 8.64 (s, 1H) 8.95 (d, J=7.28 Hz, 1H).

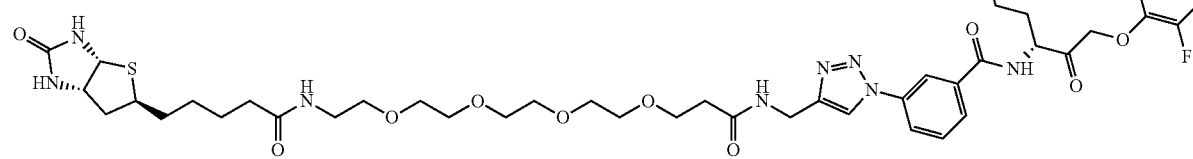

11.1

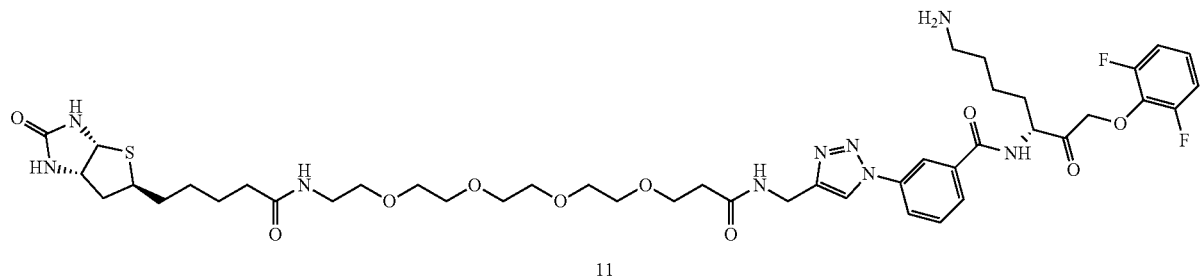

11

A solution of compound 11.1 (20.00 mg, 19.12 µmol, 1.00 eq) in TFA (1.03 g, 9.00 mmol, 666.11 µL, 470.61 eq) was stirred under $N_2$ at 20° C. for 4 hours. The mixture was filtered and concentrated under vacuum to afford compound 11 trifluoroacetate salt (18.00 mg, 16.98 µmol, 88.81% yield, TFA) as a white solid. LCMS (ESI): m/z: [M+H] calcd for $C_{44}H_{61}F_2N_9O_{16}$: 946.4; found 946.6; RT=2.076 min. $^1$H NMR (400 MHz, DMSO-$d_6$) δ ppm 1.10-1.77 (m, 14H) 1.82-1.95 (m, 1H) 2.05 (t, J=7.40 Hz, 2H) 2.17 (t, J=8.03 Hz, 1H) 2.30-2.42 (m, 2H) 2.53-2.60 (m, 3H) 2.64-2.71 (m, 2H) 2.73-2.85 (m, 3H) 3.04-3.12 (m, 2H) 3.17 (q, J=5.86 Hz, 3H) 3.44-3.52 (m, 14H) 3.63 (br t, J=6.46 Hz, 2H) 4.08-4.15 (m, 1H) 4.26-4.33 (m, 1H) 4.40 (d, J=5.52 Hz, 2H) 4.63-4.72 (m, 1H) 5.07-5.21 (m, 2H) 6.31-6.42 (m, 2H) 6.95-6.99 (m, 1H) 6.97 (s, 1H) 7.06-7.15 (m, 3H) 7.23 (s, 1H) 7.58-7.76 (m, 4H) 7.81 (br t, J=5.46 Hz, 1H) 7.95-8.01 (m, 1H) 7.98 (d, J=7.91 Hz, 1H) 8.07 (dd, J=8.03, 1.25 Hz, 1H) 8.38 (s, 1H) 8.45 (t, J=5.52 Hz, 1H) 8.63-8.66 (m, 1H) 8.64 (s, 1H) 8.98 (d, J=7.53 Hz, 1H).

Example 13. Preparation of (S)—N-(7-amino-1-(2, 6-difluorophenoxy)-2-oxoheptan-3-yl)-3-azidobenzamide (12)

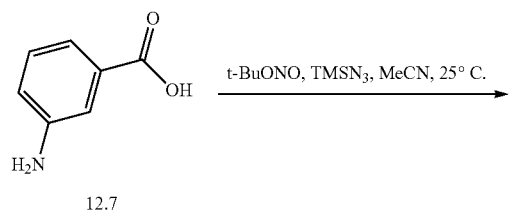

12.7

To a mixture of compound 12.7 (5.00 g, 36.46 mmol, 1.00 eq) and t-BuONO (5.64 g, 54.69 mmol, 6.48 mL, 1.50 eq) in $CH_3CN$ (70.00 mL) was added $TMSN_3$ (5.04 g, 43.75 mmol, 5.73 mL, 1.20 eq) in one portion at 18° C. under $N_2$. The mixture was stirred at 18° C. for 10 hours. The reaction mixture was diluted with $H_2O$ (100 mL) and extracted with EtOAc (3×50 mL). The combined organic layers were washed with brine (100 mL), dried over $Na_2SO_4$, filtered, and concentrated under reduced pressure to give a residue. The residue was purified by column chromatography ($SiO_2$, DCM:MeOH=10:1) to afford compound 12.6 (3.00 g, 18.39 mmol, 50.44% yield) as a yellow solid.

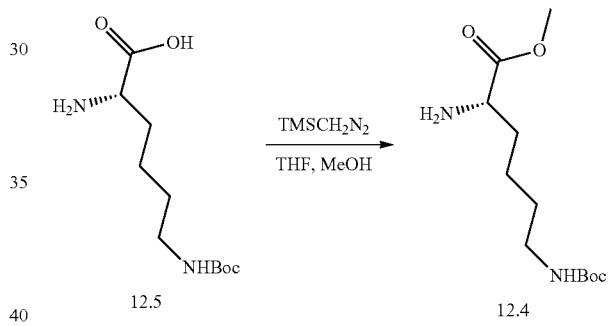

To a solution of compound 12.5 (20.00 g, 81.20 mmol, 1.00 eq) in THF (160.00 mL) and MeOH (40.00 mL) was added $TMSCHN_2$ (27.82 g, 243.60 mmol, 3.00 eq) dropwise at 25° C. under $N_2$. The mixture was stirred at 25° C. for 20 hours. The reaction mixture was concentrated under reduced pressure to give a residue. The residue was purified by column chromatography ($SiO_2$, ethyl acetate) to afford compound 12.4 (8.00 g, 30.73 mmol, 37.85% yield) as a colorless oil.

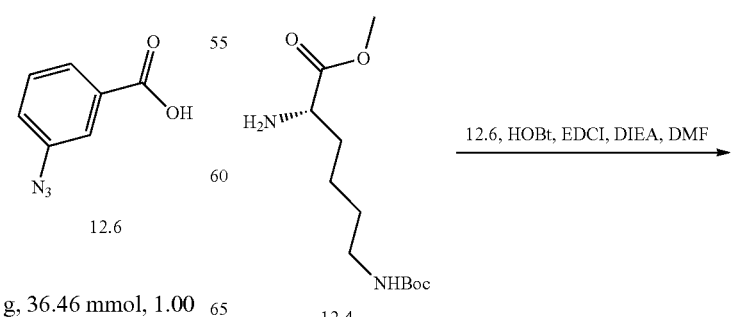

-continued

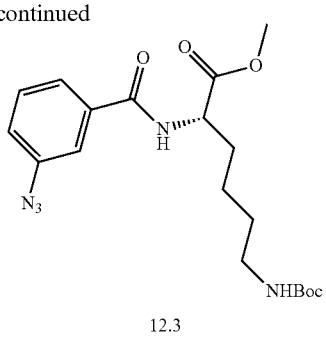

12.3

To a mixture of compound 12.6 (1.25 g, 7.68 mmol, 1.00 eq) and EDCI (1.62 g, 8.45 mmol, 1.10 eq) in DMF (20.00 mL) was added HOBt (1.14 g, 8.45 mmol, 1.10 eq) in one portion at 0° C. under $N_2$. The mixture was stirred at 0° C. for 1 hour, then the mixture was added dropwise a solution of compound 12.4 (2.00 g, 7.68 mmol, 1.00 eq) in DMF (5 mL). DIPEA (2.98 g, 23.04 mmol, 4.03 mL, 3.00 eq) was added dropwise, and the mixture was stirred at 0° C. for 1 hour. The reaction mixture was diluted with $H_2O$ (20 mL) and extracted with EtOAc (3×15 mL). The combined organic layers were washed with brine (40 mL), dried over $Na_2SO_4$, filtered and concentrated under reduced pressure to give a residue. The residue was purified by column chromatography ($SiO_2$, petroleum ether/ethyl acetate=1:1) to afford compound 12.3 (2.80 g, 6.91 mmol, 89.97% yield) as a yellow oil. $^1$H NMR (400 MHz, $CD_3OD$-d4) δ ppm 1.40 (s, 8H) 1.44-1.58 (m, 4H) 1.80-2.00 (m, 2H) 3.00-3.10 (m, 2H) 3.74 (s, 3H) 4.58 (dd, J=9.26, 5.07 Hz, 1H) 7.25 (ddd, J=8.05, 2.32, 1.10 Hz, 1H) 7.49 (t, J=7.83 Hz, 1H) 7.56 (t, J=1.76 Hz, 1H) 7.63-7.69 (m, 1H). LCMS (ESI): m/z: [M+H] calcd for $C_{19}H_{27}O_5N_5$: 405; found 350, 306; RT=0.897 min.

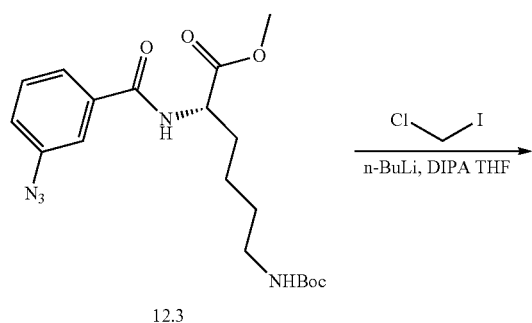

To a solution of DIPA (1.50 g, 14.80 mmol, 2.08 mL, 6 eq) in THF (15.00 mL) was added n-BuLi (2.5 M, 5.92 mL, 6.00 eq) at 0° C., and the mixture was stirred at 0° C. for 30 mins. To the mixture was added a solution of compound 12.3 (1.00 g, 2.47 mmol, 1.00 eq) and chloro(iodo)methane (2.18 g, 12.35 mmol, 895.11 μL, 5.00 eq) in THF (15.00 mL) at −78° C. The mixture was stirred at −78° C. for 30 mins. Saturated aqueous $NH_4Cl$ (10 mL) was added, and then the mixture was extracted with EtOAc (3×15 mL). The combined organic layers were washed with aqueous saturated $Na_2SO_3$ (20) and brine (20 mL), dried over $Na_2SO_4$, filtered, and concentrated under reduced pressure to provide crude compound 12.2 (2.00 g, crude) as yellow oil which was used in the next step.

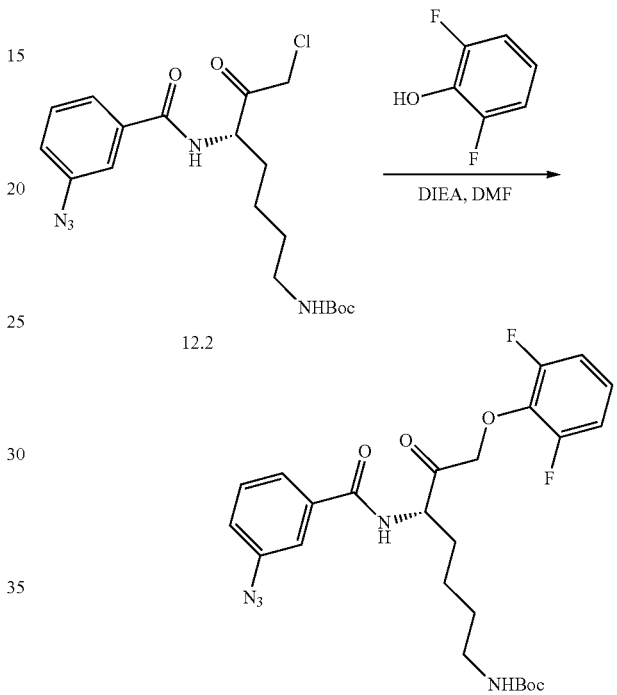

To a mixture of compound 12.2 (2.00 g, 4.72 mmol, 1.00 eq) and 2,6-difluorophenol (613.79 mg, 4.72 mmol, 1.00 eq) in DMF (5.00 mL) was added DIPEA (2.44 g, 18.87 mmol, 3.30 mL, 4.00 eq) in one portion at 20° C. under $N_2$. The mixture was stirred at 20° C. for 10 hours. The residue was purified by prep-HPLC (TFA condition) to afford compound 12.1 (200.00 mg, 386.46 μmol, 8.19% yield) as a yellow oil.

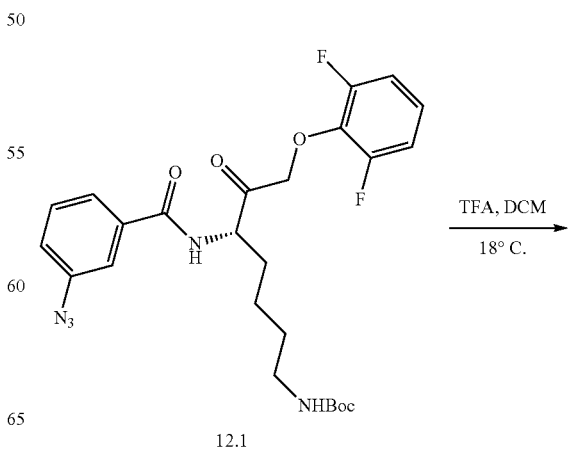

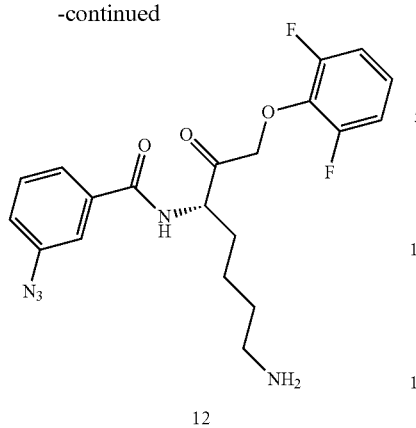

12

To a solution of compound 12.1 (100.00 mg, 193.23 μmol, 1.00 eq) in DCM (5.00 mL) was added TFA (1.54 g, 13.51 mmol, 1.00 mL, 69.90 eq) in one portion at 18° C. under N$_2$. The mixture was stirred at 18° C. for 10 hours. The reaction mixture was concentrated under reduced pressure to give a residue. The residue was purified by prep-HPLC (TFA condition) to afford compound 12 trifluoroacetate salt (80.00 mg, 191.66 μmol, 99.19% as a yellow oil. $^1$H NMR (400 MHz, methanol-d4) δ ppm 1.49-1.67 (m, 2H) 1.67-1.88 (m, 3H) 2.11 (dddd, J=13.84, 9.48, 6.78, 4.30 Hz, 1H) 2.89-2.99 (m, 2H) 4.91-5.08 (m, 3H) 6.95-7.05 (m, 2H) 7.05-7.12 (m, 1H) 7.26-7.31 (m, 1H) 7.48-7.54 (m, 1H) 7.56 (t, J=1.87 Hz, 1H) 7.64-7.70 (m, 1H). LCMS (ESI): m/z: [M+H] calcd for C$_{20}$H$_{21}$F$_2$O$_3$N$_5$: 418; found 418; RT=3.08 min.

Example 14. Preparation of (S)—N-(7-amino-2-oxo-1-(1H-tetrazol-1-yl)heptan-3-yl)cyclopentanecarboxamide (13) and (S)—N-(7-amino-2-oxo-1-(2H-tetrazol-2-yl)heptan-3-yl)cyclopentanecarboxamide (14)

15 hours. The residue was purified by prep-HPLC (TFA conditions). Compound 13.1 (5.00 mg, 12.24 μmol, 10.27% yield) was obtained as a white solid, And 5 mg of compound 14.1 was obtained as a white solid.

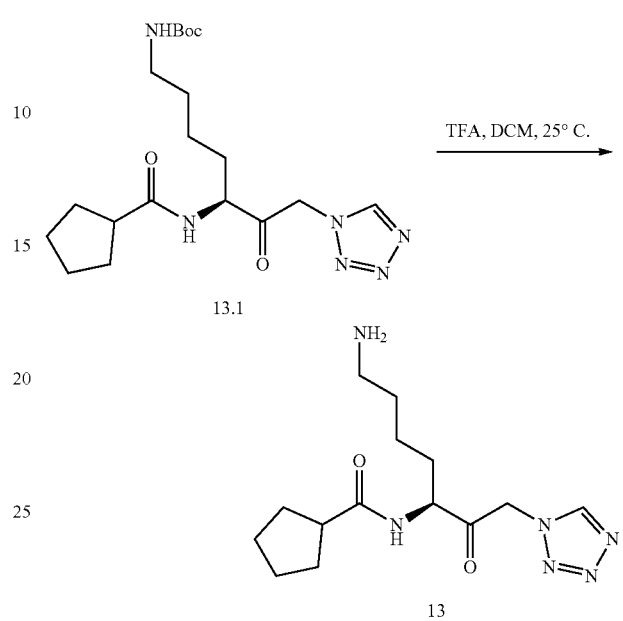

A mixture of compound 13.1 (5.00 mg, 12.24 μmol, 1.00 eq) in DCM (5.00 mL) and TFA (1.00 mL) was stirred at 25° C. for 2 hours. The mixture was concentrated under reduced pressure to afford compound 13 trifluoroacetate salt (5.00 mg, 11.84 μmol, 96.71% yield, TFA). $^1$H NMR (400 MHz, methanol-d$_4$) δ ppm 1.25-1.57 (m, 4H) 1.58-1.81 (m, 12H) 1.84-2.09 (m, 6H) 2.68-2.84 (m, 1H) 2.94 (br t, J=7.50 Hz, 3H) 4.44-4.58 (m, 1H) 5.51-5.79 (m, 2H) 9.06-9.18 (m, 1H). LCMS (ESI): m/z: [M+H] calcd for C$_{14}$H$_{24}$O$_2$N$_6$·C$_2$HF$_3$O$_2$: 423; found 309; RT=1.208 min.

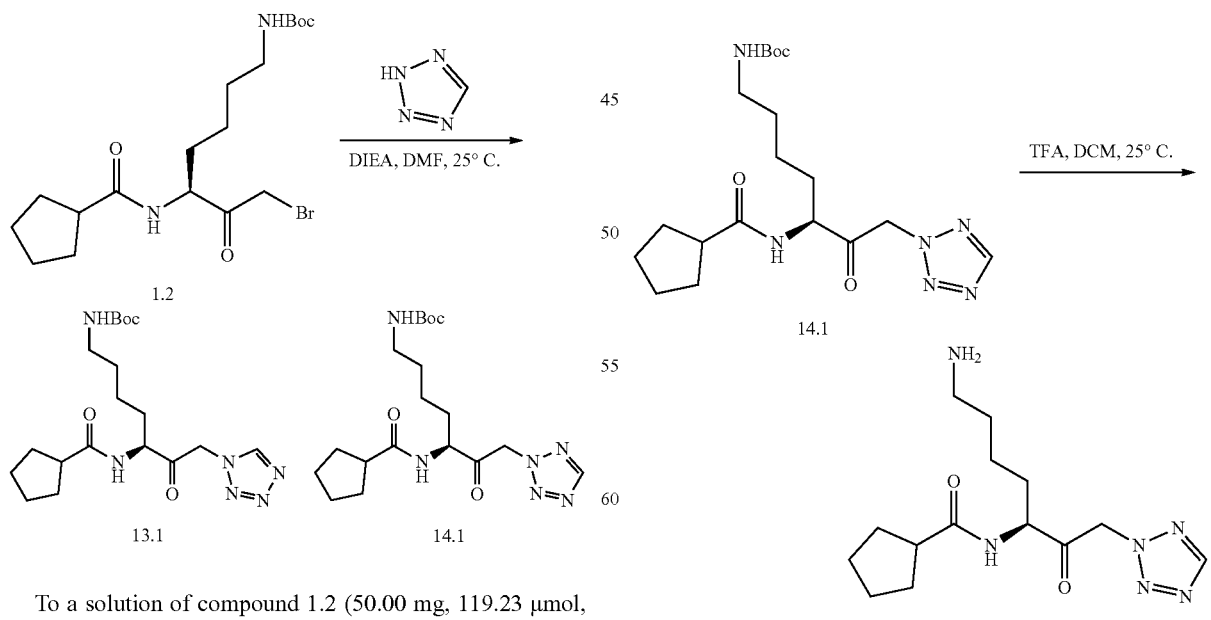

To a solution of compound 1.2 (50.00 mg, 119.23 μmol, 1.00 eq) in DMF (3.00 mL) were added DIEA (46.23 mg, 357.70 μmol, 62.47 μL, 3.00 eq) and tetrazole (0.45 M, 264.96 μL, 1.00 eq). The mixture was stirred at 25° C. for A mixture of compound 14.1 (5.00 mg, 12.24 μmol, 1.00 eq) in DCM (5.00 mL) and TFA (1.00 mL) was stirred at 25° C. for 2 hours. The mixture was concentrated under reduced pressure to afford compound 14 trifluoroacetate salt (5.00 mg, 11.84 μmol, 96.71% yield, TFA). $^1$H NMR (400 MHz, methanol-$d_4$) δ ppm 1.20-1.53 (m, 5H) 1.54-1.80 (m, 12H) 1.82-2.08 (m, 5H) 2.64-2.83 (m, 1H) 2.93 (br t, J=7.28 Hz, 3H) 4.55 (dd, J=9.37, 4.74 Hz, 1H) 5.71-5.94 (m, 2H) 8.76 (s, 1H). LCMS (ESI): m/z: [M+H] calcd for $C_{14}H_{24}N_6O_2 \cdot C_2HF_3O_2$:423; found 309; RT=1.606 min.

Example 15. Preparation of a fluorescent gingipain activity probe: (S)—N-(7-amino-1-(2,6-difluorophenoxy)-2-oxoheptan-3-yl)-3-(4-((3-(5,5-difluoro-7,9-dimethyl-5H-514,614-dipyrrolo[1,2-c:2',1'-f][1,3,2]diazaborinin-3-yl)propanamido)methyl)-1H-1,2,3-triazol-1-yl)benzamide (15)

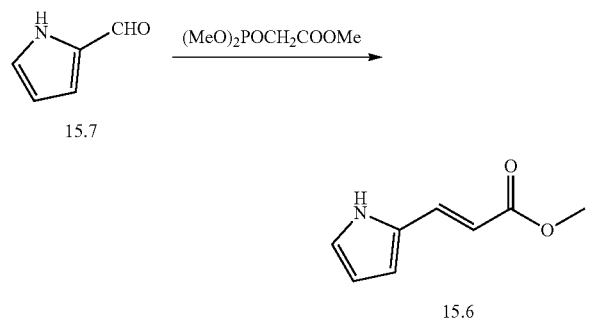

To a mixture of compound 15.7 (5.00 g, 52.58 mmol, 1.00 eq) and methyl 2-diethoxyphosphorylacetate (11.05 g, 52.58 mmol, 1.00 eq) in THF (60.00 mL) was added $K_2CO_3$ (14.53 g, 105.16 mmol, 2.00 eq) in one portion at 50° C. under $N_2$. The mixture was stirred at 50° C. for 10 hours. The reaction mixture was diluted with $H_2O$ (50 mL) and extracted with EtOAc (3×50 mL). The combined organic layers were washed with brine (100 mL), dried over $Na_2SO_4$, filtered, and concentrated under reduced pressure to give a residue. The residue was purified by column chromatography (SiO$_2$, petroleum ether/ethyl acetate=5:1) to afford 15.6 (8.60 g, 56.89 mmol, 108.20% yield) as a white solid.

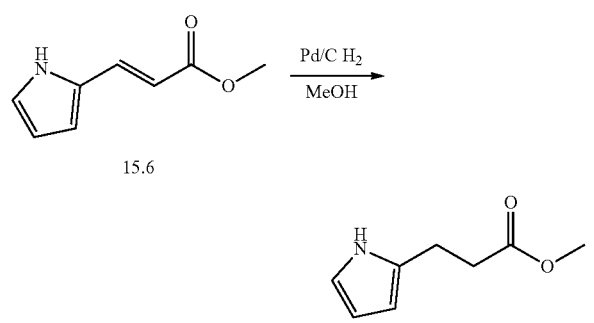

To a solution of compound 15.6 (8.60 g, 56.89 mmol, 1.00 eq) in MeOH (100.00 mL) was added Pd—C (10%, 0.9 g) under $N_2$. The suspension was degassed under vacuum and purged with $H_2$ several times. The mixture was stirred under $H_2$ (50 psi) at 18° C. for 10 hours. The reaction mixture was filtered and concentrated under reduced pressure to give a residue. The residue was purified by column chromatography (SiO$_2$, petroleum ether/ethyl acetate=5:1) to afford compound 15.5 (5.00 g, 32.64 mmol, 57.37% yield) as a colorless oil.

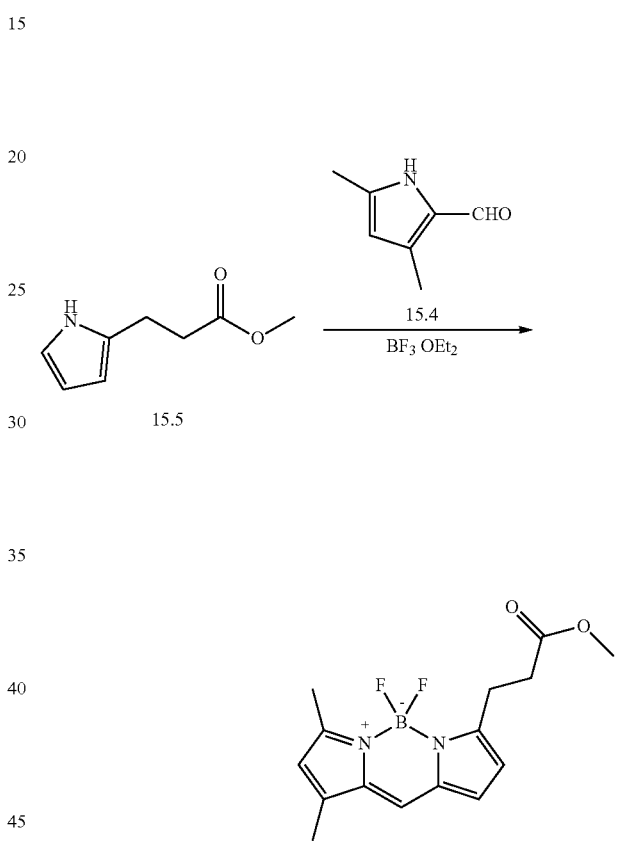

To a mixture of compound 15.5 (3.00 g, 19.58 mmol, 1.00 eq) and compound 15.4 (2.65 g, 21.54 mmol, 1.10 eq) in DCM (60.00 mL) was added POCl$_3$ (3.30 g, 21.54 mmol, 2.00 mL, 1.10 eq) in one portion at 18° C. under $N_2$. The mixture was stirred at 18° C. for 10 hours, followed by addition of BF$_3$.Et$_2$O (11.12 g, 78.32 mmol, 9.67 mL, 4.00 eq) and DIEA (10.63 g, 82.24 mmol, 14.36 mL, 4.20 eq) dropwise at 18° C. The mixture was stirred at 18° C. for 10 hours. The reaction mixture was filtered, diluted with $H_2O$ (50 mL), and extracted with DCM (3×50 mL). The combined organic layers were washed with brine (100 mL), dried over $Na_2SO_4$, filtered, and concentrated under reduced pressure to give a residue. The residue was purified by column chromatography (SiO$_2$, petroleum ether/ethyl acetate=1:4) to afford compound 15.3 (3.00 g, 9.80 mmol, 50.05% yield) as a red solid.

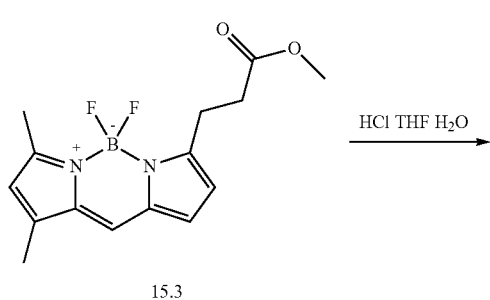

15.3

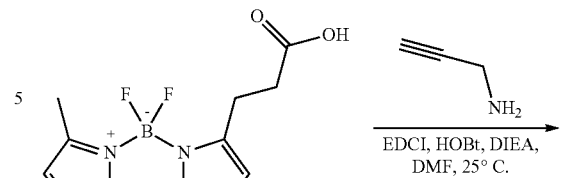

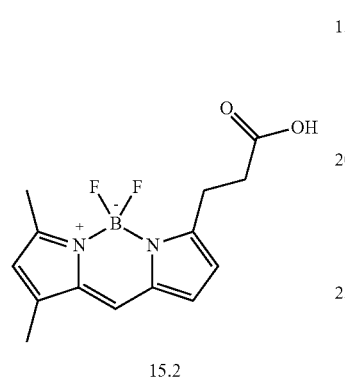

15.2

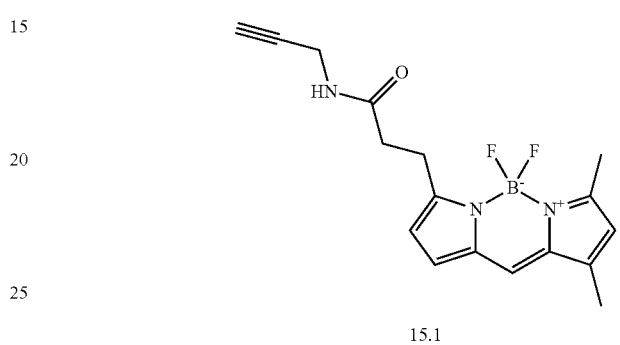

15.1

To a mixture of compound 15.3 (1.00 g, 3.27 mmol, 1.00 eq) in THF (120.00 mL) and H$_2$O (80.00 mL) was added HCl (51.11 g, 519.15 mmol, 50.11 mL, 37% purity, 158.76 eq) in one portion at 18° C. under N$_2$. The mixture was stirred at 18° C. for 10 hours. The reaction mixture was quenched by addition DCM (100 mL), then extracted with DCM (3×100 mL). The combined organic layers were washed with brine (300 mL), dried over Na$_2$SO$_4$, filtered, and concentrated under reduced pressure to give a residue. The residue was purified by column chromatography (SiO$_2$, DCM:MeOH=20:1) to afford compound 15.2 (700.00 mg, 2.40 mmol, 73.29% yield) as a red solid.

To a mixture of compound 15.2 (300.00 mg, 1.03 mmol, 1.00 eq) and HOBt (152.66 mg, 1.13 mmol, 1.10 eq) in DMF (3.00 mL) was added EDCI (216.58 mg, 1.13 mmol, 1.10 eq) in one portion at 0° C. under N$_2$. The mixture was stirred at 0° C. for 1 hour. Then, propargylamine (56.57 mg, 1.03 mmol, 65.78 µL, 1.00 eq) and DIPEA (398.22 mg, 3.08 mmol, 538.13 µL, 3.00 eq) were added in one portion at 0° C., and the mixture was stirred at 0° C. for 1 hour. The reaction mixture was diluted with EtOAc (4 mL) and extracted with EtOAc (3×3 mL). The combined organic layers were washed with brine (5 mL), dried over Na$_2$SO$_4$, filtered, and concentrated under reduced pressure to give a residue. The residue was purified by prep-TLC (SiO$_2$, DCM:MeOH=20:1) to afford compound 15.1 (150.00 mg, 455.72 µmol, 44.24% yield) as a red solid.

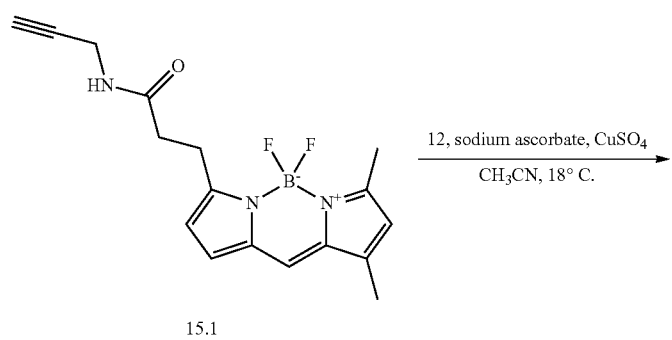

15.1

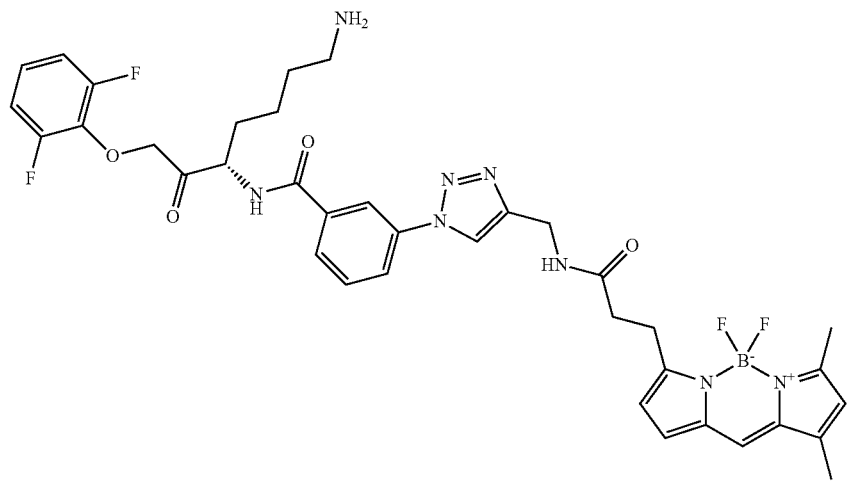

15

To a mixture of compound 15.1 (100.00 mg, 303.81 μmol, 1.00 eq) and compound 12 (126.81 mg, 303.81 μmol, 1.00 eq) in acetonitrile (2.00 mL) was added a solution of CuSO₄ (2.42 mg, 15.19 μmol, 2.33 μL, 0.05 eq) in H₂O (100.00 μL) in one portion and sodium ascorbate (120.38 mg, 607.62 μmol, 2.00 eq) at 18° C. under N₂. The mixture was stirred at 18° C. for 10 hours. The residue was purified by prep-HPLC (TFA condition) to give compound 15 trifluoroacetate salt (5.00 mg, 6.70 μmol, 2.21% yield) as a red solid. $^1$H NMR (400 MHz, methanol-d4) δ ppm 1.46-1.68 (m, 1H) 1.46-1.67 (m, 1H) 1.69-1.90 (m, 1H) 2.04-2.18 (m, 2H) 2.19-2.31 (m, 3H) 2.48 (s, 2H) 2.69 (br t, J=7.45 Hz, 2H) 2.95 (br s, 2H) 3.19-3.28 (m, 2H) 4.52 (s, 2H) 5.04 (br s, 3H) 6.19 (s, 1H) 6.31 (br d, J=3.51 Hz, 1H) 6.91-7.12 (m, 4H) 7.31-7.32 (m, 1H) 7.35 (s, 1H) 7.68 (br t, J=8.11 Hz, 1H) 7.65-7.71 (m, 1H) 7.95-8.04 (m, 2H) 8.25-8.36 (m, 2H). LCMS (ESI): m/z: [M+H] calcd for C₃₇H₃₉F₄O₄N₈B: 746; found 747; RT=2.117 min.

Example 16. Preparation of (S)—N-(7-amino-1-(methylthio)-2-oxoheptan-3-yl)cyclopentane-carboxamide (16)

To a solution of compound 1.2 (100.00 mg, 240 μmol, 1.00 eq) in DMF (2.00 mL) was added methylsulfanylsodium (16 mg, 240 μmol, 15 μL, 1.00 eq). The mixture was stirred at 25° C. for 0.5 hours. The residue was purified by prep-HPLC (TFA condition). Compound 16.1 (50.00 mg, 99.89 μmol, 55.16% yield, TFA) was obtained as a yellow oil.

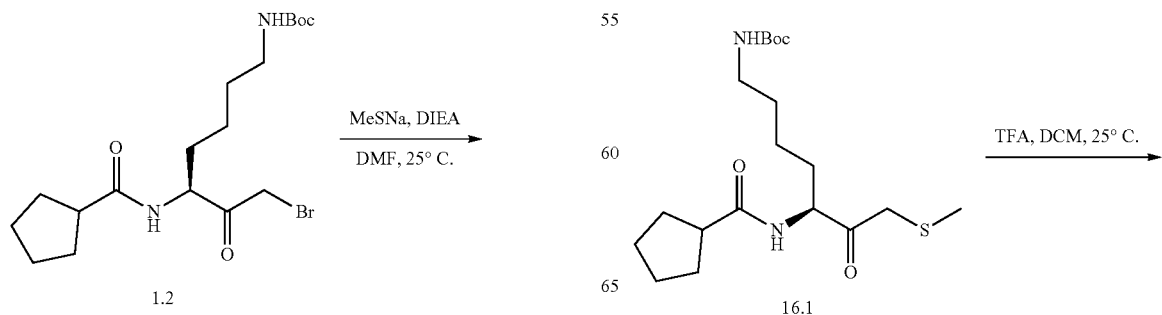

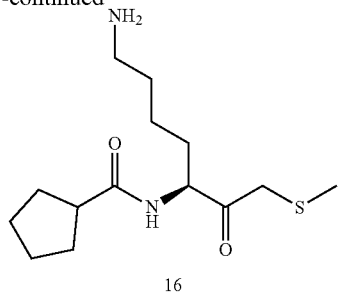

16

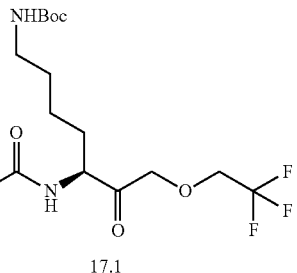

17.1

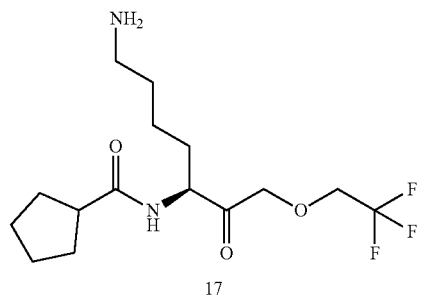

17

To a solution of compound 16.1 (50.00 mg, 129.35 μmol, 1.00 eq) in DCM (5.00 mL) was added TFA (1.00 mL). The mixture was stirred at 25° C. for 5 hours. The mixture was concentrated under reduced pressure to give compound 16 trifluoroacetate salt (5.00 mg, 17.46 μmol, 13.50% yield). $^1$H NMR (400 MHz, methanol-d4) δ ppm 1.33-1.54 (m, 2H) 1.55-1.79 (m, 11H) 1.80-1.99 (m, 4H) 2.06 (s, 3H) 2.64-2.80 (m, 1H) 2.86-2.99 (m, 2H) 3.36 (d, J=1.54 Hz, 2H) 4.67 (dd, J=9.48, 4.41 Hz, 1H). LCMS (ESI): m/z: [M+H] calcd for $C_{14}H_{26}SO_2N_2$:287; found 287; RT=1.826 min.

Example 17. Preparation of (S)—N-(7-amino-2-oxo-1-(2,2,2-trifluoroethoxy)heptan-3-yl)cyclo-pentanecarboxamide (17)

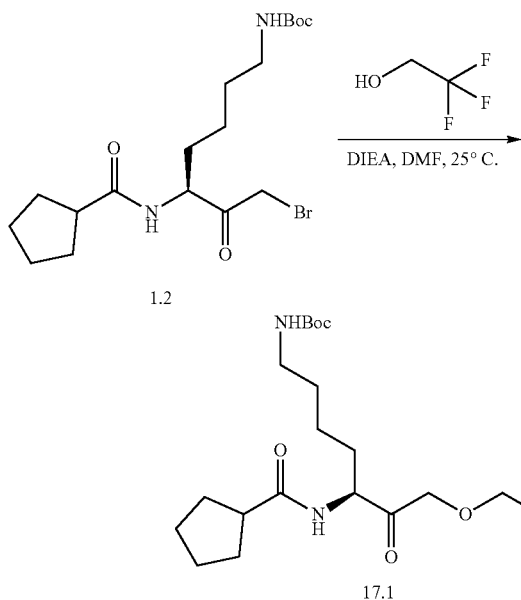

To a solution of compound 1.2 (50.00 mg, 119.23 μmol, 1.00 eq) in DMF (2.00 mL) was added $K_2CO3$ (49.44 mg, 357.69 μmol, 3.00 eq) and 2,2,2-trifluoroethan-1-ol (11.93 mg, 119.23 μmol, 8.58 μL, 1.00 eq). The mixture was stirred at 25° C. for 15 hours. The residue was purified by prep-HPLC (TFA condition). Compound 17.1 (10.00 mg, 22.81 μmol, 19.13% yield) was obtained as a yellow oil.

To a solution of tert-butyl compound 17.1 (10.00 mg, 22.81 μmol, 1.00 eq) in DCM (2.50 mL) was added TFA (500.00 μL). The mixture was stirred at 25° C. for 2 hours. The mixture was concentrated under reduced pressure to give compound 17 trifluoroacetate salt (5.00 mg, 14.78 μmol, 64.78% yield) as a yellow oil. $^1$H NMR (400 MHz, methanol-d4) δ ppm 1.32-1.51 (m, 3H) 1.53-1.78 (m, 10H) 1.80-1.96 (m, 4H) 2.72 (quin, J=7.88 Hz, 1H) 2.86-2.99 (m, 2H) 3.96-4.08 (m, 2H) 4.36-4.55 (m, 3H). LCMS (ESI): m/z: [M+H] calcd for $Ci5H_{2503}N_2F_3$: 339; found 339; RT=2.060 min.

Example 18. Preparation of (S)—N-(7-amino-1-((1,1,1,3,3,3-hexafluoropropan-2-yl)oxy)-2-oxoheptan-3-yl)cyclopentanecarboxamide (18)

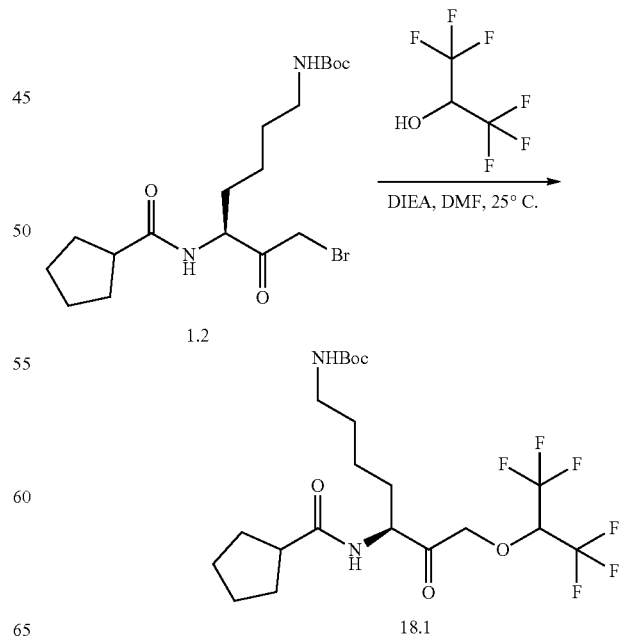

18.1

To a solution of compound 1.2 (50.00 mg, 119.23 µmol, 1.00 eq) in DMF (2.00 mL) was added K2CO3 (49.44 mg, 357.69 µmol, 3.00 eq) and 1,1,1,3,3,3-hexafluoropropan-2-ol (20.04 mg, 119.23 µmol, 1.00 eq). The mixture was stirred at 25° C. for 15 hours. The residue was purified by prep-HPLC (TFA condition). Compound 18.1 (15.00 mg, 29.62 µmol, 24.84% yield) was obtained as a yellow oil.

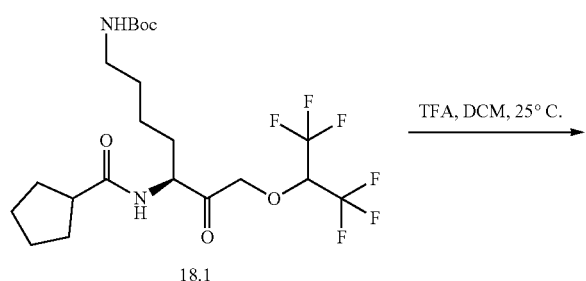

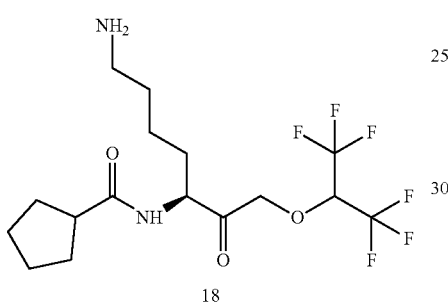

To a solution of compound 18.1 (15.00 mg, 29.62 µmol, 1.00 eq) in DCM (5.00 mL) was added TFA (1.00 mL). The mixture was stirred at 25° C. for 15 hours. The mixture was concentrated under reduced pressure to give compound 18 trifluoroacetate salt (5.00 mg, 12.30 µmol, 41.54% yield) as a yellow oil. ¹H NMR (400 MHz, methanol-d4) δ ppm 1.35-1.54 (m, 2H) 1.55-1.78 (m, 10H) 1.80-1.97 (m, 3H) 2.65-2.79 (m, 1H) 2.85-2.98 (m, 2H) 4.45-4.54 (m, 1H) 4.60-4.78 (m, 1H) 4.98-5.08 (m, 1H). LCMS (ESI): m/z: [M+H] calcd for $C_{16}H_{24}O_3N_2F_6$:407; found 407; RT=2.356 min.

Example 19. Preparation of (S)—N-(7-amino-1-(dimethylamino)-2-oxoheptan-3-yl)cyclo-pentan-ecarboxamide (19)

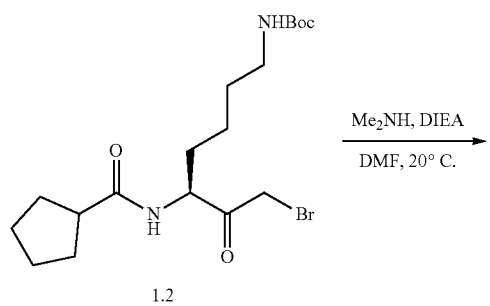

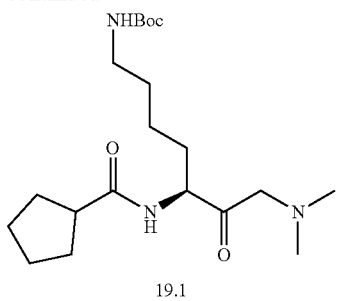

To a mixture of compound 1.2 (100.00 mg, 238.46 µmol, 1.00 eq) and N-methylmethanamine (19.44 mg, 238.46 µmol, 21.85 µL, 1.00 eq, HCl) in DMF (1.00 mL) was added DIPEA (123.28 mg, 953.86 µmol, 166.59 µL, 4.00 eq) in one portion at 20° C. under $N_2$. The mixture was stirred at 20° C. for 1 hour. The residue was purified by prep-HPLC (TFA condition) to give compound 19.1 (50.00 mg, 130.37 µmol, 54.67% yield) as a colorless oil. LCMS (ESI): m/z: [M+H] calcd for $C_{20}H_{37}O_4N_3$: 383; found 384; RT=0.672 min.

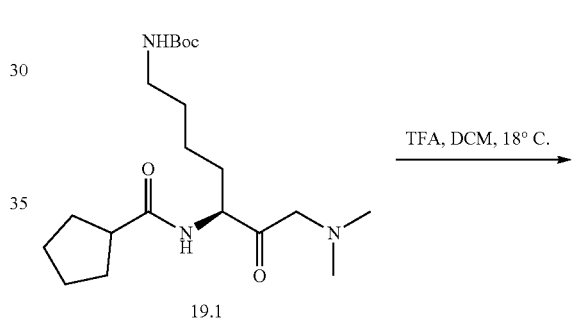

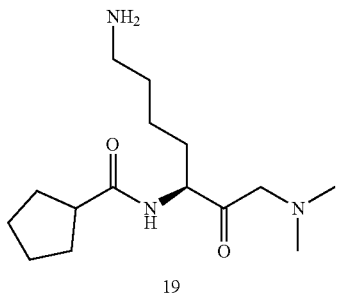

Compound 19.1 (50.00 mg, 130.37 µmol, 1.00 eq) was dissolved in DMF (1.00 mL), the mixture was added TFA (1.12 g, 9.85 mmol, 728.95 µL, 75.52 eq) and stirred at 18° C. for 10 hours. The reaction mixture concentrated under reduced pressure to give compound 19 trifluoroacetate salt (50.00 mg, crude) as a colorless oil. ¹H NMR (400 MHz, methanol-d₄) δ ppm 1.39-1.58 (m, 3H) 1.59-1.66 (m, 2H) 1.66-1.78 (m, 7H) 1.87-1.98 (m, 3H) 2.68-2.81 (m, 1H) 2.90 (s, 6H) 2.92-2.97 (m, 2H) 4.28-4.32 (m, 1H) 4.32-4.42 (m, 2H). LCMS (ESI): m/z: [M+H] calcd for $C_{15}H_{29}O_2N_3$: 283; found 284; RT=2.365 min.

191

Example 20. Preparation of (S)-3-acetamido-N-(7-amino-1-(2,6-difluorophenoxy)-2-oxoheptan-3-yl)benzamide (9)

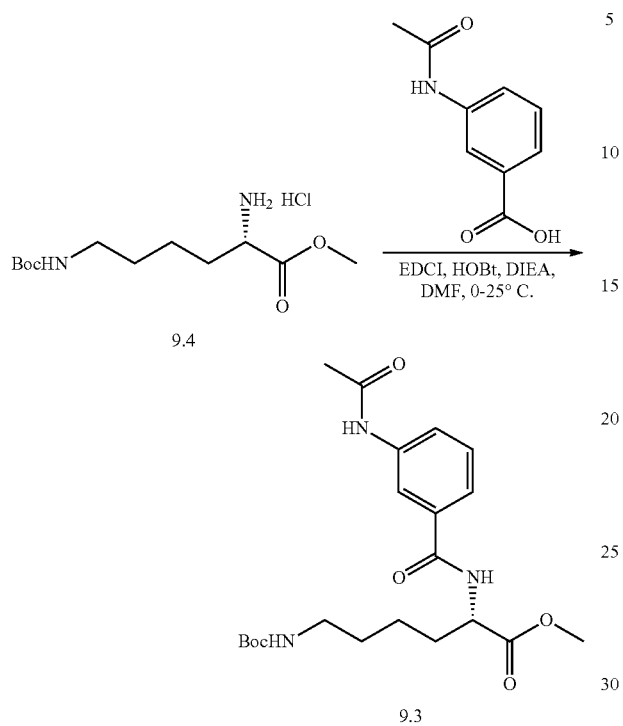

To a solution of compound 3-acetamidobenzoic acid (1.21 g, 6.74 mmol, 1.00 eq) in DMF (30.00 mL) was added HOBt (1.00 g, 7.41 mmol, 1.10 eq) and EDCI (1.42 g, 7.41 mmol, 1.10 eq). After addition, the mixture was stirred at 0° C. for 30 mins. Then added DIEA (3.48 g, 26.96 mmol, 4.71 mL, 4.00 eq) and compound 9.4 (2.00 g, 6.74 mmol, 1.00 eq) to above mixture at 0° C. under $N_2$. The resulting mixture was stirred at 25° C. for 15.5 hrs. The reaction mixture was added water (10 mL), extracted with EtOAc (30 mL*3). The organic phase was separated, washed with NaCl (10 mL) and dried over $Na_2SO_4$, filtered and concentrated under reduced pressure to give a residue. Compound 9.3 (2.30 g, 5.46 mmol, 80.96% yield) was obtained as a white solid. LCMS (ESI): m/z: [M+H] calcd for $C_{21}H_{31}N_3O_6$: 421.22; found 322.3; RT=0.748 min. $^1$H NMR (400 MHz, chloroform-d) δ ppm 1.30-1.56 (m, 14H) 1.68-1.98 (m, 2H) 2.16 (s, 3H) 2.98-3.15 (m, 2H) 3.71 (s, 3H) 4.61-4.83 (m, 2H) 7.14 (br d, J=7.50 Hz, 1H) 7.28-7.37 (m, 1H) 7.47 (br d, J=7.06 Hz, 1H) 7.74 (br s, 1H) 7.91-8.02 (m, 1H) 8.52 (br s, 1H).

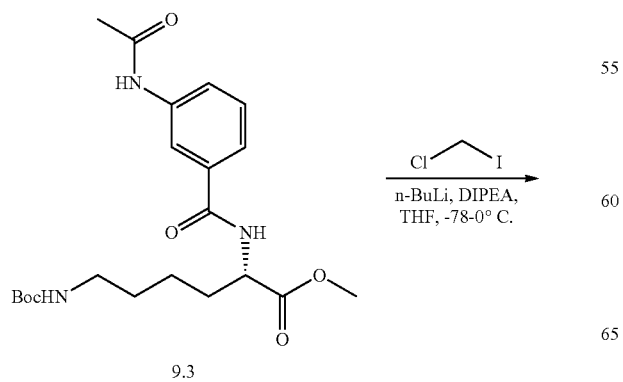

192

-continued

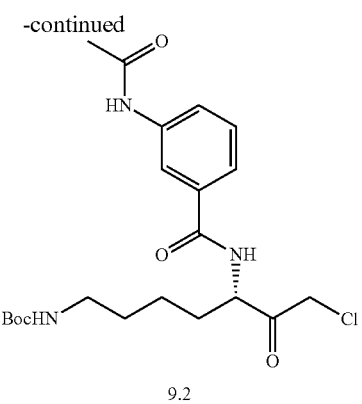

To a solution of DIPA (384.12 mg, 3.80 mmol, 533.50 μL, 4.00 eq) in THF (10.00 mL) was added n-BuLi (243.17 mg, 3.80 mmol, 4.00 eq) at 0° C. under $N_2$. After 0.5 h, compound 9.3 (400.00 mg, 949.01 μmol, 1.00 eq) and chloroiodomethane (669.55 mg, 3.80 mmol, 275.53 μL, 4.00 eq) was added to above mixture at −78° C. under $N_2$. The resulting mixture was stirred at −78° C. for 1.5 hrs. The reaction mixture was added water (20 mL), extracted with EtOAc (20 mL*3). The combined organic layers were washed with brine (10 mL*1), dried over $Na_2SO_4$, filtered and concentrated under reduced pressure to give a residue. Compound 9.2 (500.00 mg, crude) was obtained as a black brown oil.

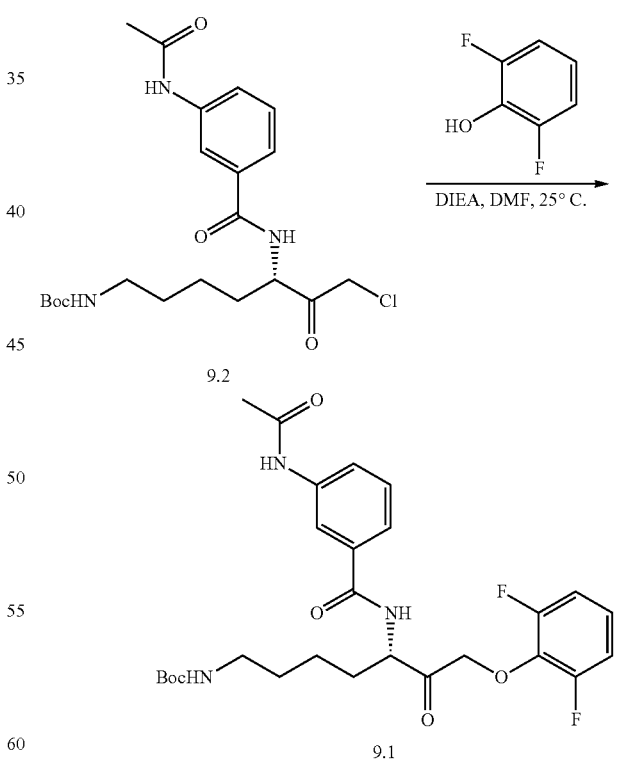

To a solution of compound 9.2 (200.00 mg, 454.62 μmol, 1.00 eq) and DIEA (176.27 mg, 1.36 mmol, 238.20 μL, 3.00 eq) in DMF (4.00 mL) was added 2,6-difluorophenol (118.28 mg, 909.24 μmol, 2.00 eq) at 25° C. under $N_2$. The resulting mixture was stirred at 25° C. for 16 hrs. The reaction mixture was added water (10 mL), extracted with EtOAc (10 mL*3). The combined organic layers were washed with brine (5 mL*1), dried over Na₂SO₄, filtered and concentrated under reduced pressure to give a residue. The crude product (500.00 mg) was obtained as a yellow oil. The residue was purified by prep-HPLC (neutral condition). Compound 9.1 (10.00 mg, 18.74 μmol, 2.00% yield) was obtained as a white solid.

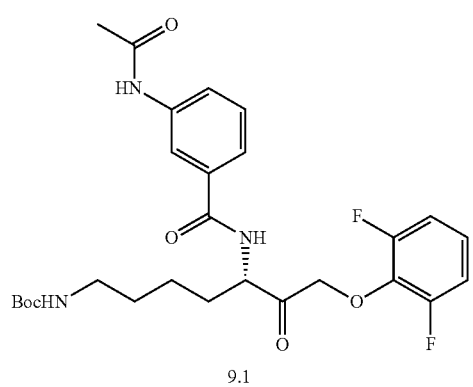

To a solution of compound 9.1 (5.00 mg, 9.37 μmol, 1.00 eq) in DCM (2.00 mL) was added TFA (2.14 mg, 18.74 μmol, 1.39 μL, 2.00 eq) under N₂. The mixture was stirred at 25° C. for 16 hours. Concentrated to afford residue. Compound 9 trifluoroacetate salt (5.00 mg, 9.13 μmol, 97.47% yield, TFA) was obtained as a red oil. LCMS (ESI): m/z: [M+H] calcd for C₂₂H₂₅F₂N₃O₄: 433.18; found 434.2; RT=2.052 min. ¹H NMR (400 MHz, methanol-d₄) δ ppm 1.44-1.88 (m, 1H) 1.44-1.51 (m, 1H) 1.51-1.84 (m, 1H) 1.52-1.82 (m, 1H) 1.52-1.85 (m, 1H) 1.83-1.85 (m, 1H) 2.07-2.20 (m, 1H) 2.94 (br t, J=6.50 Hz, 1H) 4.90-5.10 (m, 1H) 4.91-5.10 (m, 1H) 6.91-7.13 (m, 1H) 7.33-7.47 (m, 1H) 7.49-7.68 (m, 1H) 8.03-8.18 (m, 1H)

Additional compounds were synthesized according to the procedures in the preceding examples.

Example 21. Preparation of (S)—N-(7-amino-1-(methylsulfonyl)-2-oxoheptan-3-yl)-cyclopentanecarboxamide (20)

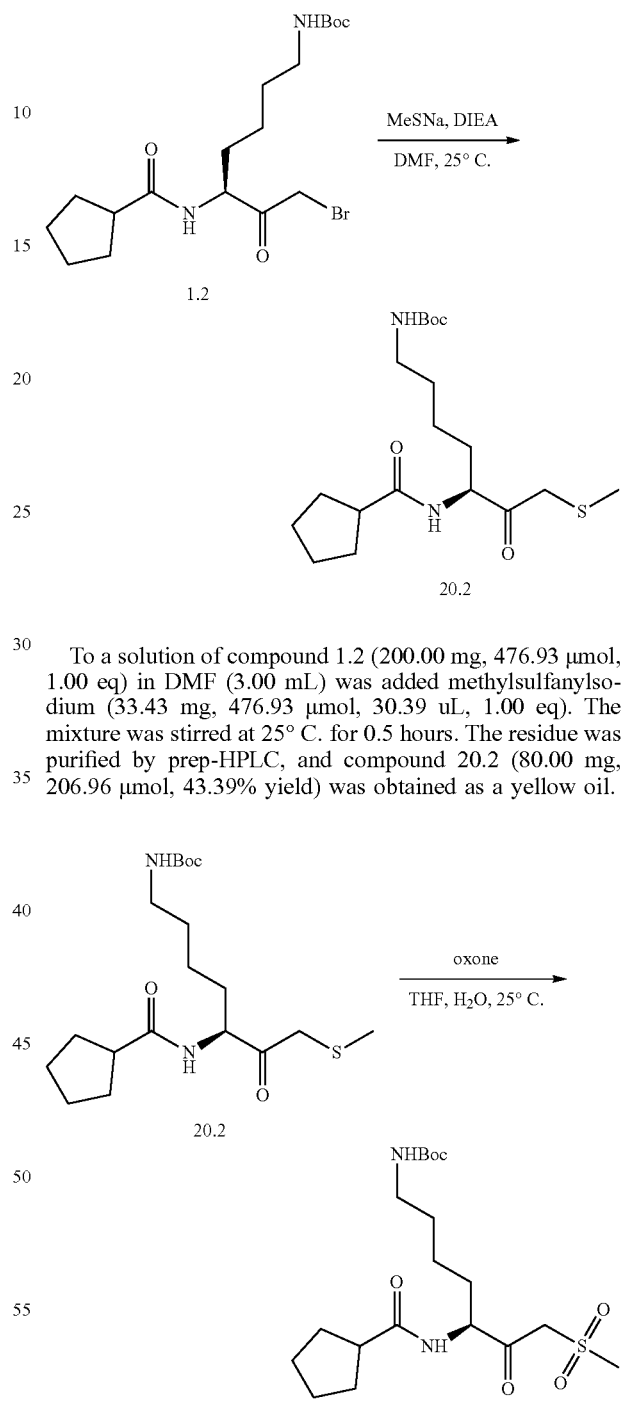

To a solution of compound 1.2 (200.00 mg, 476.93 μmol, 1.00 eq) in DMF (3.00 mL) was added methylsulfanylsodium (33.43 mg, 476.93 μmol, 30.39 uL, 1.00 eq). The mixture was stirred at 25° C. for 0.5 hours. The residue was purified by prep-HPLC, and compound 20.2 (80.00 mg, 206.96 μmol, 43.39% yield) was obtained as a yellow oil.

To a solution of compound 20.2 (60.00 mg, 155.22 μmol, 1.00 eq) in THF (2.00 mL) and H₂O (600.00 μL) was added oxone (190.85 mg, 310.44 μmol, 2.00 eq). The mixture was stirred at 25° C. for 12 hours. The residue was purified by prep-HPLC, and compound 20.1 (20.00 mg, 47.78 μmol, 30.78% yield) was obtained as a white solid

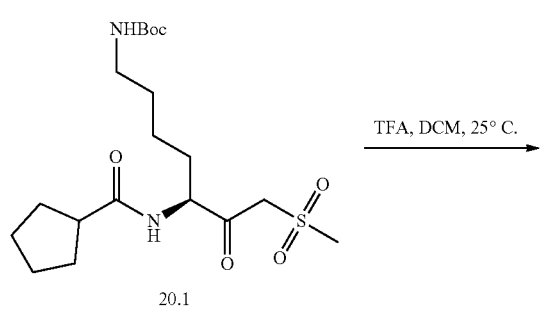

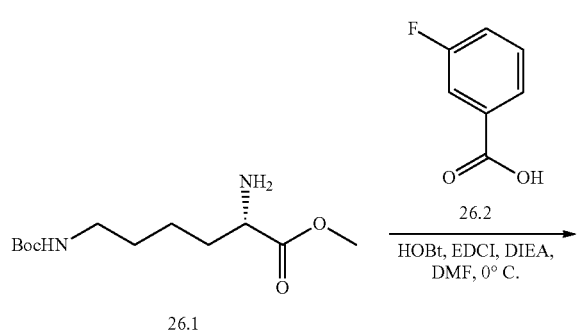

Compound 20.1 (20.00 mg, 47.78 μmol, 1.00 eq) in TFA (1.00 mL) and DCM (5.00 mL) was stirred at 25° C. for 14 hours. The mixture was concentrated under reduced pressure to provide compound 20 trifluoroacetate salt (10.00 mg, 31.40 μmol, 65.73% yield) as a yellow oil. $^1$H NMR (400 MHz, DMSO-d$_6$) δ ppm 1.18-1.39 (m, 1H) 1.18-1.39 (m, 1H) 1.39-1.66 (m, 9H) 1.67-1.88 (m, 3H) 2.58-2.86 (m, 3H) 3.08 (s, 3H) 4.15-4.32 (m, 1H) 4.39-4.61 (m, 2H) 7.70 (br s, 3H) 8.23 (d, J=7.06 Hz, 1H). LCMS (ESI): m/z: [M+H] calcd for $C_{14}H_{26}SO_4N_2$:319; found 319; RT=1.916 min.

Example 22. Preparation of (S)—N-(7-amino-1-(2, 6-difluorophenoxy)-2-oxoheptan-3-yl)-3-fluorobenzamide (26)

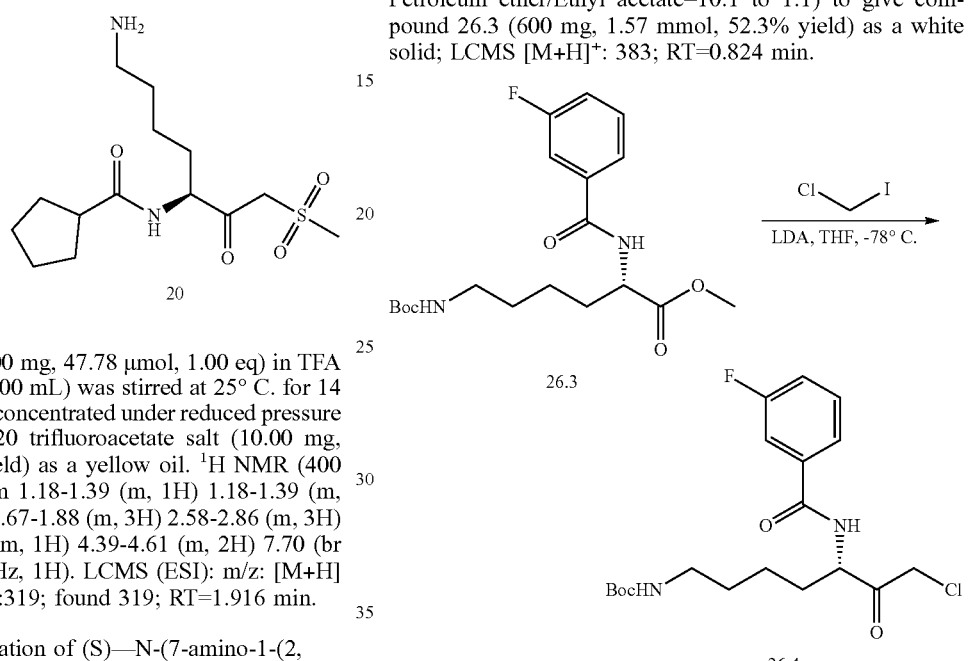

To a mixture of compound 26.1 (420.44 mg, 3.0 mmol, 1 equivalent) and EDCI (632.77 mg, 3.3 mmol, 1.1 equivalent), HOBt (446.01 mg, 3.3 mmol, 1.1 equivalent) in DMF (10 mL) was added compound 26.2 (1 g, 3 mmol, 1 equivalent) and DIEA (1.55 g, 12 mmol, 2.09 mL, 4 equivalent) in one portion at 0° C. under N$_2$. The mixture was stirred at 0° C. for 15 hours. The aqueous phase was extracted with EtOAc (20 mL×3). The combined organic phases were washed with brine (5 mL), dried with anhydrous Na$_2$SO$_4$, filtered and concentrated in vacuum. The residue was purified by column chromatography (SiO$_2$, Petroleum ether/Ethyl acetate=10:1 to 1:1) to give compound 26.3 (600 mg, 1.57 mmol, 52.3% yield) as a white solid; LCMS [M+H]$^+$: 383; RT=0.824 min.

A mixture of n-BuLi (301.51 mg, 4.71 mmol, 6 equivalent) and DIPA (476.28 mg, 4.71 mmol, 661.49 μL, 6 equivalent) in THF (6 mL) was stirred at 0° C. under N$_2$. After 0.5 h, 26.3 (300 mg, 784.46 μmol, 1 equivalent) and iodochloromethane (553.45 mg, 3.14 mmol, 227.76 μL, 4 equivalent) was added to above mixture at −78° C. under N$_2$. The resulting mixture was stirred at −78° C. for 2 hrs. To the reaction mixture was added water (20 mL) then it was extracted with EtOAc (20×mL×3). The combined organic layers were washed with brine (10 mL), dried over Na$_2$SO$_4$, filtered and concentrated under reduced pressure. 26.4 (200 mg, 499 μmol, 63.6% yield) was obtained as a brown oil.

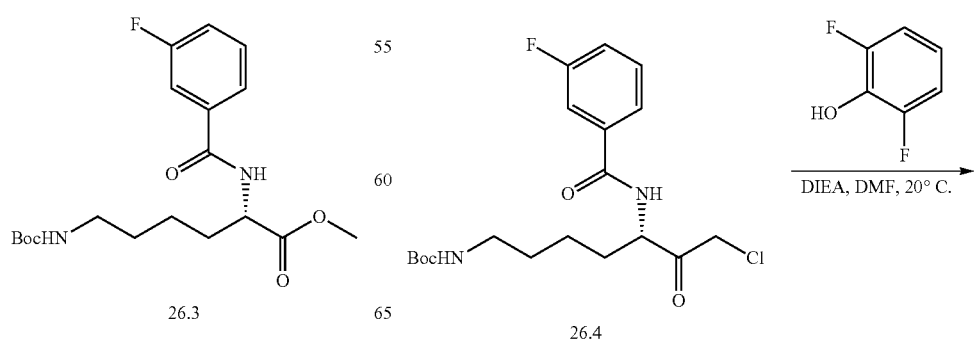

-continued

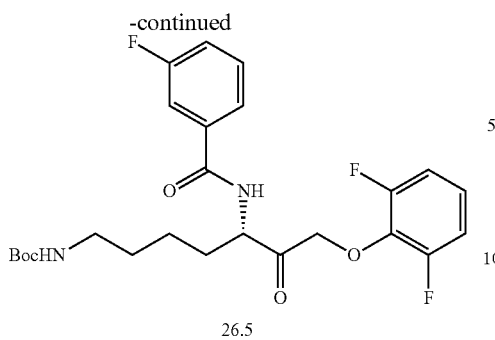

26.5

To a mixture of compound 26.4 (200 mg, 499 µmol, 1 equivalent) and 2,6-difluorophenol (64.9 mg, 499 µmol, 1 equivalent) in DMF (4 mL) was added DIEA (193.44 mg, 1.5 mmol, 261.41 µL, 3 equivalent) in one portion at 20° C. under $N_2$. The mixture was stirred at 20° C. for 15 hours. The residue was purified by preparative scale HPLC (TFA conditions). Compound 26.5 (18 mg, 36.4 µmol, 1 equivalent) was obtained as a white solid. LCMS $[M+H]^+$: 496; RT=0.886 min.

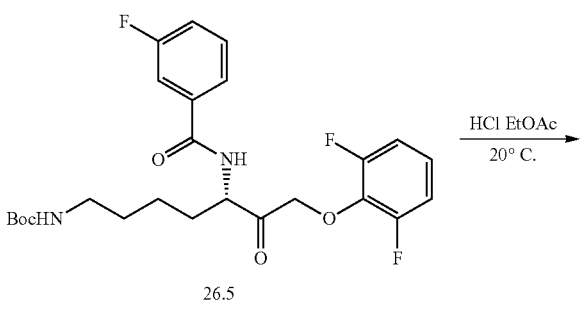

26.5

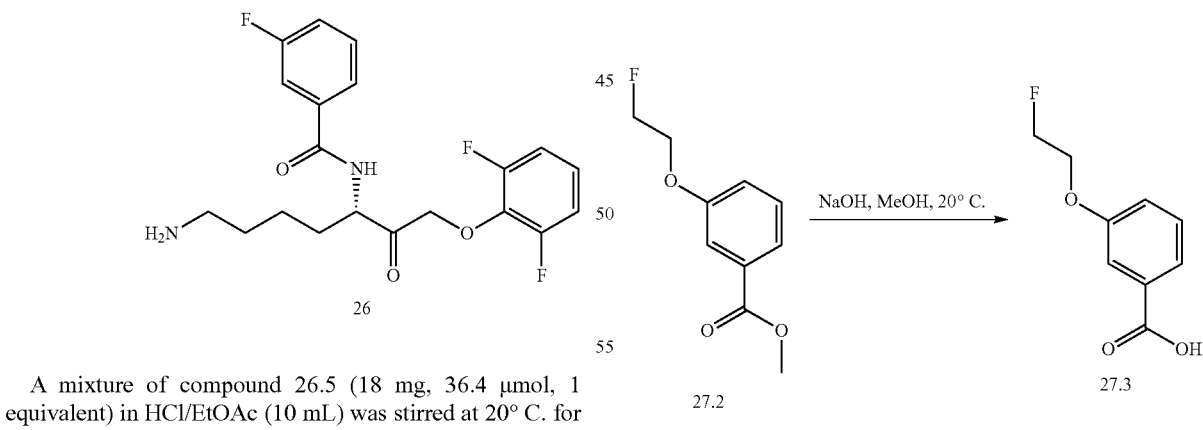

26

A mixture of compound 26.5 (18 mg, 36.4 µmol, 1 equivalent) in HCl/EtOAc (10 mL) was stirred at 20° C. for 4 hours; then filtered and concentrated under vacuum. The residue was purified by semi-preparative scale HPLC (TFA conditions) to give Compound 26 (12 mg) as a colorless oil; LCMS $[M+H]^+$: 395; RT=1.53 min. $^1$H NMR (400 MHz, METHANOL-$d_4$) δ ppm 1.48-1.63 (m, 2H), 1.67-1.86 (m, 3H), 2.07-2.18 (m, 1H), 2.89-2.99 (m, 2H), 4.92-4.96 (m, 1H), 4.96-5.06 (m, 2H), 6.95-7.03 (m, 2H), 7.03-7.12 (m, 1H), 7.29-7.35 (m, 1H), 7.51 (td, J=7.99, 5.62 Hz, 1H), 7.60 (dt, J=9.70, 2.09 Hz, 1H), 7.67-7.71 (m, 1H).

Example 23. Preparation of (S)—N-(7-amino-1-(2,6-difluorophenoxy)-2-oxoheptan-3-yl)-3-(2-fluoroethoxy)benzamide (27)

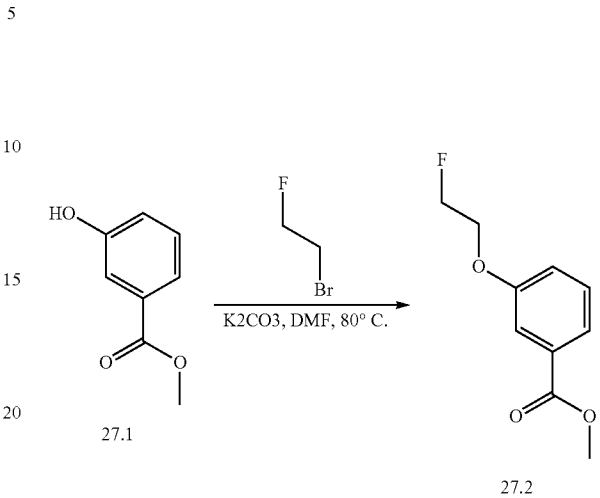

To a mixture of 27.1 (1 g, 6.57 mmol, 1 equivalent) and 1-fluoro-2-bromoethane (834.44 mg, 6.57 mmol, 1 equivalent) in DMF (10 mL) was added K2CO3 (2.72 g, 19.71 mmol, 3 equivalent) in one portion at 20° C. under $N_2$. The mixture was stirred at 80° C. for 15 hours. The aqueous phase was extracted with EtOAc (20 mL×3). The combined organic phases were washed with brine (5 mL), dried with anhydrous $Na_2SO_4$, filtered and concentrated in vacuum. The residue was purified by column chromatography (SiO$_2$, Petroleum ether/Ethyl acetate=10/1 to 2/1) to give compound 27.2 (890 mg, 4.49 mmol, 68.35% yield) as colorless oil; LCMS $[M+H]^+$: 199; RT=0.77 min.

A solution of 27.2 (890 mg, 4.49 mmol, 1 equivalent) in MeOH (27 mL) and NaOH (1 M, 8.98 mL, 2 equivalent) was stirred at 20° C. for 15 hours. The combined aqueous layers were extracted with EtOAc (40 mL×2) to remove neutral impurities. The aqueous phase was acidified with aqueous HCl to pH 5 and extracted with EtOAc (40 mL). Compound 27.3 (600 mg, 3.26 mmol, 72.6% yield) was obtained as colorless oil.

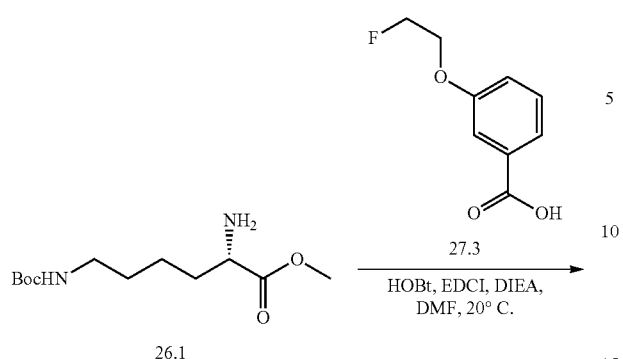

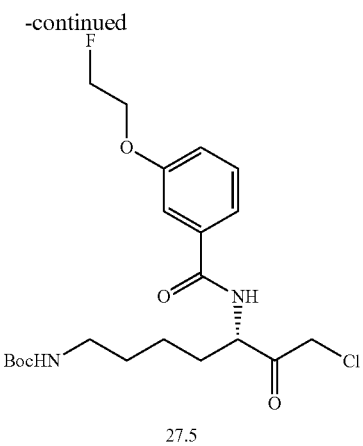

n-BuLi (270.37 mg, 4.22 mmol, 6 equivalent) was added to DIPA (427.08 mg, 4.22 mmol, 593.17 µL, 6 equivalent) in THF (6 mL) in one portion at 0° C. under N₂. After 0.5 hrs, 27.4 (300 mg, 703.43 µmol, 1 equivalent) and iodochloromethane (744.43 mg, 4.22 mmol, 306.35 µL, 6 equivalent) was added to above mixture at −78° C. under N₂. The resulting mixture was stirred at −78° C. for 2 hrs. To the reaction mixture was added water (20 mL) then it was extracted with EtOAc (20 mL×3). The combined organic layers were washed with brine (10 mL), dried over Na₂SO₄, filtered and concentrated under reduced pressure. Compound 27.5 (300 mg, crude) was obtained as a brown oil.

To a mixture of compound 27.3 (600 mg, 3.26 mmol, 1 equivalent) and HOBt (484.54 mg, 3.59 mmol, 1.1 equivalent) EDCI (687.44 mg, 3.59 mmol, 1.1 equivalent) in DMF (10 mL) was added 26.1 (967.54 mg, 3.26 mmol, 1 equivalent, HCl) and DIEA (1.69 g, 13.04 mmol, 2.28 mL, 4 equivalent) in one portion at 0° C. under N₂. The mixture was stirred at 20° C. for 15 hours. The reaction mixture was added to water (20 mL) then extracted with EtOAc (20 mL×3). The combined organic layers were washed with brine (10 mL), dried over Na₂SO₄, filtered and concentrated under reduced pressure to give 27.4 (1.17 g, 2.74 mmol, 84% yield) as a colorless oil; LCMS [M+H]⁺: 427; RT=0.825 min.

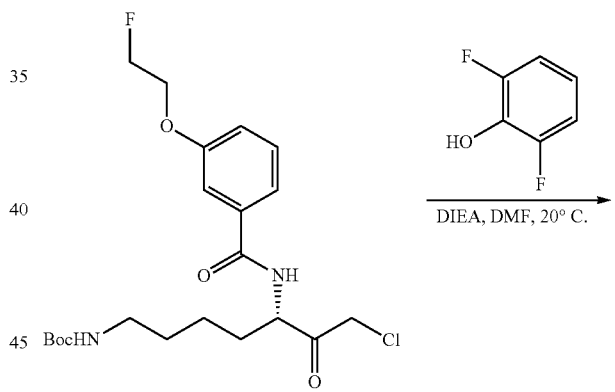

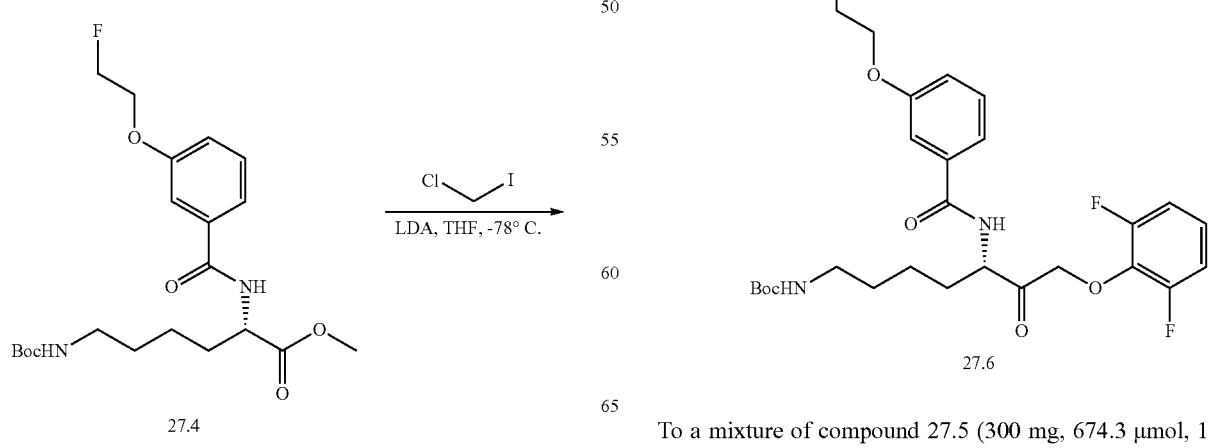

To a mixture of compound 27.5 (300 mg, 674.3 µmol, 1 equivalent) and 2,6-difluorophenol (87.72 mg, 674.28 µmol, 1 equivalent) in DMF (4 mL) was added DIEA (261.43 mg, 2.02 mmol, 353.29 µL, 3 equivalent) in one portion at 20° C. under N$_2$. The mixture was stirred at 20° C. for 15 hours. The residue was purified by prep-HPLC (TFA condition). Compound 27.6 (72 mg, 133.7 µmol, 19.8% yield) was obtained as a brown solid; LCMS [M+H]$^+$:539; RT=2.85 min.

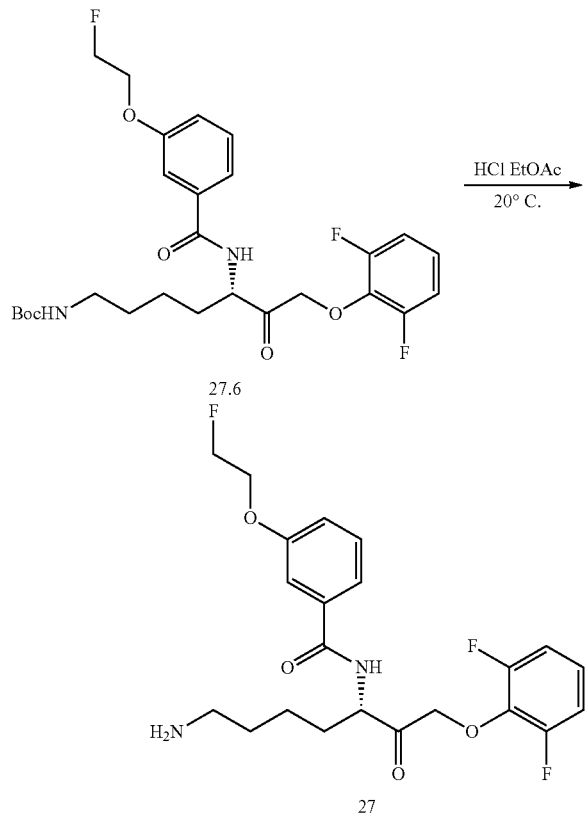

To a solution of 27.6 (72 mg, 133.7 µmol, 1 equivalent) in DCM (1 mL) was added TFA (304.87 mg, 2.67 mmol, 197.97 µL, 20 equivalent). The mixture was stirred at 20° C. for 4 hours. It was filtered and concentrated in vacuum to give Compound 27 (50 mg, 75.02 µmol, 56% yield, 2TFA); LCMS [M+H]$^+$: 667; RT=0.69 min. $^1$H NMR (400 MHz, DMSO-d$_6$) δ ppm 1.37-1.55 (m, 2H), 1.57-1.59 (m, 2H), 1.69-1.72 (m, 2H), 1.73-1.85 (m, 2H), 2.75-2.79 (t, J=8.0 Hz, 2H), 4.26-4.27 (d, J=4.0 Hz, 1H), 4.33-4.34 (d, J=3.6 Hz, 2H), 4.34-4.35 (m, 1H), 4.69-4.71 (m, 1H), 4.81-4.82 (m, 1H), 5.09-5.13 (dd, J=1.6 Hz, 2H), 7.09-7.12 (m, 4H), 7.39-7.48 (m, 4H), 7.73 (s, 2H), 8.77-8.78 (d, J=7.6 Hz, 2H).

Example 24. Preparation of (S)—N-(7-amino-1-(2, 6-difluorophenoxy)-2-oxoheptan-3-yl)-6-fluoropicolinamide (28)

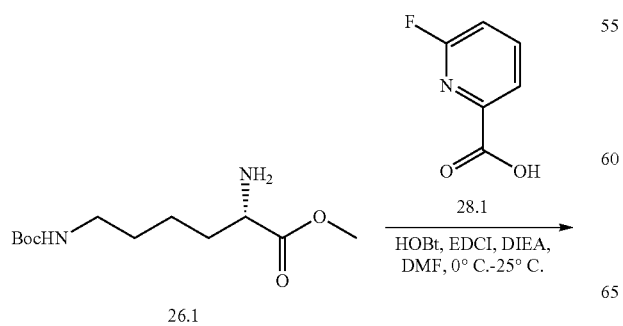

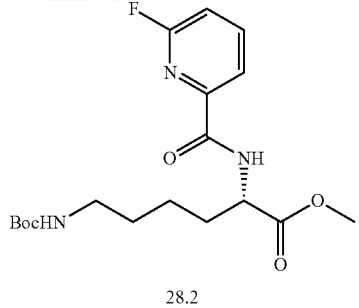

To a solution of compound 28.1 (366.07 mg, 2.6 mmol, 1.1 equivalent) in DMF (15 mL) was added HOBt (350.77 mg, 2.6 mmol, 1.1 equivalent) and EDCI (497.65 mg, 2.60 mmol, 1.1 equivalent). The mixture was stirred at 0° C. for 1 hr. Then to the mixture was added compound 26.1 (700 mg, 2.36 mmol, 1 equivalent, HCl) and DIEA (1.22 g, 9.44 mmol, 1.65 mL, 4 equivalent); the mixture was stirred at 25° C. for 14 hours. The reaction mixture was quenched by addition H$_2$O (30 mL) and extracted with ethyl acetate (30×mL×3). The combined organic layers were washed with saturated brine (5 mL), dried over anhydrous sodium sulfate, filtered and concentrated under reduced pressure. The residue was purified by column chromatography (SiO$_2$, DCM: MeOH=10:1) to give compound 28.2 (750 mg, 1.96 mmol, 83% yield) as yellow oil; LCMS [M+H-Boc]$^+$: 384; RT=0.817 min. $^1$H NMR (400 MHz, CHLOROFORM-d) δ ppm 1.42 (s, 11H), 1.53 (br d, J=6.17 Hz, 2H), 1.65 (s, 1H), 1.75-2.05 (m, 2H), 3.12 (br d, J=6.17 Hz, 2H), 3.78 (d, J=0.66 Hz, 3H), 4.57 (br s, 1H), 4.67-4.89 (m, 1H), 6.97-7.18 (m, 1H), 7.87-8.03 (m, 1H), 8.05-8.22 (m, 2H).

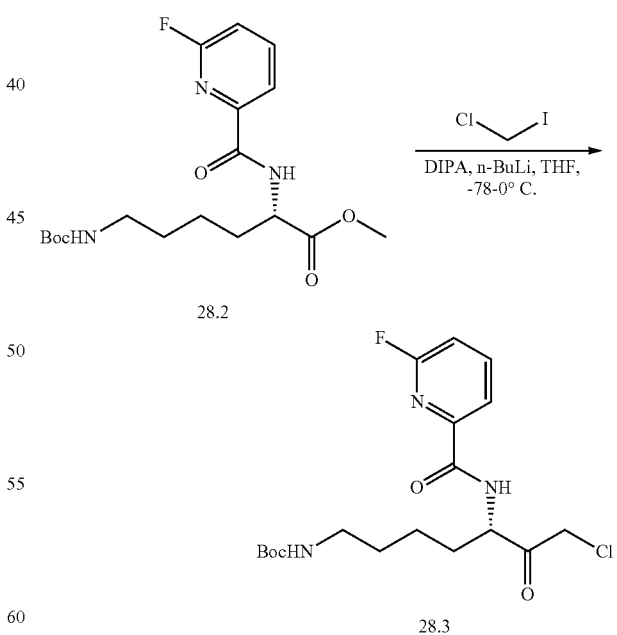

To a solution of DIPA (526.19 mg, 5.2 mmol, 730.82 µL, 5 equivalent) in THF (5 mL) was added n-BuLi (2.5 M, 2.08 mL, 5 equivalent). The mixture was stirred at 0° C. for 0.5 hr under N$_2$; then to the mixture was added to the solution of compound 28.2 (400 mg, 1.04 mmol, 1 equivalent) and chloro(iodo)methane (917.18 mg, 5.2 mmol, 377.44 µL, 5 equivalent) in THF (10 mL). This was stirred at −78° C. for 0.5 hr. The reaction mixture was quenched by addition saturated NH₄Cl (20 ml) at 25° C. and extracted with ethyl acetate (15 mL×3). The combined organic layers were washed with saturated Na₂SO₃ (10 mL), saturated NaHCO₃ (10 mL) and brine (10 mL); then it was dried over anhydrous sodium sulfate, filtered and concentrated under reduced pressure to give 28.3 (500 mg, crude) as yellow oil.

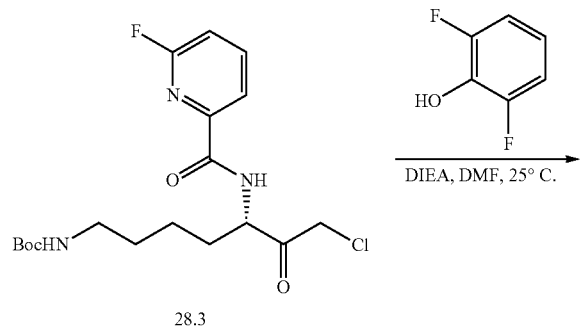

28.3

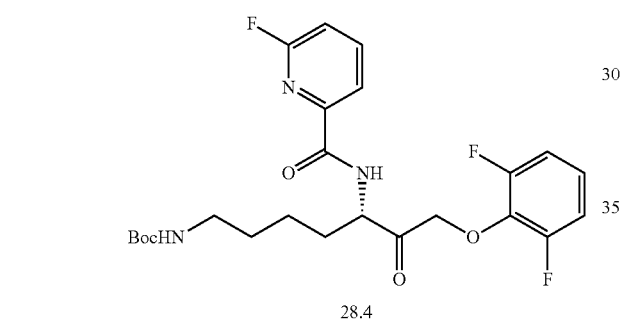

28.4

To a solution of 28.3 (500 mg, 1.24 mmol, 1 equivalent) in DMF (8 mL) was added DIEA (481 mg, 3.72 mmol, 649.69 µL, 3 equivalent) and 2,6-difluorophenol (241.97 mg, 1.86 mmol, 1.5 equivalent). The mixture was stirred at 25° C. for 15 hours. The residue was purified by semi-preparative scale HPLC (TFA conditions) to give 28.4 (50 mg, 101 µmol, 8% yield) as yellow oil; LCMS [M+H]⁺: 496; RT=2.84 min.

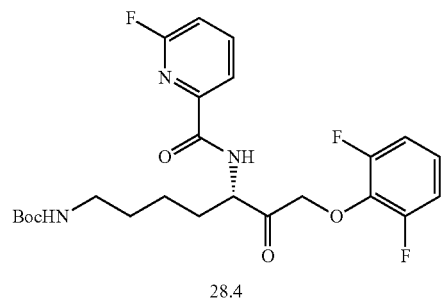

28.4

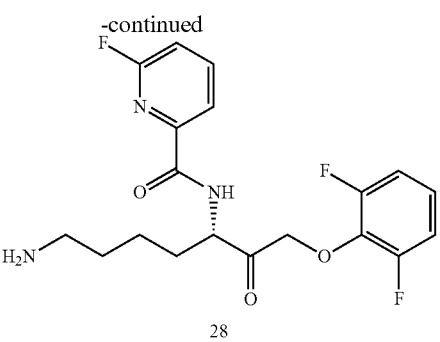

28

To a solution of 28.4 (50 mg, 101 µmol, 1 equivalent) in DCM (5 mL) was added TFA (1 mL). The mixture was stirred at 25° C. for 15 hours; then was concentrated under reduced pressure to give Compound 28 (20 mg, 50.6 µmol, 50% yield); LCMS [M+H]⁺: 396; RT=2.11 min. ¹H NMR (400 MHz, DMSO-d₆) δ ppm 1.21-1.44 (m, 2H), 1.45-1.65 (m, 2H), 1.71-2.01 (m, 2H), 2.69-2.85 (m, 2H), 4.55-4.76 (m, 2H), 4.97-5.34 (m, 2H), 7.03-7.21 (m, 2H), 7.48 (dd, J=8.27, 1.65 Hz, 1H), 7.68 (br s, 3H), 7.99 (dd, J=7.28, 1.76 Hz, 1H), 8.22 (q, J=8.08 Hz, 1H), 8.98 (d, J=8.38 Hz, 1H).

Example 25. Preparation of (S)—N-(7-amino-1-(2,6-difluorophenoxy)-2-oxoheptan-3-yl)-6-fluoronicotinamide (29)

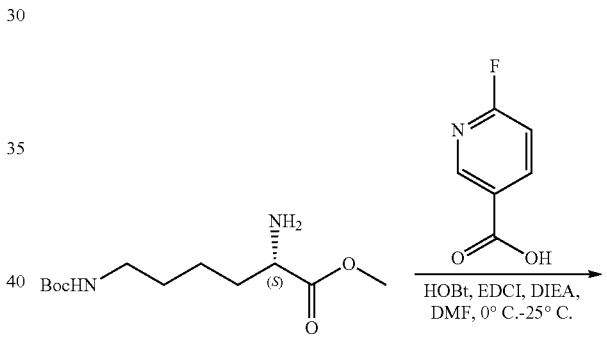

26.1

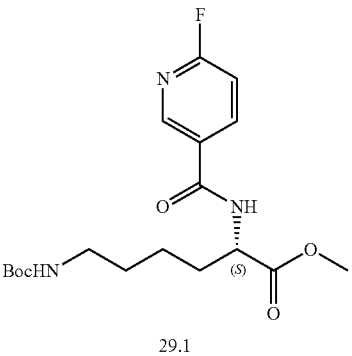

29.1

To a solution of 6-fluoronicotinic acid (366.3 mg, 2.6 mmol, 1.1 equivalent) in DMF (15 mL) was added HOBt (351 mg, 2.6 mmol, 1.1 equivalent) and EDCI (497.65 mg, 2.60 mmol, 1.1 equivalent). The mixture was stirred at 0° C. for 1 hr. Then to the mixture was added compound 26.1 (700 mg, 2.36 mmol, 1 equivalent, HCl salt) and DIEA (1.22 g, 9.44 mmol, 1.65 mL, 4 equivalent); the mixture was stirred at 25° C. for 14 hours. The reaction mixture was quenched by addition H₂O (50 mL) and extracted with ethyl acetate (30 mL×3). The combined organic layers were washed with saturated brine (5 mL), dried over anhydrous sodium sulfate, filtered and concentrated under reduced pressure. The residue was purified by column chromatography (SiO$_2$, Petroleum ether/Ethyl acetate=2/1) to give 29.1 (300 mg, 782.45 µmol, 33.15% yield); LCMS [M+H-Boc]$^+$: 384; RT=0.7 min. $^1$H NMR (400 MHz, CHLOROFORM-d) δ ppm 1.40 (s, 11H), 1.48-1.59 (m, 3H), 1.63 (s, 1H), 1.76-2.04 (m, 2H), 3.13 (br d, J=6.15 Hz, 2H), 4.47-4.86 (m, 2H), 6.93 (br s, 1H), 7.01 (dd, J=8.53, 2.76 Hz, 1H), 8.29 (td, J=7.97, 2.38 Hz, 1H), 8.72 (s, 1H).

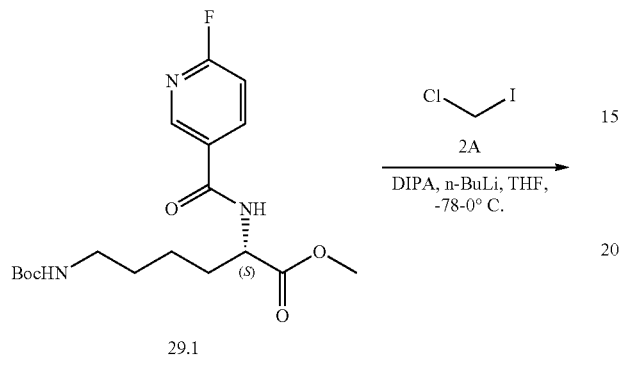

To a solution of DIPA (396 mg, 3.91 mmol, 549.82 µL, 5 equivalent) in THF (5 mL) was added n-BuLi (2.5 M, 1.56 mL, 5 equivalent). The mixture was stirred at 0° C. for 0.5 hr under N$_2$. Then the mixture was added to a solution of 29.1 (300 mg, 782.43 µmol, 1 equivalent) and chloroiodomethane (690 mg, 3.91 mmol, 284 µL, 5 equivalent) in THF (5 mL); this was stirred at −78° C. for 0.5 hr. The reaction mixture was quenched by the addition of saturated NH$_4$Cl (20 ml) then extracted with ethyl acetate (15 mL×3). The combined organic layers were washed with saturated Na$_2$SO$_3$ (10 mL), saturated NaHCO$_3$ (10 mL) and brine (10 mL). This was dried over anhydrous sodium sulfate, filtered and concentrated under reduced pressure to give 29.2 (500 mg, crude) as yellow oil.

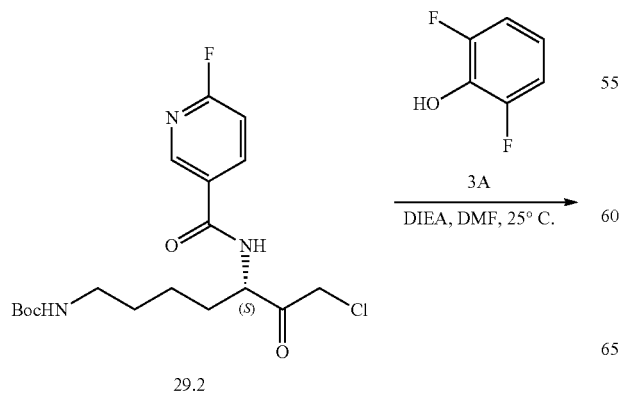

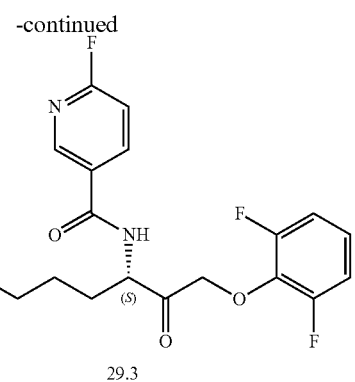

To a solution of 29.2 (300.00 mg, 746.53 µmol, 1.00 equivalent) and 2,6-difluorophenol (145.7 mg, 1.12 mmol, 1.5 equivalent) in DMF (6 mL) was added DIEA (289 mg, 2.24 mmol, 391 µL, 3 equivalent). The mixture was stirred at 25° C. for 15 hours, then it was evaporated and was purified by semi-preparative HPLC (TFA conditions) to give 29.3 (40 mg, 81 µmol, 11% yield) as yellow oil; LCMS [M+H]$^+$: 496; RT=0.874 min.

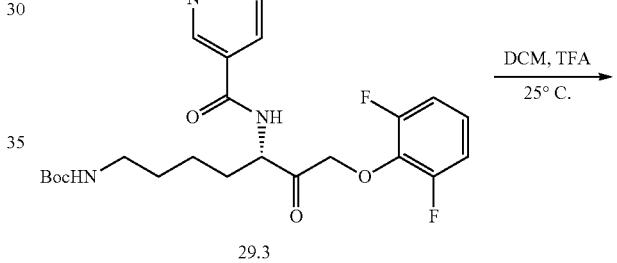

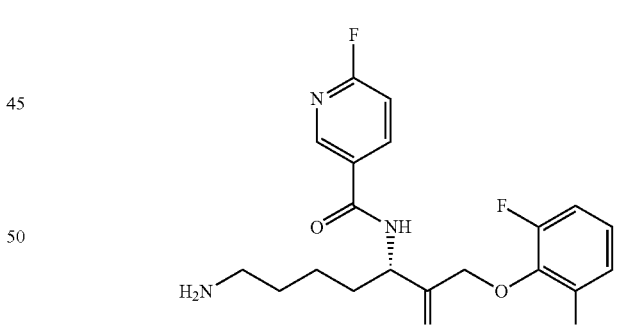

To 29.3 (40 mg, 81 µmol, 1 equivalent) in DCM (5 mL) was added TFA (1 mL). The mixture was stirred at 25° C. for 15 hours then was evaporated. The residue was purified by semi-preparative scale HPLC (TFA conditions) to give Compound 29, (10 mg, 25 µmol, 31% yield); LCMS [M+H]$^+$: 396; RT=0.7 min. $^1$H NMR (400 MHz, METHANOL-d$_4$) δ ppm 1.43-1.67 (m, 2H), 1.67-1.89 (m, 3H), 2.05-2.20 (m, 1H), 2.86-3.01 (m, 2H), 4.93-5.11 (m, 3H), 6.92-7.16 (m, 2H), 7.19 (dd, J=8.60, 2.65 Hz, 1H), 8.38 (td, J=8.05, 2.65 Hz, 1H), 8.71 (d, J=2.43 Hz, 1H).

Example 26. Preparation of (S)—N-(7-amino-1-(2,6-difluorophenoxy)-2-oxoheptan-3-yl)-3-(3-fluoropropoxy)benzamide (30)

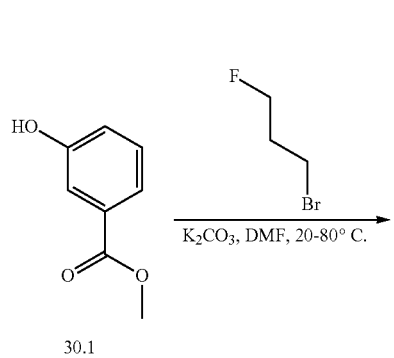

30.1

$\xrightarrow{\text{K}_2\text{CO}_3, \text{DMF}, 20\text{-}80°\text{ C.}}$

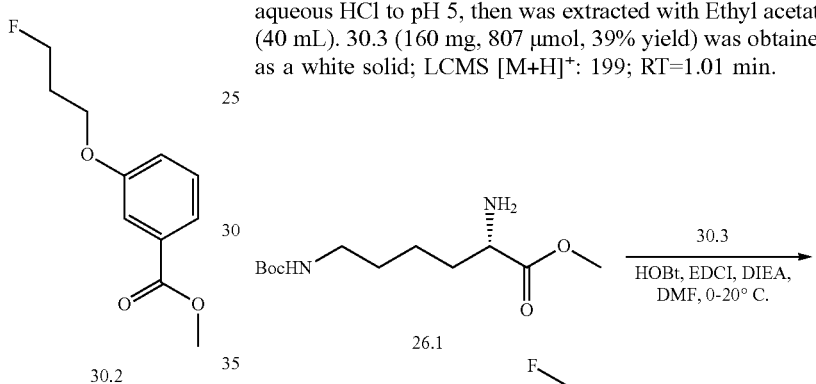

30.2

To a mixture 30.1 (540.13 mg, 3.55 mmol, 1 equivalent) and 30.2 (500 mg, 3.55 mmol, 1 equivalent) in DMF (10 mL) was added K$_2$CO$_3$ (981.29 mg, 7.1 mmol, 2 equivalent); the mixture was stirred at 80° C. for 15 hours. The reaction mixture was diluted with water (20 mL) and was extracted with EtOAc (20×mL×3). The combined organic layers were washed with brine (10 mL), dried over Na$_2$SO$_4$, filtered and concentrated under reduced pressure. The residue was purified by column chromatography (SiO2, Petroleum ether/Ethyl acetate=10/1 to 1/1) to give 30.2 (440 mg, 2.07 mmol, 58% yield) as colorless oil; LCMS [M+H]$^+$: 213; RT=0.82 min.

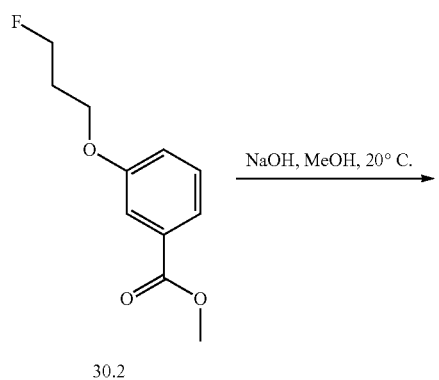

30.2

$\xrightarrow{\text{NaOH, MeOH}, 20°\text{ C.}}$

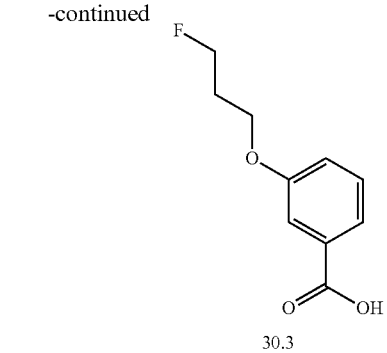

30.3

30.2 (440 mg, 2.07 mmol, 1 equivalent) in MeOH (12 mL) with NaOH (1 M, 4.14 mL, 2 equivalent) was stirred at 20° C. for 15 hours. The reaction was diluted with water (40 mL) then was extracted with EtOAc (40 mL×2) to remove neutral impurities. The aqueous phase was acidified with aqueous HCl to pH 5, then was extracted with Ethyl acetate (40 mL). 30.3 (160 mg, 807 μmol, 39% yield) was obtained as a white solid; LCMS [M+H]$^+$: 199; RT=1.01 min.

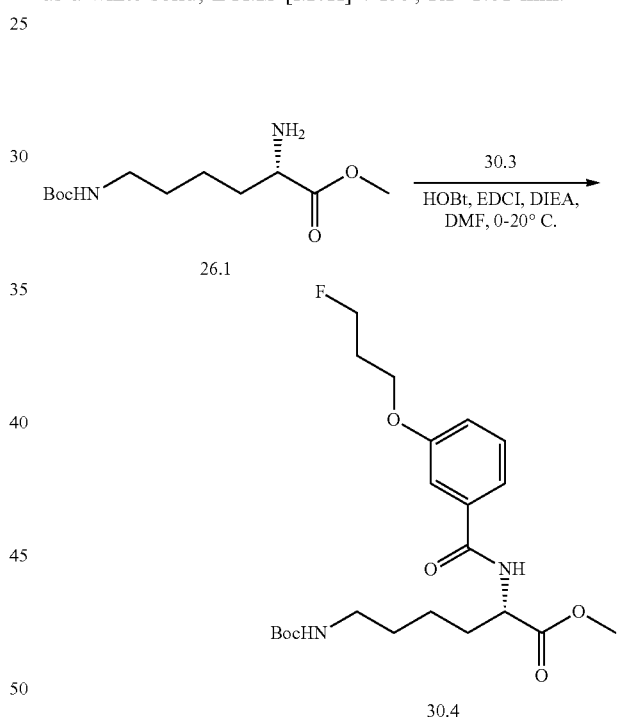

To 30.3 (160 mg, 807.31 μmol, 1 equivalent) and EDCI (170.24 mg, 888.04 μmol, 1.1 equivalent), HOBt (120 mg, 888 μmol, 1.1 equivalent) in DMF (2 mL) was added compound 26.1 (210.17 mg, 807.31 μmol, 1 equivalent) and DIEA (417.34 mg, 3.23 mmol, 563.97 μL, 4 equivalent) in one portion at 0° C. under N$_2$. The mixture was stirred at 20° C. for 15 hours. The reaction mixture was diluted with water (20 mL) and extracted with EtOAc (20 mL×3). The combined organic layers were washed with brine (10 mL), dried over Na$_2$SO$_4$, filtered and concentrated under reduced pressure. The residue was purified by column chromatography (SiO$_2$, Petroleum ether/Ethyl acetate=10/1 to 1/1) to give 30.4 (240 mg, 545 μmol, 67.5% yield) as a white solid; LCMS [M+H]$^+$: 441; RT=0.84 min.

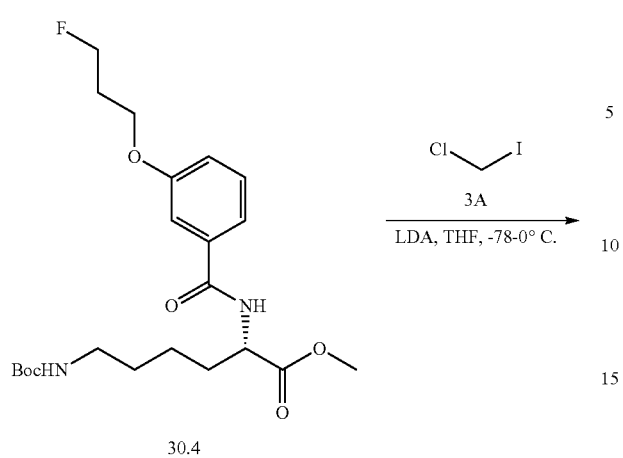

30.4

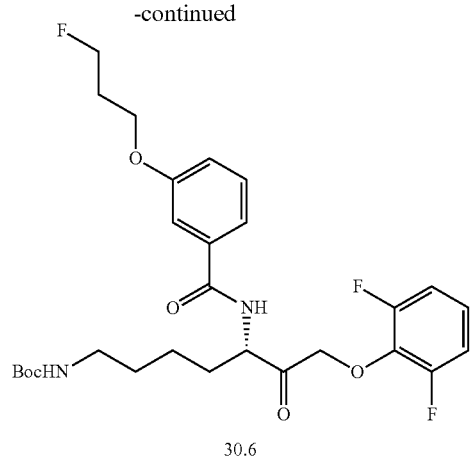

30.6

To 30.5 (200 mg, 436 µmol, 1 equivalent) and 2,5-difluorophenol (57 mg, 436 µma 1 equivalent) in DMF (4 mL) was added DIEA (168.96 mg, 1.31 mmol, 228.32 µL, 3 equivalent); the mixture was stirred at 20° C. for 15 hours. The residue was purified by semi-preparative scale HPLC (TFA conditions) to give 30.6 (13 mg, 23.5 µmol, 5.4% yield); LCMS [M+H]+: 553; RT=0.91 min.

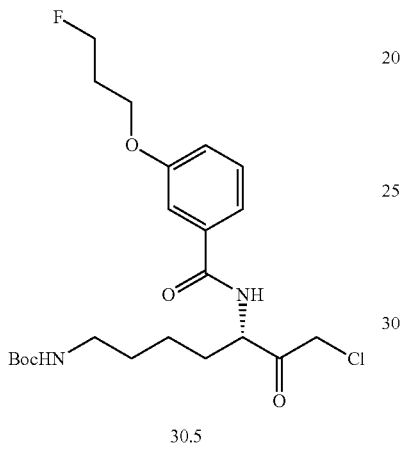

30.5

To a mixture of n-BuLi (209.41 mg, 3.27 mmol, 6 equivalent) was added to DIPA (330.8 mg, 3.3 mmol, 460 µL, 6 equivalent) in THF (6 mL) in one portion at 0° C. under N$_2$. After 0.5 h, 30.4 (240 mg, 545 µmol, 1 equivalent) and chloro(iodo)methane (577 mg, 3.3 mmol, 237.3 µL, 6 equivalent) was added to above mixture at −78° C. under N$_2$. The resulting mixture was stirred at −78° C. for 2 hrs. The reaction mixture was diluted with water (20 mL) then was extracted with EtOAc (20 mL×3). The combined organic layers were washed with brine (10 mL), dried over Na$_2$SO$_4$, filtered and concentrated under reduced pressure and 30.5 (200 mg, crude) was obtained as a brown oil.

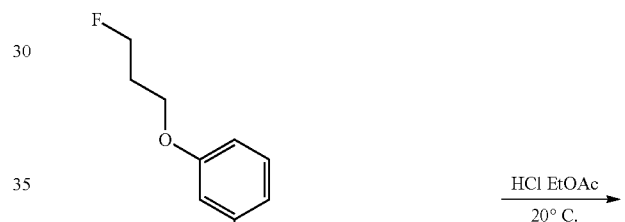

30.6

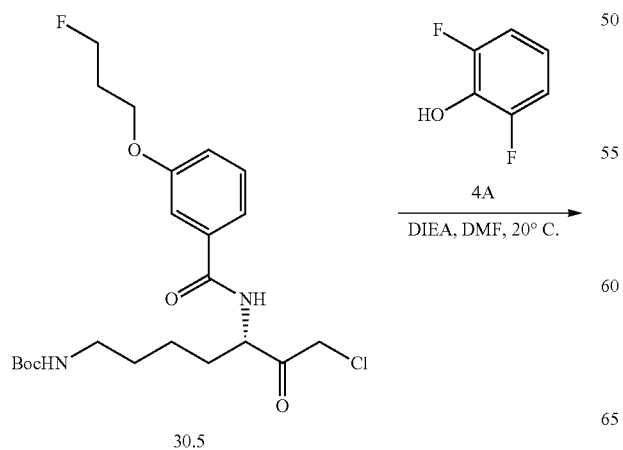

30

To 30.6 (13 mg, 23.53 µmol, 1 equivalent) in DCM (500 µL) was added TFA (160.97 mg, 1.41 mmol, 104.53 µL, 60 equivalent). The mixture was stirred at 20° C. for 3 hours. The residue was purified by semi-preparative scale HPLC (TFA conditions) to give Compound 30 (2 mg, 4.42 µmol, 19% yield) as colorless oil; LCMS [M+H]⁺:453; RT=0.7 min. ¹H NMR (400 MHz, METHANOL-d₄) δ ppm 1.47-1.63 (m, 2H), 1.67-1.86 (m, 2H), 2.10-2.23 (m, 2H), 2.85-3.01 (m, 2H), 4.10-4.20 (m, 1H), 4.11-4.20 (m, 1H), 4.57 (t, J=5.84 Hz, 1H), 4.69 (t, J=5.84 Hz, 1H), 4.90-5.07 (m, 4H), 6.95-7.03 (m, 2H), 7.03-7.11 (m, 1H), 7.14 (ddd, J=7.94, 2.54, 1.21 Hz, 1H), 7.35-7.46 (m, 3H).

Example 27. Preparation of (S)—N-(7-amino-1-(2,6-difluorophenoxy)-2-oxoheptan-3-yl)-2-fluoroisonicotinamide (31)

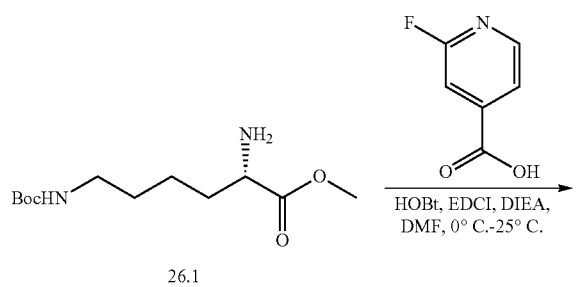

26.1

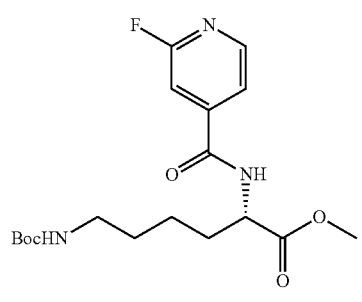

31.1

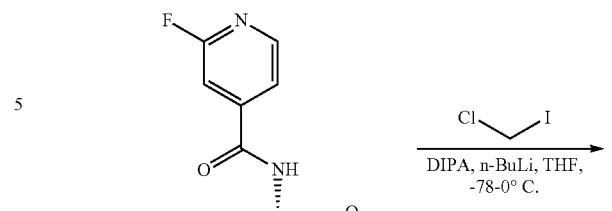

31.1

To a solution of 2-fluoro-4-carboxypyridine (523 mg, 3.71 mmol, 1.1 equivalent) in DMF (15 mL) was added HOBt (501 mg, 3.71 mmol, 1.1 equivalent) and EDCI (710.5 mg, 3.71 mmol, 1.1 equivalent). The mixture was stirred at 0° C. for 1 hr. Then to the mixture was added 26.1 (1 g, 3.37 mmol, 1 equivalent, HCl salt) and DIEA (1.74 g, 13.48 mmol, 2.35 mL, 4 equivalent); the mixture was stirred at 25° C. for 14 hours. The reaction mixture was quenched by addition of H₂O 5(0 mL) and was extracted with ethyl acetate (30 mL×3). The combined organic layers were washed with saturated brine (5 mL), dried over anhydrous sodium sulfate, filtered and concentrated. The residue was purified by column chromatography (SiO₂, Petroleum ether/Ethyl acetate=2:1) to give compound 31.1 (800 mg, 2.1 mmol, 62% yield) as yellow oil; LCMS [M+H-Boc]: 384; RT=0.8 min. ¹H NMR (400 MHz, METHANOL-d₄) δ ppm 1.27-1.62 (m, 14H), 1.69-2.08 (m, 2H), 3.05 (t, J=6.50 Hz, 2H), 3.75 (s, 3H), 4.59 (dd, J=9.37, 4.96 Hz, 1H), 7.46 (s, 1H), 7.69 (dt, J=5.29, 1.54 Hz, 1H), 8.35 (d, J=5.29 Hz, 1H)

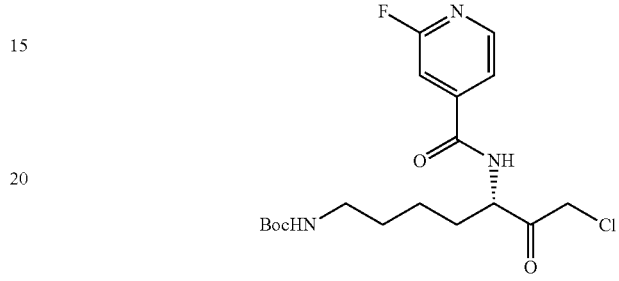

31.2

To DIPA (659.8 mg, 6.52 mmol, 916.4 μL, 5 equivalent) in THF (5 mL) was added n-BuLi (2.5 M, 2.61 mL, 5 equivalent). The mixture was stirred at 0° C. for 0.5 hr under N₂; then the mixture was added to a solution of 31.1 (500 mg, 1.3 mmol, 1 equivalent) and chloro(iodo)methane (1.15 g, 6.52 mmol, 473.3 μL, 5 equivalent) in THF (10 mL); this was stirred at -78° C. for 0.5 hr. The reaction mixture was quenched by addition of saturated NH₄Cl (20 ml) and extracted with ethyl acetate (15 mL×3). The combined organic layers were washed with saturated Na₂SO₃ (10 mL), saturated NaHCO₃ (10 mL) and brine (10 mL). This was dried over anhydrous sodium sulfate, filtered and concentrated under reduced pressure to give 31.2 (620 mg).

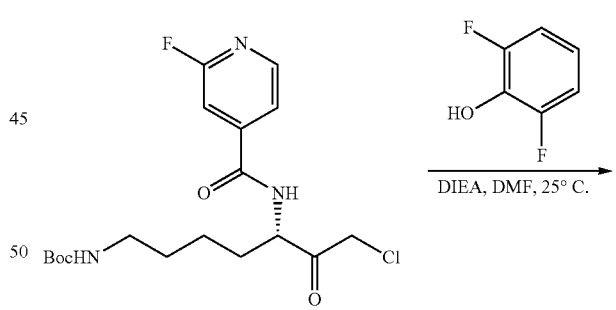

31.2

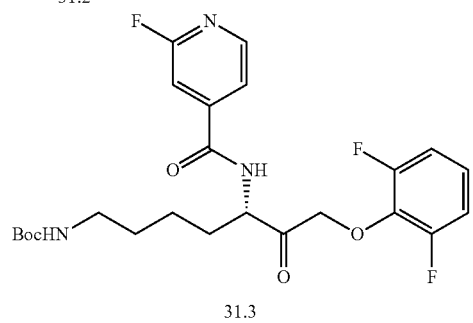

31.3

To 31.2 (620 mg, 1.54 mmol, 1 equivalent) in DMF (5 mL) was added DIEA (598.2 mg, 4.63 mmol, 808.36 µL, 3 equivalent) and 2,6-difluorophenol (301.1 mg, 2.31 mmol, 1.5 equivalent); this was stirred at 25° C. for 15 hours. Following an aqueous work up, the residue was purified by semi-preparative scale HPLC (TFA conditions) to give 31.3 (20 mg, 40.36 µmol, 3% yield).

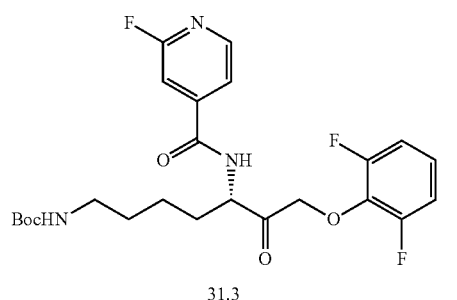

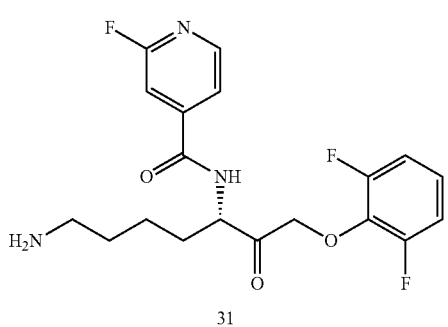

31.3 (50 mg, 101 µmol, 1 equivalent) in DCM (5 mL) and TFA (1 mL) was stirred at 25° C. for 15 hours. The residue was purified by semi-preparative scale HPLC (TFA conditions) to give Compound 31 (10 mg, 25.3 µmol, 25% yield); LCMS [M+H]: 396; RT=1.3 min. $^1$H NMR (400 MHz, METHANOL-$d_4$) δ ppm 1.40-1.91 (m, 5H), 2.03-2.22 (m, 1H), 2.83-3.03 (m, 2H), 4.87-5.15 (m, 3H), 6.90-7.17 (m, 2H), 7.38-7.53 (m, 1H), 7.60-7.74 (m, 1H), 8.24-8.39 (m, 1H).

Example 28. Preparation of (S)—N-(7-amino-1-(2,6-difluorophenoxy)-2-oxoheptan-3-yl)-2-fluoronicotinamide (32)

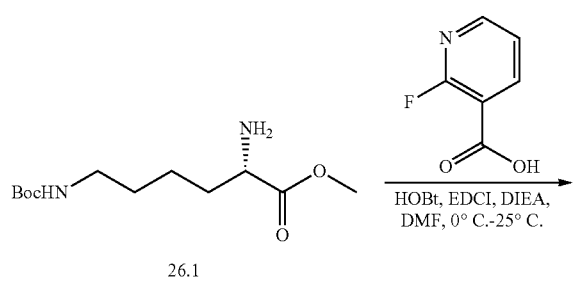

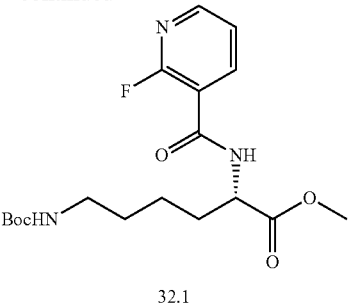

To of 2-(fluoro)nicotinic acid (366.3 mg, 2.6 mmol, 1.1 equivalent) in DMF (15 mL) was added HOBt (350.8 mg, 2.6 mmol, 1.1 equivalent) and EDCI (497.65 mg, 2.6 mmol, 1.1 equivalent). The mixture was stirred at 0° C. for 1 hr; then to the mixture was added 26.1 (700 mg, 2.36 mmol, 1 equivalent, HCl salt) and DIEA (1.22 g, 9.44 mmol, 1.65 mL, 4 equivalent). The mixture was stirred at 25° C. for 14 hours. The reaction mixture was quenched with H$_2$O (50 mL) then extracted with ethyl acetate (30 mL×3). The combined organic layers were washed with brine (5 mL), then dried over anhydrous sodium sulfate, filtered and concentrated under reduced pressure. The residue was purified by column chromatography (SiO$_2$, Petroleum ether/Ethyl acetate=2/1) to give 32.1 (600 mg, 1.56 mmol, 66% yield) as brown oil; LCMS [M+H]: 284; RT=0.7 min. $^1$H NMR (400 MHz, CHLOROFORM-d) δ ppm 1.42 (s, 11H), 1.54 (dt, J=13.68, 6.84 Hz, 3H), 1.63 (s, 1H), 1.76-2.10 (m, 2H), 3.12 (br d, J=6.15 Hz, 2H), 3.80 (s, 3H), 4.57 (br s, 1H), 4.76-4.90 (m, 1H), 7.30-7.48 (m, 2H), 8.36 (br d, J=4.52 Hz, 1H), 8.55 (ddd, J=9.66, 7.72, 1.95 Hz, 1H).

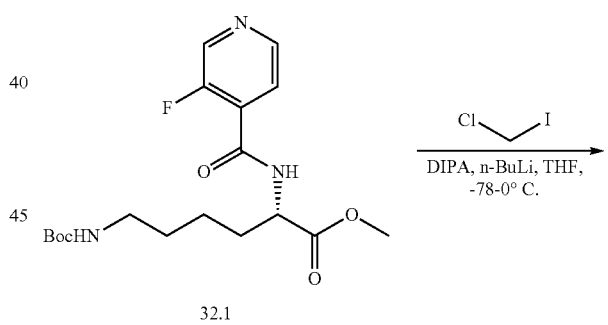

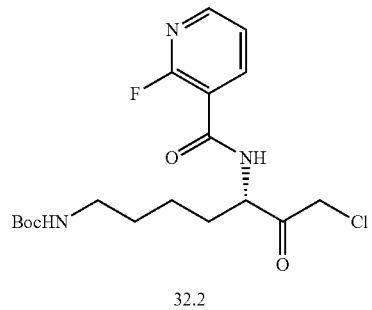

To DIPA (527.8 mg, 5.2 mmol, 733 µL, 5 equivalent) in THF (5 mL) was added n-BuLi (2.5 M, 2.1 mL, 5 equivalent); the mixture was stirred at 0° C. for 0.5 hr under N$_2$. Then the mixture was added to 32.2 (400 mg, 1.04 mmol, 1 equivalent) and chloro(iodo)methane (920 mg, 5.22 mmol, 378.6 µL, 5 equivalent) in THF (5 mL); this was stirred at −78° C. for 0.5 hours. The reaction mixture was quenched with saturated NH₄Cl (20 ml) and extracted with ethyl acetate (15×mL×3). The combined organic layers were washed with saturated Na₂SO₃ (10 mL), saturated NaHCO₃ (10 mL) and brine (10 mL); this was dried over anhydrous sodium sulfate, filtered and concentrated under reduced pressure to give 32.2 (620 mg).

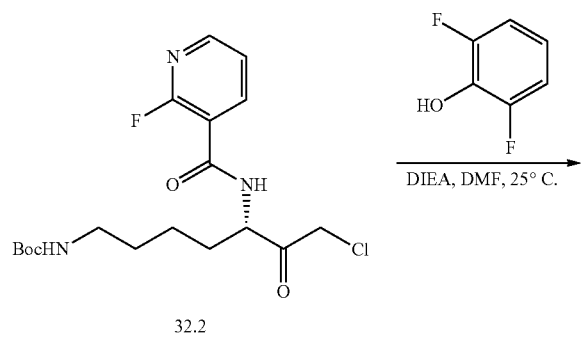

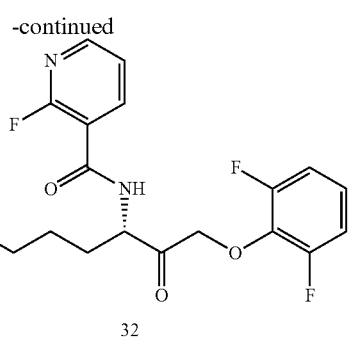

32.2 (20 mg, 40.4 µmol, 1 equivalent) in DCM (5 mL) and TFA (1 mL) was stirred at 25° C. for 15 hours. The residue was purified by semi-preparative scale HPLC (TFA conditions) to give Compound 32 (5 mg, 12.65 µmol, 31% yield); LCMS [M+H]: 396; RT=1.25 min. ¹H NMR (400 MHz, METHANOL-d₄) δ ppm 1.44-1.87 (m, 5H), 2.06-2.22 (m, 1H), 2.85-3.03 (m, 2H), 4.89-5.12 (m, 3H), 6.93-7.05 (m, 2H), 7.06-7.15 (m, 1H), 7.45 (ddd, J=7.22, 5.02, 1.87 Hz, 1H), 8.26 (ddd, J=9.48, 7.50, 1.98 Hz, 1H), 8.30-8.40 (m, 1H).

Example 29. Preparation of (S)—N-(7-amino-1-(2,6-difluorophenoxy)-2-oxoheptan-3-yl)-3-azidobenzamide (33)

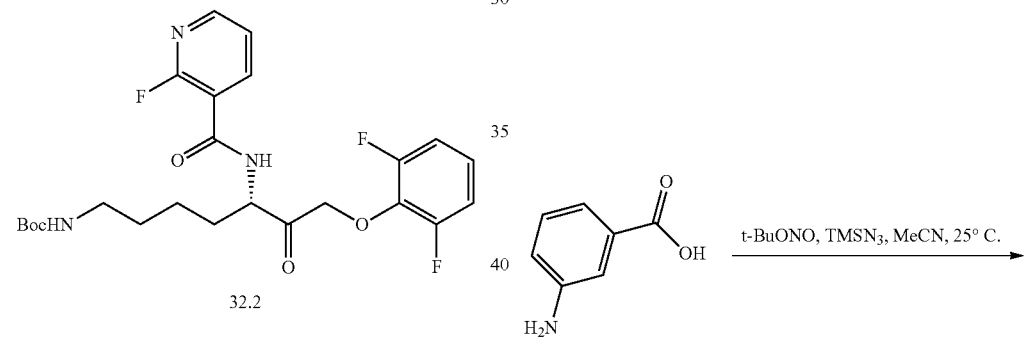

To 32.2 (500 mg, 1.24 mmol, 1 equivalent) and 2,6-difluorophenol (242.8 mg, 1.87 mmol, 1.5 equivalent) in DMF (6 mL) was added DIEA (482.41 mg, 3.73 mmol, 6524, 3 equivalent). The mixture was stirred at 25° C. for 15 hours. The residue was purified by semi-preparative scale HPLC (TFA conditions) to give 32.2 (20 mg, 40.4 µmol, 3% yield); LCMS [M+H]: 496; RT=0.86 min.

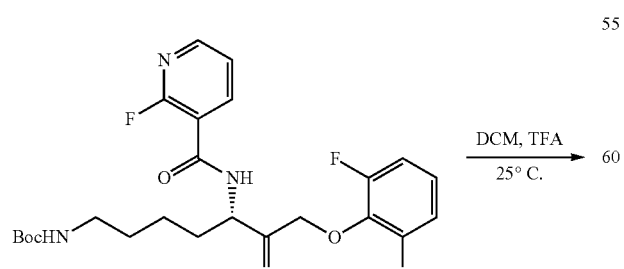

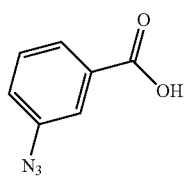

To 33.1 (5 g, 36.5 mmol, 1 equivalent) and t-BuONO (5.64 g, 54.7 mmol, 6.5 mL, 1.5 equivalent) in AcN (70 mL) was added TMSN₃ (5.04 g, 43.75 mmol, 5.73 mL, 1.2 equivalent) in one portion at 18° C. under N₂. The mixture was stirred at 18° C. for 10 hours. The reaction mixture was diluted with H₂O (100 mL) and extracted with EtOAc (50 mL×3). The combined organic layers were washed with brine (100 mL), dried over Na₂SO₄, filtered and concentrated under reduced pressure. This material was purified by column chromatography (SiO₂, DCM:MeOH=10:1) to give 33.2 (3 g, 18.4 mmol, 50% yield).

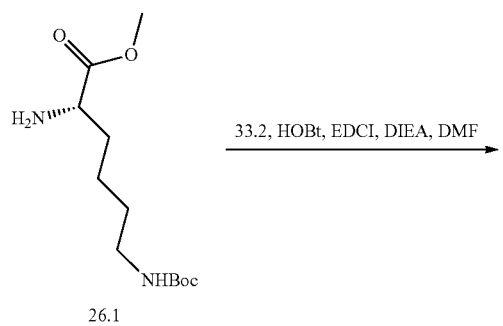

26.1

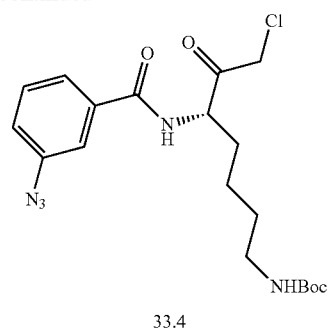

33.4

To a solution of DIPA (1.5 g, 14.8 mmol, 2.08 mL, 6 equivalent) in THF (15 mL) was added n-BuLi (2.5 M, 5.92 mL, 6 equivalent) at 0° C.; the mixture was stirred for 30 mins. This was added to 33.3 (1 g, 2.47 mmol, 1 equivalent) and chloro(iodo)methane (2.18 g, 12.35 mmol, 895.11 μL, 5 equivalent) in THF (15 mL) at −78° C. The mixture was stirred at −78° C. for 30 mins. The reaction mixture was quenched by addition of $NH_4Cl$ (10 mL), and then extracted with EtOAc (15 mL×3). The combined organic layers were washed with $Na_2SO_3$ (20 mL), and brine (20 mL), dried over $Na_2SO_4$; then filtered and concentrated to give 33.4 (2 g) which was used to next step.

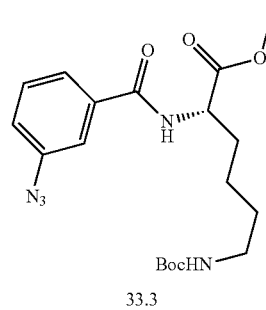

33.3

To 33.2 (1.25 g, 7.68 mmol, 1 equivalent) and EDCI (1.62 g, 8.45 mmol, 1.1 equivalent) in DMF (20 mL) was added HOBt (1.14 g, 8.45 mmol, 1.1 equivalent). The mixture was stirred at 0° C. for 1 hour; then a solution of 26.1 (2 g, 7.68 mmol, 1 equivalent) in DMF (5 mL) was added drop wise followed by the addition of DIPEA (2.98 g, 23.04 mmol, 4.03 mL, 3 equivalent). This mixture was stirred at 0° C. for 1 hour. The reaction mixture was diluted with $H_2O$ (20 mL) and extracted with EtOAc (15 mL×3). The combined organic layers were washed with brine (40 mL×1), dried over $Na_2SO_4$, filtered and concentrated. The residue was purified by column chromatography ($SiO_2$, Petroleum ether/ Ethyl acetate=1/1) to give 33.3 (2.8 g, 6.91 mmol, 90% yield). $^1$H NMR (400 MHz, METHANOL-$d_4$) δ ppm 1.40 (s, 8H), 1.44-1.58 (m, 4H), 1.80-2.00 (m, 2H), 3.00-3.10 (m, 2H), 3.74 (s, 3H), 4.58 (dd, J=9.26, 5.07 Hz, 1H), 7.25 (ddd, J=8.05, 2.32, 1.10 Hz, 1H), 7.49 (t, J=7.83 Hz, 1H), 7.56 (t, J=1.76 Hz, 1H), 7.63-7.69 (m, 1H).

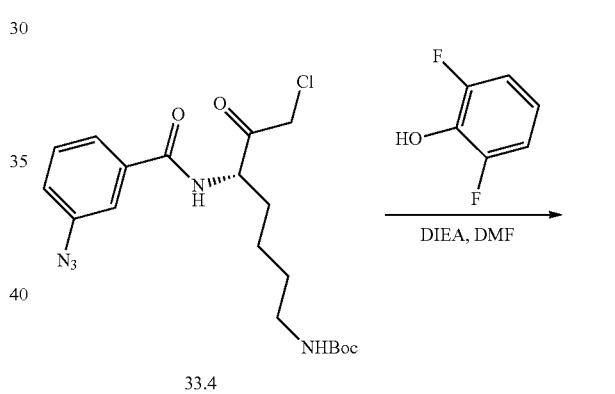

33.4

33.5

To 33.4 (2 g) and 2,6-difluorophenol (614 mg, 4.72 mmol, 1 equivalent) in DMF (5 mL) was added DIPEA (2.44 g, 18.87 mmol, 3.3 mL, 4 equivalent); this mixture was stirred at 20° C. for 10 hours. Following an aqueous work up, the residue was purified by semi-preparative HPLC (TFA conditions) to give 33.5 (200 mg, 386.46 μmol, 8% yield).

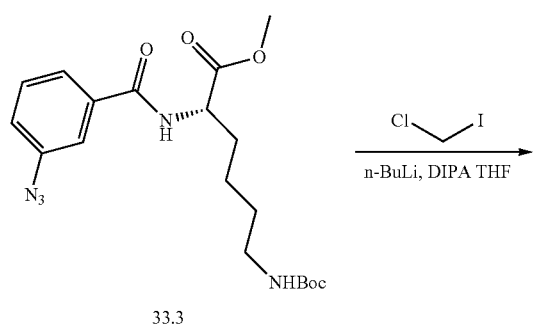

33.3

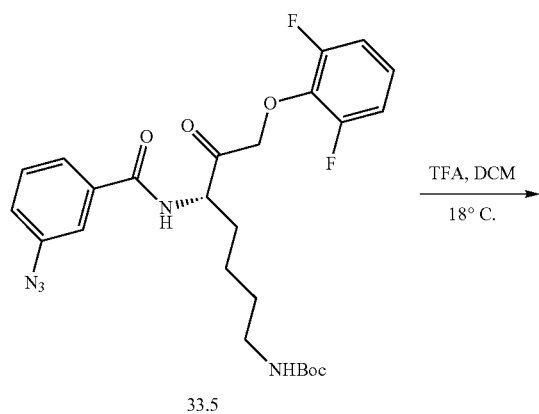

33.5

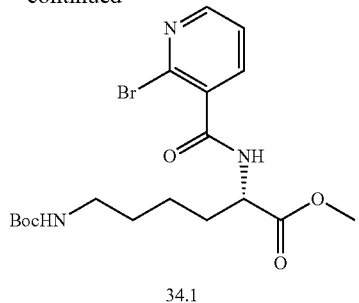

34.1

To 2-(bromo)nicotinic acid (748.71 mg, 3.71 mmol, 1.1 equivalent) in DMF (30 mL) was added HOBt (501 mg, 3.71 mmol, 1.1 equivalent) and EDCI (710.5 mg, 3.71 mmol, 1.1 equivalent); this was stirred at 0° C. for 1 hr. To this mixture was added compound 26.1 (1 g, 3.37 mmol, 1 equivalent, HCl salt) and DIEA (1.74 g, 13.48 mmol, 2.35 mL, 4 equivalent); this was stirred at 25° C. for 14 hours. The reaction mixture was quenched by addition H$_2$O (50 mL) and extracted with ethyl acetate (30 mL×3). The combined organic layers were washed with brine (5 mL), dried over anhydrous sodium sulfate, filtered and concentrated under reduced pressure. The residue was purified by column chromatography (SiO$_2$, Petroleum ether/Ethyl acetate=2/1) to give 34.1 (950 mg, 2.14 mmol, 63.5% yield) as yellow oil; LCMS [M+H]: 345; RT=0.73 min. $^1$H NMR (400 MHz, CHLOROFORM-d) δ ppm 1.29-1.60 (m, 16H), 1.76-2.04 (m, 2H), 2.98-3.27 (m, 2H), 3.80 (s, 3H), 4.59 (br s, 1H), 4.71-4.86 (m, 1H), 6.95 (br d, J=6.61 Hz, 1H), 7.36 (dd, J=7.61, 4.74 Hz, 1H), 7.92 (dd, J=7.61, 1.87 Hz, 1H), 8.45 (dd, J=4.85, 1.98 Hz, 1H)

33

33.5 5 (100 mg, 193.23 µmol, 1 equivalent) in DCM (5 mL) and TFA (1 mL) was stirred at 18° C. for 10 hours. The reaction mixture was concentrated under reduced pressure, then was purified by semi-preparative HPLC (TFA conditions) to give Compound 33 (80 mg, 192 µmol, yield 99%) as yellow oil; LCMS [M+H]: 418; RT=3.1 min. $^1$H NMR (400 MHz, METHANOL-d4) δ ppm 1.49-1.67 (m, 2H) 1.67-1.88 (m, 3H) 2.11 (dddd, J=13.84, 9.48, 6.78, 4.30 Hz, 1H) 2.89-2.99 (m, 2H) 4.91-5.08 (m, 3H) 6.95-7.05 (m, 2H) 7.05-7.12 (m, 1H) 7.26-7.31 (m, 1H) 7.48-7.54 (m, 1H) 7.56 (t, J=1.87 Hz, 1H) 7.64-7.70 (m, 1H).

Example 30. Preparation of (S)—N-(7-amino-1-(2, 6-difluorophenoxy)-2-oxoheptan-3-yl)-2-bromonicotinamide (34)

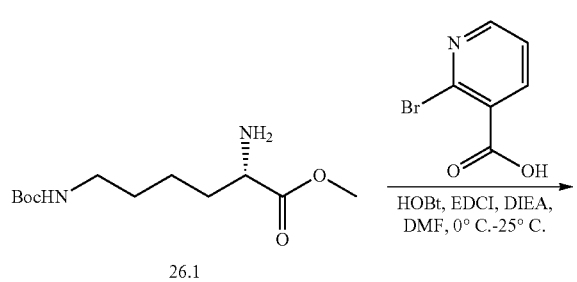

26.1

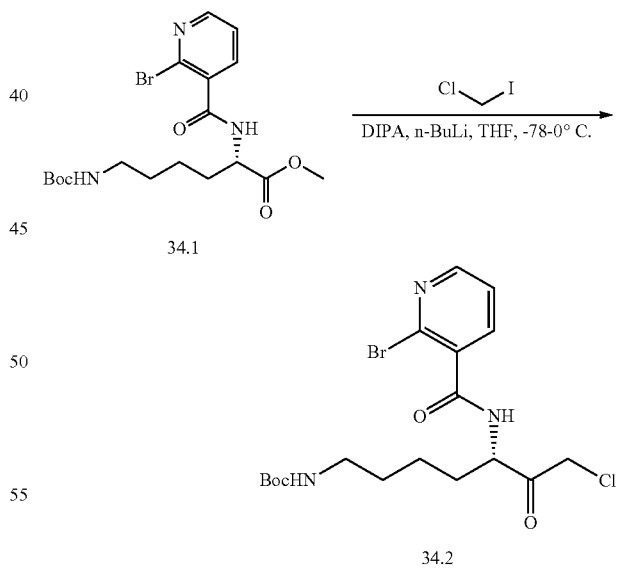

To DIPA (1.08 g, 10.69 mmol, 1.50 mL, 5 equivalent) in THF (5 mL) was added n-BuLi (2.5 M, 4.28 mL, 5 equivalent); this mixture was stirred at 0° C. for 0.5 hr under N$_2$. This mixture was added to 34.1 (950 mg, 2.14 mmol, 1 equivalent) and chloro(iodo)methane (1.89 g, 10.7 mmol, 776.65 µL, 5 equivalent) in THF (10 mL) and stirred at −78° C. for 0.5 hr. The reaction mixture was quenched with NH$_4$Cl (20 ml) at 25° C. and extracted with ethyl acetate (15 mL×3). The combined organic layers were washed with saturated Na₂SO₃ (10 mL), NaHCO₃ (10 mL) and brine (10 mL). This was dried over anhydrous sodium sulfate, filtered and concentrated under reduced pressure to give 34.2 (1.1 g).

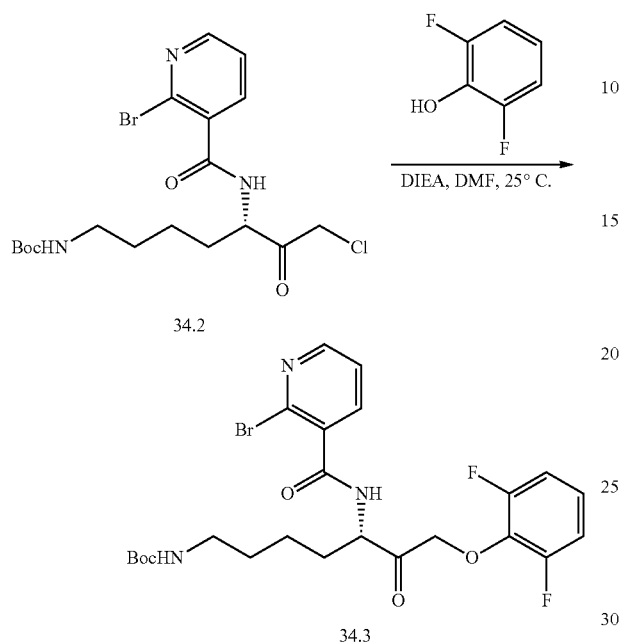

To 34.2 (1.1 g, 2.38 mmol, 1 equivalent) in DMF (10 mL) was added DIEA (921.63 mg, 7.13 mmol, 1.25 mL, 3 equivalent) and 2,6-difluorophenol (463.84 mg, 3.57 mmol, 1.5 equivalent). The mixture was stirred at 25° C. for 15 hours; following an aqueous work-up, the product was purified by semi-preparative HPLC (TFA conditions) to give 34.3 (150 mg, 269.6 μmol, 11% yield).

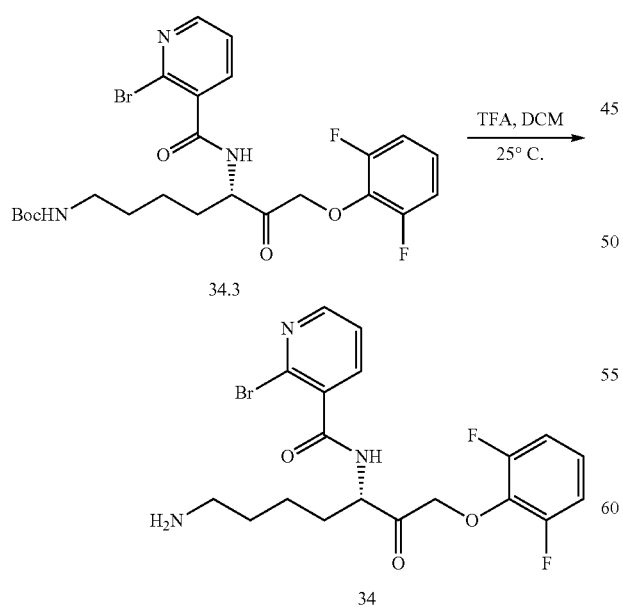

A 34.3 (150 mg, 270 μmol, 1 equivalent) in DCM (10 mL) and TFA (2 mL) was stirred at 25° C. for 14 hours. The mixture was concentrated under reduced pressure to give Compound 34 (100 mg, 219.16 μmol, 81.3% yield); LCMS [M+H]: 456; RT=2.28 min. ¹H NMR (400 MHz, METHANOL-d₄) δ ppm 1.51-1.88 (m, 6H), 1.97-2.21 (m, 1H), 2.95 (br t, J=7.50 Hz, 2H), 4.96 (dd, J=9.70, 4.19 Hz, 1H), 5.00-5.14 (m, 1H), 6.93-7.15 (m, 2H), 7.41-7.56 (m, 1H), 7.73-7.89 (m, 1H), 8.35-8.48 (m, 1H).

Example 31. Preparation of (S)—N-(7-amino-1-(2, 6-difluorophenoxy)-2-oxoheptan-3-yl)-4-fluorobenzamide (35)

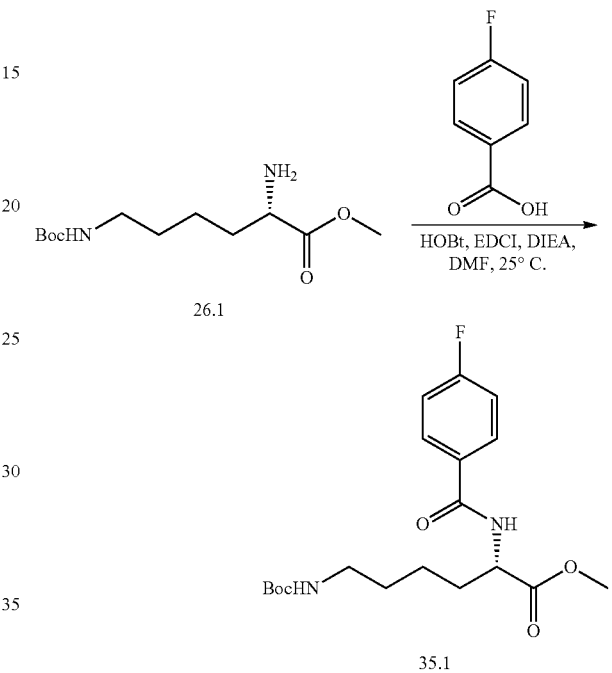

To 4-(fluoro)benzoic acid (538.2 mg, 3.84 mmol, 1 equivalent) in DMF (15 mL) was added HOBt (570.75 mg, 4.22 mmol, 1.1 equivalent) and EDCI (809.74 mg, 4.22 mmol, 1.1 equivalent); the mixture was stirred at 25° C. for 0.5h. To the mixture was added 26.1 (1 g, 3.84 mmol, 1 equivalent) and DIEA (1.99 g, 15.36 mmol, 2.68 mL, 4 equivalent); the reaction was stirred for 14h. The reaction mixture was quenched by addition H₂O (50 mL) and extracted with EtOAc (50 mL×3). The combined organic layers were washed with saturated NaHCO₃ (25 mL), dried over anhydrous sodium sulfate, filtered and concentrated under reduced pressure to give 35.1 (1.10 g); LCMS [M+H]: 369; RT=0.8 min.

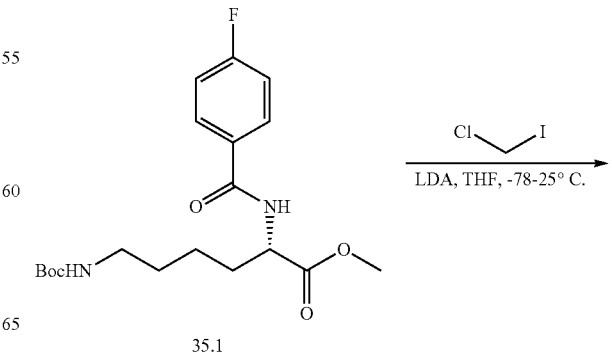

-continued

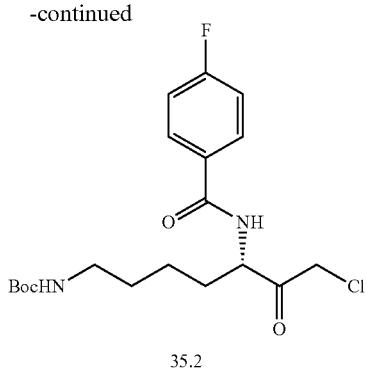

35.2

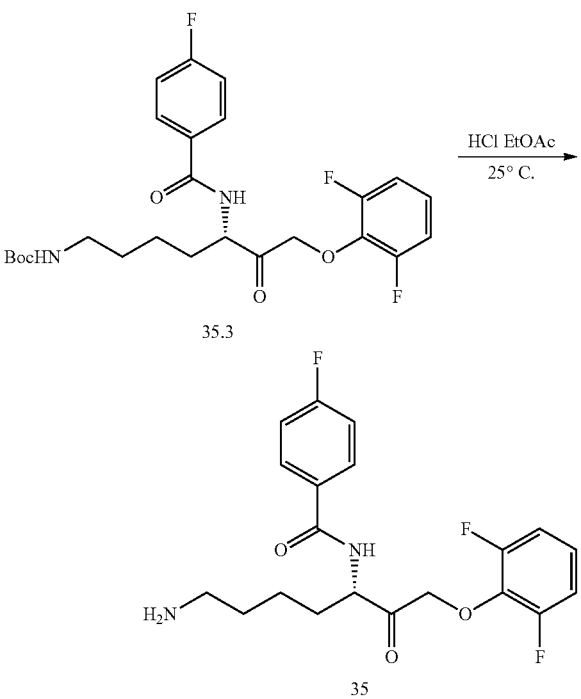

To DIPA (1.32 g, 13.05 mmol, 1.83 mL, 5 equivalent) in THF (10 mL) was added n-BuLi (835.98 mg, 13.05 mmol, 5 equivalent); this was stirred at 25° for 0.5 h under $N_2$. The mixture was added to 35.1 (1 g, 2.61 mmol, 1 equivalent) and chloro(iodo)methane (5 equivalents) in THF (10 mL), then was stirred at −78° for 2h. The reaction mixture was quenched by addition saturated ammonium chloride (30 mL) and extracted with EtOAc (50 mL×3). The combined organic layers were washed with saturated sodium hydrogen sulfite (25 mL) and brine. This was dried over anhydrous sodium sulfate, filtered and concentrated under reduced pressure to give 35.2 (800 mg, 2 mmol, 77% yield). The product used into the next step without further purification; LCMS [M+H]: 402; RT=0.8 min.

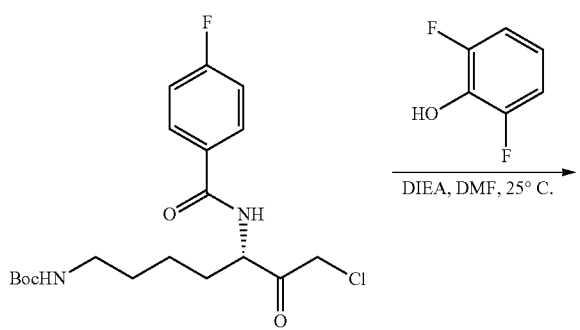

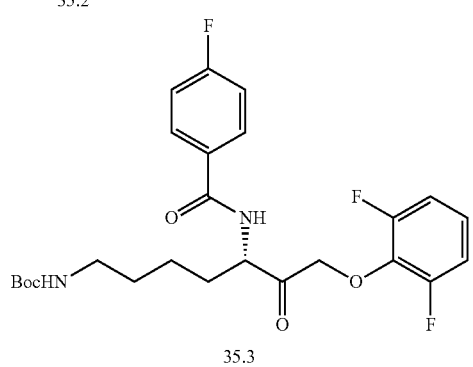

35.3

To 35.2 (800 mg, 2 mmol, 1 equivalent) in DMF (10 mL) was added DIEA (773.76 mg, 5.99 mmol, 1.05 mL, 3 equivalent) and 2,6-difluorophenol (389.42 mg, 2.99 mmol, 1.5 equivalent). The mixture was stirred at 25° C. for 15 hours. Following an aqueous work up, it was purified by semi-preparative HPLC (TFA conditions) to give 35.3 (80 mg, 161.78 μmol, 8% yield); LCMS [M+H]: 495; RT=0.94 min.

35.3 (80 mg, 232.95 μmol) in HCl/EtOAc (15 mL) was stirred at 25° C. for 14 hours. The reaction mixture was filtered and concentrated under reduced pressure to give Compound 35 (50 mg, 205.51 μmol, 88% yield); LCMS [M+H]: 244; RT=0.104 min. $^1$H NMR (400 MHz, METHANOL-$d_4$) δ ppm 1.51-1.65 (m, 2H), 1.67-1.87 (m, 3H), 2.05-2.18 (m, 1H), 2.95 (br d, J=5.29 Hz, 2H), 4.90-4.95 (m, 1H), 4.95-5.07 (m, 2H), 6.96-7.02 (m, 2H), 7.03-7.12 (m, 1H), 7.22 (t, J=8.82 Hz, 2H), 7.92 (dd, J=8.82, 5.29 Hz, 2H).

Example 32. Preparation of N-(7-amino-1,1,1-trifluoro-2-oxoheptan-3-yl)benzamide (36)

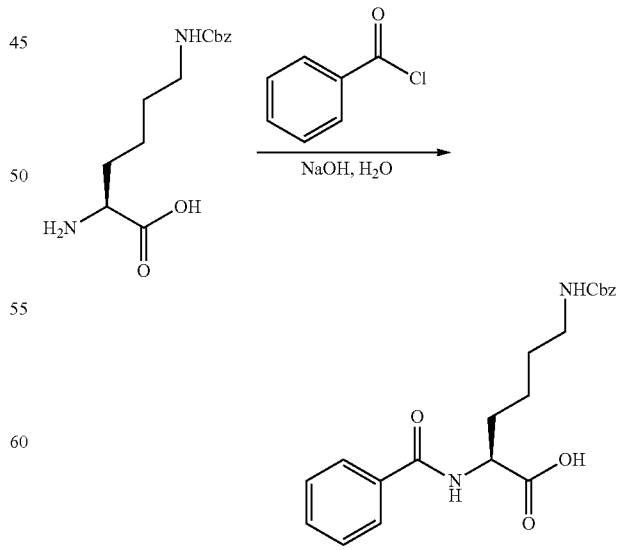

36.1

To ε-Cbz lysine (2.4 g, 8.56 mmol, 1 equivalent) in H₂O (6 mL) was added NaOH (684.93 mg, 17.12 mmol, 2 equivalent) in one portion at 0° C. under N₂. The mixture was stirred at 0° C. for 1 hour. The mixture was then added compound benzoyl chloride (1.20 g, 8.56 mmol, 994.64 µL, 1 equivalent) dropwise, and the mixture was stirred for 9 hours. The reaction mixture was filtered and the solid was washed with EtOAc (10 ml) to give 36.1 (4 g) as a white solid; LCMS [M+H]: 385; RT=0.77 min.

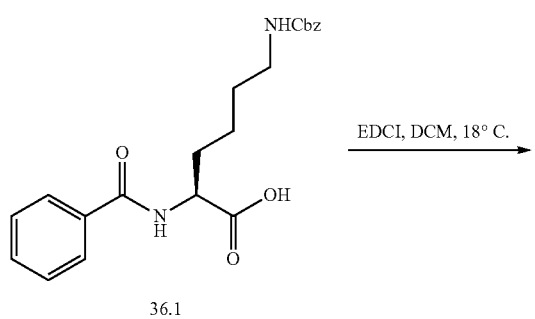

36.1

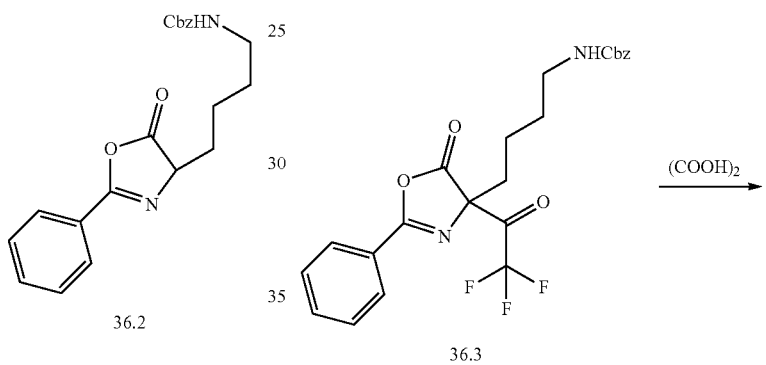

36.2

To 36.1 (4 g, 10.41 mmol, 1 equivalent) in DCM (40 mL) was added EDCI (2 g, 10.41 mmol, 1 equivalent) in one portion at 18° C. under N₂. The mixture was stirred at 18° C. for 0.5 hours. The reaction mixture was quenched by addition H₂O (40 mL) then extracted with DCM (20 mL×3). The combined organic layers were washed with NaHCO₃ (50 mL), dried over Na₂SO₄, filtered and concentrated under reduced pressure to give 36.2 (5 g); LCMS [M+H]: 367; RT=0.87 min. ¹H NMR (400 MHz, METHANOL-d₄) δ ppm 1.33-2.02 (m, 7H), 3.10-3.17 (m, 2H), 4.35-4.54 (m, 1H), 4.98-5.06 (m, 2H), 7.28-7.38 (m, 5H), 7.42-7.50 (m, 2H), 7.52-7.58 (m, 1H), 7.76-7.86 (m, 2H).

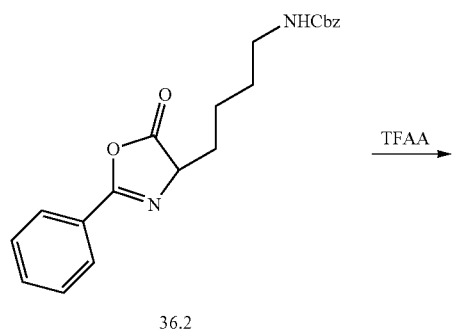

36.2

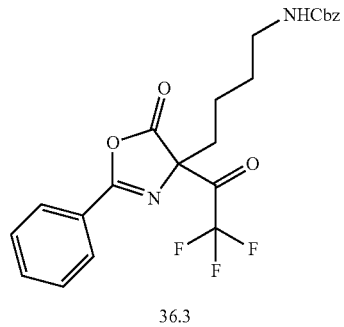

36.3

To 36.2 (3 g, 8.19 mmol, 1 equivalent) was added TFAA (2.06 g, 9.83 mmol, 1.37 mL, 1.2 equivalent); this was stirred at 40° C. for 10 hours. The reaction mixture was concentrated under reduced pressure to give 36.3 (3.5 g, 7.57 mmol, 92% yield); LCMS [M+H]: 463; RT=0.96 min.

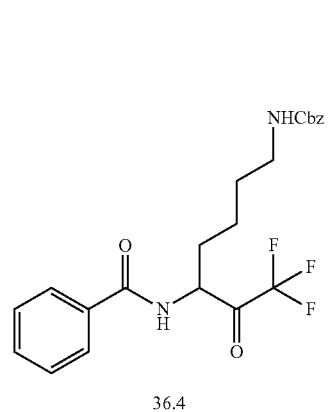

36.4

To 36.3 (3 g, 6.49 mmol, 1 equivalent) was added oxalic acid (934.53 mg, 10.38 mmol, 916 µL, 1 equivalent). The mixture was stirred at 120° C. for 5 mins. Then it was quenched by addition H₂O (20 mL) and extracted with EtOAc (20 mL×2). The combined organic layers were washed with brine (40 mL), dried over Na₂SO₄, filtered and concentrated. The residue was purified by semi-preparative HPLC (TFA conditions) to give 36.4 (200 mg, 458.27 µmol, 7% yield); LCMS [M+H]: 437; RT=0.9 min. ¹H NMR (400 MHz, METHANOL-d₄) δ ppm 1.21-1.96 (m, 7H), 3.04-3.16 (m, 2H), 4.30-4.51 (m, 1H), 4.99 (s, 1H), 7.27-7.34 (m, 3H), 7.40-7.47 (m, 1H), 7.48-7.56 (m, 1H), 7.74-7.83 (m, 1H).

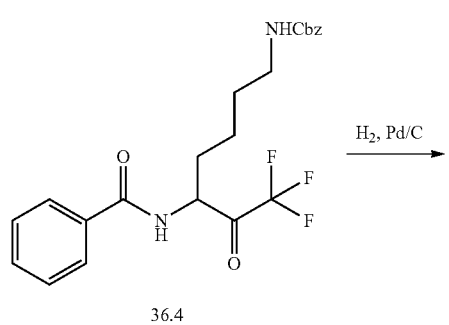

36.4

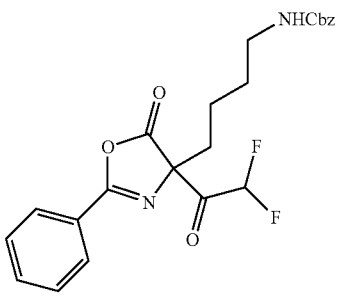

37.1

36.2 (1.2 g, 3.28 mmol, 1 equivalent) in difluoroacetic anhydride (1.71 g, 9.83 mmol, 3 equivalent) was stirred at 40° C. for 2 hours. The reaction mixture was concentrated under reduced pressure to give 37.1 (1.2 g, crude); LCMS [M+H]: 445; RT=0.91 min.

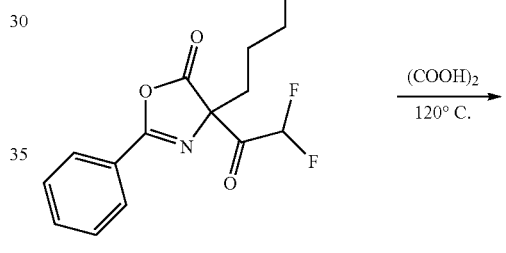

37.1

To 36.4 (100 mg, 229.14 μmol, 1.00 equivalent) in i-PrOH (10 mL) and HCl (1 M, 2 mL, 8.73 equivalent) was added Pd—C (10%, 0.02 g) under $N_2$. The suspension was degassed under vacuum and purged with $H_2$ several times. The mixture was stirred under $H_2$ (50 psi) at 18° C. for 10 hours. The reaction mixture was filtered and concentrated under reduced pressure. The residue was purified by semi-preparative HPLC (neutral conditions) to give Compound 36 (20 mg, 66.16 μmol, 29% yield); LCMS [M+H]: 303; RT=1.73 min. $^1$H NMR (400 MHz, METHANOL-$d_4$) δ ppm 1.27-2.04 (m, 6H), 2.88 (br s, 1H), 4.50 (br t, J=12.04 Hz, 1H), 7.44-7.52 (m, 2H), 7.53-7.61 (m, 1H), 7.73-7.90 (m, 2H).

Example 33. Preparation of N-(7-amino-1,1-difluoro-2-oxoheptan-3-yl)benzamide (37)

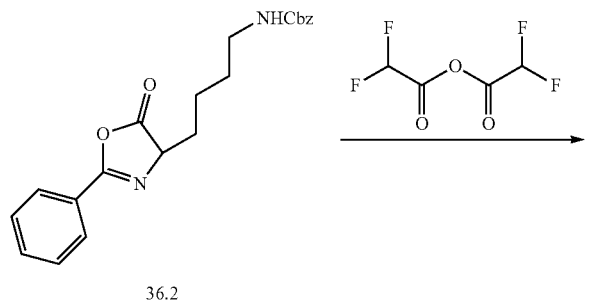

36.2

NH₂

36

37.2

37.1 (1.2 g, 2.70 mmol, 1 equivalent) and oxalic acid (486.18 mg, 5.40 mmol, 476.64 μL, 2 equivalent) was stirred at 120° C. for 10 min under $N_2$. The mixture was concentrated under reduced pressure and purified by column chromatography ($SiO_2$, Ethyl acetate) to give a crude 37.2, then was purified further by semi-preparative scale HPLC (neutral conditions) to give pure 37.2 (120 mg, 286.79 μmol, 80% yield); LCMS [M+H]: 419; RT=0.79 min.

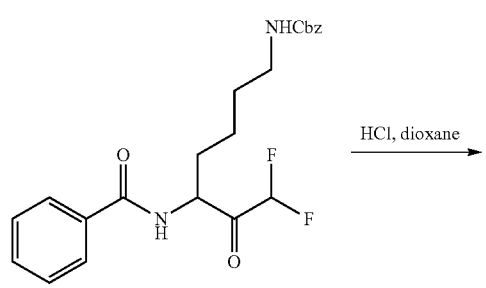

37.2

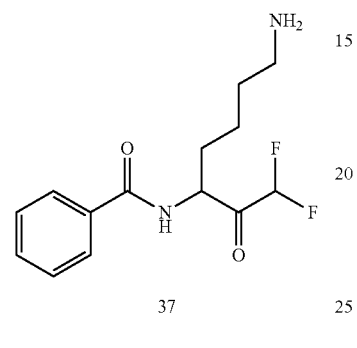

37

37.2 (10 mg, 23.9 μmol, 1 equivalent) in HCl (1 mL) and dioxane (1 mL) was stirred at 50° C. for 2 hours. The mixture was concentrated under reduced pressure and was purified by semi-preparative scale HPLC (neutral conditions) to give Compound 37 (120 mg, 287 μmol, 80% yield); LCMS [M+H]: 285; RT=2.0 min. $^1$H NMR (400 MHz, METHANOL-$d_4$) δ ppm 1.38-1.57 (m, 1H), 1.72-1.97 (m, 5H), 2.01-2.14 (m, 1H), 3.70-3.85 (m, 1H), 4.05 (br dd, J=12.35, 6.84 Hz, 1H), 5.95-6.29 (m, 1H), 7.44-7.60 (m, 4H), 7.81-7.90 (m, 2H).

Example 34. Preparation of a Fluorescent Gingipain Activity Probe with Cleavable Quencher: (S,E)-N-(7-amino-1-(4-((4-((4-(dimethylamino)phenyl)diazenyl)benzamido)-methyl)-2,6-difluorophenoxy)-2-oxoheptan-3-yl)-3-(4-((3-(5,5-difluoro-7,9-dimethyl-5H-5I4,6I4-dipyrrolo[1,2-c:2',1'-f][1,3,2]diazaborinin-3-yl)propanamido)methyl)-1H-1,2,3-triazol-1-yl)benzamide (38)

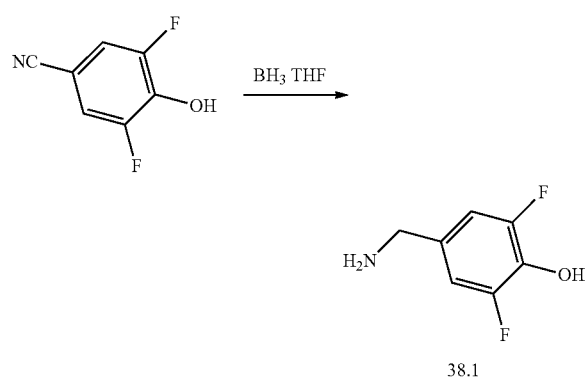

To 2,6-Difluoro-4-cyanophenol (2.5 g, 16.12 mmol, 1 equivalent) was added BH3-THF (1 M, 64.48 mL, 4 equivalent). The mixture was stirred at 70° C. for 10 hours. The reaction was quenched by addition of HCl (6 M, 5 mL) at 25° C. then it was concentrated under reduced pressure to give 38.1 (7.1 g, crude) as a white solid.

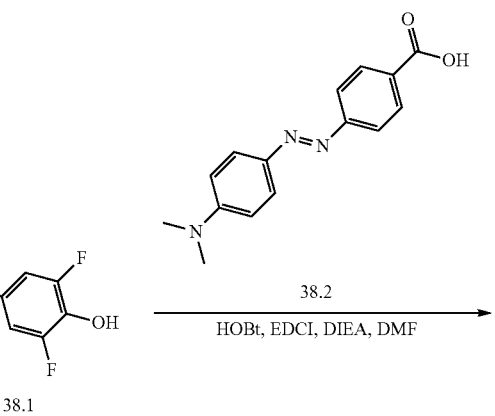

38.3

To 38.2 (6.09 g, 22.62 mmol, 1 equivalent) in DMF (15 mL) was added HOBt (3.36 g, 24.88 mmol, 1.1 equivalent) and EDCI (4.77 g, 24.88 mmol, 1.1 equivalent). The mixture was stirred at 0° C. for 1 hour, then 38.1 (3.60 g, 22.62 mmol, 1 equivalent) and DIEA (11.70 g, 90.48 mmol, 15.81 mL, 4.00 equivalent) was added; this mixture was stirred at 25° C. for 11 hours. The reaction was diluted with H$_2$O (20 mL) and extracted with EtOAc (20 mL×3). The combined organic layers were washed with brine (20 mL), dried over Na$_2$SO$_4$, filtered and concentrated under reduced pressure. This was purified by column chromatography (SiO$_2$, Petroleum ether/Ethyl acetate=1/1) to give 38.3 (400 mg, 974.6 μmol) as a red solid. $^1$H NMR (400 MHz, METHANOL-$d_4$) δ ppm 3.11 (s, 6H), 4.48 (s, 2H), 6.84 (d, J=9.29 Hz, 2H), 6.90-6.98 (m, 2H), 7.78-7.90 (m, 4H), 7.94-8.01 (m, 2H).

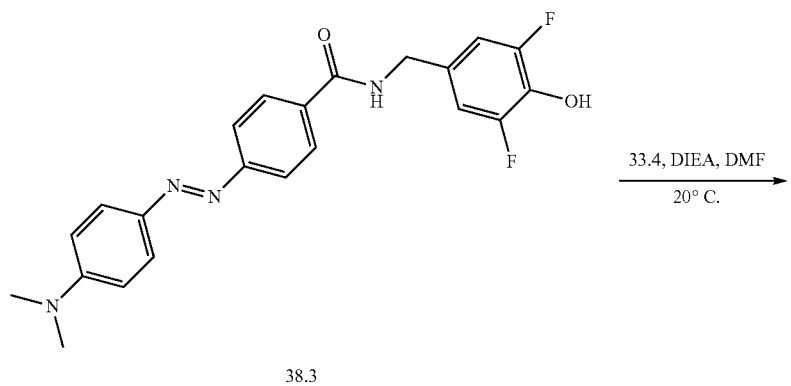

38.3

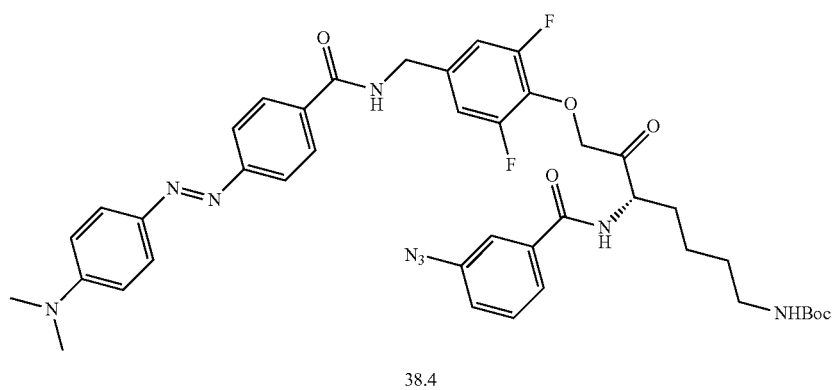

38.4

To 33.4 (1 g, 2.36 mmol, 1 equivalent) and 38.3 (100 mg, 243.65 μmol, 0.1 equivalent) in DMF (10 mL) was added DIPEA (1.22 g, 9.44 mmol, 1.65 mL, 4 equivalent) in one portion at 20° C. under $N_2$. The mixture was stirred at 20° C. for 10 hours. The reaction mixture was diluted with $H_2O$ (10 mL) and extracted with EtOAc (10 mL×3). The combined organic layers were washed with brine (30 mL), dried over $Na_2SO_4$, filtered and concentrated. This was purified by column chromatography ($SiO_2$, Petroleum ether/Ethyl acetate=1/1) to give 38.4 (250 mg, 313.34 μmop as a red solid.

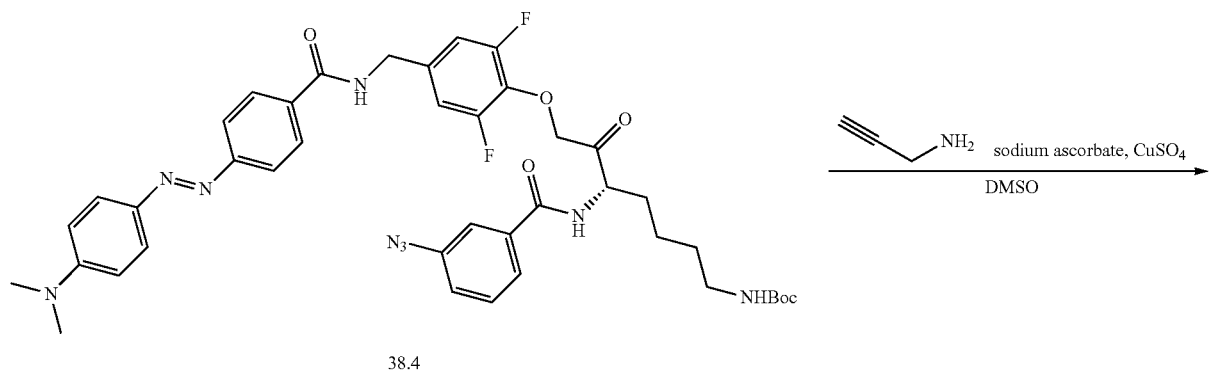

38.4

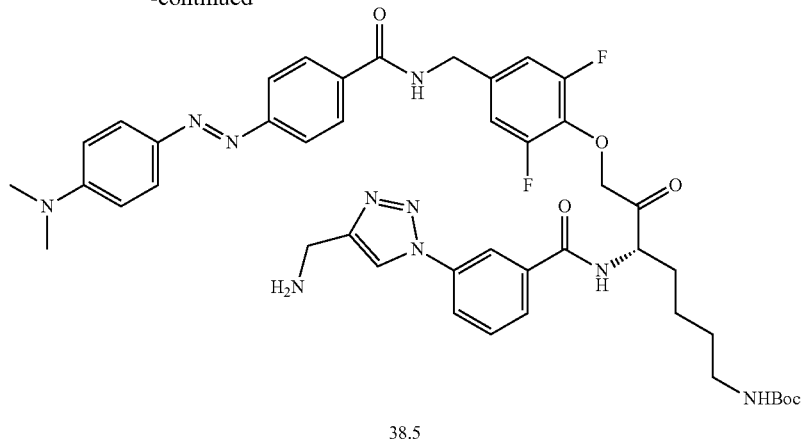

38.5

To a mixture of 38.4 (220 mg, 275.74 µmol, 1 equivalent) and prop-2-yn-1-amine (15.19 mg, 275.74 µmol, 17.66 µL, 1 equivalent) in DMSO (2 mL) was added the solution of CuSO$_4$ (8.8 mg, 55.15 µmol, 8.46 µL, 0.2 equivalent) in H$_2$O (100 µL) and sodium ascorbate (109.25 mg, 551.48 µmol, 2 equivalent) in one portion at 18° C. under N$_2$. This mixture was stirred at 18° C. for 5 mins. The reaction mixture was diluted with H$_2$O (5 mL) and extracted with EtOAc (5 mL×3). The combined organic layers were washed with brine (10 mL), dried over Na$_2$SO$_4$, filtered and concentrated to give 38.5 (250 mg) as a brown solid; LCMS [M+H]: 853; RT=1.14 min.

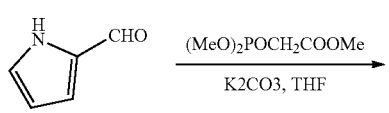

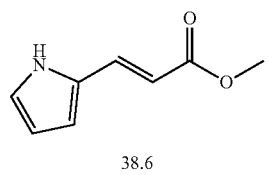

38.6

To 2-formylpyrrole (5 g, 52.58 mmol, 1 equivalent) and methyl 2-diethoxyphosphorylacetate (11.05 g, 52.58 mmol, 1 equivalent) in THF (60 mL) was added K$_2$CO$_3$ (14.53 g, 105.16 mmol, 2 equivalent) at 50° C. under N$_2$. The mixture was stirred at 50° C. for 10 hours. The reaction was diluted with H$_2$O (50 mL) and extracted with EtOAc (50 mL×3). The combined organic layers were washed with brine (100 mL), dried over Na$_2$SO$_4$, filtered and concentrated. This material was purified by column chromatography (SiO$_2$, Petroleum ether/Ethyl acetate=5/1) to give 38.6 (8.6 g, 57 mmol) as a white solid; LCMS [M+H]: 152; RT=0.68 min. $^1$H NMR (400 MHz, METHANOL-d4) δ ppm 3.69-3.76 (m, 3H), 6.04-6.13 (m, 1H), 6.15-6.21 (m, 1H), 6.31 (dt, J=3.91, 2.12 Hz, 1H) 6.45-6.57 (m, 1H), 6.92 (br d, J=1.32 Hz, 1H), 6.98-7.21 (m, 1H), 7.44-7.59 (m, 1H).

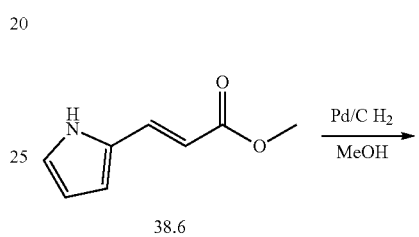

38.7

To 38.6 (8.6 g, 56.89 mmol) in MeOH (100 mL) was added Pd—C (10%, 0.9 g) under N$_2$. The suspension was degassed under vacuum and purged with H$_2$ several times. The mixture was stirred under H$_2$ (50 psi) at 18° C. for 10 hours. The reaction mixture was filtered and concentrated. This material was purified by column chromatography (SiO$_2$, Petroleum ether/Ethyl acetate=5/1) to give 38.6 (5 g, 32.64 mmol); LCMS [M+H]: 154; RT=0.55 min. $^1$H NMR (400 MHz, CHLOROFORM-d) δ ppm 2.66 (t, J=6.78 Hz, 2H), 2.93 (t, J=6.71 Hz, 2H), 3.62-3.78 (m, 3H), 5.80-5.99 (m, 1H), 6.12 (q, J=2.76 Hz, 1H) 6.60-6.76 (m, 1H), 8.54 (br s, 1H).

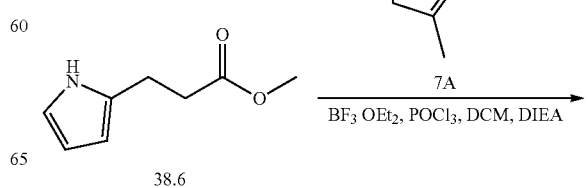

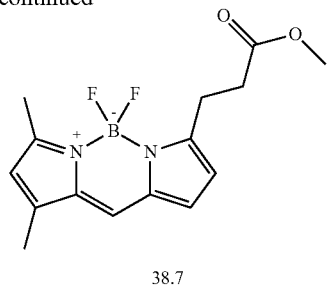

38.7

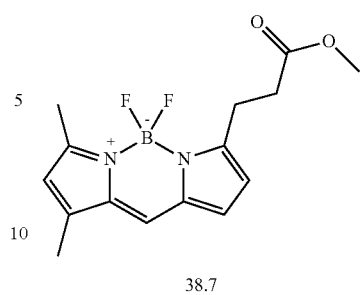

38.7

HCl THF H₂O →

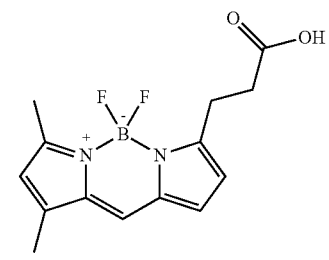

38.8

To 38.6 (3 g, 19.58 mmol, 1 equivalent) and compound 2-formyl-3,5-dimethylpyrrole (2.65 g, 21.54 mmol, 1.1 equivalent) in DCM (60 mL) was added POCl₃ (3.3 g, 21.54 mmol, 2 mL, 1.1 equivalent) in one portion at 18° C. under N₂. The mixture was stirred at 18° C. for 10 hours, then BF₃.Et₂o (11.12 g, 78.32 mmol, 9.67 mL, 4 equivalent) and DIEA (10.63 g, 82.24 mmol, 14.36 mL, 4.2 equivalent) was added drop wise at 18° C. This mixture was stirred at 18° C. for 10 hours. The reaction mixture was filtered, then diluted with H₂O (50 mL) and extracted with DCM (50 mL×3). The combined organic layers were washed with brine (100 mL), dried over Na₂SO₄, filtered and concentrated. This was purified by column chromatography (SiO₂, Petroleum ether/ Ethyl acetate=1/4) to give 38.7 (3 g, 9.80 mmol). ¹H NMR (400 MHz, CHLOROFORM-d) δ ppm 2.25 (s, 3H), 2.57 (s, 3H), 2.78 (t, J=7.59 Hz, 2H), 3.30 (t, J=7.65 Hz, 2H), 3.67-3.78 (m, 3H), 6.11 (s, 1H), 6.27 (d, J=3.89 Hz, 1H), 6.88 (d, J=3.89 Hz, 1H), 7.08 (s, 1H).

38.7 (1.2 g, 3.92 mmol, 1 equivalent) and HCl (50 mL, 37%) in THF (120 mL) and H₂O (80 mL) was stirred at 18° C. for 24 hours. The reaction mixture was partitioned with DCM (80 mL) and the aqueous layer was extracted with DCM (100 mL×2). The combined organic layers were washed with brine (300 mL), dried over Na₂SO₄, filtered and concentrated. This material was purified by preparative scale TLC (SiO₂, DCM:MeOH=10:1) to give 38.8 (700 mg, 2.4 mmol) as a red solid.

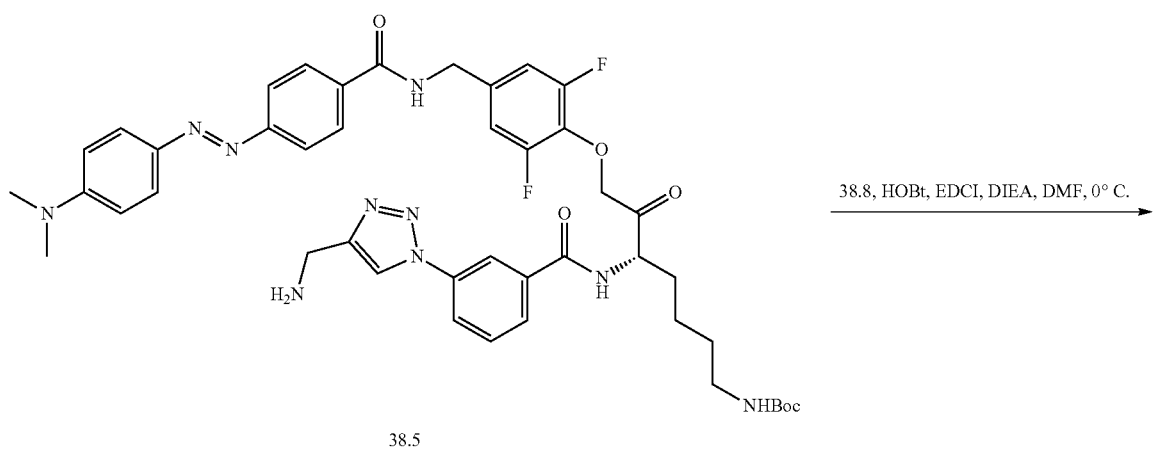

38.5

38.8, HOBt, EDCI, DIEA, DMF, 0° C. →

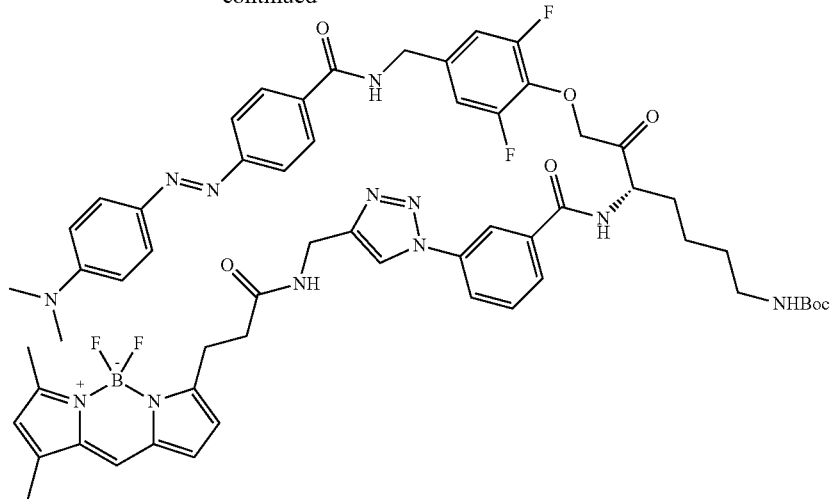

38.9

To a mixture of 38.8 (109.59 mg, 375.18 μmol, 2 equivalent) and HOBt (152.08 mg, 1.13 mmol, 6 equivalent) in DMF (2 mL) was added EDCI (215.76 mg, 1.13 mmol, 6 equivalent) at 0° C. under $N_2$. The mixture was stirred at 0° C. for 10 mins. To this mixture was added 38.5 (160 mg, 187.59 μmol, 1 equivalent) and DIPEA (145.46 mg, 1.13 mmol, 196.57 μl, 6 equivalent), this mixture was stirred at 0° C. for 20 mins. The reaction mixture was diluted with $H_2O$ (5 mL) and extracted with EtOAc (5 mL×3). The combined organic layers were washed with brine (10 mL), dried over $Na_2SO_4$, filtered and concentrated. The residue was purified by preparative scale TLC ($SiO_2$, EtOAc) to give 38.9 (60 mg, 53.24 μmol); LCMS [M+H]: 1128; RT=1.45 min.

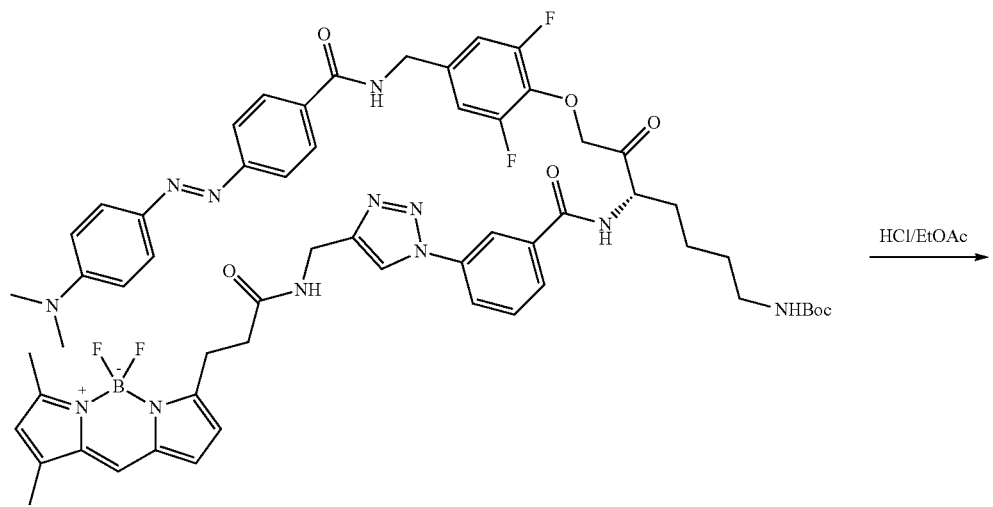

38.9

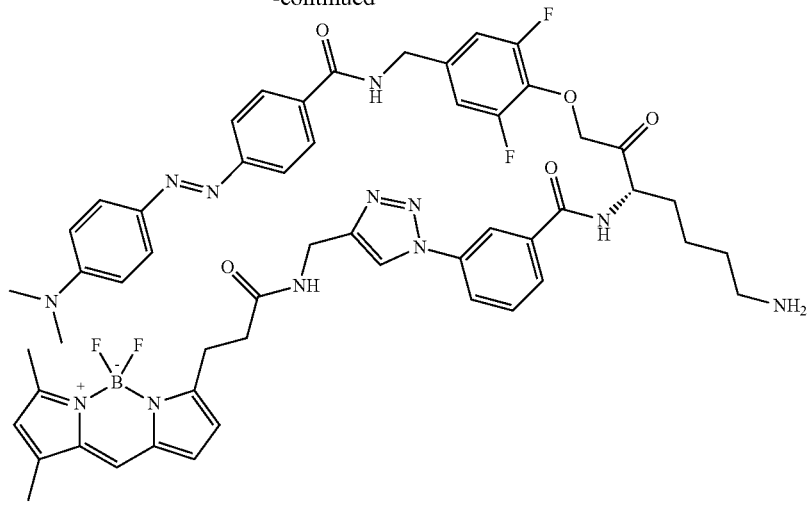

38

38.9 (50 mg, 44.37 μmol, 1 equivalent) was added to HCl/EtOAc (5 mL), and the mixture was stirred at 18° C. for 10 mins. The reaction was concentrated under reduced pressure, then was purified by semi-preparative scale HPLC (TFA condition) to give Compound 38 (10 mg, 9.74 μmol); LCMS [M+H]: 1027; RT=2.82 min. $^1$H NMR (400 MHz, DMSO-d6) δ ppm 1.23-1.59 (m, 4H), 1.67 (br d, J=9.48 Hz, 1H), 1.85 (br d, J=6.62 Hz, 1H), 2.21 (s, 2H), 2.42 (s, 3H), 2.53 (br d, J=7.94 Hz, 2H), 2.74 (br d, J=6.39 Hz, 2H), 3.04 (s, 5H), 3.06-3.11 (m, 1H), 4.39 (br d, J=5.51 Hz, 5H), 4.64 (br s, 1H), 4.99-5.20 (m, 2H), 6.25 (s, 1H), 6.32 (br d, J=3.97 Hz, 1H), 6.81 (br d, J=9.04 Hz, 2H), 6.96-7.10 (m, 2H), 7.52-7.62 (m, 3H), 7.68 (br t, J=8.05 Hz, 1H), 7.79 (br dd, J=8.60, 4.41 Hz, 3H), 7.90-8.01 (m, 2H), 8.04 (d, J=7.72 Hz, 1H), 8.36 (s, 1H), 8.47-8.58 (m, 1H), 8.64 (s, 1H), 8.96 (br d, J=7.50 Hz, 1H), 9.07-9.20 (m, 1H).

Example 35. Preparation of (S)—N-(7-amino-2-oxo-1-(6-oxopyrimidin-1(6H)-yl)heptan-3-yl)cyclopentanecarboxamide (39)

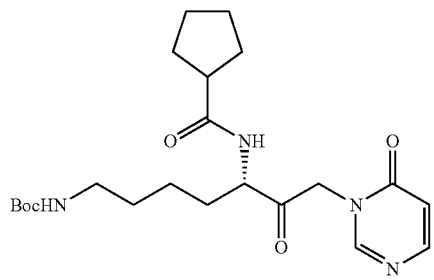

39.1

To 1.2 (150 mg, 357.7 μmol, 1 equivalent) in DMF (2 mL) was added K$_2$CO$_3$ (148.31 mg, 1.07 mmol, 3 equivalent) and 4-hydoxylpyrimidine (34.37 mg, 357.7 μmol, 1 equivalent). The mixture was stirred at 25° C. for 15 hours. The residue was purified by semi-preparative scale HPLC (TFA condition) to give 39.1 (40 mg, 92.05 μmol); LCMS [M+H]: 435; RT=0.76 min.

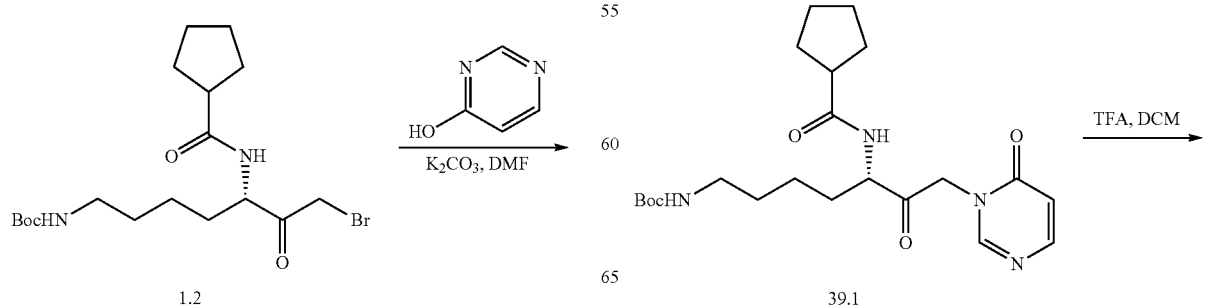

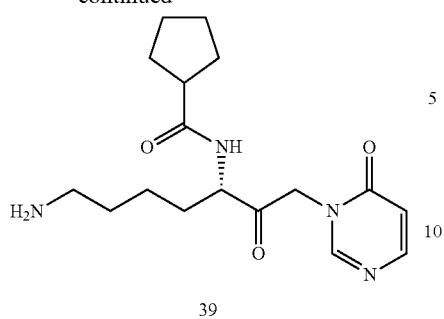

39

39.1 (40 mg, 92.05 μmol, 1 equivalent) in DCM (5 mL) and TFA (1 mL) was stirred at 25° C. for 15 hours. The mixture was concentrated under reduced pressure to give Compound 39 (20 mg, 59.8 μmol, 65% yield); LCMS [M+H]: 335; RT=0.25 min. $^1$H NMR (400 MHz, METHANOL-$d_4$) δ ppm 1.37-1.57 (m, 2H), 1.57-1.81 (m, 10H), 1.83-2.06 (m, 3H), 2.63-2.83 (m, 1H), 2.94 (br t, J=7.50 Hz, 2H), 4.52 (dd, J=8.49, 5.40 Hz, 1H), 4.95-4.99 (m, 1H), 4.97 (s, 1H), 6.51 (d, J=6.61 Hz, 1H), 8.00 (d, J=6.61 Hz, 1H), 8.32 (s, 1H).

Example 36. Preparation of (S)—N-(7-amino-2-oxo-1-(4-oxopyrimidin-1(4H)-yl)heptan-3-yl)cyclopentanecarboxamide (40)

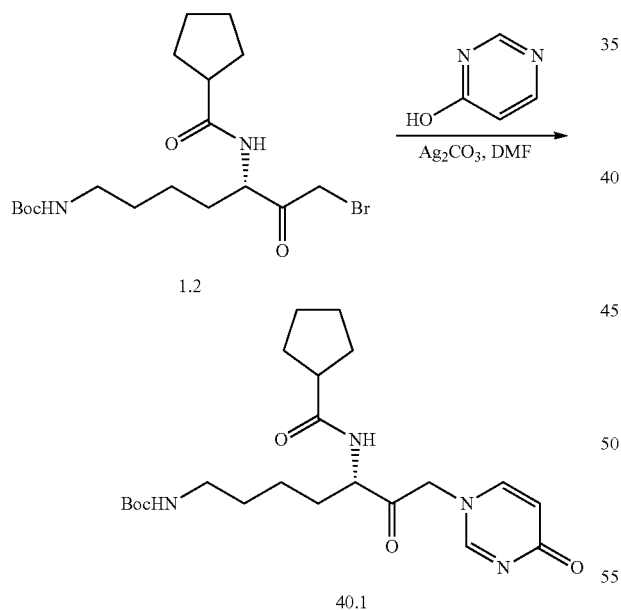

To 1.2 (100 mg, 238.46 μmol, 1 equivalent) in DMF (3 mL) was added Ag$_2$CO$_3$ (197.27 mg, 715.38 μmol, 32.45 μL, 3.00 equivalent) and 4-hydroxypyrimidine (22.91 mg, 238.46 μmol, 1 equivalent). The mixture was stirred at 25° C. for 15 hours. The residue was purified by semi-preparative scale HPLC (TFA condition) to give 40.1 (30 mg, 69.04 μmol, 29% yield) as a white solid; LCMS [M+H]: 435; RT=0.74 min.

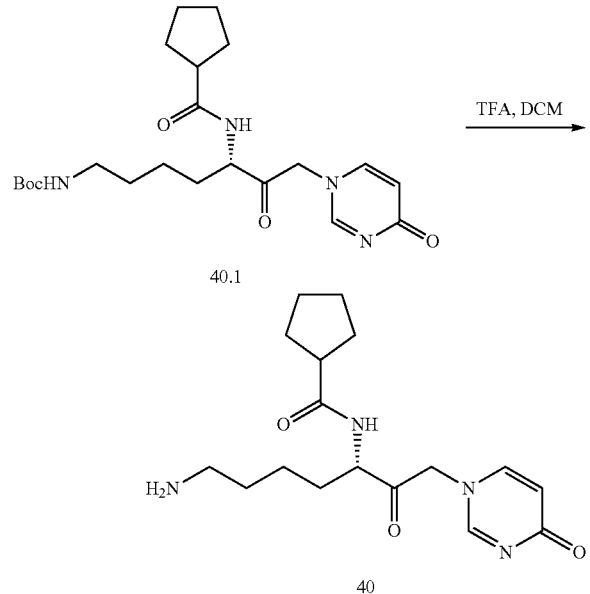

40.1 (30 mg, 69 μmol, 1 equivalent) in TFA (1 mL) and DCM (5 mL) was stirred at 25° C. for 15 hours. The mixture was concentrated under reduced pressure to give Compound 40 (2 mg, 6 μmol); LCMS [M+H]: 335; RT=0.43 min. $^1$H NMR (400 MHz, METHANOL-$d_4$) δ ppm 1.24-1.57 (m, 4H), 1.58-1.81 (m, 10H), 1.82-2.03 (m, 4H), 2.66-2.84 (m, 1H), 2.86-3.03 (m, 2H), 4.31-4.48 (m, 1H), 4.95-5.19 (m, 2H), 6.30 (d, J=7.58 Hz, 1H), 7.62 (br d, J=7.34 Hz, 1H), 8.23 (br s, 1H).

Example 37. Preparation of (S)—N-(7-amino-1-(5-fluoro-6-oxopyrimidin-1(6H)-yl)-2-oxoheptan-3-yl) cyclopentanecarboxamide (41)

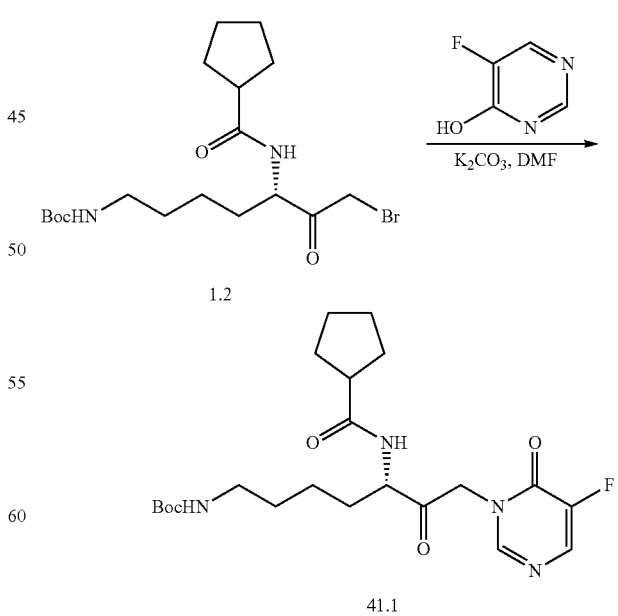

To 1.2 (150 mg, 357.7 μmol, 1 equivalent) in DMF (2 mL) was added K$_2$CO$_3$ (148.31 mg, 1.07 mmol, 3 equivalent) and 5-fluoropyrimidin-4-ol (40.81 mg, 357.7 µmol, 1 equivalent). The mixture was stirred at 25° C. for 15 hours. The residue was purified by semi-preparative scale HPLC (TFA condition) to give 41.1 (50.00 mg, 110.49 µmol, 30.89% yield) as a white solid; LCMS [M+H]: 453; RT=0.8 min.

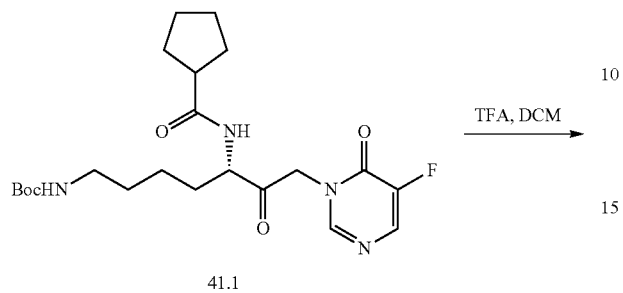

41.1

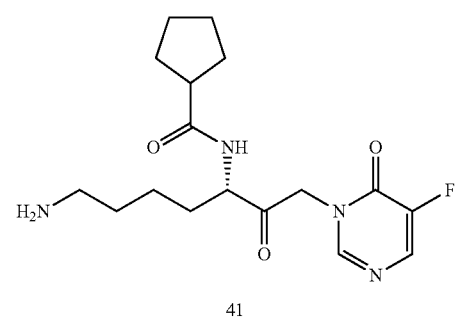

41

41.1 (50 mg, 110.49 µmol, 1. equivalent) in DCM (5 mL) and TFA (1 mL) was stirred at 25° C. for 15 hours. The mixture was concentrated under reduced pressure to give Compound 41 (30 mg, 85.13 µmol, 77% yield) as a white solid; LCMS [M+H]: 353; RT=0.16 min. $^1$H NMR (400 MHz, METHANOL-$d_4$) δ ppm 1.28-1.47 (m, 2H), 1.48-1.73 (m, 9H), 1.75-1.98 (m, 3H), 2.56-2.73 (m, 1H), 2.86 (br t, J=7.52 Hz, 2H), 4.44 (dd, J=8.56, 5.50 Hz, 1H), 4.90-5.04 (m, 2H), 7.95 (d, J=2.45 Hz, 1H), 8.05 (s, 1H).

Example 38. Preparation of (S)—N-(7-amino-2-oxo-1-(2,3,6-trifluorophenoxy)heptan-3-yl)nicotinamide (42)

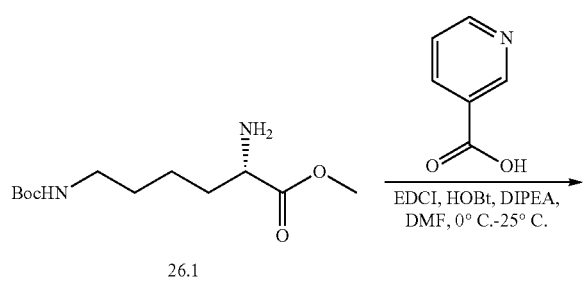

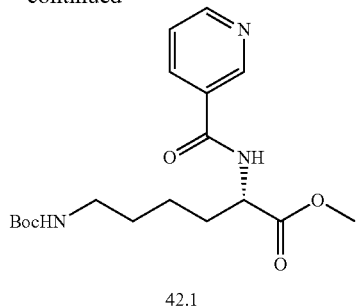

42.1

To nicotinic acid (497.86 mg, 4.04 mmol, 339 µL, 1.2 equivalent) in DMF (10 mL) was added HOBt (501 mg, 3.71 mmol, 1.1 equivalent) and EDCI (710.5 mg, 3.71 mmol, 1.1 equivalent). The mixture was stirred at 0° C. for 1 hr. Then the mixture was added to DIPEA (1.74 g, 13.48 mmol, 2.35 mL, 4 equivalent) and 26.1 (1 g, 3.37 mmol, 1.00 equivalent, HCl salt) and stirred at 25° C. for 11 hours. The reaction mixture was diluted with H$_2$O (20 mL) and extracted with EtOAc (20×mL×3). The combined organic layers were washed with brine (20 mL), dried over Na$_2$SO$_4$, filtered and concentrated. The residue was purified by column chromatography (SiO$_2$, Petroleum ether/Ethyl acetate=20/1 to 0/1) to give 42.1 (800 mg, 2.19 mmol, 65% yield) as colorless oil. 1H NMR (400 MHz, CHLOROFORM-d) δ ppm 1.41 (br s, 10H), 1.54 (br d, J=6.11 Hz, 3H), 1.81-2.06 (m, 3H), 3.14 (br s, 2H), 3.80 (br d, J=2.69 Hz, 3H), 4.06-4.20 (m, 1H), 7.04 (br s, 1H), 7.40 (br d, J=5.14 Hz, 1H), 8.16 (br s, 1H), 8.76 (br s, 1H), 9.07 (br s, 1H).

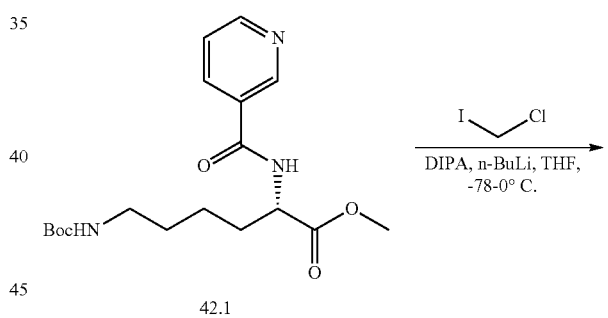

42.1

42.2

To a solution of DIPA (648 mg, 6.4 mmol, 9 µL, 6 equivalent) in THF (5 mL) was added n-BuLi (2.5 M, 2.56 mL, 6 equivalent); this was stirred at 0° C. for 1 hour. To 42.1 (390 mg, 1.07 mmol, 1 equivalent) in THF (5 mL) was added chloro(iodo)methane (1.13 g, 6.4 mmol, 464.8 µL, 6 equivalent); this was stirred at −78° C. for 30 min. Then the two mixtures were combined and stirred at −78° C. for 2 hr. The reaction was quenched by addition NH$_4$Cl solution (15 mL) and extracted with EtOAc (20 mL×3). The combined organic layers were washed with Na$_2$SO$_3$ solution (15 mL), NaHCO$_3$ solution (15 mL) and brine (15 mL); this was dried over Na$_2$SO$_4$, filtered and concentrated under reduced pressure to give 42.2 (410 mg); LCMS [M+H]: 384; RT=0.79 min.

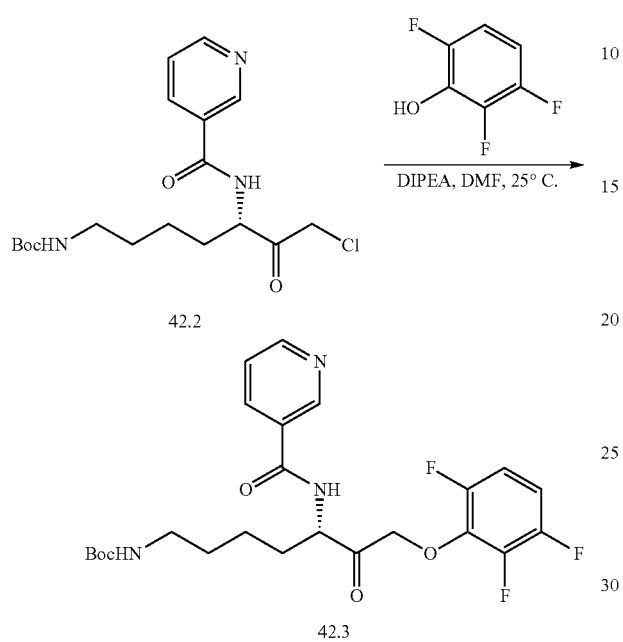

To 42.2 (410 mg, 1.07 mmol, 1 equivalent) in DMF (5 mL) was added DIPEA (553.15 mg, 4.28 mmol, 747.5 μL, 4 equivalent) and 2,3,6-trifluorophenol (158.45 mg, 1.07 mmol, 1 equivalent). The mixture was stirred at 25° C. for 12 hours. The residue was purified by semi-preparative scale HPLC (column: Waters Xbridge 150×25×5μ; mobile phase: [A: water (0.1% TFA); B: AcN]; gradient of B: 24%-65% over 12 min) to give 42.3 (40 mg, 90 μmol); LCMS [M+H]: 496; RT=0.80 min.

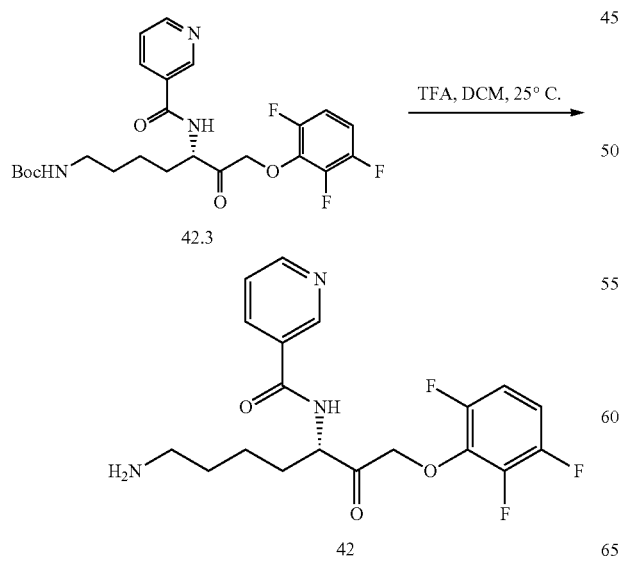

To 42.3 (40.00 mg, 80.73 μmol) in CH$_2$Cl$_2$ (5 mL) was added TFA (1 mL) and stirred at 25° C. for 12 hours. The reaction mixture was concentrated under reduced pressure to remove solvent to give Compound 42 (20 mg, 50.59 μmol, 63% yield); LCMS [M+H]: 396; RT=0.76 min. 1H NMR (400 MHz, METHANOL-d$_4$) δ ppm 1.48-1.67 (m, 2H), 1.70-1.91 (m, 3H), 2.08-2.19 (m, 1H), 2.91-3.03 (m, 1H), 2.97 (br t, J=7.03 Hz, 1H), 4.95-5.01 (m, 1H), 5.05-5.25 (m, 2H), 6.94-7.09 (m, 2H), 7.68-7.81 (m, 1H), 8.39-8.51 (m, 1H), 8.75-8.85 (m, 1H), 9.01-9.14 (m, 1H).

Example 39. Preparation of (S)—N-(7-amino-1-(2,6-difluorophenoxy)-2-oxoheptan-3-yl)nicotinamide (43)

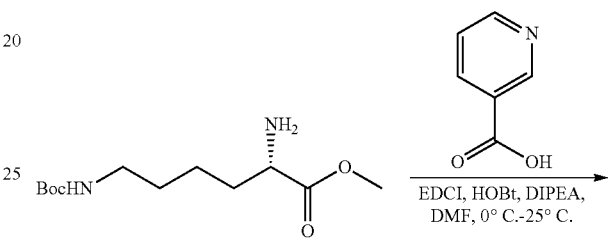

To nicotinic acid (497.86 mg, 4.04 mmol, 338.68 μL, 1.2 equivalent) in DMF (10 mL) was added HOBt (500.8 mg, 3.71 mmol, 1.1 equivalent) and EDCI (710.5 mg, 3.71 mmol, 1.1 equivalent). The mixture was stirred at 0° C. for 1 hr. To the mixture was added DIPEA (1.74 g, 13.48 mmol, 2.35 mL, 4 equivalent) and 26.1 (1 g, 3.37 mmol, 1 equivalent, HCl); this was stirred at 25° C. for 11 hours. The reaction mixture was diluted with H$_2$O (20 mL) and extracted with EtOAc (20 mL×3). The combined organic layers were washed with brine (20 mL), dried over Na$_2$SO$_4$, filtered and concentrated. The residue was purified by column chromatography (SiO$_2$, Petroleum ether/Ethyl acetate=20:1 to 0:1) to give 43.1 (800 mg, 2.19 mmol); LCMS [M+H]: 366; RT=0.69 min. $^1$H NMR (400 MHz, CHLOROFORM-d) δ ppm 1.39 (s, 9H), 1.49-1.59 (m, 2H), 1.78-2.05 (m, 5H), 3.12 (br d, J=5.70 Hz, 2H), 3.79 (s, 2H), 3.78-3.81 (m, 1H), 4.65 (br s, 1H), 4.79 (br d, J=5.26 Hz, 1H), 7.02 (br d, J=5.70 Hz, 1H), 7.39 (dd, J=7.67, 5.04 Hz, 1H), 8.15 (br d, J=7.89 Hz, 1H), 8.74 (br d, J=4.38 Hz, 1H), 9.06 (br s, 1H).

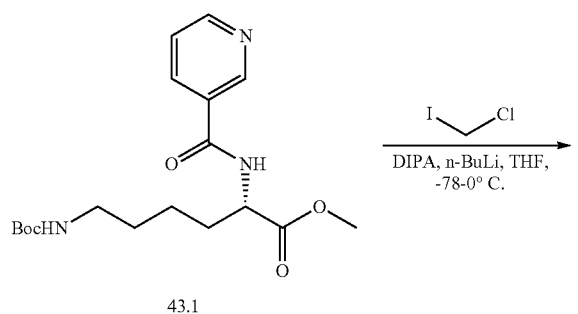
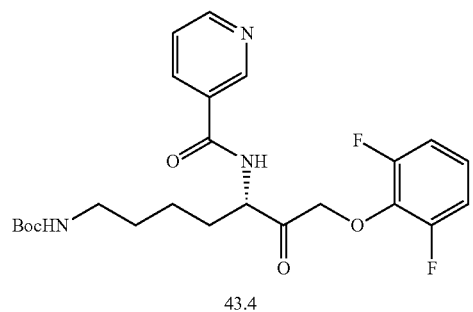

To 43.3 (500 mg, 1.30 mmol, 1 equivalent) in DMF (5 mL) was added DIPEA (672.05 mg, 5.2 mmol, 908.18 μL, 4 equivalent) and 2,6-difluorophenol (186.03 mg, 1.43 mmol, 1.1 equivalent). The mixture was stirred at 25° C. for 12 hours. The residue was purified by prep-HPLC (column: Waters Xbridge 150×25×5μ; mobile phase: [A: water (0.1% TFA), B: AcN]; gradient of B: 23% to 63%, over 12 min) to give 43.4 (40 mg, 86.30 μmol).

To a solution of DIPA (662 mg, 6.54 mmol, 919 μL, 6 equivalent) in THF (5 mL) was added n-BuLi (2.5 M, 2.62 mL, 6 equivalent); this was stirred at 0° C. for 1 hr. 43.1 (400 mg, 1.09 mmol, 1 equivalent) in THF (5 mL) was added chloro(iodo)methane (1.15 g, 6.54 mmol, 474.7 μL, 6 equivalent) and stirred at −78° C. for 30 min. Then the mixture was added the before mixture and stirred at −78° C. for 2 hours. The reaction mixture was quenched by addition NH$_4$Cl solution 15 mL at 25° C., and extracted with EtOAc (15 mL×3). The combined organic layers were washed with Na$_2$SO$_3$ solution (15 mL), NaHCO$_3$ solution (15 mL) and brine (15 mL); then dried over Na$_2$SO$_4$, filtered and concentrated to give 43.2 (500 mg).

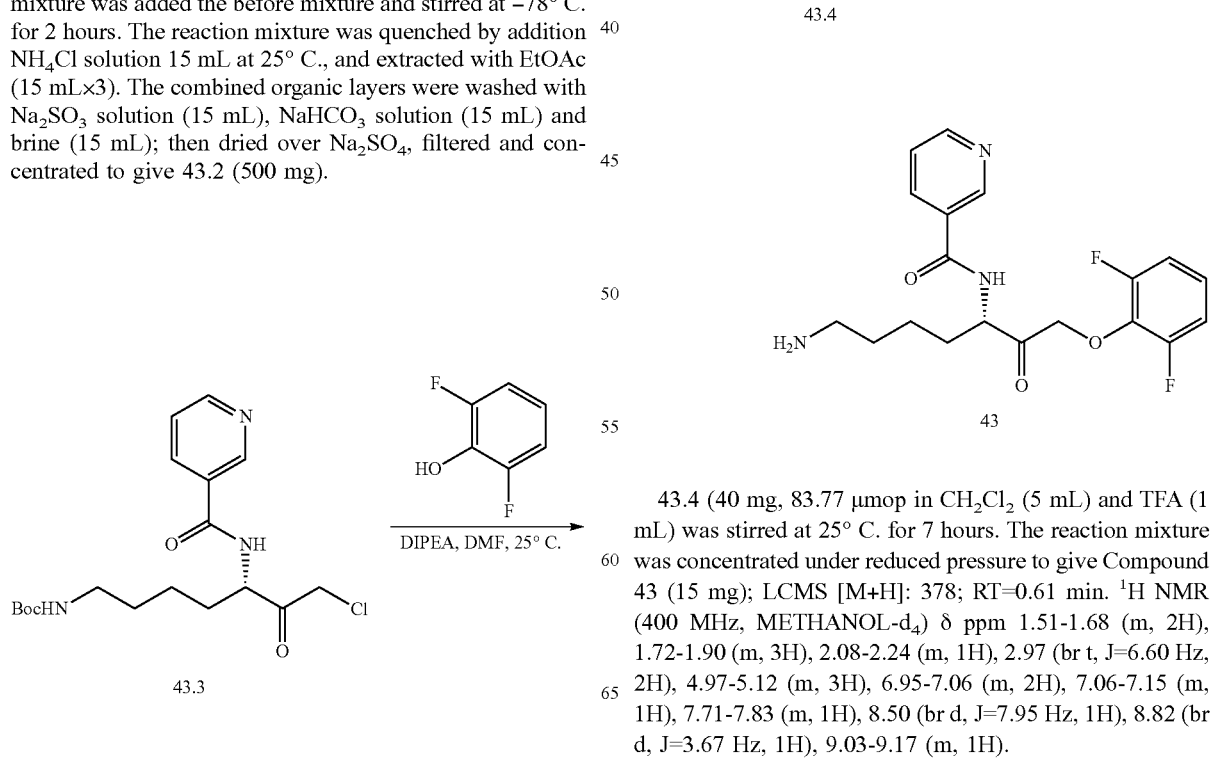

43.4 (40 mg, 83.77 μmop in CH$_2$Cl$_2$ (5 mL) and TFA (1 mL) was stirred at 25° C. for 7 hours. The reaction mixture was concentrated under reduced pressure to give Compound 43 (15 mg); LCMS [M+H]: 378; RT=0.61 min. $^1$H NMR (400 MHz, METHANOL-d$_4$) δ ppm 1.51-1.68 (m, 2H), 1.72-1.90 (m, 3H), 2.08-2.24 (m, 1H), 2.97 (br t, J=6.60 Hz, 2H), 4.97-5.12 (m, 3H), 6.95-7.06 (m, 2H), 7.06-7.15 (m, 1H), 7.71-7.83 (m, 1H), 8.50 (br d, J=7.95 Hz, 1H), 8.82 (br d, J=3.67 Hz, 1H), 9.03-9.17 (m, 1H).

Example 40. Preparation of (S,E)-N-(7-amino-1-(4-((4-((4-(dimethylamino)phenyl)diazenyl)benzamido)methyl)-2,6-difluorophenoxy)-2-oxoheptan-3-yl)-3-azidobenzamide (44)

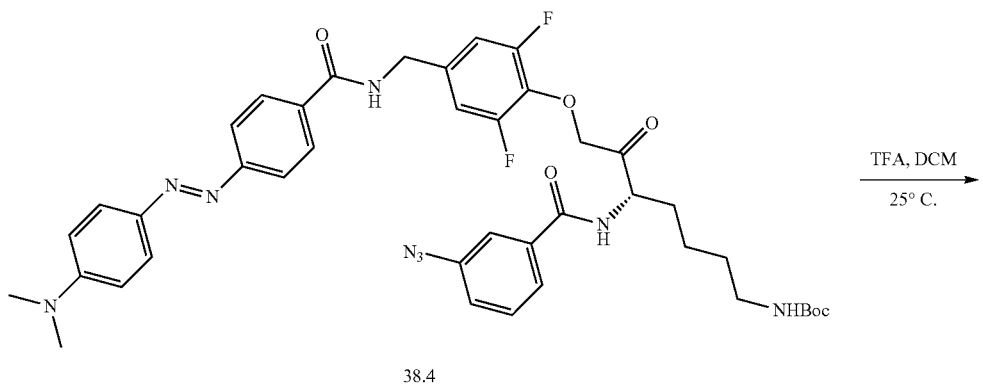

To a solution of 38.4 (100 mg, 125.34 umol, 1 equivalent) in CH$_2$Cl$_2$ (5 mL) was added TFA (1.54 g, 13.51 mmol, 1 mL, 107.76 equivalent) and was stirred at 25° C. for 12 hours. The residue was purified by prep-HPLC (Waters Xbridge 150×25×5μ; mobile phase: [A: water (0.1% TFA) & B: ACN]; B %: 31%-61%, 12 min) to give Compound 44 (40 mg, 57.33 umol, 46% yield) as a red solid; LCMS [M+H]: 698; RT=2.764 min. $^1$H NMR (400 MHz, DMSO-d6) δ ppm 1.29-1.46 (m, 2H), 1.52 (dt, J=14.28, 7.30 Hz, 2H), 1.63-1.74 (m, 1H), 1.79-1.91 (m, 1H), 2.71-2.81 (m, 2H), 3.07 (s, 5H), 4.42 (br d, J=5.73 Hz, 2H), 4.54-4.67 (m, 1H), 4.95-5.19 (m, 2H), 6.84 (br d, J=9.04 Hz, 2H), 7.01-7.11 (m, 2H), 7.30 (br d, J=7.94 Hz, 1H), 7.52 (br t, J=7.83 Hz, 1H), 7.57 (s, 1H), 7.63 (br s, 2H), 7.68 (br d, J=7.72 Hz, 1H), 7.82 (dd, J=8.71, 4.74 Hz, 3H), 7.94-8.10 (m, 1H), 8.85 (br d, J=7.50 Hz, 1H), 9.11-9.24 (m, 1H).

Example 41. Preparation of (S,E)-N-(7-amino-1-(4-(2-(4-((4-(dimethylamino)phenyl)diazenyl)benzamido)ethyl)-2,6-difluorophenoxy)-2-oxoheptan-3-yl)-3-(4-((3-(5,5-difluoro-7,9-dimethyl-5H-5$^{14}$,6$^{14}$-dipyrrolo[1,2-c:2',1'-f][1,3,2]diazaborinin-3-yl)propanamido)methyl)-1H-1,2,3-triazol-1-yl)benzamide (45)

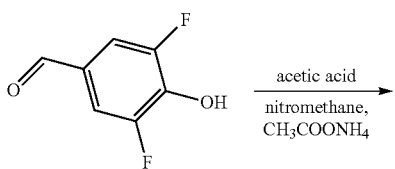

-continued

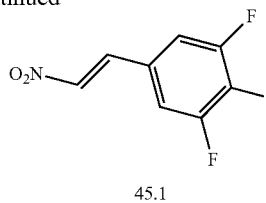

45.1

To a solution of 3,5-difluoro-4-hydroxybenzaldehyde (5 g, 31.63 mmol, 1 equivalent) in acetic acid (50.00 mL) was added nitromethane (11.58 g, 189.78 mmol, 10.25 mL, 6.00 equivalent) and $CH_3COONH_4$ (9.75 g, 126.52 mmol, 4.00 equivalent). The mixture was stirred at 110° C. for 1.5 hour. The reaction mixture was diluted with $H_2O$ (20 mL) and extracted with EtOAc (20 mL×3). The combined organic layers were washed with brine (20 mL), dried over $Na_2SO_4$, filtered and concentrated under reduced pressure to give a residue. The residue was purified by column chromatography ($SiO_2$, Petroleum ether/Ethyl acetate=20/1 to 1:1) to give 45.1 (4.60 g, 22.87 mmol, 72% yield) as a yellow solid. $^1$H NMR (400 MHz, METHANOL-$d_4$) δ ppm 7.33-7.40 (m, 2H), 7.77-7.89 (m, 1H), 7.90-8.01 (m, 1H).

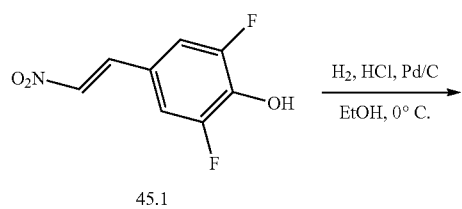

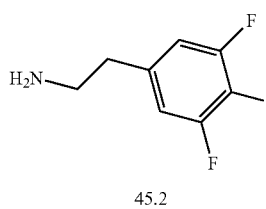

45.2

To a solution of 45.1 (2.10 g, 10.44 mmol, 1.00 equivalent) in EtOH (200.00 mL) was added HCl (6 M, 12.60 mL, 7.24 equivalent) and Pd/C (10%, 1.5 g) under Ar atmosphere at 0° C. The suspension was degassed and purged with $H_2$ for 3 times. The mixture was stirred under $H_2$ (15 Psi) at 0° C. for 3 hours. The reaction mixture was concentrated under reduced pressure to remove EtOH to give 45.2 (2.00 g, crude) as a brown solid; LCMS [M+H]: 174; RT=0.102 min. $^1$H NMR (400 MHz, METHANOL-$d_4$) δ ppm 2.88 (t, J=7.52 Hz, 2H) 3.08-3.20 (m, 2H), 6.85-6.93 (m, 2H).

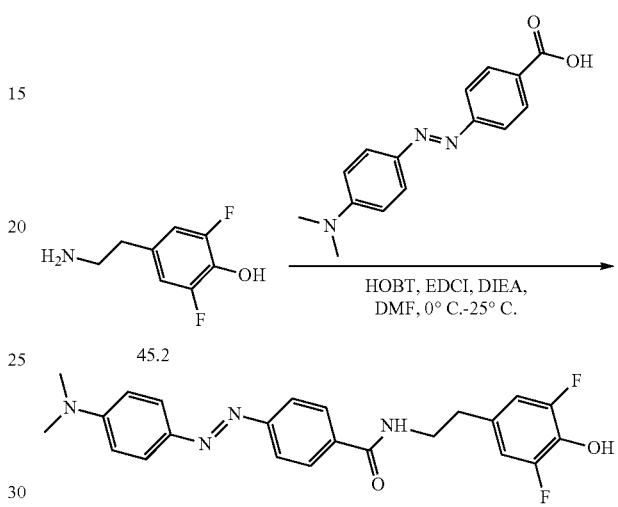

45.3

To a solution of the diazo compound (3.11 g, 11.55 mmol, 1.00 equivalent) in DMF (20.00 mL) was added EDCI (2.44 g, 12.71 mmol, 1.10 equivalent) and HOBt (1.72 g, 12.71 mmol, 1.10 equivalent) and stirred at 0° C. for 1 hr. Then the mixture was added 45.2 (2.00 g, 11.55 mmol, 1.00 equivalent) and DIPEA (5.97 g, 46.20 mmol, 8.07 mL, 4.00 equivalent) and stirred at 25° C. for 11 hr. The reaction mixture was diluted with $H_2O$ (20 mL) and extracted with EtOAc (20 mL×3). The combined organic layers were washed with brine (20 mL), dried over $Na_2SO_4$, filtered and concentrated under reduced pressure to give a residue. The residue was purified by column chromatography ($SiO_2$, Petroleum ether/Ethyl acetate=20/1 to 1:1) to give 45.3 (600 mg, 1.41 mmol). LCMS [M+H]: 425; RT=0.848 min. 1H NMR (400 MHz, DMSO-$d_6$) δ ppm 3.04-3.09 (m, 6H), 3.43-3.51 (m, 1H), 4.37 (br d, J=5.99 Hz, 1H), 4.54 (br d, J=5.75 Hz, 1H), 6.76-7.02 (m, 3H), 6.79 (br s, 1H), 7.71-7.85 (m, 4H) 7.88-8.01 (m, 2H).

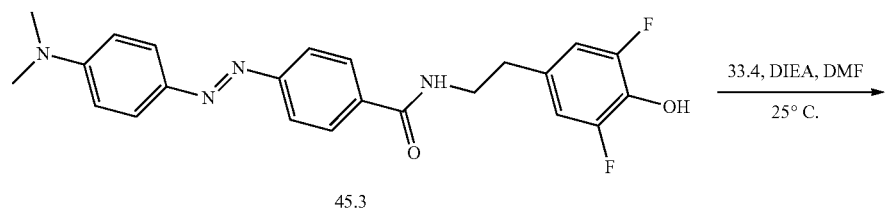

45.3

-continued

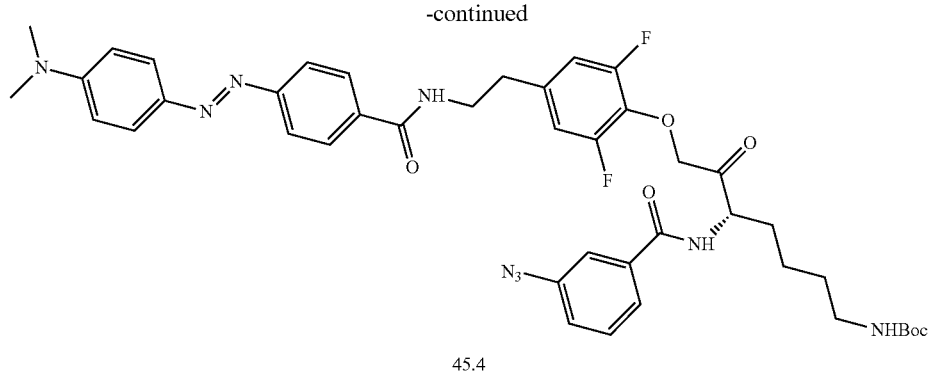

45.4

To a solution of 45.3 (310.00 mg, 730.37 μmol, 0.18 equivalent) in DMF (10.00 mL) was added 33.4 (1.70 g, 4.01 mmol, 1.00 equivalent) and DIPEA (2.07 g, 16.04 mmol, 2.80 mL, 4.00 equivalent). The mixture was stirred at 25° C. for 12 hours. The reaction mixture was diluted with H$_2$O (20 mL) and extracted with EtOAc (20 mL×3). The combined organic layers were washed with brine (20 mL), dried over Na$_2$SO$_4$, filtered and concentrated under reduced pressure to give a residue. The residue was purified by column chromatography (SiO$_2$, Petroleum ether/Ethyl acetate=20/1 to 1:1) to give 45.4 (350 mg) LCMS [M+H]: 813; RT=1.393 min.

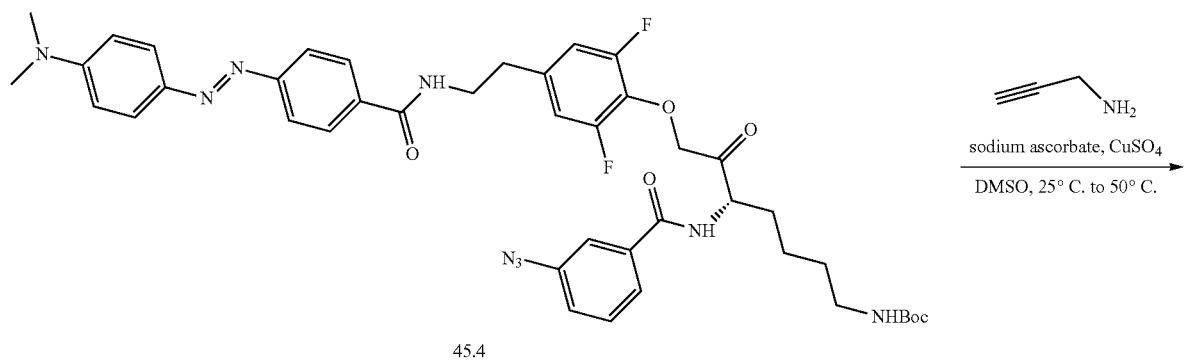

45.4

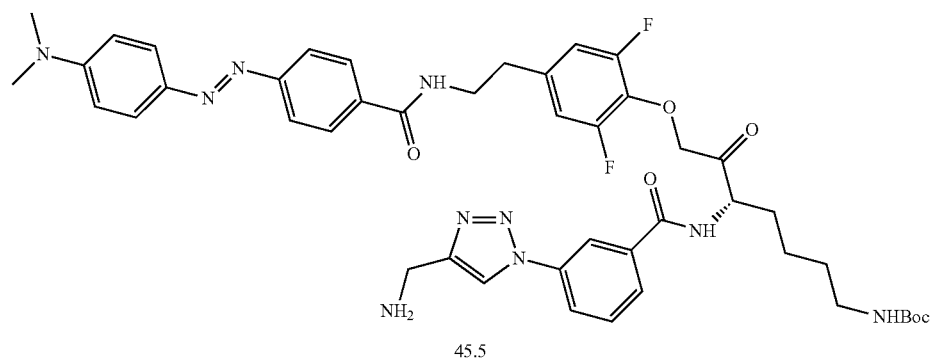

45.5

To a solution of 45.4 (200.00 mg, 246.34 µmol, 1.00 equivalent) in DMSO (2.00 mL) was added compound 14A (13.57 mg, 246.34 µmol, 15.78 µL, 1.00 equivalent) and CuSO$_4$ (1.97 mg, 12.32 µmol, 1.89 µL, 0.05 equivalent) in H$_2$O (200.00 µL) and sodium ascorbate (97.61 mg, 492.68 µmol, 2.00 equivalent). The mixture was stirred at 25° C. for 1 hour. The reaction mixture was diluted with H$_2$O (20 mL) and extracted with EtOAc (20 mL×3). The combined organic layers were washed with brine (20 mL), dried over Na$_2$SO$_4$, filtered and concentrated under reduced pressure to give a residue. The residue was purified by column chromatography (SiO$_2$, Petroleum ether/Ethyl acetate=20/1 to 1:1) to give 45.5 (130 mg).

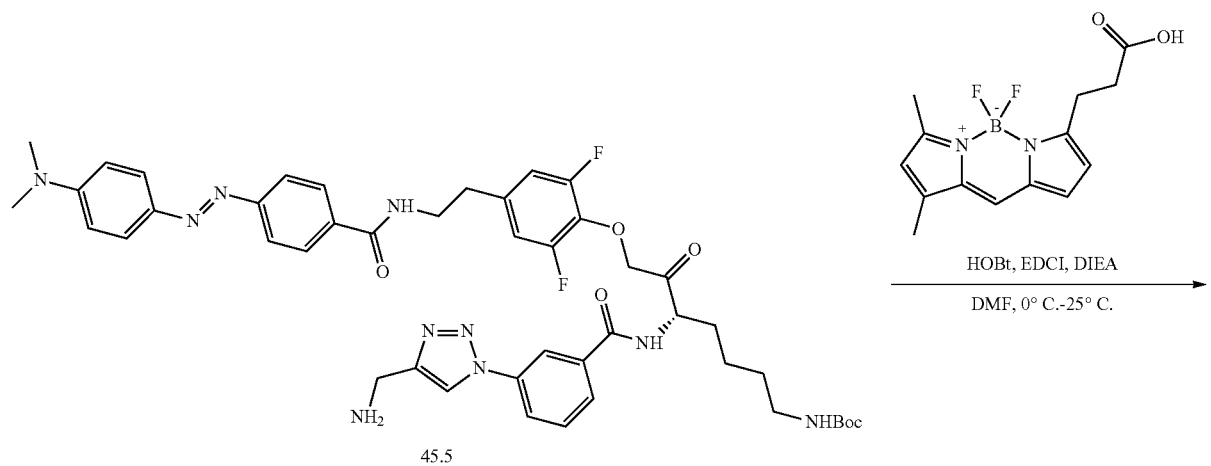

45.5

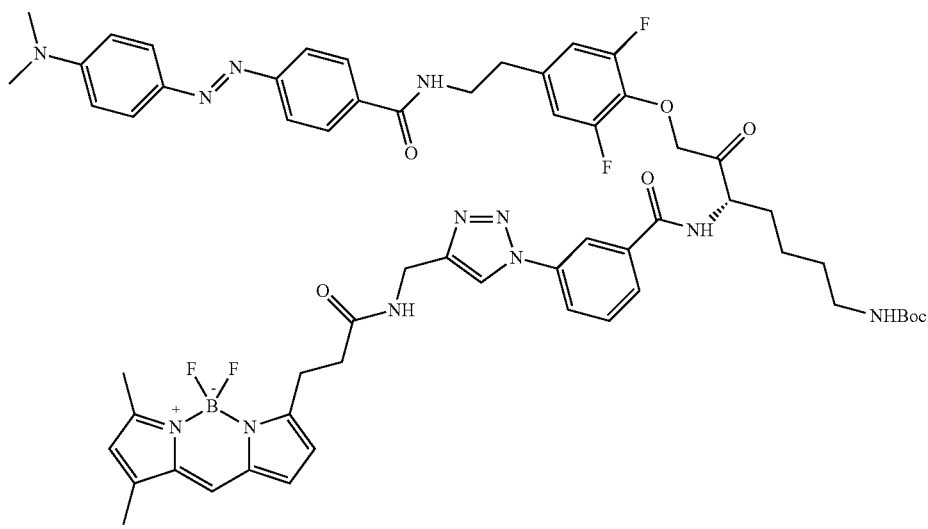

45.6

To a mixture of difluoroborate dye (48.18 mg, 164.95 µmol, 1.10 equivalent) in DMF (2.00 mL) was added EDCI (31.62 mg, 164.95 µmol, 1.10 equivalent) and HOBt (22.29 mg, 164.95 µmol, 1.10 equivalent) at 0° C. and stirred for 1 hr. Then the mixture was added 45.5 (130.00 mg, 149.95 µmol, 1.00 equivalent) and DIPEA (77.52 mg, 599.80 µmol, 104.76 µL, 4.00 equivalent) and stirred at 25° C. for 11 hr. The reaction mixture was diluted with $H_2O$ (20 mL) and extracted with EtOAc (20 mL×3). The combined organic layers were washed with brine (20 mL), dried over $Na_2SO_4$, filtered and concentrated under reduced pressure to give a residue. The residue was purified by column chromatography ($SiO_2$, Ethyl acetate) to give 45.6 (120.00 mg); LCMS [M+H]: 1142; RT=1.461 min.

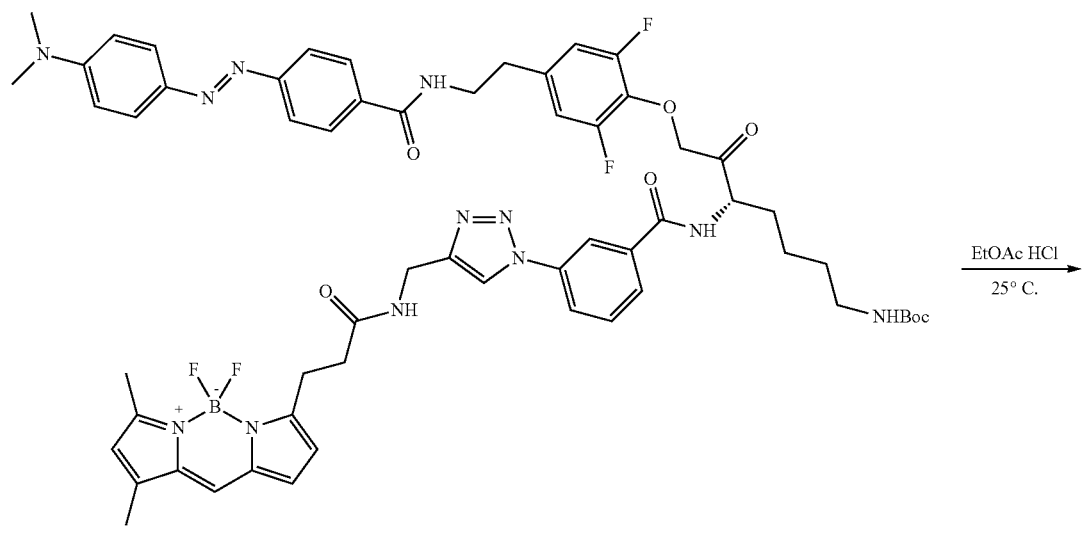

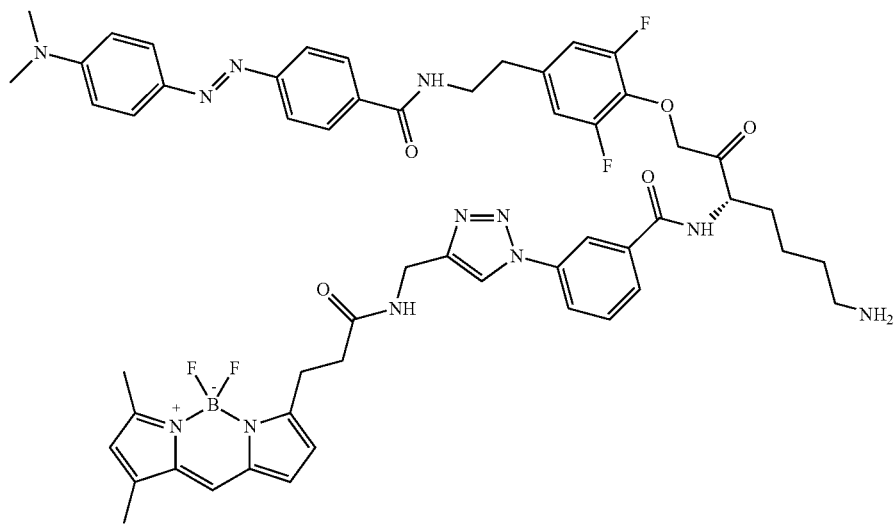

To a solution of compound 15 (120.00 mg, 105.17 μmol, 1.00 equivalent) in HCl/EtOAc (5.00 mL) was stirred at 25° C. for 0.1 hour. The residue was purified by prep-HPLC (column: Luna C18 100×30×5u; mobile phase: A: water (0.1% TFA), B: ACN; B %: 30%-60%, 10 min) to give Compound 45 (20.00 mg, 19.21 μmol, 18.27% yield) as a red solid. $^1$H NMR (400 MHz, DMSO-$d_6$) δ ppm 1.33-1.51 (m, 2H), 1.56 (dt, J=14.00, 7.06 Hz, 2H), 1.73 (br dd, J=9.29, 4.40 Hz, 1H), 1.90 (br d, J=6.24 Hz, 1H), 2.25 (s, 3H), 2.46 (s, 3H), 2.74-2.87 (m, 5H), 3.08 (s, 6H), 3.46-3.55 (m, 2H), 4.44 (br d, J=5.01 Hz, 2H), 4.64-4.73 (m, 1H), 5.01-5.18 (m, 2H), 6.30 (s, 1H), 6.36 (d, J=4.03 Hz, 1H), 6.86 (d, J=9.17 Hz, 2H), 7.01-7.11 (m, 3H), 7.62-7.76 (m, 4H), 7.78-7.87 (m, 4H), 7.92-8.11 (m, 4H), 8.40 (s, 1H), 8.57 (br t, J=5.50 Hz, 1H), 8.61-8.70 (m, 2H), 8.99 (br d, J=7.34 Hz, 1H).

Example 42. Preparation of a Fluorescent Gingipain Activity Probe with Cleavable Quencher: (S,E)-N-(7-amino-1-(4-(2-(4-((4-(dimethylamino) phenyl)diazenyl)benz-amido)ethyl)-2,6-difluorophenoxy)-2-oxoheptan-3-yl)-3-azidobenzamide (46)

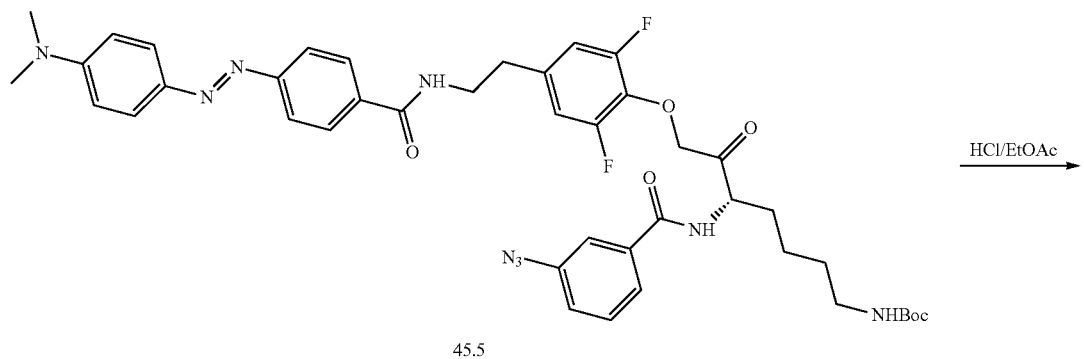

45.5

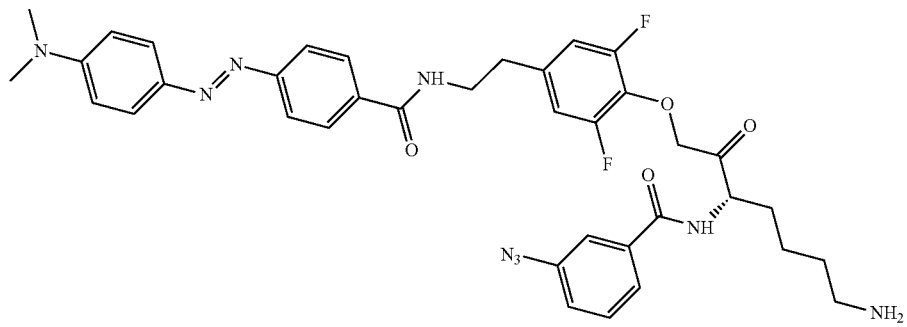

46

To a solution of 45.5 (150.00 mg, 188.01 μmol, 1.00 equivalent) in HCl/EtOAc (5.00 mL) was stirred at 25° C. for 0.2 hour. The residue was purified by prep-HPLC (column: Waters Xbridge Prep OBD C18 150×30×5 u; mobile phase: A: water (0.1% TFA), B: ACN; B %: 26%-66%, 12 min) to give Compound 46 (10.00 mg, 14.33 μmol, 7.62% yield) as a red solid; LCMS [M+H]: 712; RT=2.76 min. $^1$H NMR (400 MHz, METHANOL-$d_4$) δ ppm 1.52-1.60 (m, 2H), 1.67-1.85 (m, 4H), 2.09 (br s, 1H), 2.85-3.00 (m, 4H), 3.13 (s, 6H), 3.61 (br t, J=7.24 Hz, 2H), 4.52 (s, 1H), 4.92-5.04 (m, 2H), 6.87 (d, J=8.77 Hz, 2H), 6.95 (br d, J=9.21 Hz, 1H), 7.03 (br d, J=9.65 Hz, 1H), 7.27 (br d, J=7.89 Hz, 1H), 7.47-7.53 (m, 1H), 7.55 (br s, 1H), 7.65 (br d, J=7.02 Hz, 1H), 7.80-7.91 (m, 5H), 7.98 (d, J=8.77 Hz, 1H).

Example 43. Preparation of (S)—N-(7-amino-2-oxo-1-(2,3,6-trifluorophenoxy)heptan-3-yl)-2-methoxy-2-methylpropanamide (47)

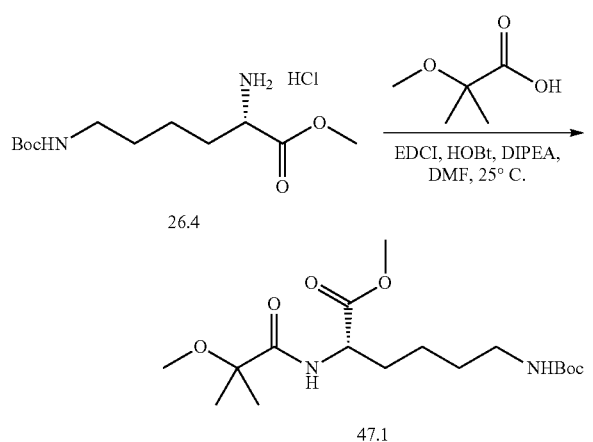

To a solution of 2-methoxy-2-methyl-propanoic acid (398.03 mg, 3.37 mmol, 1.00 equivalent) in DMF (15.00 mL) was added HOBt (500.89 mg, 3.71 mmol, 1.10 equivalent) and EDCI (710.63 mg, 3.71 mmol, 1.10 equivalent) the mixture was stirred at 25° C. for 1 hr. Then to the mixture was added DIPEA (1.74 g, 13.48 mmol, 2.35 mL, 4.00 equivalent) and 26.4 (1.00 g, 3.37 mmol, 1.00 equivalent, HCl). The mixture was stirred at 25° C. for 14 hours. The reaction mixture was diluted with H$_2$O (20 mL) and extracted with EtOAc (20 mL×3). The combined organic layers were washed with brine (20 mL), dried over Na$_2$SO$_4$, filtered and concentrated under reduced pressure to give a residue. The residue was purified by column chromatography (SiO$_2$, Petroleum ether/Ethyl acetate=2:1) to give 47.1 (1.00 g, 2.77 mmol, 82.33% yield) as yellow oil; LCMS [M+H]: 361; RT=0.780 min. $^1$H NMR (400 MHz, CHLOROFORM-d) δ ppm 1.20-1.58 (m, 17H), 1.60-1.75 (m, 1H), 1.81-1.94 (m, 1H), 3.09 (br d, J=6.17 Hz, 2H), 3.29 (s, 3H), 3.74 (s, 3H), 4.45-4.73 (m, 2H), 7.09 (br d, J=8.38 Hz, 1H).

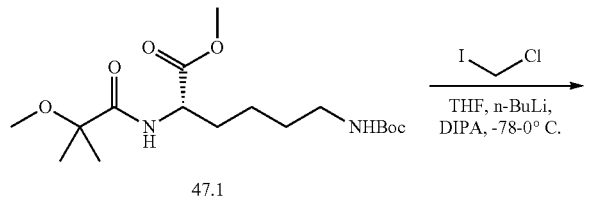

-continued

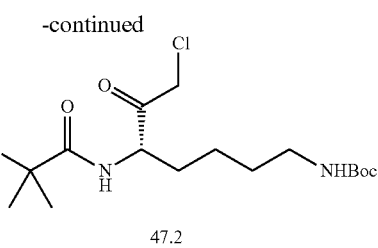

To a solution of DIPA (1.54 g, 15.24 mmol, 2.14 mL, 5.50 equivalent) in THF (10 mL) was added n-BuLi (2.5 M, 6.09 mL, 5.50 equivalent). The mixture was stirred at 0° C. for 0.5 hr under N$_2$. Then the mixture was added to the solution of compound 2 (1.00 g, 2.77 mmol, 1.00 equivalent) and chloro(iodo)methane (2.69 g, 15.24 mmol, 1.11 mL, 5.50 equivalent) in THF (10 mL) was stirred at −78° C. for 0.5 hr. The reaction mixture was diluted with H$_2$O (20 mL) and extracted with EtOAc (20 mL×3). The combined organic layers were washed with brine (20 mL), dried over Na$_2$SO$_4$, filtered and concentrated under reduced pressure to give a residue to give 47.2 (1.30 g, crude) as brown oil.

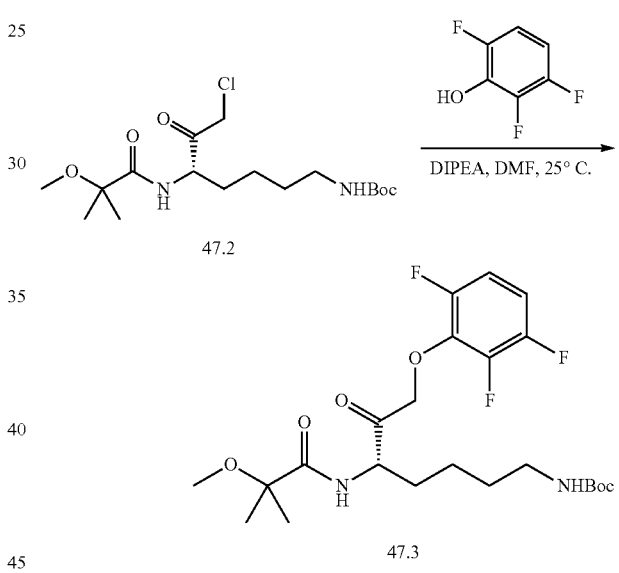

To a solution of 47.2 (650.00 mg, 1.72 mmol, 1.00 equivalent) in DMF (10.00 mL) was added DIPEA (666.88 mg, 5.16 mmol, 901.19 μL, 3.00 equivalent) and 2, 3, 6-trifluorophenol (280.17 mg, 1.89 mmol, 1.10 equivalent). The mixture was stirred at 25° C. for 15 hours. The residue was purified by prep-HPLC (TFA condition) to give 47.3 (50.00 mg, 128.07 μmol, 7.45% yield) as yellow oil; LCMS [M+H]: 391; RT=0.877 min.

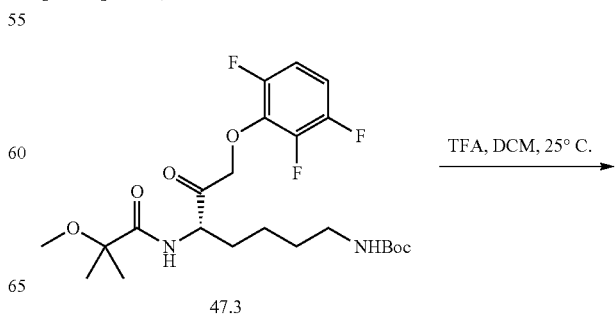

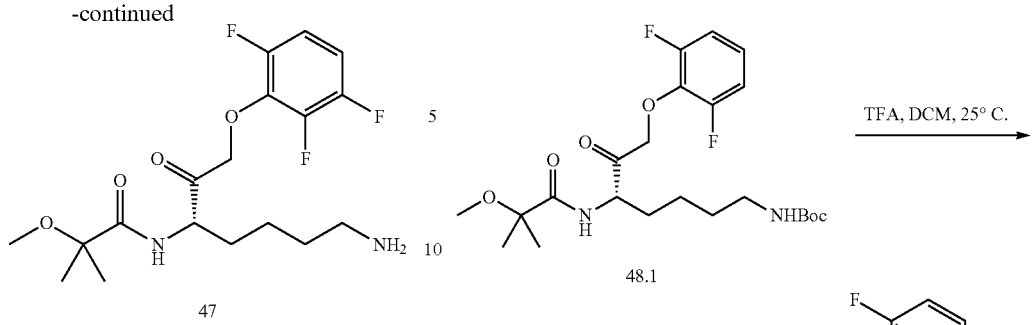

A mixture of 47.3 (50.00 mg, 101.93 μmol, 1.00 equivalent) in DCM (5.00 mL) and TFA (1.00 mL) was stirred at 25° C. for 15 hours. The mixture was concentrated under reduced pressure to give Compound 47 (30.00 mg, 76.84 μmol, 75.39% yield) as brown oil; LCMS [M+H]: 391; RT=0.681 min. $^1$H NMR (400 MHz, METHANOL-d$_4$) δ ppm 1.26-1.39 (m, 6H), 1.39-1.56 (m, 2H), 1.57-1.84 (m, 3H), 1.96-2.12 (m, 1H), 2.82-3.01 (m, 2H), 3.27-3.31 (m, 3H), 4.68 (dd, J=9.60, 4.34 Hz, 1H), 4.95-5.15 (m, 1H), 6.89-7.12 (m, 2H).

Example 44. Preparation of (S)—N-(7-amino-1-(2, 6-difluorophenoxy)-2-oxoheptan-3-yl)-2-methoxy-2-methylpropanamide (48)

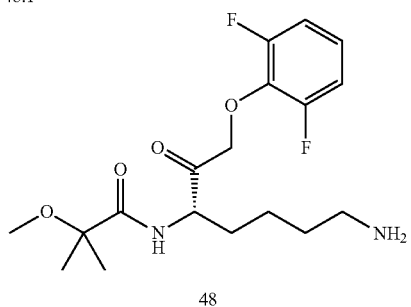

To a solution of 47.2 (650.00 mg, 1.72 mmol, 1.00 equivalent) in DMF (10.00 mL) was added DIPEA (666.88 mg, 5.16 mmol, 901.19 μL, 3.00 equivalent) and 2, 6-difluorophenol (246.13 mg, 1.89 mmol, 1.10 equivalent). The mixture was stirred at 25° C. for 14 hours. The residue was purified by prep-HPLC (TFA condition) to give 48.1 (50.00 mg, 134.26 μmol, 7.81% yield) as yellow oil; LCMS [M+H]: 473; RT=0.864 min.

48.1 (50.00 mg, 105.82 μmol, 1.00 equivalent) in DCM (5.00 mL) and TFA (1.00 mL) was stirred at 25° C. for 15 hours. The mixture was concentrated under reduced pressure to give Compound 48 (30.00 mg, 80.56 μmol, 76.13% yield); LCMS [M+H]: 373; RT=0.671 min. $^1$H NMR (400 MHz, METHANOL-d$_4$) δ ppm 1.18-1.39 (m, 6H), 1.41-1.56 (m, 2H), 1.57-1.82 (m, 3H), 1.88-2.15 (m, 1H), 2.78-3.03 (m, 2H), 3.25-3.31 (m, 3H), 4.74 (dd, J=9.54, 4.28 Hz, 1H), 4.90-5.03 (m, 2H), 6.89-7.20 (m, 3H).

Example 45. Preparation of (S)—N-(7-amino-1-(isoxazol-3-yloxy)-2-oxoheptan-3-yl)cyclopentanecarboxamide (49)

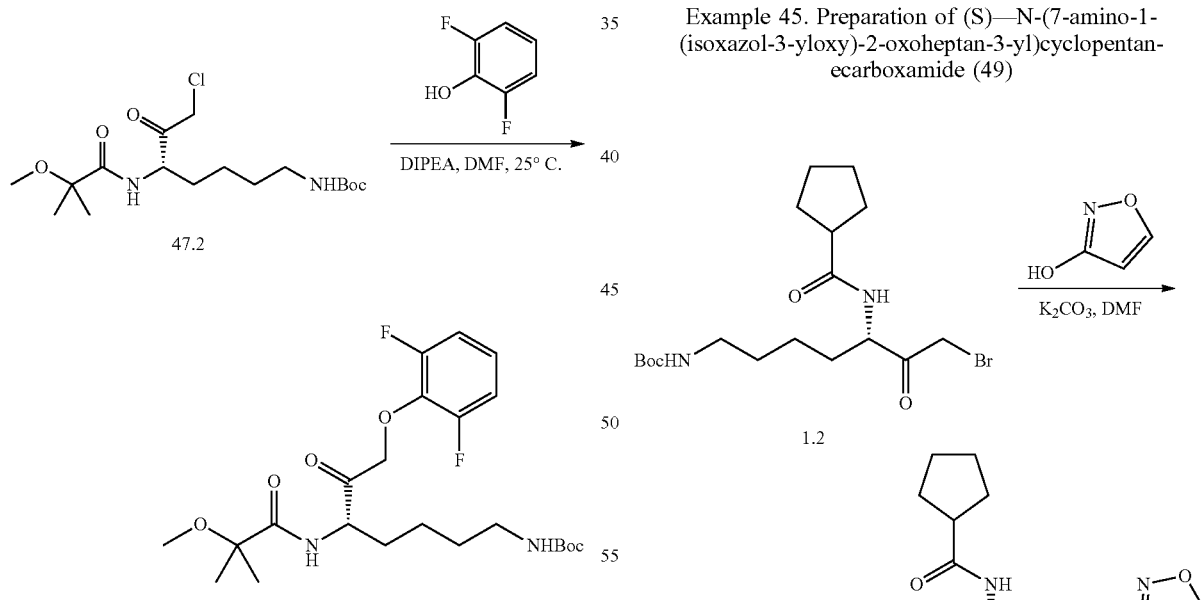

To a solution of 1.2 (0.3 g, 715.39 μmol, 1 equivalent) in DMF (5 mL) was added K$_2$CO$_3$ (296.62 mg, 2.15 mmol, 3 equivalent) and the isoxazole (66.94 mg, 786.92 μmol, 1.1 equivalent). The mixture was stirred at 25° C. for 15 hrs. The reaction mixture was quenched by addition H$_2$O (10 mL) at 25° C. and extracted with Ethyl acetate (15 mL×3). The combined organic layers were washed with brine (10 mL), dried over anhydrous sodium sulfate, filtered and concentrated under reduced pressure to give a crude product. The residue was purified by column chromatography (SiO$_2$, Petroleum ether/Ethyl acetate=2:1) to give 49.1 (100 mg, 236.13 μmol, 33.01% yield) as a yellow solid; LCMS [M+H+Na]: 446; RT=1.443 min.

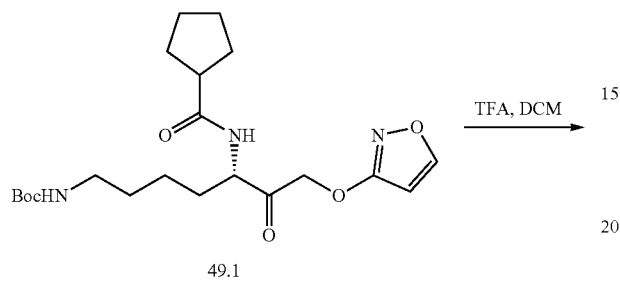

To a solution of 49.1 (0.1 g) in DCM (5 mL) was added TFA (1 mL) The mixture was stirred at 25° C. for 14 hrs. The mixture was concentrated under reduced pressure to give a residue. The residue was purified by prep-HPLC (TFA condition) to give Compound 49 (20 mg, 61.85 μmol, 26.19% yield) as yellow oil; LCMS [M+H]: 324; RT=2.072 min. $^1$H NMR (400 MHz, METHANOL-d$_4$) δ ppm 1.37-1.55 (m, 2H), 1.57-1.80 (m, 10H) 1.89, (br dd, J=12.68, 5.62 Hz, 3H), 2.73 (quin, J=7.77 Hz, 1H), 2.93 (br t, J=6.84 Hz, 2H), 4.52 (dd, J=9.04, 5.07 Hz, 1H), 4.96-5.17 (m, 2H), 6.17 (d, J=1.54 Hz, 1H), 8.38 (d, J=1.54 Hz, 1H).

Example 46. Preparation of (S)—N-(7-amino-2-oxo-1-(2,3,6-trifluorophenoxy)heptan-3-yl)picolinamide (50)

50.1 was prepared in the same fashion as 34.2, but with pyridine-2-carboxylic acid replacing 2-bromonicotinic acid.

To 50.1 (600.00 mg, 1.56 mmol, 1.00 equivalent) in DMF (5.00 mL) was added DIPEA (606.02 mg, 4.69 mmol, 818.94 μL, 3.00 equivalent) and 2, 3, 6-trifluorophenol (231.45 mg, 1.56 mmol, 1.00 equivalent). The mixture was stirred at 25° C. for 15 hours. The residue was purified by prep-HPLC (TFA condition) to give compound 50.2 (50.00 mg, 100.91 μmol, 6.47% yield) as yellow oil; LCMS [M+H]: 496; RT=1.302 min.

This reaction was run in the same fashion as Compound 34. The product obtained was purified by prep-HPLC (TFA condition) to give Compound 50 (10 mg); LCMS [M+H]: 396; RT=2.187 min. $^1$H NMR (400 MHz, METHANOL-d$_4$) δ ppm 1.43-1.62 (m, 2H), 1.62-1.93 (m, 3H), 2.06-2.24 (m, 1H), 2.93 (br t, J=7.28 Hz, 2H), 4.97 (br dd, J=9.48, 4.19 Hz, 1H), 5.03-5.21 (m, 2H), 6.91-7.07 (m, 2H), 7.60 (dd, J=6.95, 5.40 Hz, 1H), 8.00 (td, J=7.66, 1.65 Hz, 1H), 8.12 (d, J=7.72 Hz, 1H), 8.60-8.74 (m, 1H).

Example 47. Preparation of a biotinylated gingipain activity probe: N—((S)-7-amino-1-(2,6-difluorophenoxy)-2-oxoheptan-3-yl)-3-(4-((5-((3aS,4S,6aR)-2-oxohexahydro-1H-thieno[3,4-d]imidazol-4-yl)pentanamido)methyl)-1H-1,2,3-triazol-1-yl)benzamide (51)

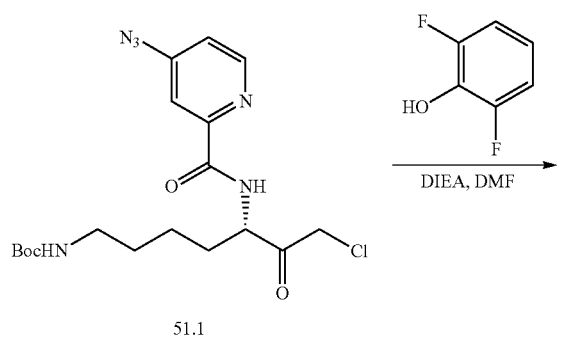

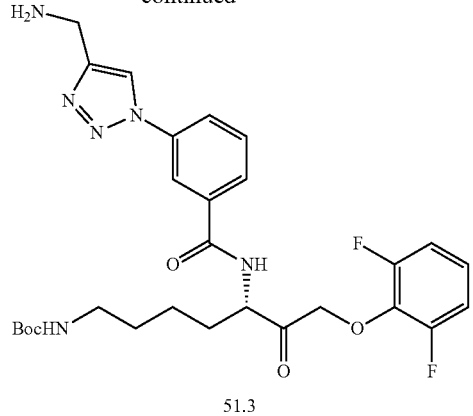

To 51.2 (140.00 mg, 270.52 μmol, 1.00 equivalent) and the aminopropyne (14.90 mg, 270.52 μmol, 17.33 μL, 1.00 equivalent) in DMSO (3.00 mL) was added the solution of CuSO4 (8.64 mg, 54.10 μmol, 8.31 μL, 0.20 equivalent) in H₂O (100.00 μL). The mixture was stirred at 18° C. for 5 mins. The reaction mixture was diluted with H₂O 10 mL and extracted with EtOAc (10 mL×3). The combined organic layers were washed with brine (30 mL), dried over Na₂SO₄, filtered and concentrated under reduced pressure to give 51.3 (150.00 mg, crude) as a red solid.

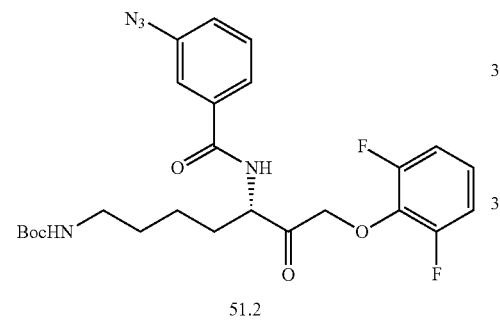

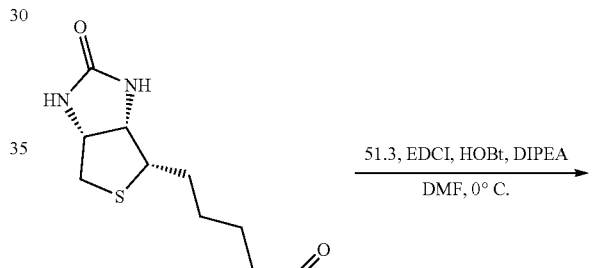

To 51.1 (2.00 g, 4.72 mmol, 1.00 equivalent) and the phenol (613.79 mg, 4.72 mmol, 1.00 equivalent) in DMF (10.00 mL) was added DIPEA (2.44 g, 18.87 mmol, 3.30 mL, 4.00 equivalent) in one portion at 20 C under N₂. The mixture was stirred at 20° C. for 10 hours. The reaction mixture was diluted with H₂O 10 mL and extracted with EtOAc (10 mL×3). The combined organic layers were washed with brine (30 mL), dried over Na₂SO₄, filtered and concentrated under reduced pressure to give a residue. The residue was purified by column chromatography (SiO₂, Petroleum ether/Ethyl acetate=1:1) to give 51.2 (160.00 mg, 309.17 μmol, 6.55% yield) as yellow oil; LCMS [M+H]: 518; RT=0.909 min.

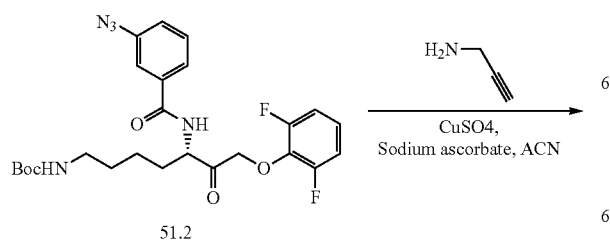

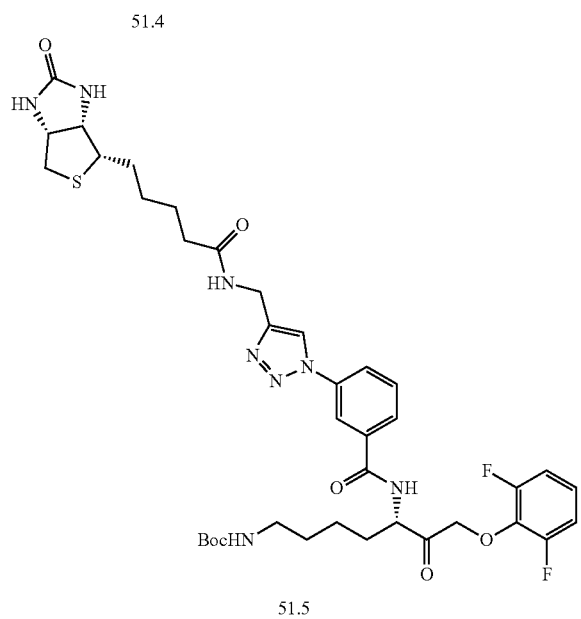

To a mixture of 51.4 (64.00 mg, 261.96 μmol, 1.00 equivalent) and HOBt (38.94 mg, 288.16 μmol, 1.10 equivalent) in DMF (2.00 mL) was added EDCI (55.24 mg, 288.16 μmol, 1.10 equivalent) in one portion at 0° C. under N₂. The mixture was stirred at 0° C. for 1 hour, then the mixture was added 51.3 (150.00 mg, 261.96 μmol, 1.00 equivalent) and DIPEA (101.57 mg, 785.88 μmol, 137.26 μL, 3.00 equivalent) in one portion at 0° C., and the mixture was stirred at 0° C. for 1 hour. The reaction mixture was diluted with H₂O 10 mL and extracted with EtOAc (10 mL×3). The combined organic layers were washed with brine (30 mL), dried over Na₂SO₄, filtered and concentrated under reduced pressure to give 51.5 (200.00 mg, 250.34 μmol, 95.57% yield) as a yellow solid; LCMS [M+H]: 799; RT=1.373 min.

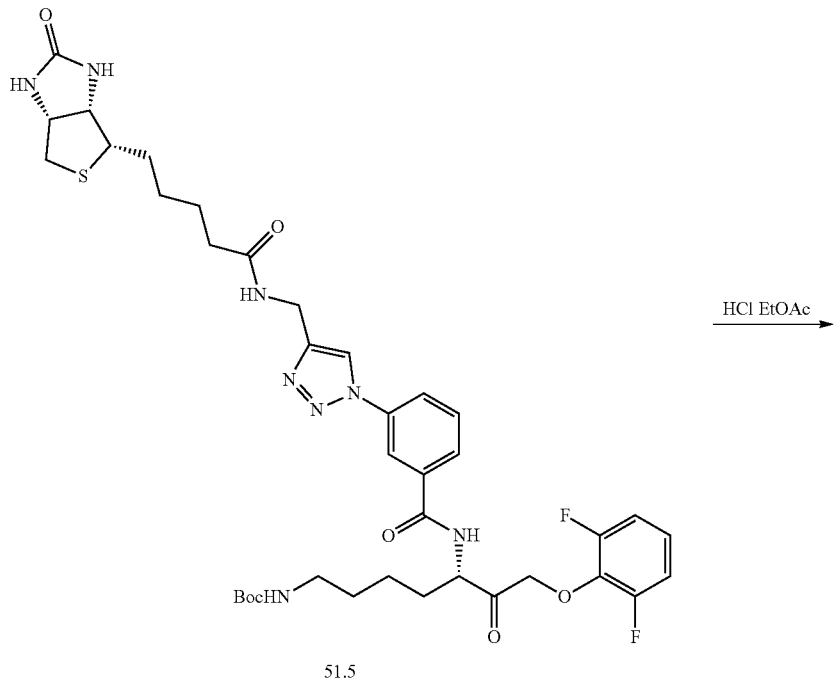

51.5

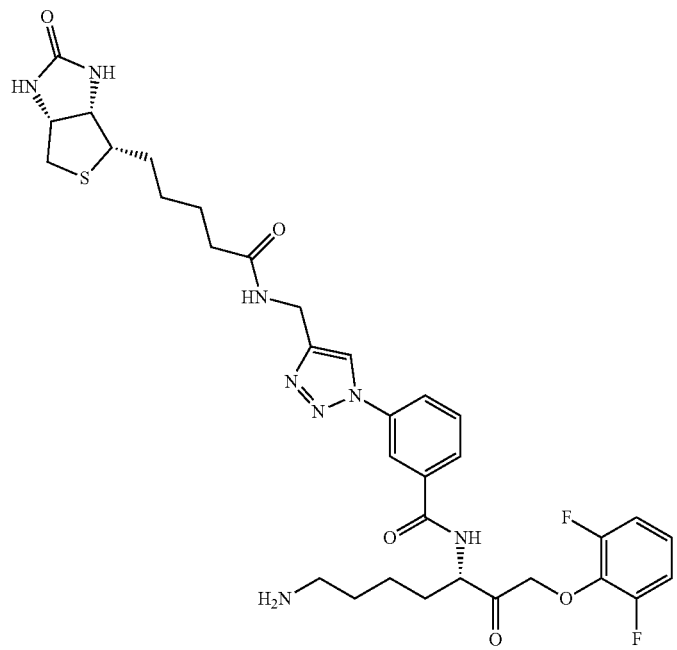

51

51.5 (200 mg) was dissolved into HCl/EtOAc (5 mL), and the mixture was stirred at 18° C. for 1 min. The reaction mixture was concentrated under reduced pressure to give a residue. The residue was purified by prep-HPLC (TFA condition) to give Compound 51 (40 mg) as a white solid; LCMS [M+H]: 699; RT=2.391 min. $^1$H NMR (400 MHz, METHANOL-d$_4$) δ ppm 1.34-1.46 (m, 2H), 1.48-1.63 (m, 3H), 1.64-1.77 (m, 4H), 1.77-1.91 (m, 2H), 2.08-2.20 (m, 1H), 2.27 (t, J=7.17 Hz, 2H), 2.62 (d, J=12.79 Hz, 1H), 2.80-2.89 (m, 1H), 2.95 (br t, J=6.50 Hz, 2H), 3.11-3.19 (m, 1H), 4.24 (dd, J=7.94, 4.41 Hz, 1H), 4.43 (dd, J=7.50, 4.63 Hz, 1H), 4.53 (s, 2H), 4.98 (br d, J=3.75 Hz, 1H), 5.00-5.10 (m, 2H), 6.96-7.05 (m, 2H), 7.06-7.13 (m, 1H), 7.68-7.74 (m, 1H), 7.95-8.00 (m, 1H), 8.02-8.08 (m, 1H), 8.35 (t, J=1.76 Hz, 1H), 8.46 (s, 1H).

Example 48. Preparation of (S)—N-(7-amino-2-oxo-1-(2,3,6-trifluorophenoxy)heptan-3-yl)isonicotinamide (52)

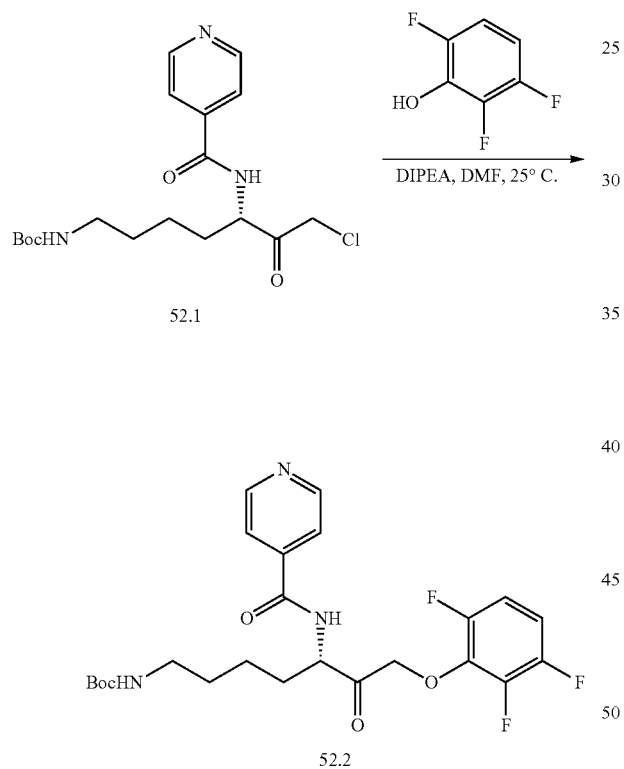

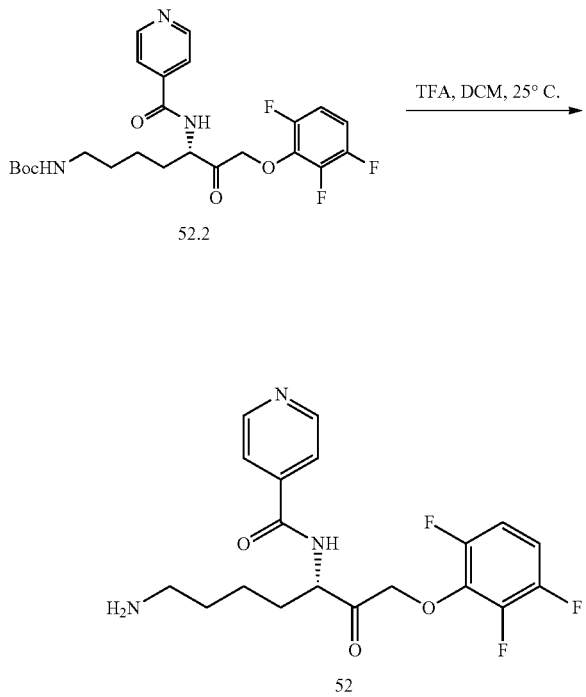

52.1 was prepared in the same fashion as 34.2, but with pyridine-4-carboxylic acid replacing 2-bromonicotinic acid.

To 52.1 (783.60 mg, 2.04 mmol, 1.00 equivalent) in DMF (10.00 mL) was added DIPEA (791.46 mg, 6.12 mmol, 1.07 mL, 3.00 equivalent) and the trifluorophenol (302.28 mg, 2.04 mmol, 1.00 equivalent). The mixture was stirred at 25° C. for 15 hours. The reaction mixture was diluted with H$_2$O (10 mL) and extracted with EtOAc (10 mL×3). The combined organic layers were washed with brine (30 mL), dried over Na$_2$SO$_4$, filtered and concentrated under reduced pressure. The residue was purified by column chromatography (SiO$_2$, Petroleum ether/Ethyl acetate=10/1 to 1/1) to give 52.2 (50.00 mg); LCMS [M+H]: 496; RT=0.777 min.

To 52.2 (10.00 mg, 20.18 μmol, 1.00 equivalent) in DCM (500.00 μL) was added TFA (154.00 mg, 1.35 mmol, 100.00 μL, 66.93 equivalent). The mixture was stirred at 25° C. for 15 hours. The reaction mixture was concentrated under reduced pressure to give Compound 52 (7.50 mg, 18.97 μmol); LCMS [M+H]: 397; RT=2.128 min. $^1$H NMR (400 MHz, METHANOL-d$_4$) δ ppm 1.49-1.66 (m, 2H), 1.67-1.92 (m, 3H), 2.04-2.21 (m, 1H), 2.94 (br t, J=7.61 Hz, 2H), 4.95 (dd, J=9.70, 4.41 Hz, 1H), 5.05-5.18 (m, 2H), 6.88-7.13 (m, 2H), 7.86-8.00 (m, 2H), 8.79 (br d, J=4.19 Hz, 2H).

Example 49. Preparation of (S)—N-(7-amino-2-oxo-1-(2H-tetrazol-2-yl)heptan-3-yl)-6-fluoronicotinamide (53)

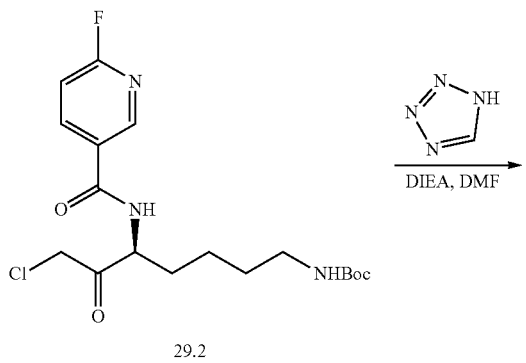

-continued

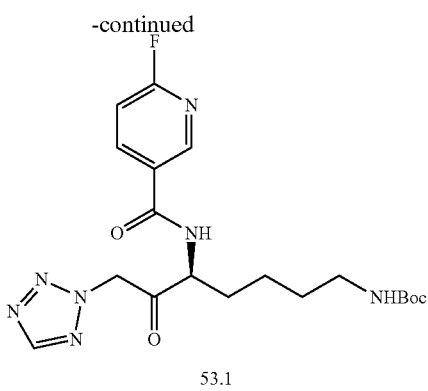

53.1

To 29.2 (1.70 g, 4.23 mmol, 1.00 equivalent) in DMF (10.00 mL) was added tetrazole (0.45 M, 10.34 mL, 1.10 equivalent) and DIPEA (2.19 g, 16.92 mmol, 2.96 mL, 4.00 equivalent). The mixture was stirred at 10° C. for 12 hours. The reaction mixture was diluted with H₂O (10 mL) and extracted with EtOAc (10 mL×3). The combined organic layers were washed with brine (30 mL), dried over Na₂SO₄, filtered and concentrated under reduced pressure. The residue was purified by prep-HPLC (column: Luna C18 100× 30×5 u; mobile phase: A: water (0.1% TFA) and B: ACN; B %: 20%-60%, 10 min) to give 53.1 (10.00 mg).

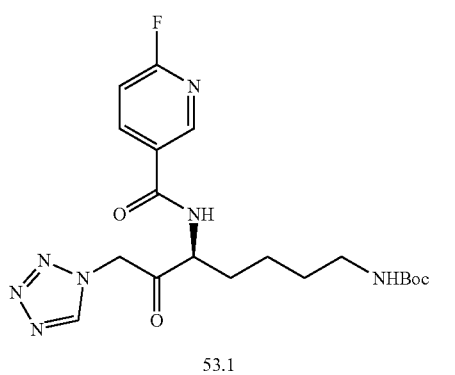

53.1

TFA, DCM →

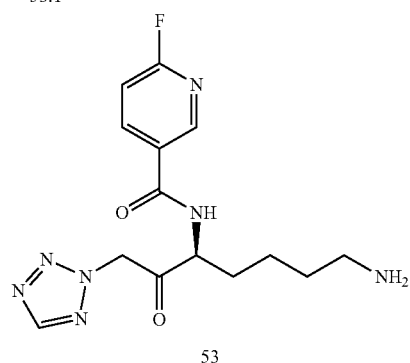

53

To 53.1 (10.00 mg) in DCM (2.50 mL) was added TFA (0.5 mL). The mixture was stirred at 10° C. for 12 hours. The reaction mixture concentrated under reduced pressure to give Compound 53 (2.00 mg, 5.96 µmol); LCMS [M+H]: 336; RT=0.593 min. ¹H NMR (400 MHz, METHANOL-d₄) δ ppm 1.49-1.66 (m, 2H), 1.67-1.80 (m, 2H), 1.83-1.93 (m, 1H), 2.06-2.16 (m, 1H), 2.89-3.00 (m, 2H), 4.79 (br s, 1H), 5.87-6.01 (m, 2H), 7.15-7.24 (m, 1H), 8.35-8.46 (m, 1H), 8.68-8.79 (m, 2H).

Example 50. Preparation of (S)—N-(7-amino-2-oxo-1-(2H-tetrazol-2-yl)heptan-3-yl)-2-fluoronicotinamide (54)

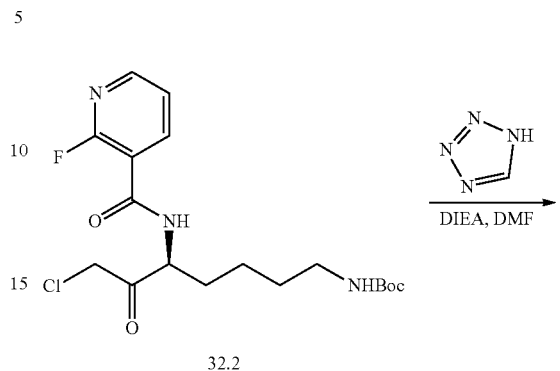

32.2

DIEA, DMF →

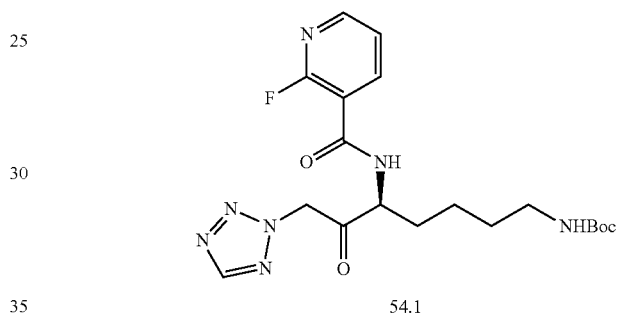

54.1

To 32.2 (1.70 g, 4.23 mmol, 1.00 equivalent) in DMF (10.00 mL) was added tetrazole (0.45 M, 10.34 mL, 1.10 equivalent) and DIPEA (2.19 g, 16.92 mmol, 2.96 mL, 4.00 equivalent). The mixture was stirred at 10° C. for 12 hours. The reaction mixture was diluted with H₂O (10 mL) and extracted with EtOAc (10 mL×3). The combined organic layers were washed with brine (30 mL), dried over Na₂SO₄, filtered and concentrated under reduced pressure. The residue was purified by prep-HPLC (column: Luna C18 100× 30×5 u; mobile phase: A: water (0.1% TFA), B: ACN; B %: 20%-60%, 10 min) to give 54.1 (5.00 mg).

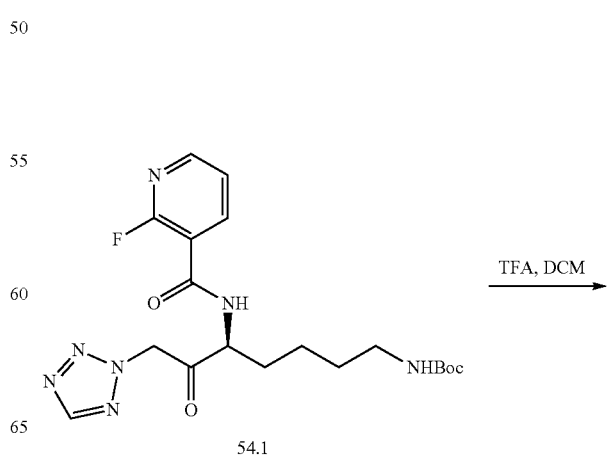

54.1

TFA, DCM →

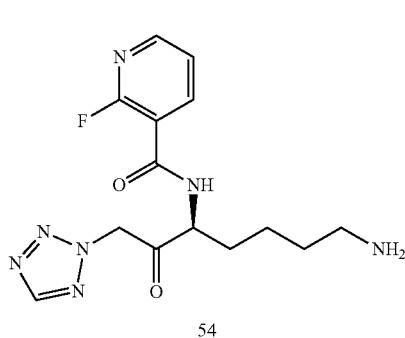

54

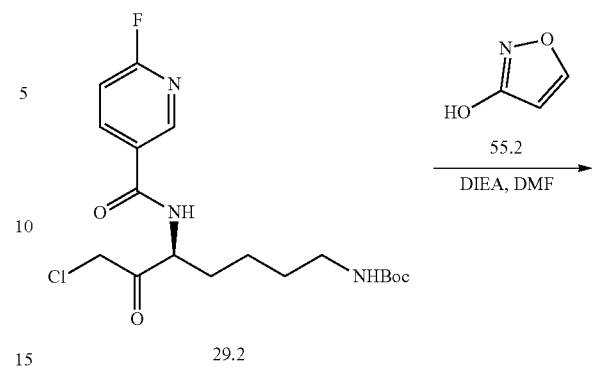

To 54.1 (5.00 mg) in DCM (2.50 mL) was added TFA (0.5 mL). The mixture was stirred at 10° C. for 12 hours. The reaction mixture concentrated under reduced pressure to give to Compound 54 (2.00 mg); LCMS [M+H]: 336; RT=3.720 min. $^1$H NMR (400 MHz, METHANOL-d4) δ ppm 1.51-1.66 (m, 2H), 1.70-1.79 (m, 2H), 1.81-1.91 (m, 1H), 2.03-2.19 (m, 1H), 2.96 (br t, J=7.61 Hz, 2H), 3.77 (s, 1H), 4.84 (br d, J=4.85 Hz, 1H), 5.96 (d, J=2.65 Hz, 2H), 7.46 (ddd, J=7.22, 5.13, 1.76 Hz, 1H), 8.25-8.41 (m, 2H), 8.68-8.80 (m, 1H).

Example 51. Preparation of (S)—N-(7-amino-1-(isoxazol-3-yloxy)-2-oxoheptan-3-yl)-6-fluoronicotinamide (55)

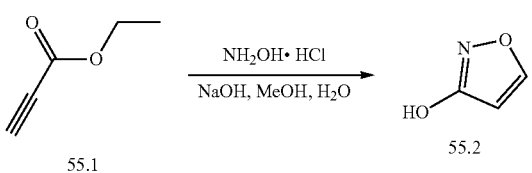

A mixture 55.1 (10.00 g, 101.94 mmol, 10.00 mL, 1.00 equivalent), hydroxylamine hydrochloride (9.21 g, 132.52 mmol, 1.30 equivalent), NaOH (15.25 g, 381.26 mmol, 3.74 equivalent) in H$_2$O (150.00 mL) and MeOH (170.00 mL) was stirred at 25° C. for 100 hours. The mixture was acidified to pH 2 with concentrated hydrochloric acid and then saturated with sodium chloride. The solution was extracted with DCM (8×150 ml), the extracts combined, dried and the solvent evaporated. The solid residue was washed with hot iso-hexane (3×100 ml) and the final suspension was allowed to cool and the resulting solid was collected by filtration, dried under vacuum to give 55.2 (4.00 g, 47.03 mmol, 46.13% yield) as a yellow solid. $^1$H NMR (400 MHz, CHLOROFORM-d) δ ppm 6.04 (d, J=1.76 Hz, 1H), 8.10 (d, J=1.76 Hz, 1H), 11.11 (br s, 1H).

To 29.2 (200.00 mg, 497.69 μmol, 1.00 equivalent) in DMF (3.00 mL) was added K$_2$CO$_3$ (206.36 mg, 1.49 mmol, 3.00 equivalent) and 55.2 (55.03 mg, 647.00 μmol, 1.30 equivalent). The mixture was stirred at 25° C. for 15 hours. The reaction mixture was diluted with H$_2$O (10 mL) and extracted with EtOAc (10 mL×3). The combined organic layers were washed with brine (30 mL), dried over Na$_2$SO$_4$, filtered and concentrated under reduced pressure. The residue was purified by column chromatography (SiO$_2$, Petroleum ether/Ethyl acetate=2:1) to give 55.3 (0.1 g, 222.00 μmol, 44.61% yield) as yellow oil; LCMS [M+H]: 451; RT=1.145 min.

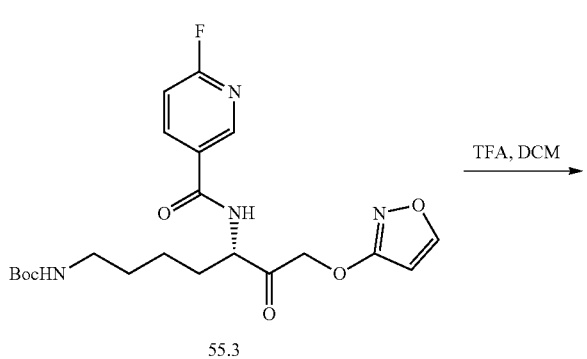

-continued

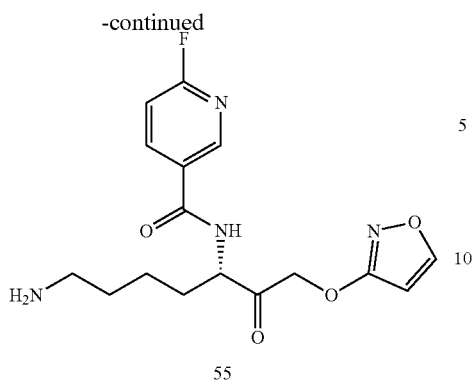

55

To a solution of 55.3 (0.1 g) in DCM (5 mL) was added TFA (1 mL). The mixture was stirred at 25° C. for 15 hours. The mixture was concentrated under reduced pressure to give a residue. The residue was purified by prep-HPLC (TFA condition) to give Compound 55 (20 mg); LCMS [M+H]: 351; RT=0.850 min. ¹H NMR (400 MHz, METHANOL-d₄) δ ppm 1.44-1.66 (m, 2H), 1.67-1.90 (m, 3H), 2.00-2.18 (m, 1H), 2.82-3.09 (m, 2H), 4.79 (dd, J=9.26, 4.85 Hz, 1H), 5.06-5.22 (m, 2H), 6.18 (d, J=1.10 Hz, 1H), 7.07-7.27 (m, 1H), 8.30-8.47 (m, 2H), 8.72 (d, J=1.98 Hz, 1H).

Example 52. Preparation of (S)—N-(7-amino-1-(isoxazol-3-yloxy)-2-oxoheptan-3-yl)-2-fluoronicotinamide (56)

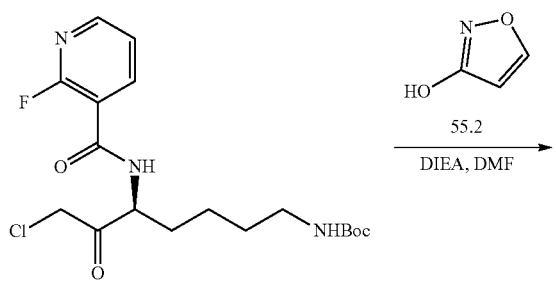

32.2

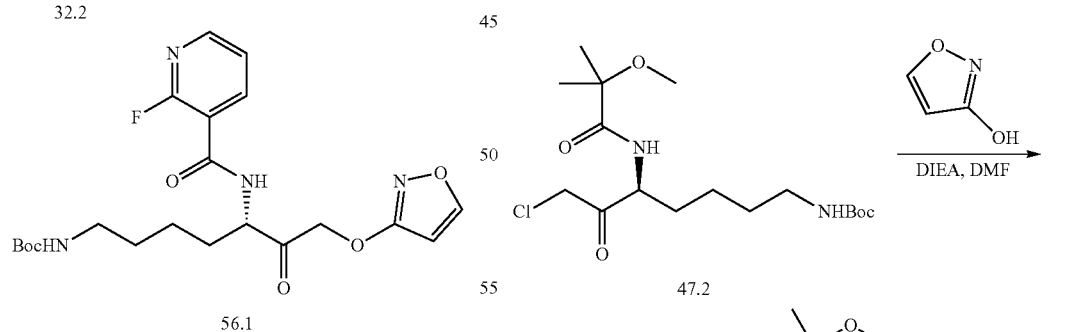

56.1

To 32.2 (1.40 g, 3.48 mmol, 1.00 equivalent) in DMF (15.00 mL) was added K₂CO₃ (1.44 g, 10.44 mmol, 3.00 equivalent) and isoxazol-3-ol (55.2, 296.01 mg, 3.48 mmol, 1.00 equivalent). The mixture was stirred at 25° C. for 15 hours. The reaction mixture was diluted with H₂O (10 mL) and extracted with EtOAc (10 mL×3). The combined organic layers were washed with brine (30 mL), dried over Na₂SO₄, filtered and concentrated under reduced pressure. The residue was purified by column chromatography (SiO₂, Petroleum ether/Ethyl acetate=2:1) to give 56.1 (300 mg); LCMS [M+H]: 453; RT=1.379 min.

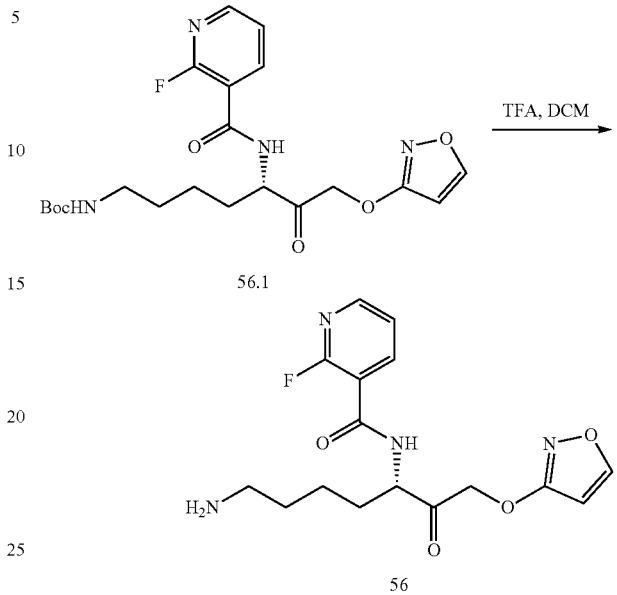

To 56.1 (0.3 g) in DCM (5 mL) was added TFA (1 mL). The mixture was stirred at 25° C. for 15 hours. The mixture was concentrated under reduced pressure to give a residue. The residue was purified by prep-HPLC (TFA condition) to give Compound 56 (20 mg); LCMS [M+H]: 351; RT=0.730 min. ¹H NMR (400 MHz, METHANOL-d₄) δ ppm 1.45-1.64 (m, 2H), 1.65-1.89 (m, 3H), 1.96-2.18 (m, 1H), 2.95 (br t, J=7.50 Hz, 2H), 4.81 (br dd, J=9.15, 4.74 Hz, 1H), 5.16 (s, 2H), 6.19 (s, 1H), 7.46 (br t, J=6.06 Hz, 1H), 8.14-8.50 (m, 3H).

Example 53. Preparation of (S)—N-(7-amino-1-(isoxazol-3-yloxy)-2-oxoheptan-3-yl)-2-methoxy-2-methylpropanamide (57)

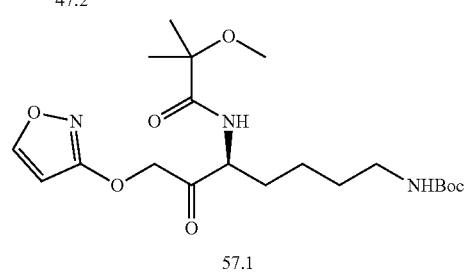

57.1

To a solution of 47.2 (893 mg, 2.36 mmol, 1 equivalent) and isoxazol-3-ol (200.48 mg, 2.36 mmol, 1 equivalent) in DMF (8 mL) was added DIPEA (913.83 mg, 7.07 mmol, 1.23 mL, 3 equivalent). The mixture was stirred at 25° C. for 10 hr. The reaction mixture was diluted with H$_2$O (10 mL) and extracted with EtOAc (10 mL×3). The combined organic layers were washed with brine (30 mL), dried over Na$_2$SO$_4$, filtered and concentrated under reduced pressure. The residue was purified by column chromatography (SiO$_2$, Petroleum ether/Ethyl acetate=10/1 to 1/1) to give 57.1 (130 mg); LCMS [M+H]: 428; RT=0.649 min.

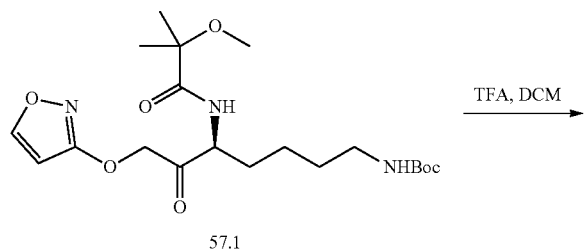

57.1

TFA, DCM

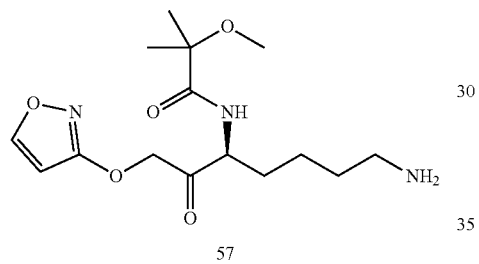

57

To a 57.1 (50 mg) in DCM (5 mL) was added TFA (1 mL). The mixture was stirred at 25° C. for 10 hours. The residue was purified by prep-HPLC (TFA condition) to give Compound 57 (10 mg); LCMS [M+H]: 328; RT=2.430 min. $^1$H NMR (400 MHz, METHANOL-d$_4$) δ ppm 1.38 (s, 7H), 1.45 (br d, J=6.84 Hz, 2H), 1.58-1.80 (m, 4H), 2.01 (br s, 1H), 2.92 (br d, J=7.28 Hz, 2H), 3.31-3.33 (m, 3H), 4.53-4.62 (m, 1H), 4.99-5.14 (m, 2H), 6.17 (s, 1H), 8.38 (s, 1H).

Example 54. Preparation of (S)—N-(7-amino-1-(dimethyl(oxo)-λ6-sulfanylidene)-2-oxoheptan-3-yl)cyclopentanecarboxamide (58)

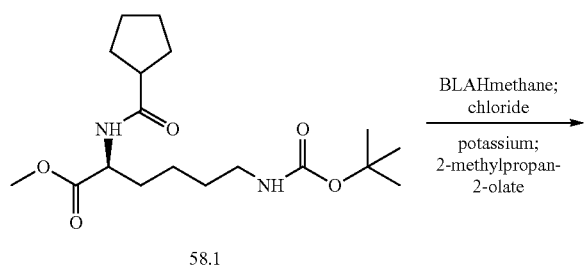

58.1

BLAHmethane; chloride potassium; 2-methylpropan-2-olate

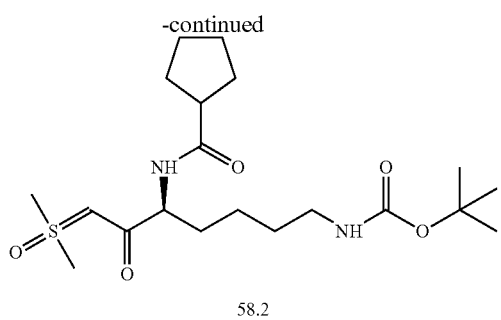

58.2

Potassium 2-methylpropan-2-olate (1 M, 5.87 mL, 2.99 equivalent) was added drop wise into a toluene (17 mL) suspension of BLAHmethane chloride (896.67 mg, 6.97 mmol, 3.55 equivalent) at 25° C. The mixture was heated to 70° C. for 4 hours and then was cooled to 0° C. A THF (15 mL) suspension of 58.1 (0.7 g, 1.96 mmol, 1 equivalent) was added dropwise at 0° C., and the resultant solution was stirred for 16 hours at 0° C. The solution was washed by MTBE for three times. The filter cake was concentrated under reduced pressure to give 58.2 (630 mg, 1.51 mmol, 38.51% yield) as a white solid; LCMS [M+H]: 417; RT=0.910 min.

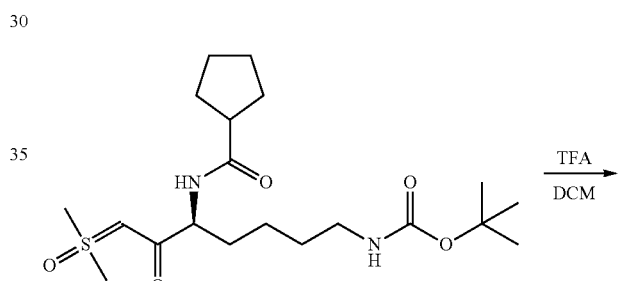

58.2

TFA / DCM

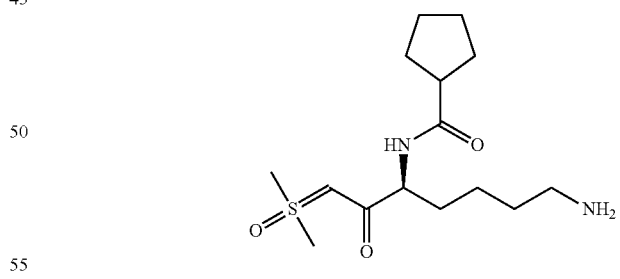

58

To a solution 58.2 (50 mg) in DCM (2 mL) was added TFA (0.4 mL) in one portion at 18° C. under N$_2$. The mixture was stirred at 18° C. for 30 mins. The reaction mixture was concentrated under reduced pressure to give Compound 58 (50 mg) as a yellow oil; LCMS [M+H]: 317; RT=1.782 min. $^1$H NMR (400 MHz, ACETONITRILE-d$_3$) δ ppm 1.39-1.51 (m, 2H), 1.56 (br d, J=6.60 Hz, 2H), 1.67 (br d, J=4.77 Hz, 6H), 1.75-1.89 (m, 4H), 2.70 (dt, J=15.68, 7.75 Hz, 1H), 2.94 (br s, 2H), 3.63 (s, 8H), 4.17-4.26 (m, 1H).

Example 55. Preparation of N—((S)-7-amino-1-(2,6-difluorophenoxy)-2-oxoheptan-3-yl)-3-(4-(15-oxo-19-((3aS,4S,6aR)-2-oxohexahydro-1H-thieno[3,4-d]imidazol-4-yl)-2,5,8,11-tetraoxa-14-azanonadecyl)-1H-1,2,3-triazol-1-yl)benzamide (59)

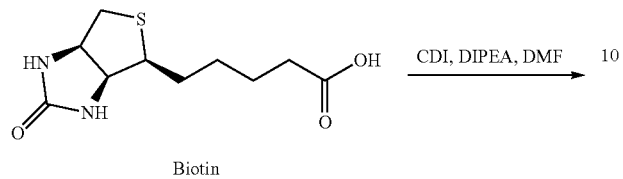

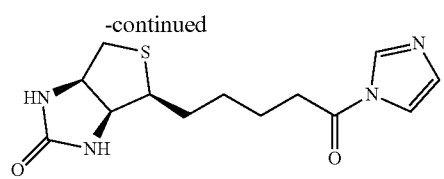

A mixture Biotin (159.29 mg, 982.36 μmol, 1.2 equivalent) in DMF (2 mL) was stirred at 25° C. for 12 hours. The mixture was filtered and concentrated under reduced pressure to give 59.1 (200 mg, crude) as a white solid; LCMS [M+H]: 295; RT=0.298 min.

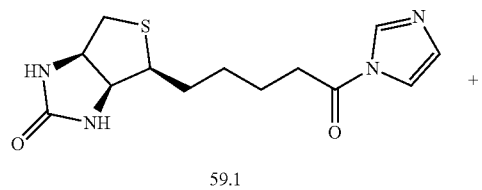

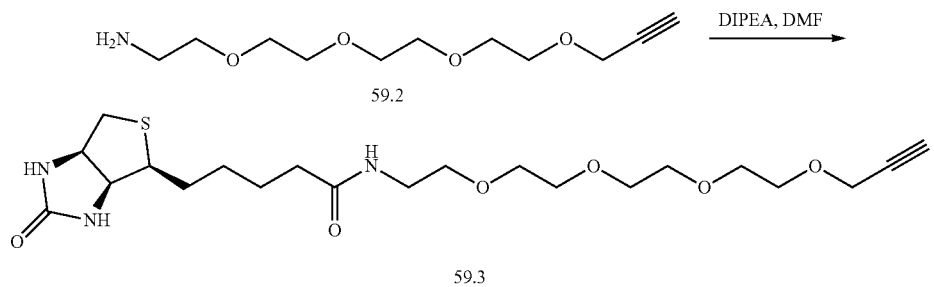

A mixture of 59.1 (127.28 mg, 432.36 μmol, 1 equivalent), 59.2 (100 mg, 432.36 μmol, 1 equivalent), DIPEA (167.64 mg, 1.30 mmol, 225.93 μL, 3 equivalent) in DMF (3 mL) was stirred at 25° C. for 12 hours. The residue was purified by prep-HPLC (TFA condition) to give 59.3 (100 mg, 218.54 μmol, 50.55% yield) as a white solid; LCMS [M+H]: 458; RT=1.052 min.

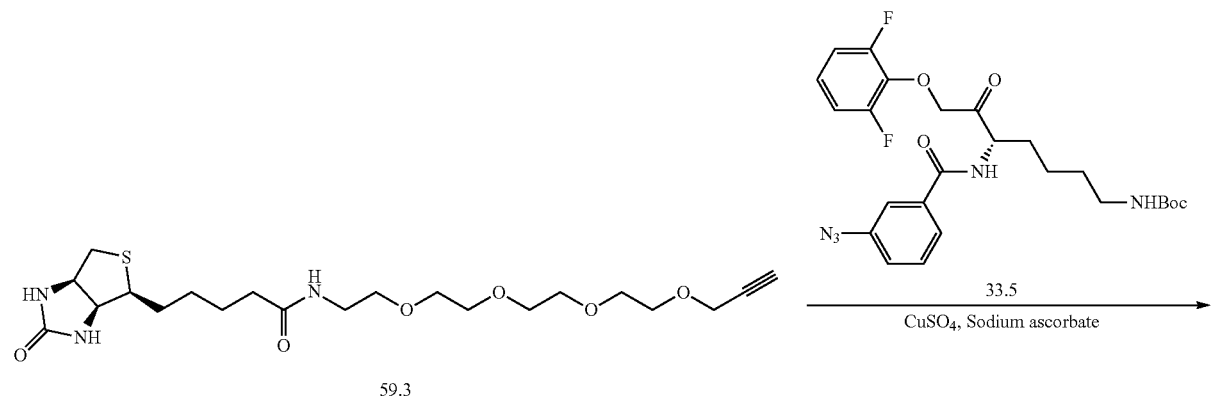

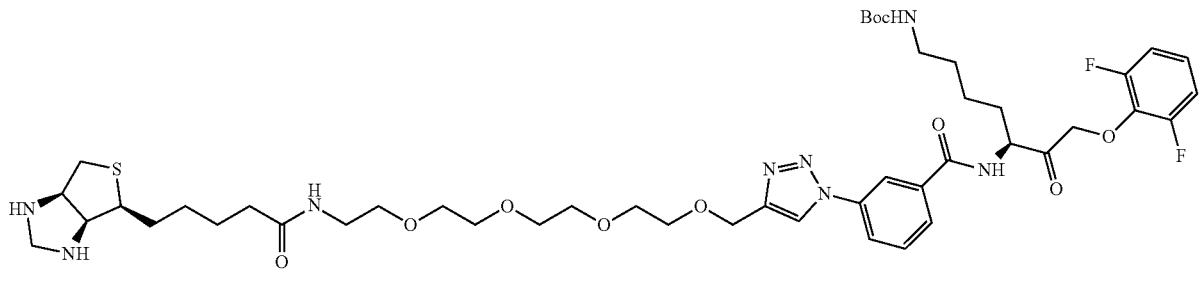

59.4

To a solution of 59.3 (80 mg, 174.83 µmol, 1 equivalent) in DMSO (2 mL) and H$_2$O (0.2 mL) was added 33.5 (90.48 mg, 174.83 µmol, 1 equivalent) and CuSO$_4$ (5.58 mg, 34.97 µmol, 5.37 µL, 0.2 equivalent) and sodium ascorbate (69.27 mg, 349.66 µmol, 2 equivalent). The mixture was stirred at 25° C. for 10 min. The reaction mixture was quenched by addition H$_2$O 10 mL at 25° C. and extracted with ethyl acetate (10 mL×3). The combined organic layers were washed with saturated brines (5 mL), dried over anhydrous sodium sulfate, filtered and concentrated under reduced pressure to give a crude product. The residue was purified by prep-TLC (SiO$_2$, DCM:MeOH=10:1) to give 59.4 (90 mg, 92.30 µmol, 52.79% yield) was obtained as yellow oil; LCMS [M+H]: 951; RT=1.160 min.

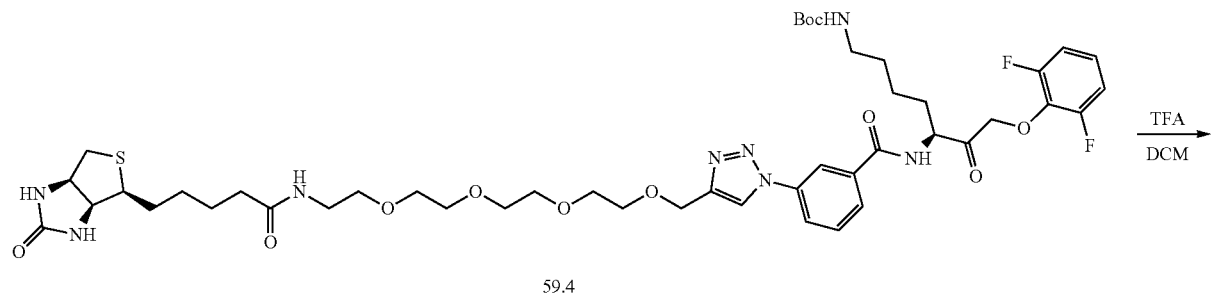

59.4

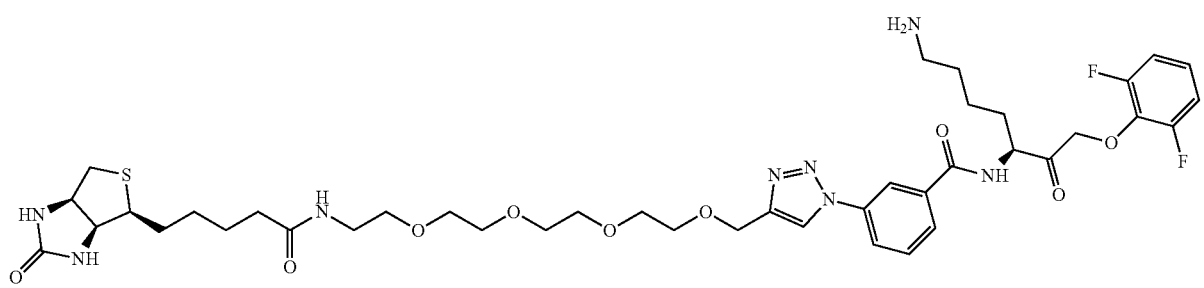

59

59.4 (90 mg, 92.30 μmop in DCM (5 mL) and TFA (1 mL) was stirred at 25° C. for 12 hours under $N_2$ atmosphere. The reaction mixture was concentrated under reduced pressure to give a residue. The residue was purified by prep-HPLC (TFA condition) to give Compound 59 (20 mg, 22.86 μmop as a white solid; LCMS [M+H]: 875; RT=0.870 min. $^1$H NMR (400 MHz, METHANOL-$d_4$) δ ppm 1.25-1.46 (m, 2H), 1.47-1.95 (m, 9H), 2.02-2.29 (m, 3H), 2.68 (d, J=12.57 Hz, 1H), 2.82-3.04 (m, 3H), 3.07-3.22 (m, 1H), 3.31-3.35 (m, 2H), 3.43-3.54 (m, 2H), 3.54-3.66 (m, 8H), 3.67-3.78 (m, 4H), 4.18-4.35 (m, 1H), 4.47 (dd, J=7.72, 4.85 Hz, 1H), 4.75 (s, 2H), 4.92-5.17 (m, 3H), 6.88-7.18 (m, 2H), 7.72 (t, J=7.94 Hz, 1H), 7.89-8.13 (m, 2H), 8.30-8.43 (m, 1H), 8.62 (s, 1H).

Example 56. Preparation of N—((S)-7-amino-1-(2,6-difluorophenoxy)-2-oxoheptan-3-yl)-3-(4-(3,43-dioxo-47-((3aS,4S,6aR)-2-oxohexahydro-1H-thieno[3,4-d]imidazol-4-yl)-6,9,12,15,18,21,24,27,30,33,36,39-dodecaoxa-2,42-diazaheptatetracontyl)-1H-1,2,3-triazol-1-yl)benzamide (60)

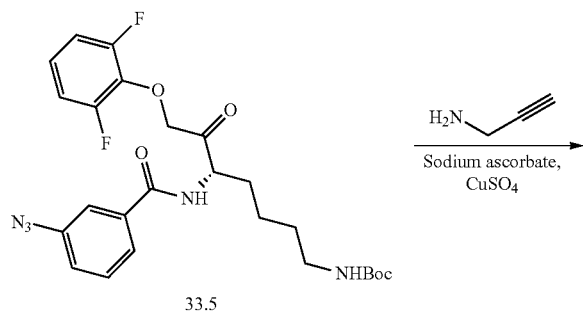

33.5

-continued

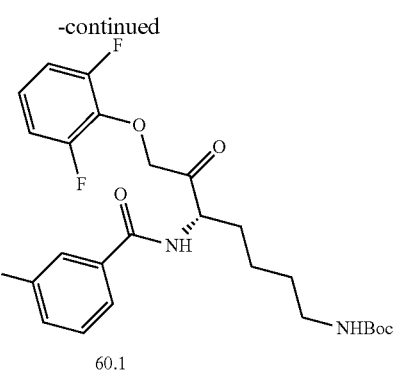

60.1

To a solution of prop-2-yn-1-amine (21.29 mg, 386.46 μmol, 24.75 μL, 1 equivalent) and 33.5 (200 mg, 386.46 μmol, 1 equivalent) in DMSO (2 mL) was added $CuSO_4$ (362.30 ug, 2.27 μmol, 3.48 μL, 0.2 equivalent) in $H_2O$ (0.1 mL) and Sodium ascorbate (153.12 mg, 772.91 μmol, 2 equivalent). The mixture was stirred at 25° C. for 15 mins. The reaction mixture was quenched by addition $H_2O$ 10 mL at 25° C. and extracted with ethyl acetate (10 mL×3). The combined organic layers were washed with saturated brines (5 mL), dried over anhydrous sodium sulfate, filtered and concentrated under reduced pressure to give a crude product. The residue was purified by column chromatography ($SiO_2$, DCM:MeOH=0:1) to give 60.1 (140 mg, 244.50 μmol, 63.27% yield) as a yellow solid; LCMS [M+H]: 573; RT=0.991 min.

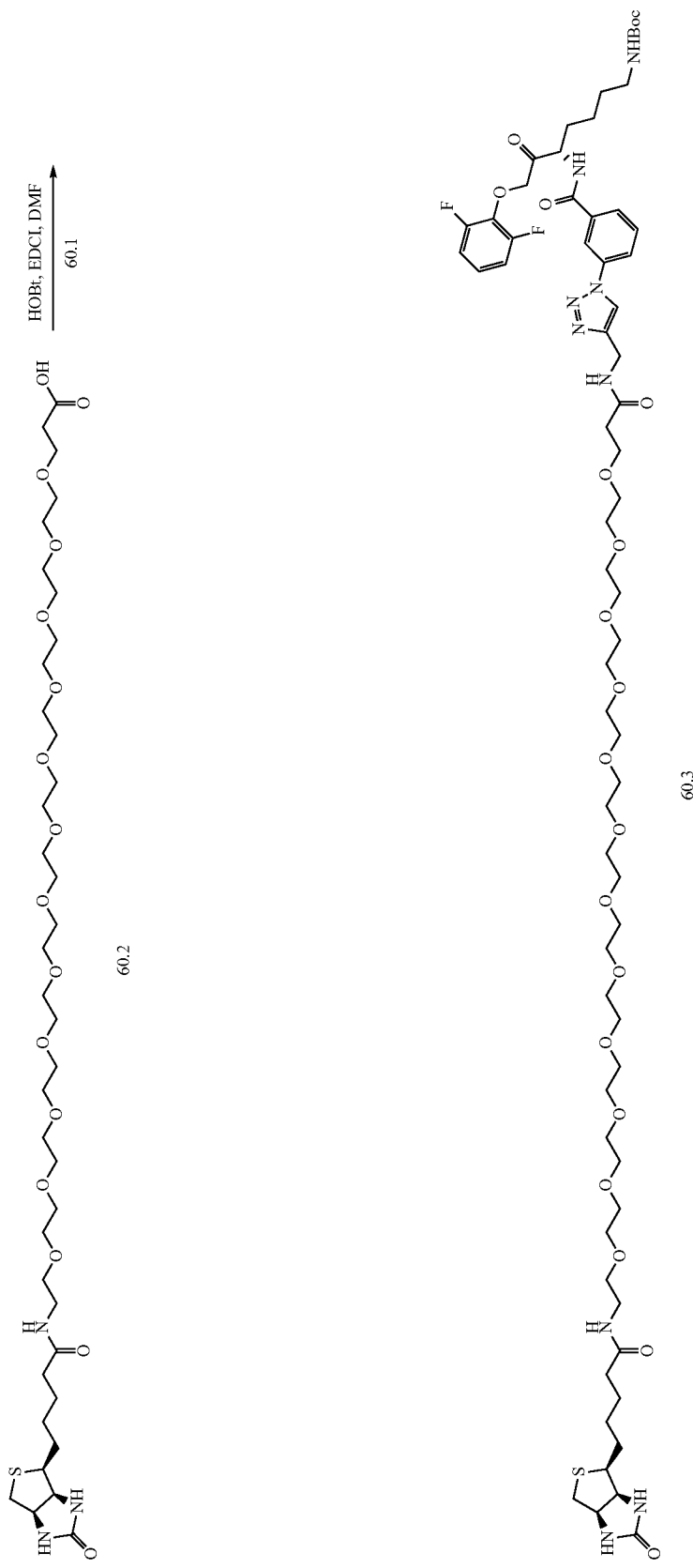

To a solution of 60.2 (200 mg, 236.96 µmol, 1 equivalent) in DMF (5 mL) was added HOBt (35.22 mg, 260.66 µmol, 1.1 equivalent) and EDCI (49.97 mg, 260.66 µmol, 1.1 equivalent). The mixture was stirred at 25° C. for 1 hr. Then to the mixture was added 60.1 (135.69 mg, 236.96 µmol, 1 equivalent) and DIPEA (122.50 mg, 947.85 µmol, 165.10 µL, 4 equivalent). The mixture was stirred at 25° C. for 11 hours. The residue was purified by prep-HPLC (TFA condition) to give 60.3 (55 mg, 39.32 µmol, 16.60% yield) as a yellow solid; LCMS [M+H]: 700; RT=1.225 min.

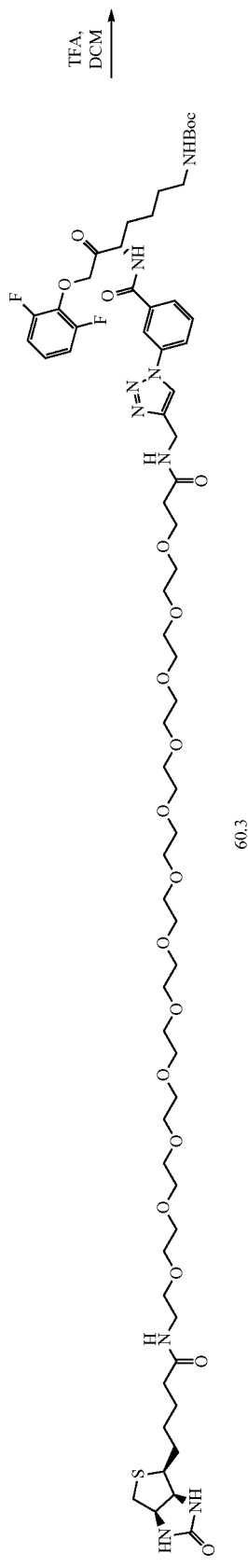
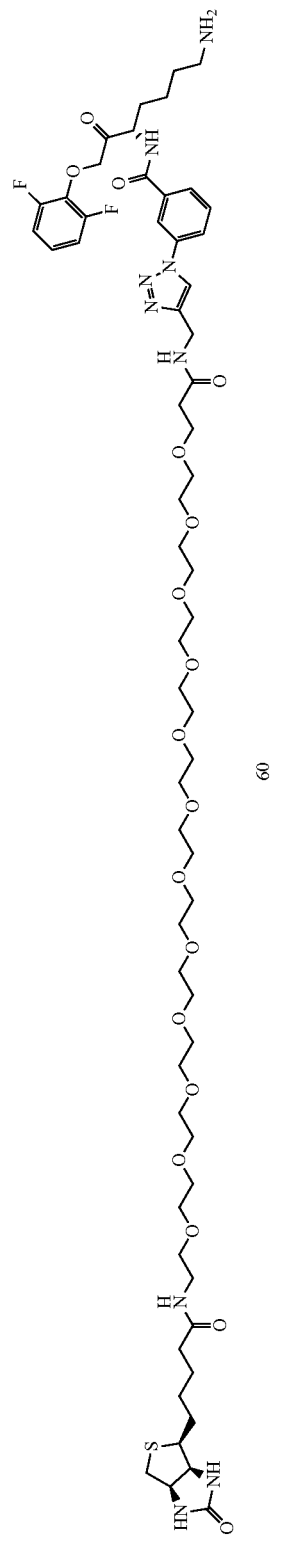
60.3
60
TFA, DCM →

A mixture of 60.3 (50 mg, 35.75 μmol) in DCM (5 mL) and TFA (1 mL), the mixture was stirred at 25° C. for 12 hours. The mixture was concentrated in vacuum to give a crude product. The residue was purified by prep-HPLC (TFA condition) to give Compound 60 (15 mg, 11.55 μmol) as yellow oil; LCMS [M+H]: 1299; RT=1.06 min. $^1$H NMR (400 MHz, METHANOL-d$_4$) δ ppm 1.32-1.93 (m, 12H), 2.06-2.27 (m, 3H), 2.52 (t, J=5.95 Hz, 2H), 2.70 (d, J=12.79 Hz, 1H), 2.86-3.05 (m, 3H), 3.14-3.24 (m, 1H), 3.32-3.38 (m, 2H), 3.45-3.68 (m, 49H), 3.77 (t, J=5.84 Hz, 2H), 4.30 (dd, J=7.83, 4.52 Hz, 1H), 4.49 (dd, J=7.72, 4.63 Hz, 1H), 4.56 (s, 2H), 4.96-5.13 (m, 2H), 6.94-7.14 (m, 3H), 7.64-7.77 (m, 1H), 7.91-8.10 (m, 2H), 8.28-8.39 (m, 1H), 8.44-8.52 (m, 1H).

Example 57. Preparation of (S)-5-((7-amino-1-(isoxazol-3-yloxy)-2-oxoheptan-3-yl)carbamoyl)-N,N,N-trimethylpyridin-2-aminium chloride (61)

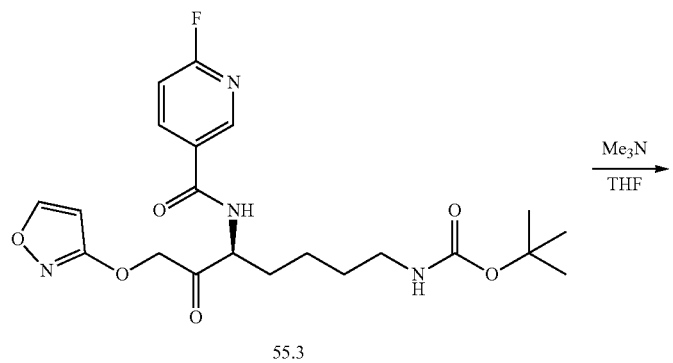

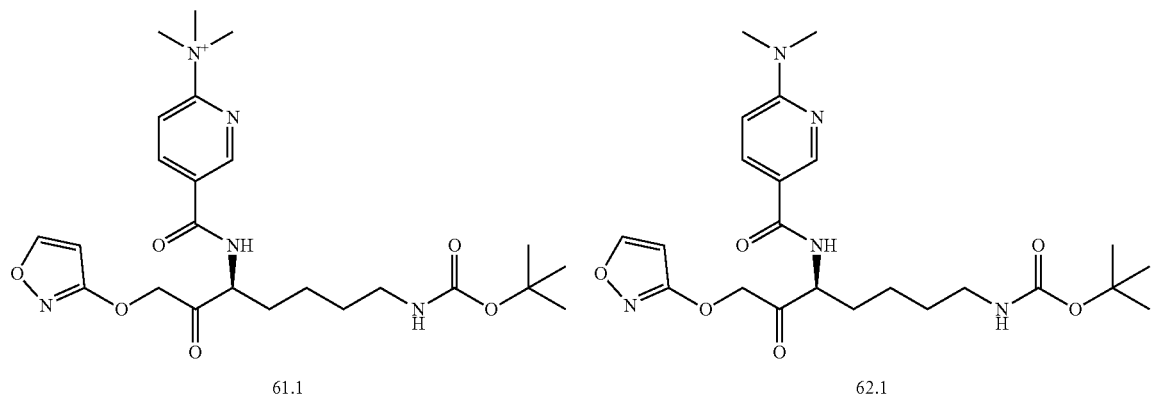

A solution of N,N-dimethylmethanamine (2 M, 4.44 mL, 20 equivalent) in THF (0.5 mL) was added 55.3 (0.2 g, 443.99 μmol, 1 equivalent) in one portion at 18° C. The mixture was stirred at 18° C. for 10 hours. The reaction mixture concentrated under reduced pressure to give a residue. The residue was purified by prep-HPLC (HCl condition) to give 61.1 (20 mg, 40.77 μmol, 9.18% yield) and 62.1 (20 mg, 42.06 μmol, 9.47% yield) as white solid; LCMS [M+H] for $C_{24}H_{37}N_5O_6+$; RT=1.136 min.

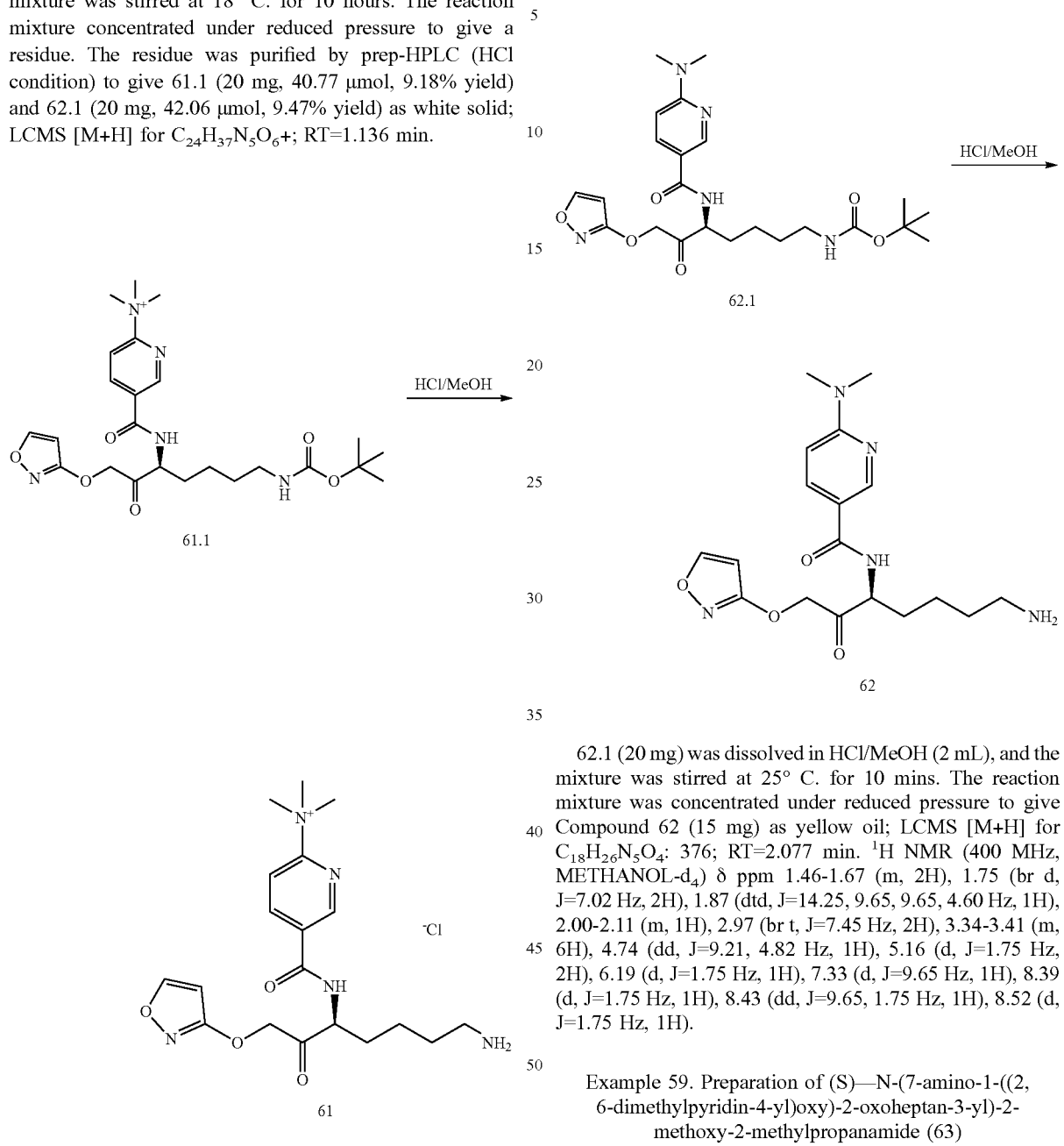

61.1 (20 mg) was dissolved in HCl/MeOH (2 mL), and the mixture was stirred at 25° C. for 10 mins. The reaction mixture was concentrated under reduced pressure to give Compound 61 (15 mg) as yellow oil; LCMS [M+H] for $C_{19}H_{29}N_5O_4+$: 391; RT=0.149 min. $^1$H NMR (400 MHz, METHANOL-$d_4$) δ ppm 1.47-1.66 (m, 2H), 1.68-1.82 (m, 2H), 1.84-1.97 (m, 1H), 2.01-2.16 (m, 1H), 2.97 (br t, J=7.45 Hz, 2H), 3.67-3.74 (m, 9H), 4.81 (dd, J=9.43, 4.60 Hz, 1H), 5.15-5.21 (m, 2H), 6.17-6.23 (m, 1H), 8.10-8.19 (m, 1H), 8.39 (d, J=1.75 Hz, 1H), 8.64 (dd, J=8.77, 2.19 Hz, 1H), 9.11 (d, J=1.75 Hz, 1H).

Example 58. Preparation of (S)—N-(7-amino-1-(isoxazol-3-yloxy)-2-oxoheptan-3-yl)-6-(dimethylamino)nicotinamide (62)

62.1 (20 mg) was dissolved in HCl/MeOH (2 mL), and the mixture was stirred at 25° C. for 10 mins. The reaction mixture was concentrated under reduced pressure to give Compound 62 (15 mg) as yellow oil; LCMS [M+H] for $C_{18}H_{26}N_5O_4$: 376; RT=2.077 min. $^1$H NMR (400 MHz, METHANOL-$d_4$) δ ppm 1.46-1.67 (m, 2H), 1.75 (br d, J=7.02 Hz, 2H), 1.87 (dtd, J=14.25, 9.65, 9.65, 4.60 Hz, 1H), 2.00-2.11 (m, 1H), 2.97 (br t, J=7.45 Hz, 2H), 3.34-3.41 (m, 6H), 4.74 (dd, J=9.21, 4.82 Hz, 1H), 5.16 (d, J=1.75 Hz, 2H), 6.19 (d, J=1.75 Hz, 1H), 7.33 (d, J=9.65 Hz, 1H), 8.39 (d, J=1.75 Hz, 1H), 8.43 (dd, J=9.65, 1.75 Hz, 1H), 8.52 (d, J=1.75 Hz, 1H).

Example 59. Preparation of (S)—N-(7-amino-1-((2,6-dimethylpyridin-4-yl)oxy)-2-oxoheptan-3-yl)-2-methoxy-2-methylpropanamide (63)

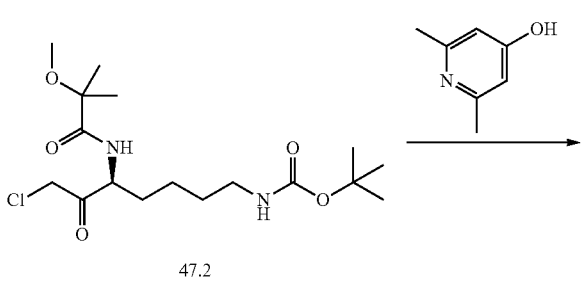

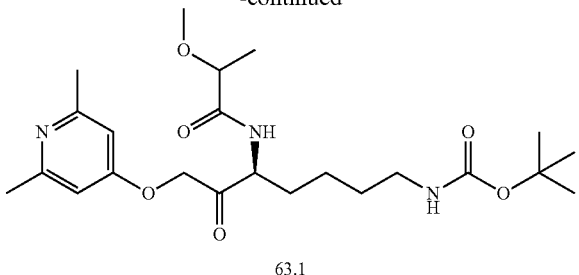

63.1

To 47.2 (423 mg, 1.12 mmol, 1 equivalent) and 2,6-dimethyl-4-hydroxypyridine (137.49 mg, 1.12 mmol, 1 equivalent) in DMF (9 mL) were added K$_2$CO$_3$ (462.89 mg, 3.35 mmol, 3 equivalent) and KI (185.33 mg, 1.12 mmol, 1 equivalent) in one portion at 25° C. under N$_2$. Then the mixture was stirred for 2 hours. The reaction mixture was quenched by addition H$_2$O (20 mL) and then diluted with EtOAc (20 mL) and extracted with EtOAc (10 mL×3). The combined organic layers were washed with H$_2$O (10 mL×3), dried over, filtered and concentrated under reduced pressure to give a residue. The residue was purified by column chromatography (SiO$_2$, Petroleum ether/Ethyl acetate=3:1) to give 63.1 (85 mg, 182.57 μmol) as a white solid; LCMS [M+H]: 466; RT=1.155 min. $^1$H NMR (400 MHz, METHANOL-d$_4$) δ ppm 1.38 (d, J=5.51 Hz, 8H), 1.43 (s, 11H), 1.50 (dt, J=13.67, 6.84 Hz, 3H), 1.64-1.77 (m, 2H), 1.88-1.99 (m, 2H), 2.41-2.46 (m, 6H), 2.99-3.09 (m, 3H), 3.31-3.32 (m, 3H), 4.55-4.62 (m, 2H), 4.92-5.04 (m, 3H), 6.66 (s, 2H).

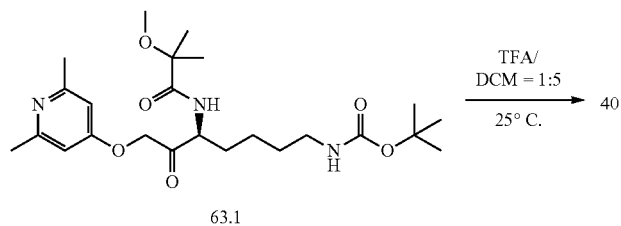

63.1 (85 mg) in DCM (5 mL) and TFA (1 mL) was stirred for 0.5 hour. The reaction mixture was concentrated under reduced pressure. The residue was purified by column chromatography (SiO$_2$, Petroleum ether/Ethyl acetate=2:1) to give compound 63 (50 mg); LCMS [M+H]: 366;

RT=1.517 min. $^1$H NMR (400 MHz, METHANOL-d$_4$) δ ppm 1.25-1.40 (m, 6H), 1.46-1.59 (m, 2H), 1.67-1.80 (m, 3H), 1.94-2.05 (m, 1H), 2.61-2.66 (m, 6H), 2.93 (br t, J=7.58 Hz, 2H), 3.30-3.32 (m, 3H), 4.47 (dd, J=9.66, 4.40 Hz, 1H), 5.22-5.40 (m, 2H), 7.13-7.22 (m, 2H).

Example 60. Preparation of (S)—N-(7-amino-2-oxo-1-(pyridin-3-yloxy)heptan-3-yl)-2-methoxy-2-methylpropanamide (64)

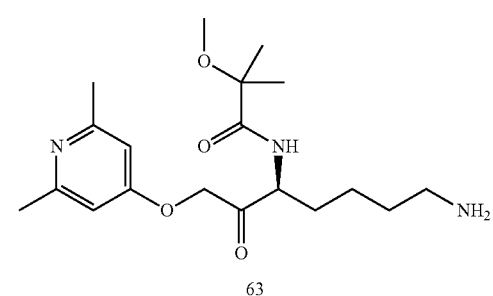

64

Compound 64 was prepared by the same methods used for Compound 63 with 3-hydrozypyridine used instead of 2,6-dimethyl-4-hydroxypyridine; LCMS [M+H]: 338; RT=4.585 min. $^1$H NMR (400 MHz, METHANOL-d$_4$) δ ppm 1.21-1.40 (m, 6H), 1.42-1.58 (m, 2H), 1.64-1.80 (m, 3H), 1.95-2.05 (m, 1H), 2.93 (br t, J=7.64 Hz, 2H), 3.30-3.32 (m, 3H), 4.51 (dd, J=9.66, 4.40 Hz, 1H), 5.14-5.29 (m, 2H), 7.86 (dd, J=8.80, 5.38 Hz, 1H), 7.98-8.03 (m, 1H), 8.41 (br d, J=5.14 Hz, 1H), 8.51 (br d, J=2.08 Hz, 1H).

Example 61. Preparation of (S)—N-(7-amino-1-((2-methylpyrimidin-5-yl)oxy)-2-oxoheptan-3-yl)-2-methoxy-2-methylpropanamide (65)

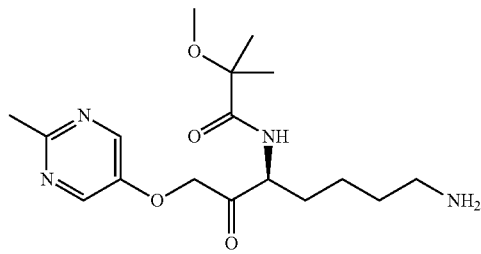

65

Compound 65 was prepared by the same methods used for Compound 63 with 5-hydroxypyrimidine used instead of 2,6-dimethyl-4-hydroxypyridine; LCMS [M+H]: 353; RT=1.98 min. $^1$H NMR (400 MHz, DMSO-d$_6$) δ ppm 1.24 (br s, 1H), 1.31 (s, 7H), 1.34 (br s, 1H), 1.45-1.58 (m, 2H), 1.65 (dtd, J=14.00, 9.48, 9.48, 4.71 Hz, 1H), 1.78-1.89 (m, 1H), 2.55 (s, 3H), 2.72-2.85 (m, 2H), 3.20 (s, 3H), 4.19-4.61 (m, 1H), 5.18 (br s, 2H), 7.68 (br s, 2H), 8.21 (d, J=7.70 Hz, 1H), 8.36 (s, 2H).

Example 62. Preparation of (S)—N-(7-amino-2-oxo-1-(pyridin-3-ylthio)heptan-3-yl)-2-methoxy-2-methylpropanamide (66)

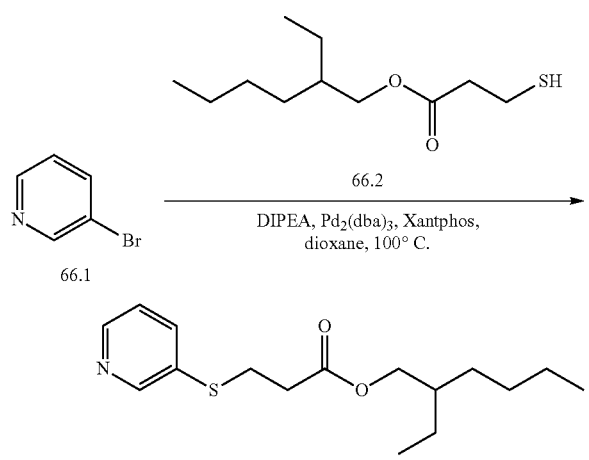

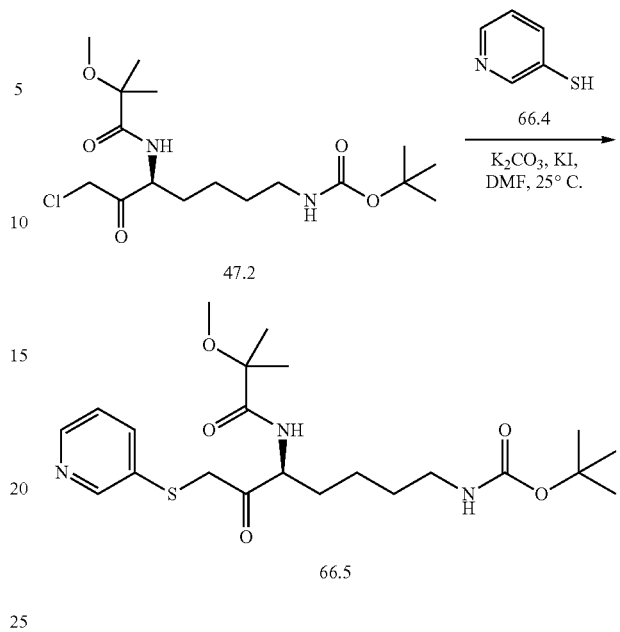

To 66.1 (2 g, 12.66 mmol, 1.22 mL, 1 equivalent) in dioxane (20 mL) was added 66.2 (2.90 g, 13.29 mmol, 1.05 equivalent), DIPEA (3.27 g, 25.32 mmol, 4.41 mL, 2 equivalent) and Xantphos (732.45 mg, 1.27 mmol, 0.1 equivalent), Pd₂(dba)₃ (579.58 mg, 632.93 μmol, 0.05 equivalent). The mixture was stirred at 100° C. for 2 hr. The reaction mixture was quenched by addition H₂O (20 mL), and extracted with EtOAc (20 mL×3). The combined organic layers were washed with brine (20 mL), dried over Na₂SO₄ and concentrated under reduced pressure to give a residue. The residue was purified by MPLC (SiO₂, Petroleum ether/Ethyl acetate=10/1 to 1:1) to give 66.3 (3.6 g, 12.19 mmol, 96.26% yield) as yellow oil.

To 47.2 (500 mg, 1.32 mmol, 1 equivalent) in DMF (5 mL) was added 66.4 (80 mg, 719.65 μmol, 5.45 equivalent), K₂CO₃ (547.15 mg, 3.96 mmol, 3 equivalent) and KI (219.06 mg, 1.32 mmol, 1 equivalent). The mixture was stirred at 25° C. for 5 h. The reaction mixture was filtered, and the desired compound was in the filtrate. The filtrate was purified by prep-HPLC (column: Phenomenex Luna C18 200×40 mm×10 um; mobile phase: A: water (0.1% TFA)-B: ACN; B %: 15%-35%, 8 min) to give 66.5 (40 mg, 88.18 μmol).

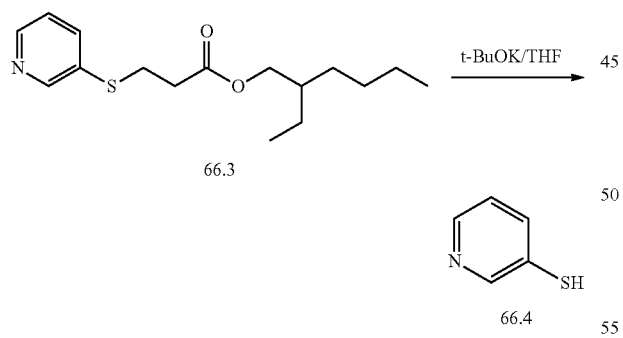

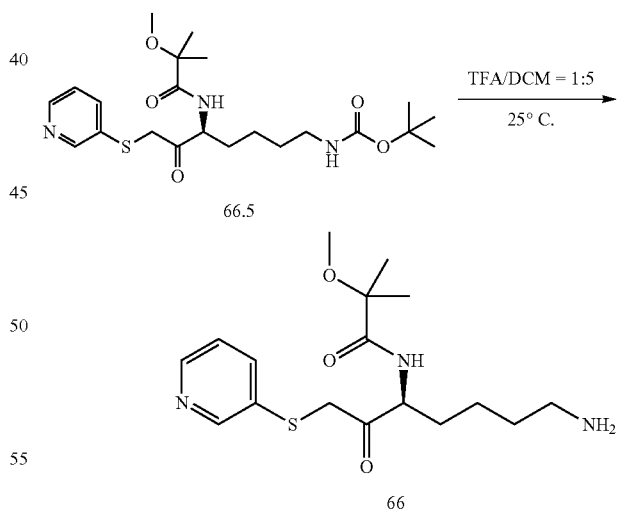

To 66.3 (800 mg, 2.71 mmol, 1 equivalent) in THF (10 mL) was added t-BuOK/THF (1 M, 4.06 mL, 1.5 equivalent). The mixture was stirred at −78° C. for 1 h. The reaction mixture was concentrated under reduced pressure to give a residue. The residue was purified by column chromatography (SiO₂, EtOAc/MEOH=10/1 to 1:1) to give 66.4 (80 mg) as yellow oil. ¹H NMR (400 MHz, DMSO-d₆) δ ppm 8.53 (d, J=1.75 Hz, 1H), 8.31 (dd, J=4.82, 1.32 Hz, 1H), 7.83-7.91 (m, 1H), 7.30 (dd, J=7.45, 4.82 Hz, 1H), 3.58 (br s, 8H) 3.38-3.73 (m, 1H).

To 66.5 in DCM (5 mL) was added TFA (1 mL). The mixture was stirred at 25° C. for 1 h. The reaction mixture was concentrated under reduced pressure to give a residue to give Compound 66 (12 mg); LCMS [M+H]: 354; RT=1.83 min. ¹H NMR (400 MHz, METHANOL-d4) δ ppm 8.62 (br s, 1H), 8.49 (br s, 1H), 8.14 (d, J=8.33 Hz, 1H), 7.62 (dd, J=8.33, 4.82 Hz, 1H), 4.60 (dd, J=9.43, 4.17 Hz, 1H), 4.10-4.21 (m, 1H), 3.29 (br s, 3H), 2.90 (br t, J=7.45 Hz, 2H), 1.97 (br d, J=10.09 Hz, 1H), 1.62-1.74 (m, 3H), 1.42 (br d, J=4.39 Hz, 1H), 1.36 (d, J=4.38 Hz, 8H), 1.27-1.33 (m, 1H).

Example 63. Preparation of (S)—N-(7-amino-1-((2, 6-dimethylpyridin-4-yl)thio)-2-oxoheptan-3-yl)-2-methoxy-2-methylpropanamide (67)

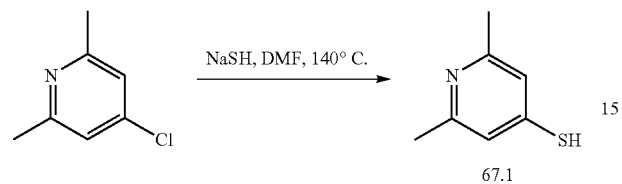

To 2,6-dimethyl-4-chloropyridine (2 g, 14.12 mmol, 1 equivalent) in DMF (20 mL) was added NaSH (1.98 g, 35.31 mmol, 2.5 equivalent). The mixture was stirred at 140° C. for 2 h. The reaction mixture was concentrated under reduced pressure to give a residue. The residue was purified by MPLC (Dichloromethane: Methanol SiO$_2$, =10/1 to 1:1) to give 67.1 (2.7 g) as a yellow solid.

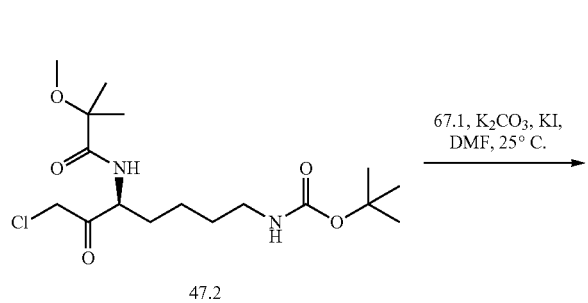

To 67.1 (367.44 mg, 2.64 mmol, 1 equivalent) in DMF (7 mL) was added 47.2 (1 g, 2.64 mmol, 1 equivalent), K$_2$CO$_3$ (1.09 g, 7.92 mmol, 3 equivalent) and KI (438.12 mg, 2.64 mmol, 1 equivalent). The mixture was stirred at 25° C. for 2h. The reaction mixture was filtered, and the desired compound was in the filtrate. The filtrate was purified by prep-HPLC (column: Phenomenex Luna (2) C18, 250×50× 10 u; mobile phase A: water (0.1% TFA) and B: ACN; gradient B %: 10%-40% over 20 min) to give 67.2 (353 mg).

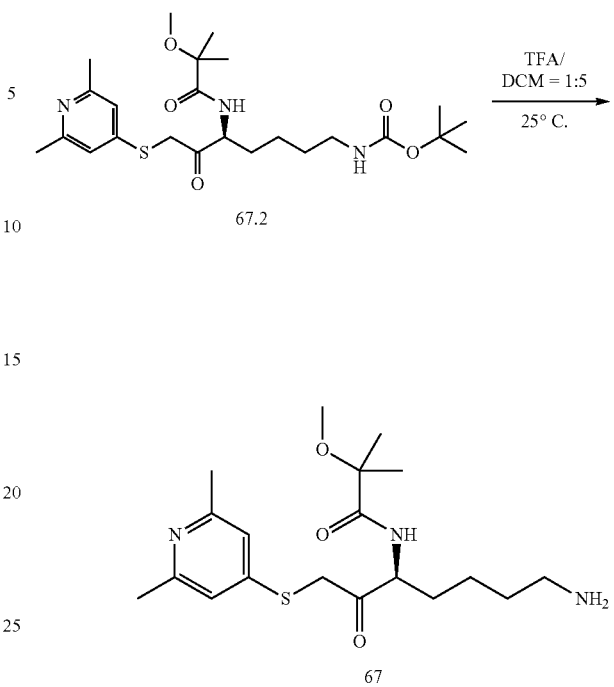

To 67.2 (353 mg) in DCM (5 mL) was added TFA (1 mL). The mixture was stirred at 25° C. for 1 h. The reaction mixture was concentrated under reduced pressure to give Compound 67 (350 mg); LCMS [M+H]: 382; RT=1.799 min. $^1$H NMR (400 MHz, METHANOL-d$_4$) δ ppm 7.40-7.52 (m, 2H), 4.32-4.57 (m, 3H), 3.32 (br s, 3H), 2.94 (br t, J=7.64 Hz, 2H), 2.63 (s, 6H), 1.95-2.08 (m, 1H), 1.65-1.83 (m, 3H), 1.43-1.57 (m, 2H), 1.39 (d, J=5.62 Hz, 6H).

Example 64. Preparation of (S)—N-(7-amino-1-((2-methylpyrimidin-5-yl)thio)-2-oxoheptan-3-yl)-2-methoxy-2-methylpropanamide (68)

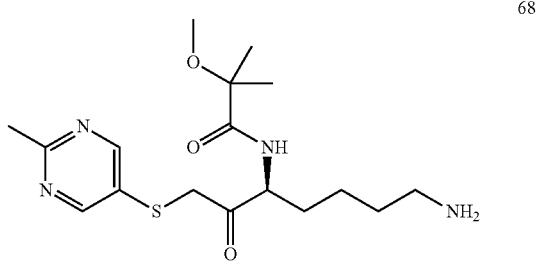 [SMILES: COC(C)(C)C(=O)N[C@@H](CCCCN)C(=O)COc1cnc(C)nc1]

Compound 68 was prepared by the same methods used for Compound 66 with 2-methyl-5-bromopyrimidine used instead of 3-bromopyridine; LCMS [M+H]: 369; RT=2.0 min. $^1$H NMR (400 MHz, METHANOL-d$_4$) δ ppm 1.36 (s, 8H), 1.38-1.48 (m, 2H), 1.60-1.74 (m, 3H), 1.90-2.01 (m, 1H), 2.65 (s, 3H), 2.90 (br t, J=6.80 Hz, 2H), 3.29 (s, 3H), 3.91-4.10 (m, 2H), 4.62 (dd, J=9.43, 4.60 Hz, 1H), 8.68 (s, 2H).

Example 65. Preparation of (S)—N-(7-amino-1-((1,1,1,3,3,3-hexafluoropropan-2-yl)oxy)-2-oxoheptan-3-yl)-2-methoxy-2-methylpropanamide (69)

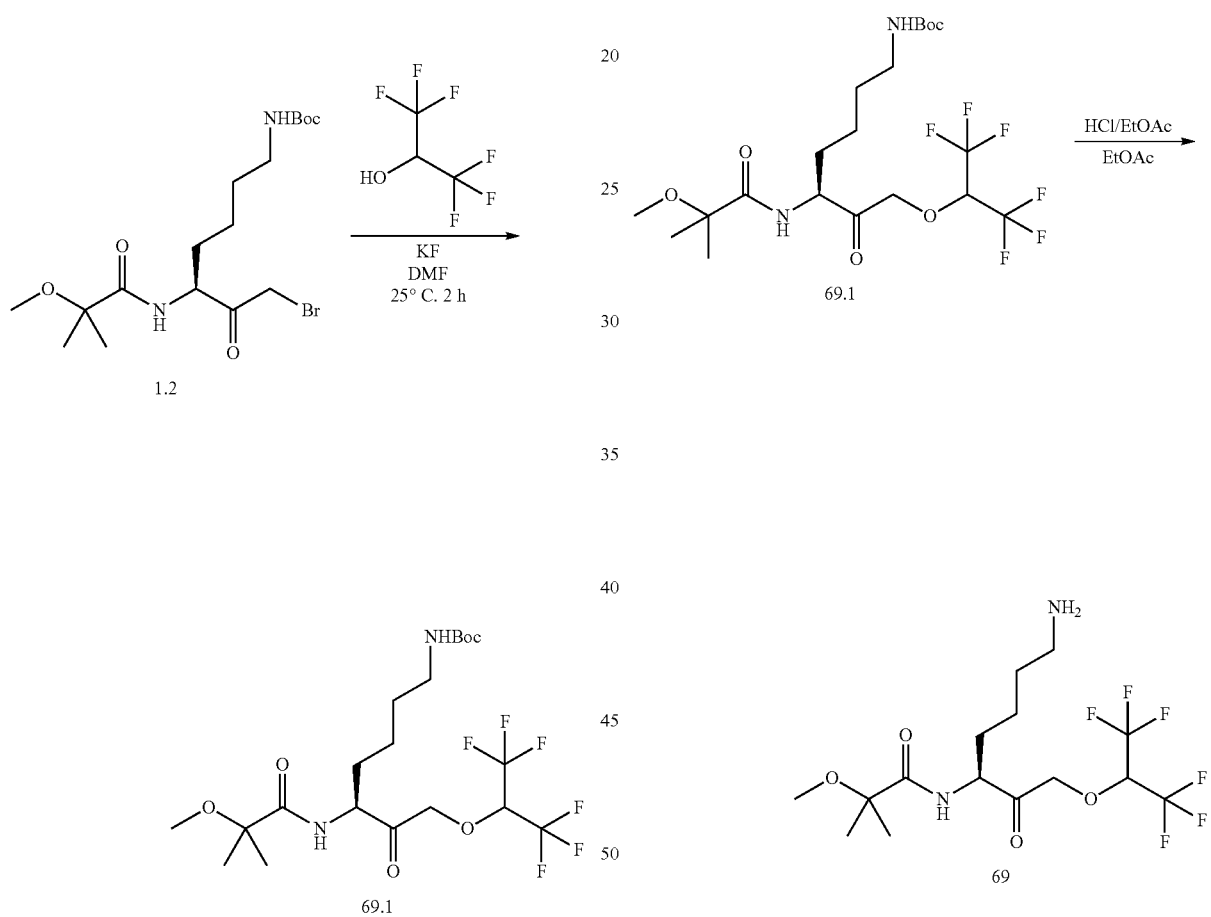

A suspension of compound 1.2 (1.0 g, 2.36 mmol, 1.0 equivalent), 1,1,13,3,3-hexafluoroisopropanol (595 mg, 3.54 mmol, 1.5 equivalent), KF (411 mg, 7.09 mmol, 3.0 equivalent) in DMF (7 mL) was degassed and purged with N$_2$ for 3 times, and then the suspension was stirred at 25° C. for 2 hr under N$_2$ atmosphere. LCMS indicated compound 1.2 was consumed completely. The reaction was quenched with water (21 mL) slowly and then extracted with EtOAc (20 mL×2). The combined organic phase was washed with brine (10 mL), dried over anhydrous Na$_2$SO$_4$, filtered and concentrated in vacuo. The residue was purified by column chromatography (SiO$_2$, Petroleum ether: Ethyl acetate=15:1 to 3:1) to give 69.1 (0.90 g, 1.67 mmol, 70% yield) as a colorless gum. $^1$H NMR (400 MHz, DMSO-d$_6$) δ 8.05 (d, J=8.4 Hz, 1H), 6.73 (broad s, 1H), 5.42-5.50 (m, 1H), 4.65 (dd, J=1.2 Hz, J=1.2 Hz, 2H), 4.26-4.32 (m, 1H), 3.15 (s, 3H), 2.80-2.91 (m, 2H), 1.67-1.75 (m, 1H), 1.52-1.58 (m, 1H), 1.33 (s, 11H), 1.25 (s, 6H) ppm.

To a solution of compound 3 (0.90 g, 1.76 mmol, 1.0 equivalent) in EtOAc (10 mL) was added HCl/EtOAc (4 M, 10 mL, 22 equivalent) at 0° C. The solution was stirred at 0° C. for 1 hr. LCMS indicated compound 69.1 was consumed completely. The reaction mixture was concentrated under reduced pressure to give a residue. This was dried by freeze dryer to give compound Compound 69 (0.78 g, total yield: 63.7%, HCl salt) as a yellow gum. $^1$H NMR (400 MHz, DMSO-d$_6$) δ 8.09 (d, J=8.4 Hz, 1H), 7.91 (br.s, 3H), 5.47-5.54 (m, 1H), 4.61-4.79 (m, 2H), 3.15 (s, 3H), 2.64-2.72 (m, 2H), 1.58-1.74 (m, 1H), 1.52-1.58 (m, 3H), 1.33-1.34 (m, 2H), 1.33 (s, 6H) ppm.

Example 66. Preparation of Cyanine Gingipain Activity Probes 70, 71, and 72
Probe compound 70 was prepared according to the following scheme.
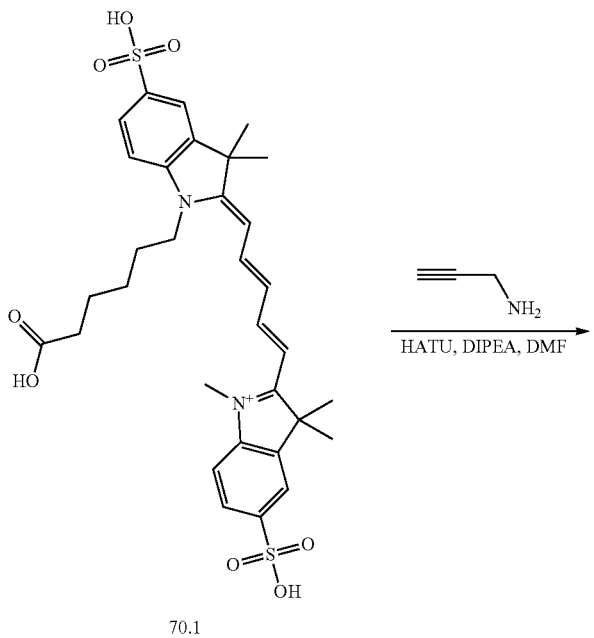
70.1
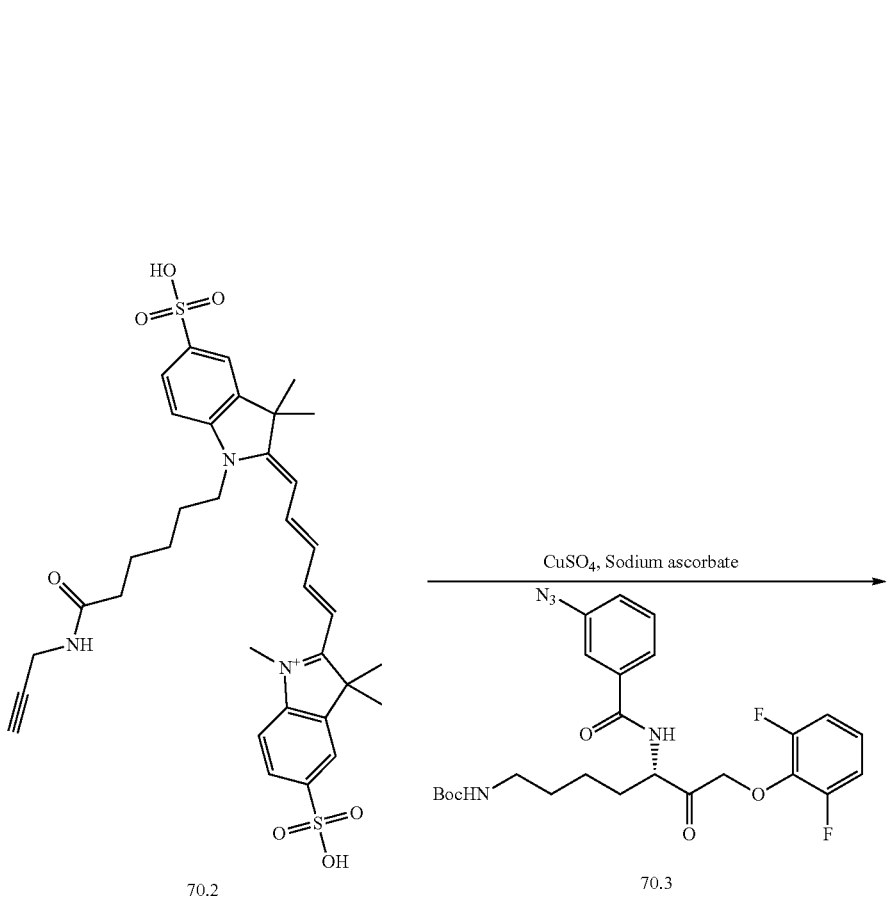
70.2
70.3

-continued
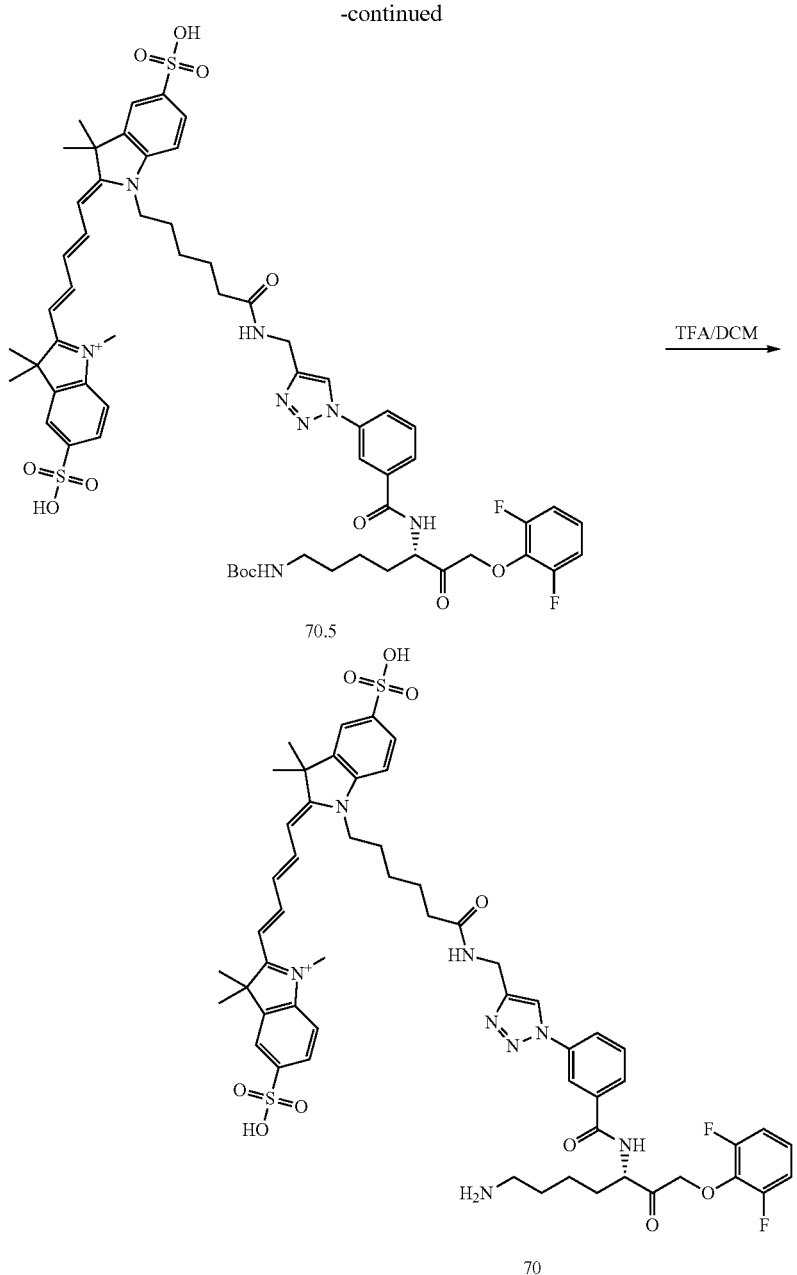
Probe compound 71 was prepared according to the following scheme.

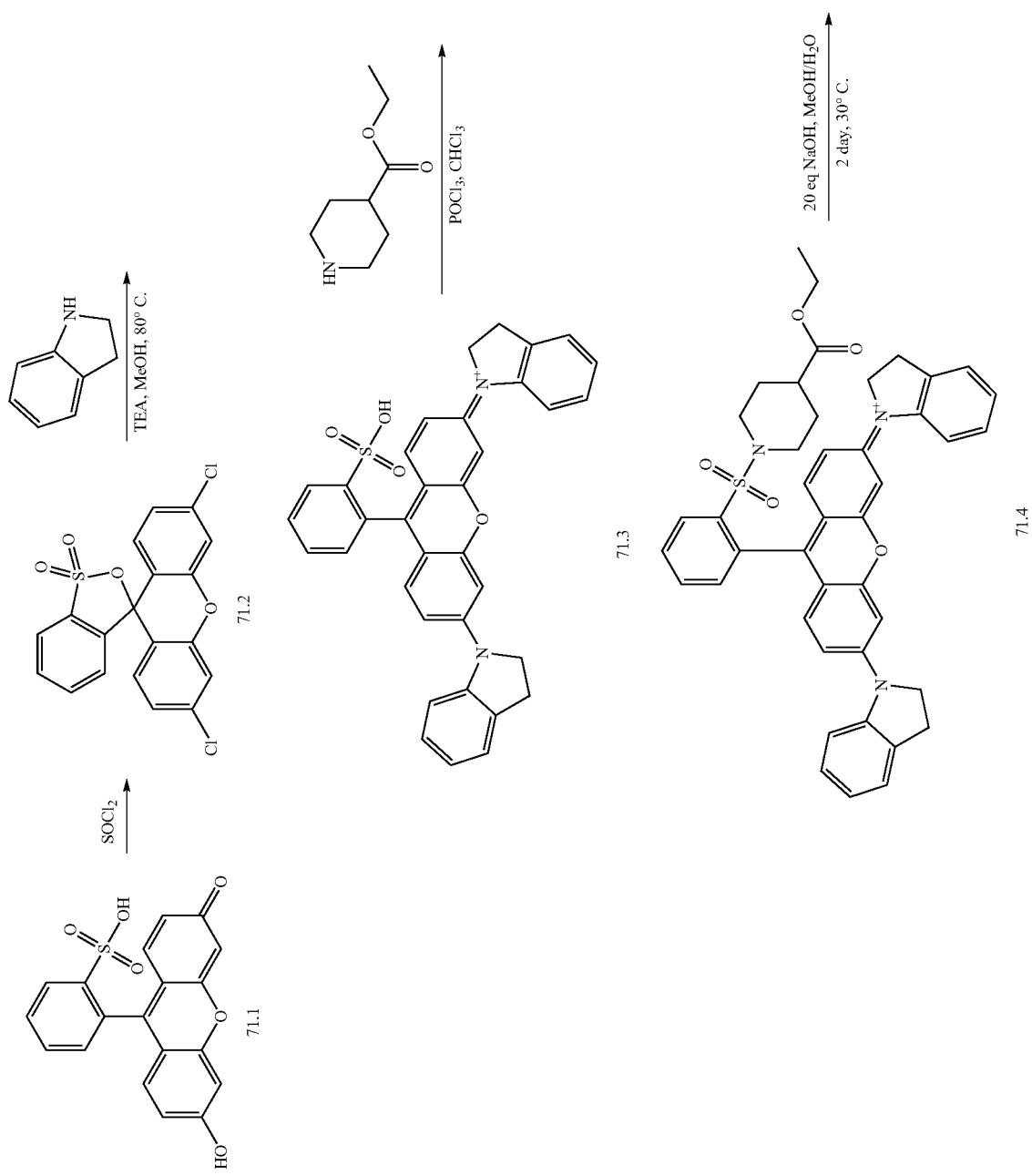

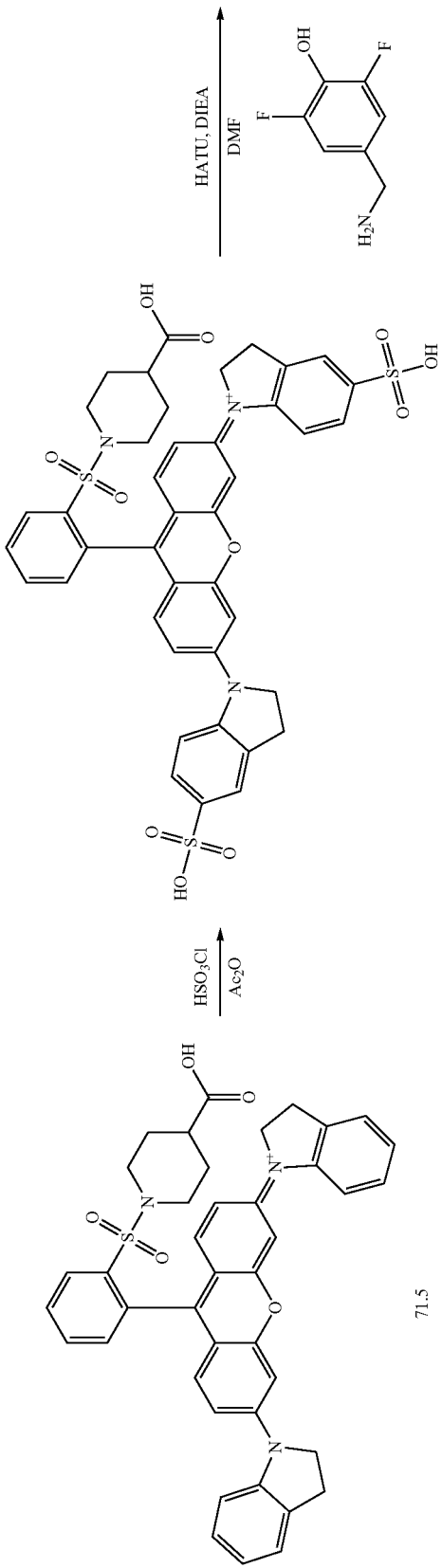
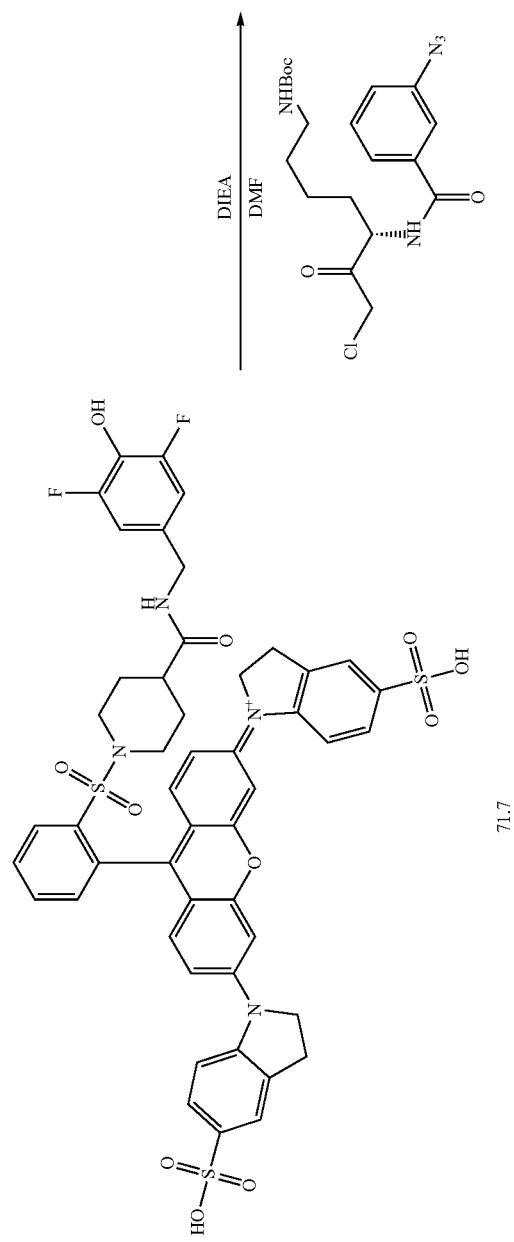

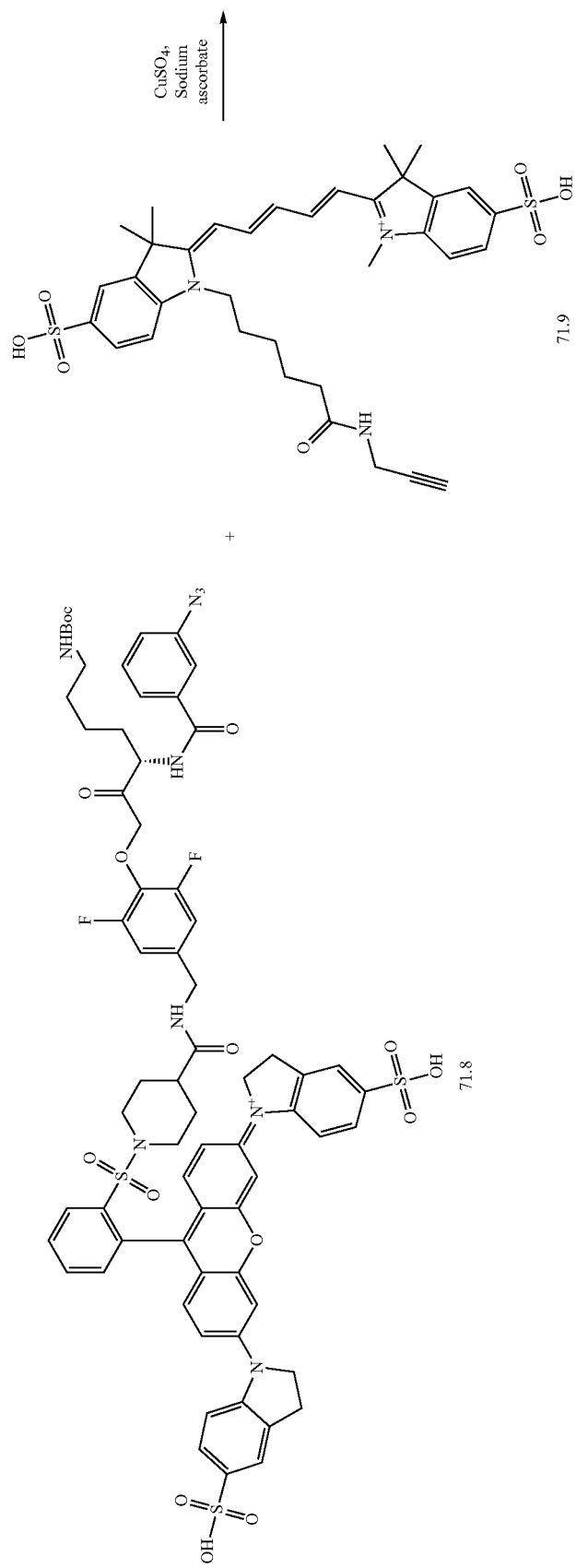

-continued
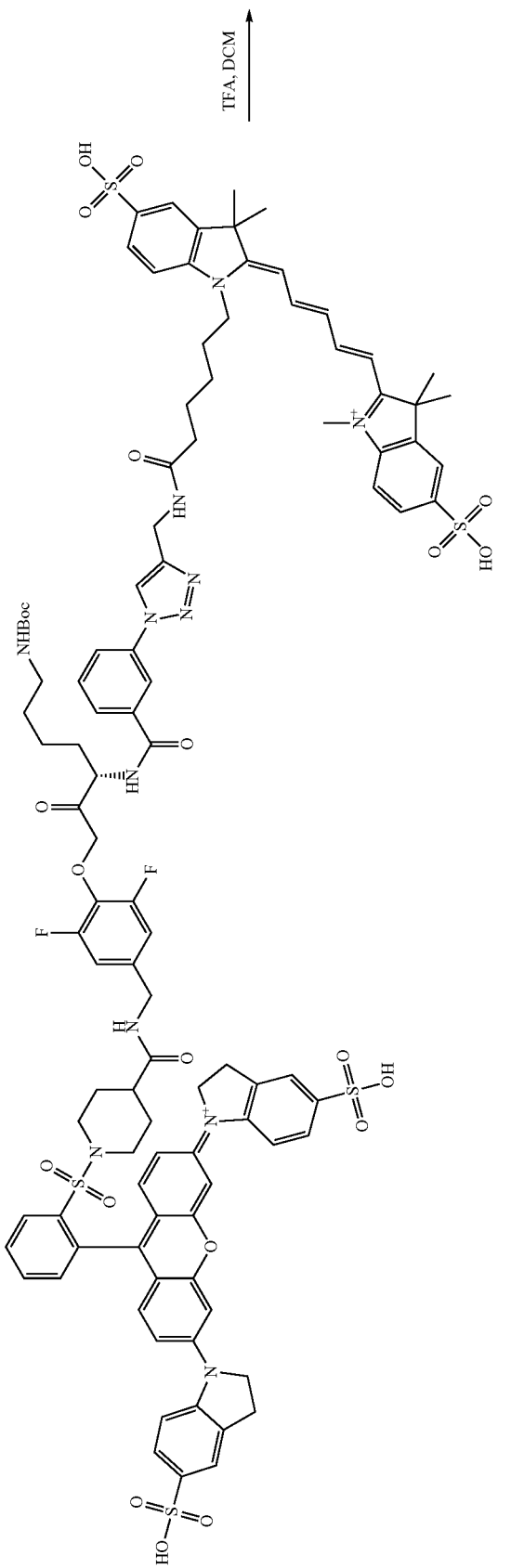
TFA, DCM →
71.91

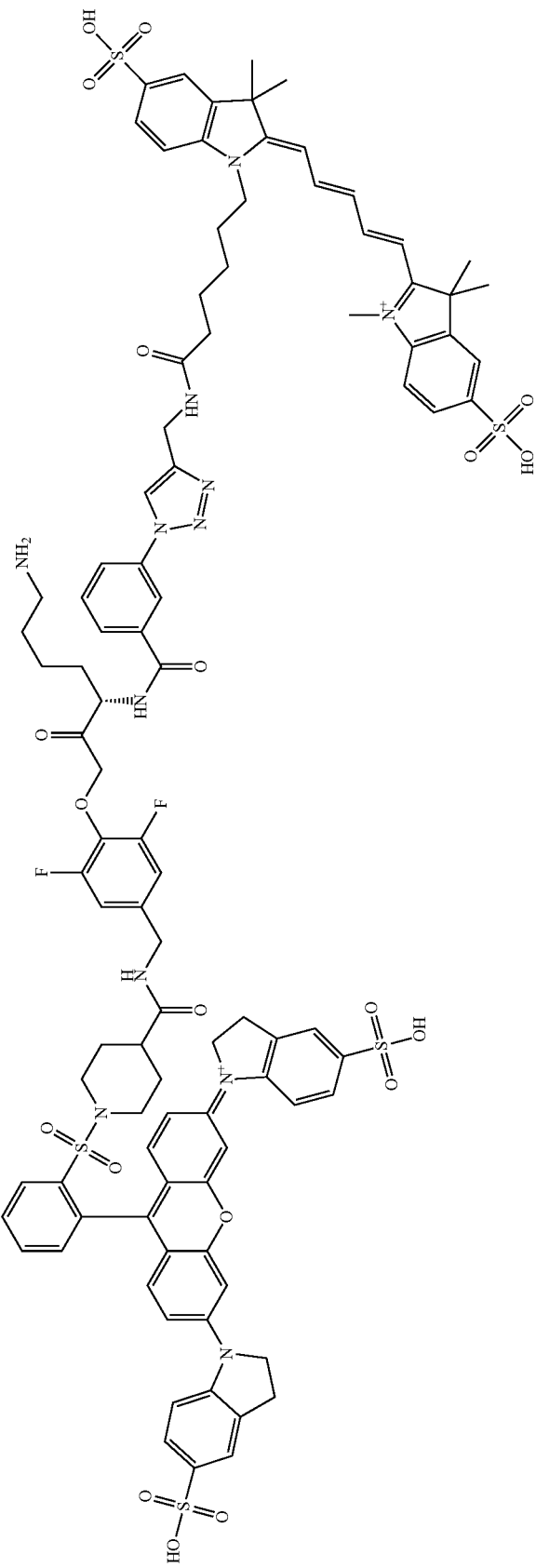
71
-continued

Probe compound 72 was prepared according to the following scheme.

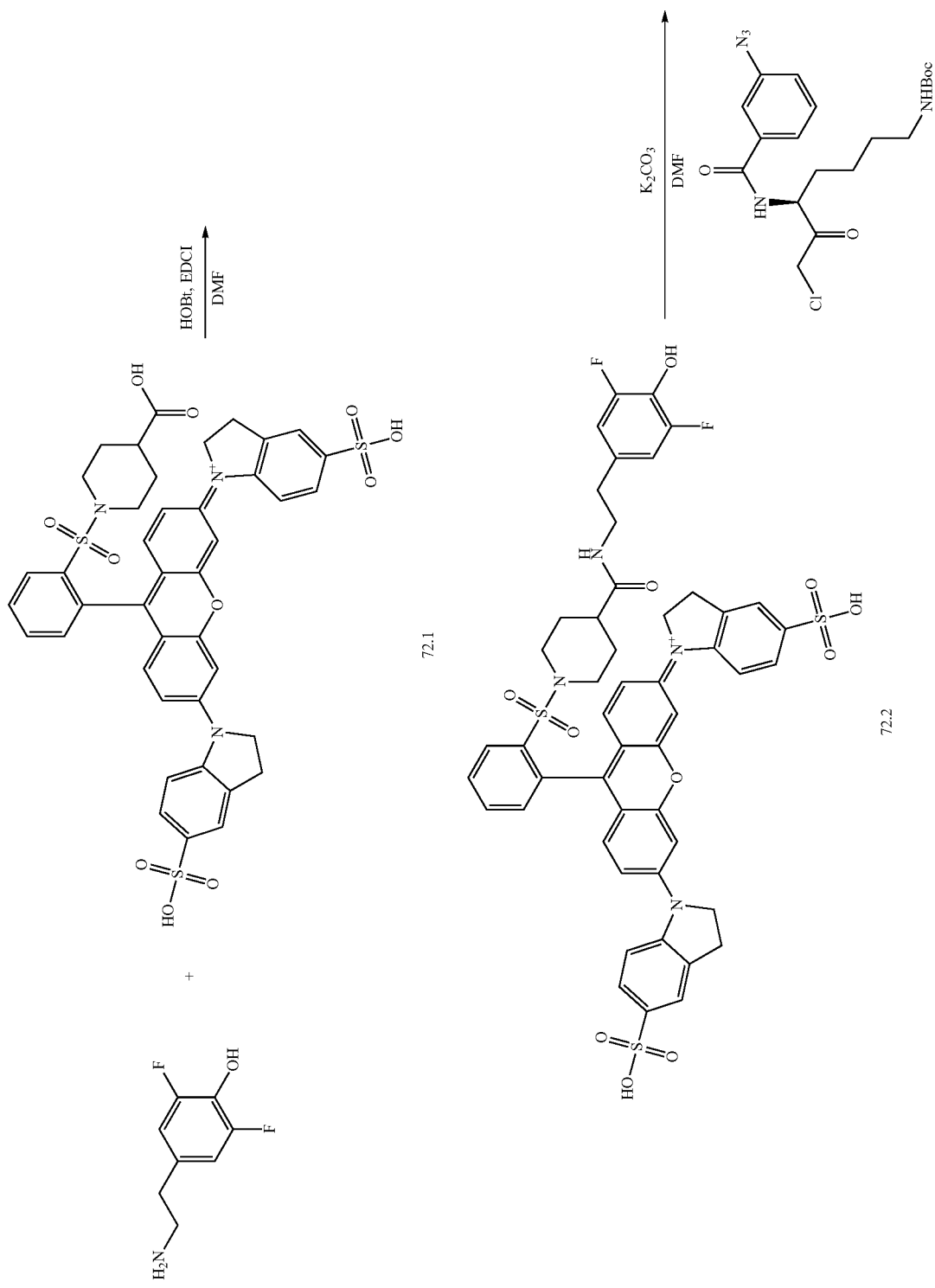

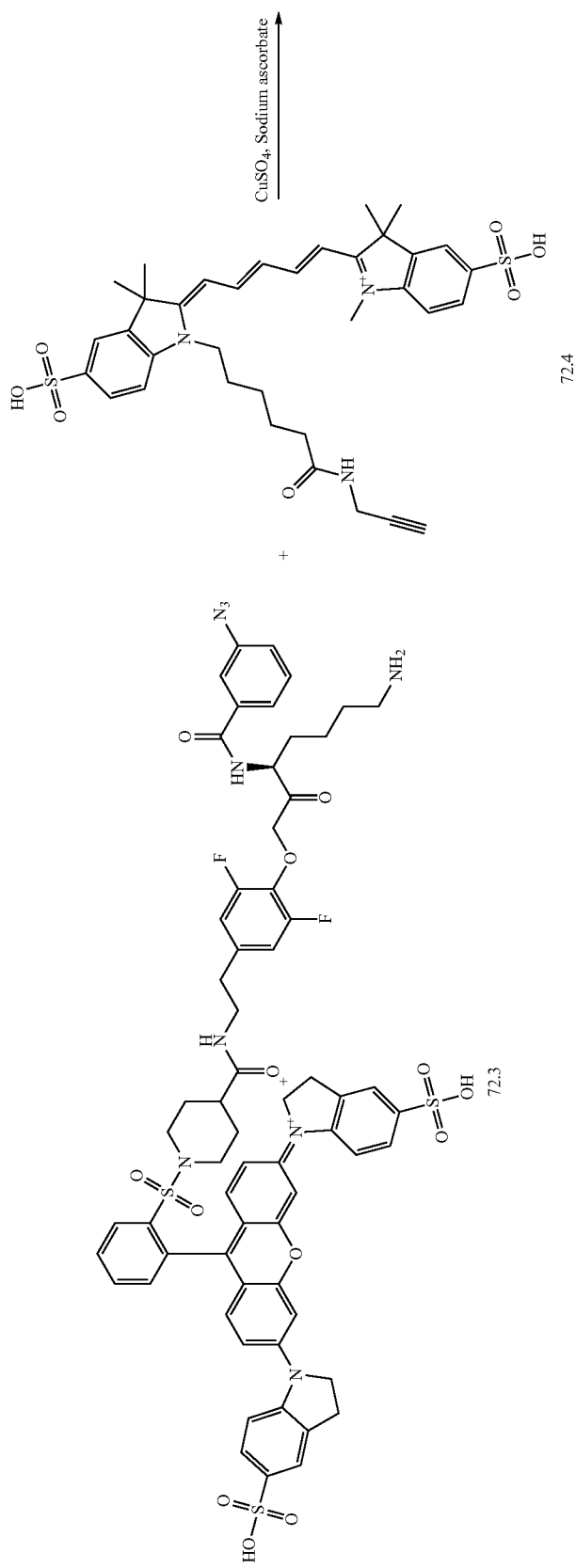

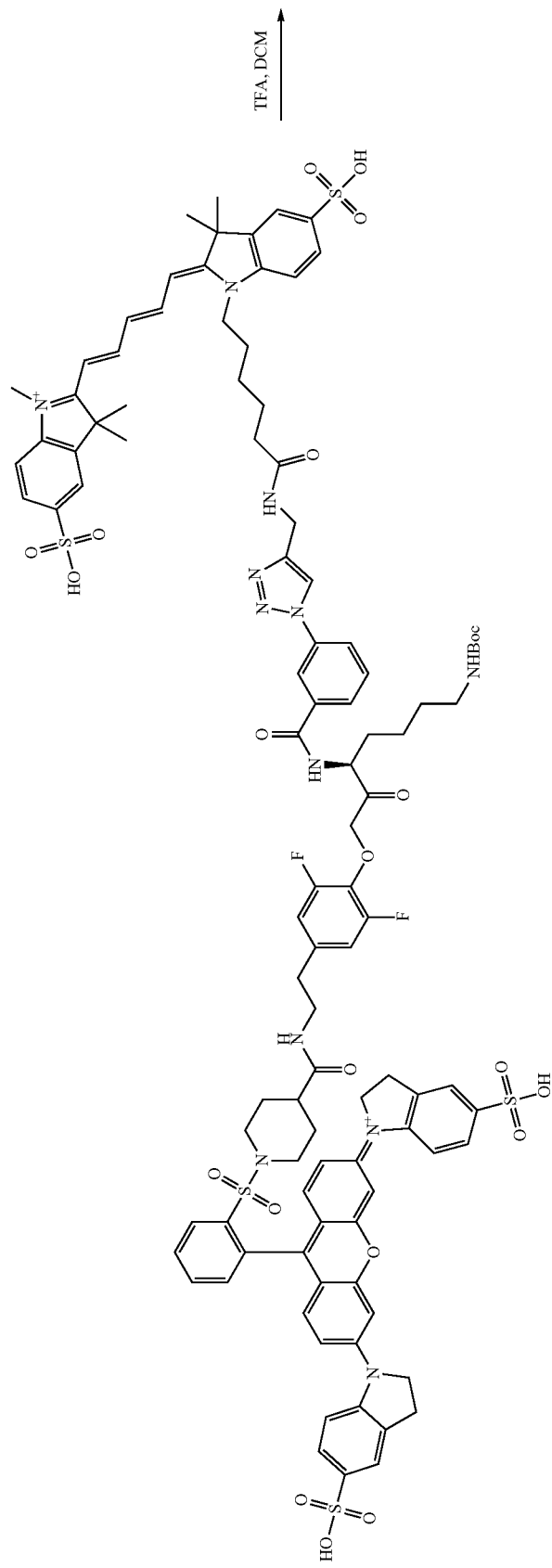

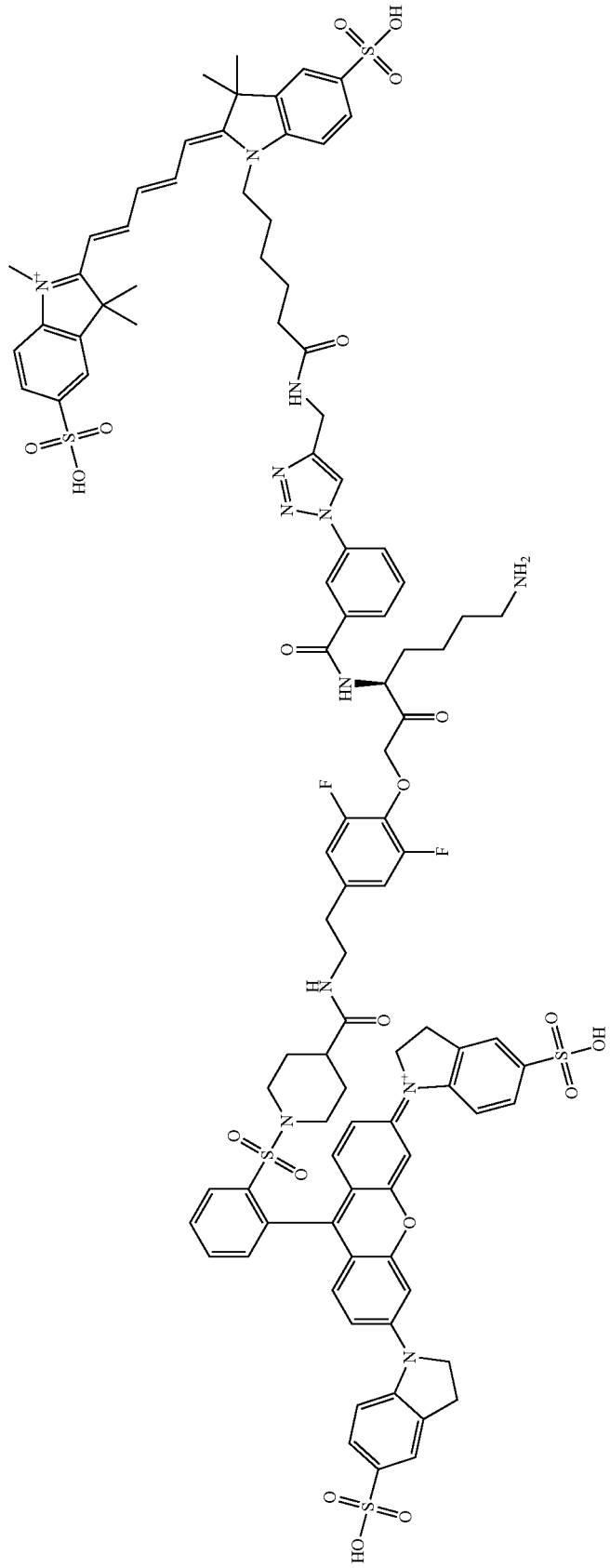
72

Example 67. Inhibition of Lysine Gingipain

The capacities of compounds of the present invention to inhibit the activity of lysine gingipain were measured in a fluorogenic assay similar to those described by Barret (*Biochemical Journal*. 1980, 187(3), 909). The specific assay conditions were as follows. Buffer: pH=7.5, 100 mM Tris-HCl, 75 mM NaCl, 2.5 mM $CaCl_2$), 10 mM cysteine, 1% DMSO after all additions. Protein: 0.1 nM Kgp, isolated from culture of *Porphyromonas gingivalis*, as described by Pike et al. (*J. Biol. Chem.* 1994, 269(1), 406), and Potempa and Nguyen (*Current Protocols in Protein Science*. 2007, 21.20.1-21.20.27). Fluorogenic substrate: 10 μM Z-His-Glu-Lys-MCA. Time=90 minutes. Temperature=37° C. Each compound: 10 concentrations, starting at either 100 μM or 100 nM, with lower concentrations generated by serial 3-fold dilutions. By testing a range of concentrations for each compound, the concentration required to inhibit the activity of lysine gingipain by 50% (the "$IC_{50}$") was determined. Under the described assay conditions, the signal-to-noise ratio was excellent, and the Z factor was greater than 0.6. Compounds in Table 1 were tested, as well as the compounds set forth in Table 2 below.

The capacities of compounds of the present invention to inhibit the activity of cathepsins B, H, K, L, and S were measured in similar assays. Boc-Leu-Arg-Arg-AMC (20 μM) in sodium acetate buffer (50 mM, pH 5.5) containing DTT (1 mM) and EDTA (2 mM) was used for the Cathepsin B assay. L-Arg-AMC (20 μM) in sodium acetate buffer (50 mM, pH 5.5) containing DTT (1 mM) and EDTA (2 mM) was used for the Cathepsin H assay. Z-Phe-Arg-AMC (10 μM) in HEPES buffer (50 mM, pH 7.4) containing DTT (2.5 mM) and EDTA (1 mM) was used for the Cathepsin K assay. Z-Phe-Arg-AMC (20 μM) in sodium acetate buffer (50 mM, pH 5.5) containing DTT (1 mM) and EDTA (2 mM) was used for the Cathepsin L assay. Z-Leu-Arg-AMC (10 μM) in sodium acetate buffer (25 mM, pH 4.5) containing DTT (2.5 mM) and NaCl (50 mM) was used for the Cathepsin S assay. The capacities of the compounds to inhibit the activity of cathepsins F, V, and Z were also measured. Compounds in Table 1 were tested, as well as the compounds set forth in Table 2 below.

TABLE 2

Comparative Lysine gingipain inhibitors.

| Compound No. | Compound Structure |
|---|---|
| 73 | (structure) |
| 74 | (structure) |
| 75 | (structure) |

$IC_{50}$ values for inhibition of Kgp and cathepsins by compounds of the invention are set forth in Table 3. The results show that the compounds of the invention and reference compound 73 are comparable with respect to Kgp inhibition activity, having sub-nanomolar Kgp $IC_{50}$ values. Surprisingly, the compounds of the invention exhibit superior selectivity for Kgp. For example, the CatH and CatS $IC_{50}$ values for compound 2 are more than ten times higher than the $IC_{50}$ values for reference compound 73, indicating that compound 2 is a less effective cathepsin inhibitor than reference compound 73. The CatB $IC_{50}$ value for compound 2 is more than 20 times higher than the CatB $IC_{50}$ value for reference compound 73. The CatK and CatL $IC_{50}$ values for compound 2 are more than 100 times higher than the $IC_{50}$ values for reference compound 73.

The decreased cathepsin inhibition activity of the compounds is advantageous because cathepsins are lysosomal proteases implicated in a number of important physiological processes including MHC-II-mediated antigen presentation, bone remodeling, keratinocyte differentiation, and prohormone activation. The compounds of the invention can therefore be used to selectively inhibit Kgp in a subject, resulting from invasive *P. gingivalis*, without perturbing endogenous cathepsin activity in the subject.

TABLE 3

Inhibition of Lysine Gingipain and Cathepsins by compounds of the invention.

| Compound No. | $IC_{50}$ (nM) | | | | | |
|---|---|---|---|---|---|---|
| | Kgp | CatB | CatS | CatK | CatL | CatH |
| 1a - non-racemic | ≤0.05 | 380 | 29,470 | 170 | 4680 | 560 |
| 1a - racemic | ≤0.05 | | | | | |
| 2a | ≤0.05 | >$10^4$ | >$10^5$ | 2290 | >$10^5$ | 1550 |
| 2a | 0.11 | | | | | |
| 3a | 0.64 | 52181 | >$10^5$ | >$10^5$ | >$10^5$ | |
| 4a | 0.07 | 2645 | >$10^5$ | >$10^5$ | >$10^5$ | |
| 5a | 0.15 | 21517 | >$10^5$ | >$10^5$ | >$10^5$ | |

TABLE 3-continued

Inhibition of Lysine Gingipain and Cathepsins by compounds of the invention.

| Compound No. | IC$_{50}$ (nM) | | | | | |
|---|---|---|---|---|---|---|
| | Kgp | CatB | CatS | CatK | CatL | CatH |
| 6a | 0.19 | 20337 | 42763 | >10$^5$ | >10$^5$ | |
| 7a | 1.3 | 49578 | 24054 | 20239 | 5526 | |
| 8a | 0.34 | 68264 | >10$^5$ | >10$^5$ | >10$^5$ | |
| 9a | 0.08 | | | | | |
| 10a | 0.12 | | | | | |
| 11a | 3.39 | | | | | |
| 12a | 0.08 | | | | | |
| 13a | 2.56 | | | | | |
| 14a | 6.42 | | | | | |
| 15a | 3.89 | | | | | |
| 16a | >100 | | | | | |
| 17a | >100 | | | | | |
| 18a | 0.50 | | | | | |
| 19a | >100 | | | | | |
| 20a | >100 | | | | | |
| 73 | ≤0.05 | 485 | 9980 | 20 | 700 | 110 |
| 74 | ≤0.05 | | | | | |
| 75 | 2.29 | | | | | |

Example 68. Neuroprotective Effects of Compounds of the Invention

Human neuroblastoma SH-SY5Y cells at thirteen passages were inoculated and cultured in complete medium, DMEM/F12 (Invitrogen 11330-032) supplemented with 2 mM L-glutamine (Invitrogen 25030164), 10% heat-inactivated fetal bovine serum (Invitrogen-10099141), and 1% penicillin-streptomycin (Pen/Strep; Invitrogen-15140122) in a 5% CO$_2$ incubator (Thermal Fisher 371). The cells were seeded at a density of 2-4×10$^4$ cells/well (200 µl of 1-2×10$^5$ cell/mL) in a 96-well black/flat bottom plates (Greiner-655090) manually coated with collagen type I. The plates were incubated in a CO$_2$ incubator at 37° C.

When the cell culture in the wells reached 70-80% confluency (~6×10$^4$ cells/well), they were challenged with P. gingivalis in the presence of test compounds at various concentrations, or in the absence of test compounds. Compound stock solutions were prepared via serial dilution with DMSO in a sterile v-bottom 96-well plate (2.8, 6.4, 3.2, 1.6, 0.8, 0.4, 0.2, 0.1, 0.05 and 0 mg/ml). Stock solutions (6 µL) were then transferred into a 96-deep well plate filled with 594 µL complete medium-Pen/Strep to provide working solutions for further testing (128, 64, 32, 16, 8, 4, 2, 1, 0.5 and 0 µg/mL).

The strain P. gingivalis ATCC BAA-308 was streaked out from −80° C. stock onto a brain heart infusion agar (BHA) (BD-211065). The plate was incubated for 72 h at 37° C. in an anaerobic workstation (Shanghaiyuejin, YQX-II). The atmosphere was kept at 80% N$_2$, 10% CO$_2$, and 10% H$_2$. At the time of testing, the plates were taken out of the anaerobic work station and processed in ambient atmosphere. The bacteria were harvested and suspended in complete medium-Pen/Strep (without Pen/Strep). The turbidity of the suspension was adjusted to 0.5 by Siemens MicroScan® Turbidity Meter (Siemens), which is equivalent to ~6×10$^8$ cfu/mL. The bacterial suspension was diluted in complete medium-Pen/Strep to the final bacterial density of 6×10$^8$ cfu/ml (for MOI 1:1000) including one well with no bacteria as a negative control.

The cells in testing plate were washed once with 200 µL complete medium-Pen/Strep. Then 100 µL of working solution was added. Immediately after this step, 100 µL of bacterial suspension was added. The final concentrations of the test compounds were 64, 32, 16, 8, 4, 2, 1, 0.5, 0.025 and 0 µg/mL with 1% DMSO. The testing plates were incubated at 37° C. in a 5% CO$_2$ incubator for 24 hrs.

Cell viability was determined using AlamarBlue (Invitrogen-527026). The cells in the testing plates were washed twice using complete medium-Pen/Strep to removed bacteria from the suspension. Immediately after this, 220 µL AlamarBlue/medium mix (consisting of 200 µL complete medium-Pen/Strep and 20 µL AlamarBlue) was added to each well of the testing plates using a multi-pipette. The testing plates were then incubated in a 37° C. CO$_2$ incubator for fluorescent reduced-AlamarBlue to develop, which was readable after 5-6 hours of development using a SpectraMax M2e plate reader (Molecular Devices) without saturation. Excitation and emission wavelengths were set to 530 nm and 590 nm, respectively, according to the supplier's manual (Invitrogen).

Kgp inhibitors of the invention protected SH-SY5Y neuroblastoma cells from P. gingivalis-induced cell death, as shown in FIG. 1.

Example 69. Prevention of Iron Acquisition by P. Gingivalis

Three days prior to the day of test, bacterial strains were streaked out from −80° C. glycerol stock onto Brain Heart Infusion Agar (BHA) (BD-211065) plates and incubated at 37° C. for 72 h in a YQX-II anaerobic workstation. The single colonies were picked using an inoculation loop (Greiner-731175) and suspended into 5 ml sterile saline. The turbidity of the suspension was adjusted to 0.2 (Siemens MicroScan turbidity meter), equal to ~2×10$^8$ cfu/mL. The bacterial suspension was then diluted 100× in testing media. This was used for inoculating daughter plates.

An aliquot of 100 µl of the bacterial suspension was inoculated into each well of the daughter plates. Each well contained ~1.0×10$^6$ cfu/mL bacteria, 1% DMSO, and serially diluted compounds in 200 µL Brucella Broth (BRU). The plates were incubated for 6 days at 37° C. in a YQX-II anaerobic workstation. Results of iron acquisition were read by visualizing conversion of the color of the bacteria to black.

Figure 2:
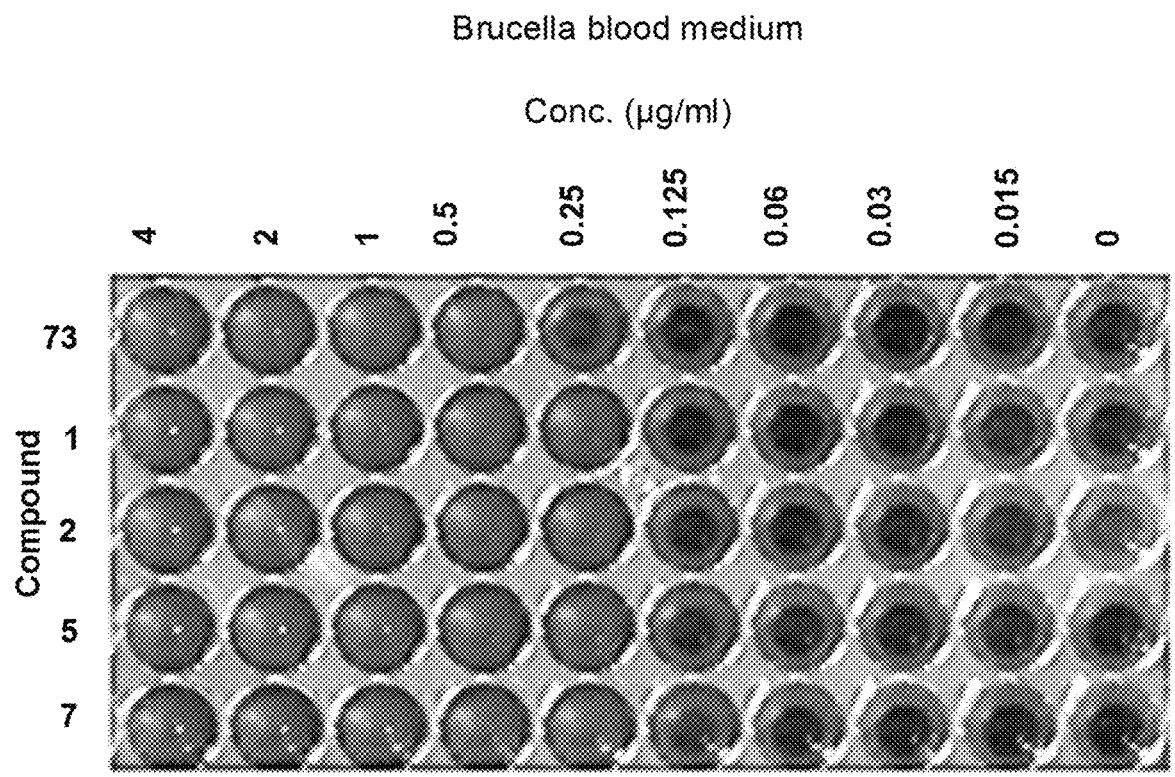
FIG. 2 shows that Kgp inhibitors of the invention prevent hemoglobin breakdown and acquisition of iron, a key survival-enhancing mechanism of *P. gingivalis*.

FIG. 2 shows that compounds of the present invention are approximately twice as effective in preventing hemoglobin breakdown and iron acquisition, a key survival mechanism of P. gingivalis, as compared to reference compound 73.

Example 70. Improved Pharmacokinetic Properties of Kgp Inhibitors

Adult male Balb/C mice (20-25 grams, Harlan Laboratories, USA) were anesthetized using isoflurane (2%, 800 mL/min O2). Bupivacaine/epinephrine was used for local analgesia and carprofen was used for peri-/post-operative analgesia. The animals were placed in a stereotaxic frame (Kopf instruments, USA). MetaQuant (MQ) microdialysis probes (regenerated cellulose membrane, 3 mm exposed surface, BrainLink, the Netherlands) were inserted into the hippocampus and a cannula was inserted into the jugular vein. Coordinates for the tips of the hippocampal probes were: anterior-posterior (AP)=−3.1 mm from bregma, lateral (L)=−2.8 mm from midline and ventral (V)=−4.1 mm from dura, the toothbar set at 0 mm. After surgery, animals were housed individually in cages and provided food and water ad libitum.

Compound 1 and reference compound 73 were prepared fresh in 2% DMSO and 98% Saline at 2 mg/mL and dosed p.o. at 5 mL/kg resulting in a final dosing concentration of 10 mg/kg.

Microdialysis sampling was initiated one day after surgery. On the day of the experiment, the probes were connected with flexible PEEK tubing to a microperfusion pump (Harvard PHD 2000 Syringe pump, Holliston, Mass. or similar). Microdialysis probes were perfused with aCSF containing 147 mM NaCl, 3.0 mM KCl, 1.2 mM $CaCl_2$), 1.2 mM $MgCl_2$, and 0.15% BSA, at a slow flow rate of 0.15 µL/min and a carrier flow (UP water, 0.04% ascorbic acid, and 0.15% BSA) at a rate of 0.8 µL/min. Microdialysis samples were collected for 15- or 30-minute periods by an automated fraction collector (820 Microsampler, Univentor, Malta) into 300 µL. After stabilization, one baseline sample was collected and reference compound 73 (10 mg/kg; PO) was administered to all animals. Samples were collected for an additional 8 hours. Plasma was also collected via the tail vein at 15, 30, 60, 120, 240 360, 480 and 720 minutes after administration of reference compound 73. All the samples were stored at −80° C. awaiting analysis by Brains On-Line. After the completion of the experiment, the mice were sacrificed, brains were collected for probe verification.

Concentrations of drug in dialysate and plasma were determined by HPLC with tandem mass (MS/MS) detection. Microdialysis samples were injected without any sample pretreatment onto the LC system (LC20XR, Shimadzu, Japan) by an automated sample injector (Sil20ACHT, Shimadzu, Japan). Plasma samples were precipitated with a mixture containing 80% ACN. Samples were further diluted with water containing 0.1% formic acid.

Chromatographic separation was performed on a reversed phase column (2.1×50 mm, particle size: 2.5 µm, Xbridge C8, Waters, USA). Components were separated using a linear gradient of acetonitrile containing 0.1% formic acid in ultrapurified H2O containing 0.1% formic acid (flow rate 0.2 mL/min).

MS analyses were performed using an API 4000 triple-quadropole system consisting of an API 4000 triple-quadro-pole detector and a Turbo Ion Spray interface (both from Applied Biosystems, USA). The acquisitions were performed in positive ionization mode, with optimized settings for the analytes. The instrument was operated in multiple-reaction-monitoring (MRM) mode using a mass transition of 405.2-to-221.3. Data were calibrated and quantified using the Analyst™ data system (Applied Biosystem) using the response of the analyte versus the concentration.

Figure 3:
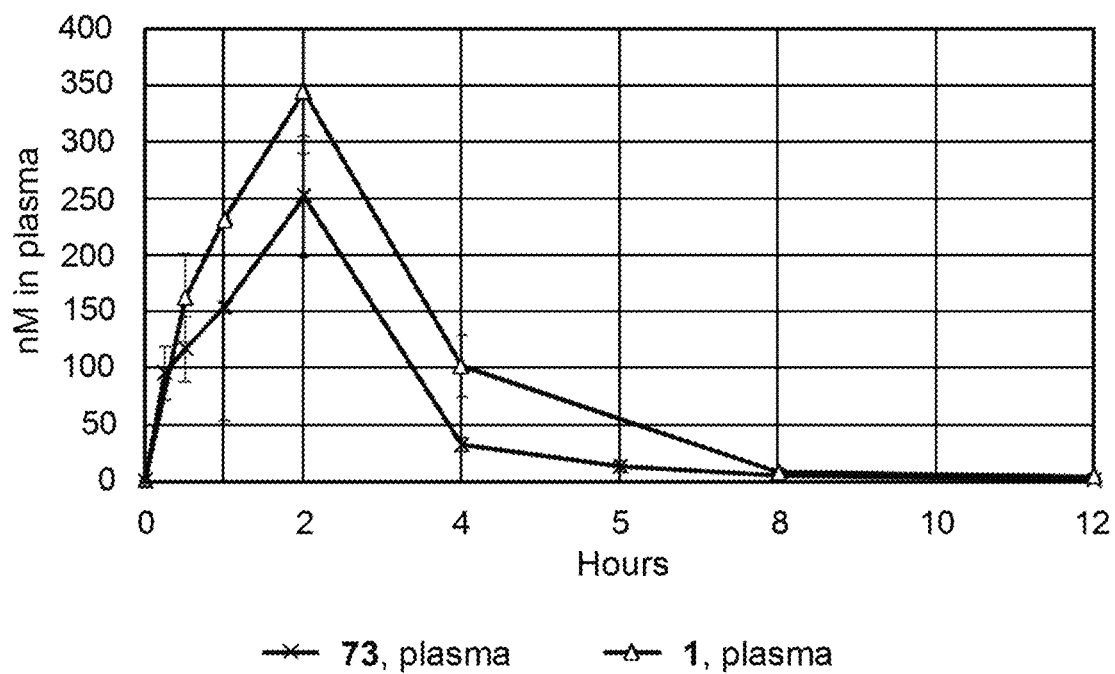
FIG. 3 shows that compounds of the invention provide increased plasma concentrations in mice.
Figure 4:
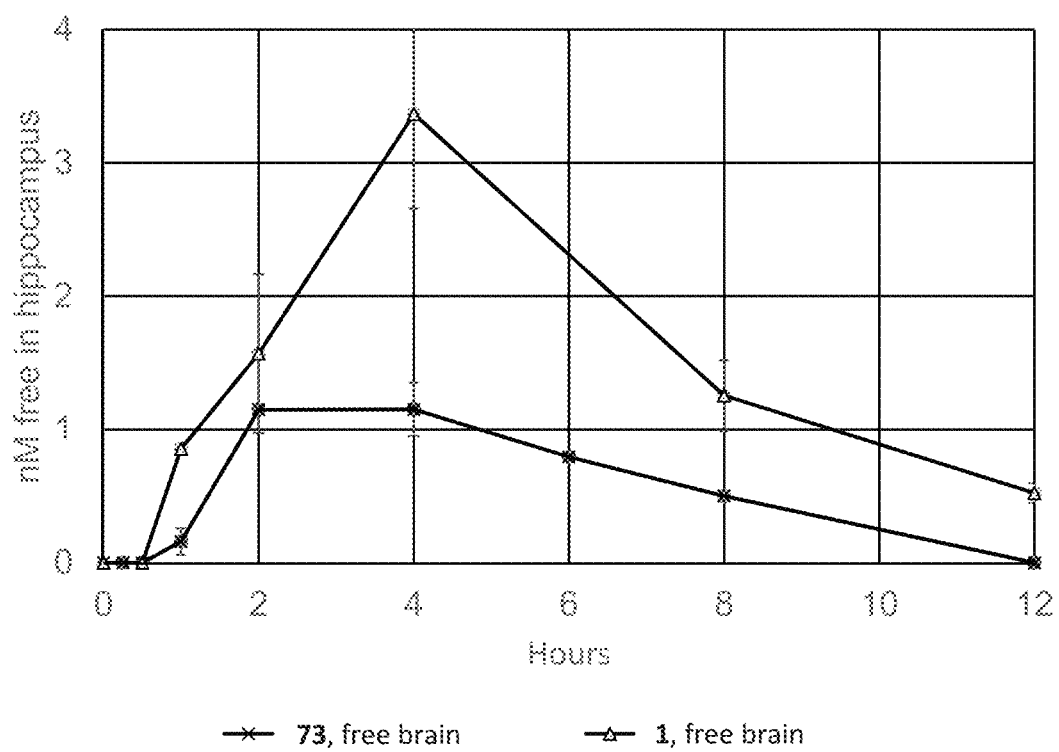
FIG. 4 shows that compounds of the invention provide increased free brain concentrations in mice.

The compounds of the invention provide increased plasma concentrations and free brain concentrations in mice as shown in FIG. 3 and FIG. 4, respectively.

Example 71. Inhibition of Lysine Gingipain

Further assays to measure the inhibitory activity of compounds of the present invention against Kgp and cathepsins B, H, K, L, and S were conducted as described in Example 66. The capacities of the compounds to inhibit the activity of cathepsins F, V, and Z were also measured. Taken together, the results of Example 66 and Example 70 show that the compounds described herein are very effective inhibitors of Kgp exhibiting nanomolar and picomolar $IC_{50}$ values. Furthermore, as shown in Table 4, a number of compounds—including compounds 1, 2, 7, and 50—show increased selectivity for Kgp over endogenous cathepsin as compared to reference compound 73. Compounds 18, 47, 55, and 69, in particular, are far more selective for Kgp over endogenous cathepsins as compared to reference compound 73.

The compounds also displayed other important advantages. For example, compounds 1, 47, 48, and 69 exhibited improved oral availability and increased plasma concentrations upon administration to male CD-1 mice (dosed p.o. at 10 mg/kg) as compared to reference compound 73. Compounds 47 and 69 produced increased concentrations in the brain and cerebrospinal fluid (CSF), as compared to reference compound 73, which can be particularly useful for treating brain conditions such as Alzheimer's disease. Other compounds, including compound 49, exhibited reduced concentrations in the brain and/or cerebrospinal fluid. Such compounds can be useful for treating peripheral conditions that do not affect the brain, such as periodontal disease or arthritis.

TABLE 4

Inhibition of Lysine Gingipain and Cathepsins by compounds of the invention.

| Cmpd. No. | $IC_{50}$ (nM) | | | | | | | | |
|---|---|---|---|---|---|---|---|---|---|
| | Kgp | CatK | CatH | CatB | CatF | CatL | CatV | CatS | CatZ |
| 73 | <0.05 | 20 | 110 | 485 | 500 | 700 | 5720 | >$10^4$ | >$10^4$ |
| 1 97% S enantiomer | <0.05 | 117 | 560 | 380 | 6,100 | 4680 | >$10^4$ | >$10^4$ | >$10^4$ |
| 21 | 0.09 | | | | | | | | |
| 2a | <0.05 | 2290 | 1550 | >$10^4$ | | >$10^4$ | >$10^4$ | >$10^4$ | |
| 7a | 1.3 | >$10^4$ | | >$10^4$ | | >$10^4$ | | >$10^4$ | |
| 18a | 0.5 | >$10^4$ | >$10^4$ | >$10^4$ | >$10^4$ | >$10^4$ | >$10^4$ | >$10^4$ | |
| 47a | 0.06 | 9000 | >$10^4$ | >$10^4$ | >$10^4$ | >$10^4$ | >$10^4$ | >$10^4$ | |
| 50a | 0.09 | 1,000 | >$10^4$ | >$10^4$ | >$10^4$ | >$10^4$ | >$10^4$ | >$10^4$ | |
| 55a | 0.12 | 1,000 | >$10^4$ | >$10^4$ | | 6,380 | >$10^4$ | >$10^4$ | |
| 69a | 0.21 | >$10^4$ | >$10^4$ | >$10^4$ | >$10^4$ | >$10^4$ | | >$10^4$ | >$10^4$ |
| 48a | 0.07 | | | | | | | | |
| 49a | 0.23 | | | | | | | | |
| 57a | 0.09 | | | | | | | | |
| 26a | 0.09 | | | | | | | | |
| 27a | 0.27 | | | | | | | | |
| 28a | 0.34 | | | | | | | | |
| 29a | 0.31 | | | | | | | | |
| 30a | 0.21 | | | | | | | | |
| 31a | 0.15 | | | | | | | | |
| 32a | 0.08 | | | | | | | | |

TABLE 4-continued

Inhibition of Lysine Gingipain and Cathepsins by compounds of the invention.

| Cmpd. No. | Kgp | CatK | CatH | CatB | CatF | CatL | CatV | CatS | CatZ |
|---|---|---|---|---|---|---|---|---|---|
| | | | | IC$_{50}$ (nM) | | | | | |
| 33a | 0.08 | | | | | | | | |
| 34a | 0.13 | | | | | | | | |
| 35a | 0.10 | | | | | | | | |
| 36a | 71.36 | | | | | | | | |
| 37a | >100 | | | | | | | | |
| 38a | 12.09 | | | | | | | | |
| 39a | >100 | | | | | | | | |
| 40a | 30.3 | | | | | | | | |
| 41a | >100 | | | | | | | | |
| 42a | 0.06 | | | | | | | | |
| 43a | 0.09 | | | | | | | | |
| 44a | 3.04 | | | | | | | | |
| 45a | 54.16 | | | | | | | | |
| 46a | 13.12 | | | | | | | | |
| 51a | 0.44 | | | | | | | | |
| 52a | 0.06 | | | | | | | | |
| 53a | 71.25 | | | | | | | | |
| 54a | 49.02 | | | | | | | | |
| 56a | 0.10 | | | | | | | | |
| 58a | 4.66 | | | | | | | | |
| 59a | 1.94 | | | | | | | | |
| 60a | 4.41 | | | | | | | | |
| 61a | 0.43 | | | | | | | | |
| 62a | 0.14 | | | | | | | | |
| 63a | 0.09 | | | | | | | | |
| 64a | 0.40 | | | | | | | | |
| 65a | 0.16 | | | | | | | | |
| 66a | 359.6 | | | | | | | | |
| 67a | 531.2 | | | | | | | | |
| 68a | 258.4 | | | | | | | | |

Example 72. Measurement of Kgp Inhibition Activity by Probe Compounds

The capacities of compounds of the present invention to inhibit the activity of lysine gingipain (Kgp) were measured in a fluorogenic assay similar to those described by Barret (*Biochemical Journal.* 1980, 187(3), 909) using 10 µM Z-His-Glu-Lys-MCA as a fluorogenic substrate at 37° C. By testing a range of concentrations for each compound, the concentration required to inhibit the activity of lysine gingipain by 50% (the "IC$_{50}$") was determined, as set forth in Table 5.

TABLE 5

Comparative Lysine gingipain inhibitors.

| Compound | Kgp IC$_{50}$ (nM) |
|---|---|
| 15a | 4 |
| 38a | 12 |
| 44a | 3 |
| 45a | 54 |
| 46a | 13 |
| 51a | 0.4 |
| 73 | <0.05 |

Example 73. Analysis of Bacterial Smears Using Gingipain Activity Probes

Figure 5A:
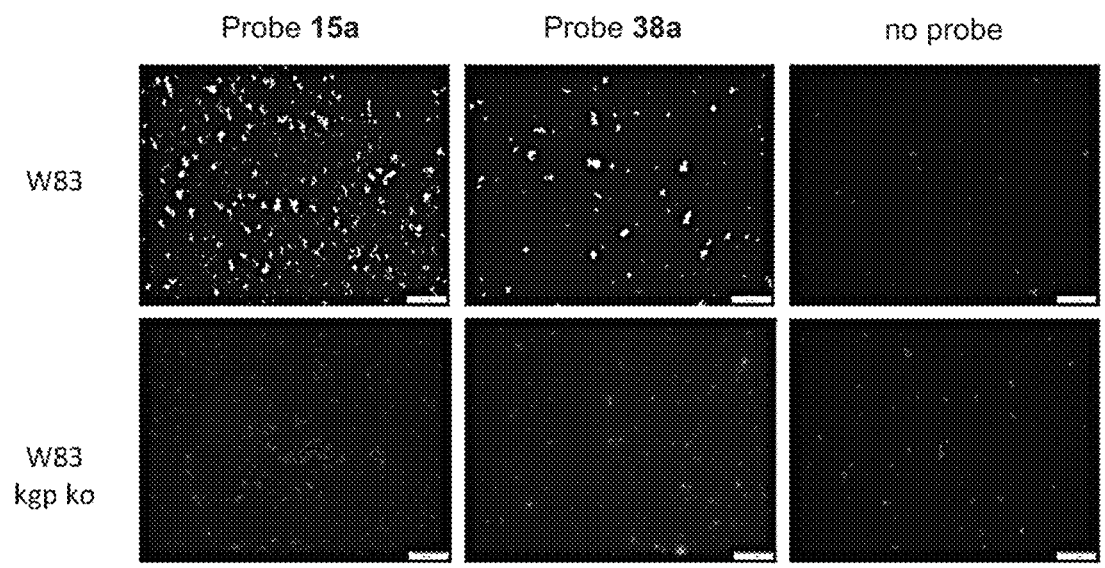
FIG. 5A shows that activity probes of the invention are useful for characterization of bacterial smears. A bacterial smear of *P. gingivalis* exposed to activity probe 15a or 38a can be detected by fluorescence microscopy. The signal is dependent on the presence of Kgp and is not detected in a bacterial smear of *P. gingivalis* W83 strain with a knockout of the Kgp gene.

W83 bacteria or a W83 Kgp knockout strain of bacteria was incubated with 1 µM activity probe 15a or activity probe 38a for 1 hr at 37° C. Bacteria were then pelleted and resuspended in 20 µl of PBS, which was dropped onto a poly-L-lysine coated slide and kept in a dark box at room temperature for about 2 hrs in order for the droplet to dry. The slide was then washed 3 times in PBS. Slides were mounted with a mounting media containing DAPI stain for bacterial DNA and visualized under fluorescence microscopy. W83 bacteria are fluorescent after exposure to activity probe 15a or activity probe 38a based on the expression of active Kgp. Kgp knockout bacteria and bacteria without exposure to activity probes show only blue DAPI fluorescence, confirming presence of the bacterial nuclei (FIG. 5A). This example demonstrates that the activity probes stain the bacteria, allowing their detection, by specific covalent reaction with Kgp.

Example 74. Analysis of Gingival Tissue Samples Using Gingipain Activity Probes

Figure 5B:
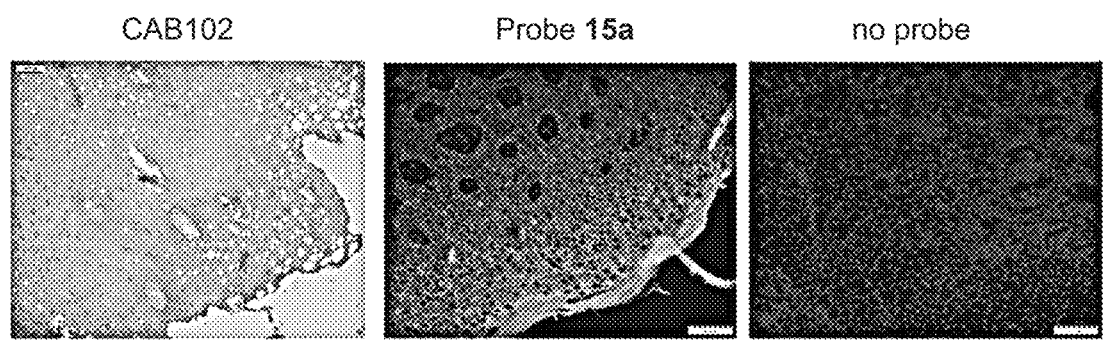

Slides of fresh frozen gingival tissue (5 micron thickness) were removed from a −80° C. freezer and thawed at RT for 10 min. Then, the tissues were immediately immersed with activity probe 15a (1 µM in PBS) in a humidified chamber, and the chamber was covered from light and incubated at 37° C. for 1 hr. Slides were then washed three times in PBS, 5 min each, then fixed in fresh 4% PFA for 15 min at RT, then washed again three times in PBS. Then slides were incubated with a 1× working Trueblack solution (Biotium) for 30 min at RT. Slides were then washed three times in PBS and mounted with anti-fade mounting media containing DAPI (FIG. 5B). The resulting micrographs demonstrated that the activity probes can be used to visualize the presence of active Kgp in human tissue samples.

Example 75. Analysis of Infected Cells Using Gingipain Activity Probes

Figure 6A:
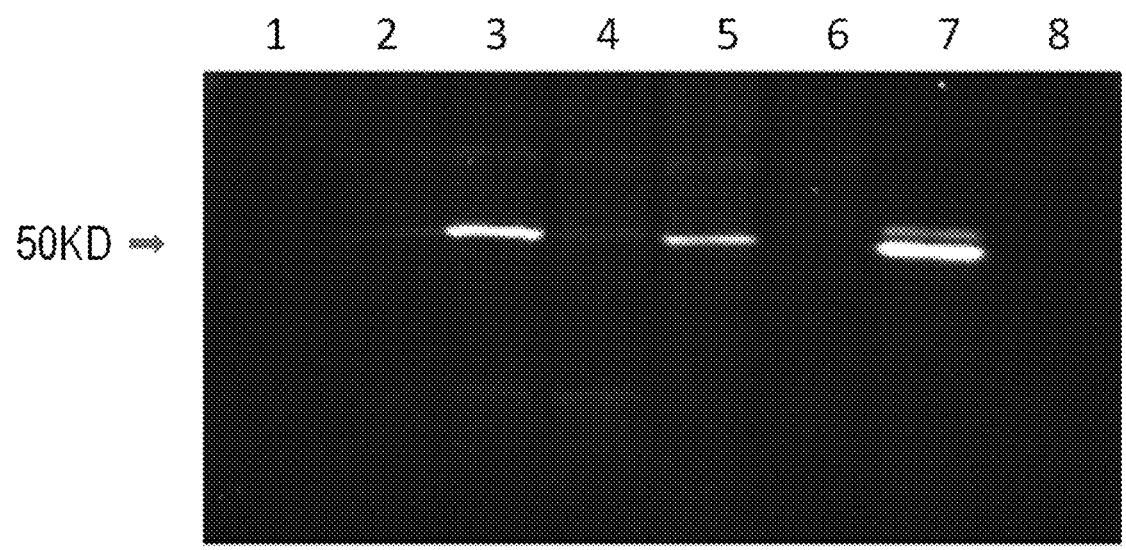

Human Jurkat cells, with and without infection by *P. gingivalis* W83 or the W83 Kgp knockout strain, were exposed to activity probe 15a. Some infected cells were pre-incubated with a non-fluorescent active site Kgp inhibitor 73 (N-[7-amino-2-oxo-1-(2,3,5,6-tetrafluorophenoxy)heptan-3-yl]cyclopentanecarboxamide) for 1 hour prior to exposure to activity probe 15a. As shown in FIG. 6A, probe 15a irreversibly binds to purified Kgp and to a protein in infected cells corresponding to the size of Kgp. The identity of this labeled protein in *P. gingivalis*-infected cells was confirmed to be Kgp by Western blot. In addition, preincubation of compound 70 (N-[7-amino-2-oxo-1-(2,3,5,6-tetrafluorophenoxy)heptan-3-yl]cyclopentanecarboxamide) with the infected cells prior to the addition of activity probe 15a blocked the binding of the probe 15a to Kgp, confirming that the probe is specific for Kgp.

Figure 6B:
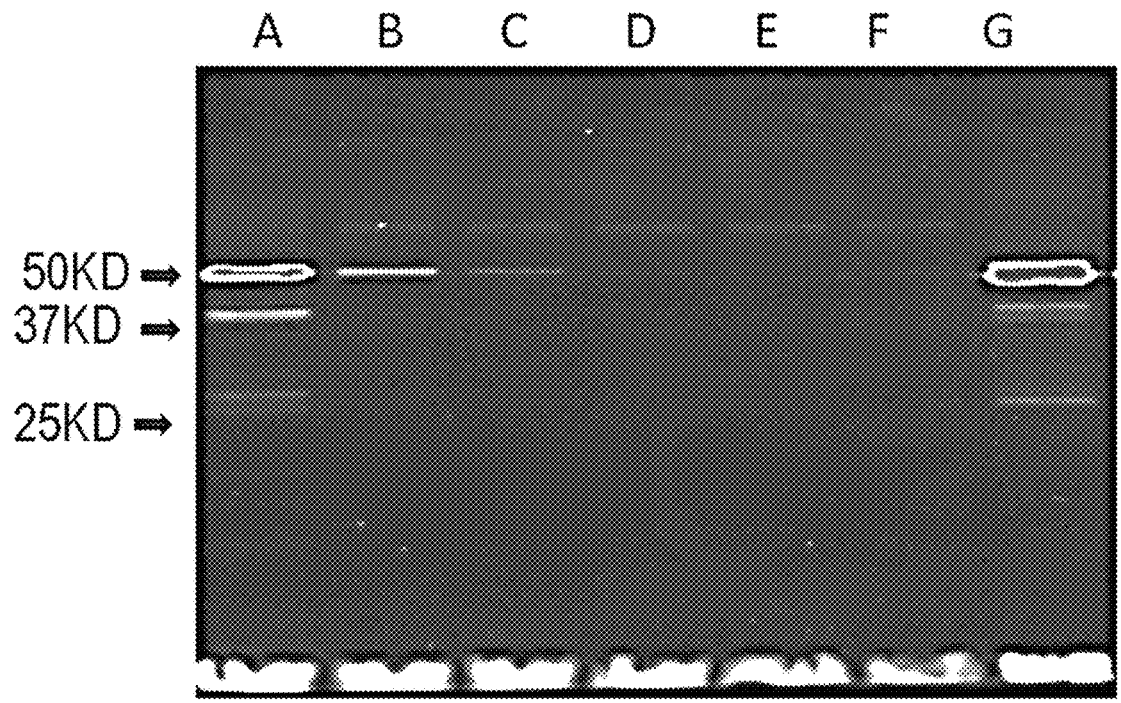
FIG. 6B shows a fluorescence image of an SDS-PAGE gel containing titrated amounts of *P. gingivalis* W83. Lane A: $10^7$ colony forming units (CFU); Lane B: $10^6$ CFU; Lane C: $10^5$ CFU; Lane D: $10^4$ CFU; Lane E: $10^3$ CFU; Lane F: $10^2$ CFU: 10; Lane G: purified Kgp. The titrated fluorescence data can be used to quantify *P. gingivalis* infection in biological samples.

A titration of the bacteria in the Jurkat cell growth allowed for quantitative determination Kgp levels in infected cells (FIG. 6B). This example demonstrates that Kgp can be quantitatively detected in the bacteria and bacteria infected cells and that it can also be used to measure target engagement of an inhibitor.

Example 76. Analysis of Buccal Cell Samples Using Gingipain Activity Probes

Figure 7:
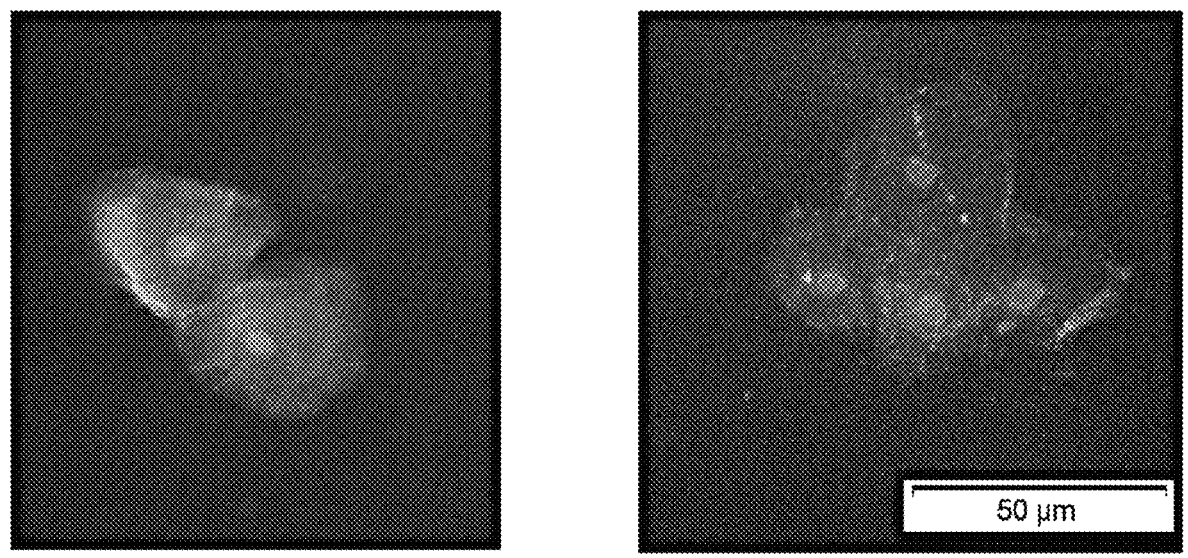
FIG. 7 shows fluorescence microscope imaging of buccal cells, obtained from the oral cavity of human subjects, incubated with activity probe 15a and analyzed for activity probe binding. Punctate staining with activity probe 15a indicates the presence of Kgp in some cells. The left image shows this punctate staining whereas the cells in the right panel show cells that do not stain with the probe and are presumed to be uninfected with *P. gingivalis*. The blue dye is a DAPI stain for cell nuclei.

Buccal cells harvested from several human donors with a sterile loop were suspended in a solution of activity probe 15a (1 µM in PBS). Cells were incubated for 1 hr at 37° C. and pelleted. Cells were resuspended in 20 µL of PBS and placed on poly-L-lysine coated slides, washed, and dried. Slides were mounted with antifade mounting media containing DAPI and visualized under a fluorescence microscope. Some buccal cells incubated with activity probe 15a showed pronounced, punctate staining while others did not (FIG. 7), indicating the presence of Kgp in some cells. This example demonstrates that *P. gingivalis* and the presence of Kgp could be detected in oral human buccal cell samples.

Example 77. Use of Biotinylated Activity Probes for Isolation and Analysis of Gingipains

Figure 8:
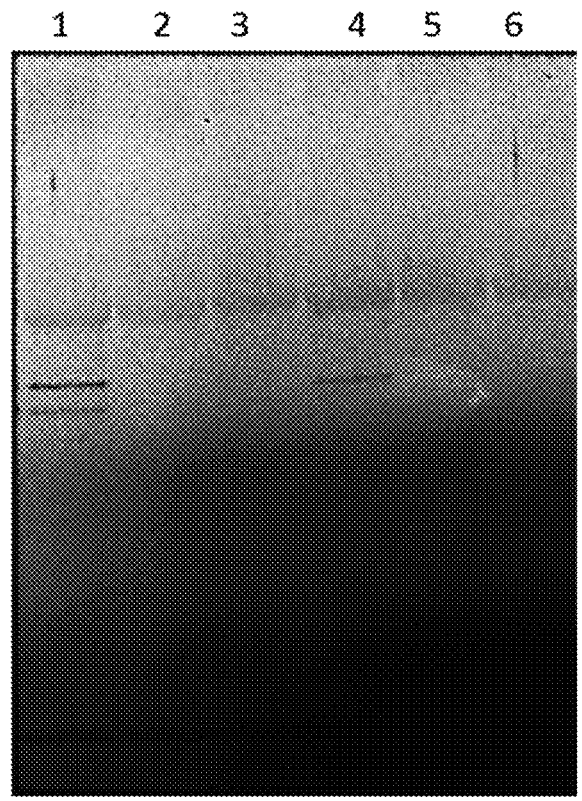
FIG. 8 shows that biotin activity probe 51a can be used to covalently label Kgp in *P. gingivalis* lysates for subsequent binding of labeled Kgp to streptavidin beads. After release from the beads, labeled Kgp was analyzed by SDS-PAGE and detected on a Western blot with the polyclonal Kgp antibody CAB102. Kgp was pulled-down via this method and detected from at least $10^6$ CFU of *P. gingivalis*. Lane 1: purified Kgp. Lane 2: *P. gingivalis* W83, $10^2$ CFU. Lane 3: W83, $10^4$ CFU. Lane 4: W83, $10^6$ CFU. Lane 5: Kgp knockout strain, $10^6$ CFU. Lane 6: probe 51a only.

*P. gingivalis* W83 was lysed with B-Per buffer for 15 min at 4° C. The resulting supernatant was spiked with biotin Kgp activity probe 51a, 2 mM, and incubated at room temperature for 1 hr. 5 mg of streptavidin-beads were incubated with all samples for 1 hr at room temperature on an inverting platform. The beads were collected after 1 hr and heated at 100° C. for 5 min with 0.1% SDS to disrupt biotin-streptavidin binding. The resulting supernatants were analyzed by SDS-PAGE and Western blotting for specific detection of Kgp with CAB102 (FIG. 8). This example demonstrates that a biotin probe can be used for pull down and quantification of active Kgp.

Example 78. Detection of Kgp Using a Cy5 Activity-Based Probe

This example demonstrates the detection of active Kgp utilizing probe compound 71, a Cy5-conjugated activity based probe that irreversibly binds to Kgp. It has a warhead that binds to the Kgp active site, a peptide-based core, and a Cy5 fluorophore for detection. Labeled target proteins can be visualized by biochemical separation of a sample with fractionation by 2-D gel electrophoresis and detection of fluorescent signals from Cy5 at the appropriate excitation and emission wavelength. Incubation of a fixed concentration of the probe following binding of Kgp to a test compound (e.g., a candidate Kgp inhibitor) results in binding of the activity probe to Kgp active sites not already bound by the test compound.

Preparation of *P. gingivalis* Lysate.

$10^8$ bacteria were collected and centrifuged at 5000 g for 10 min at 4° C., and the supernatant was discarded. The bacterial cell pellet was lysed with 1 mL of B-Per lysis buffer (Thermo Fischer) on ice for 10 min, then centrifuged for 10 min at 14000 g, 4° C. Supernatant-containing protein lysate was collected. Biological samples were lysed with B-Per lysis buffer for 10 min at 4° C.

Cy5 Direct Labeling of Kgp.

Biological samples, *P. gingivalis* lysate or purified Kgp were incubated with quenchable Cy5 probe compound 71 (1 µM) for 1 h at 37° C. with shaking. Then, samples were denatured with NUPAGE LDS sample buffer (Thermo Fisher) containing 50 mM DTT at 95° C. for 10 min and subjected to SDS-PAGE electrophoresis using a Criterion 4-15% precast gel (Bio-Rad) and Tris/Glycine/SDS running buffer (Bio-Rad). The gel was run at 75V for 10 min and then 125V for 1.5 h. The gel was then removed from the plastic cassette and subjected to Cy5 visualization with a ChemiDoc imaging system (Bio-Rad).

Immunoprecipitation of Kgp Labeled with Cy5 Probe.

Samples were labeled with quenchable Cy5 probe compound 71 (1 µM) for 1 h at 37° C. with shaking. For immunoprecipitation of Cy5 labeled Kgp, the samples were then incubated with 10 µg of rabbit polyclonal CAB102 antibody with rotation overnight at 4° C. Then, samples were incubated with prewashed Dynabead Protein G beads with rotation for 20 min at room temperature. The samples were washed 4 times with 200 µL of washing buffer, using a magnetic rack. The beads were suspended in 20 µL, of elution buffer and 10 µL NUPAGE LDS sample buffer, 50 mM DTT, heated at 70° C. for 10 min. The immunoprecipitated proteins were then eluted from the magnetic beads using a magnetic rack. Samples were then subjected to SDS-PAGE electrophoresis and the Cy5 signal was visualized with a ChemiDoc imaging system (Bio-Rad).

Western Blot Analysis of Cy5 Labeled Samples.

After imaging with Cy5 detection, the SDS-PAGE gel was subjected to Western blot analysis by using a Trans-blot Turbo transfer system (Bio-Rad) to transfer proteins to PVDF membrane. The membrane was then washed with TBS for 5 min and blocked with 3% BSA in TBST buffer for 1 h or longer. The blot was then incubated with 1:1000 primary antibody CAB102 for 2 h at RT or overnight at 4° C. in blocking buffer. The blot was then washed 3 times with TBST buffer, 5 min each, then incubated with 1:50,000 Goat anti-rabbit IgG absorbed HRP conjugated antibody (Thermo Fisher, #31462) in TBST for 45 min, RT. The blot was then washed 4 times with TBST and subjected to chemiluminescent imaging using SuperSignal West Femto Maximum Sensitivity Substrate (Thermo Fisher) and a ChemiDoc imaging system.

Results.

Figure 9A:
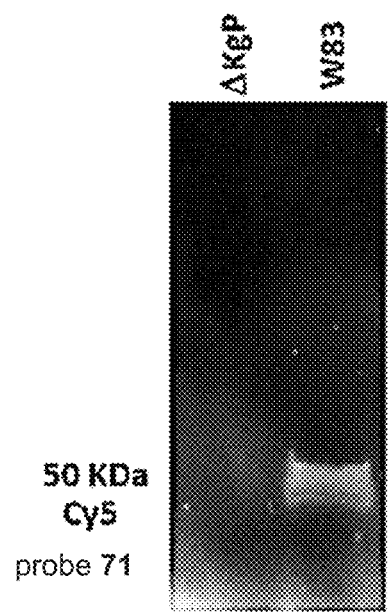
FIG. 9A shows the visualization of *P. gingivalis* W83 lysate and a *P. gingivalis* Kgp knockout strain lysate by SDS-PAGE following incubation with probe compound 71.

Detection of Kgp using probe compound 71 was sensitive, with an apparent limit of detection of 500 CFU. The detection was specific for Kgp, as was demonstrated by three experiments. First, as shown in FIG. 9A, there was specific detection of a single band of Kgp protein (50 kDa in molecular weight) in wild-type W83 *P. gingivalis* bacterial culture samples and no detection in samples from a Kgp knockout strain of *P. gingivalis*.

Figure 9B:
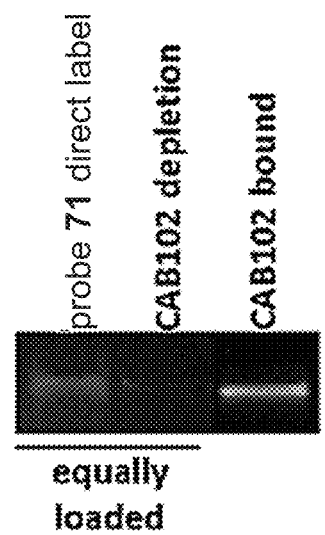
FIG. 9B shows the visualization of *P. gingivalis* lysate by SDS-PAGE following incubation with probe compound 71 with or without pre-incubation with CAB102 antibody-conjugated beads.

Second, labeling of Kgp by probe compound 71 was specifically depleted by preincubation and immune-depletion with CAB102, a Kgp-specific polyclonal antibody. Lane 1 in FIG. 9B shows the labeling of wild-type *P. gingivalis* with probe compound 71, while land 2 in FIG. 9B shows sample analysis after immune-depletion of labeled Kgp with rabbit polyclonal antibody CAB102-conjugated beads. Lanes 1 and 2 were equally loaded with one-tenth of the total sample volume. Lane 3 of FIG. 9B shows the elution of labeled Kgp from CAB102-conjugated beads. Two-thirds of the total elution volume was loaded in lane 3.

Figure 9C:
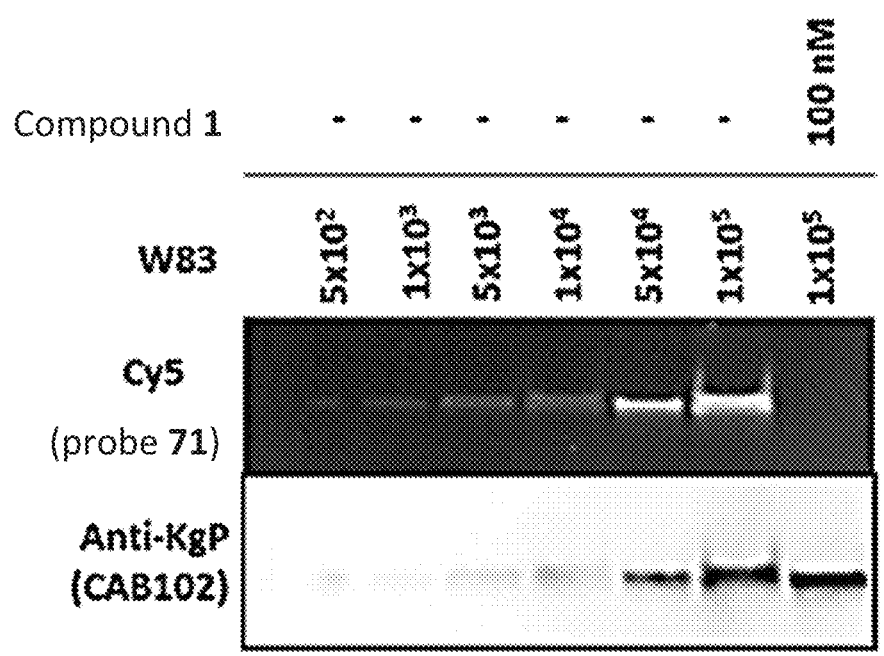
FIG. 9C shows the analysis of labeled *P. gingivalis* W83 lysate by SDS-PAGE and Cy5 signal visualization (top panel) or Western blot with detection by CAB102 primary antibody and chemiluminescent detection (bottom panel).

Finally, detection is completed by preincubation with compound 1 (100 nM), a concentration that is selective for Kgp and does not inhibit the homologous arginine gingipain, Rgp. FIG. 9C shows labeling and detection of wild-type *P. gingivalis* at different concentrations to determine the limit of detection of the labeling assay. The highest CFU (colony forming unit) sample was also incubated with compound 1 at 100 nM. Samples were detected by western blotting with the CAB102 antibody as well as by visualizing the Cy5 signal. This last study demonstrates that compound 1 competes for active site binding with probe compound 71, enabling detection of the level of Kgp target engagement by a Kgp small molecule inhibitor such as compound 1. These data establish labeling of Kgp protein in intact bacterial cultures and purified protein by probe compound 71 and establish a method to assess target engagement in compound-treated samples.

Example 79. Multiple Aspects of *P. gingivalis* Infection are Treated by Inhibiting Kgp

*P. gingivalis* applied over several weeks directly to the gingiva of mice has been used as a model for periodontitis. Alveolar bone resorption, a hallmark of periodontitis progression, is typically observed when this model employed. More recently, use of the model has also led to the discovery of a significant amount *P. gingivalis* in the brain, which accumulates concomitantly with oral colonization and which subsequently leads to detrimental effects such as inflammation and loss of hippocampal neurons. As described below, Compound 1 and other compounds disclosed herein can prevent these effects when used to treat subjects infected with *P. gingivalis*.

At the beginning of the study, eight week old BALB/C female mice received antibiotic in drinking water (sulfamethoxazolum 0.87 mg/mL, trimethoprimum 0.17 mg/mL) for 10 days to reduce microbiome protection from experiment infection. Experimental periodontitis was induced by ligature placement followed by multiple exposures to *P. gingivalis*. During the ligature procedure mice were anesthetized with an intraperitoneal injection of ketamine (200 mg/kg) and xylazine (10 mg/kg), and eyes were lubricated with ointment (Puralube Vet; Pharmaderm, Melville, N.Y.). Next, a 5-0 silk ligature (Roboz Surgical Instrument Co.) was tied around the upper maxillary left and right second molar. Sutures were applied and tied gently to prevent damage to the periodontal tissue. The ligature was left in position for the entire experimental period so that inflammation could be constantly induced by colonization of bacteria inside of it.

Mice (n=8-10/arm) were infected for 6 weeks every other day. For infection, 100 ft. of bacteria solution were applied topically to the buccal surface of the maxillae. For preparation of the bacteria, *P. gingivalis* W83 (ATCC, Rockville, Md.) was streaked on Tryptic Soy Broth (TSB) agar plates (5% sheep blood, supplemented with 0.5 mg/mL L-cysteine, 5 μg/mL hemin, and 0.5 μg/mL vitamin K) and grown under anaerobic conditions at 37° C. for 5-7 days. Samples were then inoculated in TSB with hemin, vitamin K and L-cysteine (TSB-HKC) until mid-log phase ($OD_{600}$=0.5-0.7). Bacteria were washed in PBS and prepared at final concentration of $1\times10^{10}$ cells/mL in PBS+2% methylcellulose (CMC).

Mice received vehicle or compound 1 for 5 weeks (day 36-70). Compound 1 was administered orally b.i.d. in PBS at 3, 10, or 30 mg/kg into the oral cavity. Vehicle-treated animals received PBS only. At 5 weeks, a subgroup of animals (n=16) were euthanized to gather baseline measurements before the start of treatment. After 10 weeks, mice were euthanized and the brain, serum, and maxillary tissues were harvested and frozen in liquid nitrogen.

Figure 10:
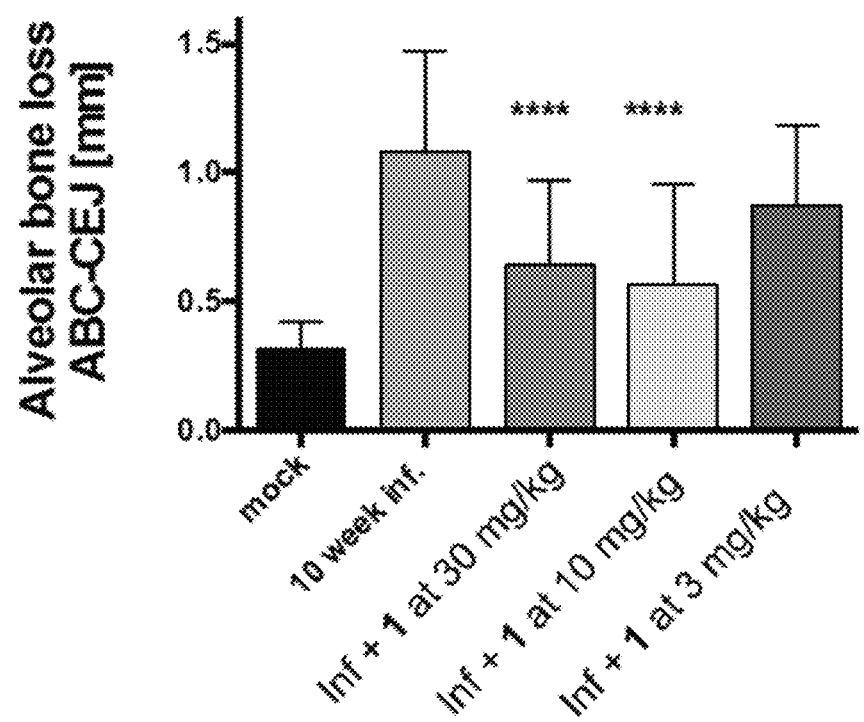
FIG. 10 shows alveolar bone loss in mice infected with *P. gingivalis*, with or without treatment with Compound 1.

Bone loss in the maxillae was measured ex vivo blinded using OsiriX MD software (PixmeoSARL, Bernex, Switzerland). Point of measurements were obtained using 3D Multi Planar Reconstruction (MPR) view where the maxillae were sliced straight along the superficial roots of second molar and the posterior root of first molar, with a tangent of the anterior root of the first molar. The distance between the cementoenamel junction (CEJ) and the alveolar bone crest (ABC) was measured from the CEJ to a reference line on the ABC which was placed perpendicular to the superficial root one each side of the second molar. FIG. 10 shows infection-induced alveolar bone loss at the 10 week endpoint in mice treated with vehicle or Compound 1 (### $p<0.0001$). Bone loss was improved by treatment with Compound 1 (30 mg/kg or 10 mg/kg) during week 5-10. Treatment with Compound 1 at 3 mg/kg trended to improvement but did not result in significant improvement over vehicle treated mice. (ANOVA: $F (5, 24)=15.71$, $p<0.0001$; t-test with Bonferroni correction: $p<0.005$, *$p<0.001$).

Figure 11:
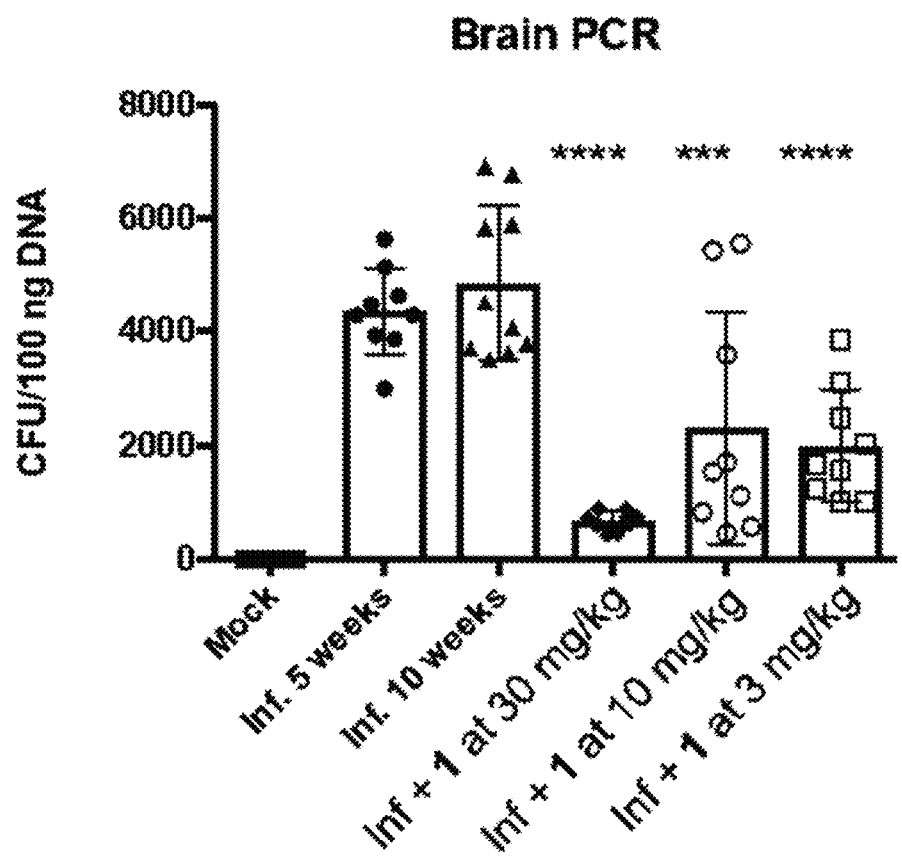
FIG. 11 shows a reduction of *P. gingivalis* DNA in the brain tissue of infected mice upon treatment with Compound 1.

DNA was extracted from brain tissue using the DNeasyBLOOD & TISSUE KIT (Qiagen, Germany) according to manufacturer's protocol. Taqman qPCR was performed with Kapa Probe fast qPCR Mix (Rox Low) on a Bio-Rad CFX96 Real-Time System C1000 Touch ThermalCycler with forward and reverse primers (5'-AGCAACCAGCTACCG-TT-TAT-3' and 5'-GTACCTGTCGGTTTACCATCTT-3', respectively), and a detection probe (6-FAM-TACCAT-GTTTCGCAGAAGCCCTGA-TAMRA). The primers were based on a single copy of *P. gingivalis* arginine-specific cysteine-proteinase gene. Duplicate samples were assayed in a total volume of 10 μL, containing 100 ng of template brain genomic DNA solution, TaqMan Universal PCR Master Mix (2×) (Kapa Biosystems, USA), and the specific set of primers (final concentration 5 μM) and probe (final concentration 4 μM) (GenoMed, Poland), corresponding to 562.5 nM for the forward and reverse primers and 100 nM for the probe primer. After an initial incubation step of 2 min at 50° C. and denaturation for 95° C. for 20 sec, 40 PCR cycles (95° C. for 20 s, 60° C. for 30 sec) were performed. The number of copies of the *P. gingivalis* genome was calculated by matching Cq values with a standard curve prepared from serial dilutions of cultured *P. gingivalis* W83 (WT). As shown in FIG. 11, significant copy numbers of the *P. gingivalis*-specific RgpB gene were found in brain tissue after 5 and 10 weeks of infection. Treatment with 30 mg/kg Compound 1 between week 5 and 10 resulted in a ~80% reduction (*$p<0.001$) in the DNA copy number. Treatment with 10 mg/kg or 3 mg/kg resulted in a ~50% reduction ($p<0.01$, ***$p<0.001$) in the copy number. ANOVA: $F (6, 59)=23.31$, $p<0.0001$; t-test with Bonferroni correction.

Figure 12:
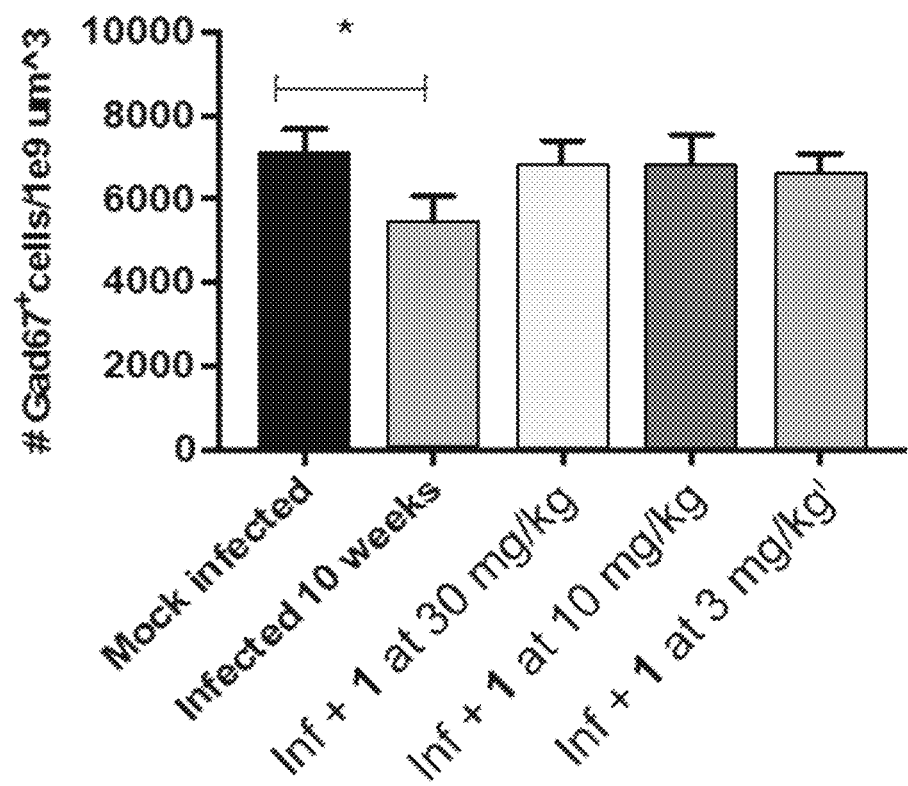
FIG. 12 shows a reduction in hippocampal neuron loss in the brain tissue of infected mice upon treatment with Compound 1.

Quantification of GAD67 positive interneurons was performed with CellSens 1.5. Software. The area of the hilus was defined as the area between the blades of the dentate gyrus connected by a straight line on the open side. The number of cells on every 40th section through the hippocampus was counted. As shown in FIG. 12, quantification of GAD67 positive interneurons in the dentate gyrus revealed a ~25% loss of interneurons in infected mice (*p<0.05) at 10 weeks, compared to mock-infected controls. In contrast, GAD67+ cells in mice treated with Compound 1 were at the same level as the GAD67+ cells in the mock-infected mice. The results are in FIG. 12 are presented as the number of cells per volume tissue.

Taken together, the results in this example show that Compound 1 treats multiple aspects of P. gingivalis infection, including alveolar bone loss, bacterial levels in brain tissue, and hippocampal neuron loss. Compound 1 was also observed to reduce induction of brain abeta42 and neuroinflammation in related studies. By inhibiting Kgp, the compounds disclosed herein can treat P. gingivalis infection itself, as well as the detrimental effects of neurological disease and other infection-associated conditions.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:
1. A compound according to Formula I:

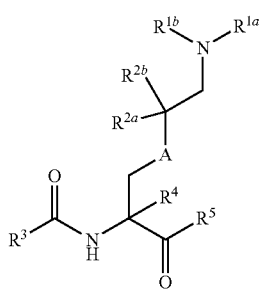

(I)

or a pharmaceutically acceptable salt thereof, wherein:
A is —CH$_2$—;
R$^{1a}$, R$^{1b}$, R$^{2a}$, R$^{2b}$, and R$^4$ are hydrogen;
R$^3$ is selected from the group consisting of C$_{3-8}$ cycloalkyl, C$_{3-8}$ alkyl,
3- to 12-membered heterocyclyl, C$_{6-10}$ aryl, and 5- to 12-membered heteroaryl, wherein R$^3$ is optionally substituted with one or more R$^{3a}$ substituents;
each R$^{3a}$ is independently selected from the group consisting of halogen, —N$_3$, C$_{1-4}$ alkyl, C$_{1-4}$ haloalkyl, C$_{1-4}$ alkoxy, C$_{1-4}$ haloalkoxy, —N(R$^c$)$_2$, —N$^+$(R$^b$)$_3$, and —NR$^c$C(O)R$^b$;
each R$^b$ is independently selected from the group consisting of C$_{1-4}$ alkyl, C$_{1-4}$ haloalkyl, and C$_{1-4}$ deuteroalkyl;
each R$^c$ is independently selected from the group consisting of hydrogen and C$_{1-8}$ alkyl;
R$^5$ is —CH$_2$R$^{5a}$; and
R$^{5a}$ is —O-phenyl, wherein phenyl is substituted with 1-5 halogens;

provided that R$^5$ is other than 2,3,5, 6-tetrafluorophenoxymethyl.

2. The compound of claim 1, or a pharmaceutically acceptable salt thereof, having a structure according to Formula Ia:

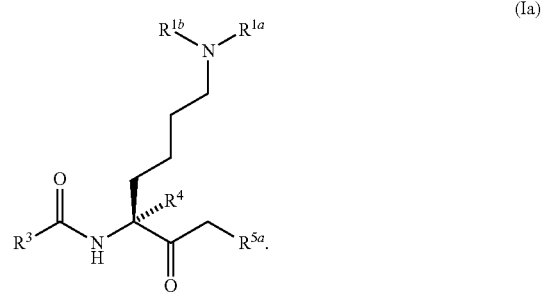

(Ia)

3. The compound of claim 1, or a pharmaceutically acceptable salt thereof, wherein R$^3$ is C$_{3-8}$ cycloalkyl.

4. The compound of claim 1, or a pharmaceutically acceptable salt thereof, wherein R$^{5a}$ is selected from the group consisting of 2,3,6-trifluorophenoxy; 2,3,5-trifluorophenoxy; 2,3,4-trifluorophenoxy; 3,4,5-trifluorophenoxy; 2,3-difluorophenoxy; 2,4-difluorophenoxy; 2,5-difluorophenoxy; 2,6-difluorophenoxy; 3,4-difluorophenoxy; 3,5-difluorophenoxy; 2-fluorophenoxy; 3-fluorophenoxy; and 4-fluorophenoxy.

5. The compound of claim 3, or a pharmaceutically acceptable salt thereof, wherein R$^{5a}$ is selected from the group consisting of 2,3,6-trifluorophenoxy; 2,3,5-trifluorophenoxy; 2,3,4-trifluorophenoxy; 3,4,5-trifluorophenoxy; 2,3-difluorophenoxy; 2,4-difluorophenoxy; 2,5-difluorophenoxy; 2,6-difluorophenoxy; 3,4-difluorophenoxy; 3,5-difluorophenoxy; 2-fluorophenoxy; 3-fluorophenoxy; and 4-fluorophenoxy.

6. The compound of claim 5, or a pharmaceutically acceptable salt thereof, wherein R$^{5a}$ is selected from the group consisting of 2,3,6-trifluorophenoxy; 2,3,5-trifluorophenoxy; 2,3,4-trifluorophenoxy; and 3,4,5-trifluorophenoxy.

7. The compound of claim 1, or a pharmaceutically acceptable salt thereof, which is selected from the group consisting of:

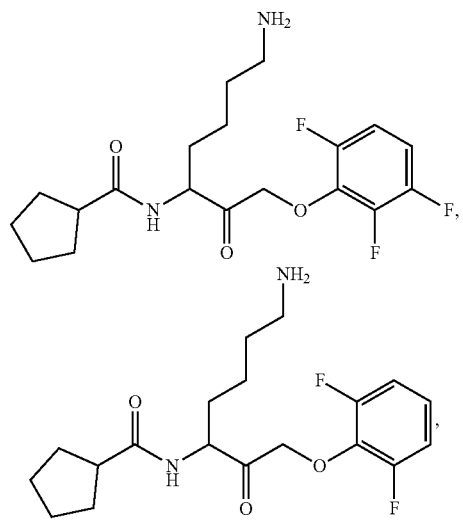

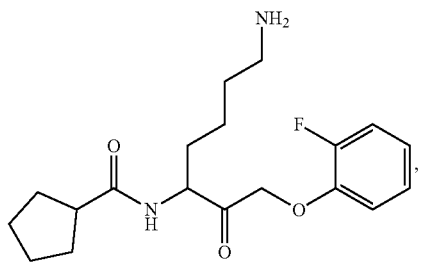,
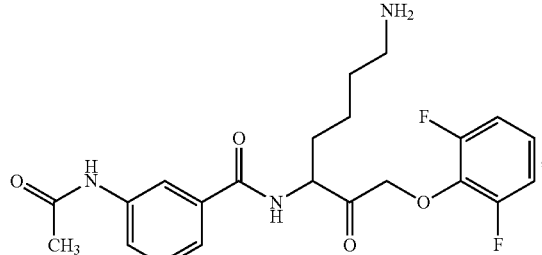,
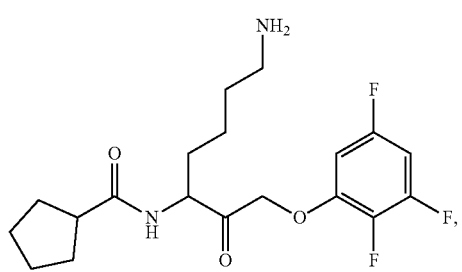,
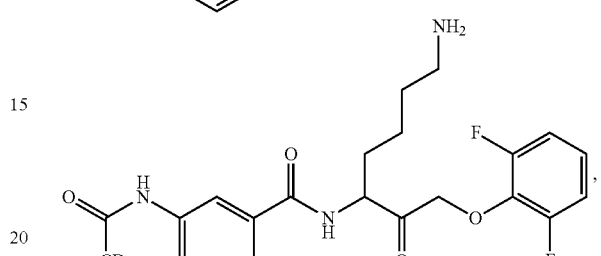,
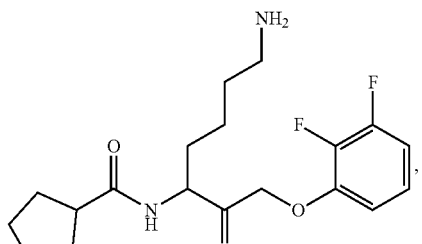,
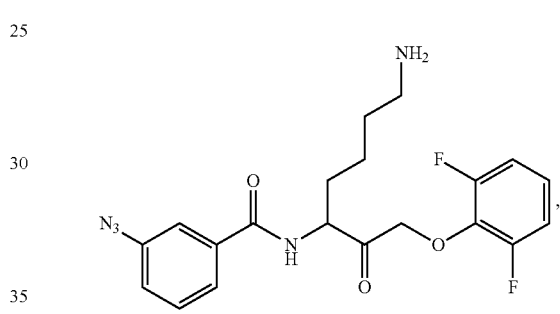,
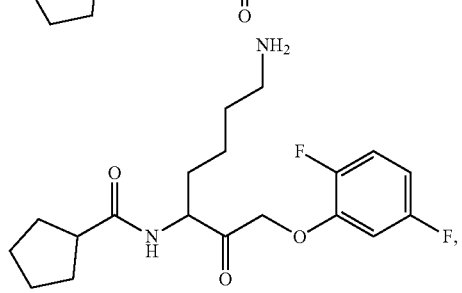,
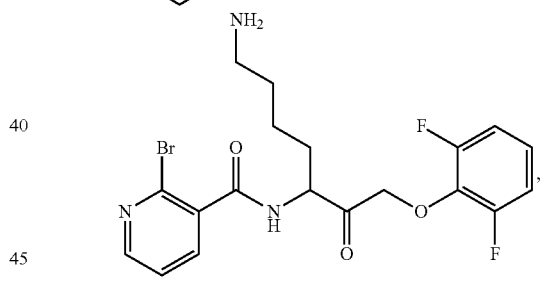,
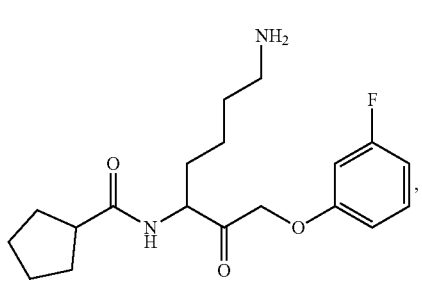,
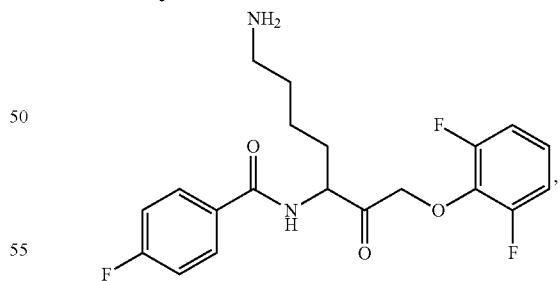,
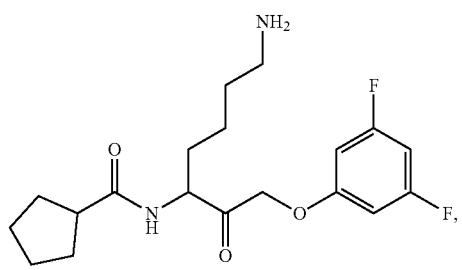,
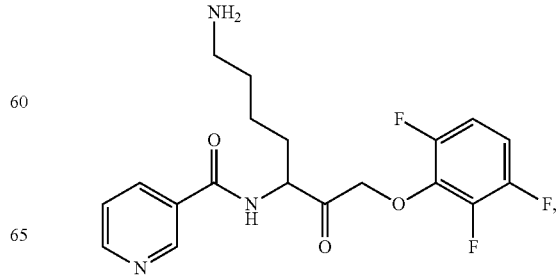,

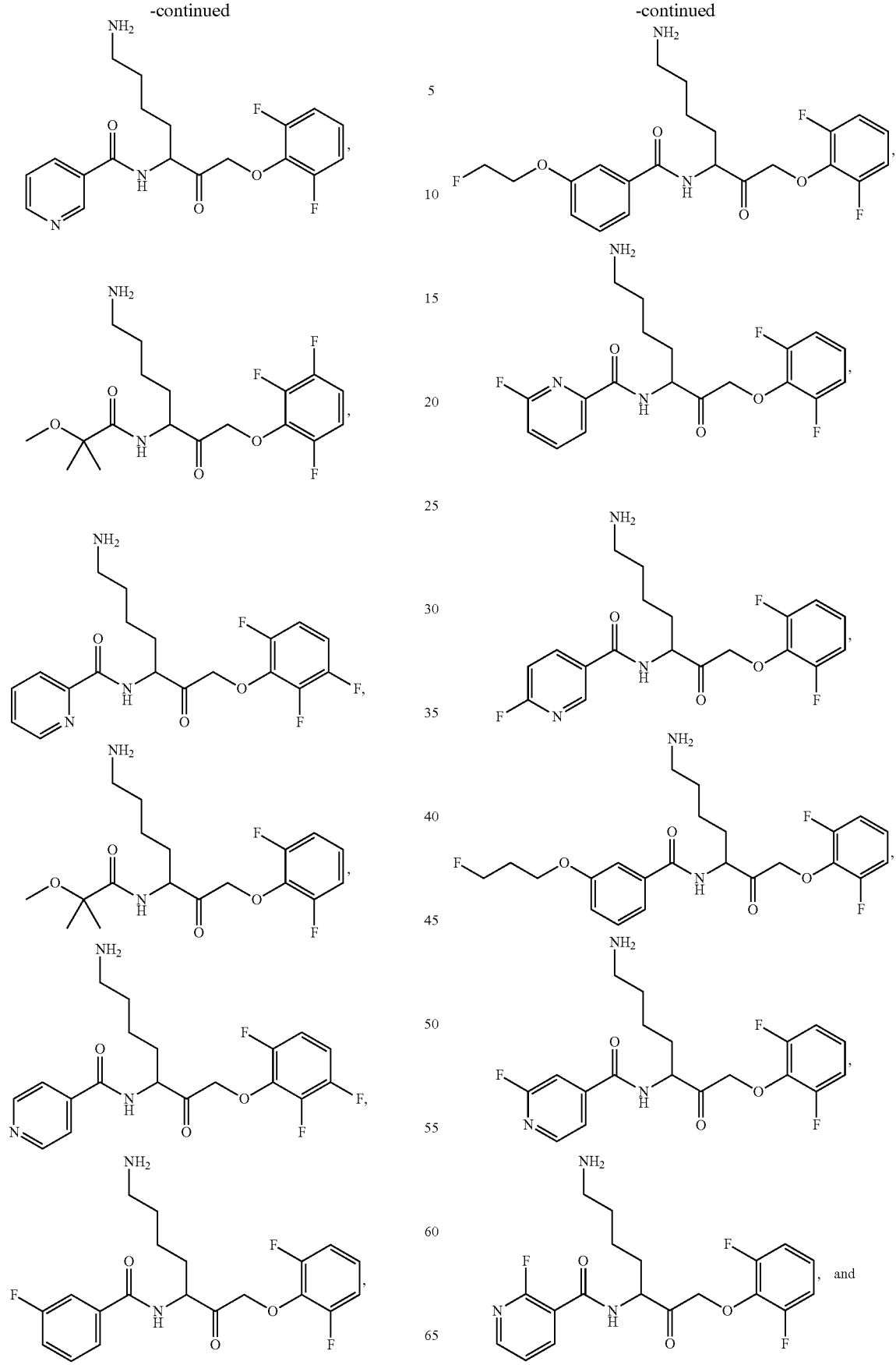

347
-continued
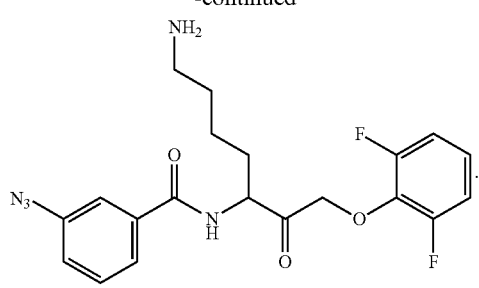
348
-continued
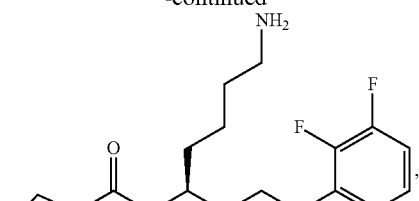
8. The compound of claim 1, or a pharmaceutically acceptable salt thereof, which is selected from the group consisting of:
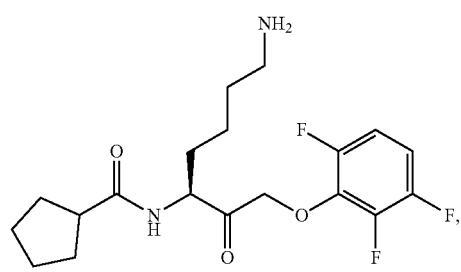
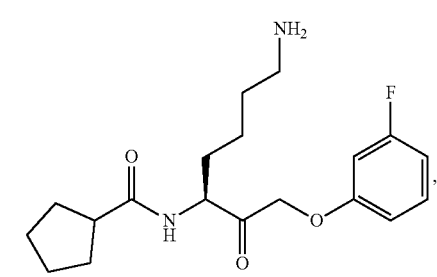
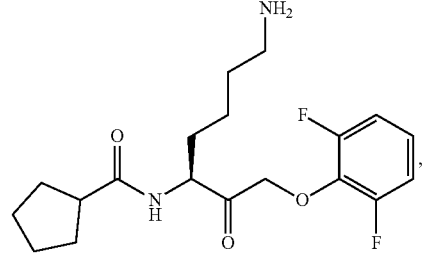
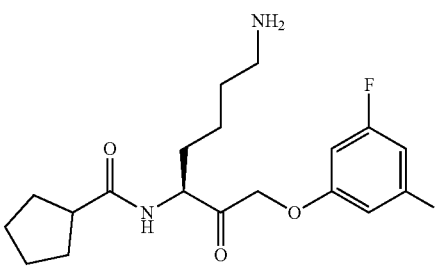
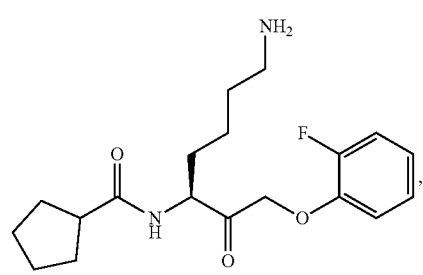
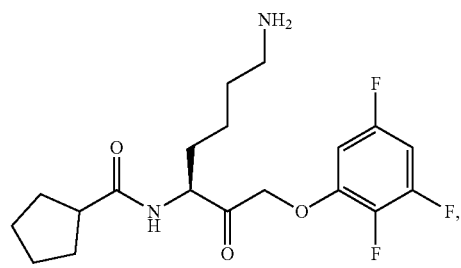
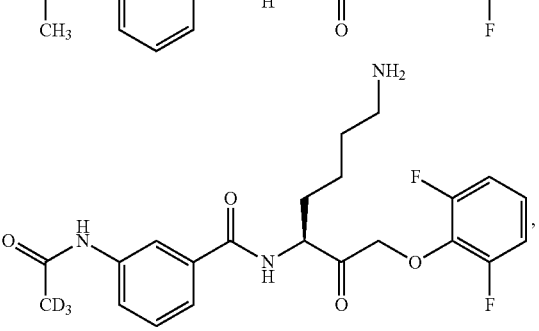

349
-continued
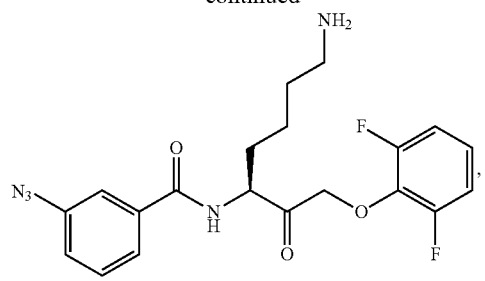
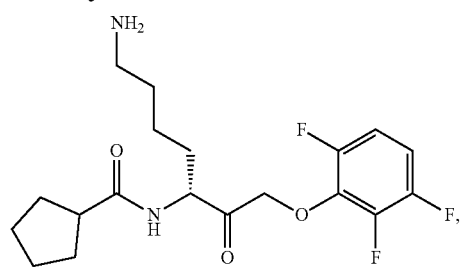
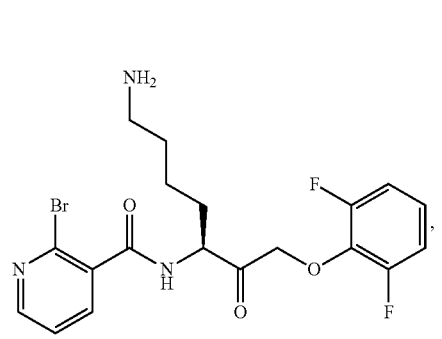
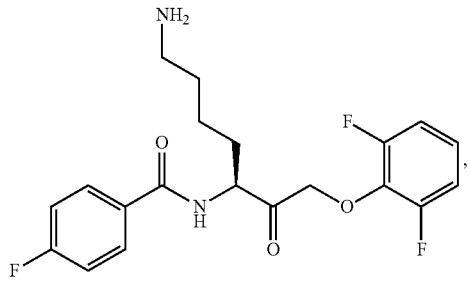 [SMILES: NCCCCC(NC(=O)c1ccc(F)cc1)C(=O)COc1c(F)cccc1F]
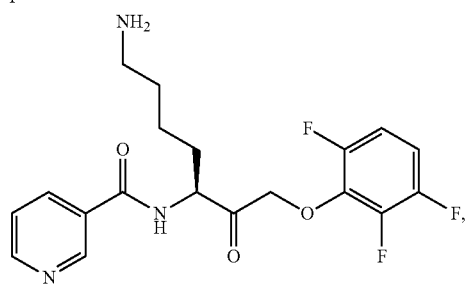
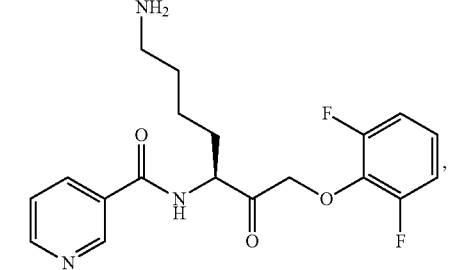
350
-continued
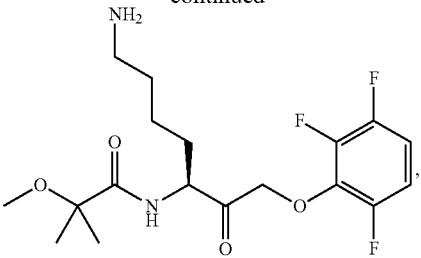
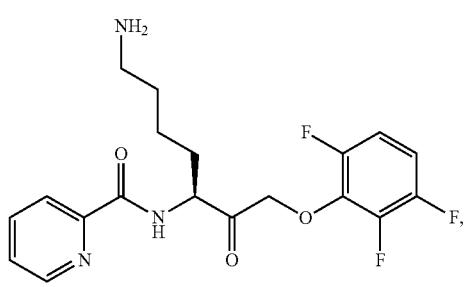
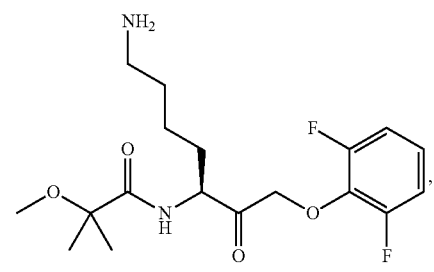
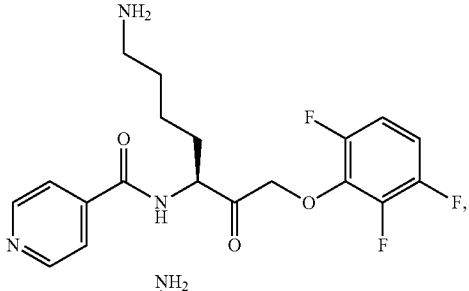
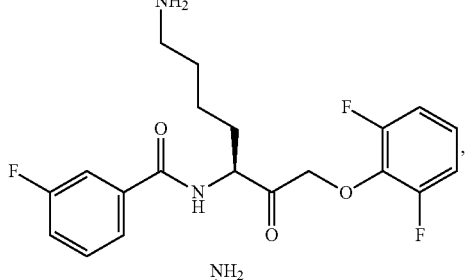
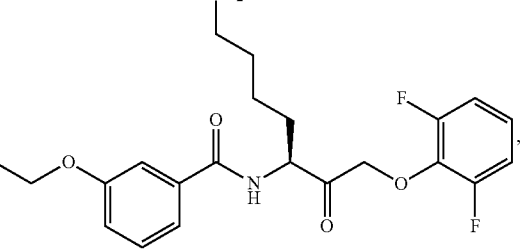

351

-continued

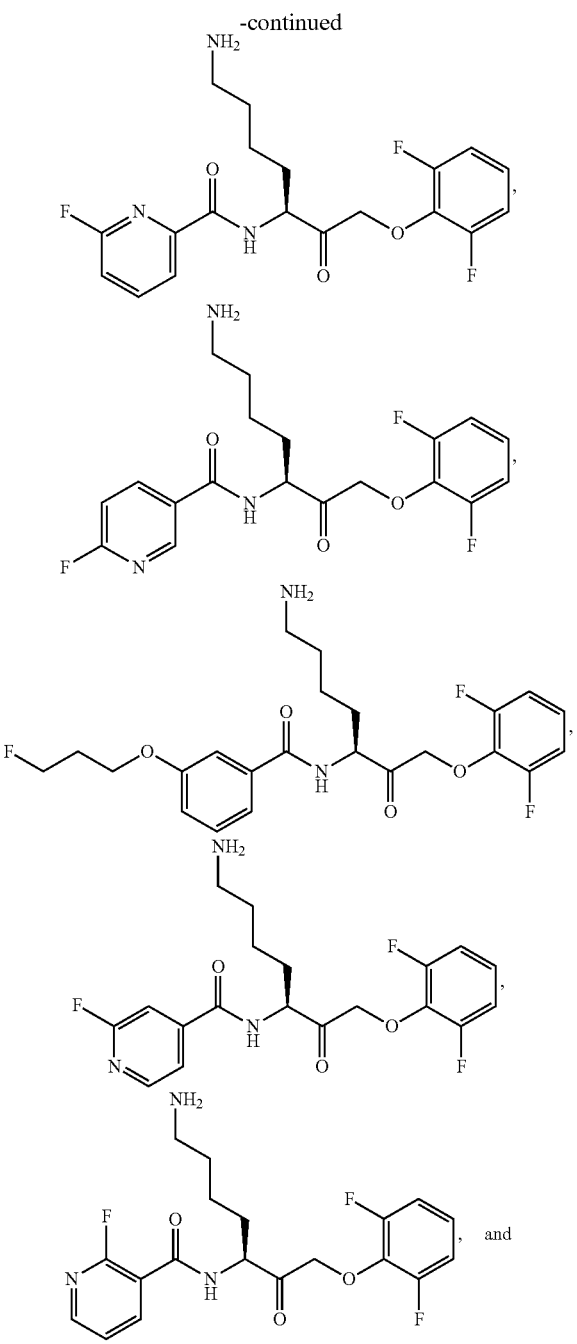
, and

352

-continued

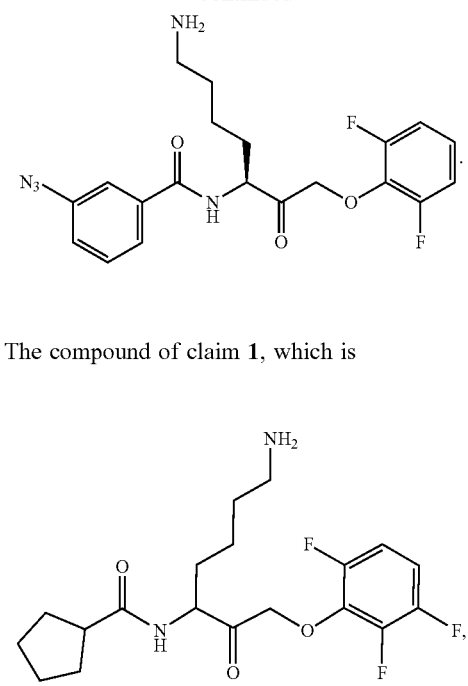
.

9. The compound of claim 1, which is

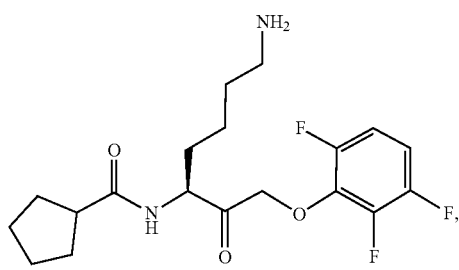 [SMILES: NCCCC[C@H](NC(=O)C1CCCC1)C(=O)COc1c(F)ccc(F)c1F]

or a pharmaceutically acceptable salt thereof.

10. The compound of claim 1, which is

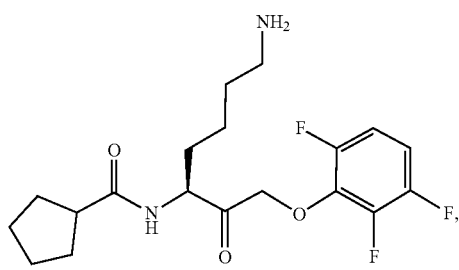 [SMILES: NCCCC[C@H](NC(=O)C1CCCC1)C(=O)COc1c(F)ccc(F)c1F]

or a pharmaceutically acceptable salt thereof.

11. A pharmaceutical composition comprising according to any one of the preceding claims, or a pharmaceutically acceptable salt thereof, and a pharmaceutically acceptable excipient.

* * * * *